(12) United States Patent
Seifermann

(10) Patent No.: US 12,187,711 B2
(45) Date of Patent: *Jan. 7, 2025

(54) ORGANIC MOLECULES FOR USE IN OPTOELECTRONIC DEVICES

(71) Applicant: SAMSUNG DISPLAY CO., LTD., Yongin-si (KR)

(72) Inventor: Stefan Seifermann, Bühl (DE)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/314,060

(22) Filed: May 8, 2023

(65) Prior Publication Data

US 2023/0278992 A1 Sep. 7, 2023

Related U.S. Application Data

(62) Division of application No. 16/759,844, filed as application No. PCT/EP2018/079019 on Oct. 23, 2018, now Pat. No. 11,718,608.

(30) Foreign Application Priority Data

Oct. 30, 2017 (EP) .................................. 17199193

(51) Int. Cl.
  *C07D 409/14* (2006.01)
  *C07D 403/14* (2006.01)
  *C07D 405/14* (2006.01)
  *H10K 85/60* (2023.01)

(52) U.S. Cl.
  CPC .......... *C07D 409/14* (2013.01); *C07D 403/14* (2013.01); *C07D 405/14* (2013.01); *H10K 85/654* (2023.02); *H10K 85/6572* (2023.02); *H10K 85/6574* (2023.02); *H10K 85/6576* (2023.02)

(58) Field of Classification Search
  CPC .................................................... C07D 409/14
  USPC ........................................................ 257/40
  See application file for complete search history.

(56) References Cited

FOREIGN PATENT DOCUMENTS

| KR | 10-2015-0129282 A | 11/2015 |
|---|---|---|
| WO | WO 2016/089080 A1 | 6/2016 |

OTHER PUBLICATIONS

International Search Report and Written Opinion of PCT/EP2018/079019 A1, Mar. 6, 2019.

*Primary Examiner* — Taofiq A Solola
(74) *Attorney, Agent, or Firm* — Lewis Roca Rothgerber Christie LLP

(57) ABSTRACT

An organic molecule is disclosed having:
  one first chemical moiety with a structure of formula I:

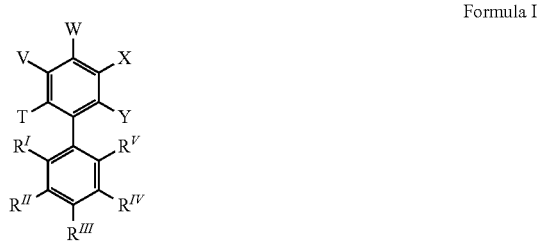

Formula I and
  one second chemical moiety with a structure of formula II:

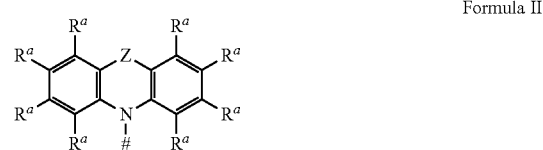

Formula II wherein the first chemical moiety is linked to the second chemical moiety via a single bond; and
  one third chemical moiety with a structure of Formula III:

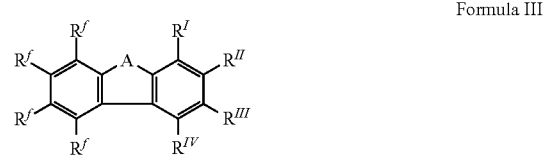

Formula III wherein the first chemical moiety is linked to the third chemical moiety via a single bond.

20 Claims, 4 Drawing Sheets

ORGANIC MOLECULES FOR USE IN OPTOELECTRONIC DEVICES

CROSS-REFERENCE TO RELATED APPLICATIONS

This application is a divisional of, and claims priority to and the benefit of U.S. application Ser. No. 16/759,844, filed on Apr. 28, 2020, which is a National Phase Patent Application of International Patent Application No. PCT/EP2018/079019, filed on Oct. 23, 2018, which claims priority to and the benefit of European Patent Application No. 17199193.8, filed on Oct. 30, 2017, the entire contents of all of which are incorporated herein by reference.

FIELD OF INVENTION

The invention relates to light-emitting organic molecules and their use in organic light-emitting diodes (OLEDs) and in other optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTIONS

Figure 1:
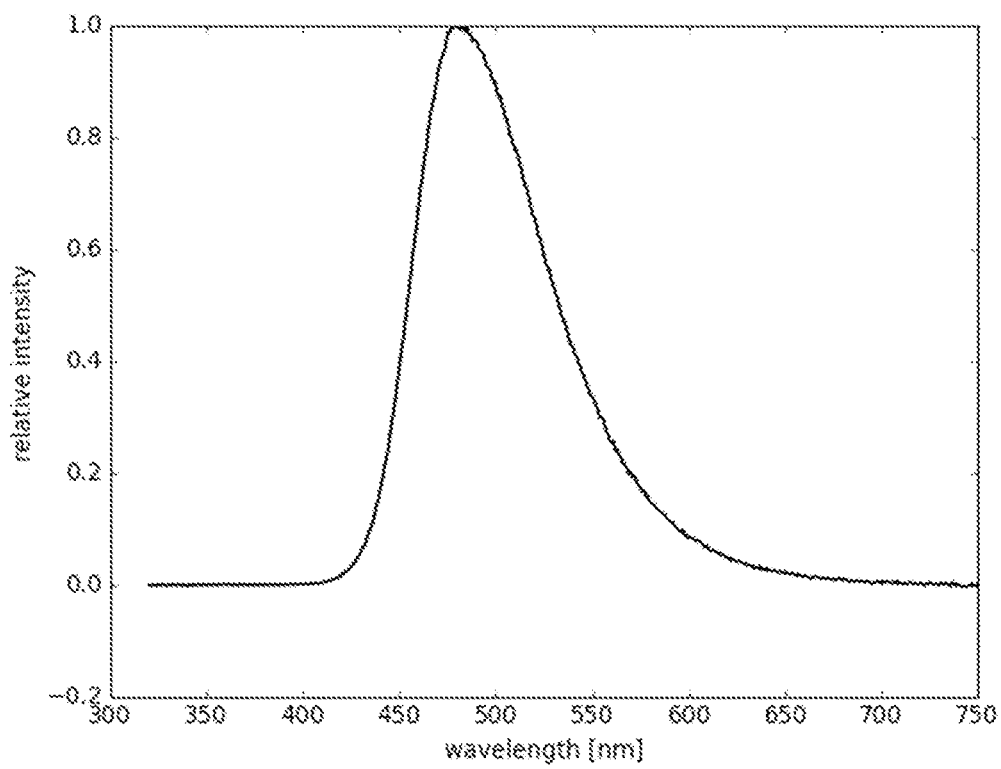
FIG. 1 is an emission spectrum of example 1 (10% by weight) in PMMA.

Exemplary embodiments of the invention will now be discussed in further detail. This invention may, however, be embodied in many different forms and should not be construed as limited to the embodiments set forth herein.

The object of the present invention is to provide molecules which are suitable for use in optoelectronic devices. This object is achieved by the invention which provides a new class of organic molecules.

According to the invention, the organic molecules are purely organic molecules, i.e. they do not contain any metal ions in contrast to metal complexes known for use in organic optoelectronic devices.

According to the present invention, the organic molecules exhibit emission maxima in the blue, sky-blue or green spectral range. The organic molecules exhibit in particular emission maxima between 420 nm and 520 nm, preferably between 440 nm and 495 nm, more preferably between 450 nm and 470 nm. The photoluminescence quantum yields of the organic molecules according to the invention are, in particular, 70% or more. The molecules according to the invention exhibit in particular thermally activated delayed fluorescence (TADF). The use of the molecules according to the invention in an optoelectronic device, for example an organic light-emitting diode (OLED), leads to higher efficiencies of the device. Corresponding OLEDs have a higher stability than OLEDs with known emitter materials and comparable color.

The organic light-emitting molecules according to the invention comprise or consist of
one first chemical moiety comprising or consisting of a structure of Formula I,

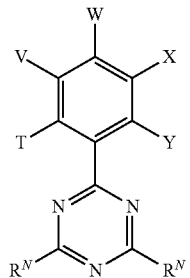

Formula I and
one second chemical moiety comprising or consisting of a structure of Formula II,

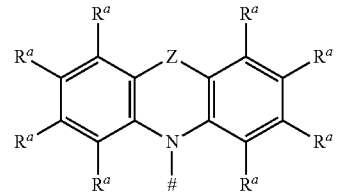

Formula II wherein the first chemical moiety is linked to the second chemical moiety via a single bond; and
one third chemical moiety comprising or consisting of a structure of Formula III,

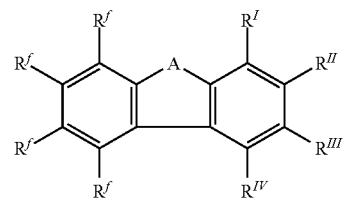

Formula III wherein the first chemical moiety is linked to the third chemical moiety via a single bond.

T is selected from the group consisting of
the binding site of a single bond linking the first chemical moiety to the second chemical moiety,
the binding site of a single bond linking the first chemical moiety to the third chemical moiety, and $R^1$.

V is selected from the group consisting of
the binding site of a single bond linking the first chemical moiety to the second chemical moiety,
the binding site of a single bond linking the first chemical moiety to the third chemical moiety, and $R^1$.

W is selected from the group consisting of
the binding site of a single bond linking the first chemical moiety to the second chemical moiety, the binding site of a single bond linking the first chemical moiety to the third chemical moiety, and $R^1$.

X is selected from the group consisting of $R^1$ and the binding site of a single bond linking the first chemical moiety to the third chemical moiety.

Y is selected from the group consisting of $R^1$ and the binding site of a single bond linking the first chemical moiety to the third chemical moiety.

\# represents the binding site of a single bond linking the first chemical moiety to the second chemical moiety.

A is selected from the group consisting of O, S and N-Ph.

Z is selected from the group consisting of a direct bond, $CR^3R^4$, $C=CR^3R^4$, $C=O$, $C=NR^3$, $NR^3$, O, $SiR^3R^4$, S, S(O) and $S(O)_2$.

$R^N$ is at each occurrence independently from another selected from the group consisting of hydrogen, deuterium,
 $C_1$-$C_5$-alkyl,
  wherein one or more hydrogen atoms are optionally substituted by deuterium;
 $C_2$-$C_8$-alkenyl,
  wherein one or more hydrogen atoms are optionally substituted by deuterium;
 $C_2$-$C_8$-alkynyl,
  wherein one or more hydrogen atoms are optionally substituted by deuterium;
 $C_6$-$C_{18}$-aryl,
  which is optionally substituted with one or more substituents $R^6$; and
 $C_3$-$C_{17}$-heteroaryl,
  which is optionally substituted with one or more substituents $R^6$.

$R^I$, $R^{II}$, $R^{III}$, and $R^{IV}$ is at each occurrence independently from another selected from the group consisting of \$ and $R^d$.

$R^d$ is at each occurrence independently from another selected from the group consisting of hydrogen, deuterium,
 $C_6$-$C_{18}$-aryl,
  which is optionally substituted with one or more substituents independently from another selected from the group consisting of
   $C_1$-$C_5$-alkyl,
    wherein optionally one or more hydrogen atoms are independently from each other substituted by deuterium, CN, $CF_3$, or F;
   and
   $C_6$-$C_{18}$-aryl,
    which is optionally substituted with one or more $C_1$-$C_5$-alkyl substituents.

\$ represents the binding site of a single bond linking the first chemical moiety to the third chemical moiety.

$R^1$ is at each occurrence independently from another selected from the group consisting of
 hydrogen,
 deuterium,
 $C_1$-$C_5$-alkyl,
  wherein one or more hydrogen atoms are optionally substituted by deuterium;
 $C_2$-$C_3$-alkenyl,
  wherein one or more hydrogen atoms are optionally substituted by deuterium;
 $C_2$-$C_3$-alkynyl,
  wherein one or more hydrogen atoms are optionally substituted by deuterium; and
 $C_6$-$C_{13}$-aryl,
  which is optionally substituted with one or more substituents independently from another selected from the group consisting of
   $C_1$-$C_5$-alkyl,
    wherein optionally one or more hydrogen atoms are independently from each other substituted by deuterium, CN, $CF_3$, or F;
   and
   $C_5$-$C_{13}$-aryl,
    which is optionally substituted with one or more $C_1$-$C_5$-alkyl substituents.

$R^a$, $R^3$ and $R^4$ is at each occurrence independently from another selected from the group consisting of hydrogen, deuterium,
 $N(R^5)_2$,
 $OR^5$,
 $Si(R^5)_3$,
 $B(OR^5)_2$,
 $OSO_2R^5$,
 $CF_3$,
 CN,
 F,
 Br,
 I,
 $C_1$-$C_{40}$-alkyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
 $C_1$-$C_{40}$-alkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
 $C_1$-$C_{40}$-thioalkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
 $C_2$-$C_{40}$-alkenyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
 $C_2$-$C_{40}$-alkynyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
 $C_6$-$C_{60}$-aryl,
  which is optionally substituted with one or more substituents $R^5$; and
 $C_3$-$C_{57}$-heteroaryl,
  which is optionally substituted with one or more substituents $R^5$.

$R^5$ is at each occurrence independently from another selected from the group consisting of
 hydrogen,
 deuterium,
 $N(R^6)_2$,
 $OR^6$, Si(R$^6$)$_3$,
B(OR$^6$)$_2$,
OSO$_2$R$^6$,
CF$_3$,
CN,
F,
Br,
I,
C$_1$-C$_{40}$-alkyl,
   which is optionally substituted with one or more substituents R$^6$ and
   wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;
C$_1$-C$_{40}$-alkoxy,
   which is optionally substituted with one or more substituents R$^6$ and
   wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;
C$_1$-C$_{40}$-thioalkoxy,
   which is optionally substituted with one or more substituents R$^6$ and
   wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;
C$_2$-C$_{40}$-alkenyl,
   which is optionally substituted with one or more substituents R$^6$ and
   wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;
C$_2$-C$_{40}$-alkynyl,
   which is optionally substituted with one or more substituents R$^6$ and
   wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;
C$_6$-C$_{60}$-aryl,
   which is optionally substituted with one or more substituents R$^6$; and
C$_3$-C$_{57}$-heteroaryl,
   which is optionally substituted with one or more substituents R$^6$.

R$^f$ is at each occurrence independently from another selected from the group consisting of
hydrogen,
deuterium,
N(R$^{5f}$)$_2$,
OR$^{5f}$,
Si(R$^{5f}$)$_3$,
B(OR$^{5f}$)$_2$,
OSO$_2$R$^{5f}$,
CF$_3$,
CN,
F,
Br,
I,
C$_1$-C$_{40}$-alkyl,
   which is optionally substituted with one or more substituents R$^{5f}$ and
   wherein one or more non-adjacent CH$_2$-groups are optionally substituted by R$^{5f}$C=CR$^{5f}$, C≡C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^5$a, O, S or CONR$^{5f}$;
C$_1$-C$_{40}$-alkoxy,
   which is optionally substituted with one or more substituents R$^{5f}$ and
   wherein one or more non-adjacent CH$_2$-groups are optionally substituted by R$^{5f}$C=CR$^{5f}$, C≡C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$; O, S or CONR$^{5f}$;
C$_1$-C$_{40}$-thioalkoxy,
   which is optionally substituted with one or more substituents R$^{5f}$ and
   wherein one or more non-adjacent CH$_2$-groups are optionally substituted by R$^{5f}$C=CR$^{5f}$, C≡C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$; O, S or CONR$^{5f}$;
C$_2$-C$_{40}$-alkenyl,
   which is optionally substituted with one or more substituents R$^{5f}$ and
   wherein one or more non-adjacent CH$_2$-groups are optionally substituted by R$^{5f}$C=CR$^{5f}$, C≡C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$; O, S or CONR$^{5f}$;
C$_2$-C$_{40}$-alkynyl,
   which is optionally substituted with one or more substituents R$^{5f}$ and
   wherein one or more non-adjacent CH$_2$-groups are optionally substituted by R$^{5f}$C=CR$^{5f}$, C≡C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$; O, S or CONR$^{5f}$;
C$_6$-C$_{60}$-aryl,
   which is optionally substituted with one or more substituents R$^{5f}$; and
C$_3$-C$_{57}$-heteroaryl,
   which is optionally substituted with one or more substituents R$^{5f}$.

R$^{5f}$ is at each occurrence independently from another selected from the group consisting of
hydrogen,
deuterium,
N(R$^6$)$_2$,
OR$^6$,
Si(R$^6$)$_3$,
B(OR$^6$)$_2$,
OSO$_2$R$^6$,
CF$_3$,
CN,
F,
Br,
I,
C$_1$-C$_{40}$-alkyl,
   which is optionally substituted with one or more substituents R$^6$ and
   wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;
C$_1$-C$_{40}$-alkoxy,
   which is optionally substituted with one or more substituents R$^6$ and wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_1$-C$_{40}$-thioalkoxy,
which is optionally substituted with one or more substituents R$^6$ and
wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_2$-C$_{40}$-alkenyl,
which is optionally substituted with one or more substituents R$^6$ and
wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_2$-C$_{40}$-alkynyl,
which is optionally substituted with one or more substituents R$^6$ and
wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_6$-C$_{60}$-aryl,
which is optionally substituted with one or more substituents R$^6$; and C$_3$-C$_7$-heteroaryl,
which is optionally substituted with one or more substituents R$^6$.

R$^6$ is at each occurrence independently from another selected from the group consisting of
hydrogen,
deuterium,
OPh,
CF$_3$,
CN,
F,
C$_1$-C$_5$-alkyl,
wherein optionally one or more hydrogen atoms are independently from each other substituted by deuterium, CN, CF$_3$, or F;
C$_1$-C$_5$-alkoxy,
wherein optionally one or more hydrogen atoms are independently from each other substituted by deuterium, CN, CF$_3$, or F;
C$_1$-C$_5$-thioalkoxy,
wherein optionally one or more hydrogen atoms are independently from each other substituted by deuterium, CN, CF$_3$, or F;
C$_2$-C$_5$-alkenyl,
wherein optionally one or more hydrogen atoms are independently from each other substituted by deuterium, CN, CF$_3$, or F;
C$_2$-C$_5$-alkynyl,
wherein optionally one or more hydrogen atoms are independently from each other substituted by deuterium, CN, CF$_3$, or F;
C$_6$-C$_{13}$-aryl,
which is optionally substituted with one or more C$_1$-C$_5$-alkyl substituents;
C$_3$-C$_{17}$-heteroaryl,
which is optionally substituted with one or more C$_1$-C$_5$-alkyl substituents;
N(C$_6$-C$_{18}$-aryl)$_2$;
N(C$_3$-C$_{17}$-heteroaryl)$_2$; and
N(C$_3$-C$_{17}$-heteroaryl)(C$_6$-C$_{18}$-aryl).

Optionally, one or more of the substituents R$^a$, R$^3$, R$^4$ or R$^5$ independently from each other form a mono- or polycyclic, aliphatic, aromatic and/or benzo-fused ring system with one or more other substituents R$^a$, R$^3$, R$^4$ or R$^5$.

Optionally, one or more of the substituents R$^f$ or R$^{5f}$ independently from each other form a mono- or polycyclic, aliphatic, aromatic and/or benzo-fused ring system with one or more other substituents R$^f$ or R$^{5f}$.

According to the invention, exactly one (one and only one) substituent selected from the group consisting of T, V, W, X, and Y is the binding site of a single bond linking the first chemical moiety to the third chemical moiety, and exactly one substituent selected from the group consisting of T, V and W represents the binding site of a single bond linking the first chemical moiety to the second chemical moiety.

According to the invention, T is hydrogen in case W is the binding site of a single bond linking the first chemical moiety and the third chemical moiety and V represents the binding site of a single bond linking the first chemical moiety and the second chemical moiety; and W is hydrogen in case T is the binding site of a single bond linking the first chemical moiety and the third chemical moiety and V represents the binding site of a single bond linking the first chemical moiety and the second chemical moiety.

According to the invention, exactly one substituent selected from the group consisting of R$^I$, R$^{II}$ R$^{III}$ and R$^{IV}$ is the binding site of a single bond linking the first chemical moiety to the third chemical moiety (represented by $).

In some embodiments of the invention, the second chemical moiety and the third chemical moiety of the organic molecule are not both in a meta position to the triazine ring shown in formula I. In other words, the substitution pattern of the central phenyl group shown in formula I is not "meta-meta-meta" with respect to the triazine moiety, the second chemical moiety, and the third chemical moiety in these embodiments.

In one embodiment, the organic molecules according to the invention comprise or consist of a first chemical moiety comprising or consisting of a structure of Formula I,

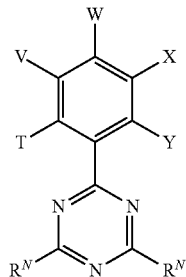

Formula I wherein
X is R$^1$ in case V is the binding site of a single bond linking the first chemical moiety and the second chemical moiety;
and apart from that the aforementioned definitions apply.

In one embodiment, the organic molecules according to the invention comprise or consist of a first chemical moiety comprising or consisting of a structure of Formula I,

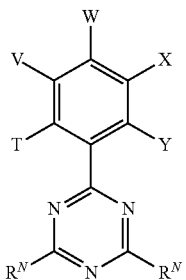

Formula I

X is H in case V is the binding site of a single bond linking the first chemical moiety and the second chemical moiety;
and apart from that the aforementioned definitions apply.
In one embodiment, the organic molecules according to the invention comprise or consist of a first chemical moiety comprising or consisting of a structure of Formula I-YY,

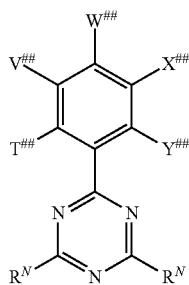

Formula I-YY wherein $R^N$ is defined as above,
$T^{\#\#\#}$ is selected from the group consisting of
the binding site of a single bond linking the first chemical moiety to the second chemical moiety,
the binding site of a single bond linking the first chemical moiety to the third chemical moiety, and $R^1$;
$V^{\#\#\#}$ is selected from the group consisting of
the binding site of a single bond linking the first chemical moiety to the third chemical moiety, and $R^1$;
$W^{\#\#\#}$ is selected from the group consisting of
the binding site of a single bond linking the first chemical moiety to the second chemical moiety,
the binding site of a single bond linking the first chemical moiety to the third chemical moiety, and $R^1$;
$X^{\#\#\#}$ is selected from the group consisting of
the binding site of a single bond linking the first chemical moiety to the third chemical moiety, and $R^1$;
$Y^{\#\#\#}$ is selected from the group consisting of
the binding site of a single bond linking the first chemical moiety to the third chemical moiety, and $R^1$;
exactly one substituent selected from the group consisting of $T^{\#\#\#}$ and $W^{\#\#\#}$ represents the binding site of a single bond linking the first chemical moiety and the second chemical moiety,
exactly one substituent selected from the group consisting of $T^{\#\#\#}$, $V^{\#\#\#}$, $W^{\#\#\#}$, $X^{\#\#\#}$ and $Y^{\#\#\#}$ represents the binding site of a single bond linking the first chemical moiety and the third chemical moiety and exactly one substituent selected from the group consisting of $R^I$, $R^{II}$, $R^{III}$ and $R^{IV}$ is the binding site of a single bond linking the first chemical moiety to the third chemical moiety (represented by $).

In one embodiment, the organic molecules according to the invention comprise or consist of a first chemical moiety comprising or consisting of a structure of Formula I-Y,

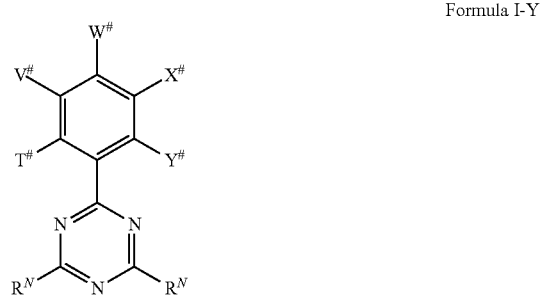

Formula I-Y wherein $R^1$, $R^N$ are defined as above,
$X^\#$ is the binding site of a single bond linking the first chemical moiety to the third chemical moiety,
$T^\#$ is the binding site of a single bond linking the first chemical moiety to the second chemical moiety or is $R^1$,
$W^\#$ is the binding site of a single bond linking the first chemical moiety to the second chemical moiety or is $R^1$,
exactly one substituent selected from the group consisting of $T^\#$ and $W^\#$ represents the binding site of a single bond linking the first chemical moiety and the second chemical moiety, and exactly one substituent selected from the group consisting of $R^I$, $R^{II}$, $R^{III}$ and $R^{IV}$ is the binding site of a single bond linking the first chemical moiety to the third chemical moiety (represented by $).

In one embodiment, A is selected from group consisting of O and S.
In one embodiment, A is O.
In one embodiment, A is S.
In one embodiment, $R^1$ is at each occurrence independently from another selected from the group consisting of H, methyl and phenyl.
In one embodiment, $R^1$ is H.
In one embodiment, $R^N$ is Ph, which is optionally substituted with one or more substituents independently from each other selected from the group consisting of Me, $^iPr$, $^tBu$, CN, $CF_3$, and Ph.
In one embodiment, $R^N$ is Ph.
In one embodiment, X represents the binding site of a single bond linking the first chemical moiety and the third chemical moiety and T represents the binding site of a single bond linking the first chemical moiety and the second chemical moiety.
In one embodiment, V is the binding site of a single bond linking the first chemical moiety to the second chemical moiety or is hydrogen.
In one embodiment, $R^d$ is at each occurrence independently from another selected from the group consisting of H and phenyl.
In one embodiment, $R^d$ is H.

In one embodiment, $R^f$ is at each occurrence independently from another selected from the group consisting of H and phenyl.

In one embodiment, $R^f$ is H.

In further embodiments of the invention, one of the group consisting of $R^I$, $R^{II}$, $R^{III}$ and $R^{IV}$ the binding site of a single bond linking the first chemical moiety to the third chemical moiety (represented by $) and H.

In one embodiment of the invention, $R^{III}$ is the binding site of a single bond linking the first chemical moiety to the third chemical moiety (represented by $).

In another embodiment of the invention, $R^I$ is the binding site of a single bond linking the first chemical moiety to the third chemical moiety (represented by $).

In another embodiment of the invention, $R^{II}$ is the binding site of a single bond linking the first chemical moiety to the third chemical moiety (represented by $).

In another embodiment of the invention, $R^{IV}$ is the binding site of a single bond linking the first chemical moiety to the third chemical moiety (represented by $).

In one embodiment of the invention, T represents the binding site of a single bond linking the first chemical moiety and the third chemical moiety.

In one embodiment of the invention, W represents the binding site of a single bond linking the first chemical moiety and the third chemical moiety.

In one embodiment of the invention, X represents the binding site of a single bond linking the first chemical moiety and the third chemical moiety.

In one embodiment of the invention, Y represents the binding site of a single bond linking the first chemical moiety and the third chemical moiety.

In a further embodiment of the invention, the second chemical moiety comprises or consists of a structure of Formula IIa:

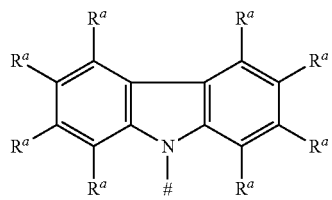

Formula IIa wherein # and $R^a$ are defined as above.

In a further embodiment of the invention, $R^a$ is at each occurrence independently from another selected from the group consisting of hydrogen,
Me,
$^iPr$,
$^tBu$
CN,
$CF_3$,
Ph, which is optionally substituted with one or more substituents independently from each other selected from the group consisting of Me, $^iPr$, $^tBu$, CN, $CF_3$, and Ph,
pyridinyl, which is optionally substituted with one or more substituents independently from each other selected from the group consisting of Me, $^iPr$, $^tBu$, CN, $CF_3$, and Ph,
pyrimidinyl, which is optionally substituted with one or more substituents independently from each other selected from the group consisting of Me, $^iPr$, $^tBu$, CN, $CF_3$, and Ph,
carbazolyl, which is optionally substituted with one or more substituents independently from each other selected from the group consisting of Me, $^iPr$, $^tBu$, CN, $CF_3$, and Ph,
triazinyl, which is optionally substituted with one or more substituents independently from each other selected from the group consisting of Me, $^iPr$, $^tBu$, CN, $CF_3$, and Ph,
and $N(Ph)_2$.

In a further embodiment of the invention, $R^a$ is at each occurrence independently from another selected from the group consisting of hydrogen,
Me,
$^iPr$,
$^tBu$
CN,
$CF_3$,
Ph, which is optionally substituted with one or more substituents independently from each other selected from the group consisting of Me, $^iPr$, $^tBu$, CN, $CF_3$, and Ph,
pyridinyl, which is optionally substituted with one or more substituents independently from each other selected from the group consisting of Me, $^iPr$, $^tBu$, CN, $CF_3$, and Ph,
pyrimidinyl, which is optionally substituted with one or more substituents independently from each other selected from the group consisting of Me, $^iPr$, $^tBu$, CN, $CF_3$, and Ph, and
triazinyl, which is optionally substituted with one or more substituents independently from each other selected from the group consisting of Me, $^iPr$, $^tBu$, CN, $CF_3$, and Ph.

In a further embodiment of the invention, the second chemical moiety comprises or consists of a structure of Formula IIb, a structure of Formula IIb-2, a structure of Formula IIb-3 or a structure of Formula IIb-4:

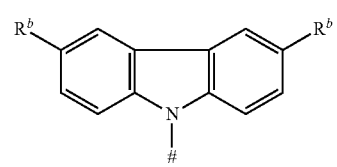

Formula IIb

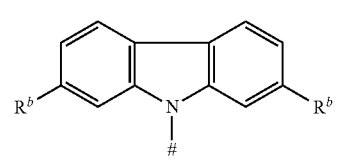

Formula IIb-2

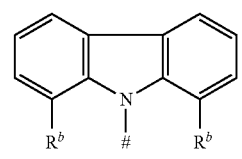

Formula IIb-3

-continued

Formula IIb-4

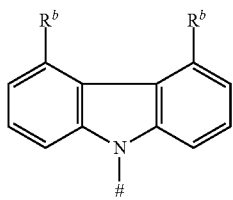

wherein
$R^b$ is at each occurrence independently from another selected from the group consisting of deuterium,
$N(R^5)_2$,
$OR^5$,
$Si(R^5)_3$,
$B(OR^5)_2$,
$OSO_2R^5$,
$CF_3$,
CN,
F,
Br,
I,
$C_1$-$C_{40}$-alkyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-alkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-thioalkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkenyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkynyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_6$-$C_{60}$-aryl,
  which is optionally substituted with one or more substituents $R^5$; and
$C_3$-$C_{57}$-heteroaryl,
  which is optionally substituted with one or more substituents $R^5$.
For additional variables, the aforementioned definitions apply.

In one additional embodiment of the invention, the second chemical moiety comprises or consists of a structure of Formula Ic, a structure of Formula IIc-2, a structure of Formula IIc-3 or a structure of Formula IIc-4:

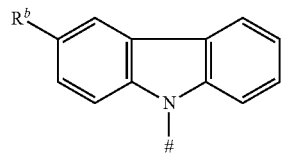

Formula IIc

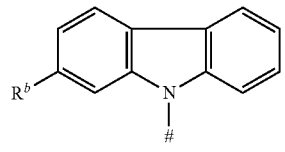

Formula IIc-2


Formula IIc-3

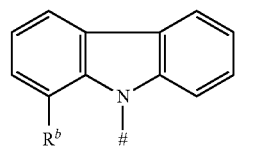

Formula IIc-4

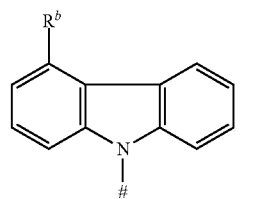

wherein the aforementioned definitions apply.
In a further embodiment of the invention, $R^b$ is at each occurrence independently from another selected from the group consisting of
  Me,
  $^i$Pr,
  $^t$Bu
  CN,
  $CF_3$,
  Ph, which is optionally substituted with one or more substituents independently from each other selected from the group consisting of Me, $^i$Pr, $^t$Bu, CN, $CF_3$, and Ph,
  pyridinyl, which is optionally substituted with one or more substituents independently from each other selected from the group consisting of Me, $^i$Pr, $^t$Bu, CN, $CF_3$, and Ph,
  pyrimidinyl, which is optionally substituted with one or more substituents independently from each other selected from the group consisting of Me, $^i$Pr, $^t$Bu, CN, $CF_3$, and Ph,
  carbazolyl, which is optionally substituted with one or more substituents independently from each other selected from the group consisting of Me, $^i$Pr, $^t$Bu, CN, $CF_3$, and Ph,
  triazinyl, which is optionally substituted with one or more substituents independently from each other selected from the group consisting of Me, $^i$Pr, $^t$Bu, CN, $CF_3$, and Ph,
  and $N(Ph)_2$.
In a further embodiment of the invention, $R^b$ is at each occurrence independently from another selected from the group consisting of Me,
$^i$Pr,
$^t$Bu,
CN,
CF$_3$,
Ph, which is optionally substituted with one or more substituents independently from each other selected from the group consisting of Me, $^i$Pr, $^t$Bu, CN, CF$_3$, and Ph,
pyridinyl, which is optionally substituted with one or more substituents independently from each other selected from the group consisting of Me, $^i$Pr, $^t$Bu, CN, CF$_3$, and Ph,
pyrimidinyl, which is optionally substituted with one or more substituents independently from each other selected from the group consisting of Me, $^i$Pr, $^t$Bu, CN, CF$_3$, and Ph, and
triazinyl, which is optionally substituted with one or more substituents independently from each other selected from the group consisting of Me, $^i$Pr, $^t$Bu, CN, CF$_3$, and Ph.

In the following, exemplary embodiments of the second chemical moiety are shown:

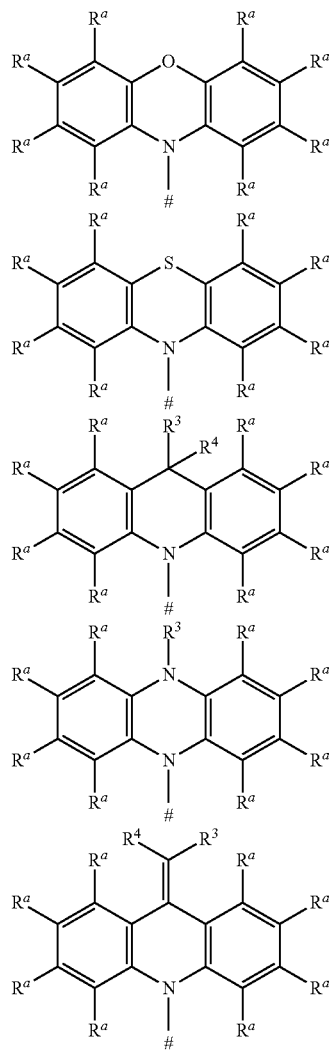

-continued

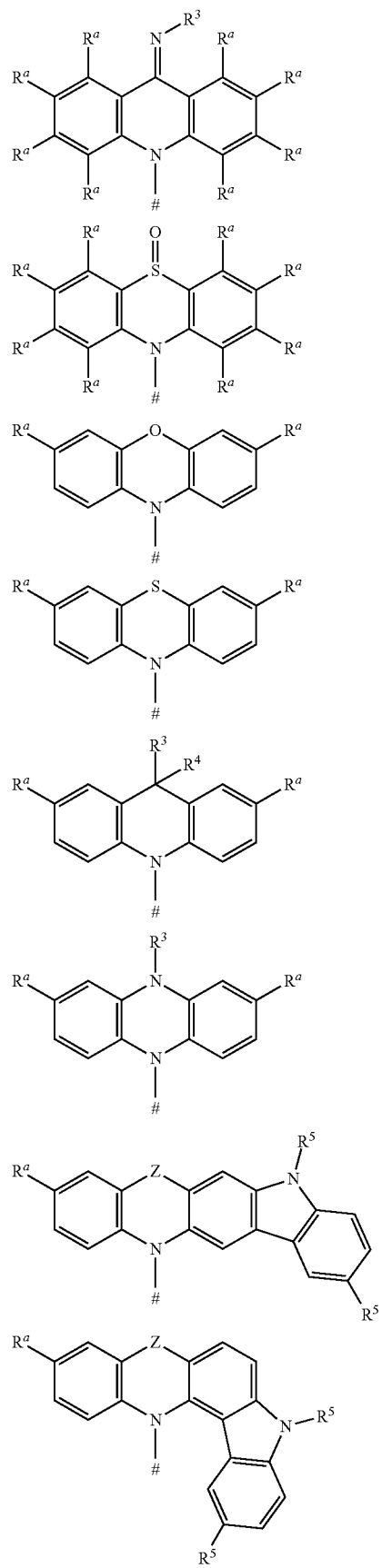

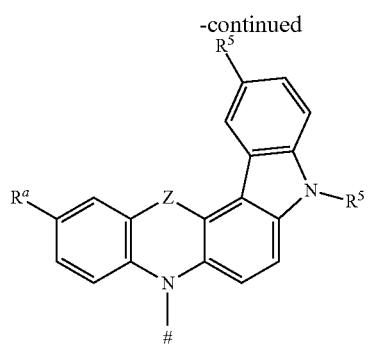
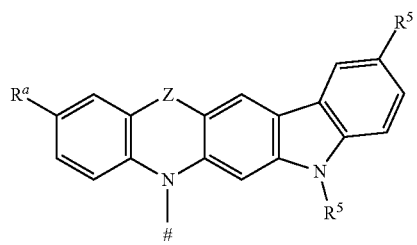

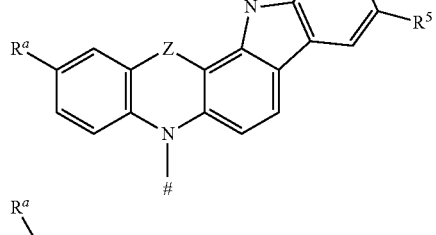
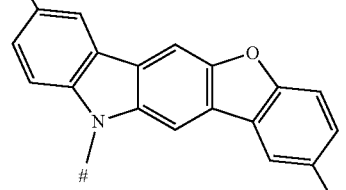
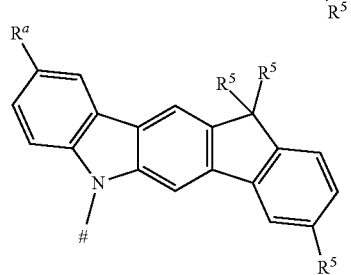
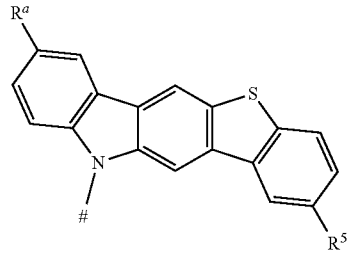
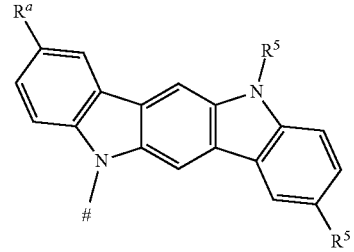
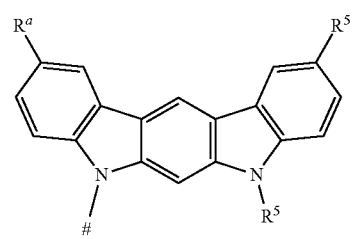
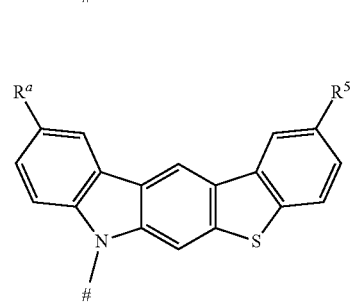
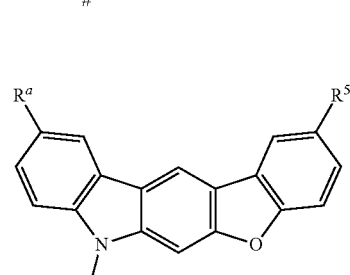
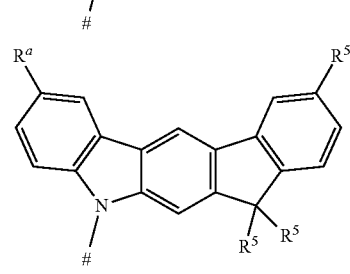
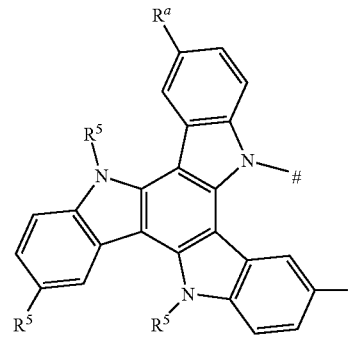

-continued
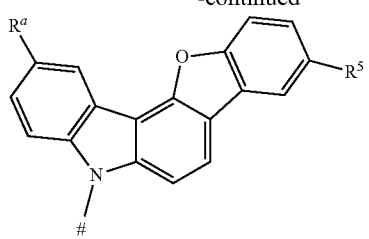
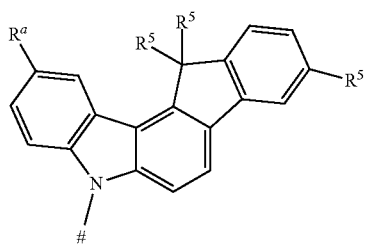
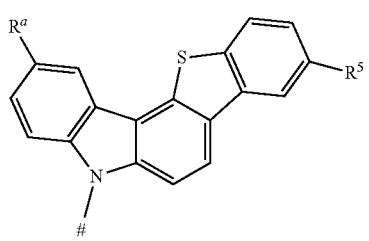
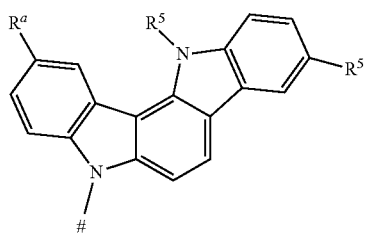
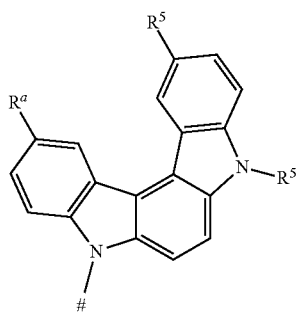
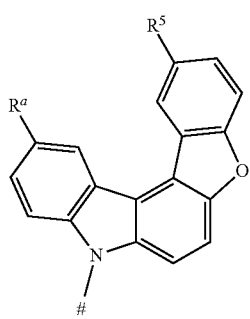
-continued
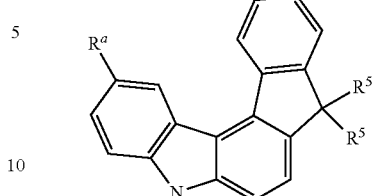
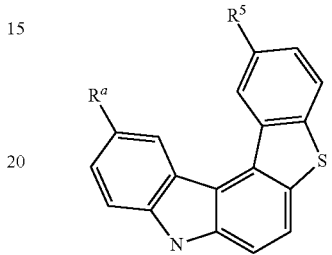
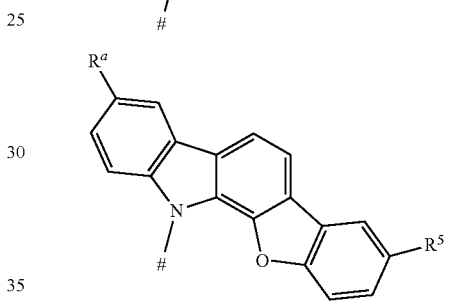
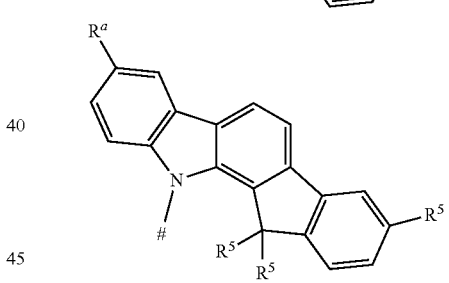
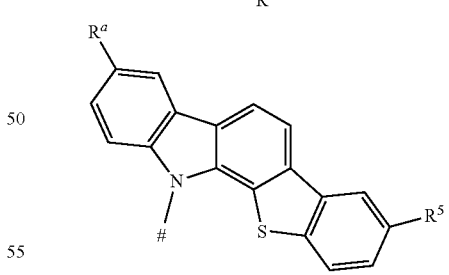
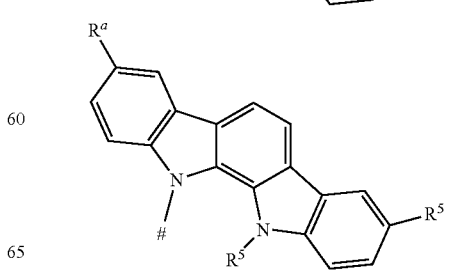

-continued

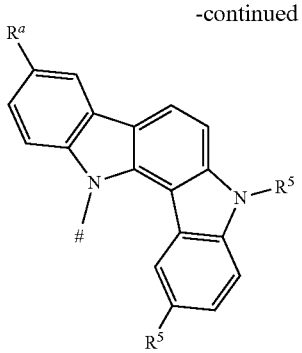

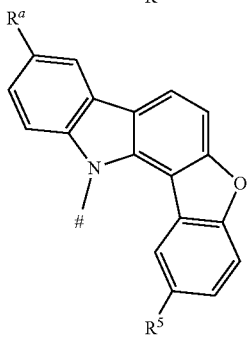

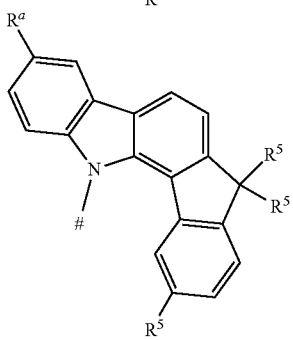

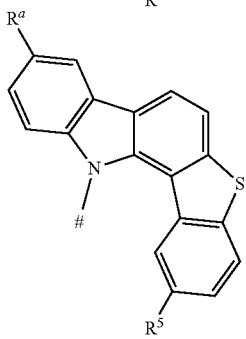

wherein for #, Z, $R^a$, $R^3$, $R^4$ and $R^5$, the aforementioned definitions apply.

In one embodiment, $R^a$ and $R^5$ is at each occurrence independently from another selected from the group consisting of hydrogen (H), methyl (Me), i-propyl (CH(CH$_3$)$_2$) ($^i$Pr), t-butyl ($^t$Bu), phenyl (Ph), triazinyl, which is optionally substituted with one or more substituents independently from each other selected from the group consisting of Me, $^i$Pr, $^t$Bu, CN, CF$_3$, and Ph; and diphenylamine (NPh$_2$).

In a further embodiment of the invention, the third chemical moiety comprises or consists of a structure selected from the group of Formula III-I, Formula III-II, Formula III-III, Formula III-IV:

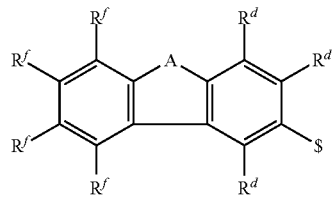
Formula III-I

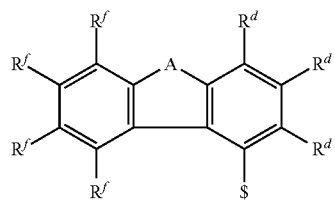
Formula III-II

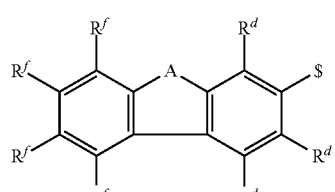
Formula III-III

Formula III-IV wherein A, $R^d$ and $R^f$ are defined as above.

In a preferred embodiment of the invention, the third chemical moiety comprises or consists of a structure of Formula III-I.

In one embodiment of the invention, the organic molecules comprise or consist of a structure of Formula III-1, Formula III-2, Formula III-3 or Formula III-4:

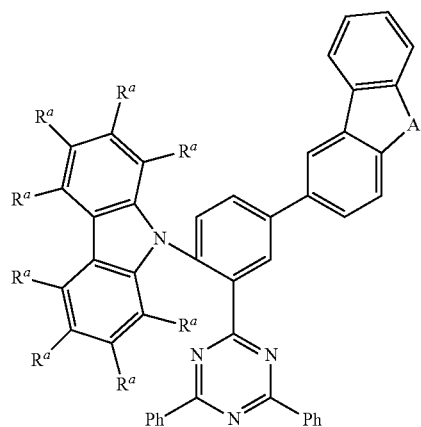
Formula III-1

Formula III-2

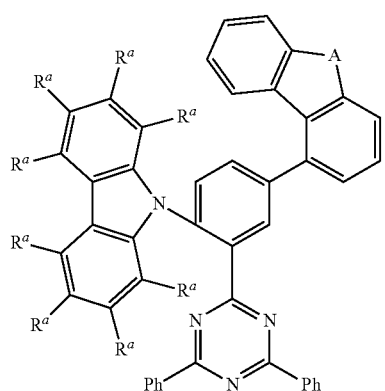

Formula IIIa-1

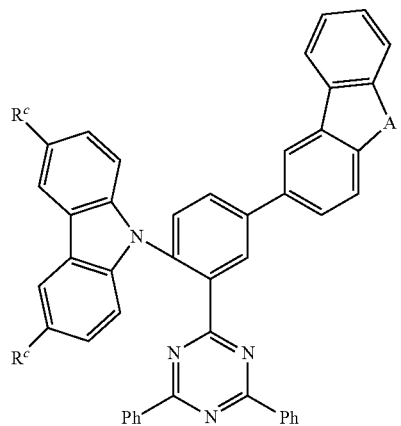

Formula III-3

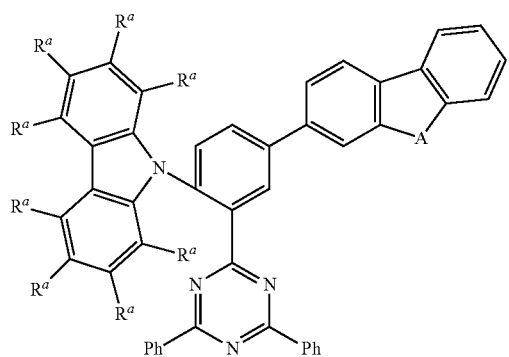

Formula IIIa-2

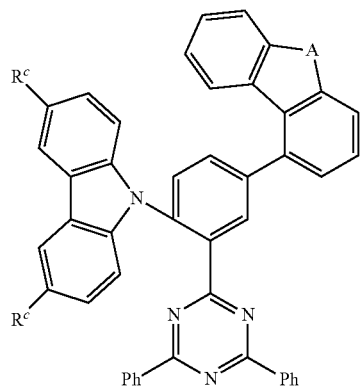

Formula IIIa-3

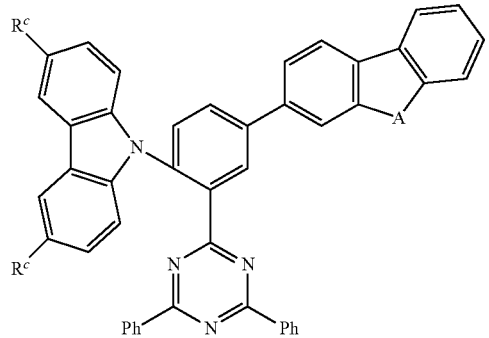

Formula III-4

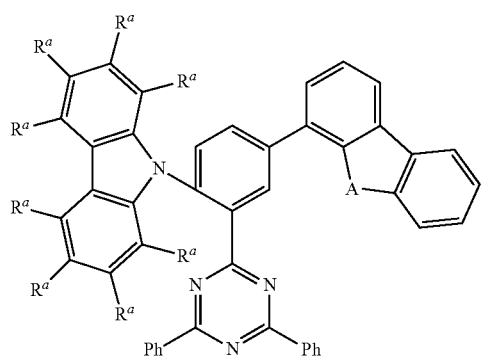

Formula IIIa-4

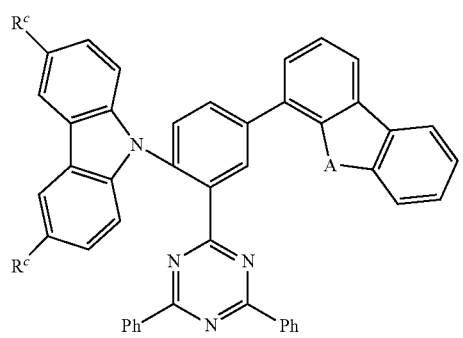

wherein the aforementioned definitions apply.

In a preferred embodiment of the invention, the organic molecules comprise or consist of a structure of Formula III-1.

In one embodiment of the invention, the organic molecules comprise or consist of a structure of Formula IIIa-1, Formula IIIa-2, Formula IIIa-3 or Formula IIIa-4:

wherein $R^c$ is at each occurrence independently from another selected from the group consisting of Me,
$^i$Pr,
$^t$Bu
Ph, which is optionally substituted with one or more substituents independently from each other selected from the group consisting of Me, $^i$Pr, $^t$Bu, CN, CF$_3$, and Ph,
pyridinyl, which is optionally substituted with one or more substituents independently from each other selected from the group consisting of Me, $^i$Pr, $^t$Bu, CN, CF$_3$, and Ph,
pyrimidinyl, which is optionally substituted with one or more substituents independently from each other selected from the group consisting of Me, $^i$Pr, $^t$Bu, CN, CF$_3$, and Ph,
carbazolyl, which is optionally substituted with one or more substituents independently from each other selected from the group consisting of Me, $^i$Pr, $^t$Bu, CN, CF$_3$, and Ph,
triazinyl, which is optionally substituted with one or more substituents independently from each other selected from the group consisting of Me, $^i$Pr, $^t$Bu, CN, CF$_3$, and Ph,
and N(Ph)$_2$.

In a preferred embodiment, the organic molecules comprise or consist of a structure of Formula III-1.

In one additional embodiment of the invention, the organic molecules comprise or consist of a structure of Formula IIIb-1, Formula IIIb-2, Formula IIIb-3 or Formula IIIb-4:

Formula IIIb-1
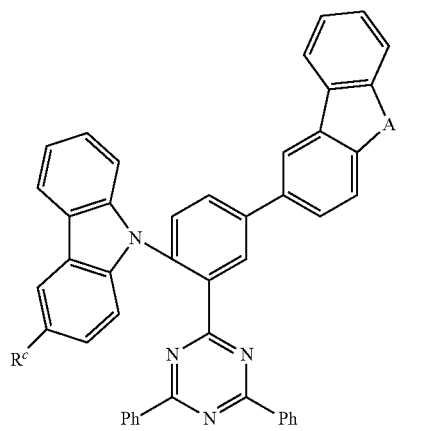

Formula IIIb-2
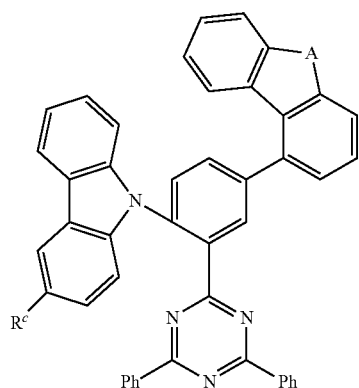

Formula IIIb-3
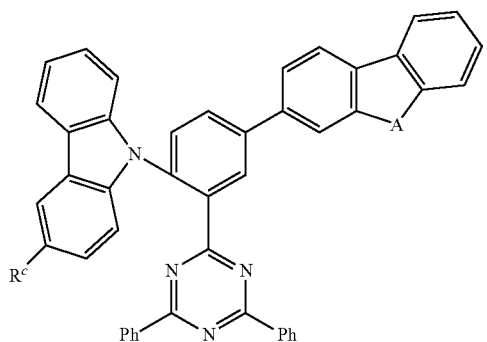

Formula IIIb-4
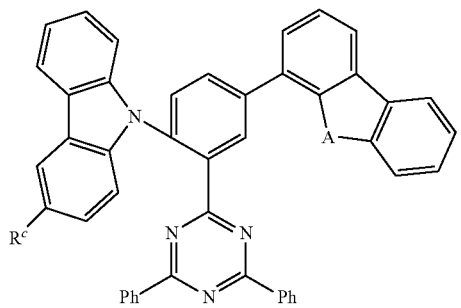

wherein the aforementioned definitions apply.

In a preferred embodiment, the organic molecules comprise or consist of a structure of Formula IIIb-1.

In one embodiment of the invention, the organic molecules comprise or consist of a structure of Formula IV-1, Formula IV-2, Formula IV-3 or Formula IV-4:

Formula IV-1
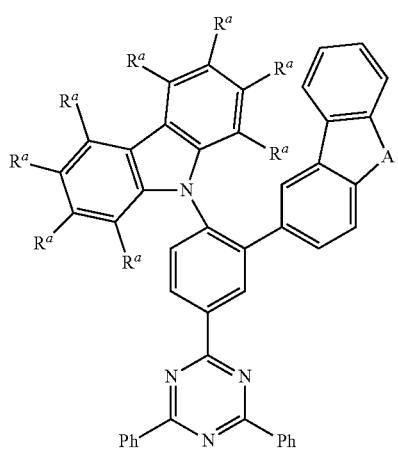

Formula IV-2

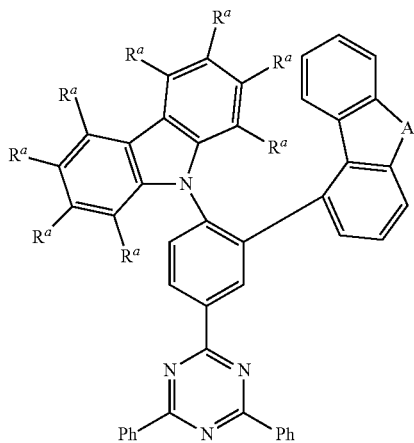

Formula IVa-1

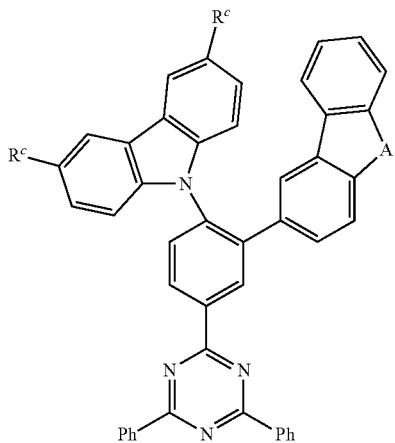

Formula IV-3

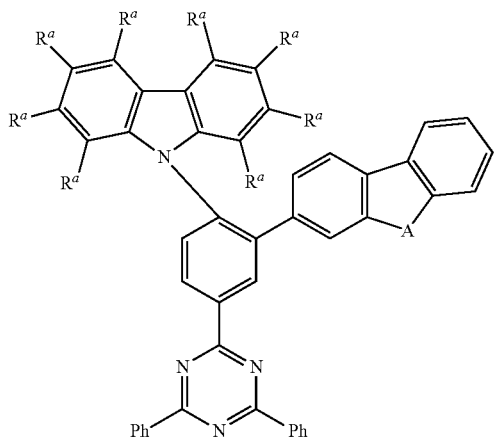

Formula IVa-2

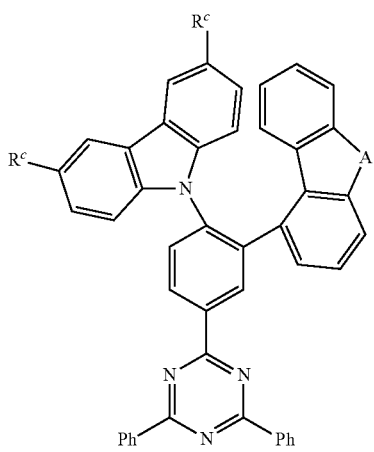

Formula IV-4

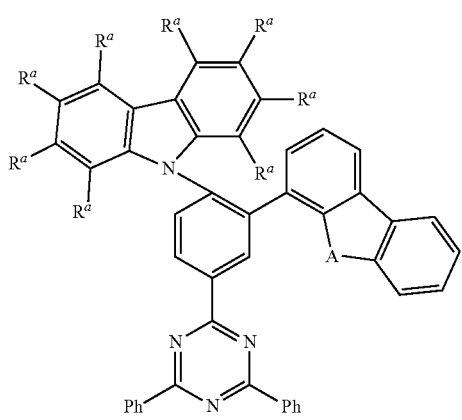

wherein the aforementioned definitions apply.

In a preferred embodiment of the invention, the organic molecules comprise or consist of a structure of Formula IV-1.

In one embodiment of the invention, the organic molecules comprise or consist of a structure of Formula IVa-1, Formula IVa-2, Formula IVa-3 or Formula IVa-4:

Formula IVa-3

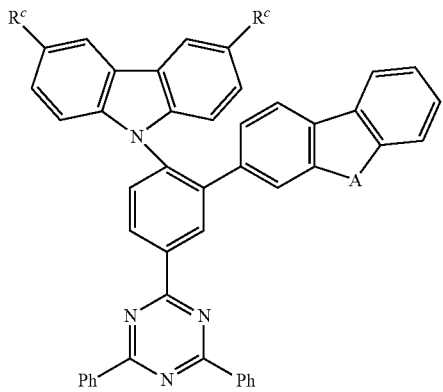

Formula IVa-4

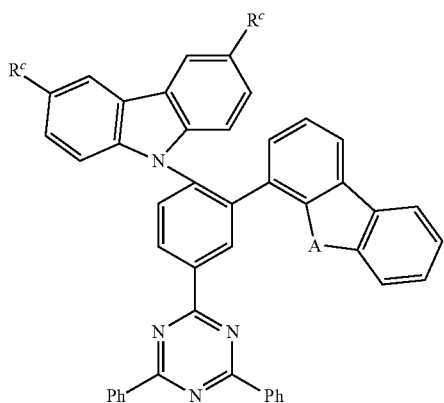

wherein the aforementioned definitions apply.

In a preferred embodiment, the organic molecules comprise or consist of a structure of Formula IVa-1.

In one additional embodiment of the invention, the organic molecules comprise or consist of a structure of Formula IVb-1, Formula IVb-2, Formula IVb-3 or Formula IVb-4:

Formula IVb-1

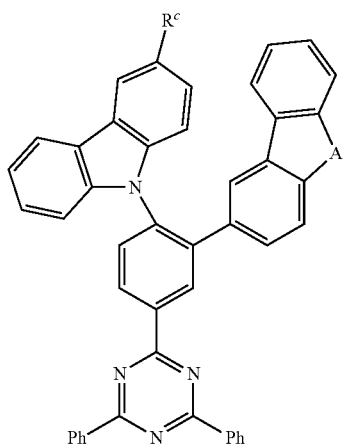

Formula IVb-2

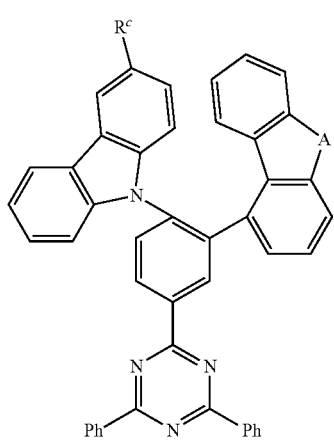

Formula IVb-3

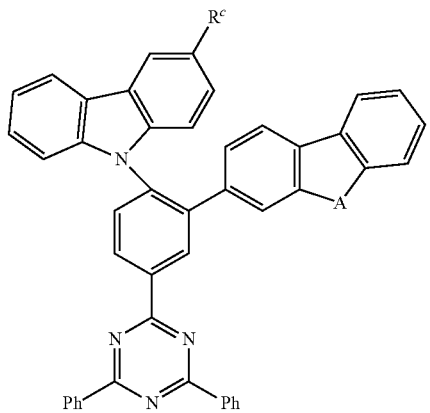

Formula IVb-4

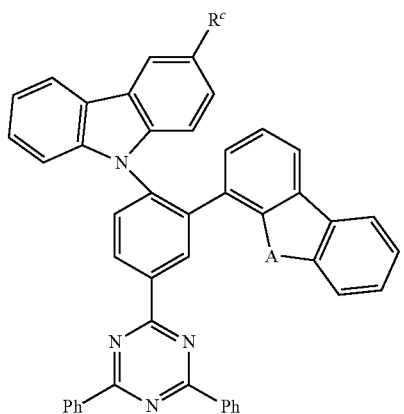

wherein the aforementioned definitions apply.

In a preferred embodiment, the organic molecules comprise or consist of a structure of Formula IVb-1.

In one embodiment of the invention, the organic molecules comprise or consist of a structure of Formula V-1, Formula V-2, Formula V-3 or Formula V-4:

Formula V-1

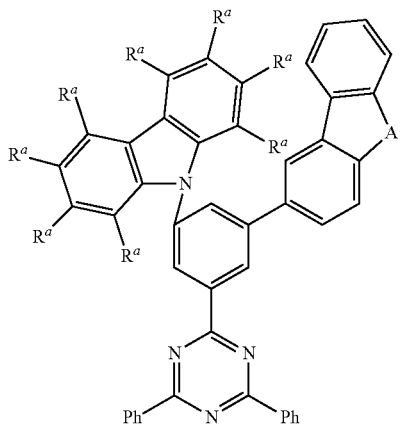

Formula V-2

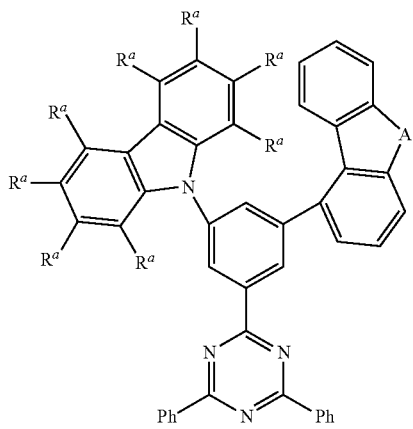

Formula Va-1

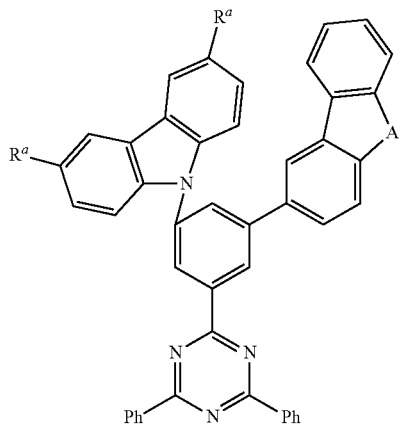

Formula V-3

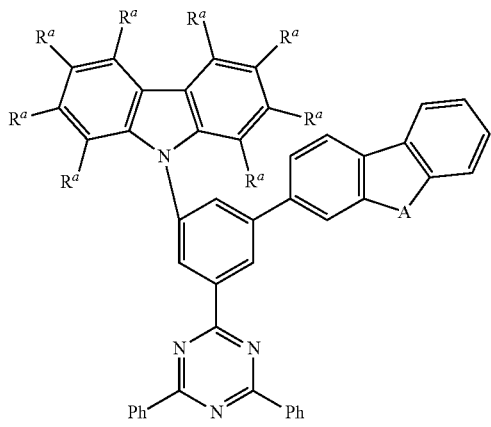

Formula Va-2

Formula V-4

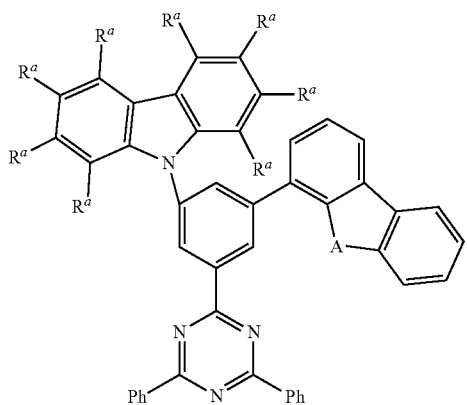

Formula Va-3

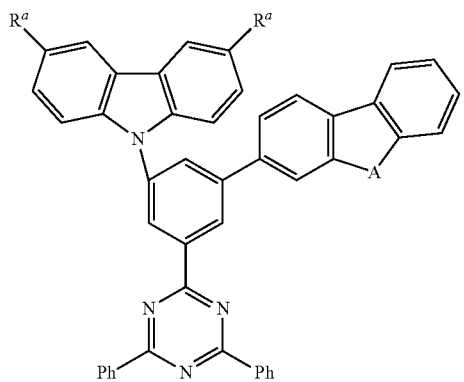

wherein the aforementioned definitions apply.

In a preferred embodiment of the invention, the organic molecules comprise or consist of a structure of Formula V-1.

In one embodiment of the invention, the organic molecules comprise or consist of a structure of Formula Va-1, Formula Va-2, Formula Va-3 or Formula Va-4:

Formula Va-4

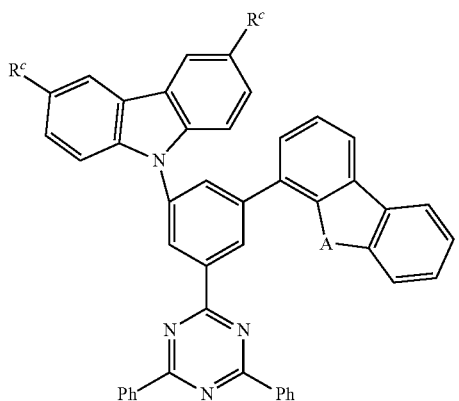

wherein the aforementioned definitions apply.

In a preferred embodiment, the organic molecules comprise or consist of a structure of Formula Va-1.

In one additional embodiment of the invention, the organic molecules comprise or consist of a structure of Formula Vb-1, Formula Vb-2, Formula Vb-3 or Formula Vb-4:

Formula Vb-1

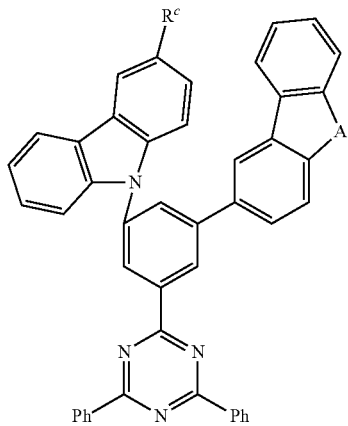

Formula Vb-2

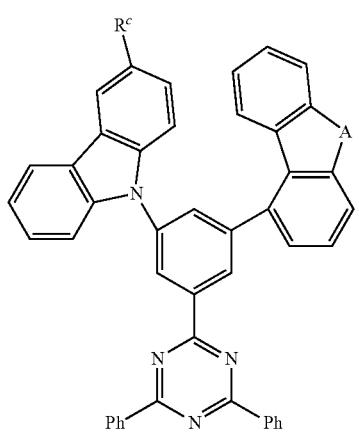

Formula Vb-3

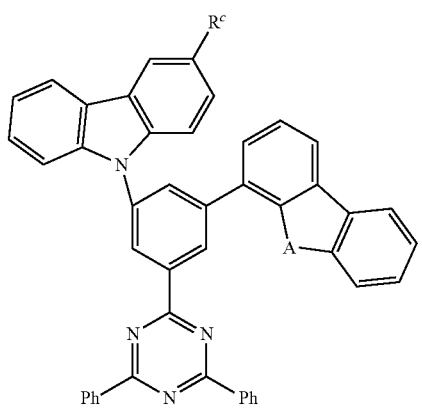

Formula Vb-4

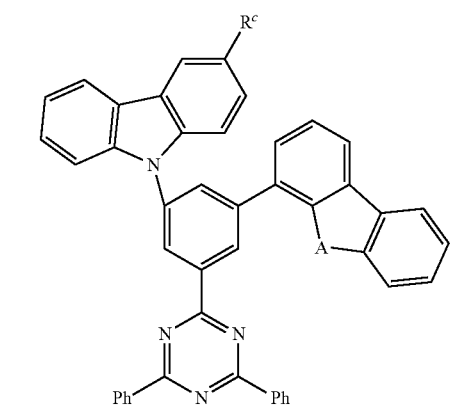

wherein the aforementioned definitions apply.

In a preferred embodiment, the organic molecules comprise or consist of a structure of Formula Vb-1.

In one embodiment of the invention, the organic molecules comprise or consist of a structure of Formula VI-1, Formula VI-2, Formula VI-3 or Formula VI-4:

Formula VI-1

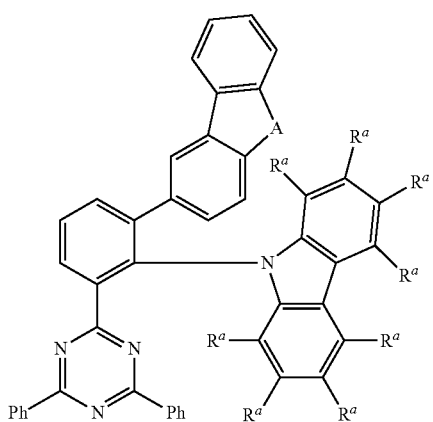

Formula VI-2

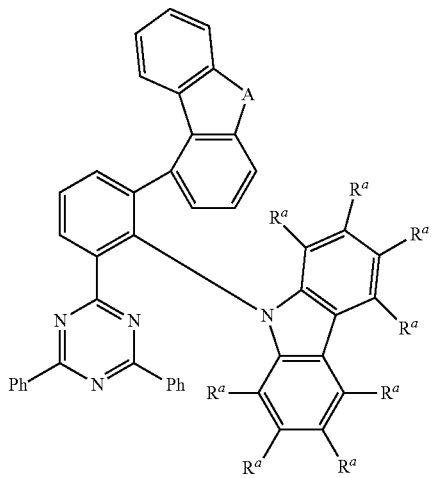

Formula VI-3

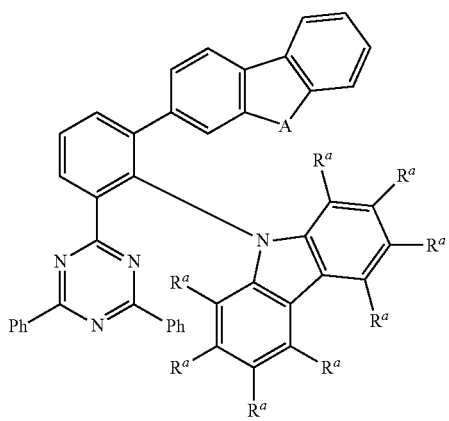

Formula VI-4

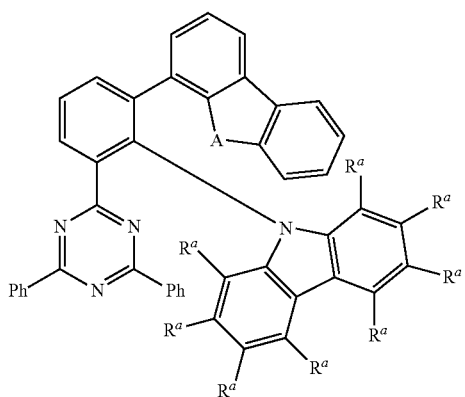

wherein the aforementioned definitions apply.

In a preferred embodiment of the invention, the organic molecules comprise or consist of a structure of Formula VI-1.

In one embodiment of the invention, the organic molecules comprise or consist of a structure of Formula VIa-1, Formula VIa-2, Formula VIa-3 or Formula VIa-4:

Formula VIa-1

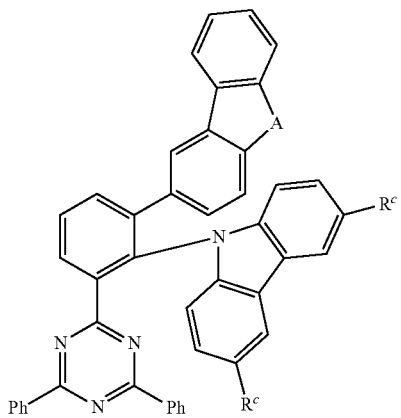

Formula VIa-2

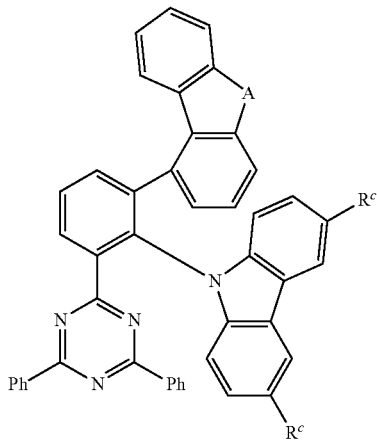

Formula VIa-3

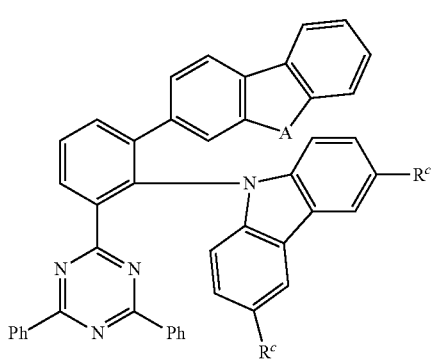

Formula VIa-4

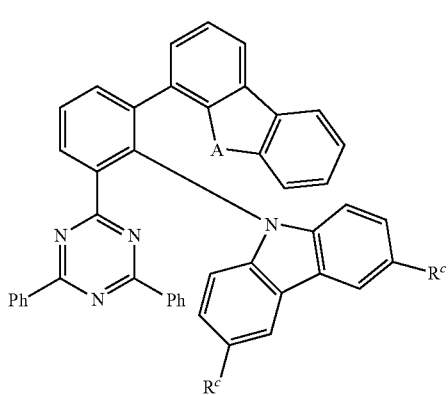

wherein the aforementioned definitions apply.

In a preferred embodiment, the organic molecules comprise or consist of a structure of Formula VIa-1.

In one additional embodiment of the invention, the organic molecules comprise or consist of a structure of Formula VIb-1, Formula VIb-2, Formula VIb-3 or Formula VIb-4:

Formula VIb-1

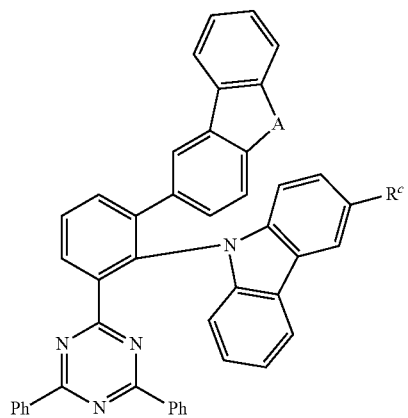

Formula VIb-2

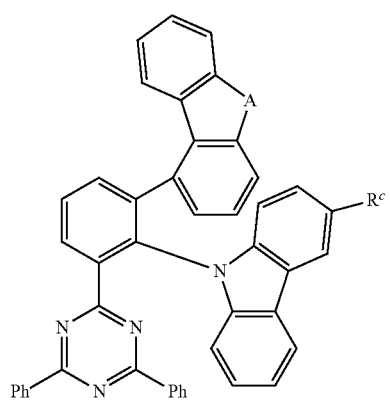

Formula VIb-3

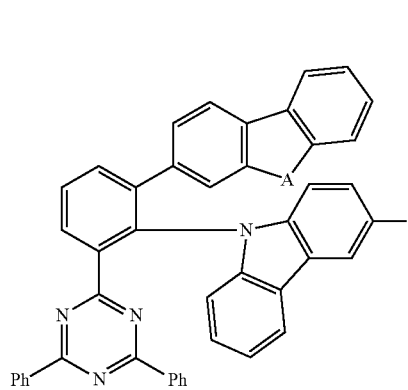

Formula VIb-4

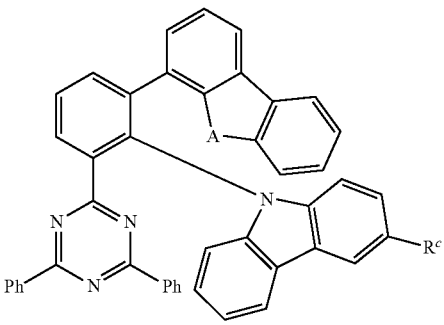

wherein the aforementioned definitions apply.

In a preferred embodiment, the organic molecules comprise or consist of a structure of Formula VIb-1.

In one embodiment of the invention, the organic molecules comprise or consist of a structure of Formula VII-1, Formula VII-2, Formula VII-3 or Formula VII-4:

Formula VII-1

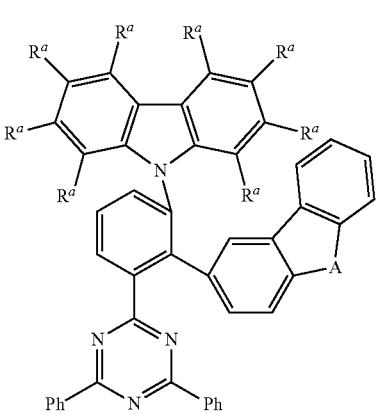

Formula VII-2

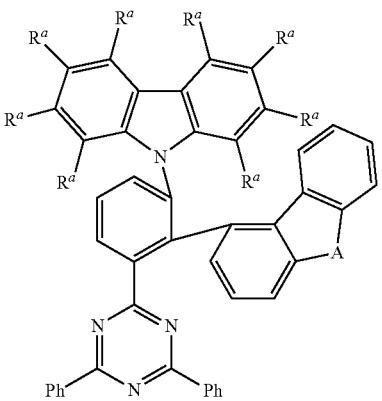

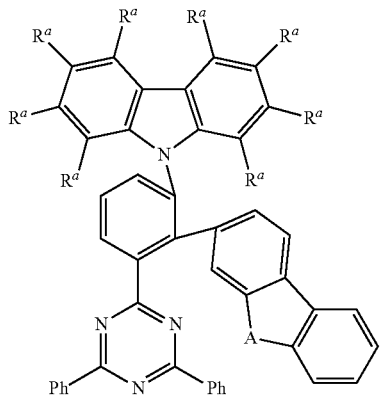

Formula VII-3

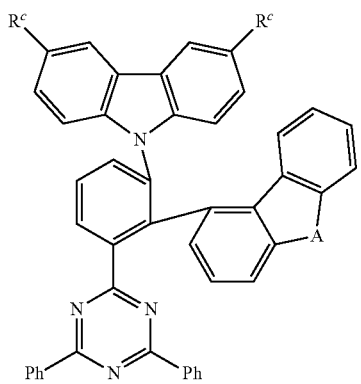

Formula VIIa-2

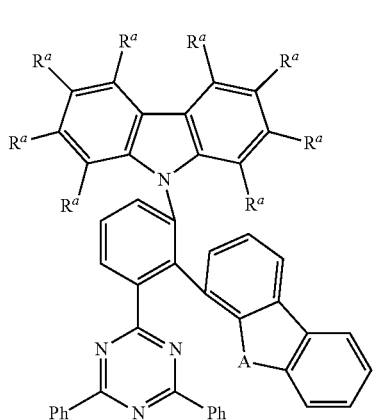

Formula VII-4

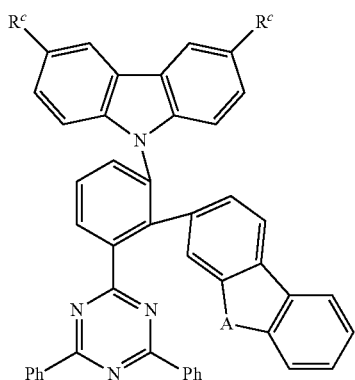

Formula VIIa-3 wherein the aforementioned definitions apply.

In a preferred embodiment of the invention, the organic molecules comprise or consist of a structure of Formula VII-1.

In one embodiment of the invention, the organic molecules comprise or consist of a structure of Formula VIIa-1, Formula VIIa-2, Formula VIIa-3 or Formula VIIa-4:

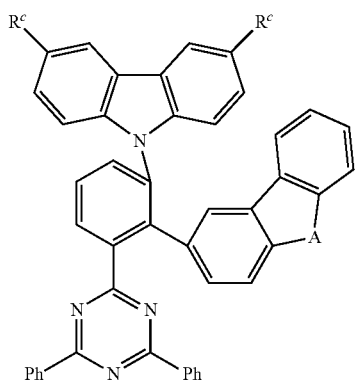

Formula VIIa-1

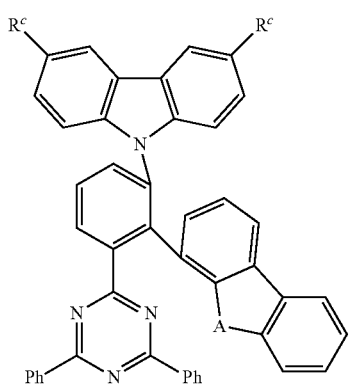

Formula VIIa-4 wherein the aforementioned definitions apply.

In a preferred embodiment, the organic molecules comprise or consist of a structure of Formula VIIa-1.

In one additional embodiment of the invention, the organic molecules comprise or consist of a structure of Formula VIIb-1, Formula VIIb-2, Formula VIIb-3 or Formula VIIb-4:

Formula VIIb-1

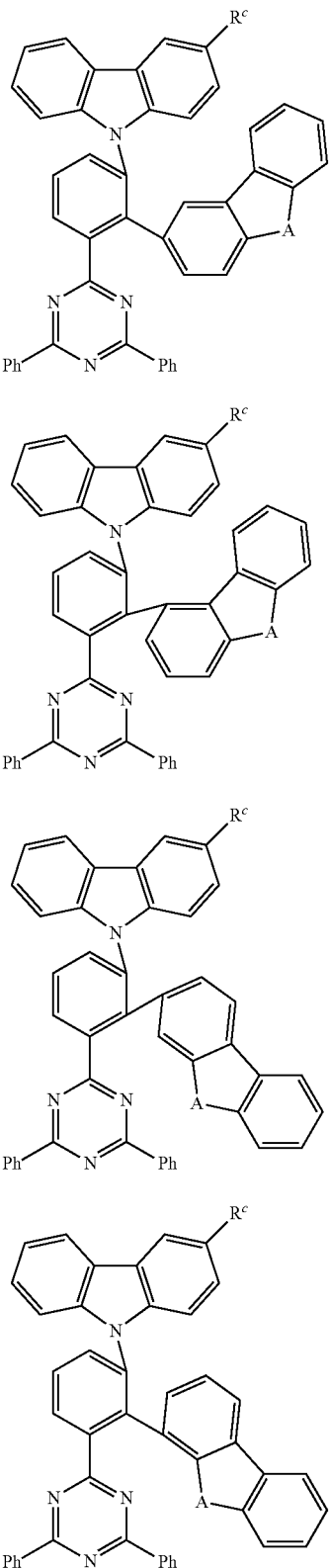

Formula VIIb-2

Formula VIIb-3

Formula VIIb-4 wherein the aforementioned definitions apply.

In a preferred embodiment, the organic molecules comprise or consist of a structure of Formula VIIb-1.

In one embodiment of the invention, the organic molecules comprise or consist of a structure of Formula VIII-1, Formula VIII-2, Formula VIII-3 or Formula VIII-4:

Formula VIII-1

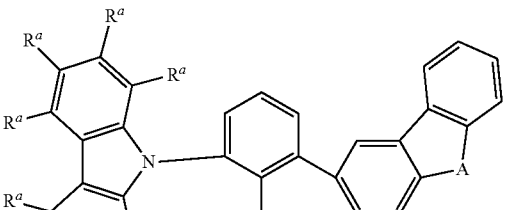

Formula VIII-2

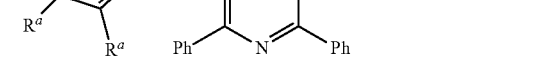

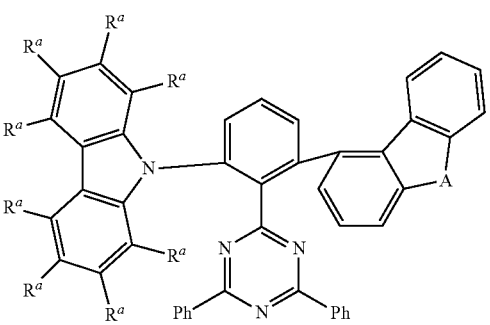

Formula VIII-3

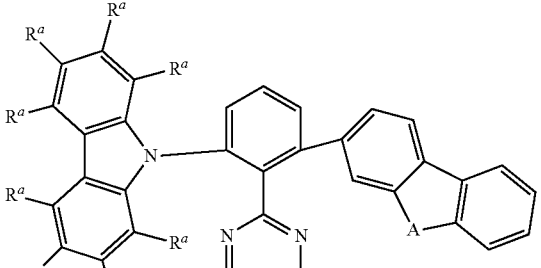

Formula VIII-4

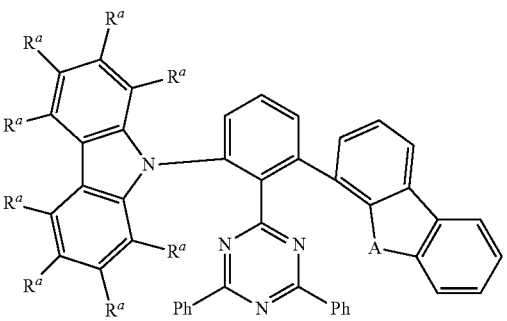

wherein the aforementioned definitions apply.

In a preferred embodiment of the invention, the organic molecules comprise or consist of a structure of Formula VIII-1.

In one embodiment of the invention, the organic molecules comprise or consist of a structure of Formula VIIIa-1, Formula VIIIa-2, Formula VIIIa-3 or Formula VIIIa-4:

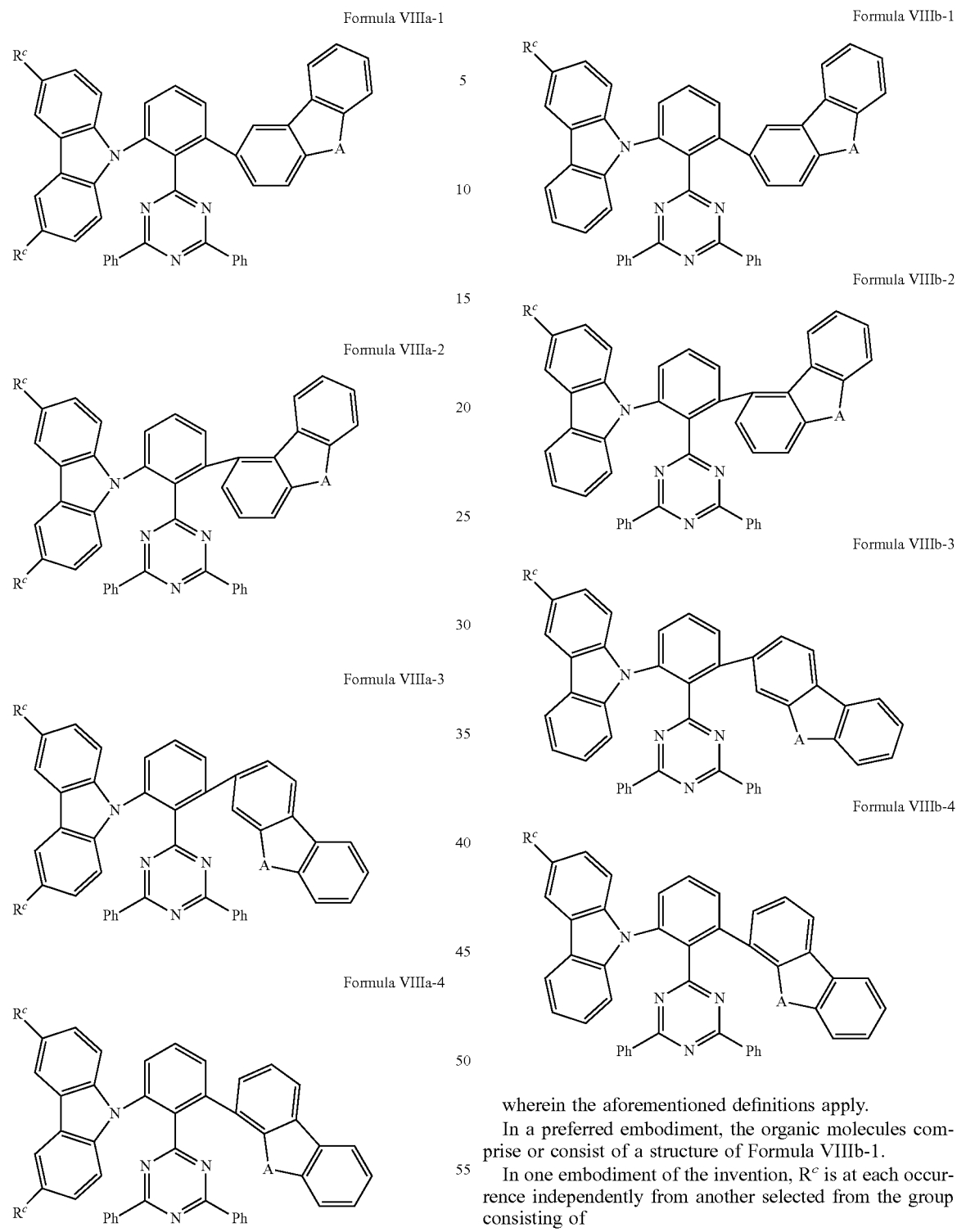

wherein the aforementioned definitions apply.

In a preferred embodiment, the organic molecules comprise or consist of a structure of Formula VIIIa-1.

In one additional embodiment of the invention, the organic molecules comprise or consist of a structure of Formula VIIIb-1, Formula VIIIb-2, Formula VIIIb-3 or Formula VIIIb-4:

wherein the aforementioned definitions apply.

In a preferred embodiment, the organic molecules comprise or consist of a structure of Formula VIIIb-1.

In one embodiment of the invention, $R^c$ is at each occurrence independently from another selected from the group consisting of
Me,
$^i$Pr,
$^t$Bu
CN,
$CF_3$,
Ph, which is optionally substituted with one or more substituents independently from each other selected from the group consisting of Me, $^i$Pr, $^t$Bu, CN, $CF_3$, and Ph, pyridinyl, which is optionally substituted with one or more substituents independently from each other selected from the group consisting of Me, $^i$Pr, $^t$Bu, CN, CF$_3$, and Ph, pyrimidinyl, which is optionally substituted with one or more substituents independently from each other selected from the group consisting of Me, $^i$Pr, $^t$Bu, CN, CF$_3$, and Ph, and triazinyl, which is optionally substituted with one or more substituents independently from each other selected from the group consisting of Me, $^i$Pr, $^t$Bu, CN, CF$_3$, and Ph.

In one embodiment of the invention, R$^c$ is at each occurrence independently from another selected from the group consisting of Me,
$^i$Pr,
$^t$Bu Ph, which is optionally substituted with one or more substituents independently from each other selected from the group consisting of Me, $^i$Pr, $^t$Bu, CN, CF$_3$ and Ph; and triazinyl, which is optionally substituted with one or more substituents independently from each other selected from the group consisting of Me, $^i$Pr, $^t$Bu, CN, CF$_3$ and Ph.

As used throughout the present application, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application the term aryl group or heteroaryl group comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine und benzothiadiazole or combinations of the abovementioned groups.

As used throughout the present application the term cyclic group may be understood in the broadest sense as any mono-, bi- or polycyclic moieties.

As used throughout the present application the term alkyl group may be understood in the broadest sense as any linear, branched, or cyclic alkyl substituent. In particular, the term alkyl comprises the substituents methyl (Me), ethyl (Et), n-propyl ($^n$Pr), i-propyl ($^i$Pr), cyclopropyl, n-butyl ($^n$Bu), i-butyl ($^i$Bu), s-butyl ($^s$Bu), t-butyl ($^t$Bu), cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl und 1-(n-decyl)-cyclohex-1-yl.

As used throughout the present application the term alkenyl comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used throughout the present application the term alkynyl comprises linear, branched, and cyclic alkynyl substituents. The term alkynyl group exemplarily comprises ethynyl, propynyl, butynyl, pentynyl, hexynyl, heptynyl or octynyl.

As used throughout the present application the term alkoxy comprises linear, branched, and cyclic alkoxy substituents. The term alkoxy group exemplarily comprises methoxy, ethoxy, n-propoxy, i-propoxy, n-butoxy, i-butoxy, s-butoxy, t-butoxy and 2-methylbutoxy.

As used throughout the present application the term thioalkoxy comprises linear, branched, and cyclic thioalkoxy substituents, in which the O of the exemplarily alkoxy groups is replaced by S.

As used throughout the present application, the terms "halogen" and "halo" may be understood in the broadest sense as being preferably fluorine, chlorine, bromine or iodine.

Whenever hydrogen is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 150 µs, of not more than 100 µs, in particular of not more than 50 µs, more preferably of not more than 10 µs or not more than 7 µs in a film of poly(methyl methacrylate) (PMMA) with 10% by weight of organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (S1) and the first excited triplet state (T1), of less than 5000 cm$^{-1}$, preferably less than 3000 cm$^{-1}$, more preferably less than 1500 cm$^{-1}$, even more preferably less than 1000 cm$^{-1}$ or even less than 500 cm$^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of poly(methyl methacrylate) (PMMA) with 10% by weight of organic molecule at room temperature.

In a further embodiment of the invention, the organic molecules according to the invention have a "blue material index" (BMI), calculated by dividing the photoluminescence quantum yield (PLQY) in % by the CIEy color coordinate of the emitted light, of more than 150, in particular more than 200, preferably more than 250, more preferably of more than 300 or even more than 500.

In a further embodiment of the invention, the organic molecules according to the invention have a highest occupied molecular orbital with the energy $E^{HOMO}$, which is higher in energy than –6.2 eV, preferably higher in energy than –6.1 eV and even more preferably higher in energy than –6.0 eV or even –5.9 eV.

Orbital and excited state energies can be determined either by means of experimental methods or by calculations employing quantum-chemical methods, in particular density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is determined as the onset of the absorption spectrum.

The onset of an absorption spectrum is determined by computing the intersection of the tangent to the absorption spectrum with the x-axis. The tangent to the absorption spectrum is set at the low-energy side of the absorption band and at the point at half maximum of the maximum intensity of the absorption spectrum.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of) PMMA with 10% by weight of emitter. Both for host and emitter compounds, the energy of the first excited singlet state S1 is determined from the onset of the emission spectrum, if not otherwise stated measured in a film of PMMA with 10% by weight of host or emitter compound. The onset of an emission spectrum is determined by computing the intersection of the tangent to the emission spectrum with the x-axis. The tangent to the emission spectrum is set at the high-energy side of the emission band, i.e., where the emission band rises by going from higher energy values to lower energy values, and at the point at half maximum of the maximum intensity of the emission spectrum.

A further aspect of the invention relates to a process for synthesizing organic molecules according to the invention (with an optional subsequent reaction), wherein a cyanophenylboronic acid is used as a reactant:

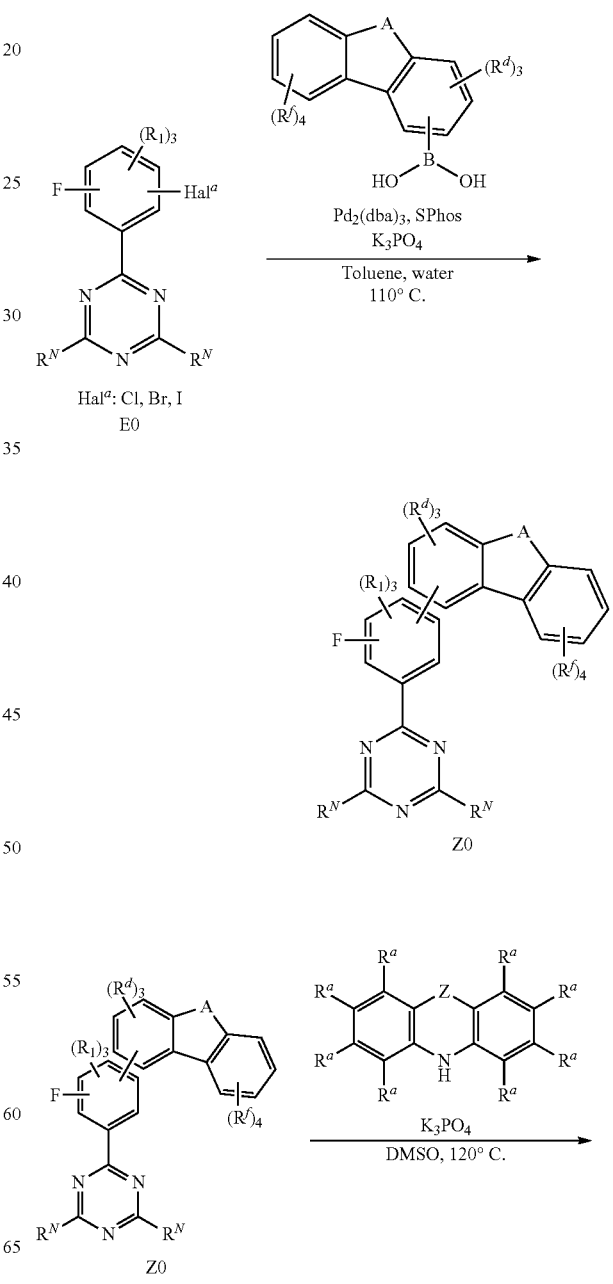

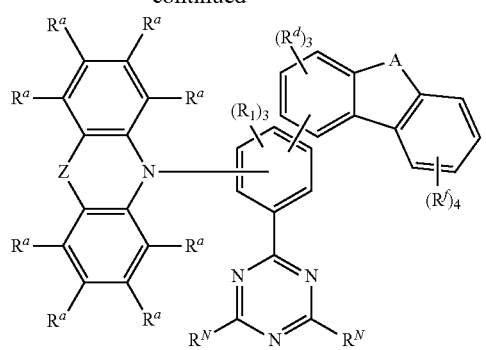
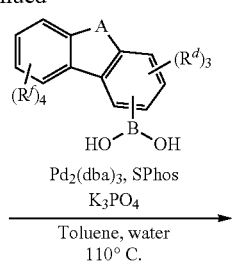

According to the invention, in the reaction for the synthesis of Z0 a boronic acid ester can be used instead of a boronic acid.

An alternative synthesis route comprises the introduction of a nitrogen heterocycle via copper- or palladium-catalyzed coupling to an aryl halide or to an aryl pseudohalide, preferably an aryl bromide, an aryl iodide, aryl triflate, or an aryl tosylate.

Additionally, organic molecules (with an optional subsequent reaction) according to the invention can be synthesized via the following synthesis route:

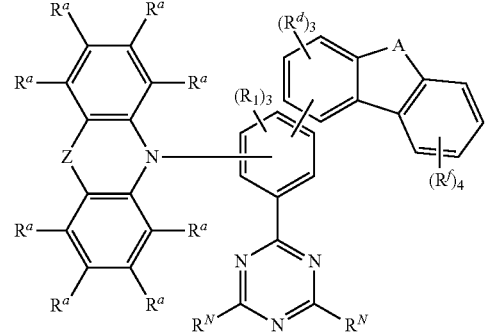

E0 can be synthesized via the following synthesis routes:

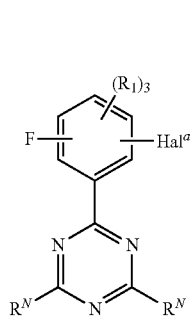
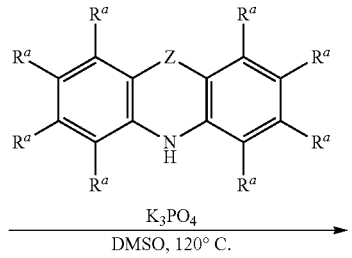
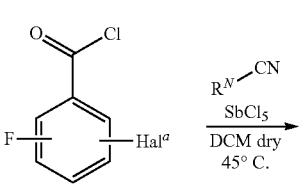

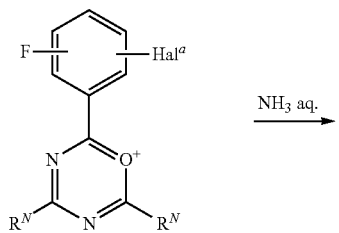

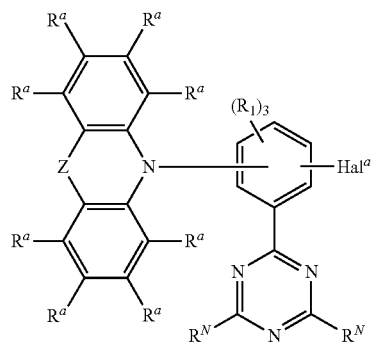
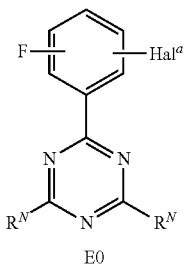

-continued

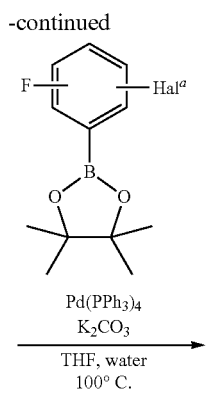

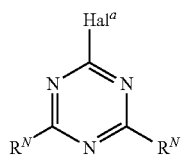

Alternatively, Z0 can be synthesized via the following synthesis route, wherein $E^{ALT}$ is used as a reactant:

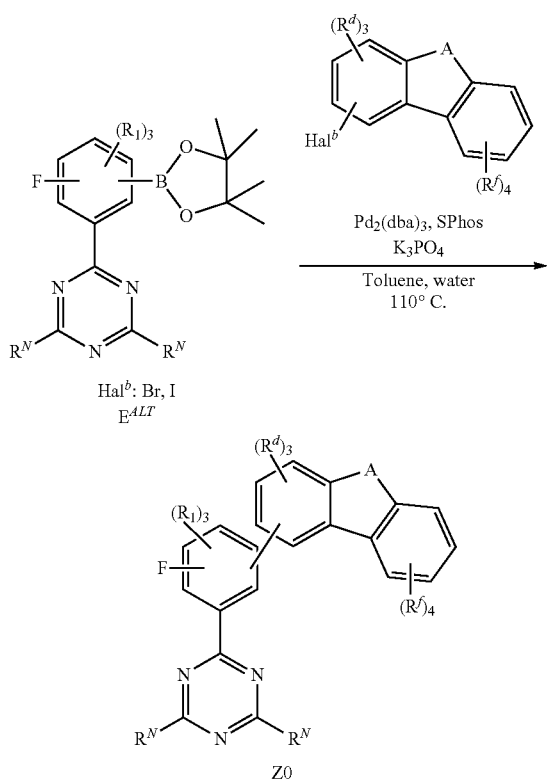

For the reaction of a nitrogen heterocycle in a nucleophilic aromatic substitution with an aryl halide, preferably an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

A further aspect of the invention relates to the use of an organic molecule according to the invention as a luminescent emitter or as an absorber, and/or as host material and/or as electron transport material, and/or as hole injection material, and/or as hole blocking material in an optoelectronic device.

The optoelectronic device may be understood in the broadest sense as any device based on organic materials that is suitable for emitting light in the visible or nearest ultraviolet (UV) range, i.e., in the range of a wavelength of from 380 to 800 nm. More preferably, the optoelectronic device may be able to emit light in the visible range, i.e., of from 400 to 800 nm.

In the context of such use, the optoelectronic device is more particularly selected from the group consisting of:
  organic light-emitting diodes (OLEDs),
  light-emitting electrochemical cells,
  OLED sensors, especially in gas and vapour sensors not hermetically externally shielded,
  organic diodes,
  organic solar cells,
  organic transistors,
  organic field-effect transistors,
  organic lasers and
  down-conversion elements.

In a preferred embodiment in the context of such use, the optoelectronic device is a device selected from the group consisting of an organic light emitting diode (OLED), a light emitting electrochemical cell (LEC), and a light-emitting transistor.

In the case of the use, the fraction of the organic molecule according to the invention in the emission layer in an optoelectronic device, more particularly in OLEDs, is 1% to 99% by weight, more particularly 5% to 80% by weight. In an alternative embodiment, the proportion of the organic molecule in the emission layer is 100% by weight.

In one embodiment, the light-emitting layer comprises not only the organic molecules according to the invention but also a host material whose triplet (T1) and singlet (S1) energy levels are energetically higher than the triplet (T1) and singlet (S1) energy levels of the organic molecule.

A further aspect of the invention relates to a composition comprising or consisting of:
  (a) at least one organic molecule according to the invention, in particular in the form of an emitter and/or a host, and
  (b) one or more emitter and/or host materials, which differ from the organic molecule according to the invention and
  (c) optional one or more dyes and/or one or more solvents.

In one embodiment, the light-emitting layer comprises (or (essentially) consists of) a composition comprising or consisting of:
  (a) at least one organic molecule according to the invention, in particular in the form of an emitter and/or a host, and
  (b) one or more emitter and/or host materials, which differ from the organic molecule according to the invention and
  (c) optional one or more dyes and/or one or more solvents.

In a particular embodiment, the light-emitting layer EML comprises (or (essentially) consists of) a composition comprising or consisting of:

(i) 1-50% by weight, preferably 5-40% by weight, in particular 10-30% by weight, of one or more organic molecules according to the invention;
(ii) 5-99% by weight, preferably 30-94.9% by weight, in particular 40-89% by weight, of at least one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules according to the invention, in particular transferred from the first excited triplet state T1(H) of the host compound H to the first excited triplet state T1(E) of the one or more organic molecules according to the invention and/or from the first excited singlet state S1(H) of the host compound H to the first excited singlet state S1(E) of the one or more organic molecules according to the invention.

In a further embodiment, the light-emitting layer EML comprises (or (essentially) consists of) a composition comprising or consisting of:
(i) 1-50% by weight, preferably 5-40% by weight, in particular 10-30% by weight, of one organic molecule according to the invention;
(ii) 5-99% by weight, preferably 30-94.9% by weight, in particular 40-89% by weight, of one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

In one embodiment, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$ wherein $E^{HOMO}(H) > E^{HOMO}(D)$ In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H) > E^{LUMO}(D)$.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and
the at least one further host compound D has a highest occupied molecular orbital HOMO(D) having an energy $E^{HOMO}(D)$ and a lowest unoccupied molecular orbital LUMO(D) having an energy $E^{LUMO}(D)$
the organic molecule according to the invention has a highest occupied molecular orbital HOMO(E) having an energy $E^{HOMO}(E)$ and a lowest unoccupied molecular orbital LUMO(E) having an energy $E^{LUMO}(E)$,
wherein
$E^{HOMO}(H) > E^{HOMO}(D)$ and the difference between the energy level of the highest occupied molecular orbital HOMO(E) of organic molecule according to the invention ($E^{HOMO}(E)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and $E^{LUMO}(H) > E^{LUMO}(D)$ and the difference between the energy level of the lowest unoccupied molecular orbital LUMO(E) of organic molecule according to the invention ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

In a further aspect, the invention relates to an optoelectronic device comprising an organic molecule or a composition of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the optoelectronic device is a device selected from the group consisting of an organic light emitting diode (OLED), a light emitting electrochemical cell (LEC), and a light-emitting transistor.

In one embodiment of the optoelectronic device of the invention, the organic molecule according to the invention is used as emission material in a light-emitting layer EML.

In one embodiment of the optoelectronic device of the invention the light-emitting layer EML consists of the composition according to the invention described here.

For example, when the optoelectronic device is an OLED, it may exhibit the following layer structure:
1. substrate
2. anode layer A
3. hole injection layer, HIL
4. hole transport layer, HTL
5. electron blocking layer, EBL
6. emitting layer, EML
7. hole blocking layer, HBL
8. electron transport layer, ETL
9. electron injection layer, EIL
10. cathode layer,
wherein the OLED comprises each layer, selected from the group consisting of HIL, HTL, EBL, HBL, ETL and EIL, only optionally, different layers may be merged and the OLED may comprise more than one layer of each layer type defined above.

Furthermore, the optoelectronic device optionally comprises one or more protective layers protecting the device from damaging exposure to harmful species in the environment including, for example, moisture, vapor and/or gases.

In one embodiment of the invention, the optoelectronic device is an OLED, which exhibits the following inverted layer structure:
1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A Wherein the OLED with an inverted layer structure comprises each layer, selected from the group consisting of HIL, HTL, EBL, HBL, ETL and EIL, only optionally, different layers may be merged and the OLED may comprise more than one layer of each layer types defined above.

In one embodiment of the invention, the optoelectronic device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the anode layer.

In one embodiment of the invention, the optoelectronic device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The anode layer A is mostly composed of materials allowing to obtain an (essentially) transparent film. As at least one of both electrodes should be (essentially) transparent in order to allow light emission from the OLED, either the anode layer A or the cathode layer C is transparent. Preferably, the anode layer A comprises a large content or even consists of transparent conductive oxides (TCOs). Such anode layer A may exemplarily comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

Particularly preferably, the anode layer A (essentially) consists of indium tin oxide (ITO) (e.g., $(InO_3)0.9(SnO_2)0.1$). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may exemplarily comprise PEDOT:PSS (poly-3,4-ethylendioxy thiophene: polystyrene sulfonate), PEDOT (poly-3,4-ethylendioxy thiophene), mMTDATA (4,4',4"-tris[phenyl(m-tolyl)amino]triphenylamine), Spiro-TAD (2,2', 7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL) typically a hole transport layer (HTL) is located. Herein, any hole transport compound may be used. Exemplarily, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. Exemplarily the hole transport layer (HTL) may comprise a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N,N-bis(4-methylphenyl)benzenamine]), 2-TNATA (4,4',4"-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane (F4-TCNQ), copper-pentafluorobenzoate (Cu(I)pFBz) or transition metal complexes may exemplarily be used as organic dopant.

The EBL may exemplarily comprise mCP (1,3-bis(carbazol-9-yl)benzene), TCTA, 2-TNATA, mCBP (3,3-di(9H-carbazol-9-yl)biphenyl), SiMCP (3,5-Di(9H-carbazol-9-yl)phenyl]triphenylsilane), DPEPO, tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), typically, the light-emitting layer EML is located. The light-emitting layer EML comprises at least one light emitting molecule. Particular, the EML comprises at least one light emitting molecule according to the invention. In one embodiment, the light-emitting layer comprises only the organic molecules according to the invention. Typically, the EML additionally comprises one or more host material. Exemplarily, the host material is selected from CBP (4,4'-Bis-(N-carbazolyl)-biphenyl), mCP, mCBP Sif87 (dibenzo[b,d]thiophen-2-yltriphenylsilane), CzSi, SimCP ([3,5-Di(9H-carbazol-9-yl)phenyl]triphenylsilane), Sif88 (dibenzo[b,d]thiophen-2-yl) diphenylsilane), DPEPO (bis[2-(diphenylphosphino) phenyl] ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting molecule according to the invention and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML an electron transport layer (ETL) may be located. Herein, any electron transporter may be used. Exemplarily, compounds poor of electrons such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a holeblocking layer (HBL) is introduced.

The HBL may exemplarily comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris(carbazol)-9-yl)benzene).

Adjacent to the electron transport layer (ETL), a cathode layer C may be located. Exemplarily, the cathode layer C may comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of (essentially) non-transparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), $Li_2O$, $BaF_2$, MgO and/or NaF.

Optionally, also the electron transport layer (ETL) and/or a hole blocking layer (HBL) may comprise one or more host compounds.

In order to modify the emission spectrum and/or the absorption spectrum of the light-emitting layer EML further, the light-emitting layer EML may further comprise one or more further emitter molecule F. Such an emitter molecule F may be any emitter molecule known in the art. Preferably such an emitter molecule F is a molecule with a structure differing from the structure of the molecules according to the invention. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. Exemplarily, the triplet and/or singlet excitons may be transferred from the emitter molecule according to the invention to the emitter molecule F before relaxing to the ground state S0 by emitting light typically red-shifted in comparison to the light emitted by emitter molecule E. Optionally, the emitter molecule F may also provoke two-photon effects (i.e., the absorption of two photons of half the energy of the absorption maximum).

Optionally, an optoelectronic device (e.g., an OLED) may exemplarily be an essentially white optoelectronic device. For example, such white optoelectronic device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:
  violet: wavelength range of >380-420 nm;
  deep blue: wavelength range of >420-480 nm;
  sky blue: wavelength range of >480-500 nm;
  green: wavelength range of >500-560 nm;
  yellow: wavelength range of >560-580 nm;
  orange: wavelength range of >580-620 nm;
  red: wavelength range of >620-800 nm.

With respect to emitter molecules, such colors refer to the emission maximum. Therefore, exemplarily, a deep blue emitter has an emission maximum in the range of from >420 to 480 nm, a sky blue emitter has an emission maximum in the range of from >480 to 500 nm, a green emitter has an emission maximum in a range of from >500 to 560 nm, a red emitter has an emission maximum in a range of from >620 to 800 nm.

A deep blue emitter may preferably have an emission maximum of below 480 nm, more preferably below 470 nm, even more preferably below 465 nm or even below 460 nm. It will typically be above 420 nm, preferably above 430 nm, more preferably above 440 nm or even above 450 nm.

Accordingly, a further aspect of the present invention relates to an OLED, which exhibits an external quantum efficiency at 1000 cd/m2 of more than 8%, more preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 cd/m2 of more than 100 h, preferably more than 200 h, more preferably more than 400 h, even more preferably more than 750 h or even more than 1000 h. Accordingly, a further aspect of the present invention relates to an OLED, whose emission exhibits a CIEy color coordinate of less than 0.45, preferably less than 0.30, more preferably less than 0.20 or even more preferably less than 0.15 or even less than 0.10.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.50 eV, preferably less than 0.48 eV, more preferably less than 0.45 eV, even more preferably less than 0.43 eV or even less than 0.40 eV.

A further aspect of the present invention relates to an OLED, which emits light with CIEx and CIEy color coordinates close to the CIEx (=0.131) and CIEy (=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. In commercial applications, typically top-emitting (top-electrode is transparent) devices are used, whereas test devices as used throughout the present application represent bottom-emitting devices (bottom-electrode and substrate are transparent). The CIEy color coordinate of a blue device can be reduced by up to a factor of two, when changing from a bottom- to a top-emitting device, while the CIEx remains nearly unchanged (Okinaka et al. (2015), 22.1: *Invited Paper: New Fluorescent Blue Host Materials for Achieving Low Voltage in OLEDs, SID Symposium Digest of Technical Papers,* 46; doi:10.1002/sdtp.10480). Accordingly, a further aspect of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a CIEy color coordinate of between 0.00 and 0.45, preferably between 0.01 and 0.30, more preferably between 0.02 and 0.20 or even more preferably between 0.03 and 0.15 or even between 0.04 and 0.10.

In a further aspect, the invention relates to a method for producing an optoelectronic component. In this case an organic molecule of the invention is used.

The optoelectronic device, in particular the OLED according to the present invention can be produced by any means of vapor deposition and/or liquid processing. Accordingly, at least one layer is
  prepared by means of a sublimation process,
  prepared by means of an organic vapor phase deposition process,
  prepared by means of a carrier gas sublimation process, solution processed or printed.

The methods used to produce the optoelectronic device, in particular the OLED according to the present invention are known in the art. The different layers are individually and successively deposited on a suitable substrate by means of subsequent deposition processes. The individual layers may be deposited using the same or differing deposition methods.

Vapor deposition processes exemplarily comprise thermal (co)evaporation, chemical vapor deposition and physical vapor deposition. For active matrix OLED display, an AMOLED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

General synthesis scheme I

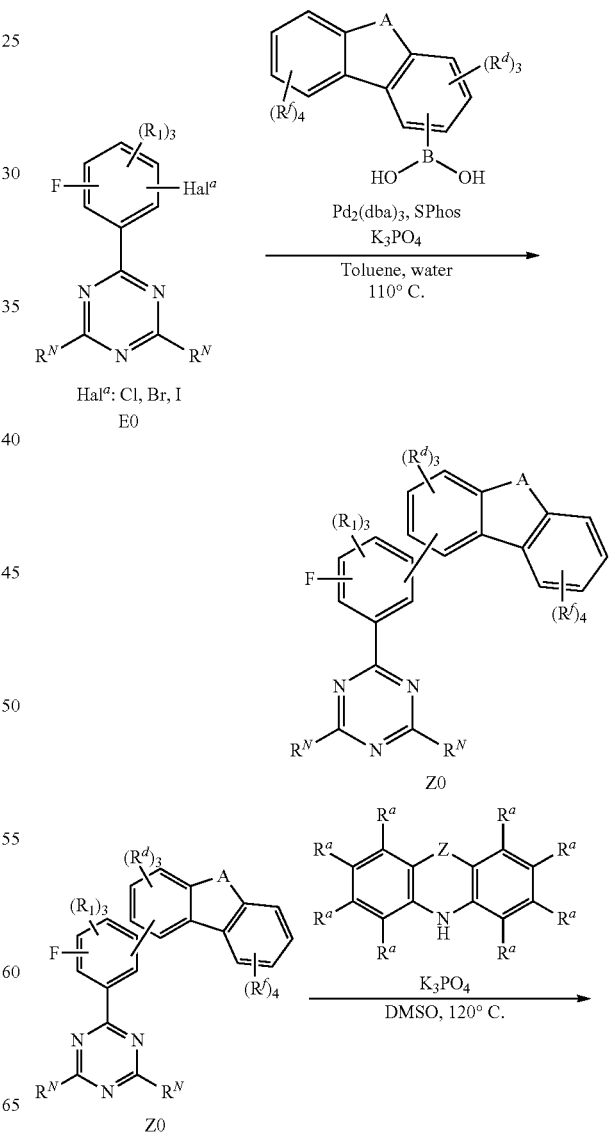

-continued

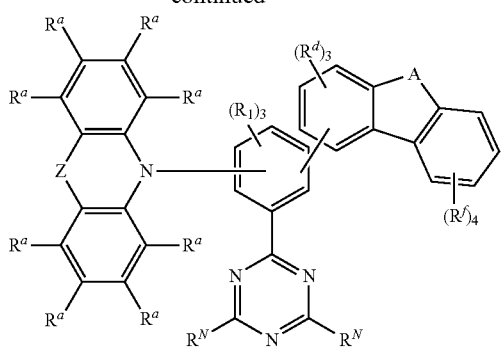

General Procedure for Synthesis AAV1

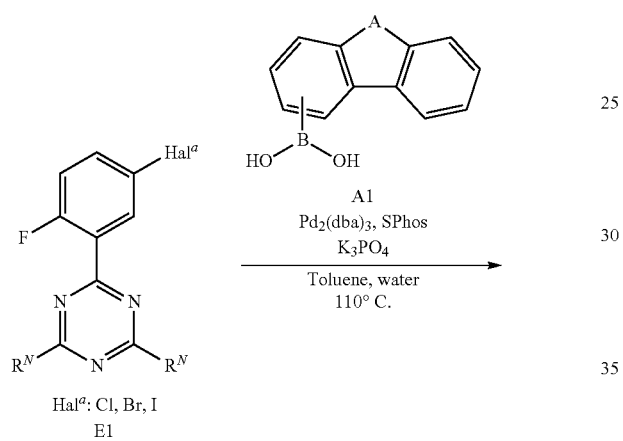

2-(2-fluoro-5-Hal$^a$-phenyl)-4,6-di-R$^N$-1,3,5-triazine E1 (1.00 equivalents), boronic acid A1 (1.50 equivalents), Pd$_2$(dba)$_3$ (0.01 equivalents), 2-(dicyclohexylphosphino)-2',6'-dimethoxy-1-1'-biphenyl (S-Phos) (0.04 equivalents) and tribasic potassium phosphate (3.00 equivalents) are stirred under nitrogen atmosphere in a mixture of toluene and water (10:1) at 110° C. until completion of the reaction (monitoring with LC/MS, usually finished within 4-16 h). After cooling to rt the reaction mixture is filtered through a fiber glass filter. Subsequently, the biphasic filtrate is added brine. The phases are separated and the aqueous phase extracted with dichloromethane. The combined organic layers are dried over MgSO$_4$, filtered and concentrated in vacuo. The obtained crude product is purified via flash chromatography or recrystallization, giving Z1 as solid.

General Procedure for Synthesis AAV2

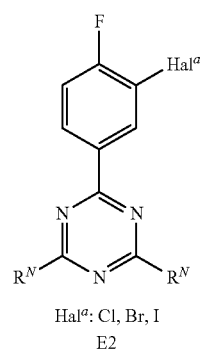
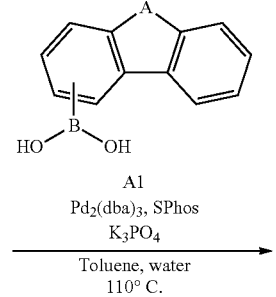

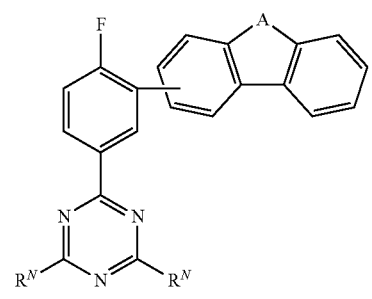

The synthesis of Z2 is carried out according to AAV1, wherein 2-(4-fluoro-5-Hal$^a$-phenyl)-4,6-di-R$^N$-1,3,5-triazine is used as reactant.

General Procedure for Synthesis AAV3

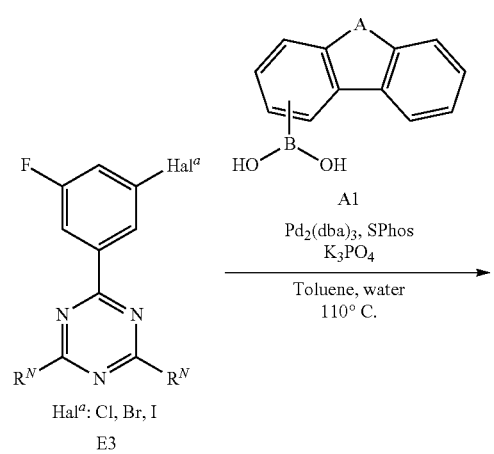

-continued

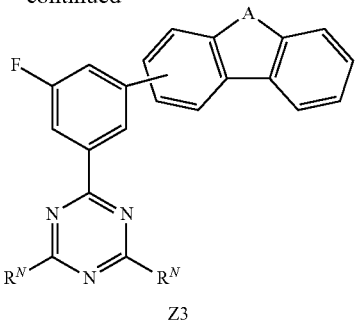

Z3

The synthesis of Z3 is carried out according to AAV1, wherein 2-(3-fluoro-5-Hal$^a$-phenyl)-4,6-di-R$^N$-1,3,5-triazine is used as reactant.

General Procedure for Synthesis AAV4

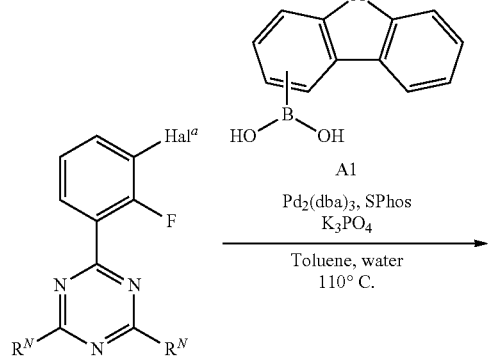

Hal$^a$: Cl, Br, I

E4

General Procedure for Synthesis AAV5

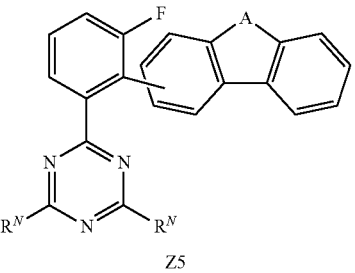

Hal$^a$: Cl, Br, I

E5

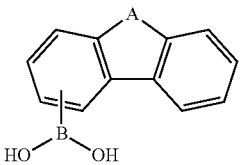

Z5

The synthesis of Z5 is carried out according to AAV1, wherein 2-(3-fluoro-2-Hal$^a$-phenyl)-4,6-di-R$^N$-1,3,5-triazine is used as reactant.

General Procedure for Synthesis AAV6

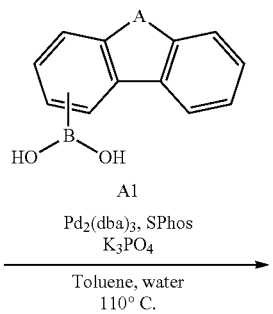

Hal$^a$: Cl, Br, I

E6

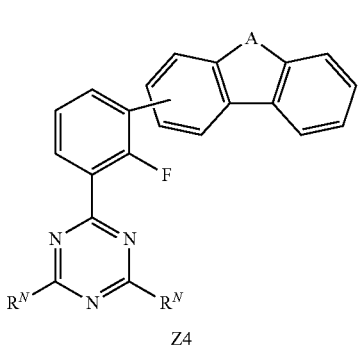

Z4

The synthesis of Z4 is carried out according to AAV1, wherein 2-(2-fluoro-3-Hal$^a$-phenyl)-4,6-di-R$^N$-1,3,5-triazine is used as reactant.

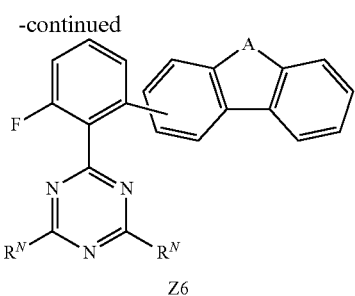

Z6

The synthesis of Z6 is carried out according to AAV1, wherein 2-(2-fluoro-6-Hal$^a$-phenyl)-4,6-di-R$^N$-1,3,5-triazine is used as reactant.

General Procedure for Synthesis AAV7

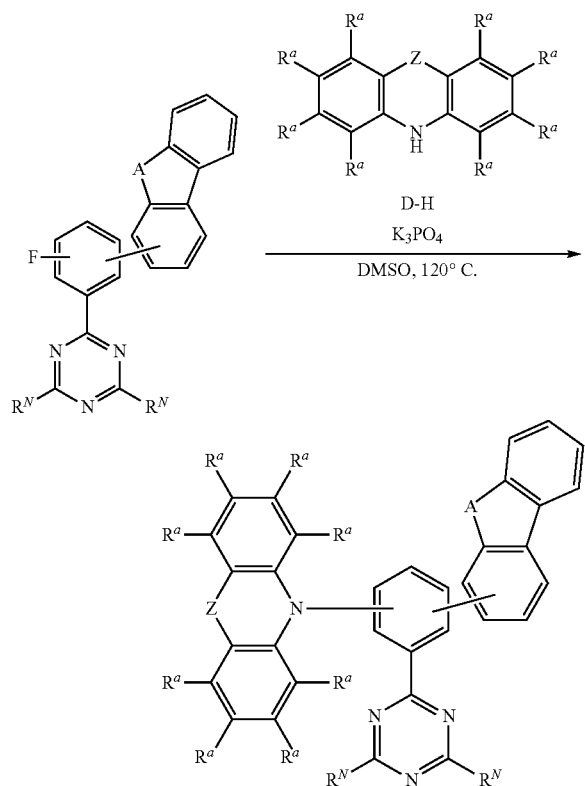

Z1, Z2, Z3, Z4, Z5 or Z6 (1 equivalent), the corresponding donor molecule D-H (1.00 equivalents) and tribasic potassium phosphate (2.00 equivalents) are suspended under nitrogen atmosphere in DMSO and stirred at 120° C. (12-16 h). Subsequently the reaction mixture is poured into an excess of water in order to precipitate the product. The precipitate is filtered off, washed with water and dried under vacuum. The crude product is purified by recrystallization or by flash chromatography. The product is obtained as a solid.

In particular, the donor molecule D-H is a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butylcarbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

Exemplarily a halogen-substituted carbazole, particularly 3-bromocarbazole, can be used as D-H.

In a subsequent reaction a boronic acid ester functional group or boronic acid functional group may be exemplarily introduced at the position of the one or more halogen substituents, which was introduced via D-H, to yield the corresponding carbazol-3-ylboronic acid ester or carbazol-3-ylboronic acid, e.g., via the reaction with bis(pinacolato)diboron (CAS No. 73183-34-3). Subsequently, one or more substituents R$^a$ may be introduced in place of the boronic acid ester group or the boronic acid group via a coupling reaction with the corresponding halogenated reactant R$^a$-Hal, preferably R$^a$—Cl and R$^a$—Br.

Alternatively, one or more substituents R$^a$ may be introduced at the position of the one or more halogen substituents, which was introduced via D-H, via the reaction with a boronic acid of the substituent R$^a$ [R$^a$—B(OH)$_2$] or a corresponding boronic acid ester.

HPLC-MS

HPLC-MS spectroscopy is performed on a HPLC by Agilent (1100 series) with MS-detector (Thermo LTQ XL). A reverse phase column 4.6 mm×150 mm, particle size 5.0 µm from Waters (without pre-column) is used in the HPLC. The HPLC-MS measurements are performed at room temperature (rt) with the solvents acetonitrile, water and THF in the following concentrations:

| solvent A: | H$_2$O (90%) | MeCN (10%) |
| solvent B: | H$_2$O (10%) | MeCN (90%) |
| solvent C: | THF (50%) | MeCN (50%) |

From a solution with a concentration of 0.5 mg/ml an injection volume of 15 µL is taken for the measurements. The following gradient is used:

| Flow rate [ml/min] | time [min] | A[%] | B[%] | C[%] |
| --- | --- | --- | --- | --- |
| 3 | 0 | 40 | 50 | 10 |
| 3 | 10 | 15 | 25 | 60 |
| 3 | 14 | 15 | 25 | 60 |
| 3 | 14.01 | 40 | 50 | 10 |
| 3 | 18 | 40 | 50 | 10 |
| 3 | 19 | 40 | 50 | 10 |

Ionisation of the probe is performed by APCI (atmospheric pressure chemical ionization).

Cyclic Voltammetry

Cyclic voltammograms are measured from solutions having concentration of 10$^{-3}$ mol/l of the organic molecules in dichloromethane or a suitable solvent and a suitable supporting electrolyte (e.g. 0.1 mol/l of tetrabutylammonium hexafluorophosphate). The measurements are conducted at room temperature under nitrogen atmosphere with a three-electrode assembly (Working and counter electrodes: Pt wire, reference electrode: Pt wire) and calibrated using FeCp$_2$/FeCp$_2^+$ as internal standard. The HOMO data was corrected using ferrocene as internal standard against SCE.

Density Functional Theory Calculation

Molecular structures are optimized employing the BP86 functional and the resolution of identity approach (RI).

Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating

Apparatus: Spin150, Sps Euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are tried at 70° C. for 1 min.

Photoluminescence spectroscopy and TCSPC (Time-correlated single-photon counting) Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation sources:

NanoLED 370 (wavelength: 371 nm, puls duration: 1.1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0.

Emission maxima are given in nm, quantum yields Φ in % and CIE coordinates as x,y values. PLQY is determined using the following protocol:

1) Quality assurance: Anthracene in ethanol (known concentration) is used as reference
2) Excitation wavelength: the absorption maximum of the organic molecule is determined and the molecule is excited using this wavelength
3) Measurement
   Quantum yields are measured for sample of solutions or films under nitrogen atmosphere. The yield is calculated using the equation:

$$\Phi_{PL} = \frac{n_{photon}, \text{emited}}{n_{photon}, \text{absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

wherein $n_{photon}$ denotes the photon count and Int. the intensity.

Production and Characterization of Optoelectronic Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc.

Accelerated lifetime measurements are performed (e.g. applying increased current densities). Exemplarily LT80 values at 500 cd/m² are determined using the following equation:

$$LT80\left(500\ \frac{cd^2}{m^2}\right) = LT80(L_0)\left(\frac{L_0}{500\ \frac{cd^2}{m^2}}\right)^{1.6}$$

wherein $L_0$ denotes the initial luminance at the applied current density.

The values correspond to the average of several pixels (typically two to eight), the standard deviation between these pixels is given. Figures show the data series for one OLED pixel.

Example 1

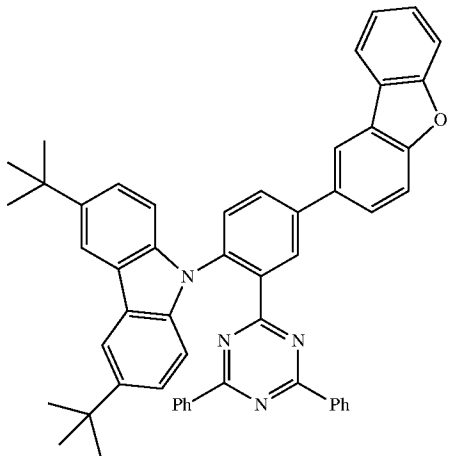 [SMILES: CC(C)(C)c1ccc2c(c1)c1cc(C(C)(C)C)ccc1n2-c1ccc(-c2ccc3oc4ccccc4c3c2)cc1-c1nc(-c2ccccc2)nc(-c2ccccc2)n1]

Example 1 was synthesized according to AAV1 (62% yield) and AAV7 (34% yield). MS (HPLC-MS), m/z (retention time): 752.62 (12.90 min).

FIG. 1 depicts the emission spectrum of example 1 (10% by weight in PMMA). The emission maximum is at 479 nm. The photoluminescence quantum yield (PLQY) is 86%, the full width at half maximum is 0.40 eV and the emission lifetime is 8 μs. The resulting $CIE_x$ coordinate is determined at 0.18 and the $CIE_y$ coordinate at 0.34.

In mCBP the full width at half maximum is reduced to 0.37 eV.

Example 2

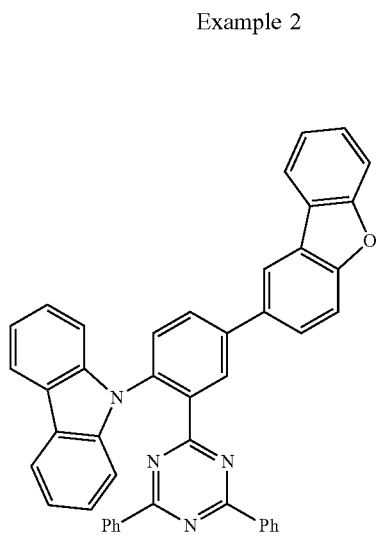

Example 2 was synthesized according to AAV1 (62% yield) and AAV7 (67% yield). MS (HPLC-MS), m/z (retention time): 640.34 (11.82 min).

Figure 2:
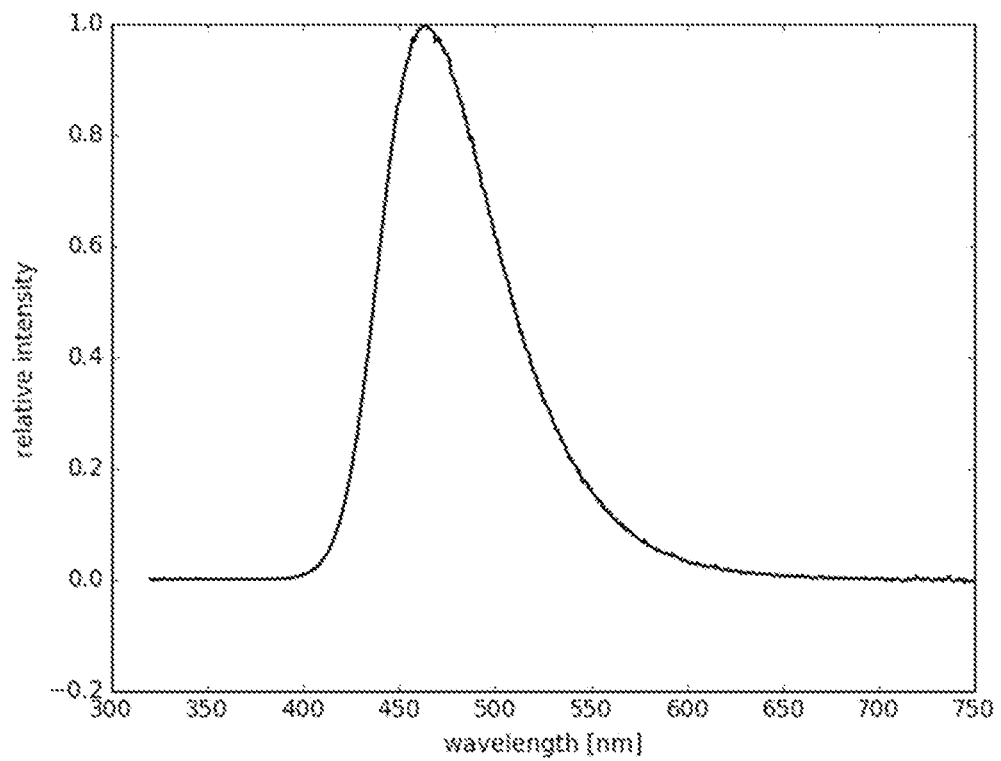
FIG. 2 is an emission spectrum of example 2 (10% by weight) in PMMA.

FIG. 2 depicts the emission spectrum of example 2 (10% by weight in PMMA). The emission maximum is at 464 nm. The photoluminescence quantum yield (PLQY) is 80% and the full width at half maximum is 0.41 eV. The resulting $CIE_x$ coordinate is determined at 0.16 and the $CIE_y$ coordinate at 0.19.

Example 3

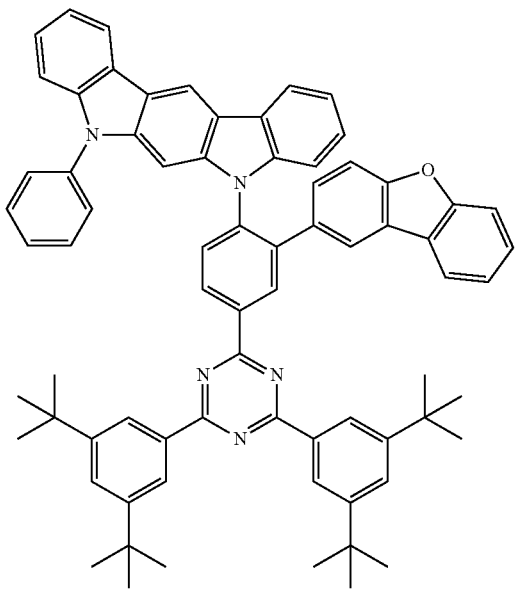 [SMILES: CC(C)(C)c1cc(-c2nc(-c3cc(C(C)(C)C)cc(C(C)(C)C)c3)nc(-c3ccc(-n4c5ccccc5c5cc6c7ccccc7n(-c7ccccc7)c6cc54)c(-c4ccc5oc6ccccc6c5c4)c3)n2)cc(C(C)(C)C)c1]

Example 3 was synthesized according to

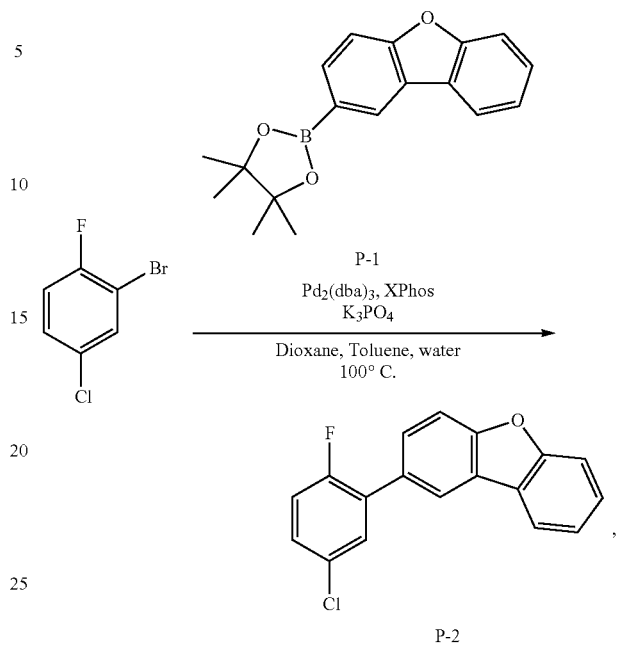

In a two-necked flask 2-bromo-4-chloro-1-fluorobenzene [1996-30-1] (1.0 equiv.), the benzofuryl boronic pinacol ester P-1 (1.2 equiv.), tris(dibenzylideneacetone)dipalladium(0) [CAS 51364-51-3] (0.02 equiv.), XPhos [CAS 564483-18-7] (0.08 equiv.) and K$_3$PO$_4$ (3.5 equiv.) were suspended in a mixture of toluene/dioxane/water (5:5:1) and subsequently heated at 100° C. overnight. After cooling down to room temperature (rt), the reaction mixture was added brine and extracted with dichloromethane. The organic layer was dried over MgSO$_4$, filtered and concentrated. The crude product was purified by MPLC using cyclohexane as the eluent (solid, yield: 67%).

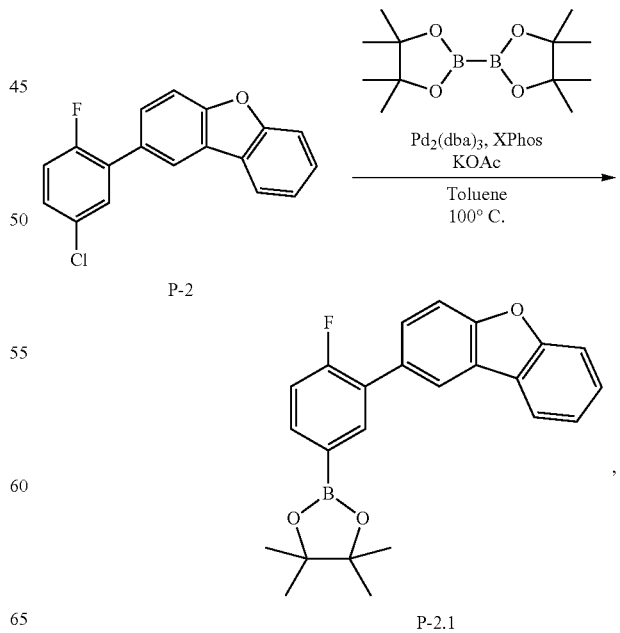

In a two-necked flask, aryl chloride P-2 (1.0 equiv.), bis(pinacolato)diboron [CAS 73183-34-3](1.3 equiv.), tris(dibenzylideneacetone)dipalladium(0) [CAS 51364-51-3] (0.02 equiv.), XPhos [CAS 564483-18-7] (0.08 equiv.) and potassium acetate (3.0 equiv.) were suspended in dry toluene and heated at 100° C. for 4 h (monitored by GC-MS). After cooling down to rt, the mixture were added brine and dichloromethane. The phases were separated, the organic layer dried over MgSO₄, filtered and concentrated. The crude product was purified by stirring with refluxing EtOH and subsequent hot filtration (solid, yield: 89%).

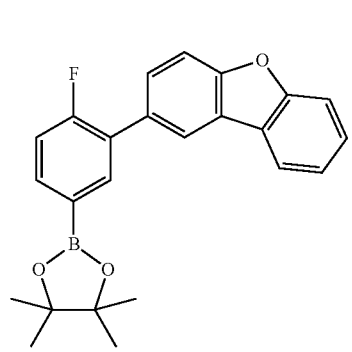

P-2.1

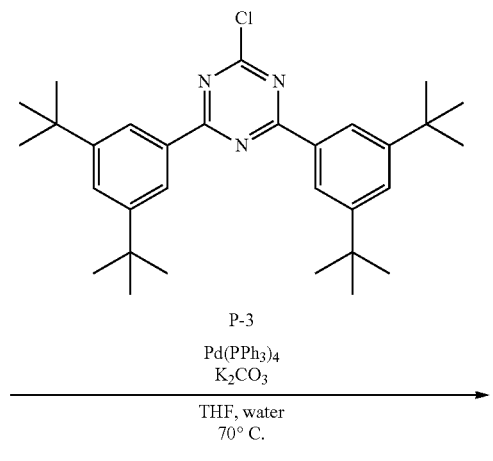

P-3

Pd(PPh₃)₄
K₂CO₃
———————→
THF, water
70° C.

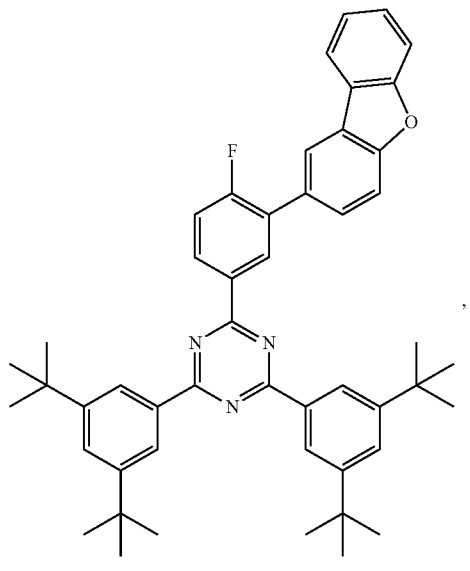

P-4

In a two-necked flask, the triazine derivative P-3 (1.0 equiv.), boronic ester P-2.1 (1.2 equiv.), tetrakis(triphenylphosphine)palladium(0) [CAS 14221-01-3] (0.1 equiv.) and potassium carbonate (3.0 equiv.) were suspended in THF/water (3:1). The mixture was heated at 70° C. overnight. After cooling down to rt the mixture were added brine and dichloromethane and the phases were separated. The organic layer was dried over MgSO₄, filtered and concentrated. The crude product was purified by recrystallization from EtOH (solid, yield: 87%).

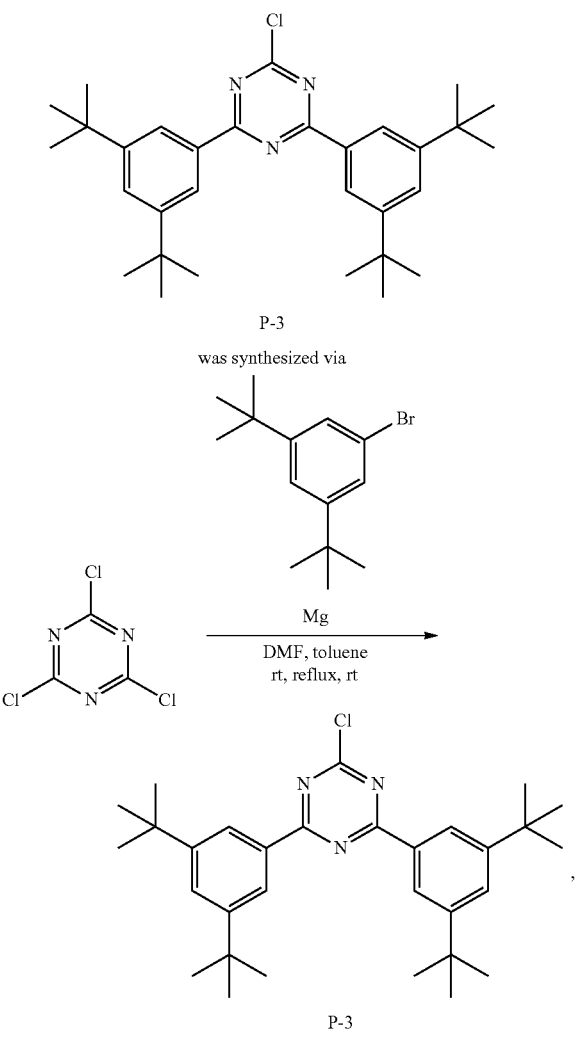

P-3 was synthesized via

P-3

In a flame-dried three-necked flask, equipped with a reflux condenser and a septum, pre-dried Mg turnings (4.0 equiv.) and iodine (~5 mg) were suspended in dry THF. The mixture was stirred at rt until the color had changed from purple to light brownish. Subsequently, a solution of 1-bromo-3,5-di-tert-butylbenzene [CAS 22385-77-9] (2.5 equiv.) was added dropwise. After stirring at rt for 30 min, the mixture was refluxed for 3 h (bleaching of the color). After cooling down to rt, with a transfer cannula, the mixture was slowly transferred into another flask containing a solution of cyanuric chloride [CAS 108-77-0] (1.0 equiv.) in dry THF. Subsequently, the solution was heated under reflux overnight. After cooling down to rt, followed by quenching with water, the mixture was extracted with dichloromethane. The organic layer was dried over $MgSO_4$, filtered and concentrated. The crude product was purified by MPLC using a gradient of n-hexane and dichloromethane as the eluent (white solid, yield: 71%).

Further, synthesis was performed according to AAV7 (91% yield).

MS (HPLC-MS), m/z (retention time): 1029 (31.99 min).

Figure 3:
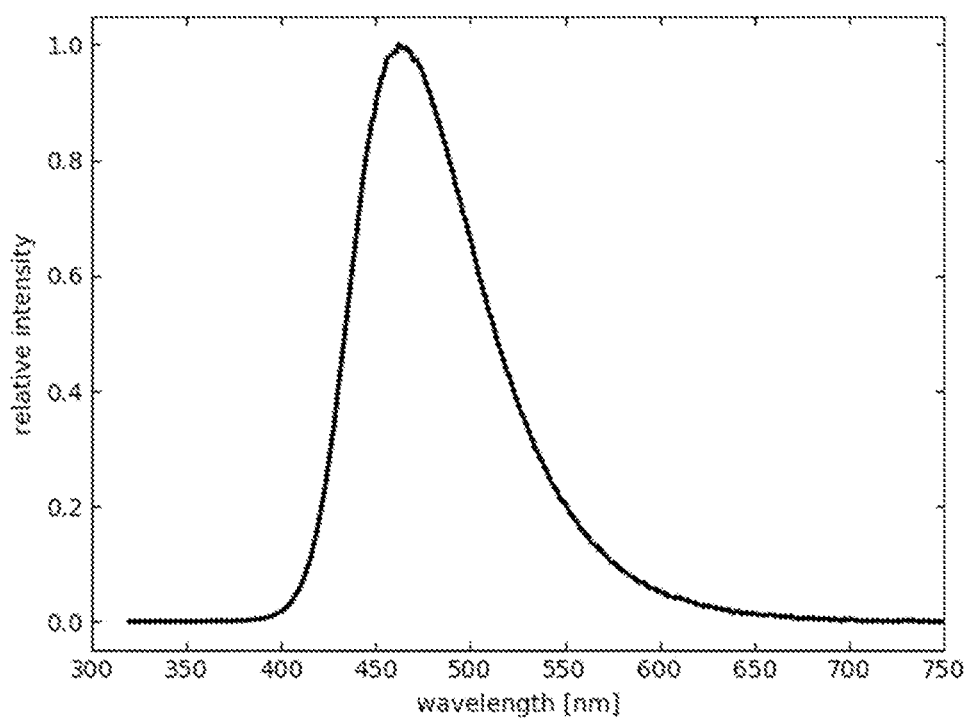
FIG. 3 is an emission spectrum of example 3 (10% by weight) in PMMA.

FIG. 3 depicts the emission spectrum of example 3 (10% by weight in PMMA). The emission maximum is at 462 nm. The photoluminescence quantum yield (PLQY) is 62% and the full width at half maximum is 0.45 eV. The resulting $CIE_x$ coordinate is determined at 0.16 and the $CIE_y$ coordinate at 0.20.

Example 4

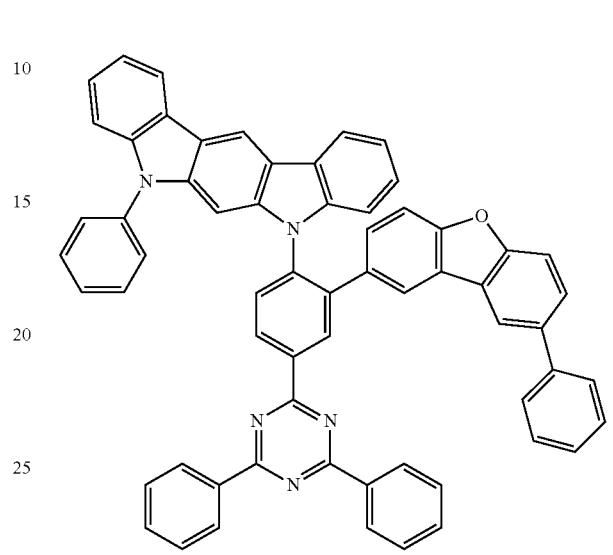

Example 4 was synthesized according to

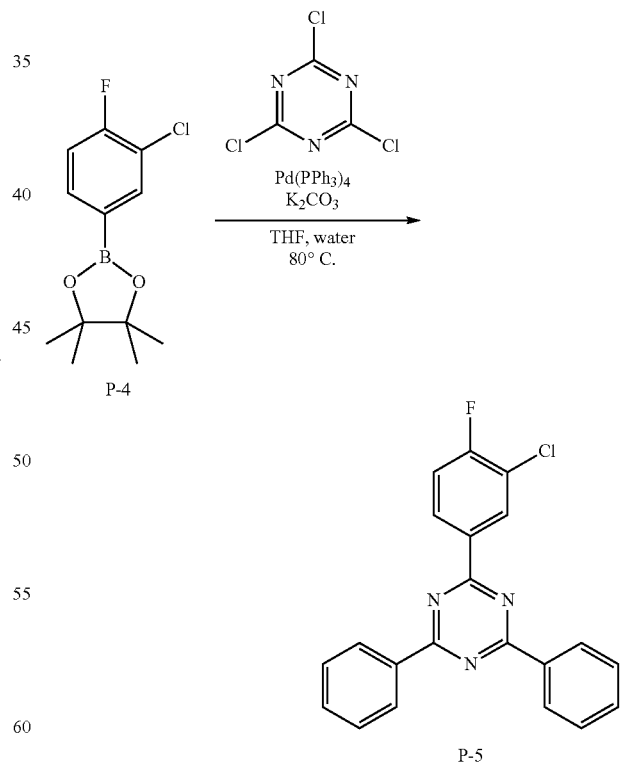

The synthesis of P-5 was performed by reacting boronic ester P-4 with 2-chloro-4,6-diphenyl-1,3,5-triazine [CAS 3842-55-5] following the same procedure as described above for the synthesis of P-4 (solid, yield: 92%).

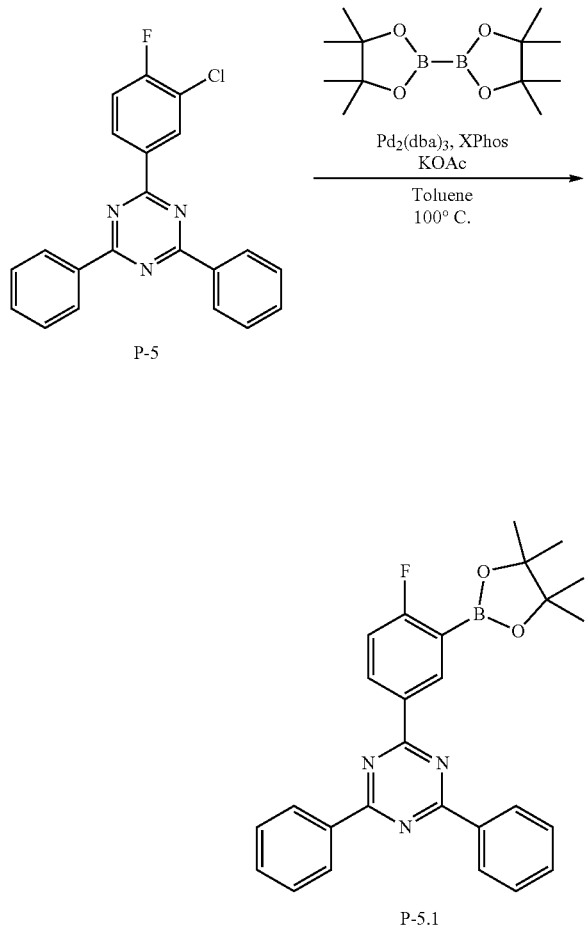

P-5

P-5.1

The boronic ester P-5.2 was synthesized from aryl chloride P-5 according to the procedure described above for the synthesis of P-2.1 (solid, yield: 85%).

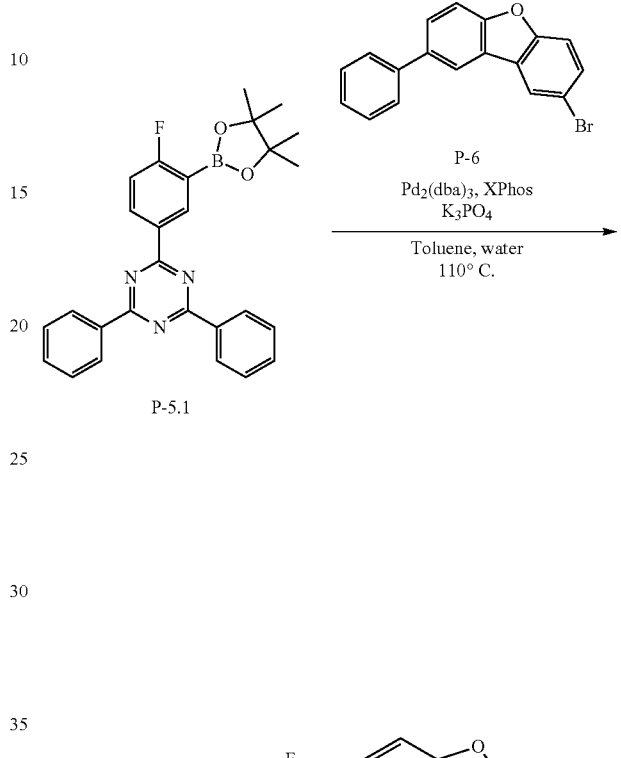

P-5.1

Compound P-6 was synthesized from 2,8-dibromodibenzofuran [CAS 10016-52-1] and 4,4,5,5-tetramethyl-2-phenyl-1,3,2-dioxaborolane [CAS 24388-23-6] following the protocol described above for the synthesis of P-4 (solid, yield: 55%).

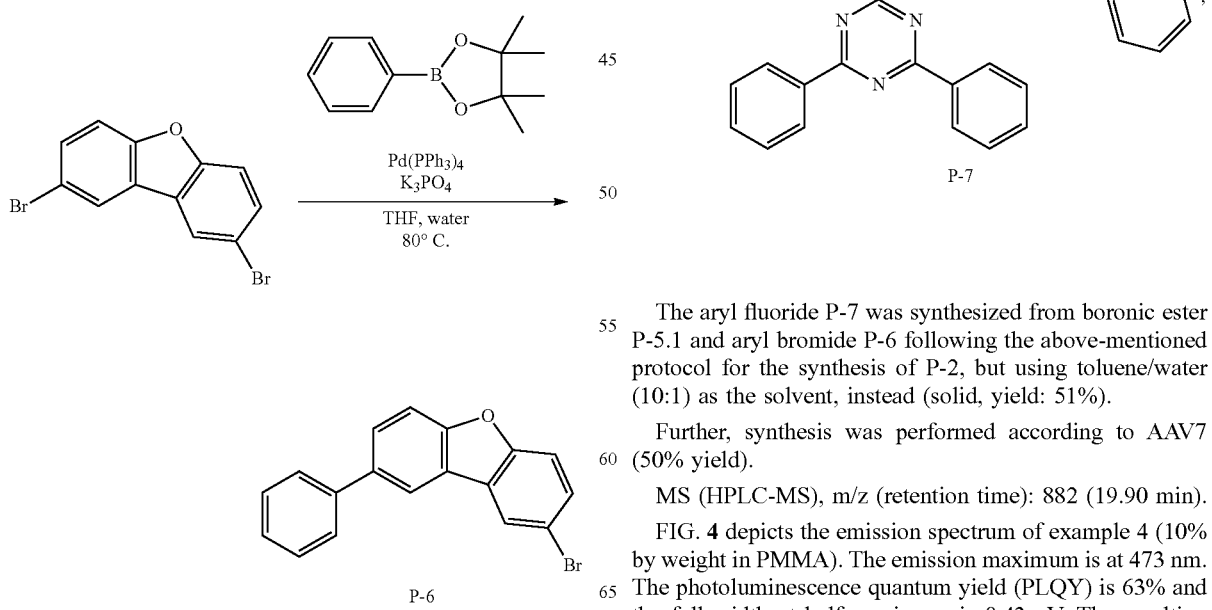

P-7

The aryl fluoride P-7 was synthesized from boronic ester P-5.1 and aryl bromide P-6 following the above-mentioned protocol for the synthesis of P-2, but using toluene/water (10:1) as the solvent, instead (solid, yield: 51%).

Further, synthesis was performed according to AAV7 (50% yield).

MS (HPLC-MS), m/z (retention time): 882 (19.90 min).

Figure 4:
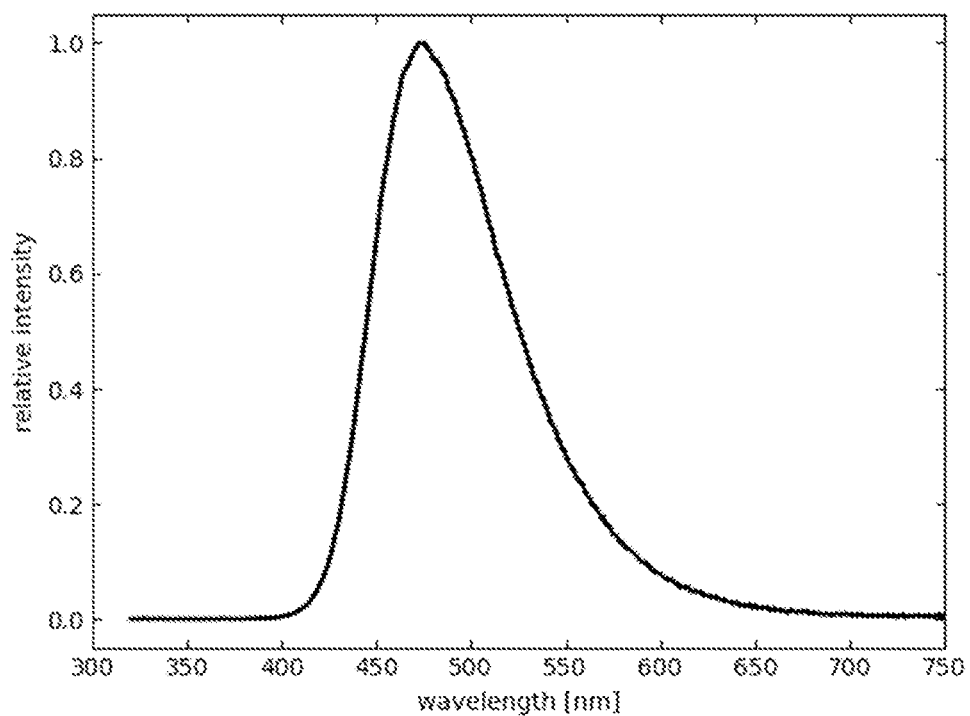
FIG. 4 is an emission spectrum of example 4 (10% by weight) in PMMA.

FIG. 4 depicts the emission spectrum of example 4 (10% by weight in PMMA). The emission maximum is at 473 nm. The photoluminescence quantum yield (PLQY) is 63% and the full width at half maximum is 0.43 eV. The resulting CIEx coordinate is at 0.17 and the $CIE_y$ coordinate at 0.27.

Example 5

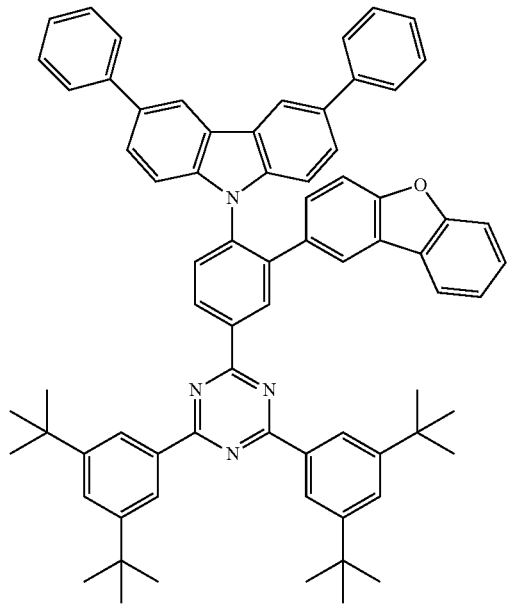 [SMILES: CC(C)(C)c1cc(-c2nc(-c3cc(C(C)(C)C)cc(C(C)(C)C)c3)nc(-c3ccc(-n4c5ccc(-c6ccccc6)cc5c5cc(-c6ccccc6)ccc54)c(-c4ccc5oc6ccccc6c5c4)c3)n2)cc(C(C)(C)C)c1]

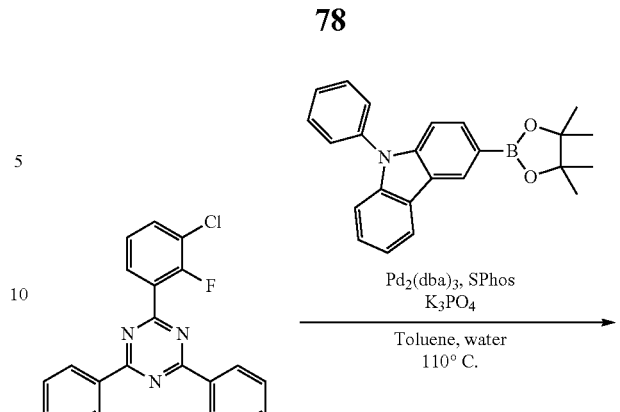

P-8

Example 5 was synthesized as described in Example 3 and AAV7 (94% yield).

MS (HPLC-MS), m/z (retention time): 1016.9 (33.08 min).

Figure 5:
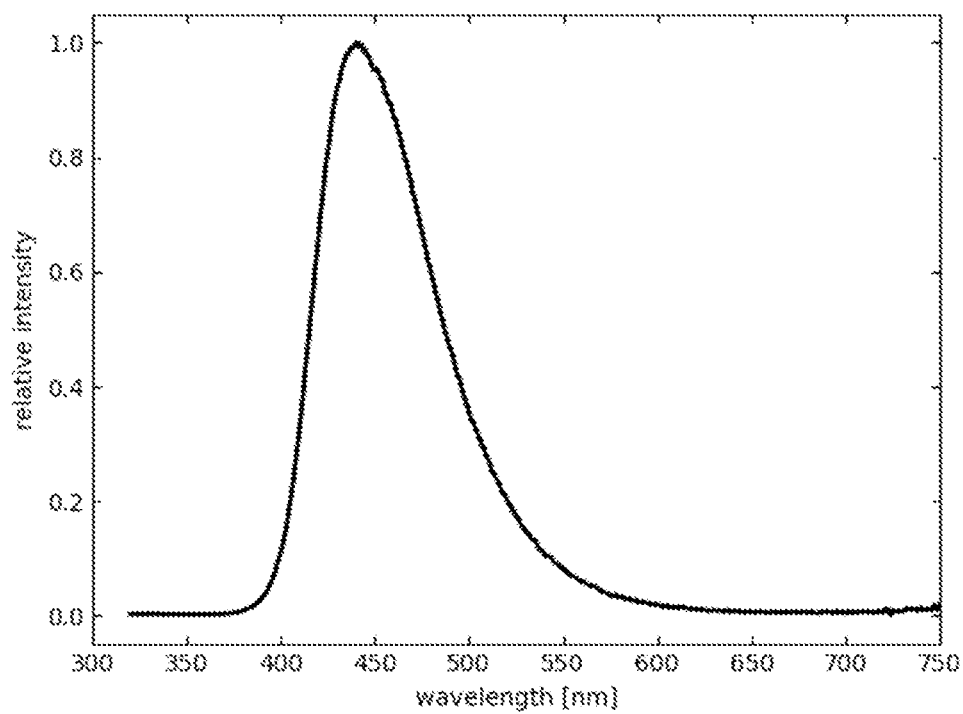
FIG. 5 is an emission spectrum of example 5 (10% by weight) in PMMA.

FIG. 5 depicts the emission spectrum of example 5 (10% by weight in PMMA). The emission maximum is at 440 nm. The photoluminescence quantum yield (PLQY) is 58% and the full width at half maximum is 0.43 eV. The resulting $CIE_x$ coordinate is at 0.16 and the $CIE_y$ coordinate is at 0.11.

Example 6

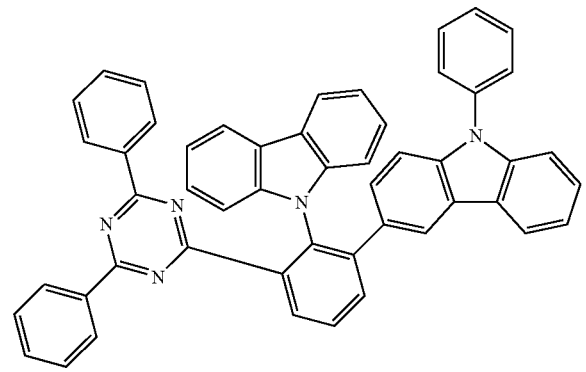 [SMILES: c1ccc(-c2nc(-c3ccccc3)nc(-c3cccc(-c4ccc5c(c4)c4ccccc4n5-c4ccccc4)c3-n3c4ccccc4c4ccccc43)n2)cc1]

Example 6 was synthesized as described by AAV4 from aryl chloride P-8 and 9-phenyl-3-(4,4,5,5-tetramethyl-[1,3,2]dioxaborolan-2-yl)-9H-carbazole [CAS 1126522-69-7] with 64% yield.

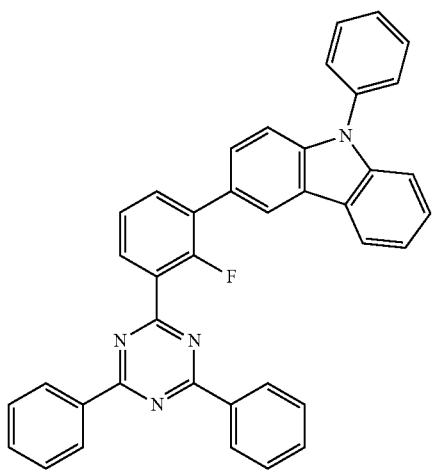

Aryl chloride P-8 was synthesized from boronic ester P-9 and 2-chloro-4,6-diphenyl-1,3,5-triazine [CAS 3842-55-5], following the procedure described for the synthesis of P-5 (solid, yield: 99%).

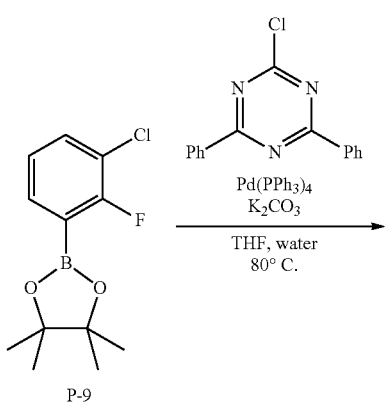

P-9

-continued

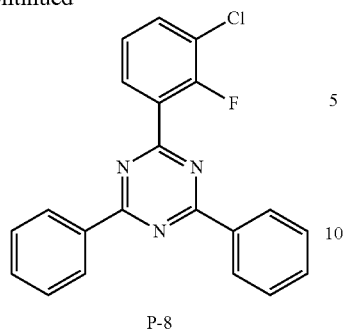

P-8

Further, synthesis was performed according to AAV7 (41% yield).

MS (HPLC-MS), m/z (retention time): 715 (15.56 min).

Figure 6:
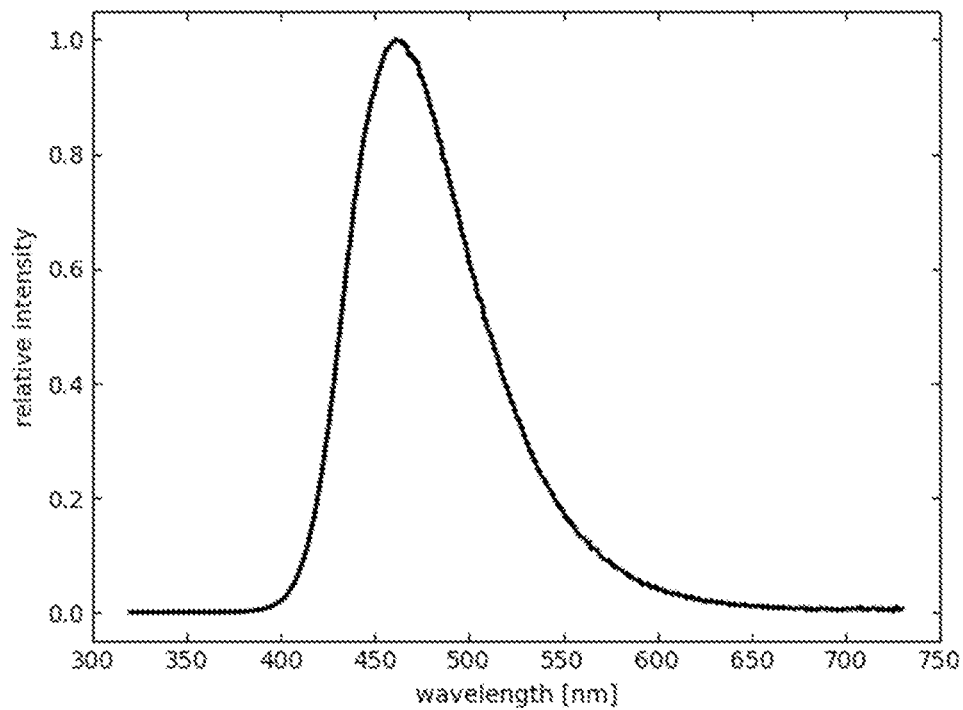
FIG. 6 is an emission spectrum of example 6 (10% by weight) in PMMA.

FIG. 6 depicts the emission spectrum of example 6 (10% by weight in PMMA). The emission maximum is at 462 nm. The photoluminescence quantum yield (PLQY) is 59% and the full width at half maximum is 0.44 eV. The resulting CIEx coordinate is determined at 0.16 and the $CIE_y$ coordinate at 0.19.

Example 7

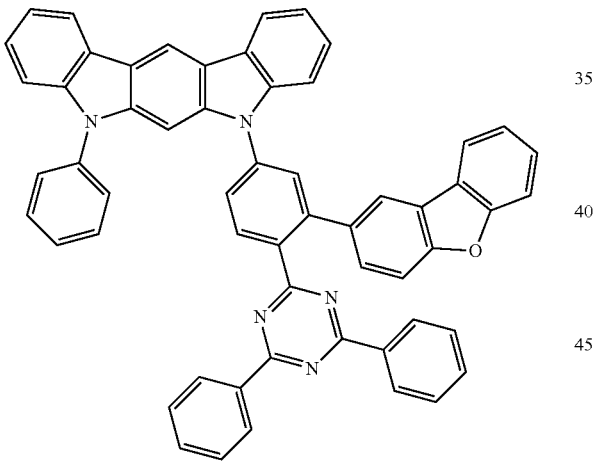

Example 7 was synthesized according to AAV1 (62% yield) and AAV7 (80% yield).

MS (HPLC-MS), m/z (retention time): 806 (18.03 min).

Figure 7:
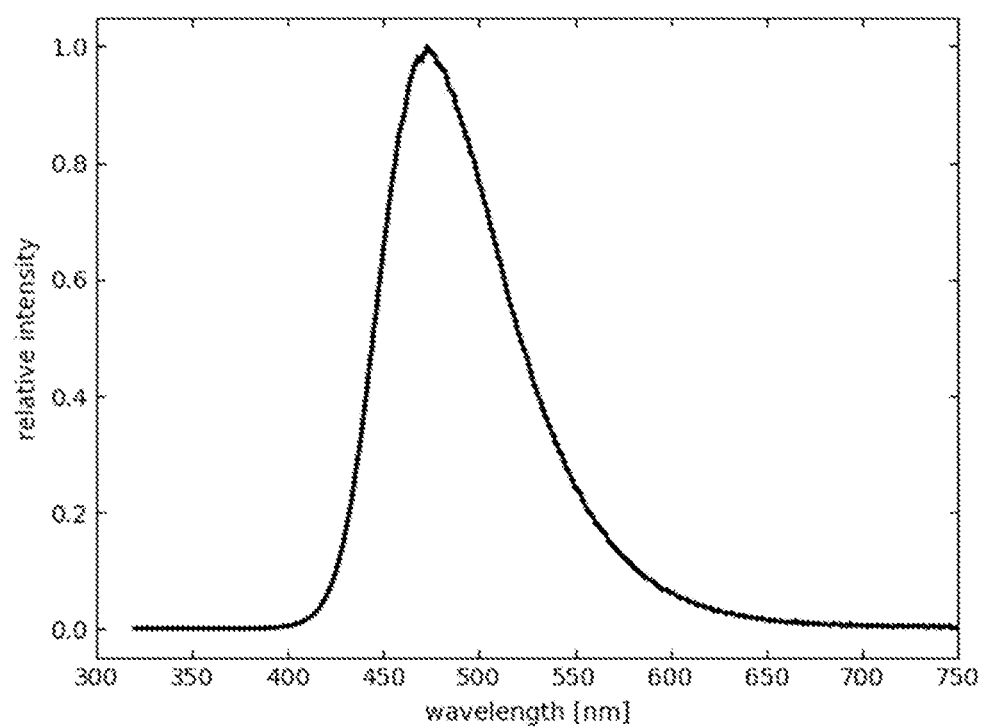
FIG. 7 is an emission spectrum of example 7 (10% by weight) in PMMA.

FIG. 7 depicts the emission spectrum of example 7 (10% by weight in PMMA). The emission maximum is at 473 nm. The photoluminescence quantum yield (PLQY) is 39% and the full width at half maximum is 0.41 eV. The resulting $CIE_x$ coordinate is determined at 0.17 and the $CIE_y$ coordinate at 0.26.

Device D1

Example 1 was tested in an OLED-device D1 with the following layer structure:

| Layer | Thickness | |
|---|---|---|
| 8 | 100 nm | Al |
| 7 | 2 nm | Liq |
| 6 | 30 nm | NBPhen |
| 5 | 50 nm | Example 1 (20%):mCBP (80%) |
| 4 | 10 nm | mCBP |
| 3 | 10 nm | TCTA |
| 2 | 100 nm | NPB |
| 1 | 130 nm | ITO |
| Substrate | | Glass |

For D1, an external quantum efficiency (EQE) at 1000 cd/m$^2$ of 9.0±0.2% was determined and the emission maximum is at 478 nm, CIEx is 0.17 and CIEy 0.33 at 8.0 V.

Additional Examples of Organic Molecules of the Invention

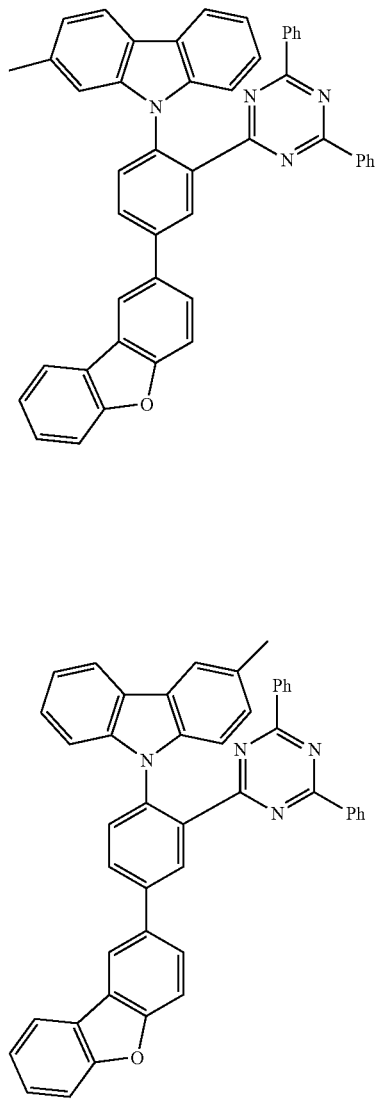

81
-continued
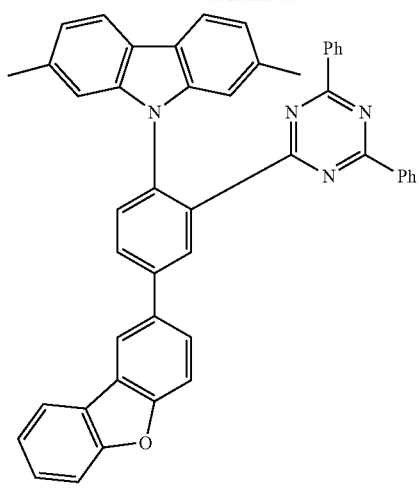
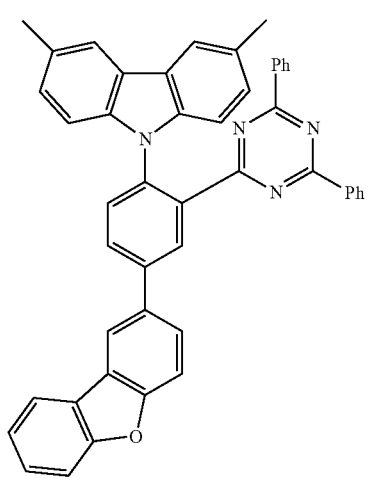
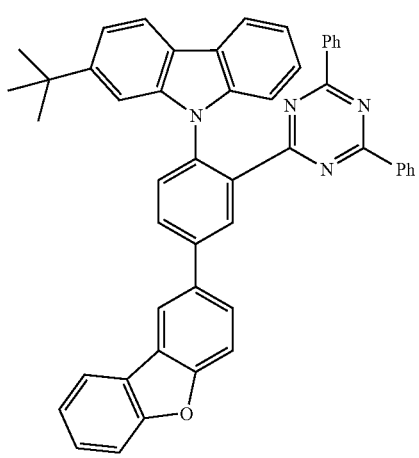
82
-continued
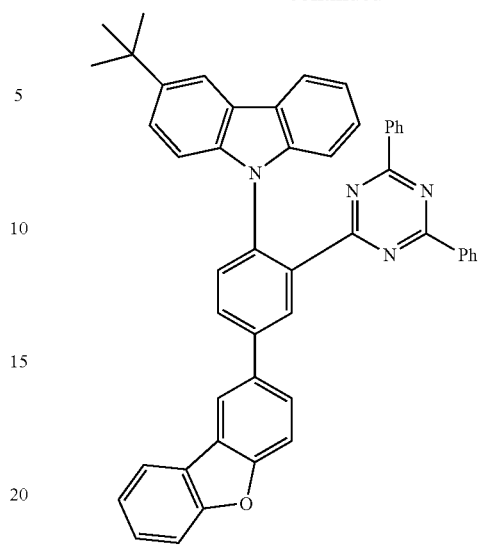
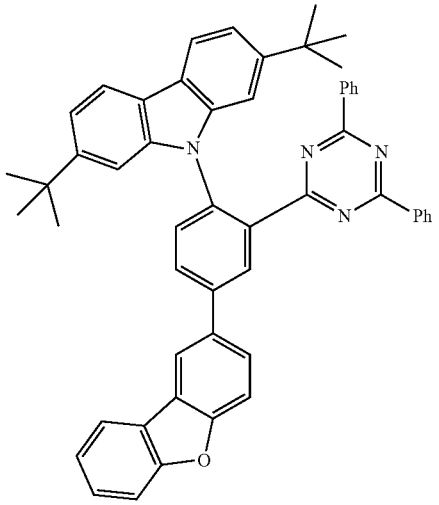

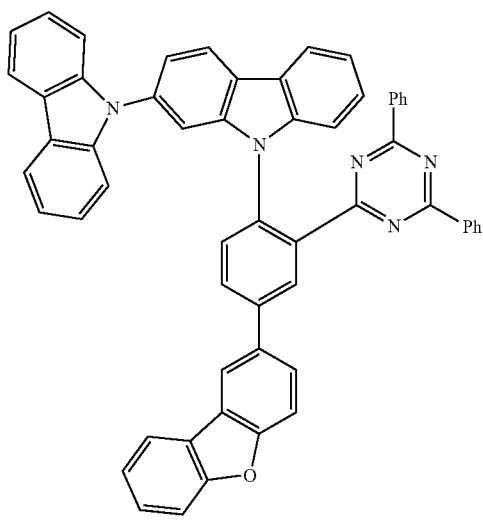
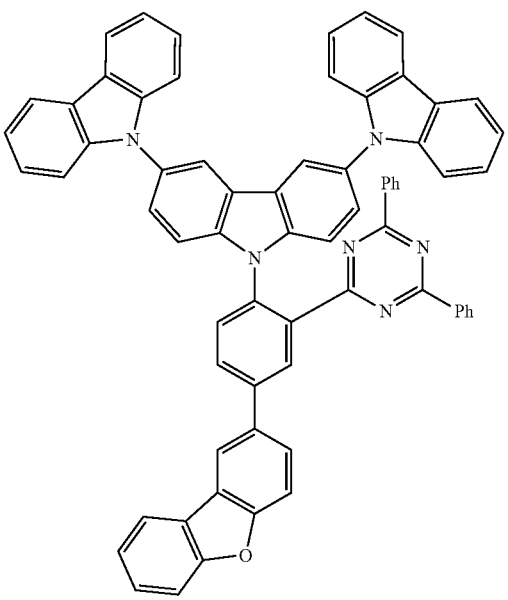

85
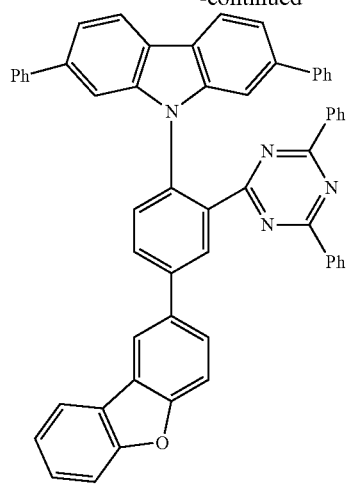
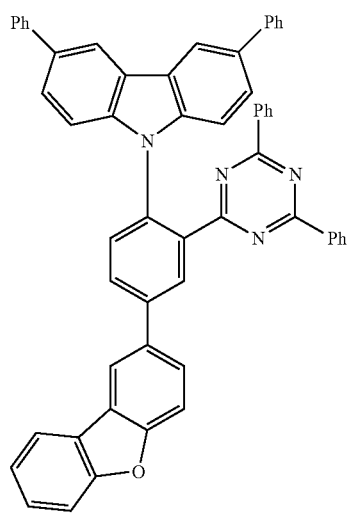
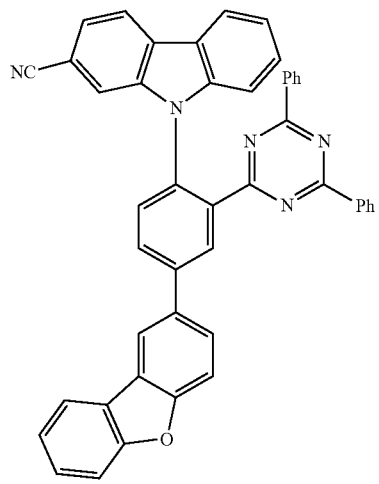
86
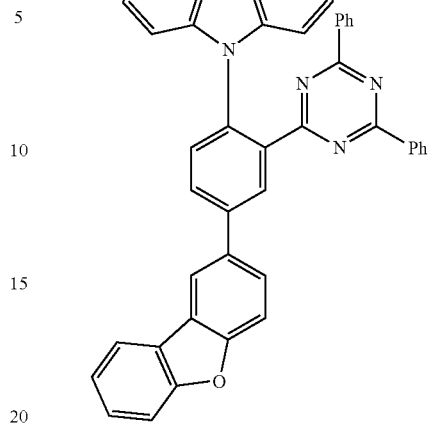
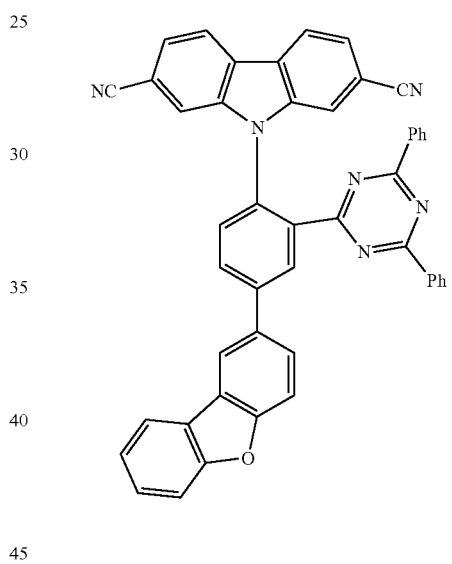
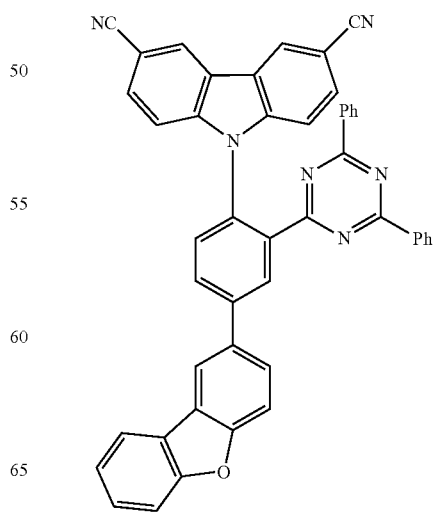

87
-continued
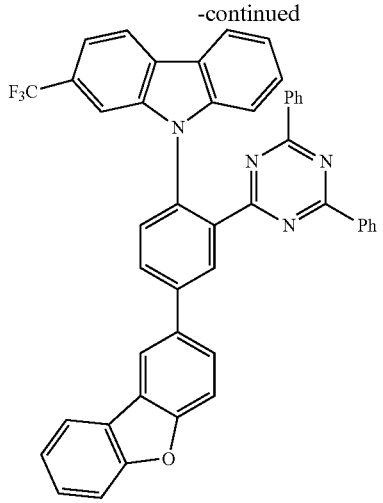
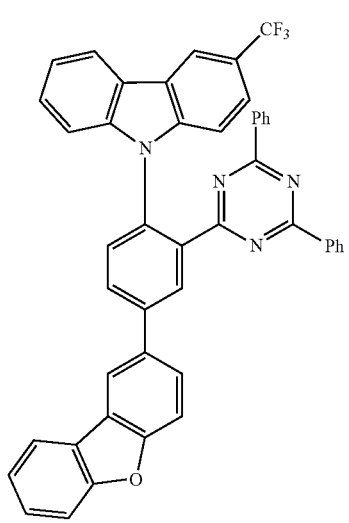
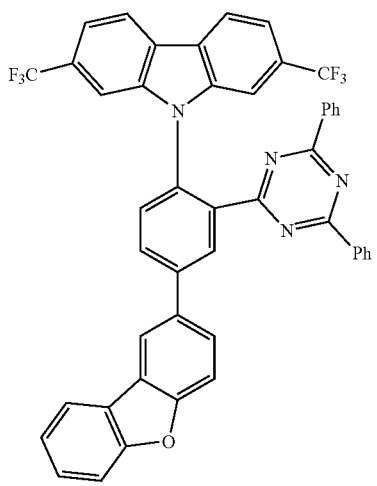
88
-continued
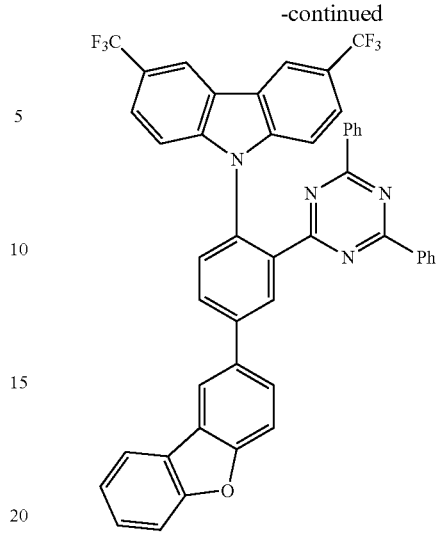
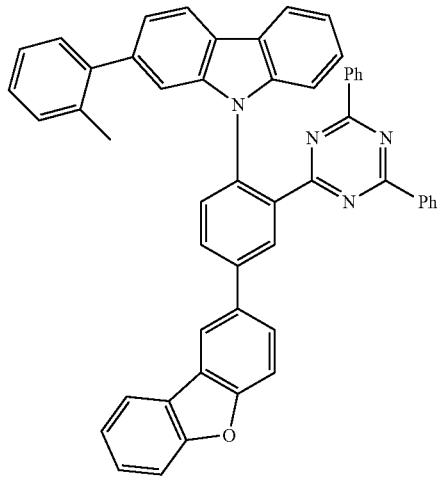
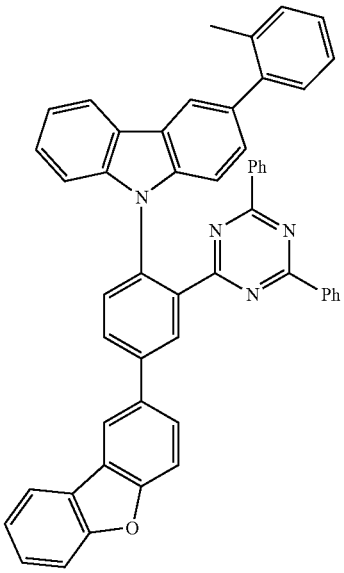

89
-continued
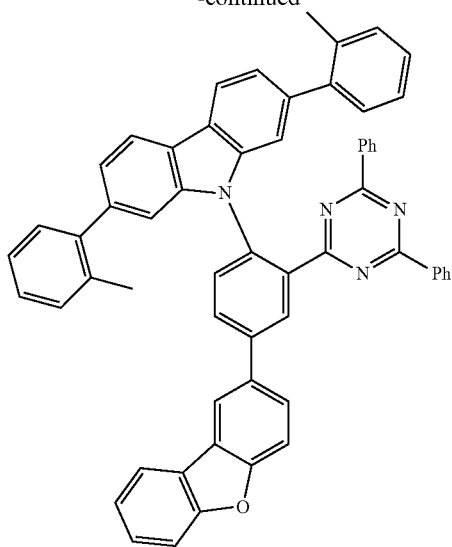
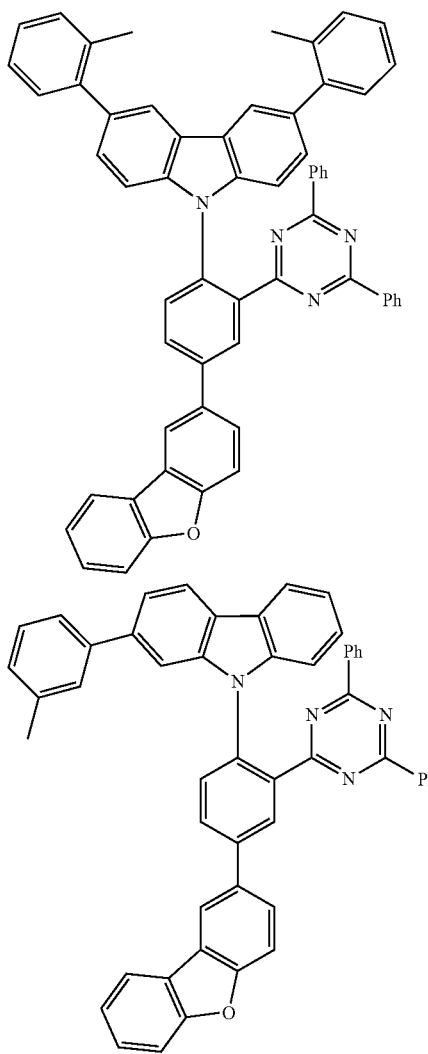
90
-continued
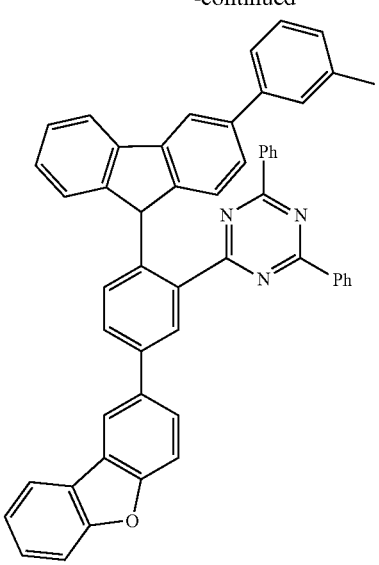
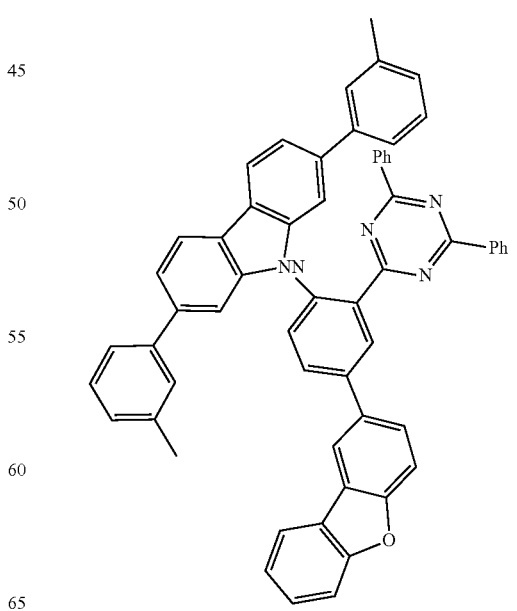

91
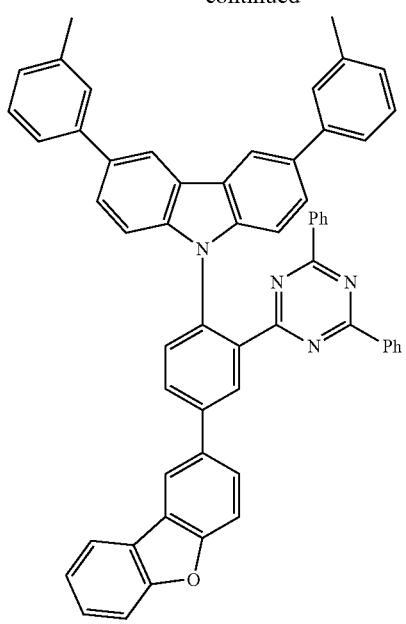
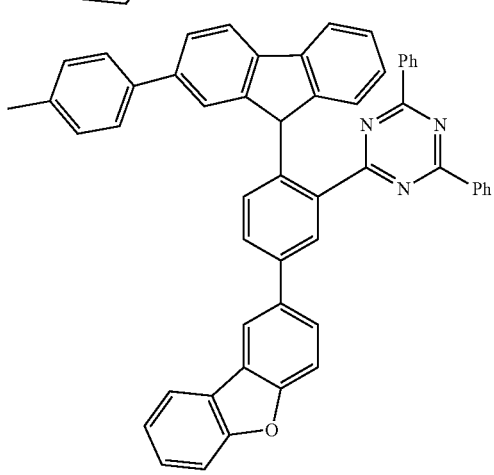
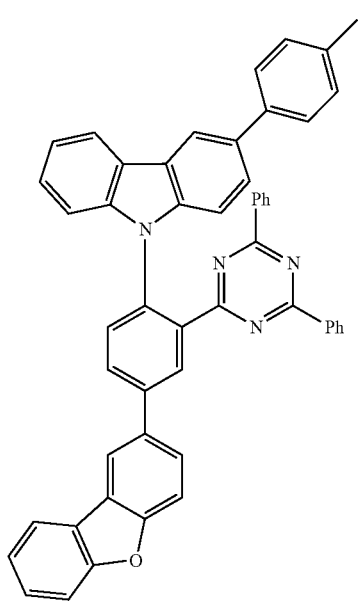
92
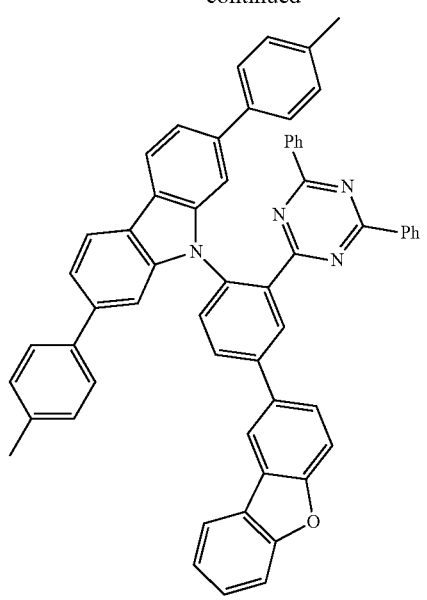
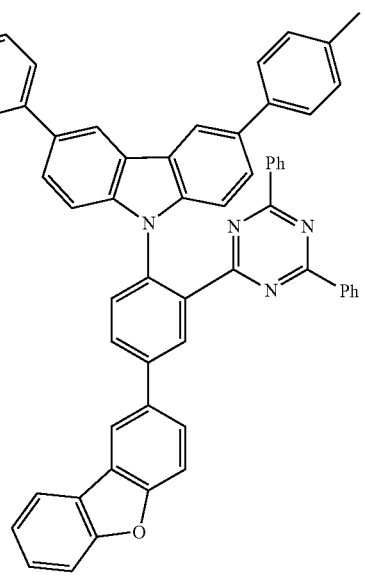

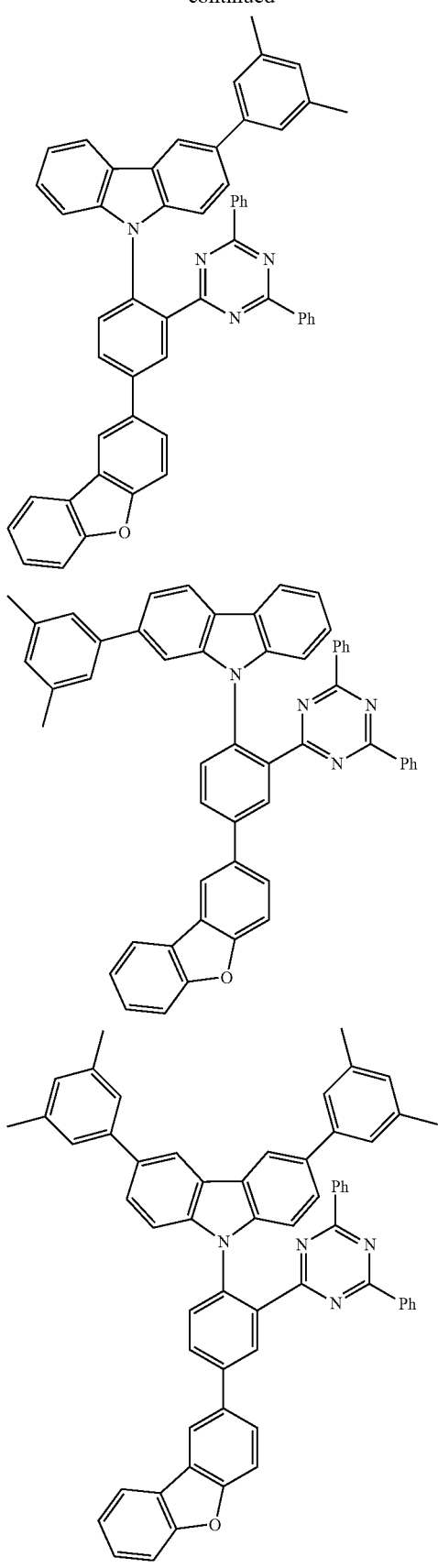
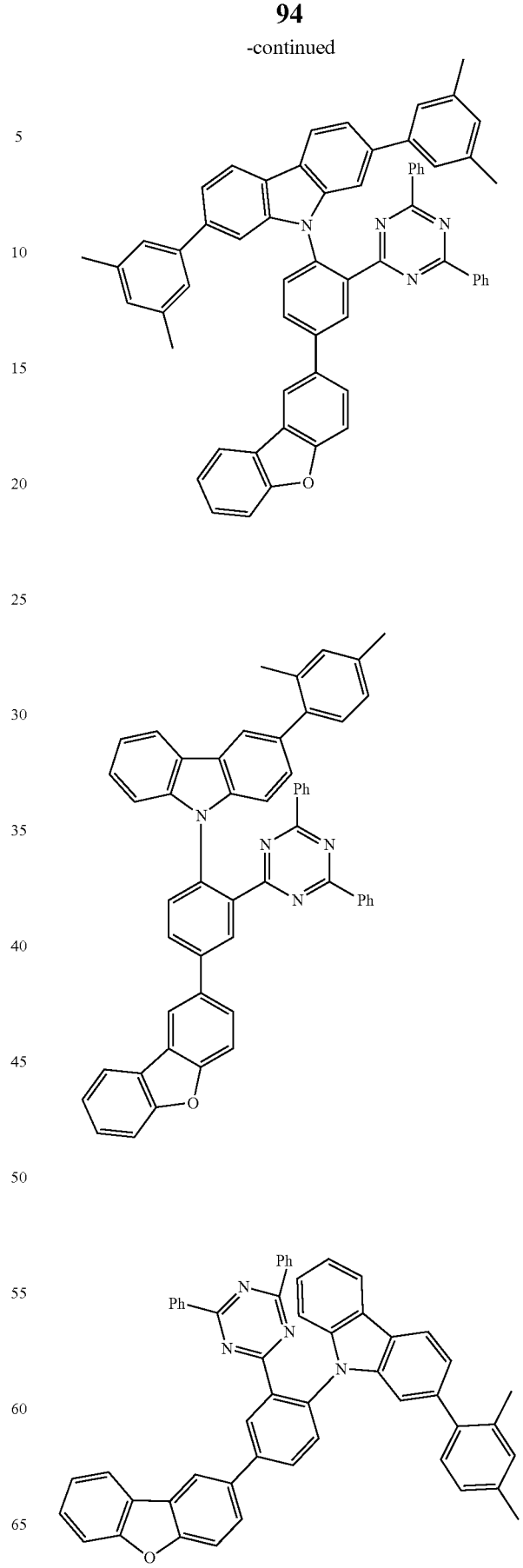

95
-continued
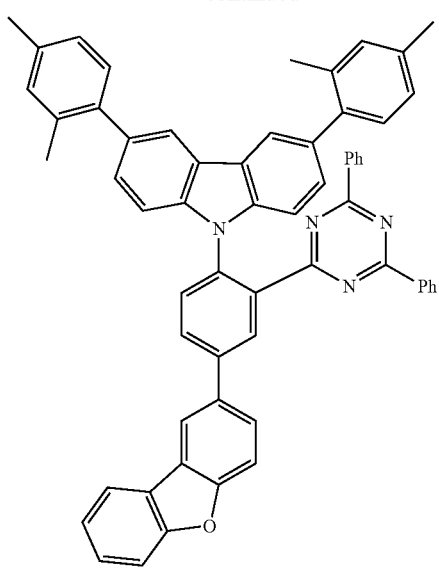
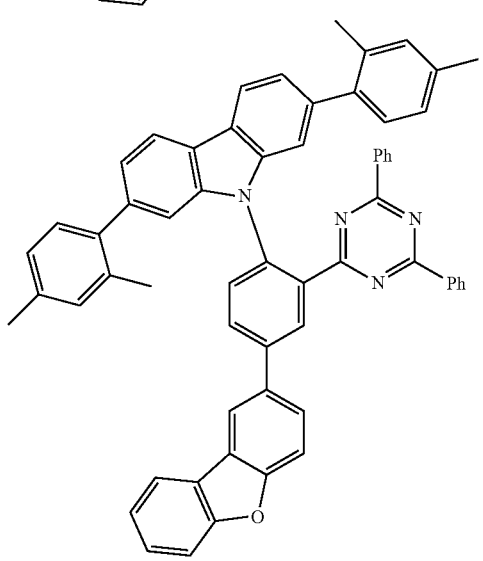
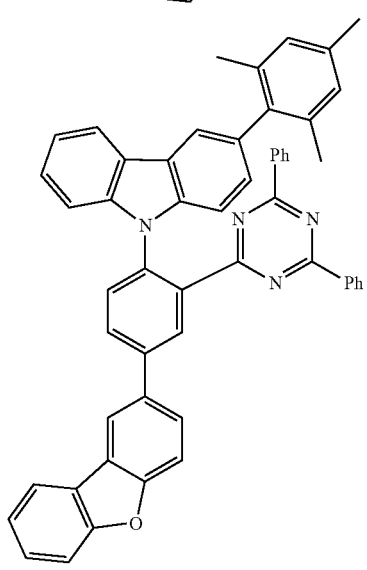
96
-continued
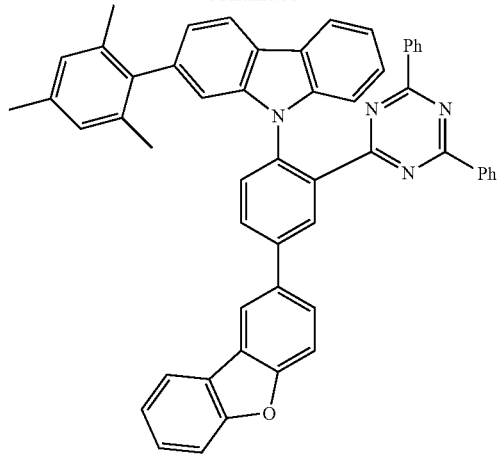
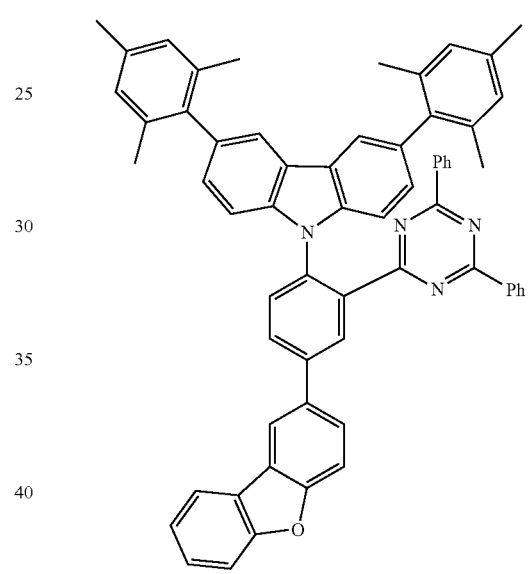
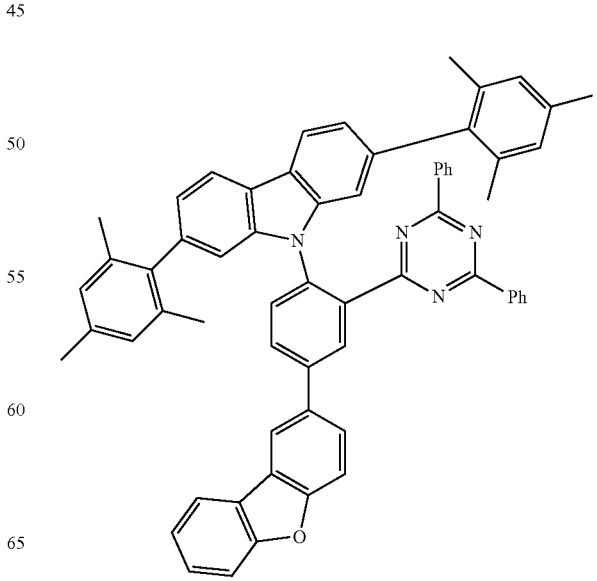

97
-continued
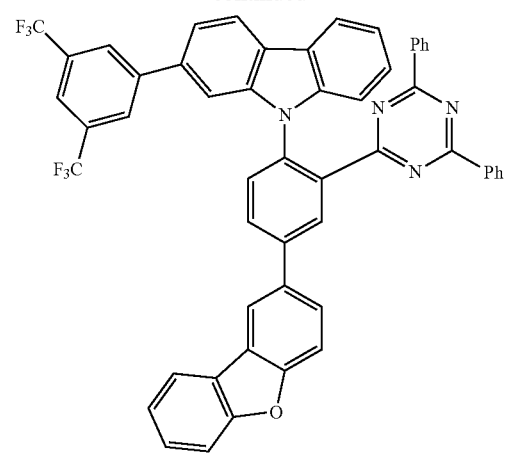
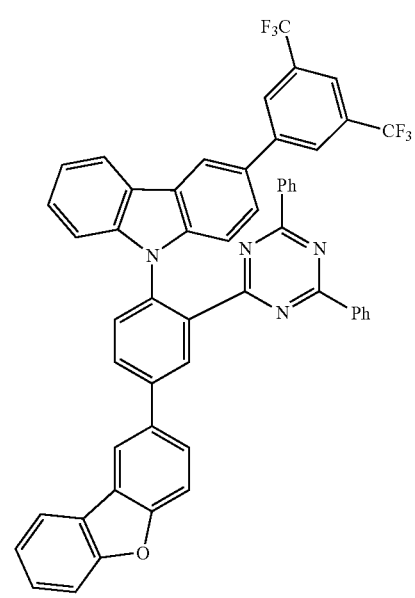
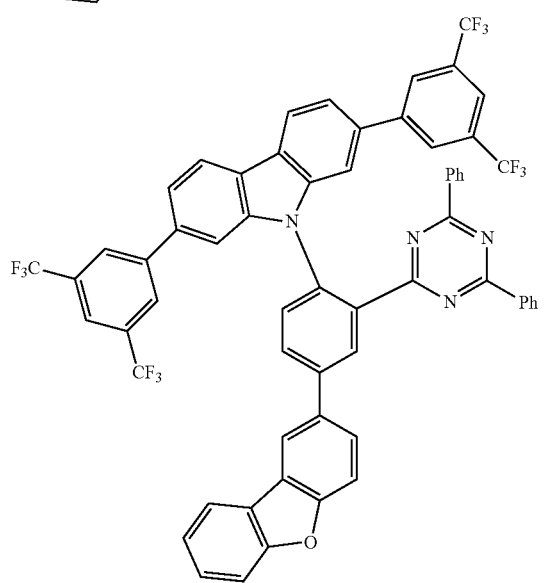
98
-continued
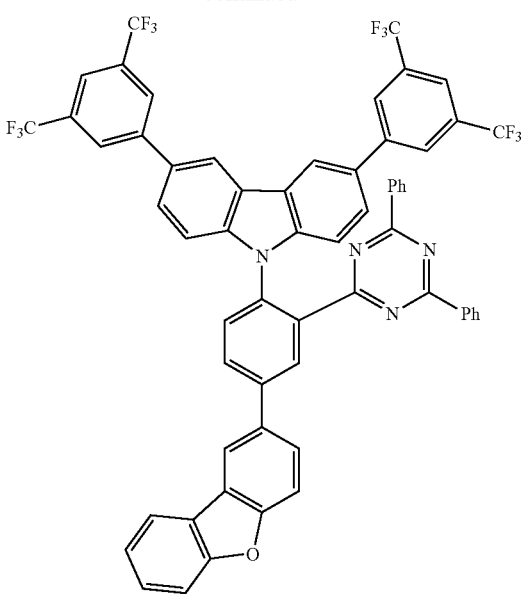
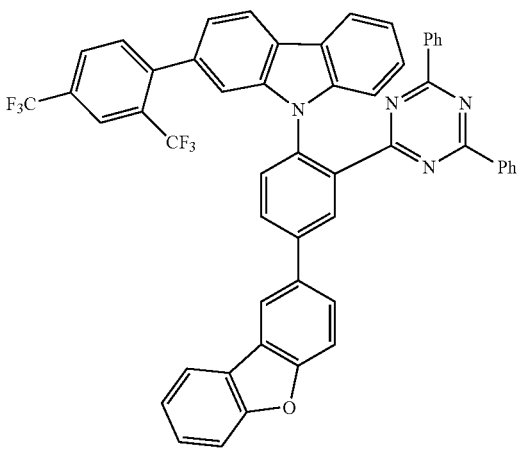

-continued
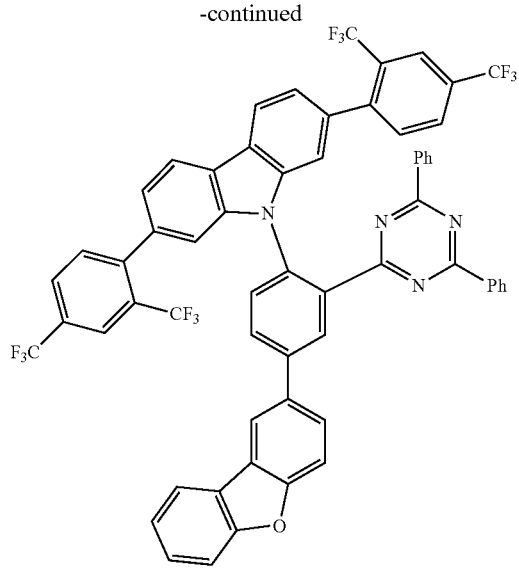
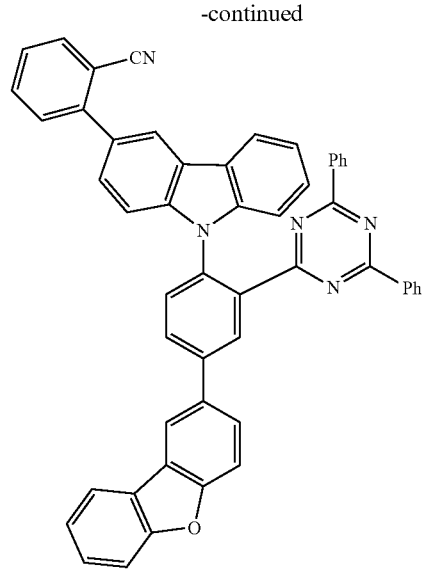
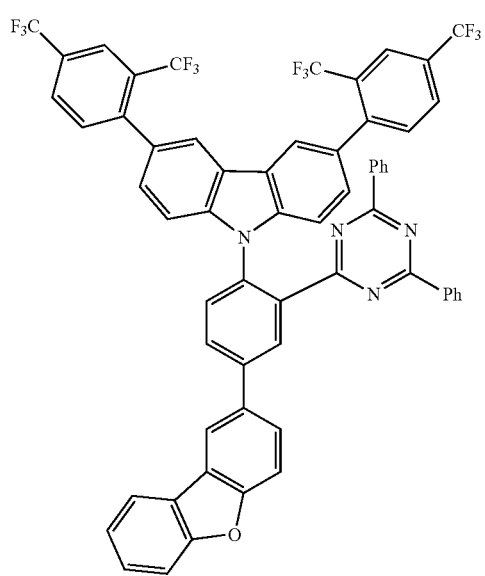
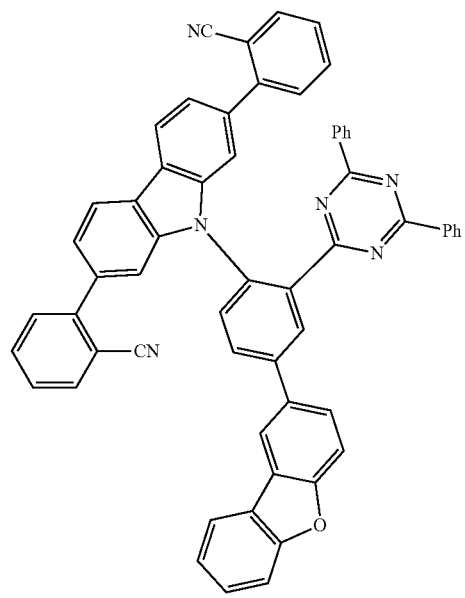
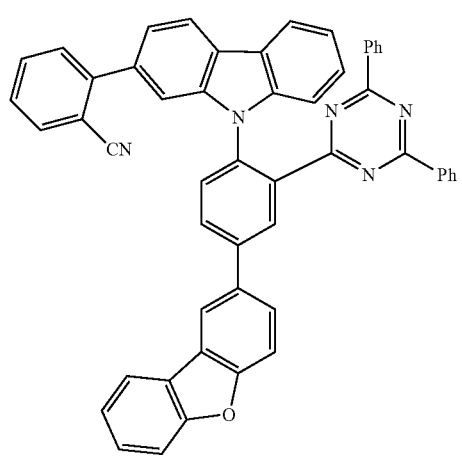
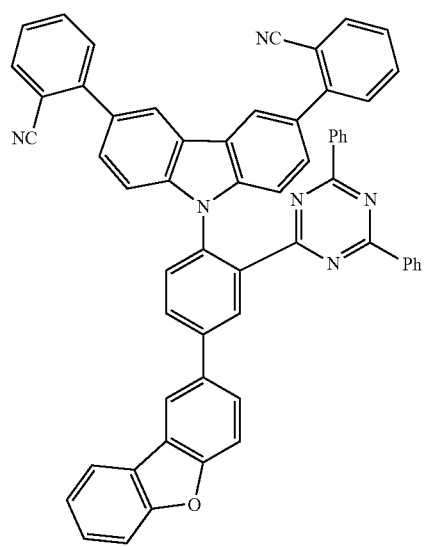

| 101 | 102 |
|---|---|
| 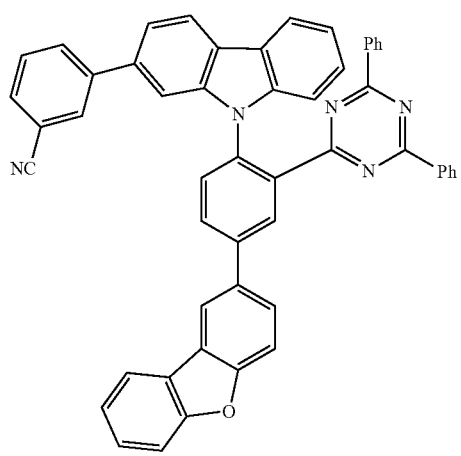 | 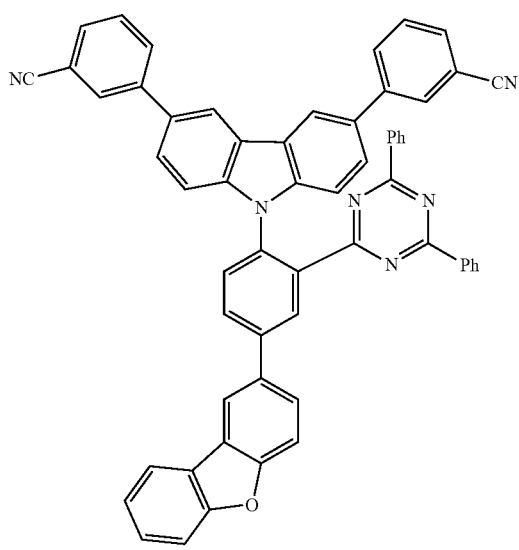 |
| 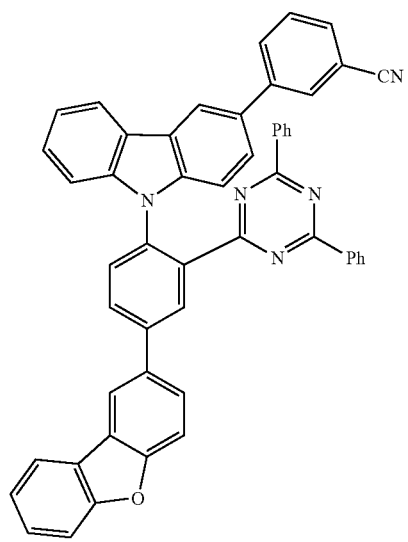 | 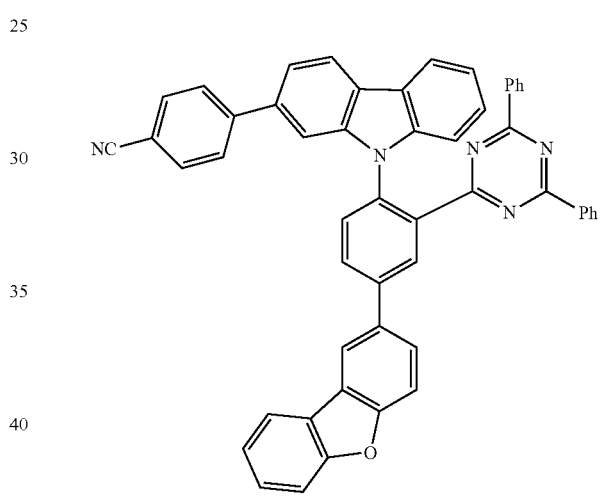 |
| 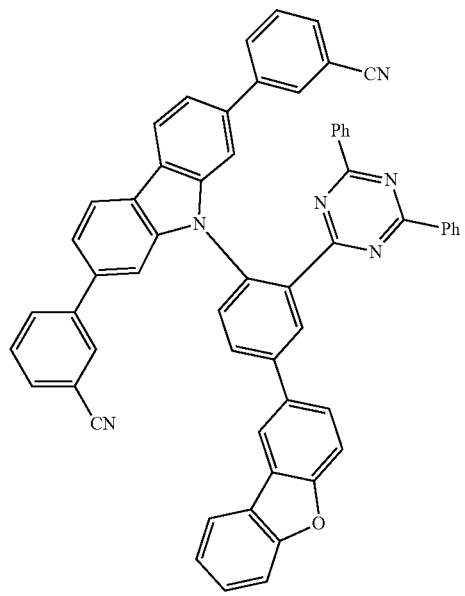 | 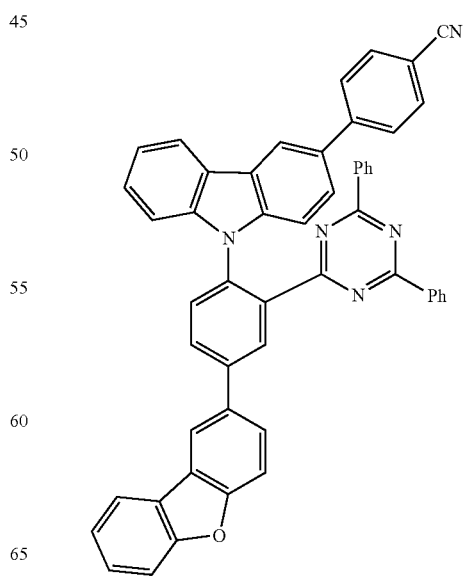 |

103
-continued
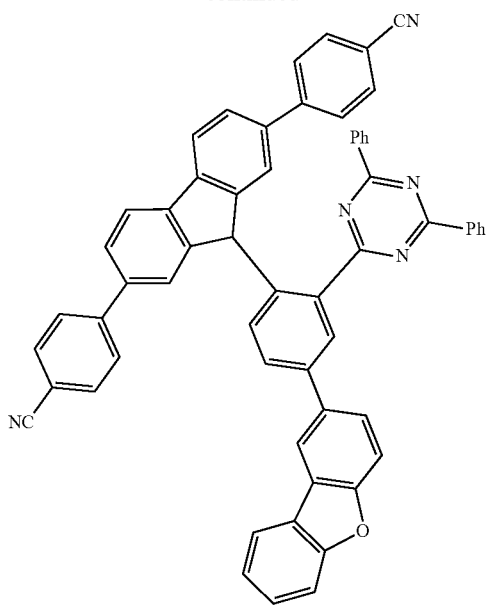
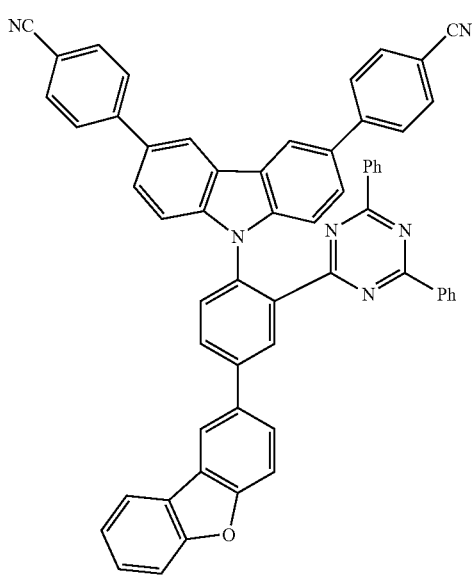
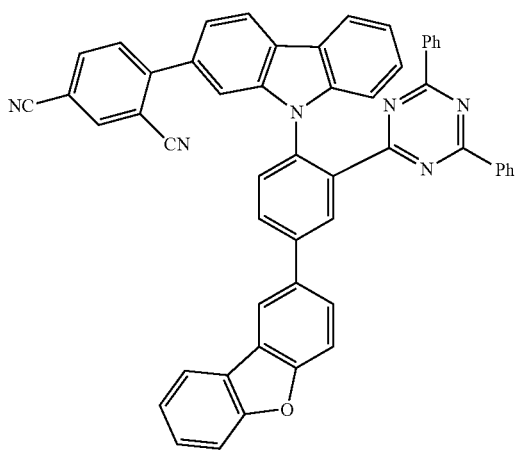
104
-continued
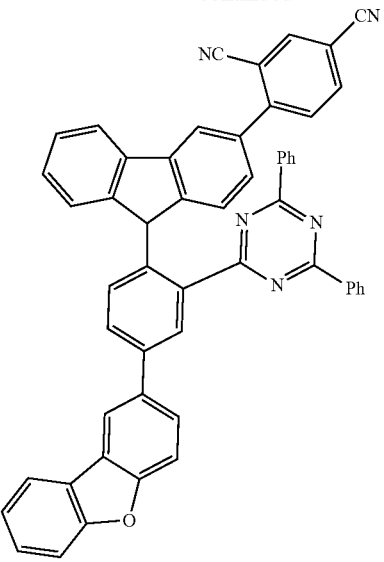
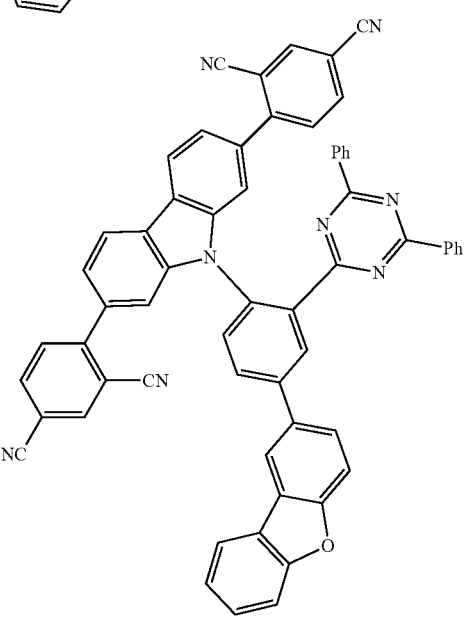
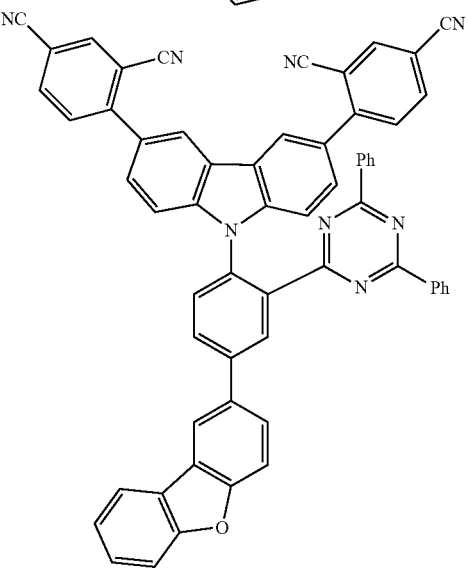

105
-continued
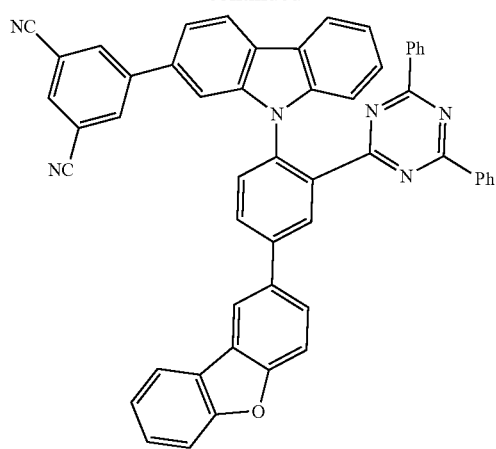
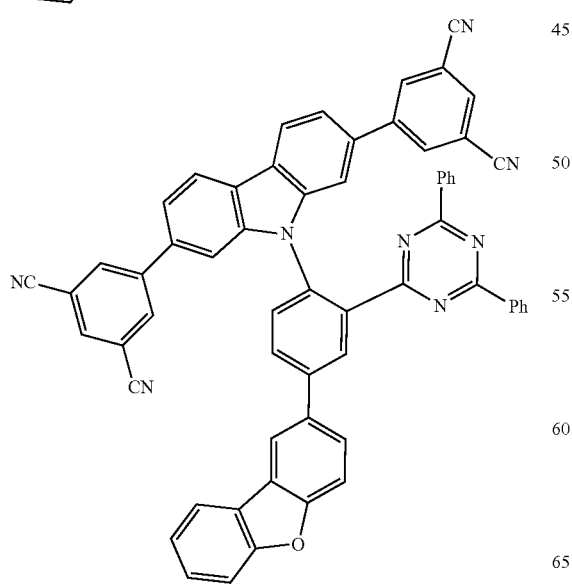
106
-continued
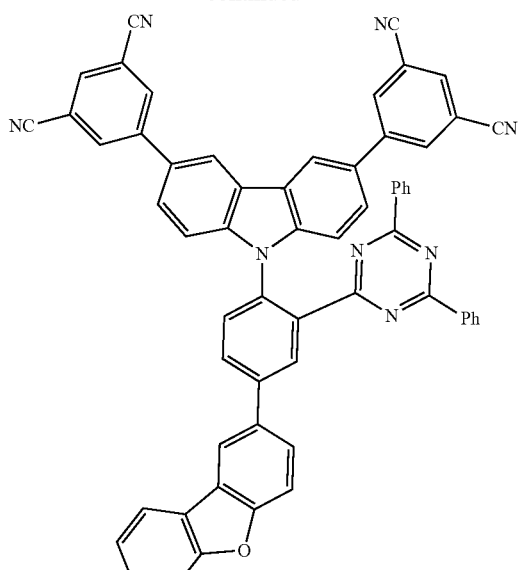
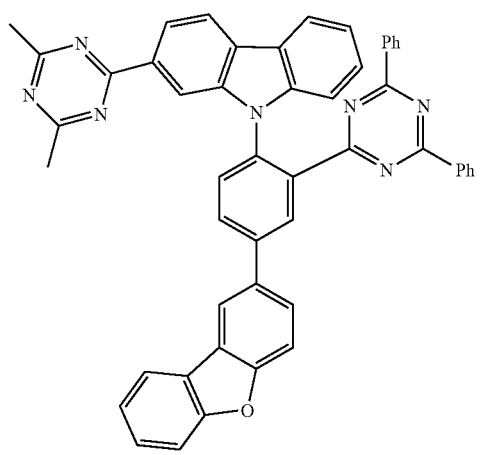
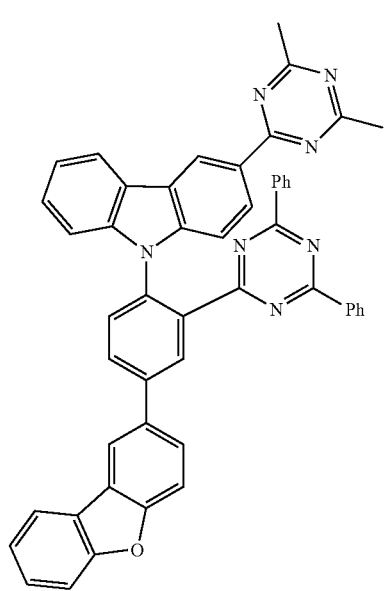

107
-continued
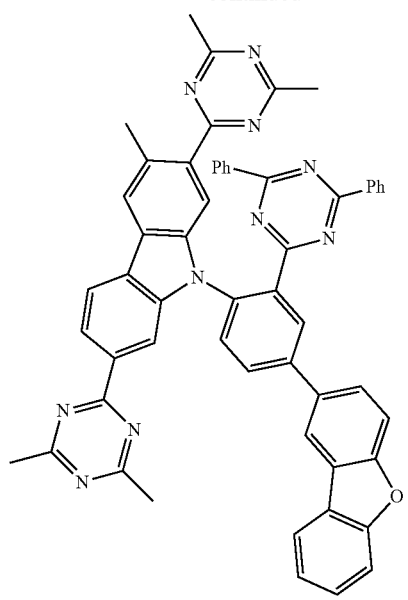
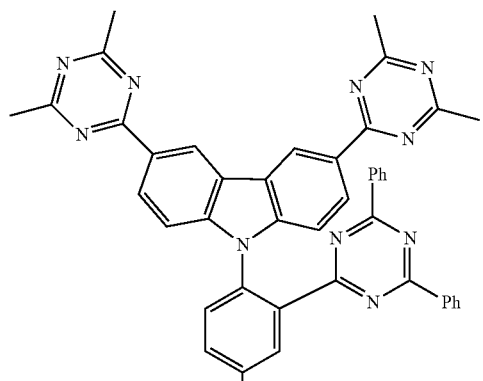
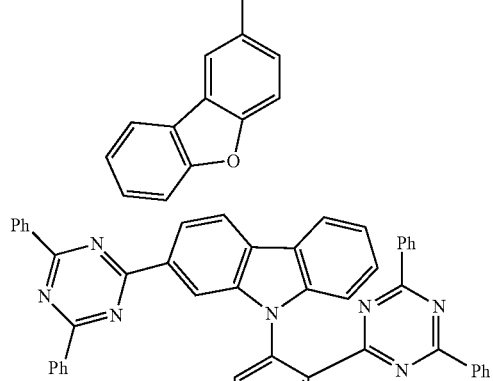
108
-continued
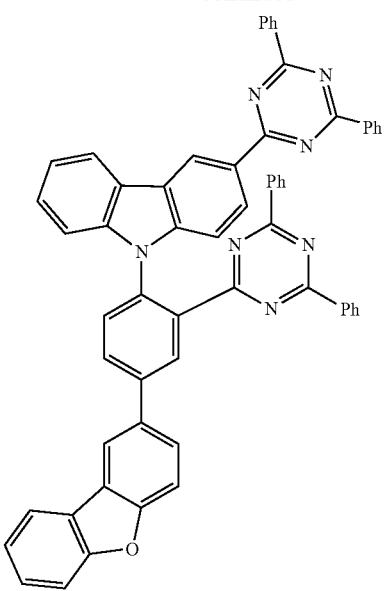
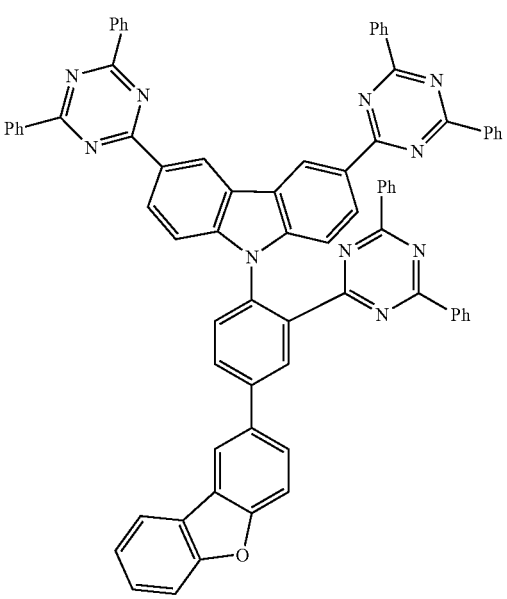

109
-continued
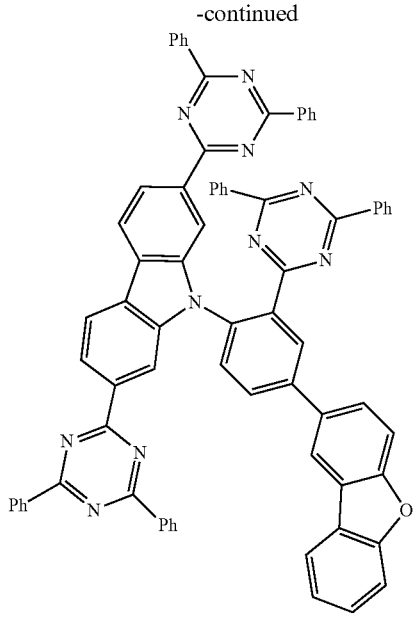
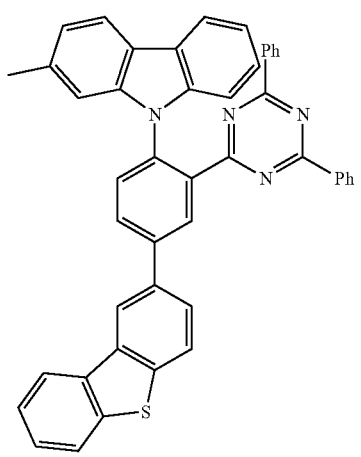
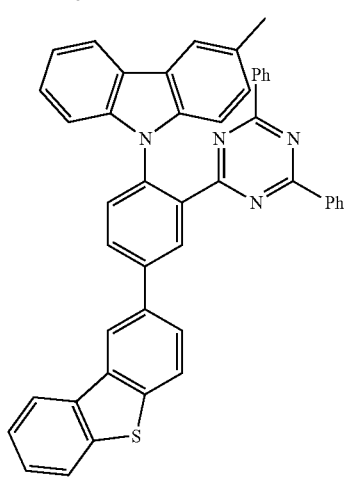
110
-continued
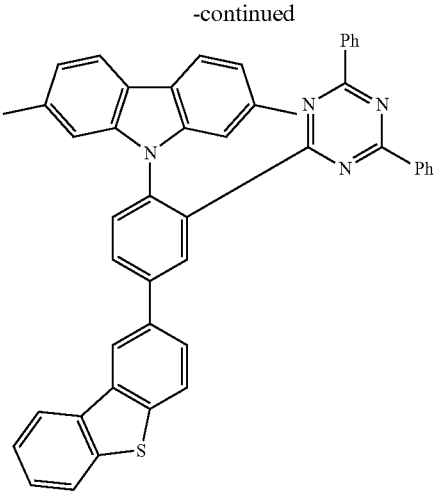
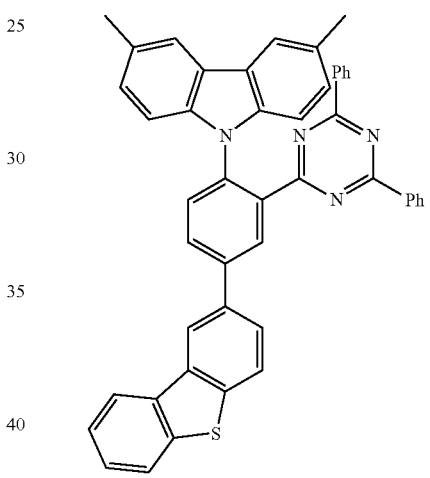
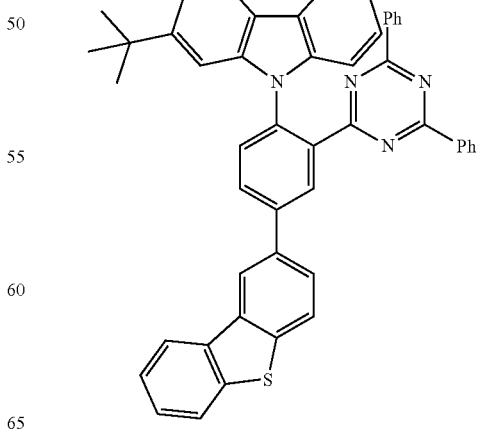

111
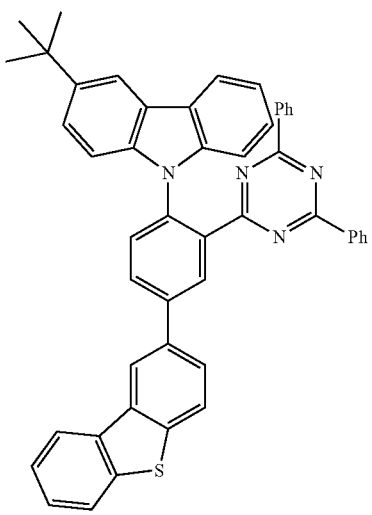
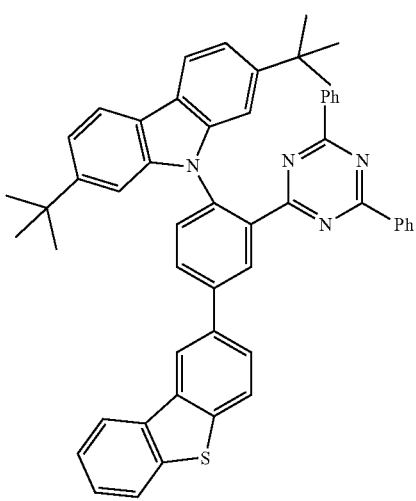
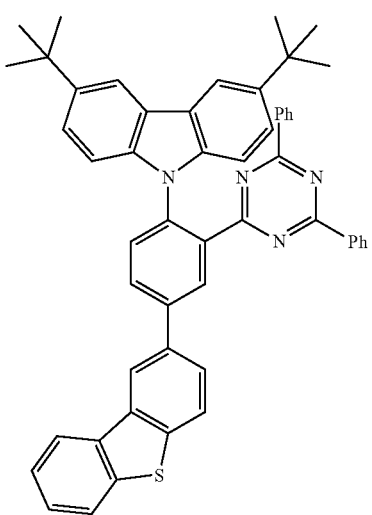
112
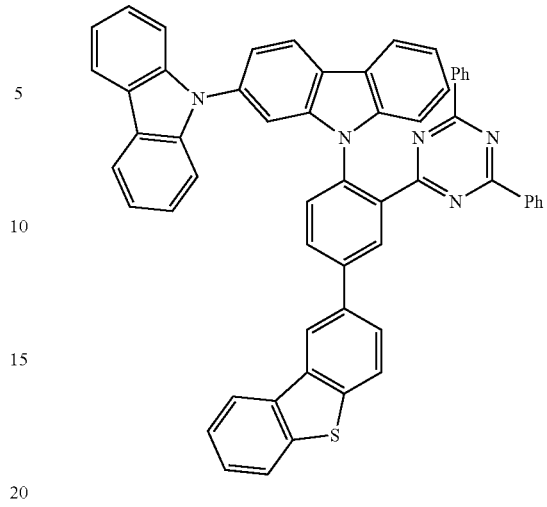
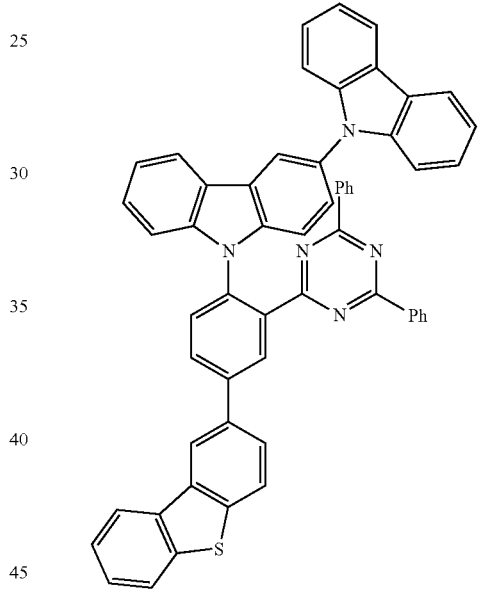
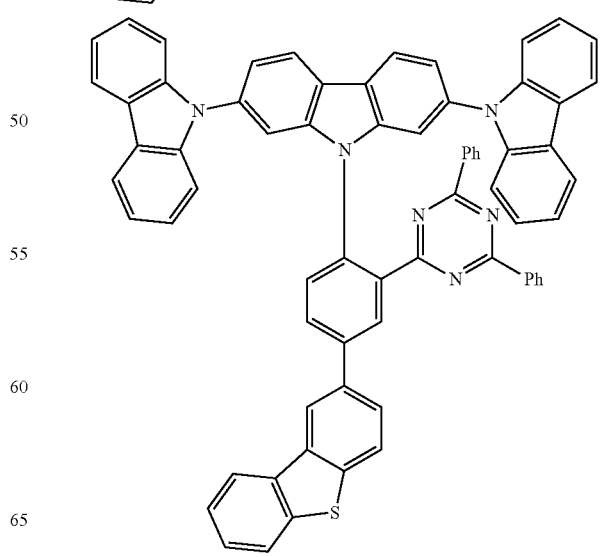

113
-continued
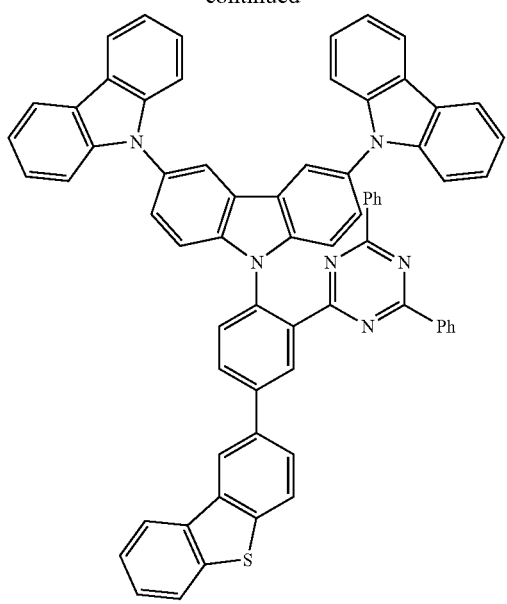
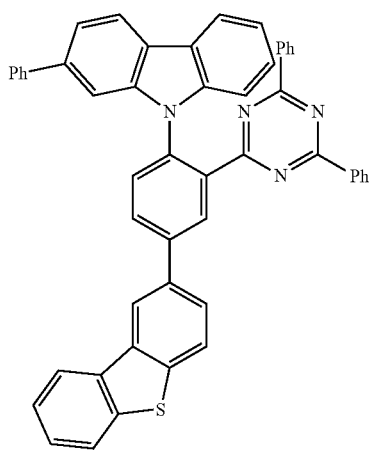
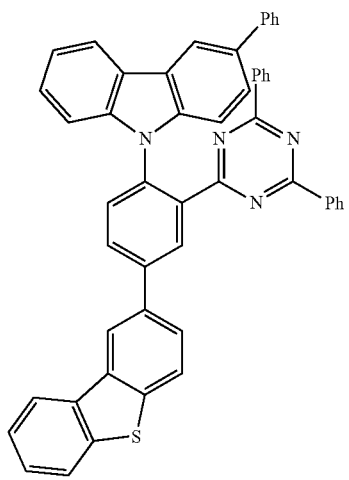
114
-continued
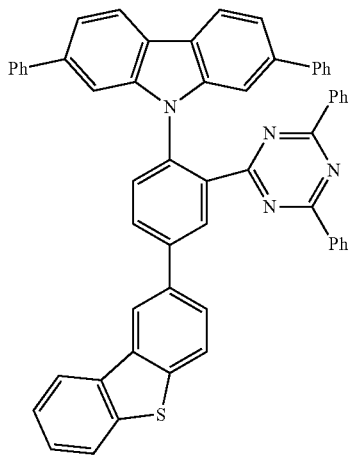
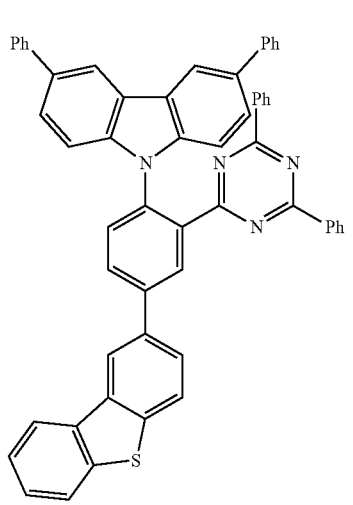
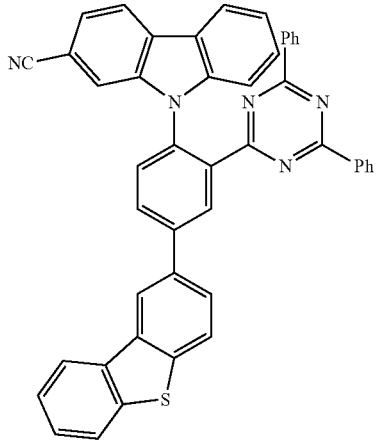

115
-continued
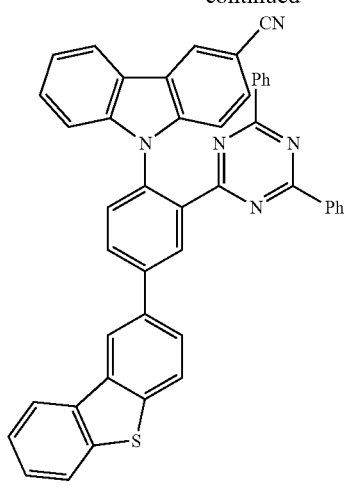
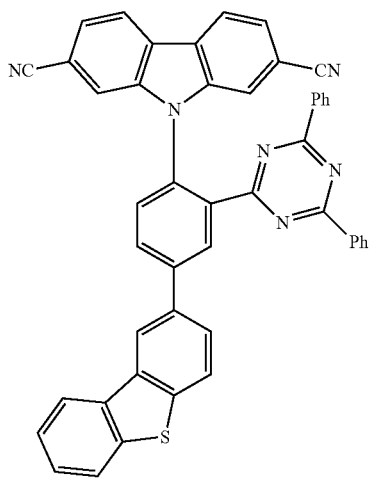
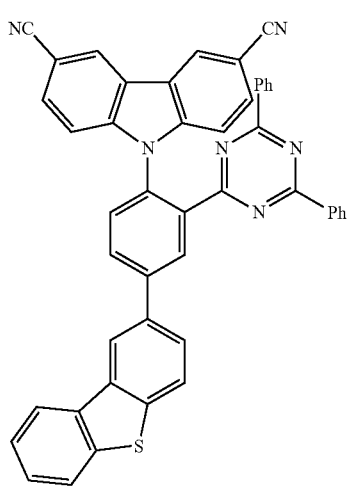
116
-continued
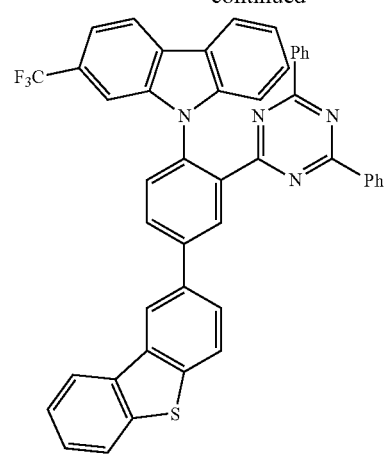
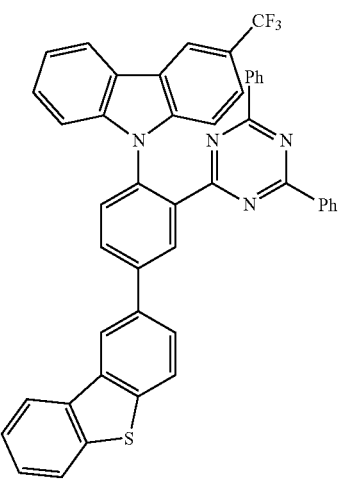
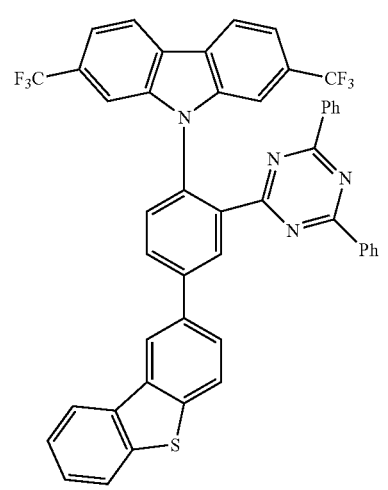

117
-continued
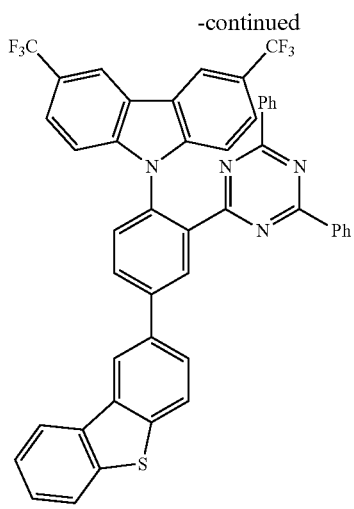
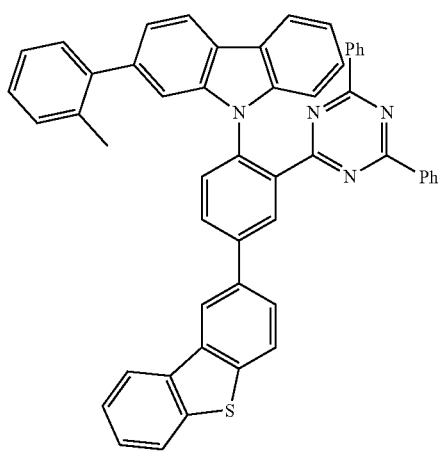
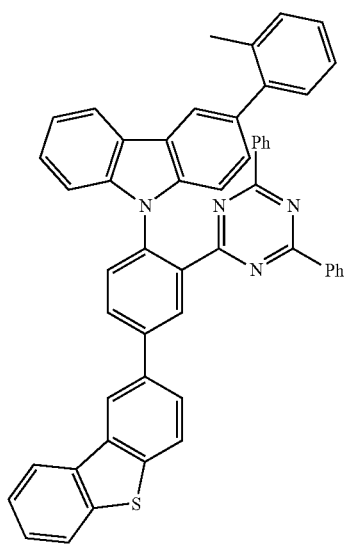
118
-continued
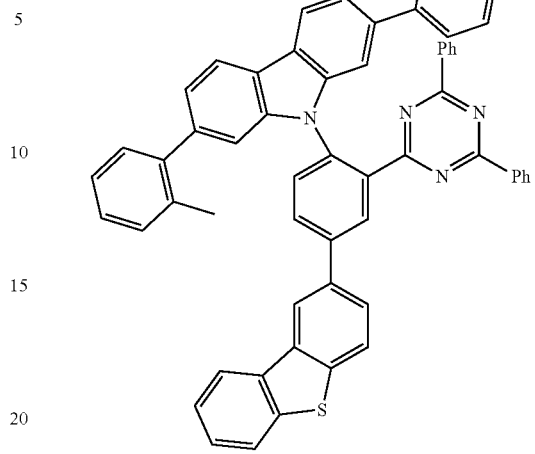
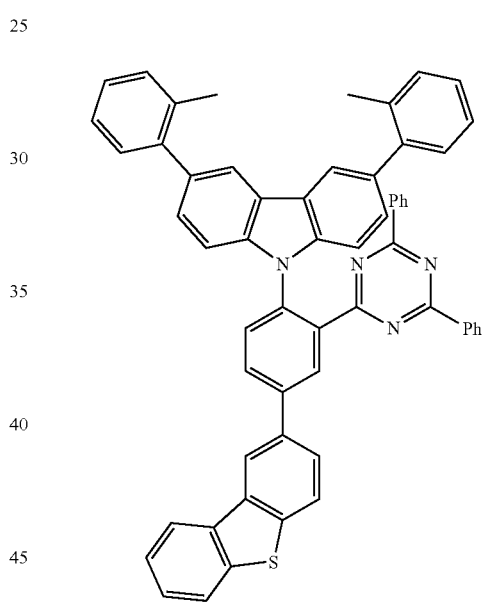
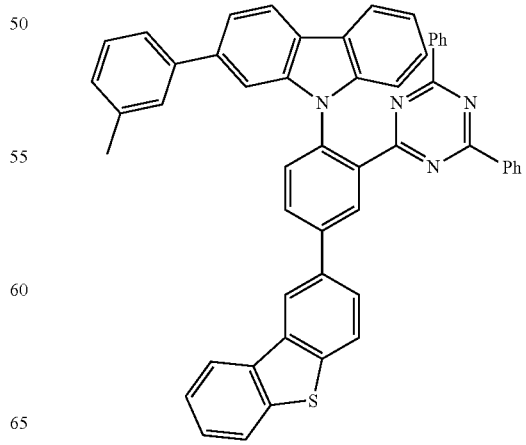

-continued
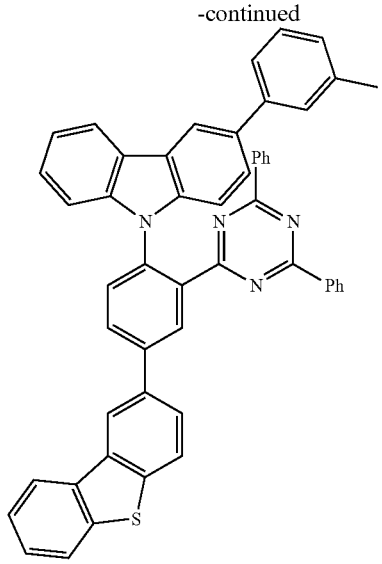
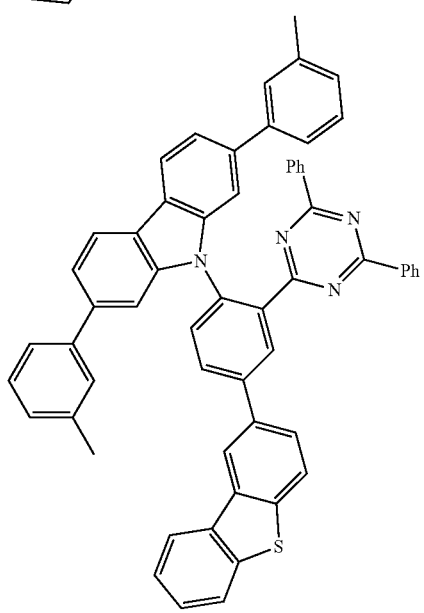
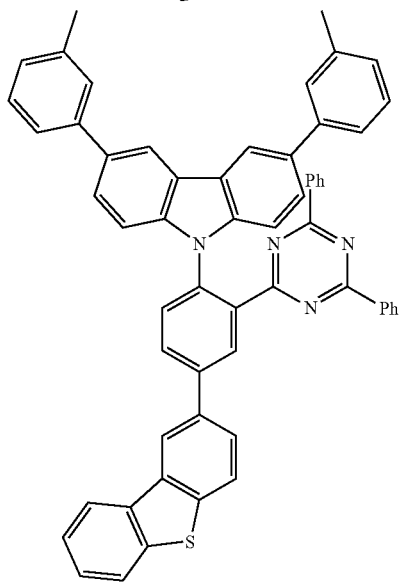
-continued
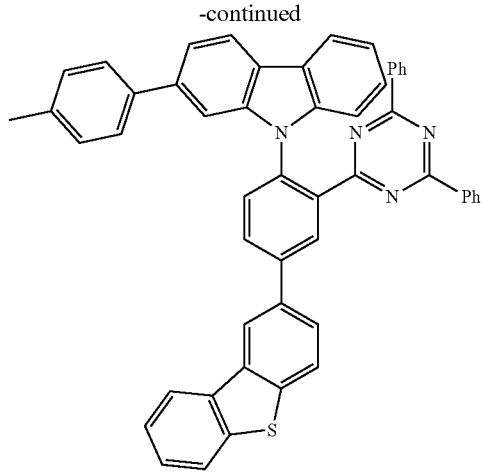
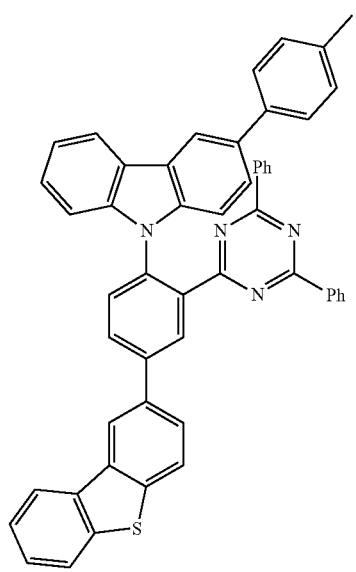
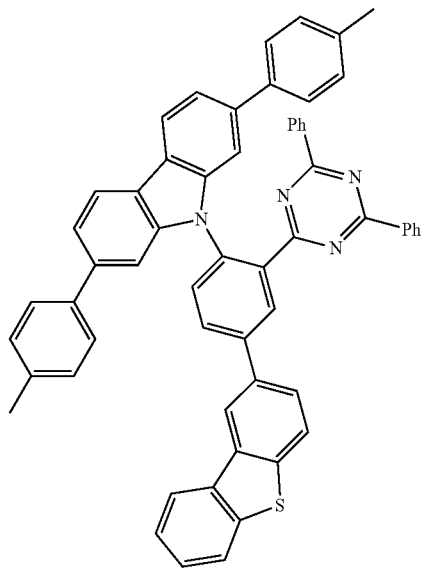

121
-continued
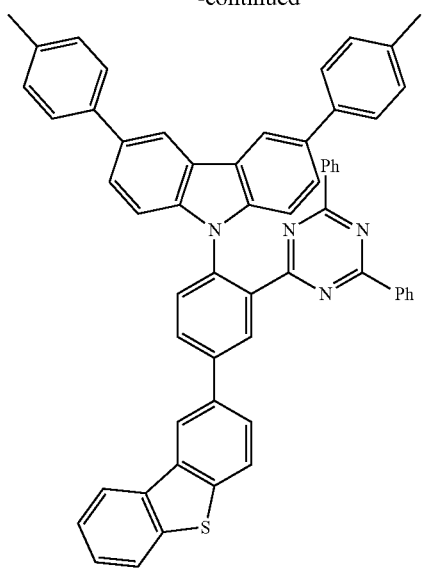
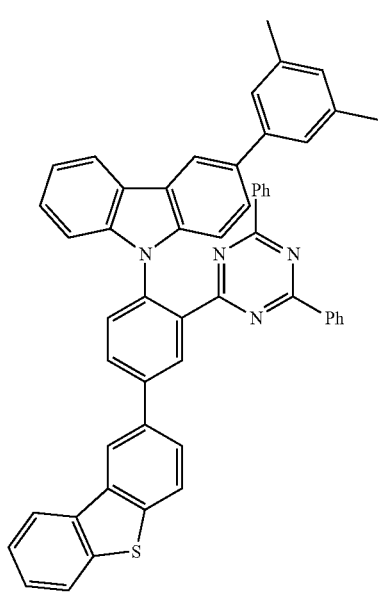
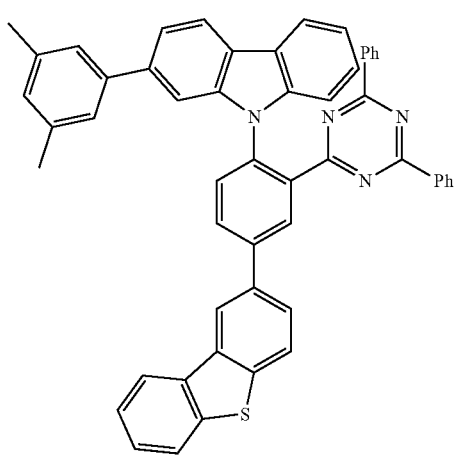
122
-continued
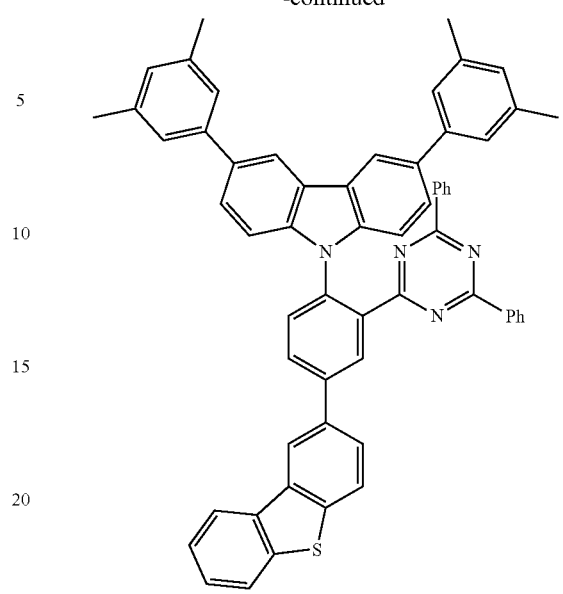
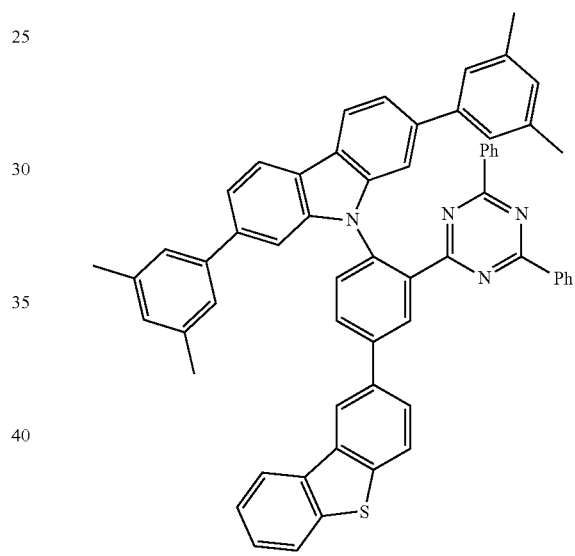
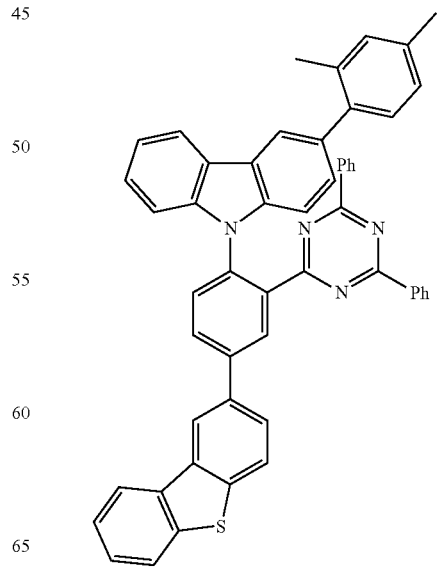

123
-continued
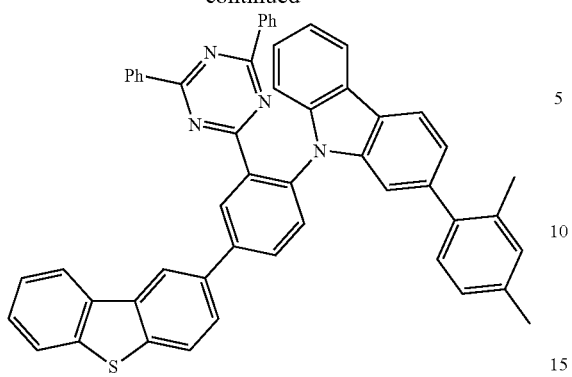
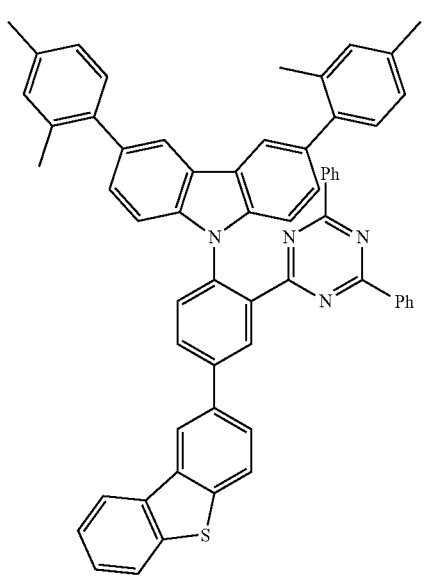
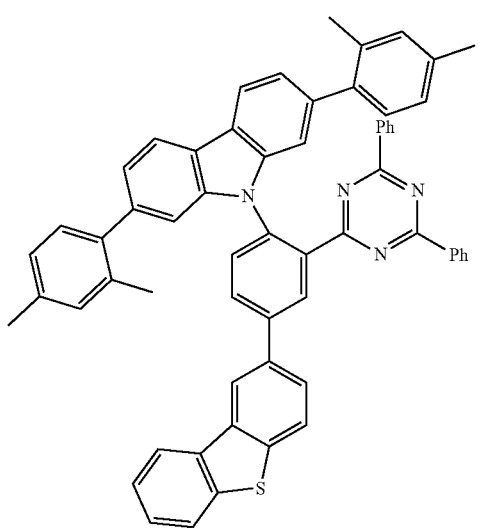
124
-continued
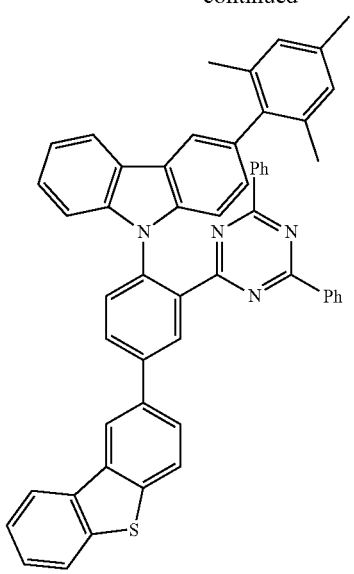
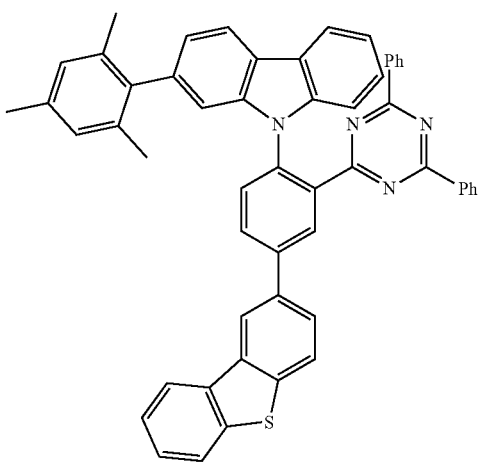
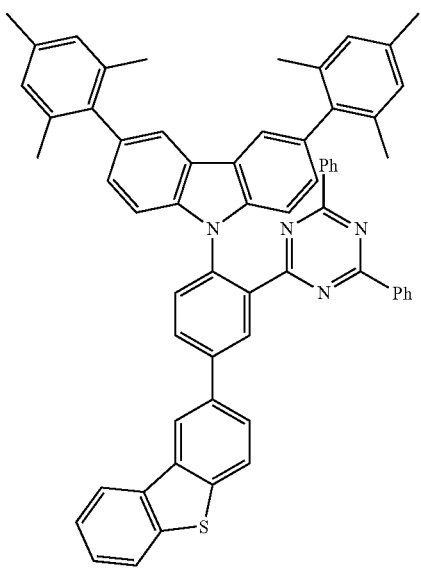

125
-continued
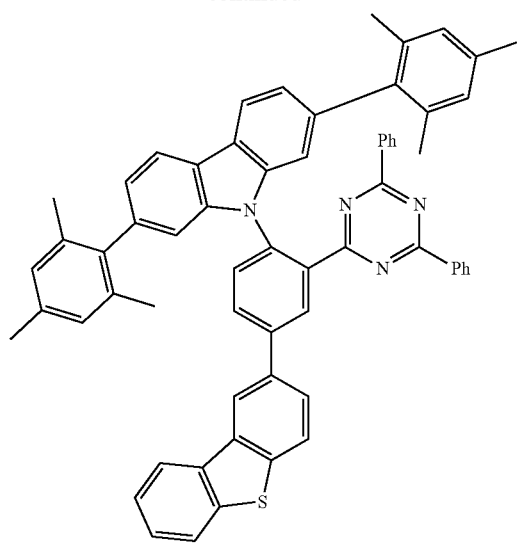
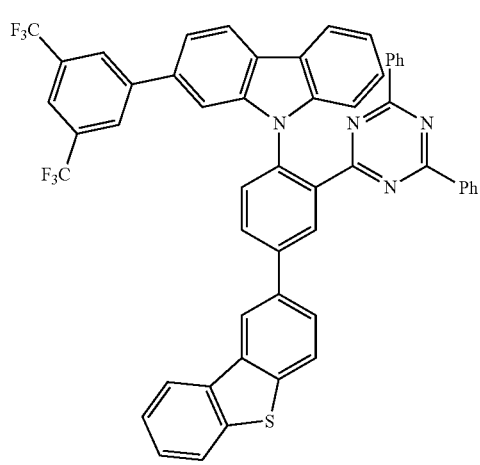
126
-continued
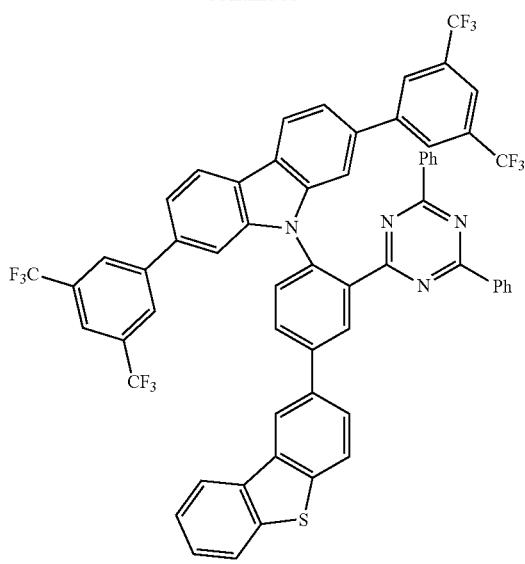
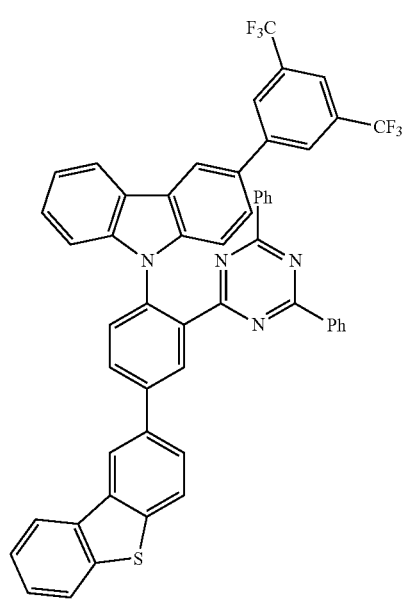

127
-continued
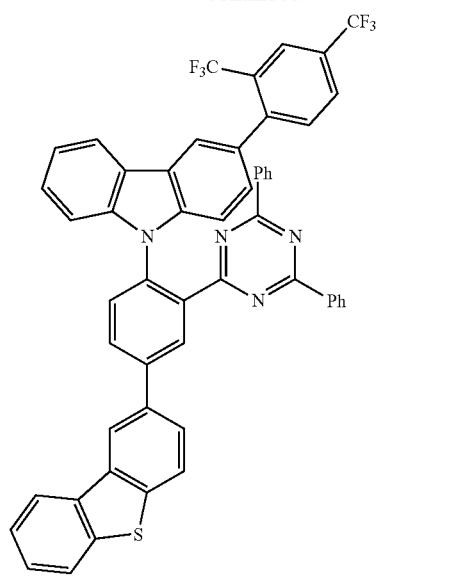
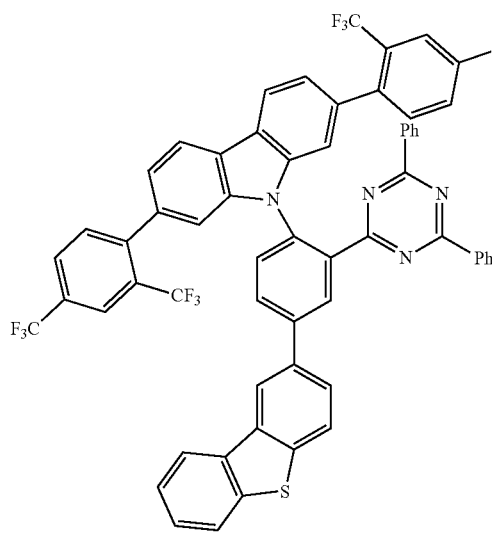
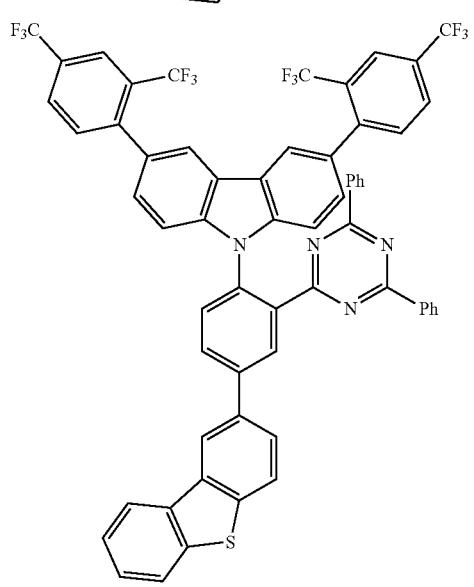
128
-continued
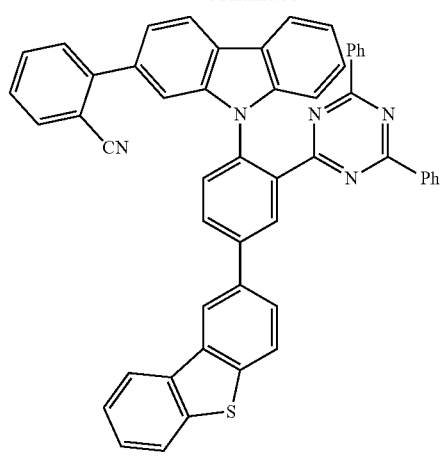
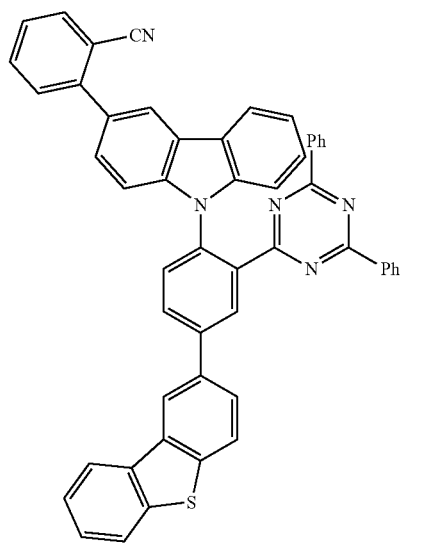
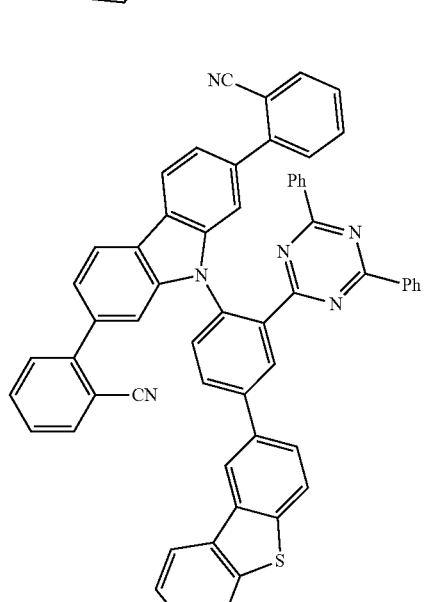

129
-continued
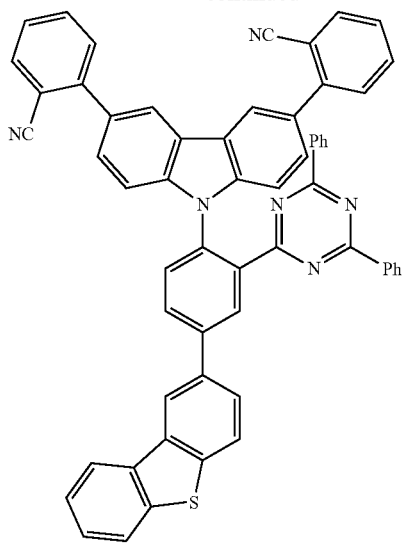
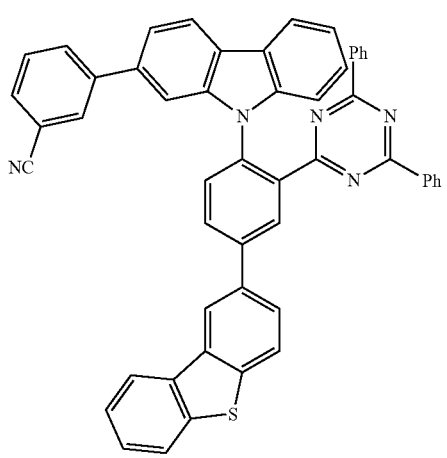
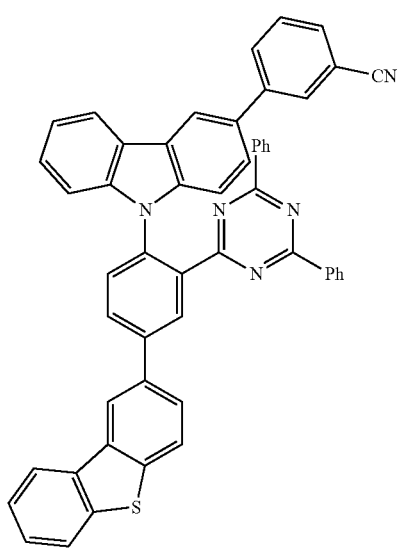
130
-continued
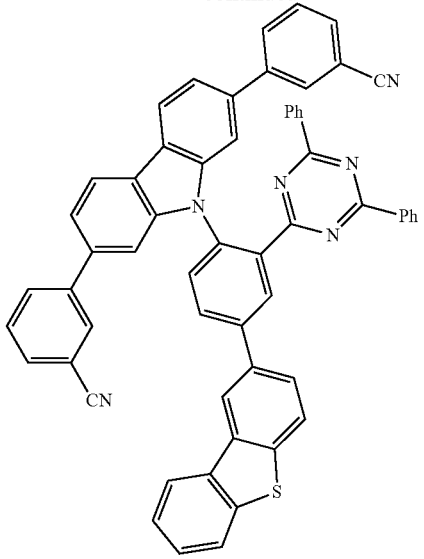
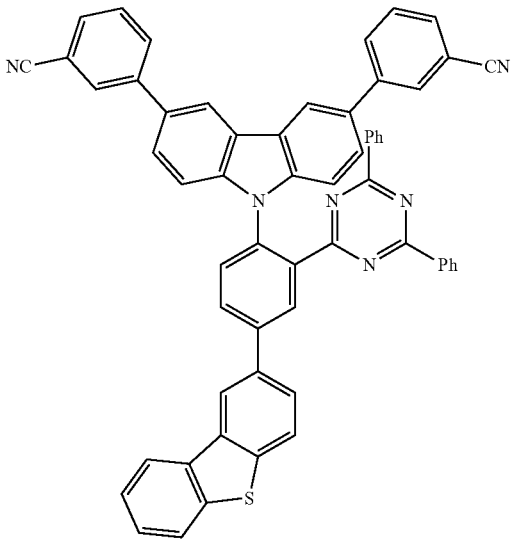
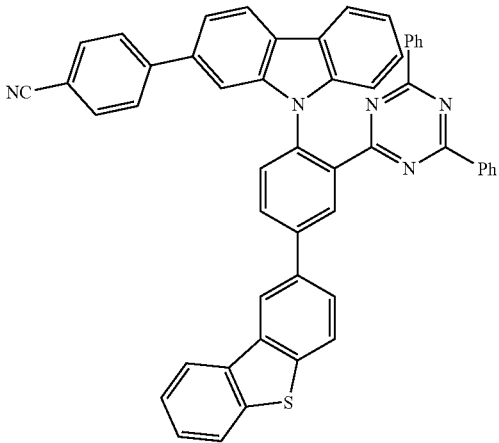

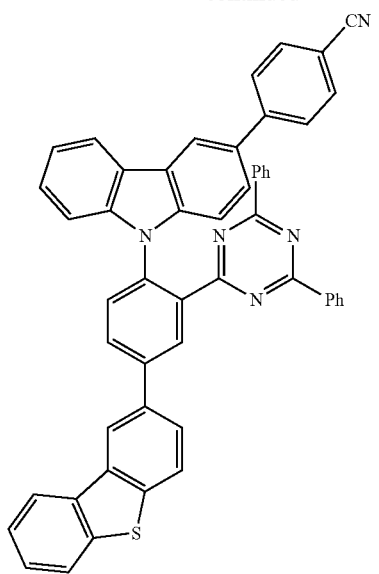
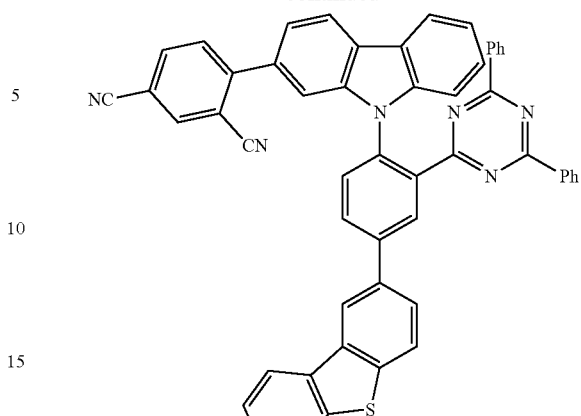
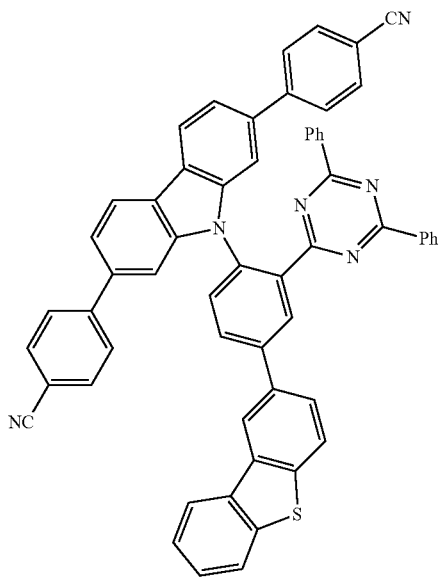
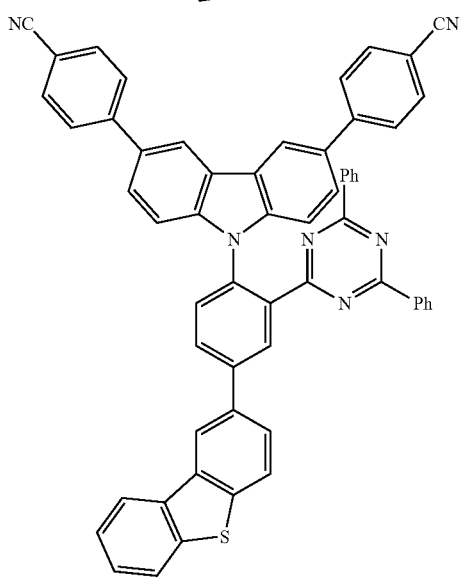
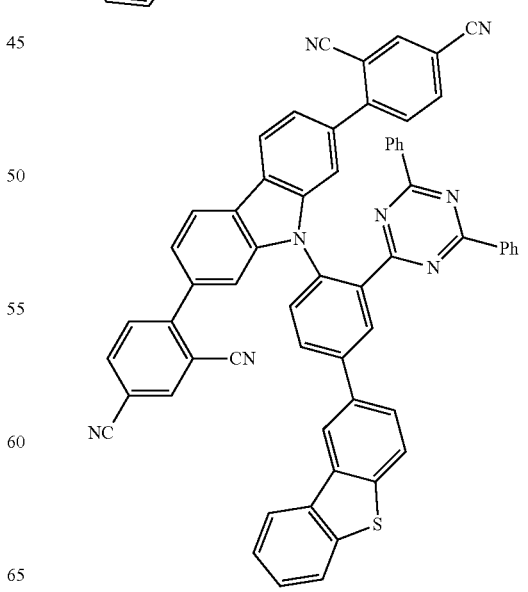

133
-continued
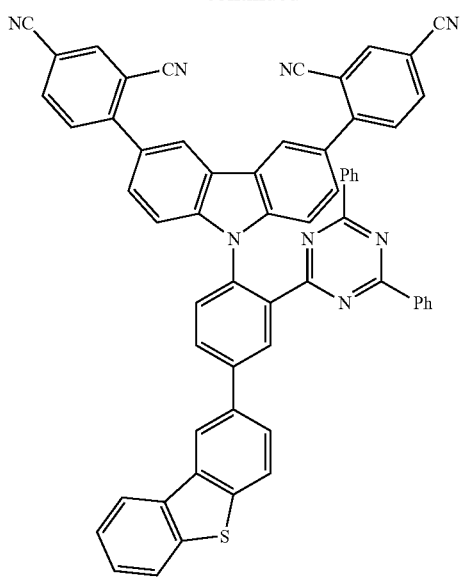
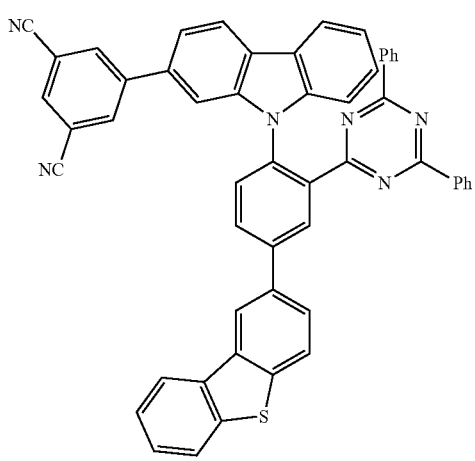
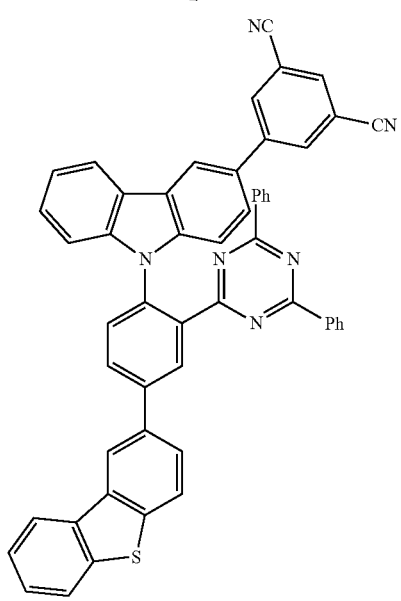
134
-continued
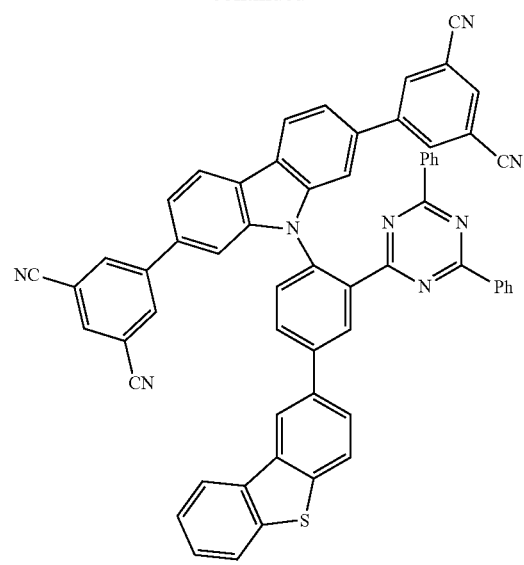
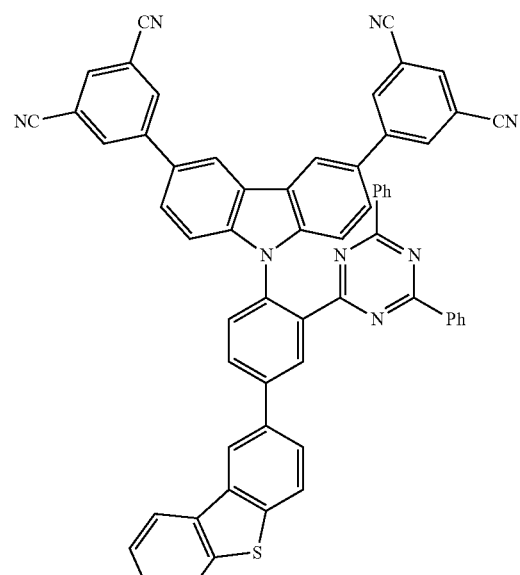
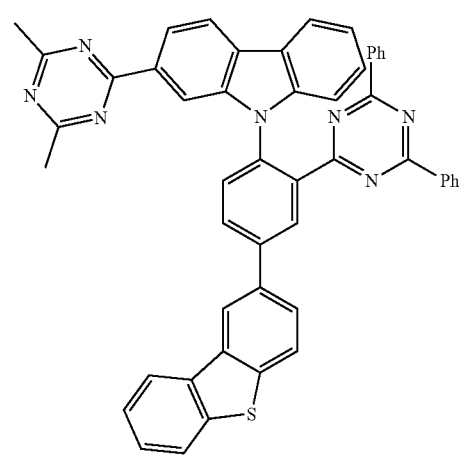

135
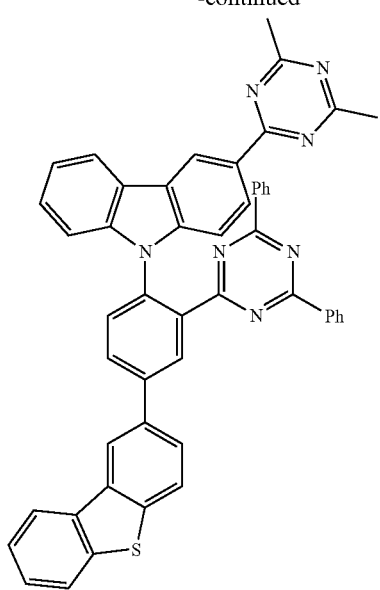
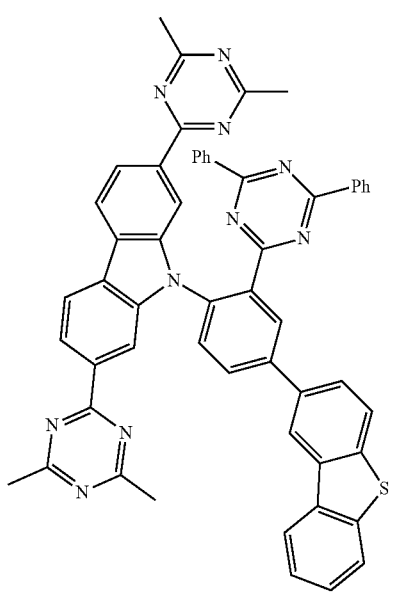
136
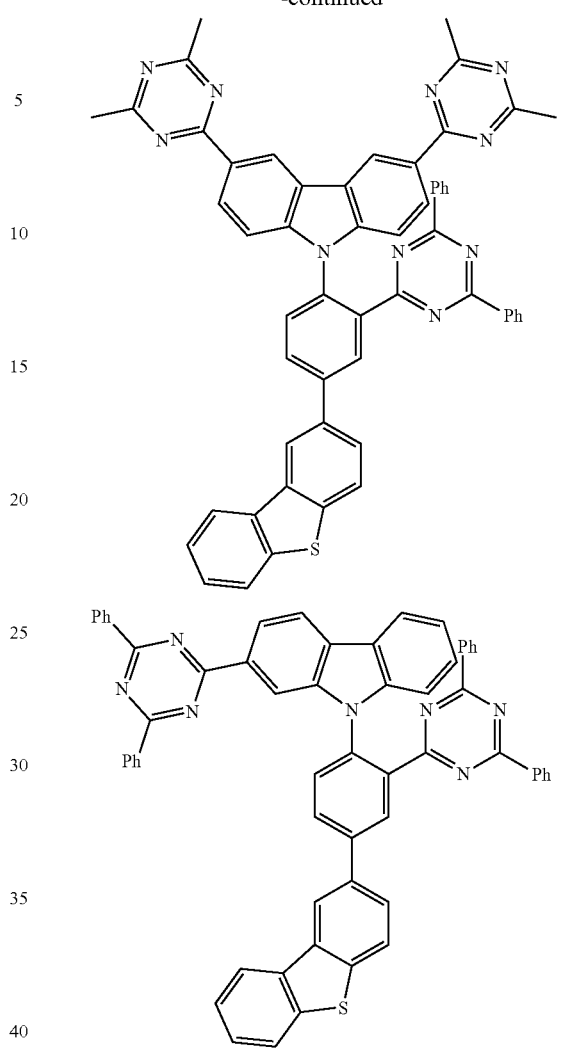

137
-continued
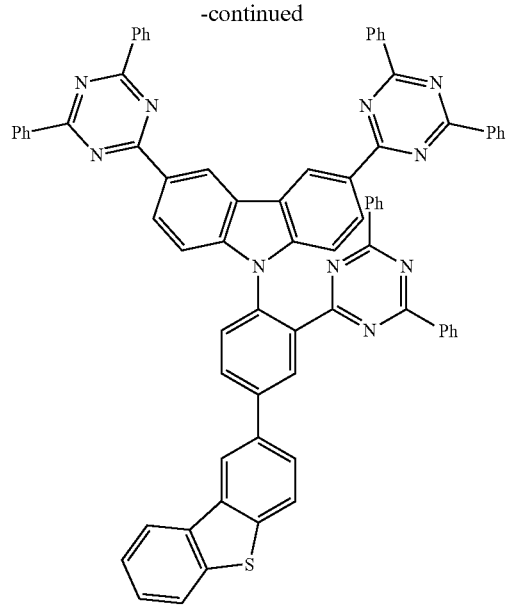
138
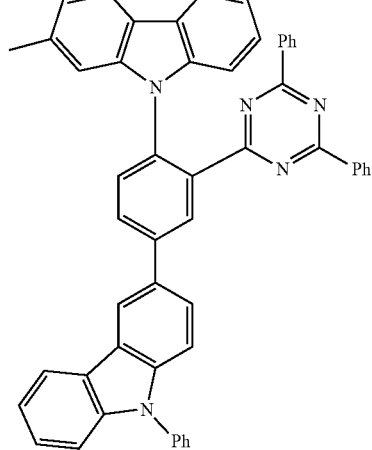
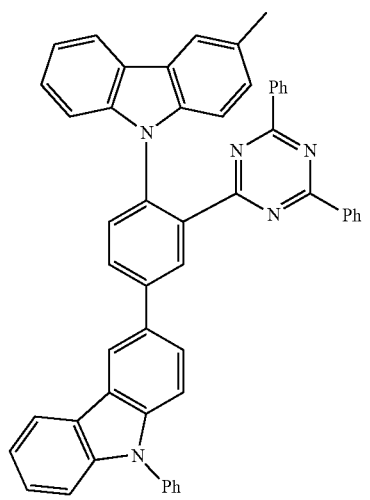
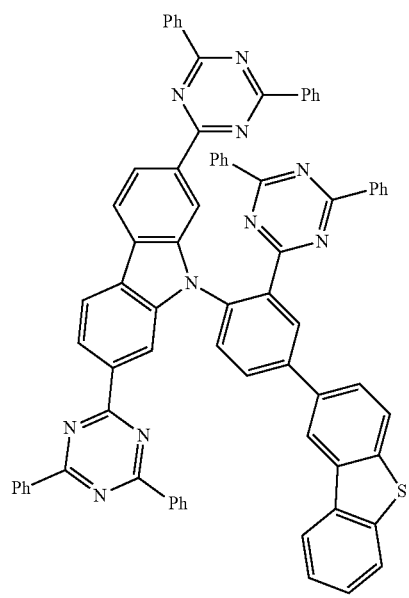
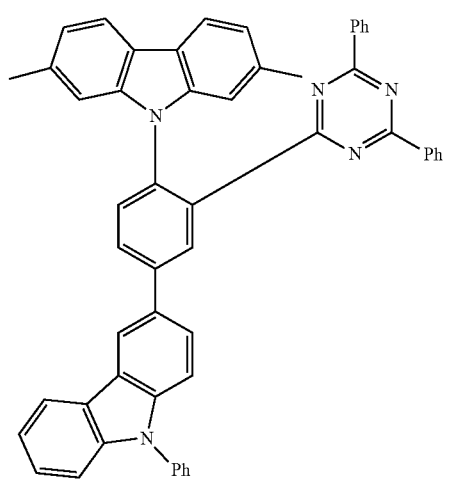

139
-continued
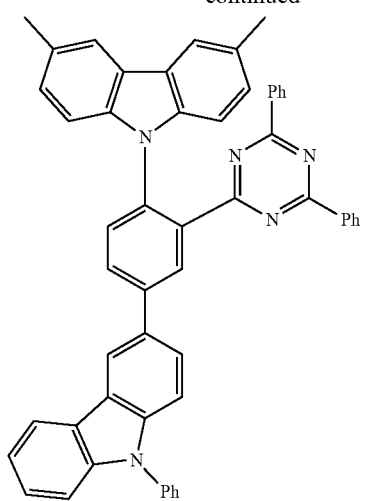
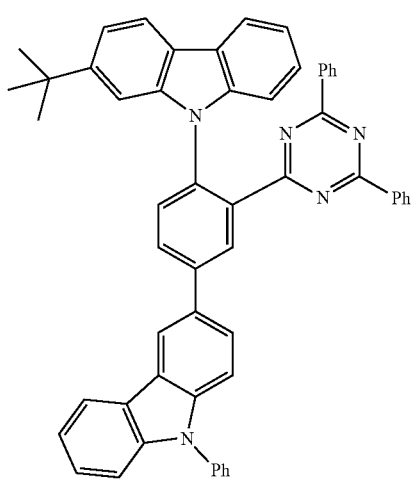
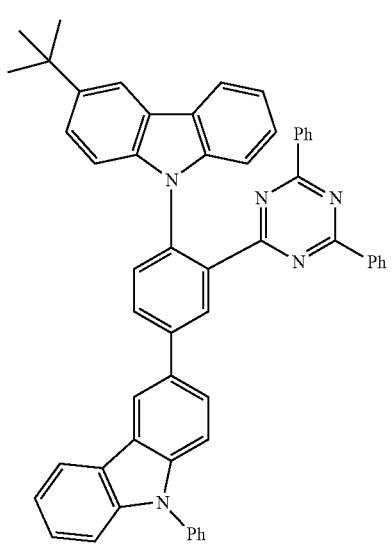
140
-continued
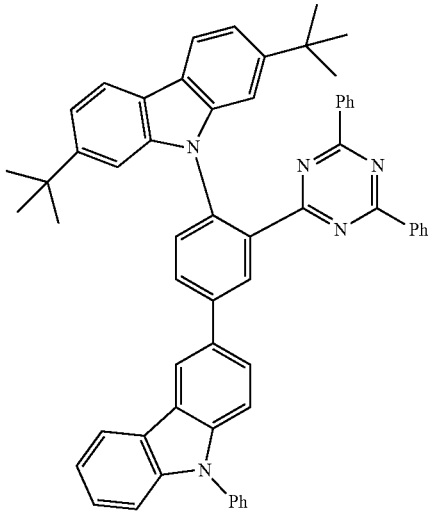
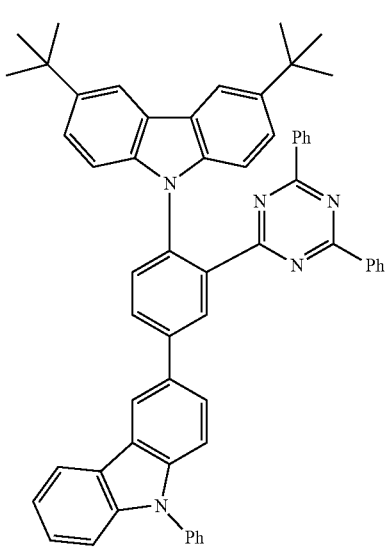
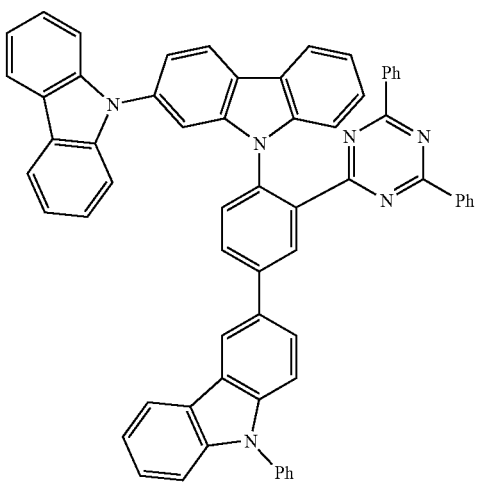

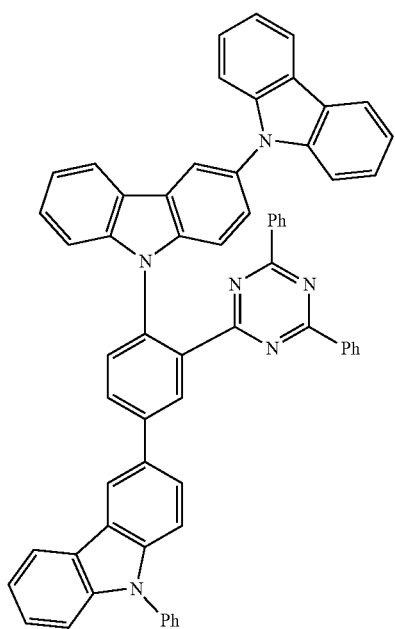
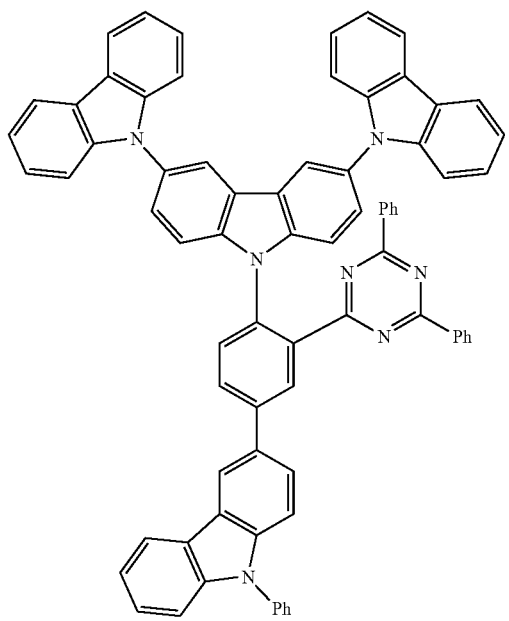
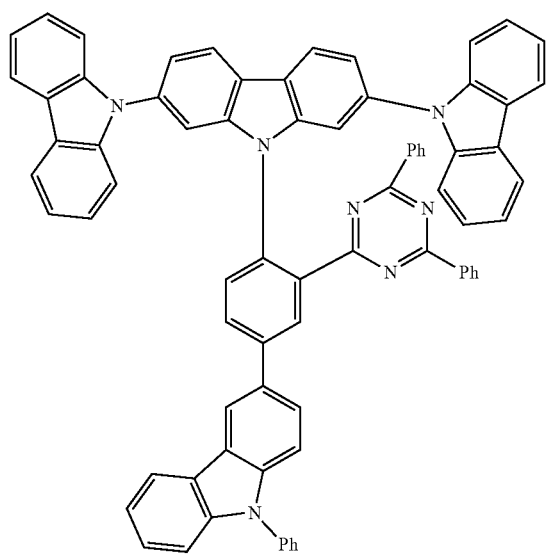
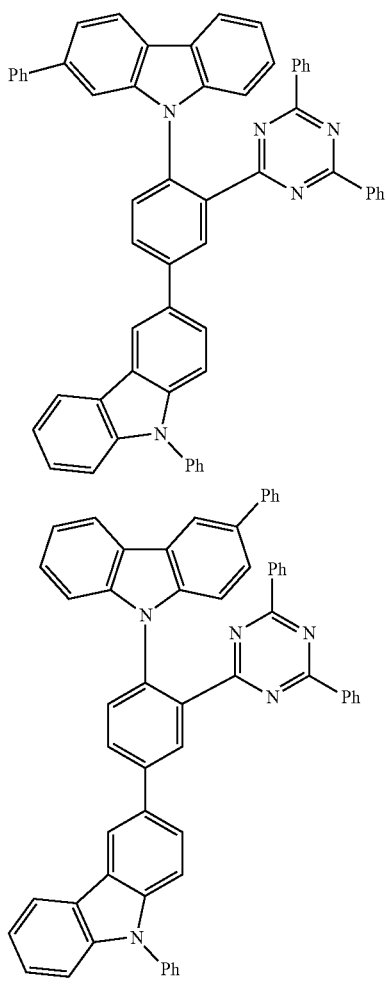

143
-continued
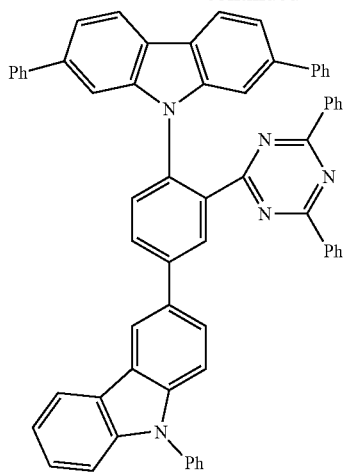
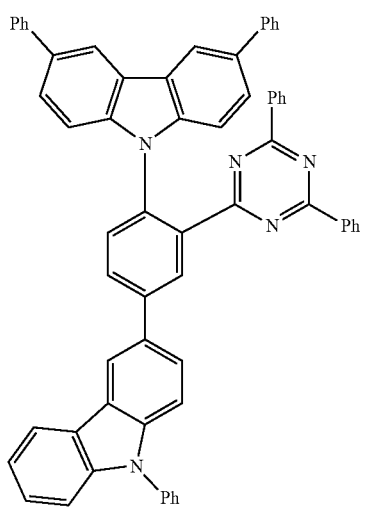
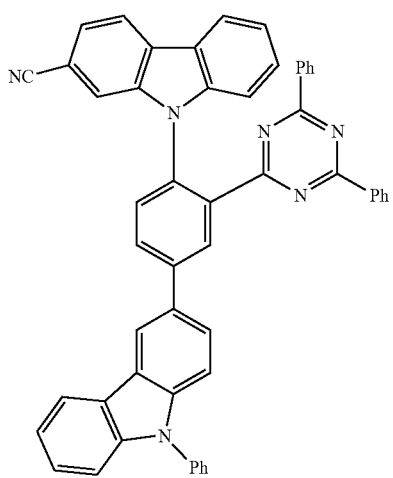
144
-continued
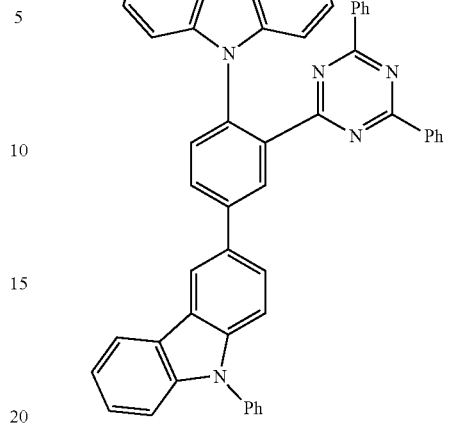
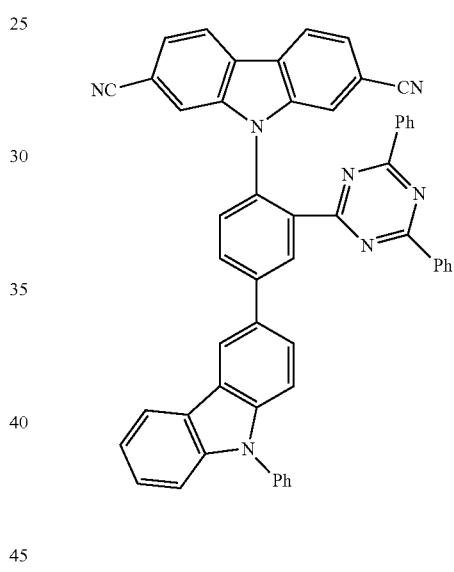
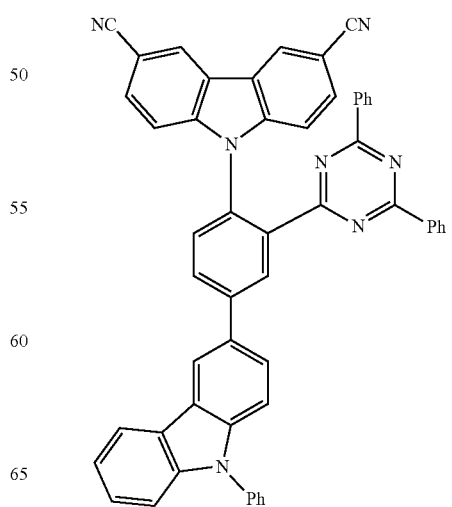

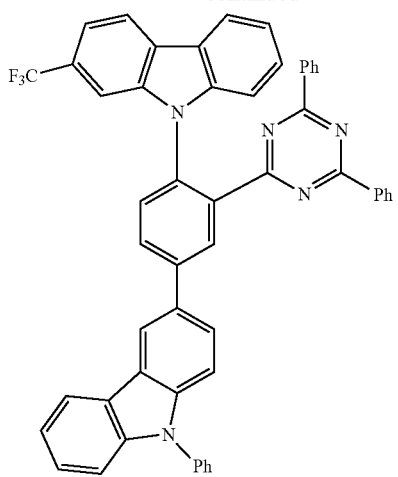
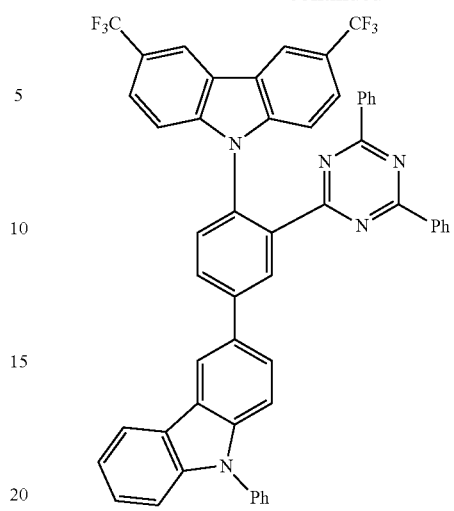
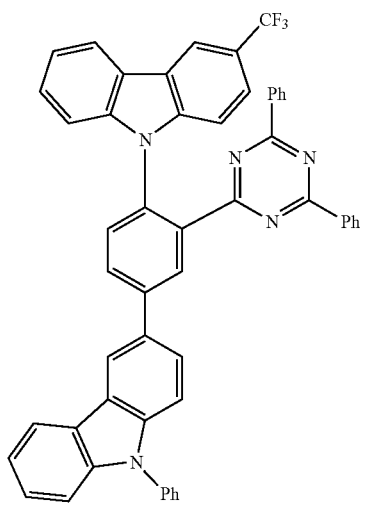
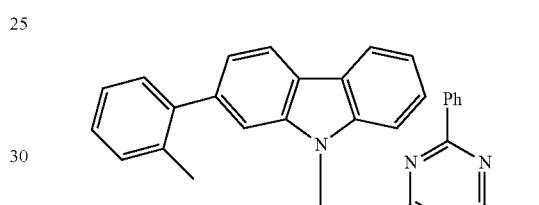
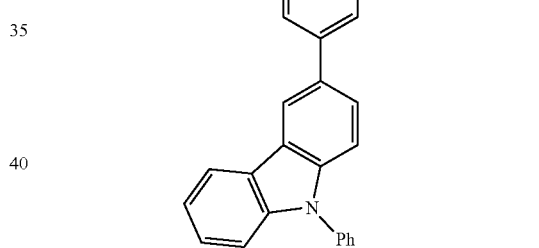
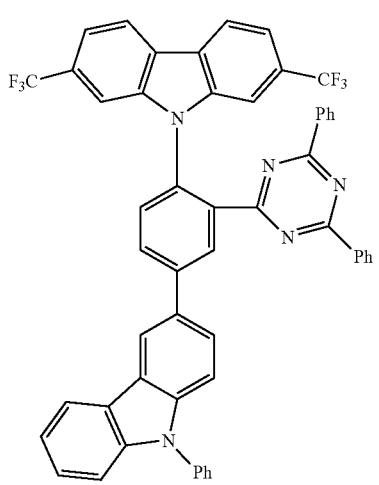
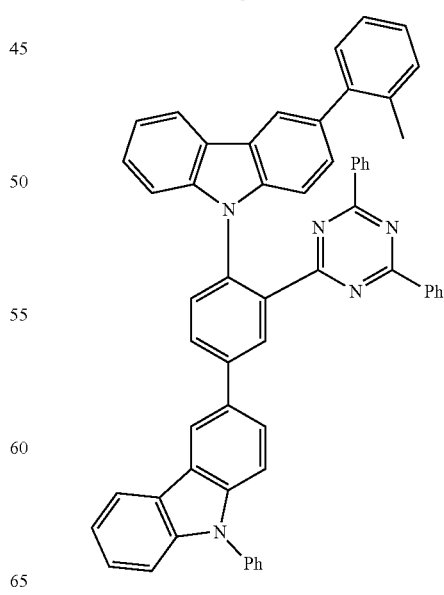

147
-continued
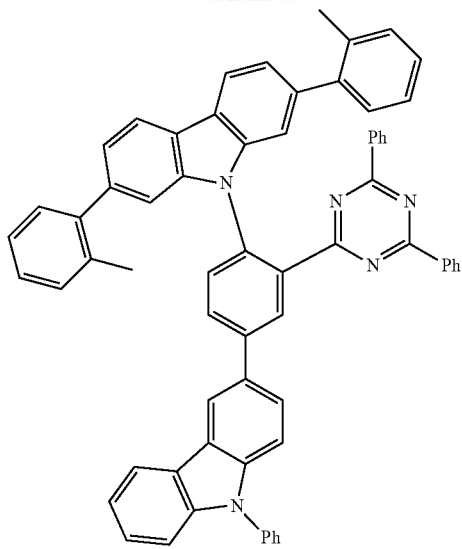
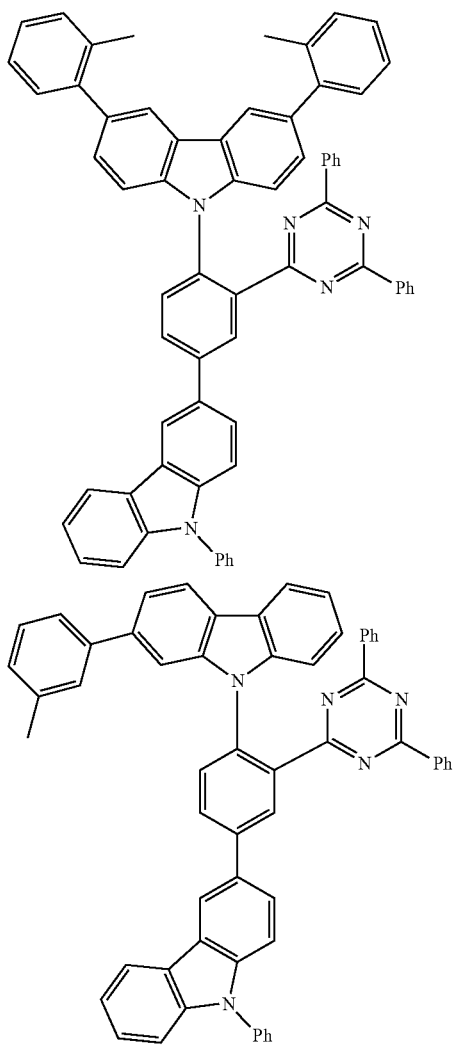
148
-continued
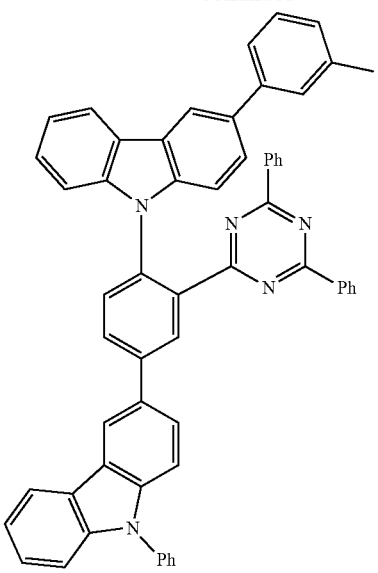
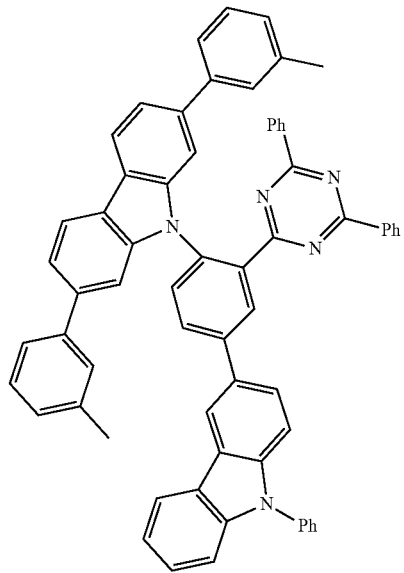

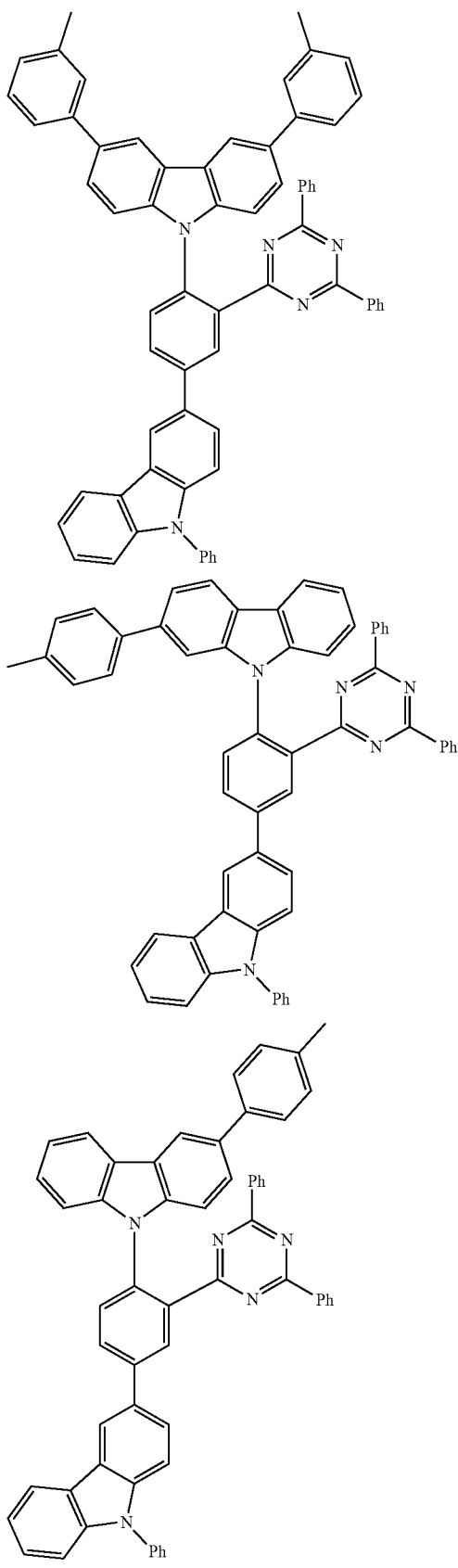

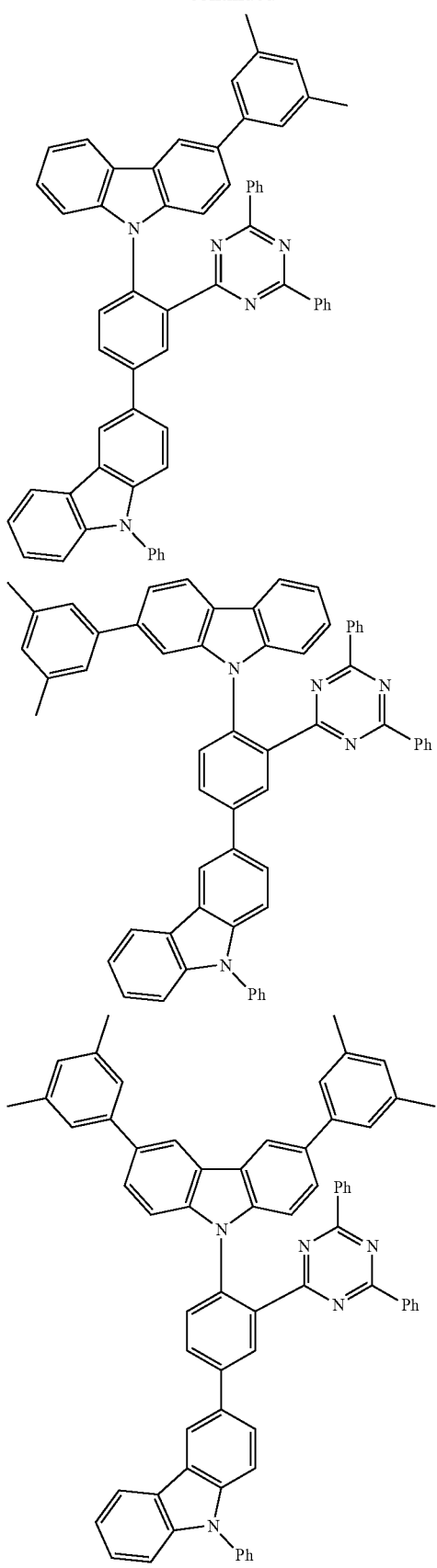
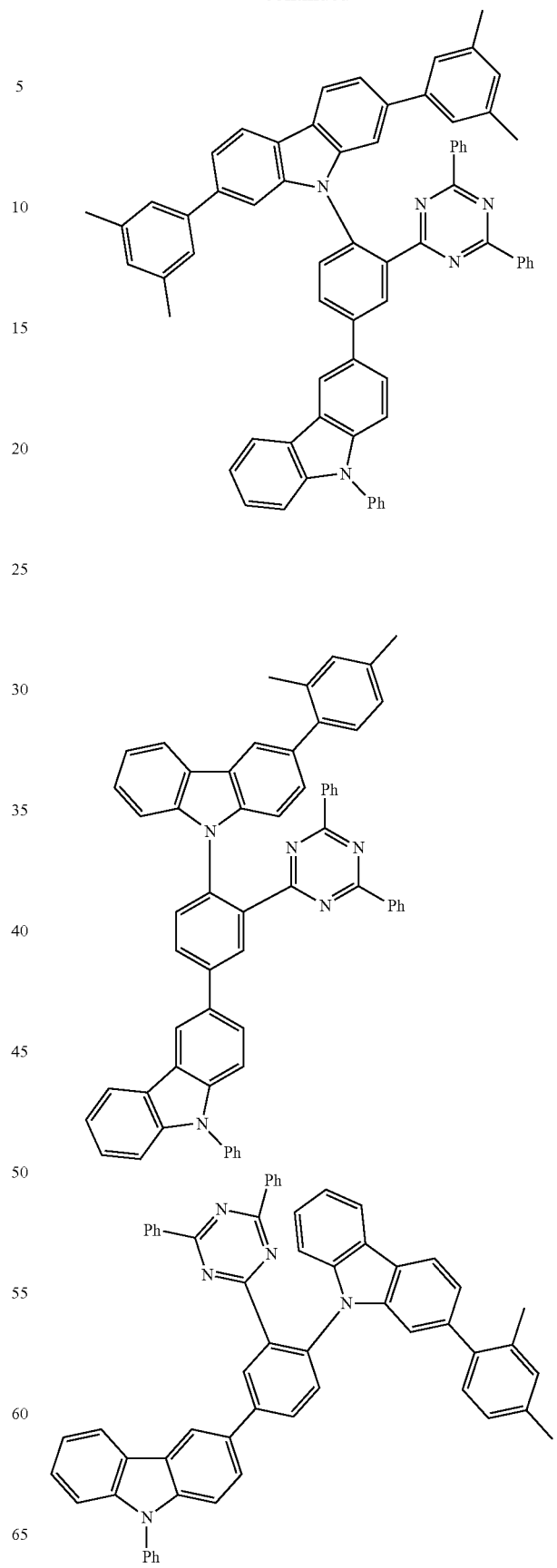

153
-continued
154
-continued
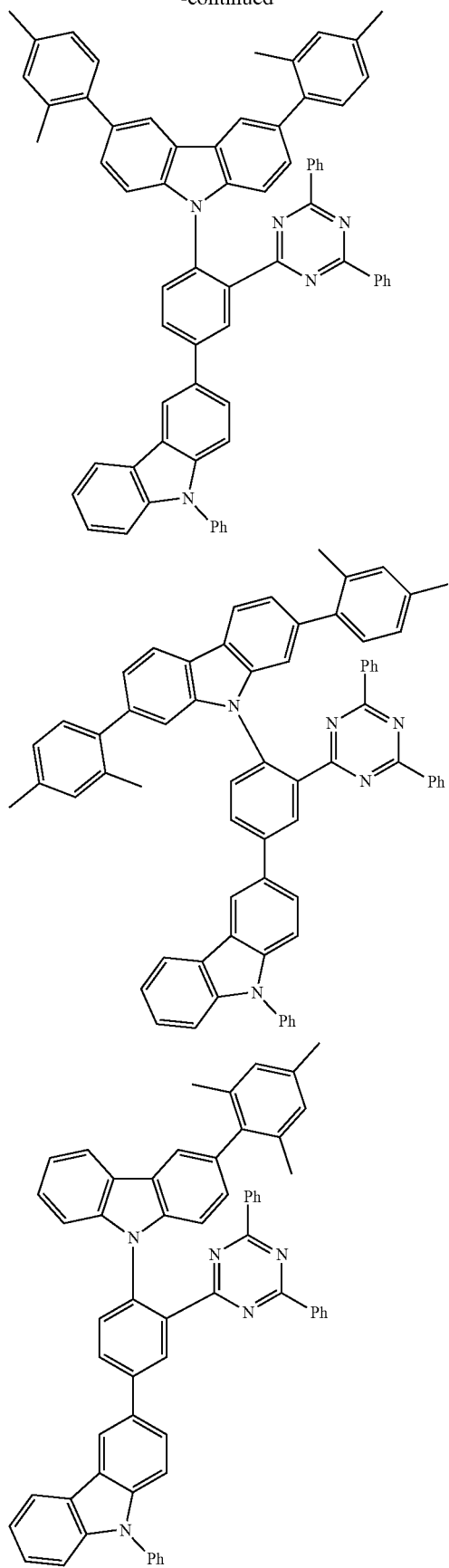
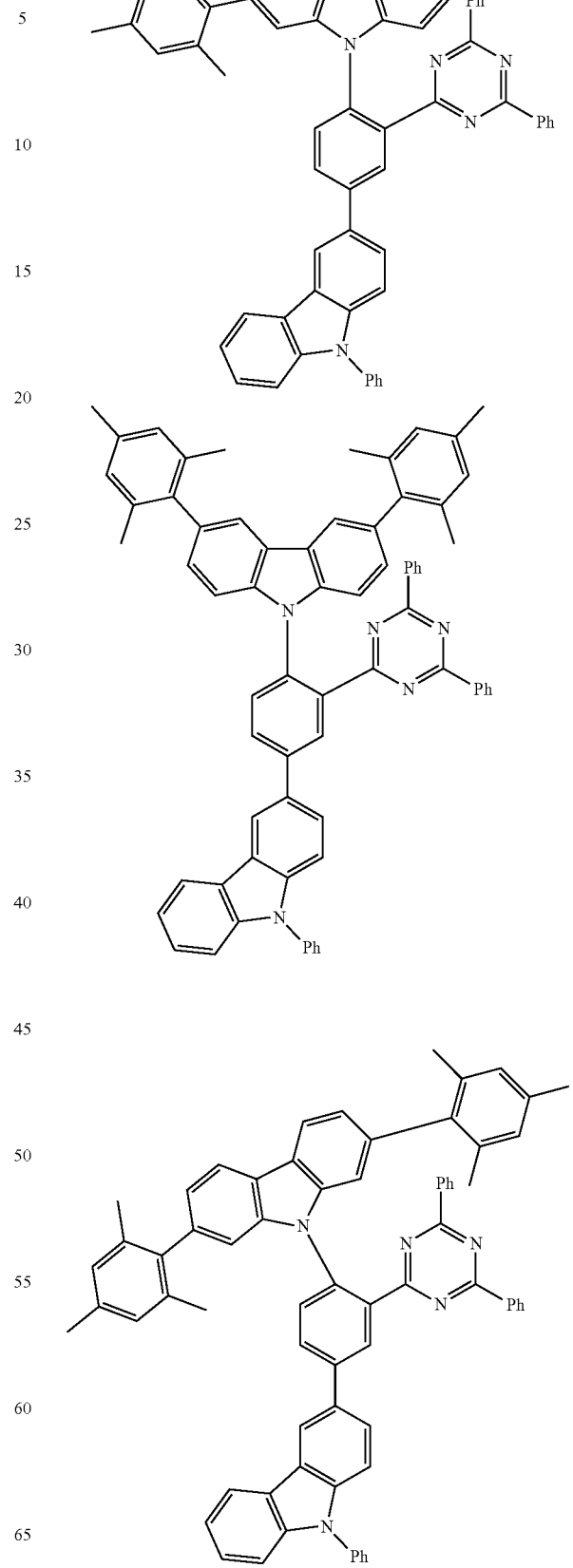

155
-continued
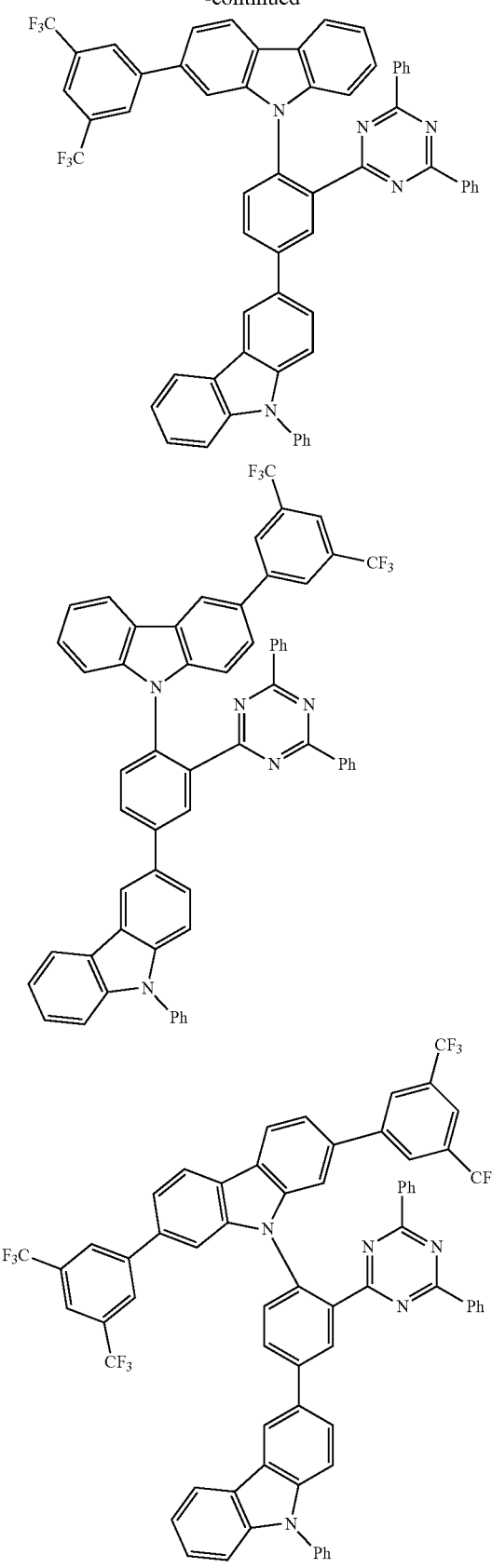
156
-continued
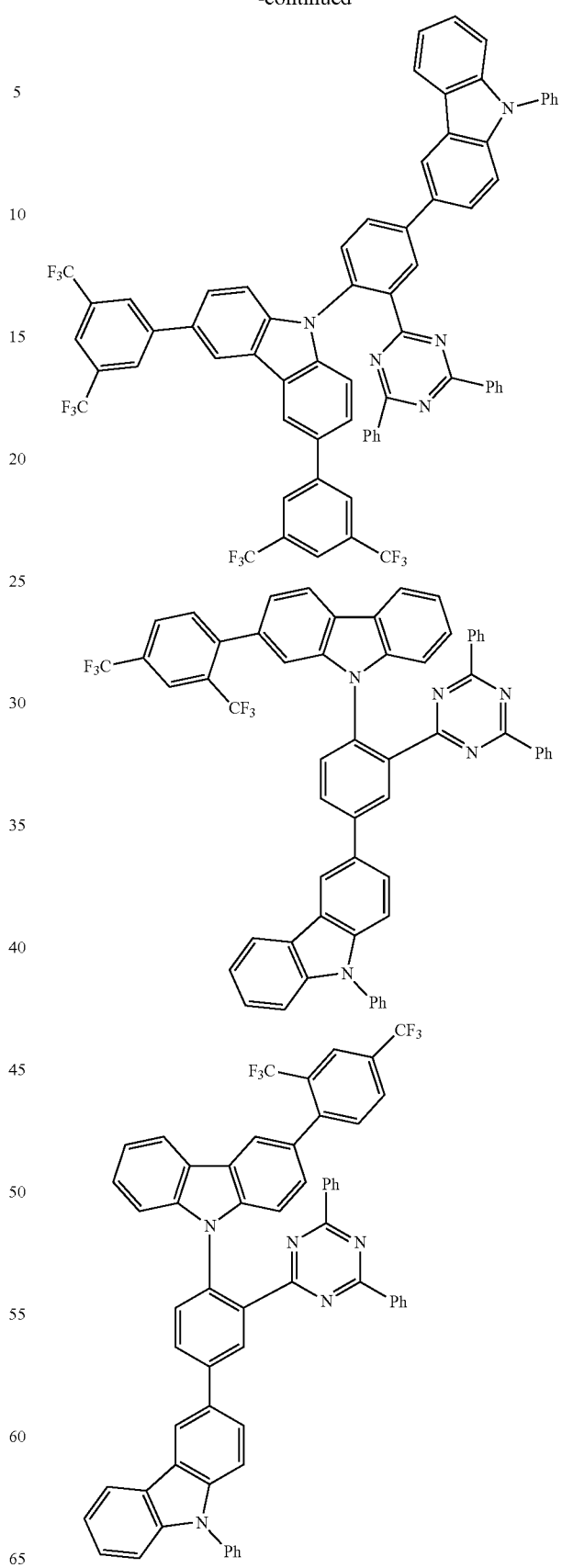

157
-continued
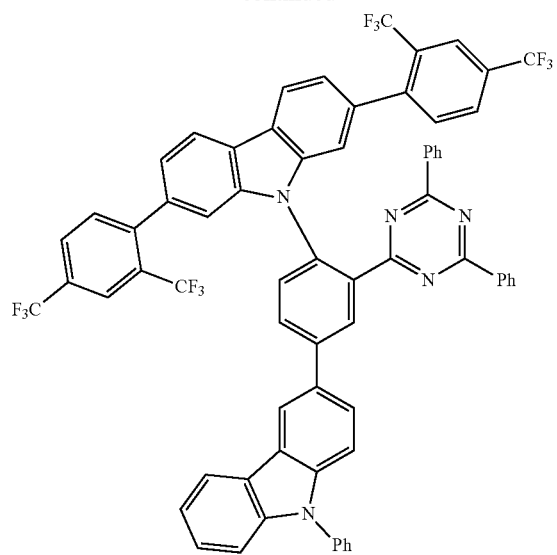
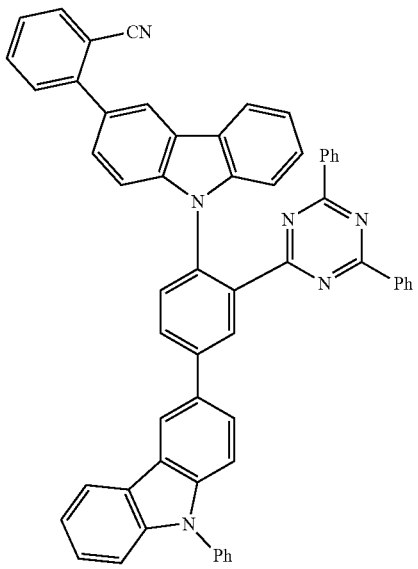
158
-continued
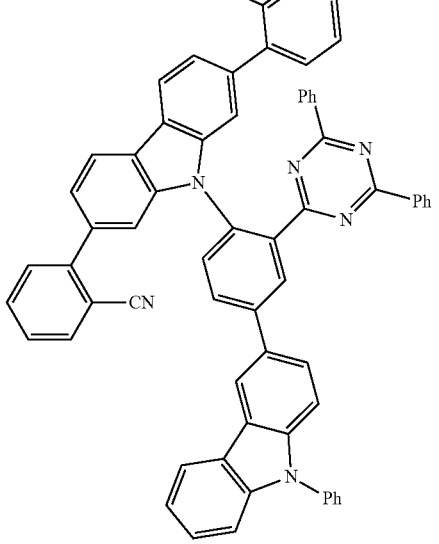
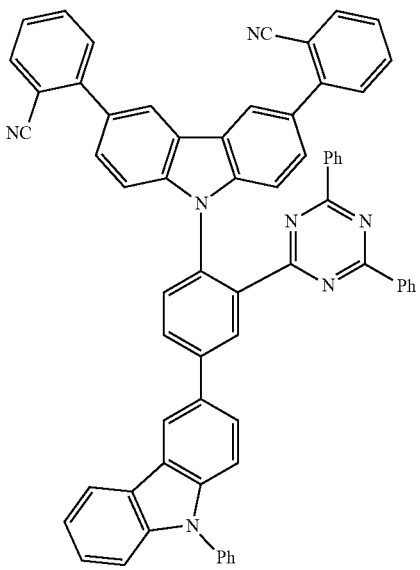

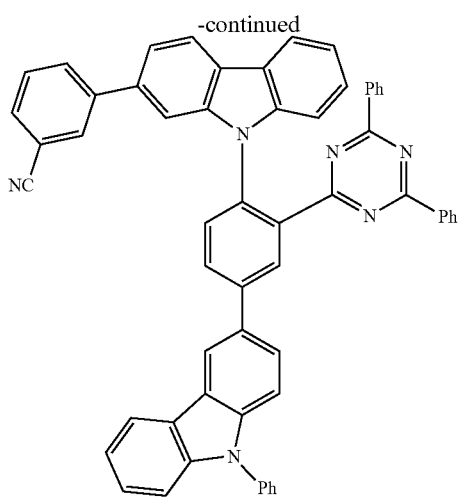
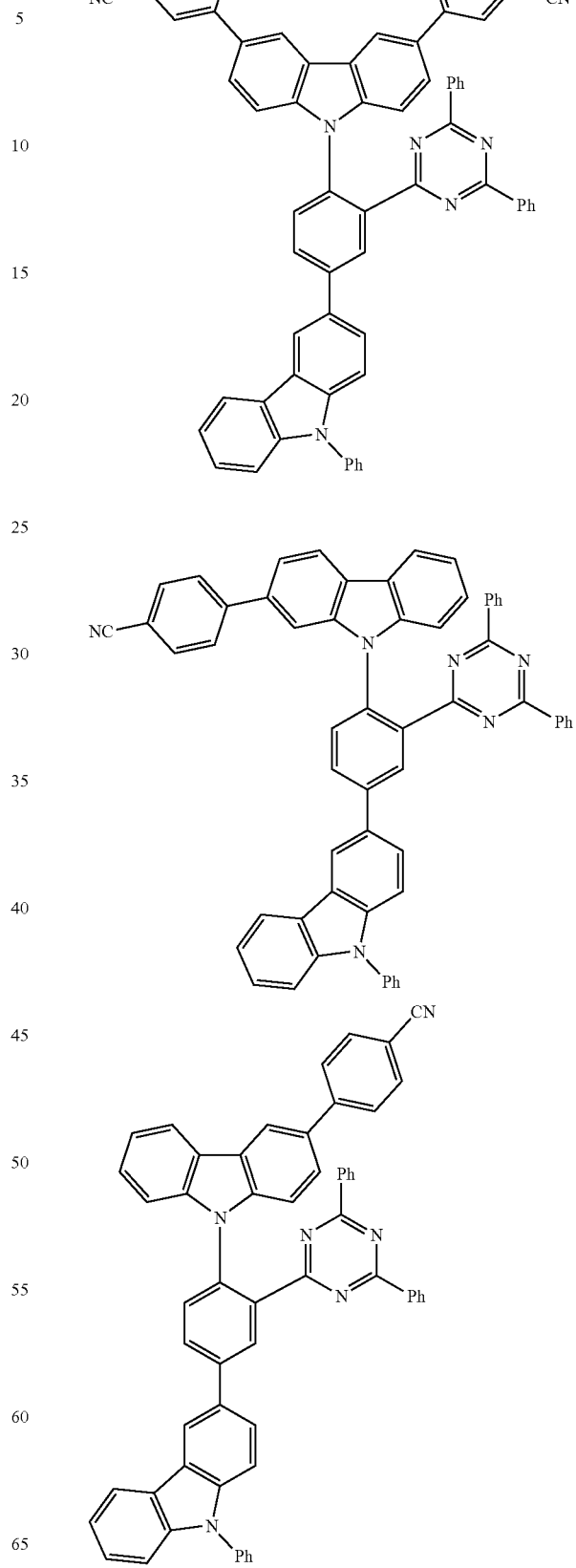

161
-continued
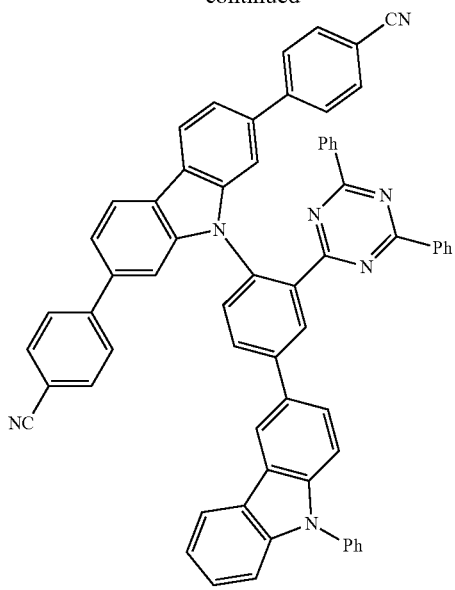
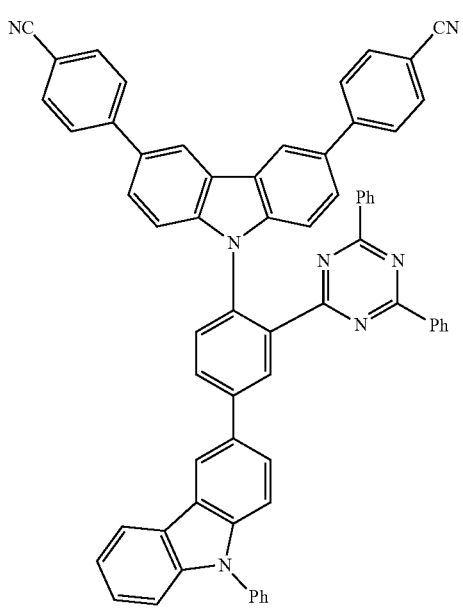
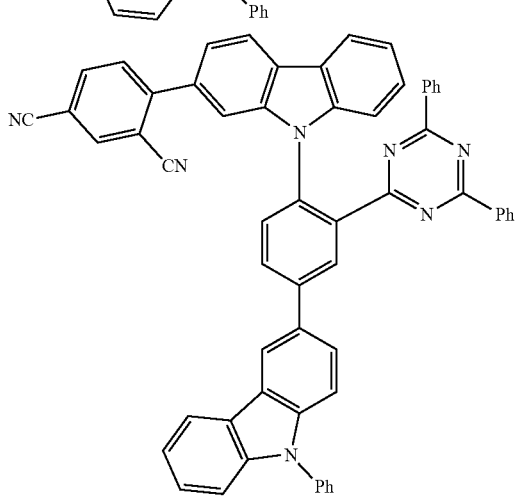
162
-continued
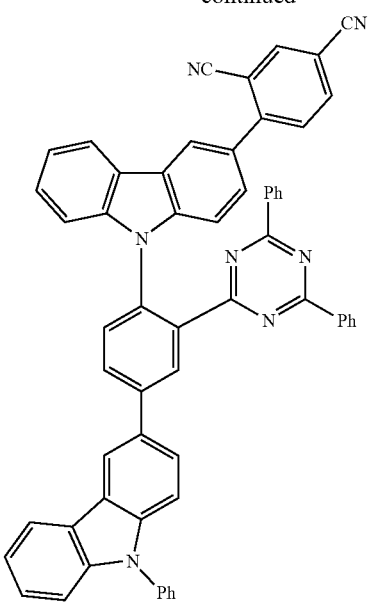
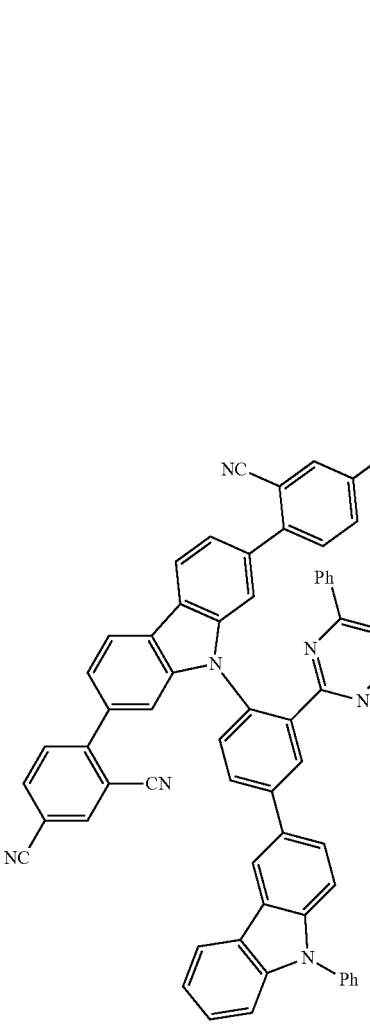

163
-continued
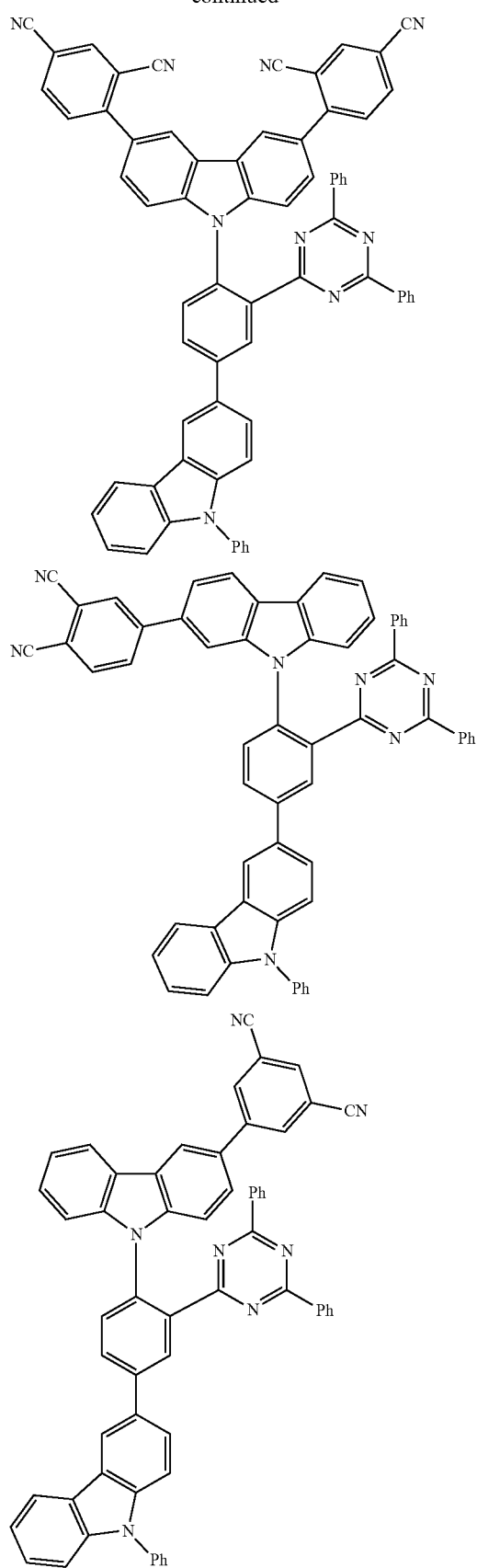
164
-continued
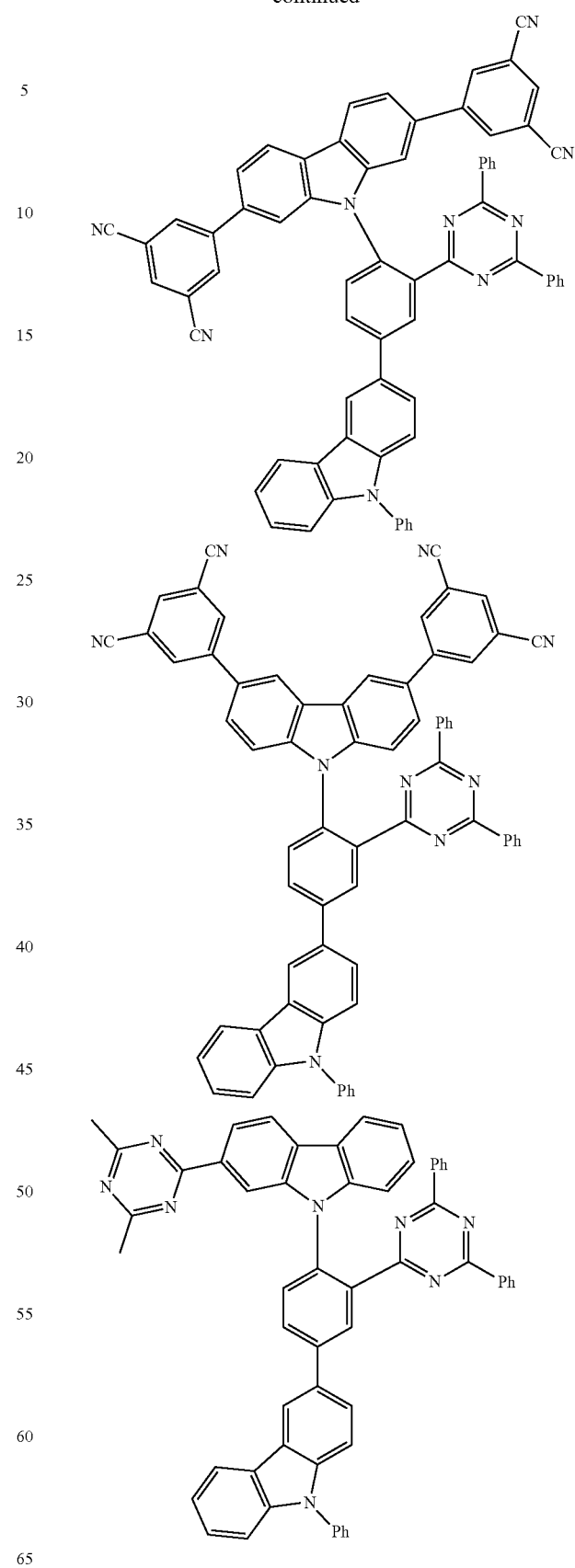

165
-continued
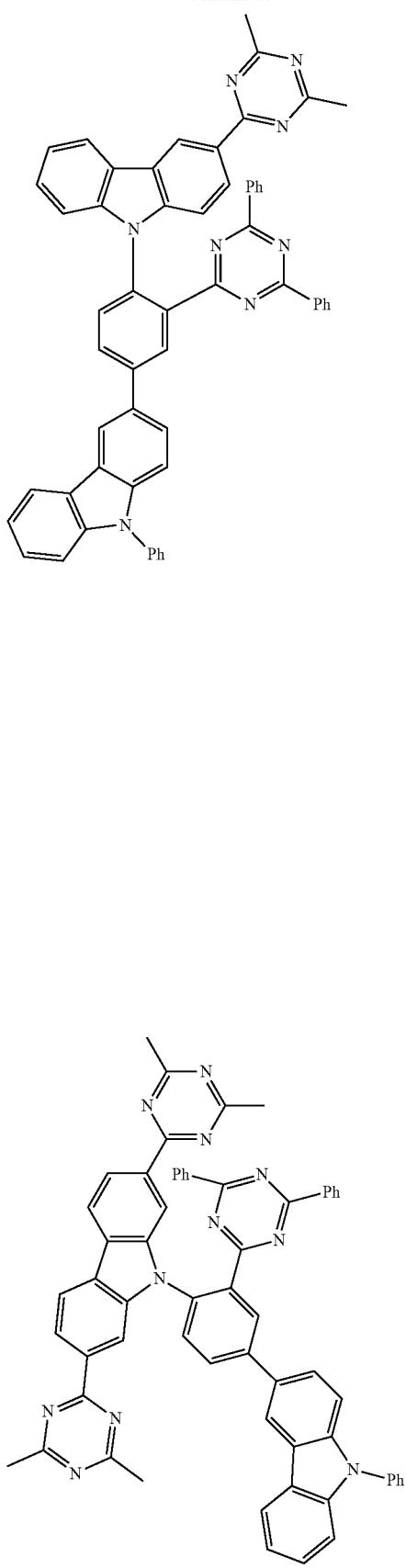
166
-continued
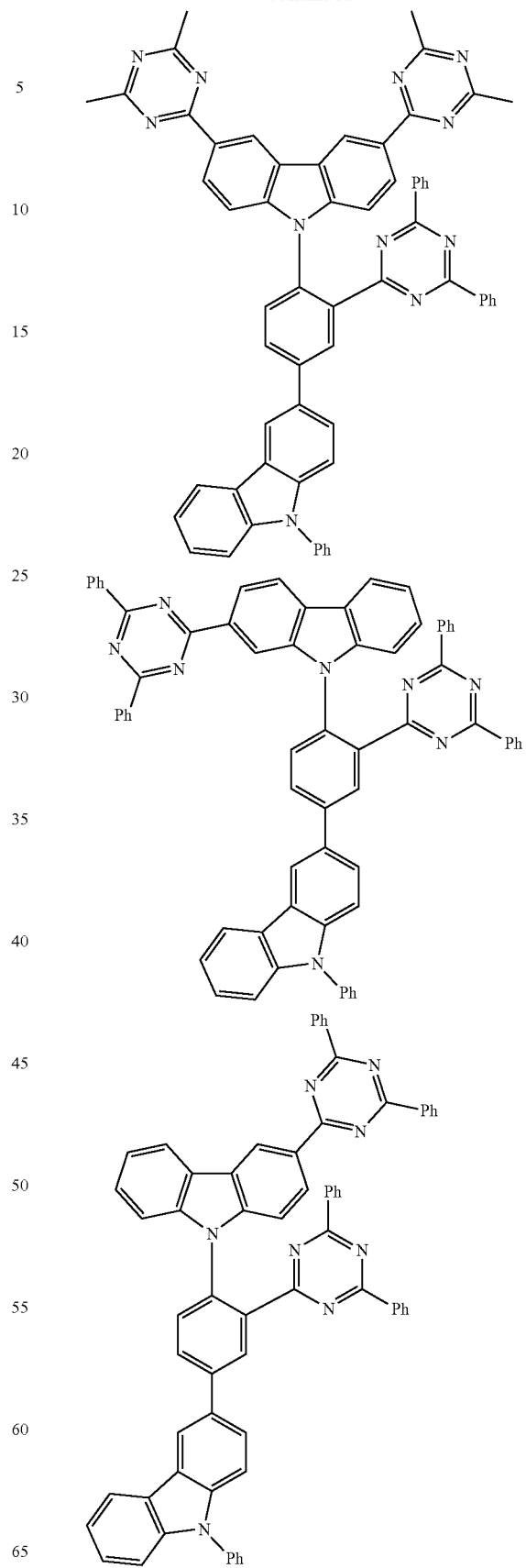

-continued
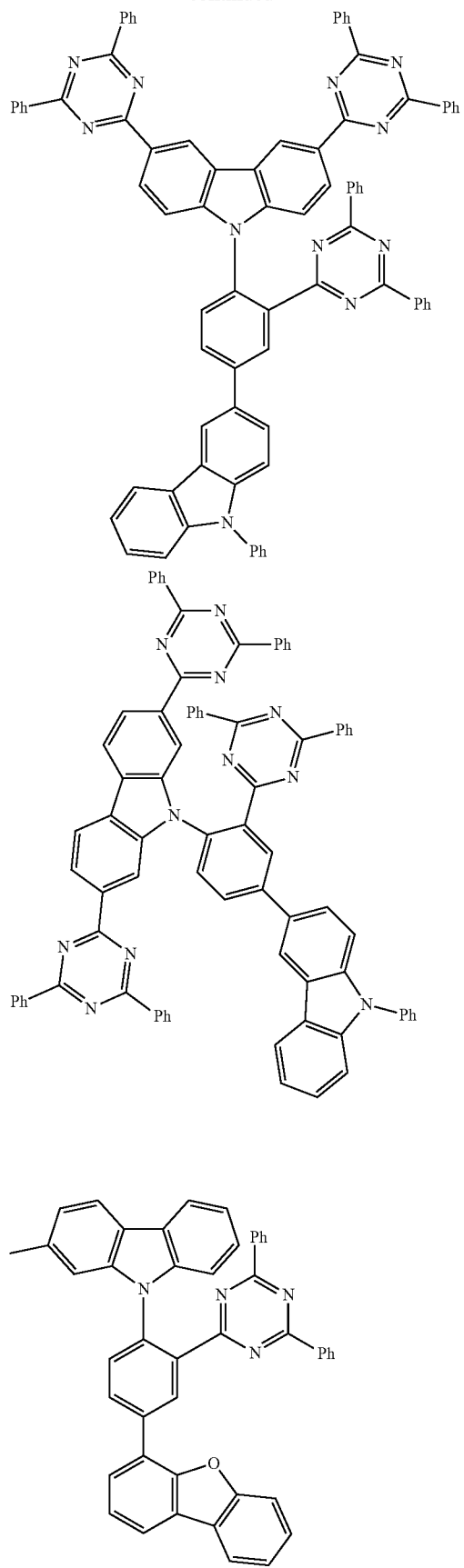
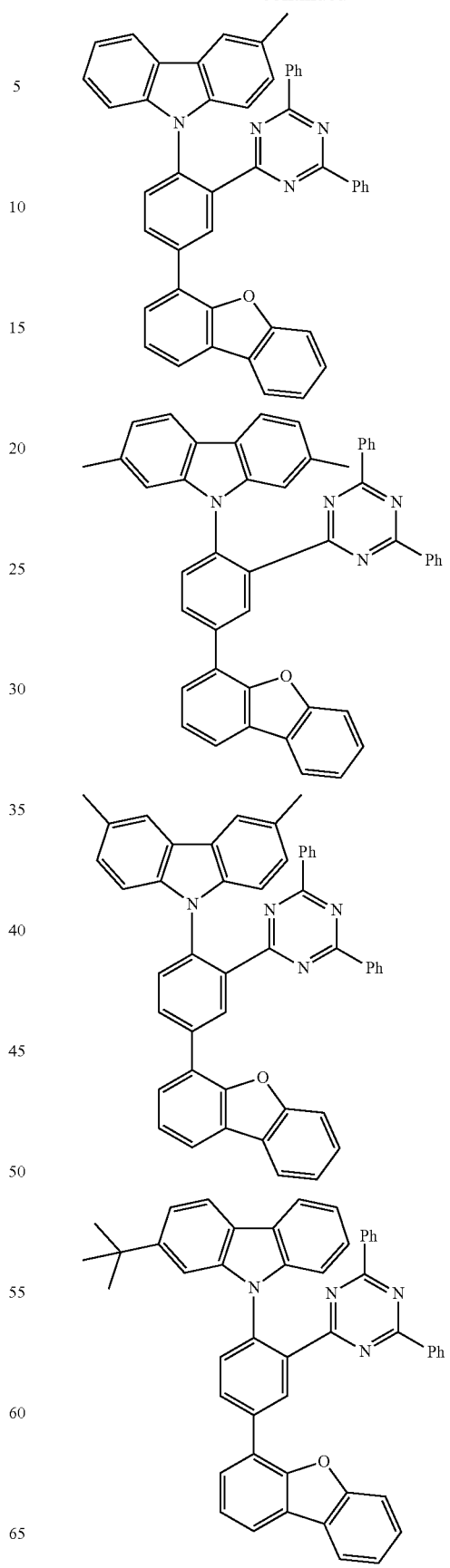

169
-continued
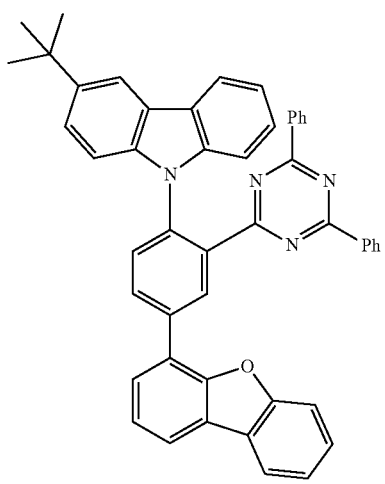
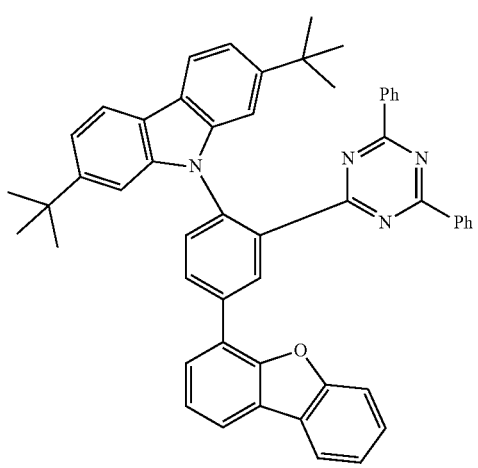
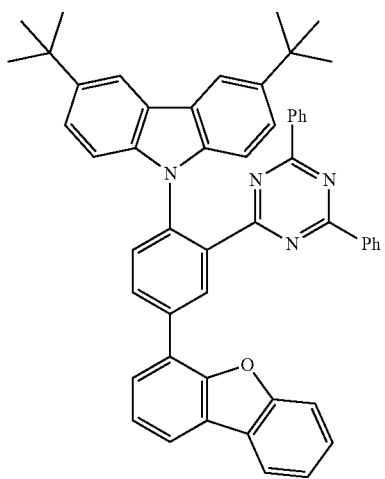
170
-continued
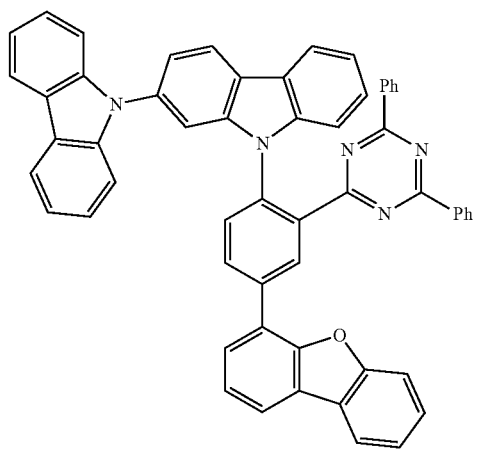
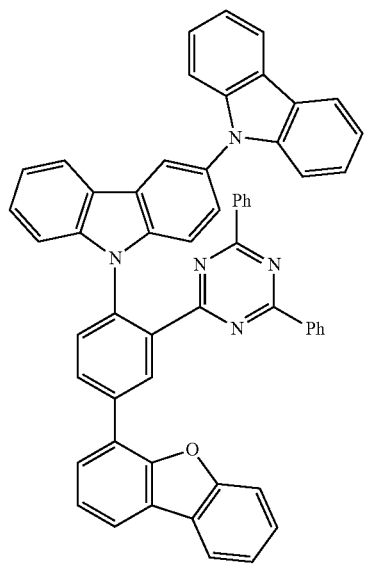
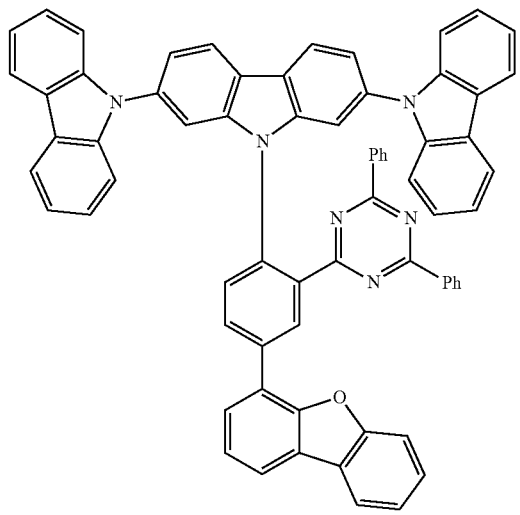

171
-continued
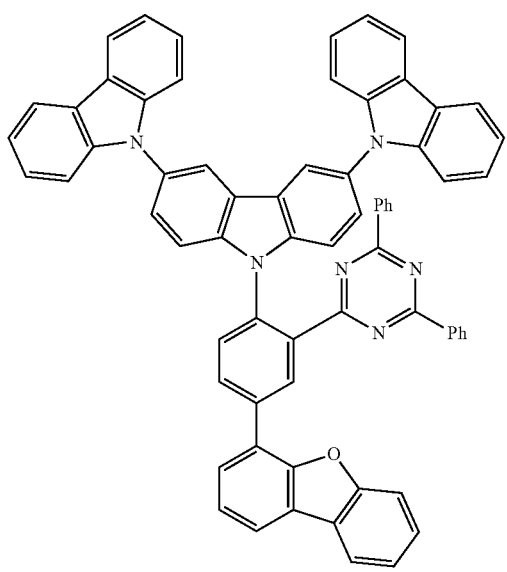
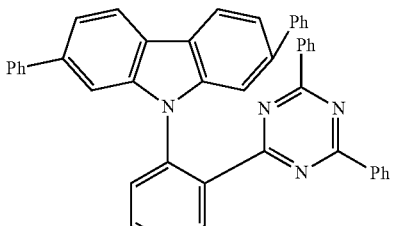
172
-continued
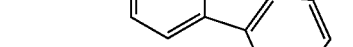
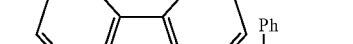
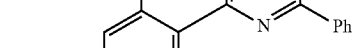
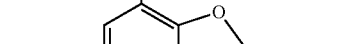
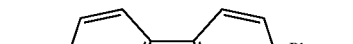
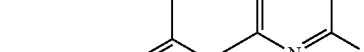
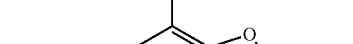
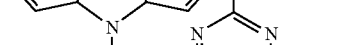
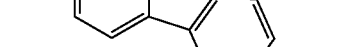

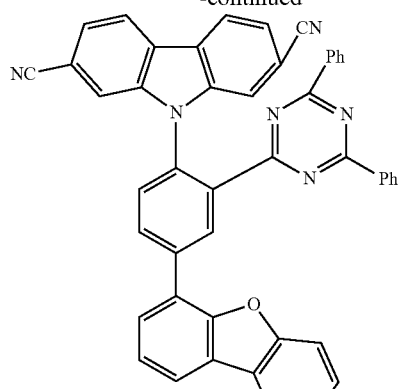
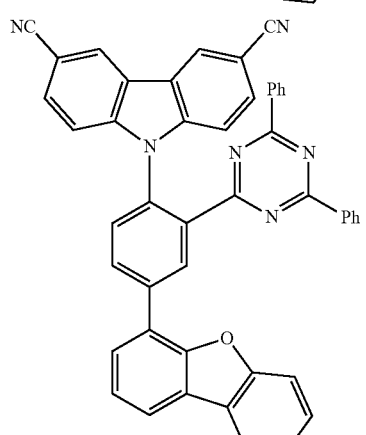
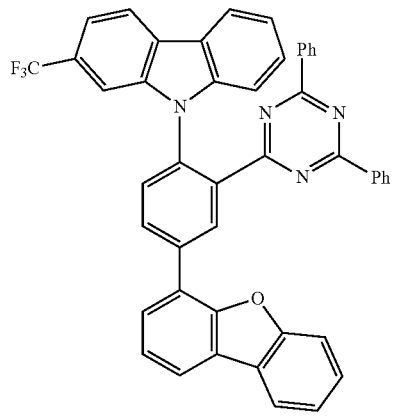
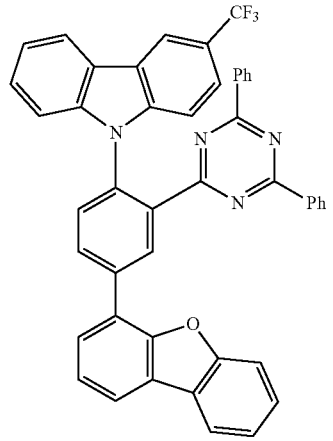
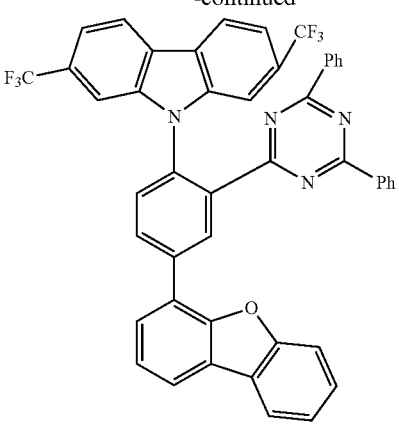
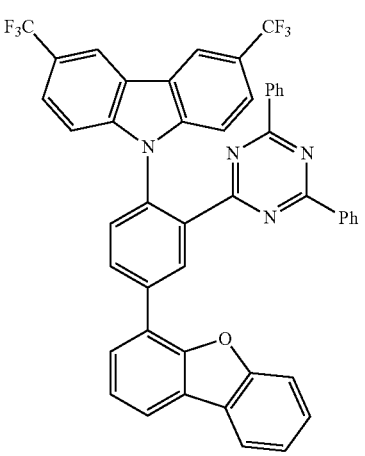
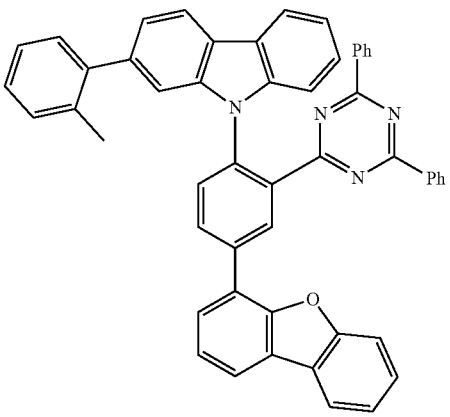

175
-continued
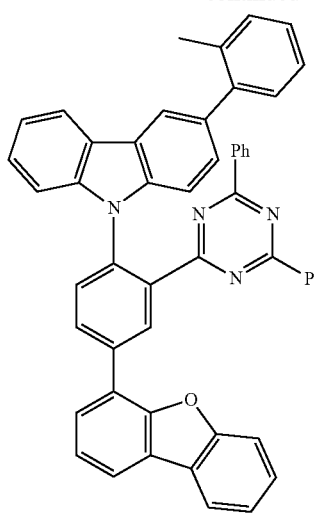
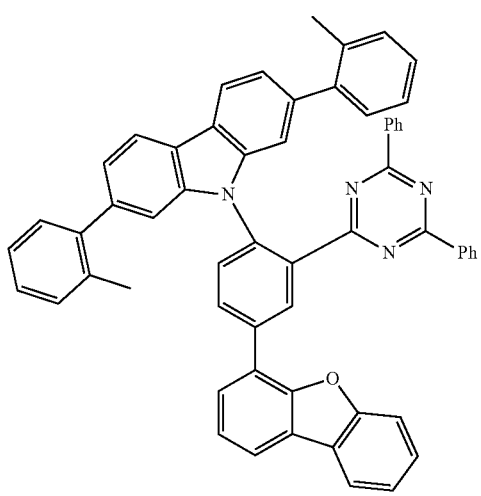
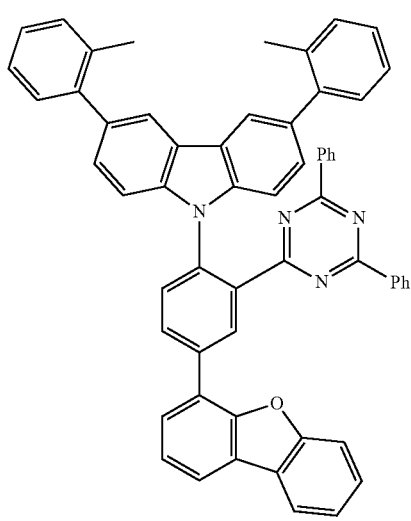
176
-continued
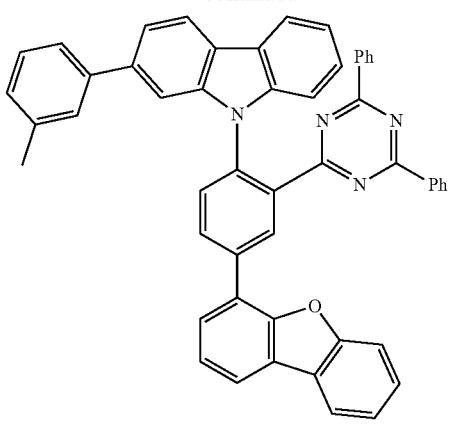
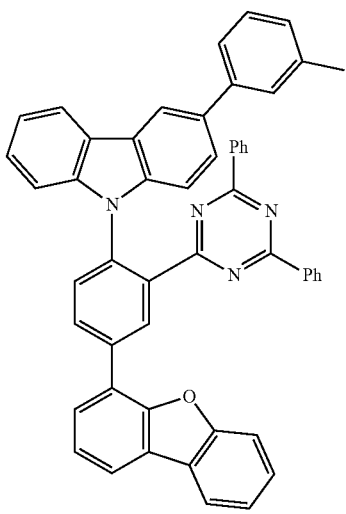
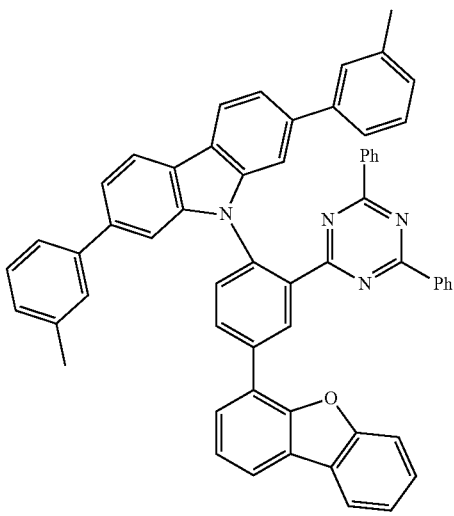

177
-continued
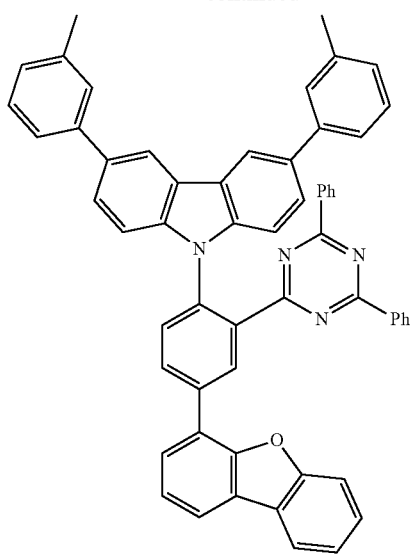
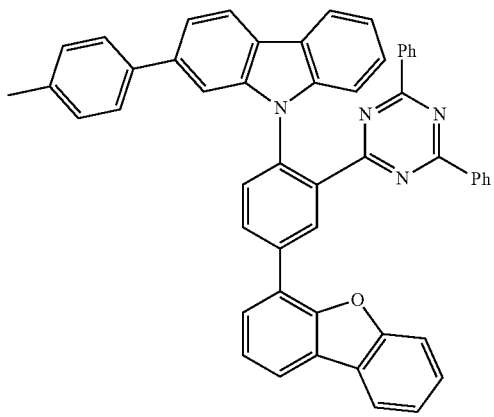
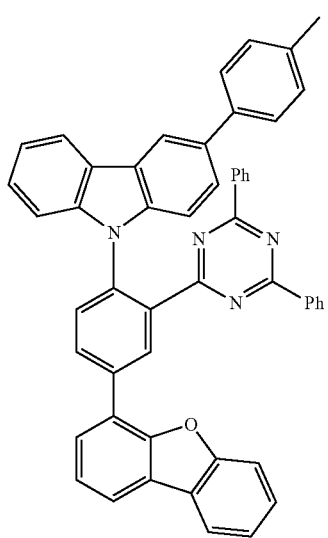
178
-continued
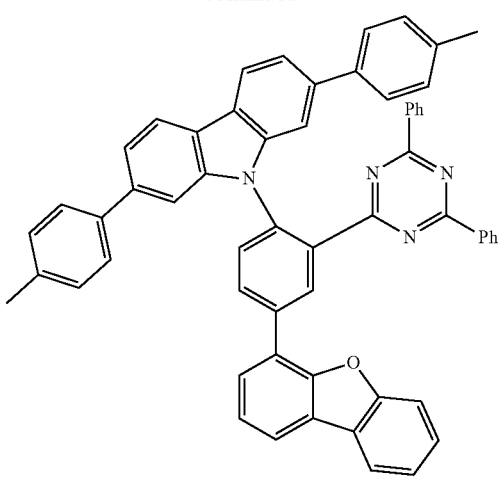
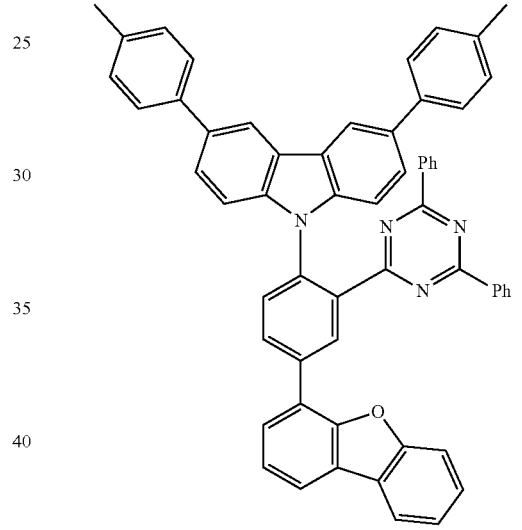
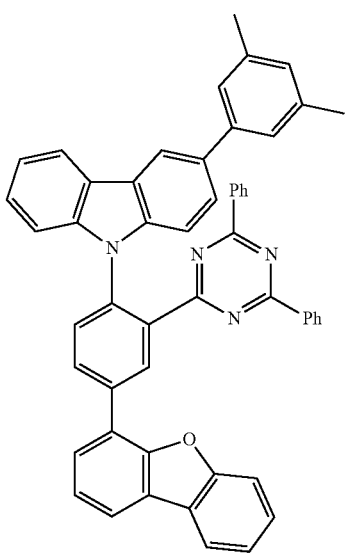

179
-continued
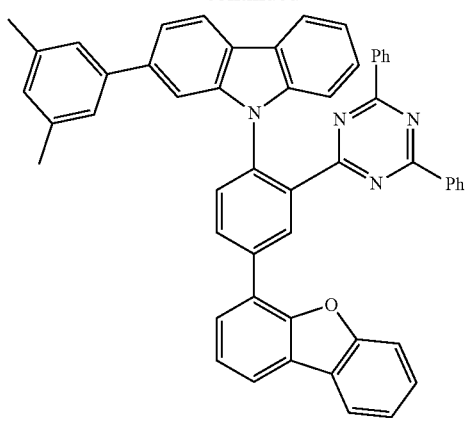
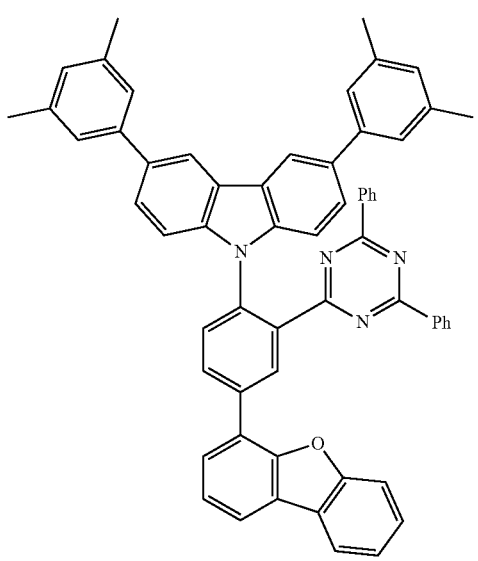
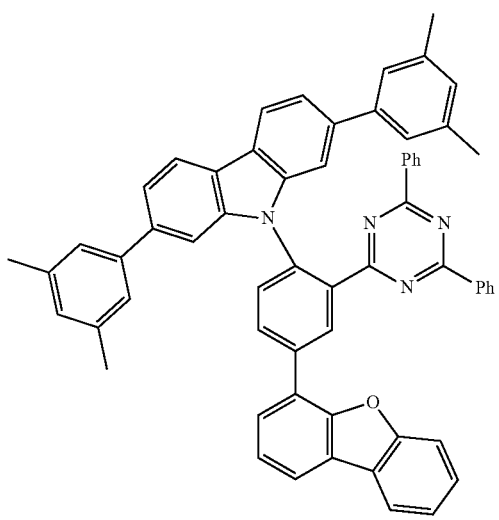
180
-continued
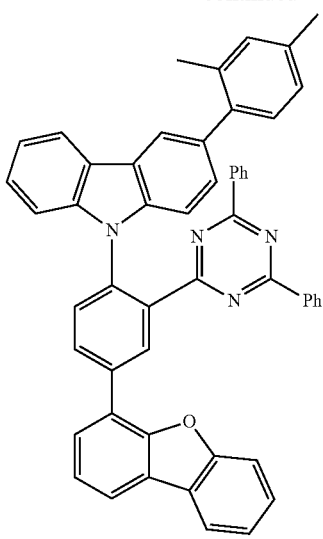
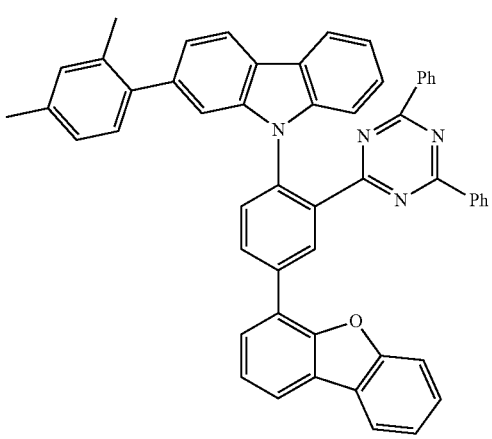
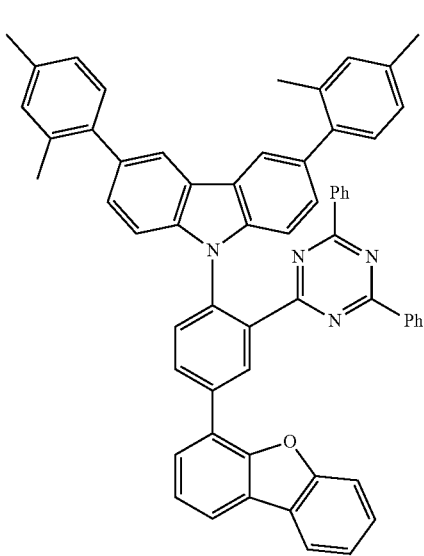

181
-continued
182
-continued
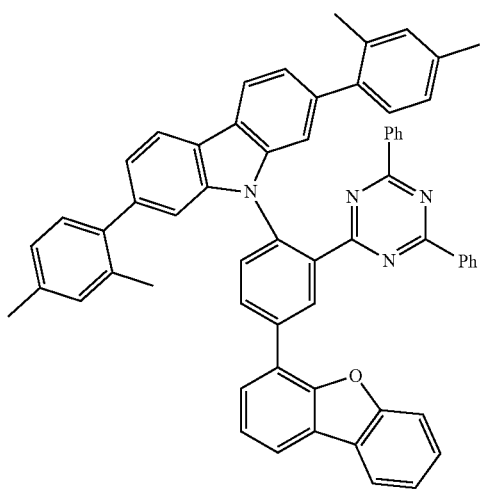
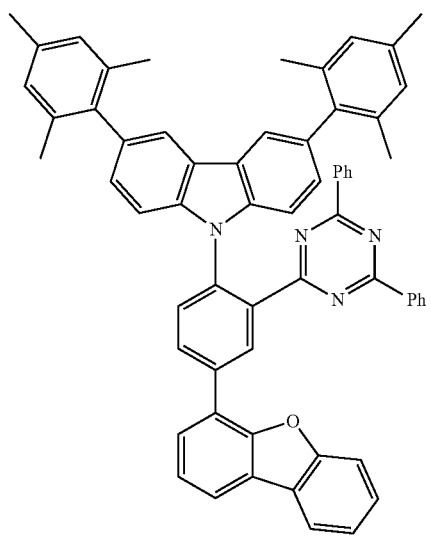
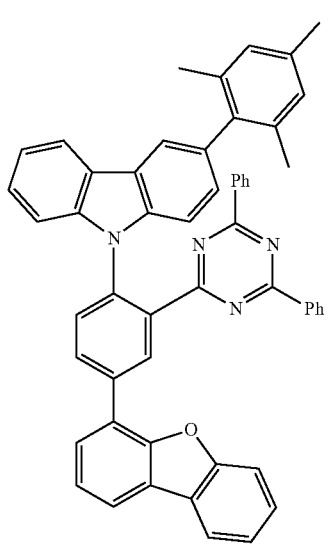
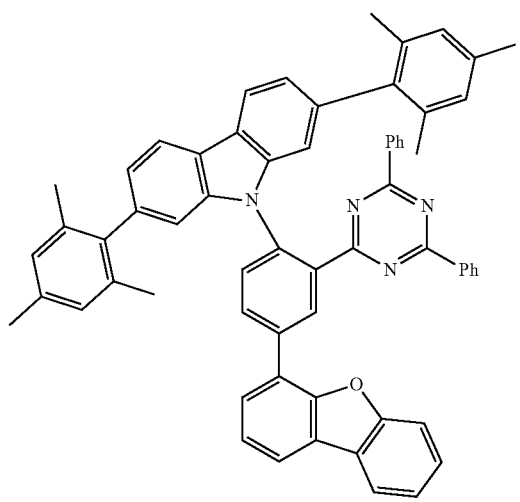
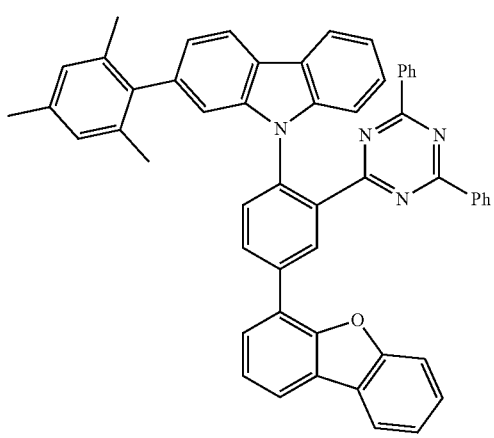
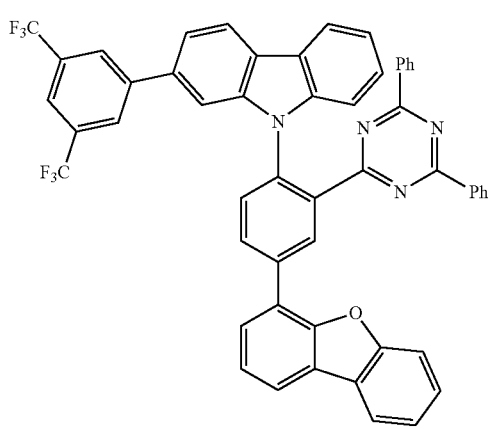

183
-continued
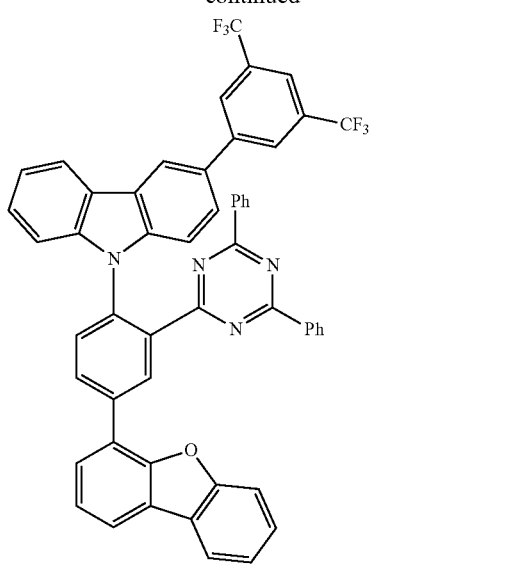
184
-continued
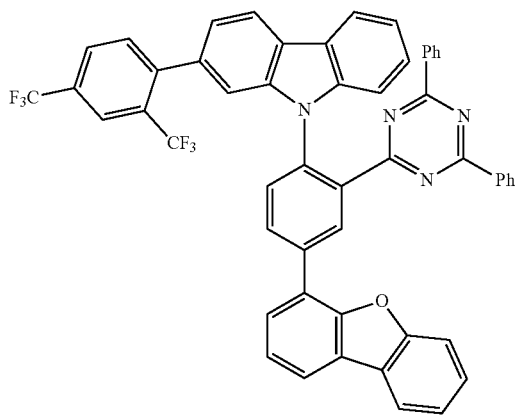
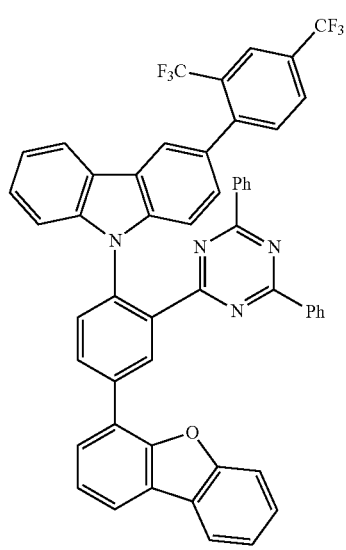
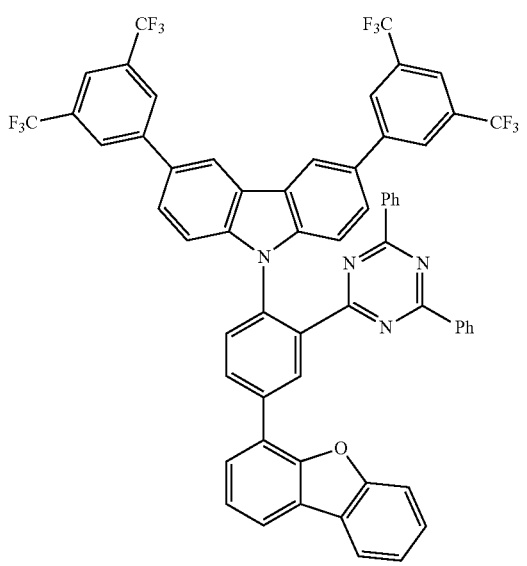
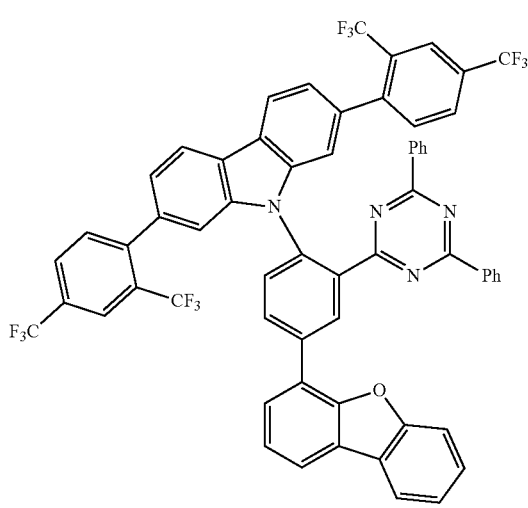

185
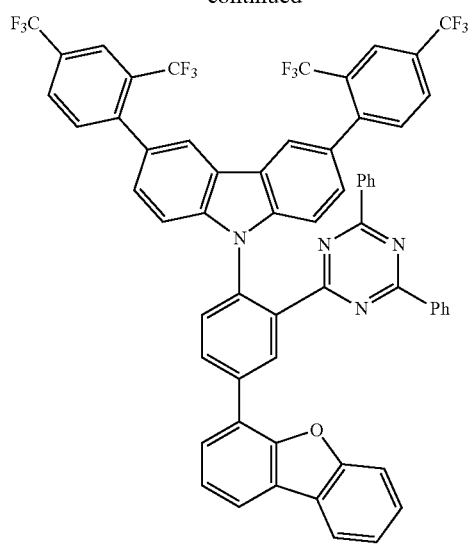
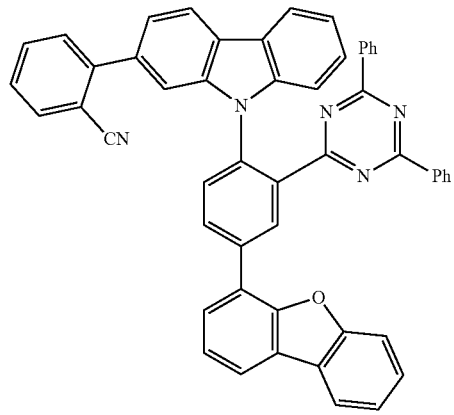
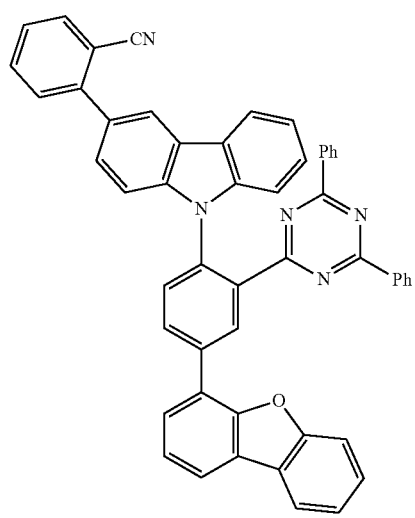
186
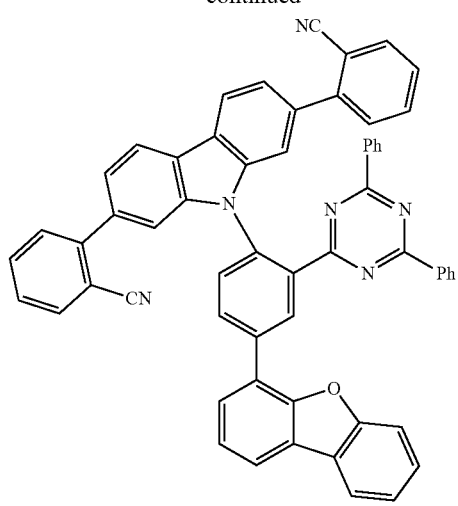
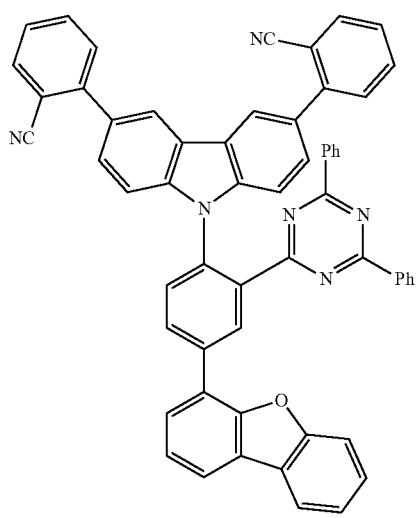
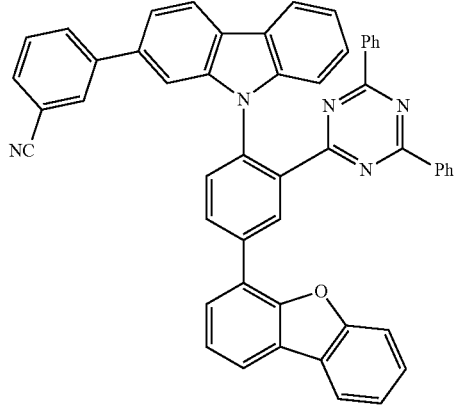

187
-continued
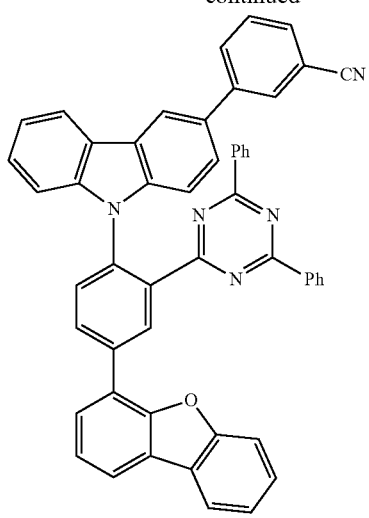
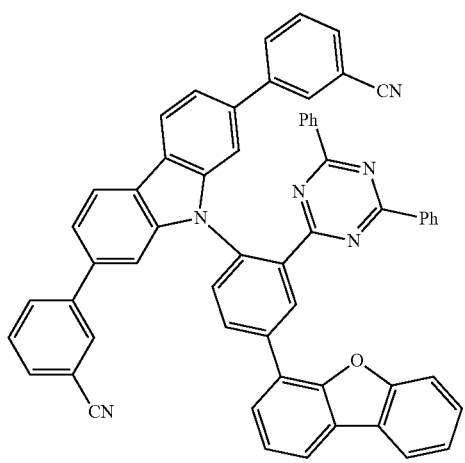
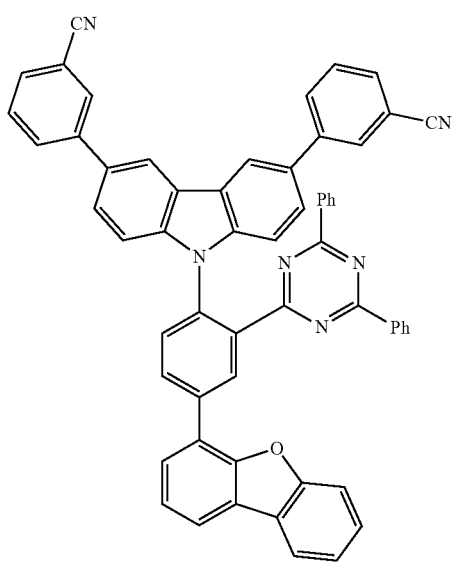
188
-continued
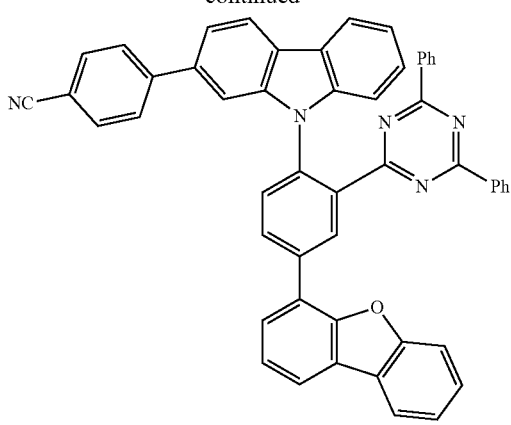
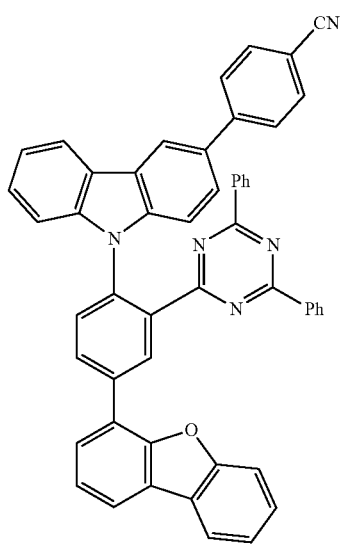
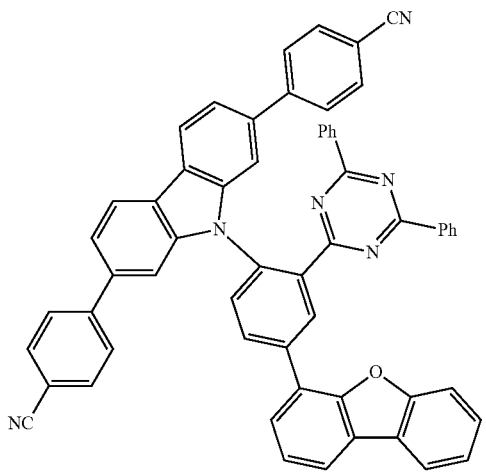

189
-continued
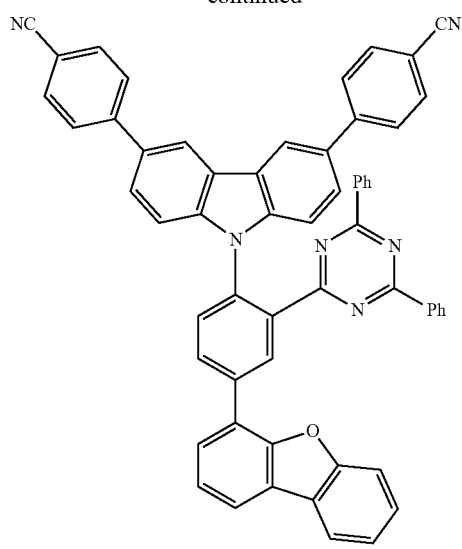
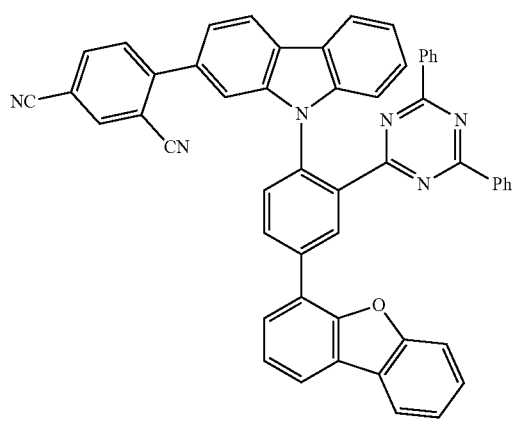
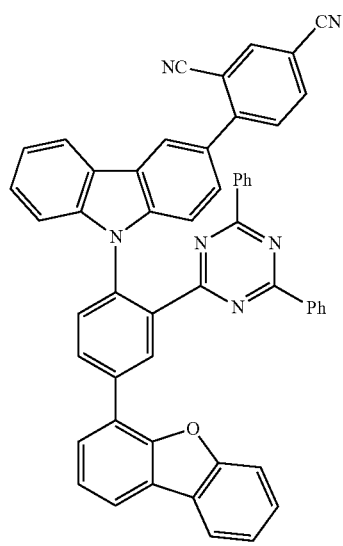
190
-continued
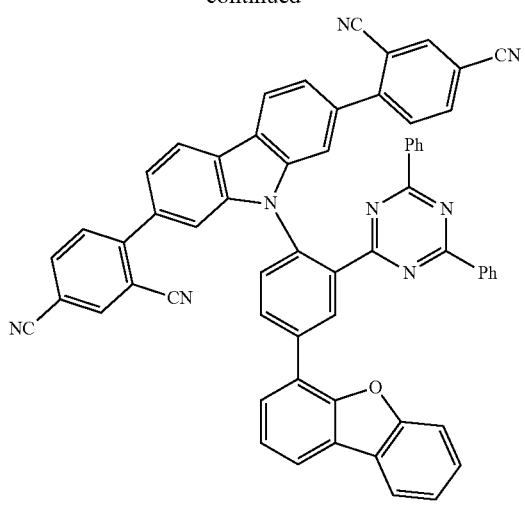
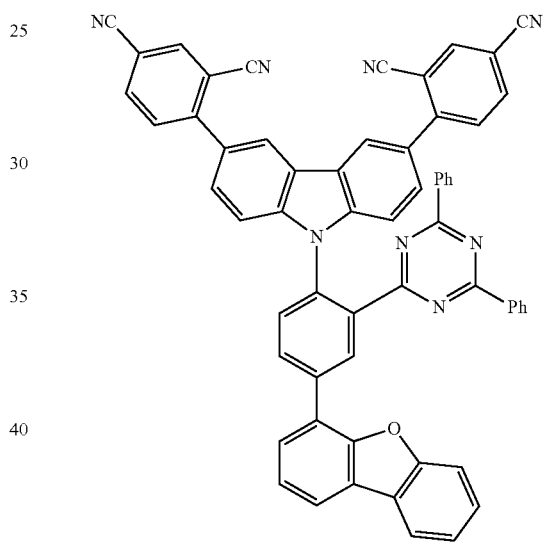
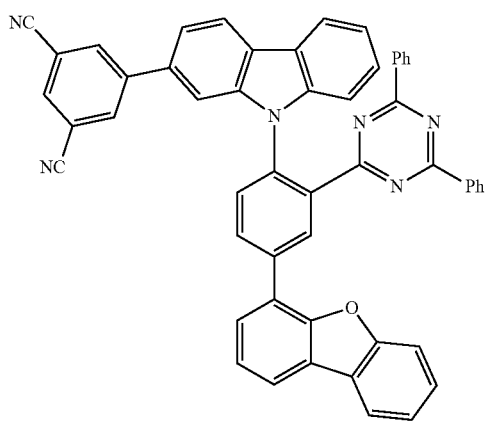

-continued
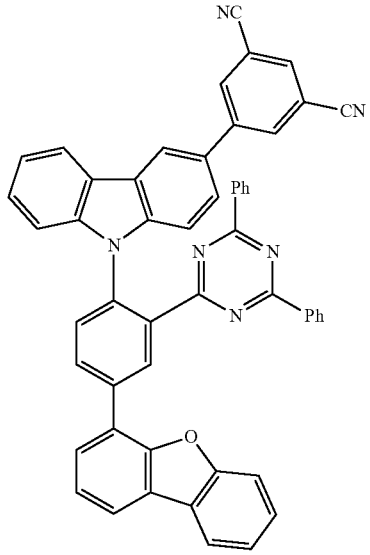
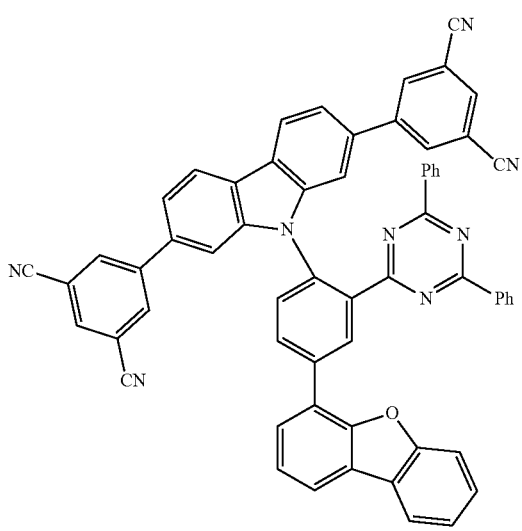
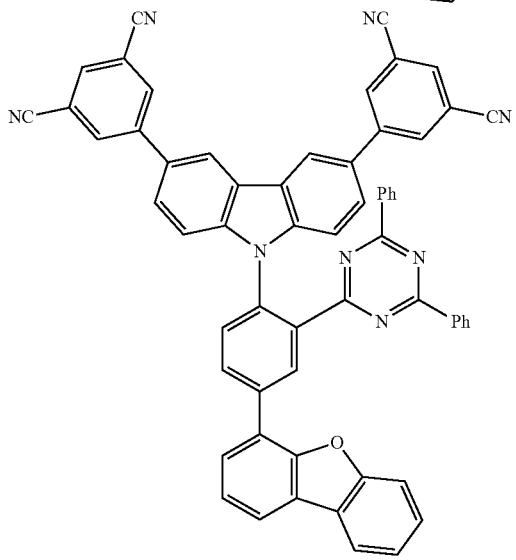
-continued
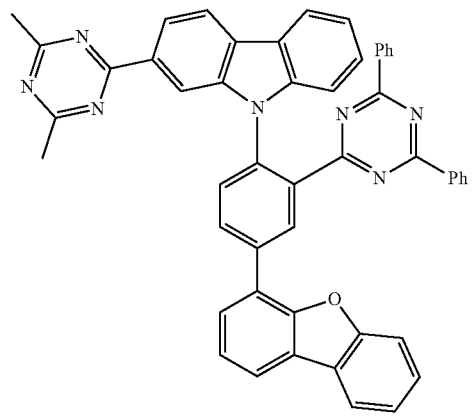
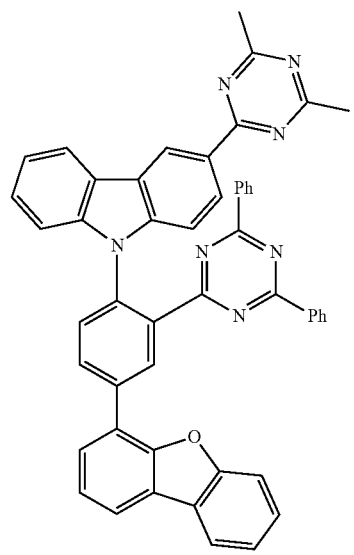
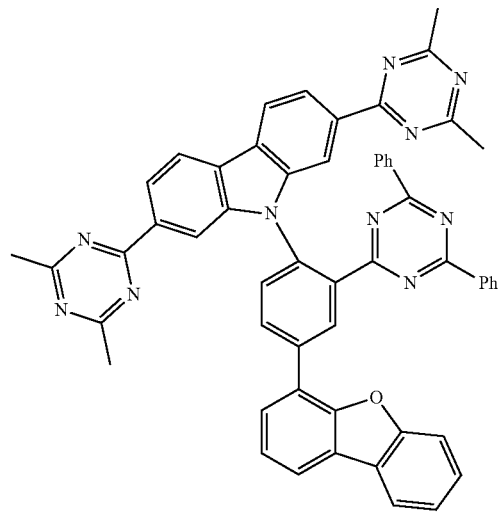

193
-continued
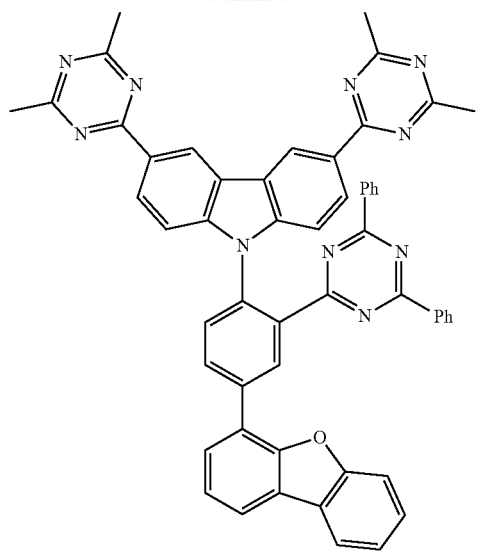
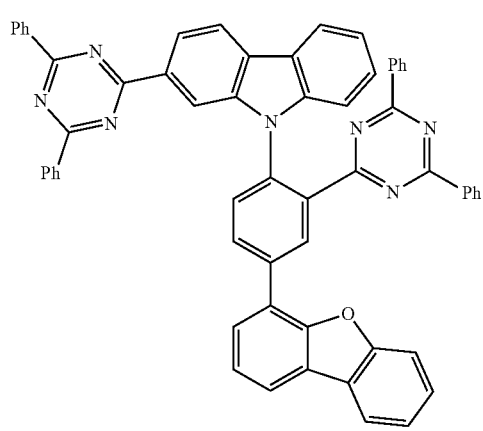
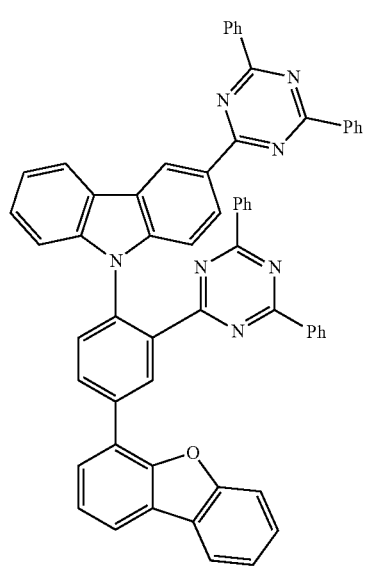
194
-continued
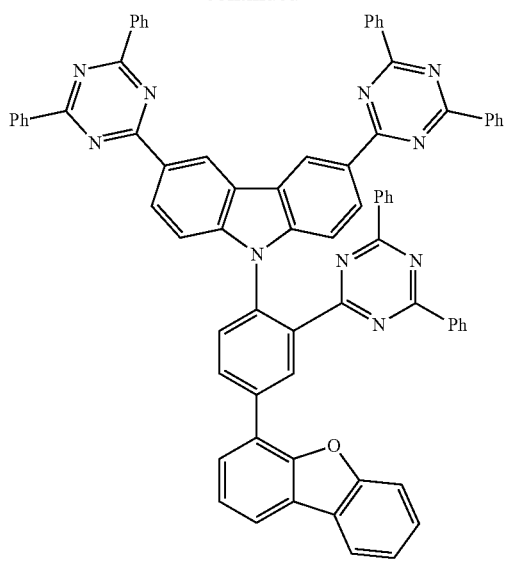
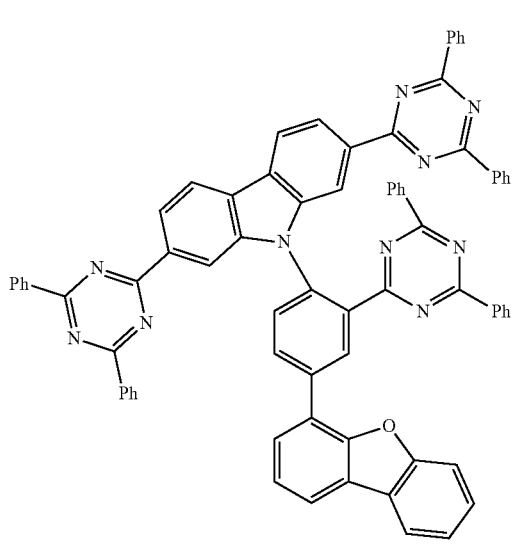 [SMILES: c1ccc(-c2nc(-c3ccccc3)nc(-c3ccc4c5ccc(-c6nc(-c7ccccc7)nc(-c7ccccc7)n6)cc5n(-c5ccc(-c6cccc7c6oc6ccccc67)cc5-c5nc(-c6ccccc6)nc(-c6ccccc6)n5)c4c3)n2)cc1]
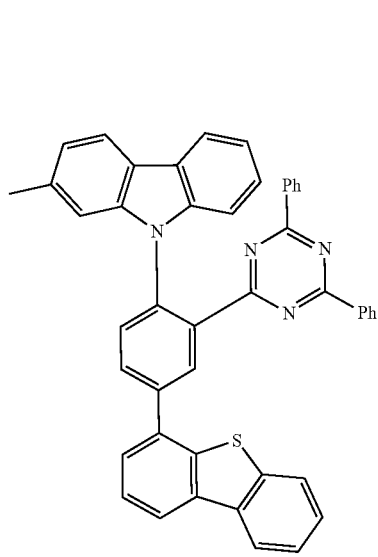

-continued
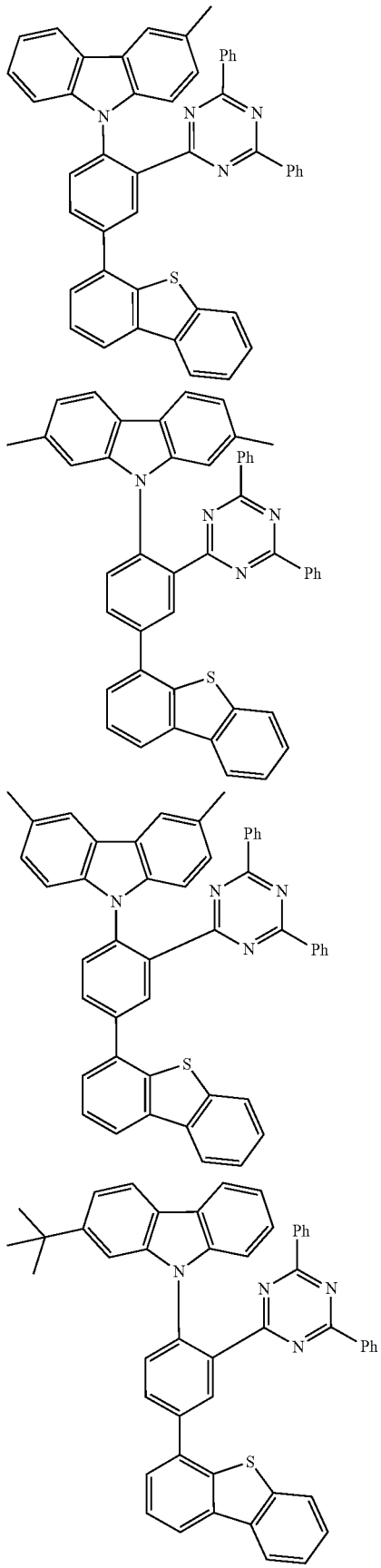
-continued
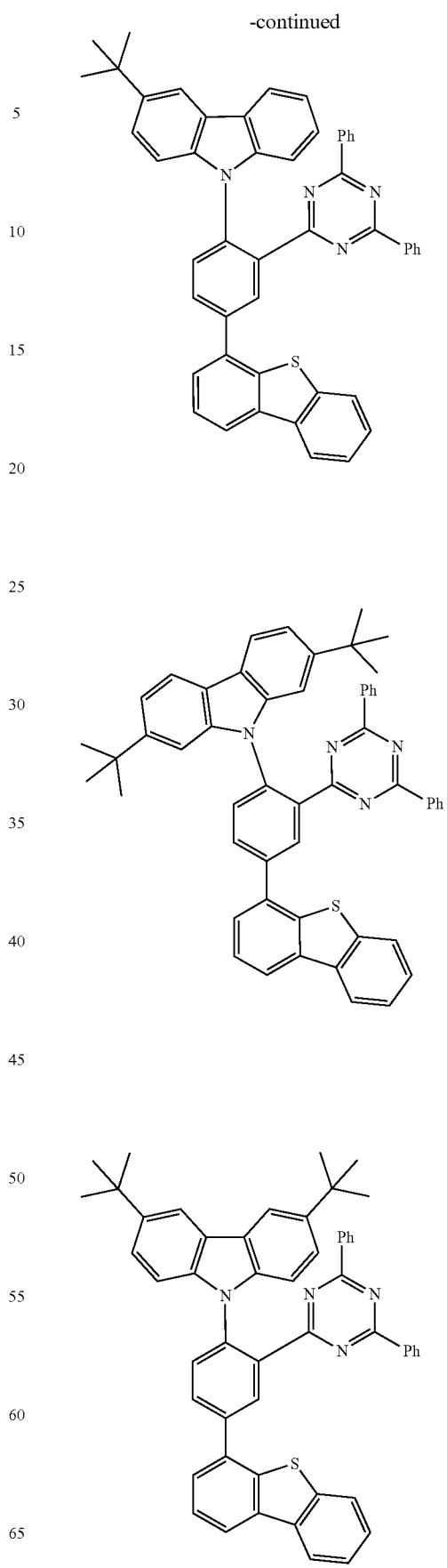

197
-continued
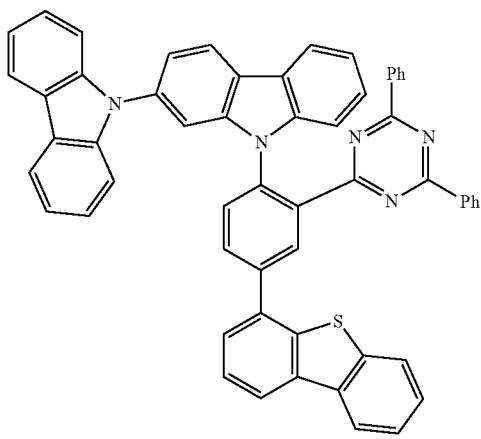
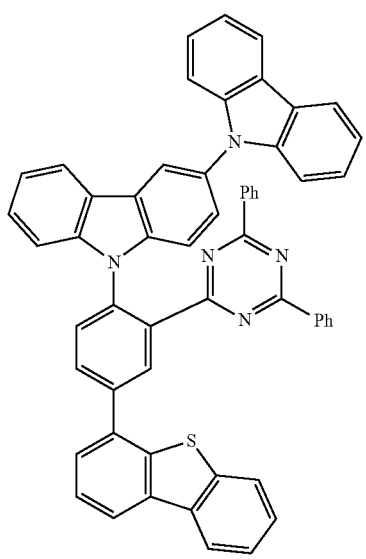
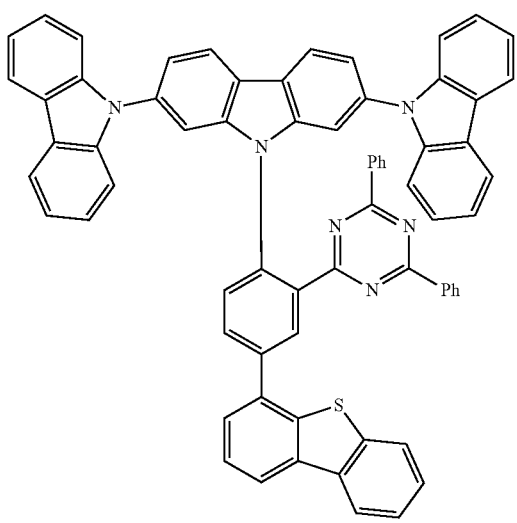
198
-continued
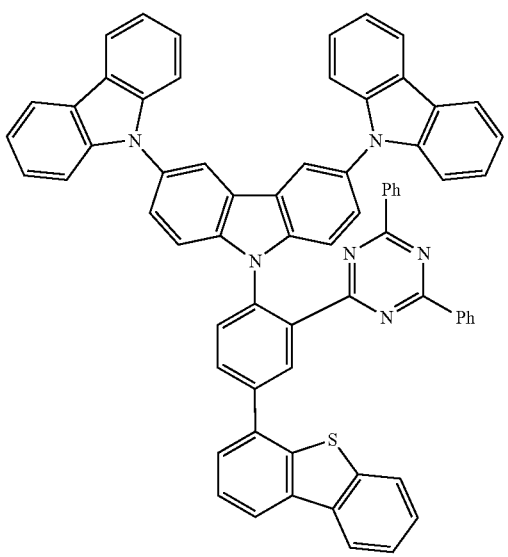
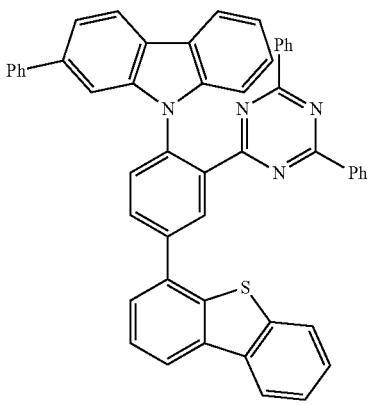
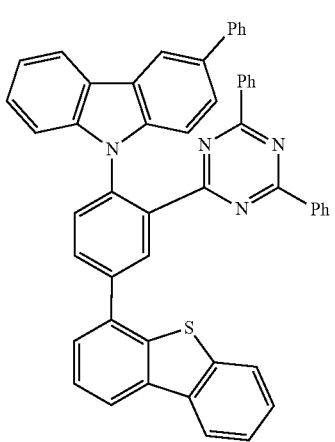

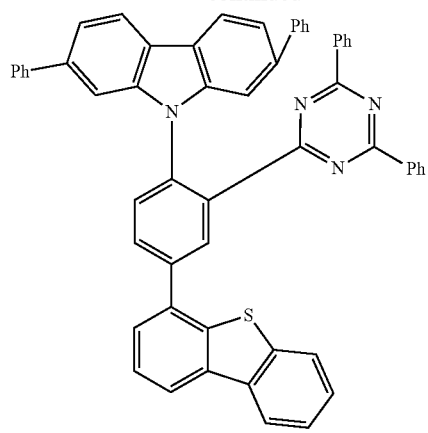
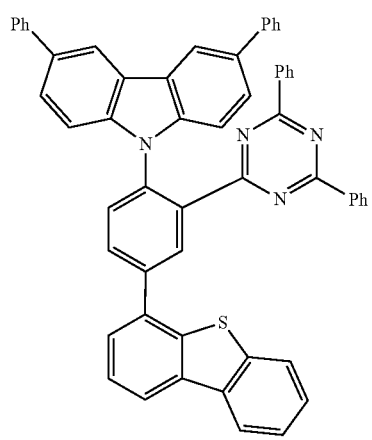
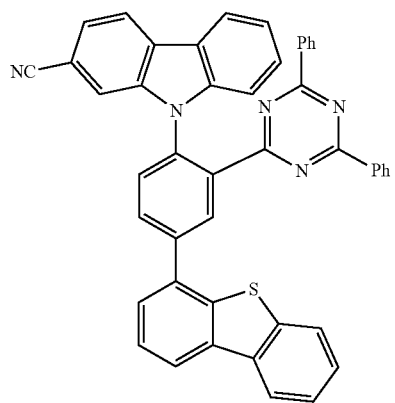
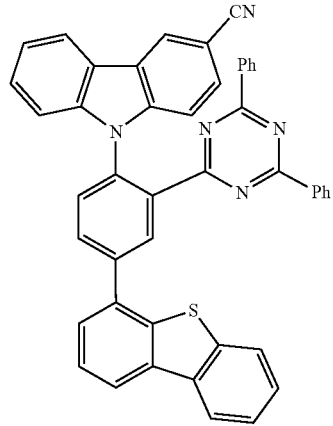
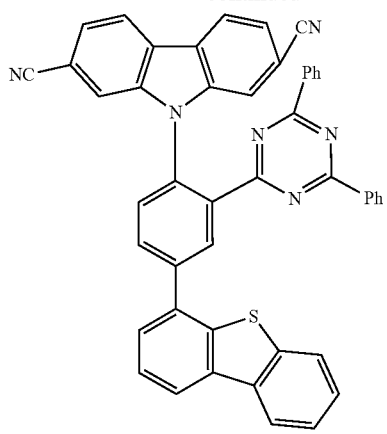
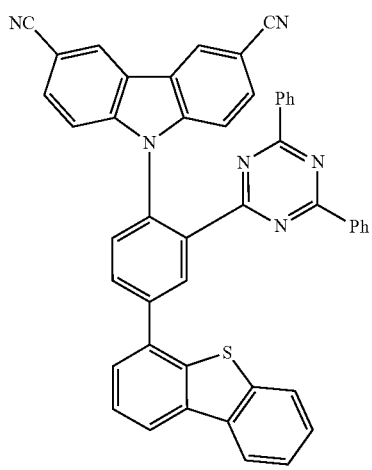
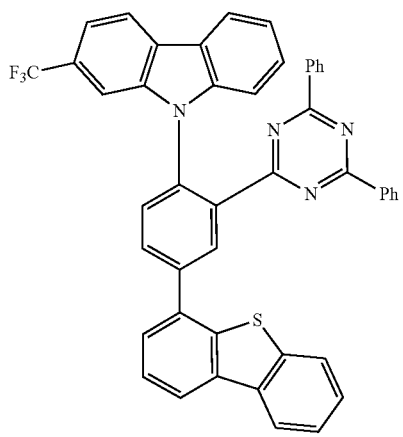

201
-continued
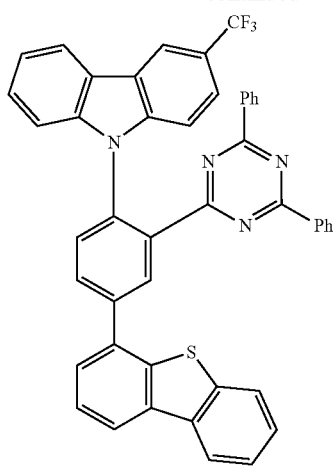
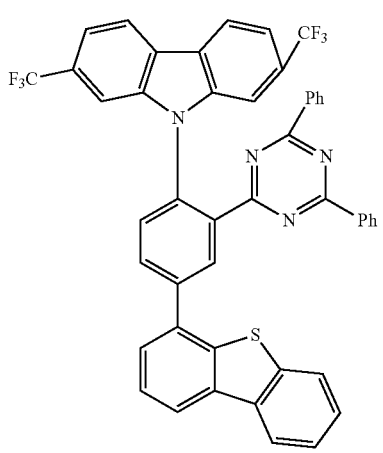
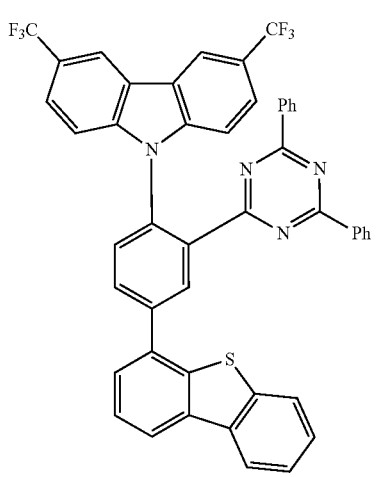
202
-continued
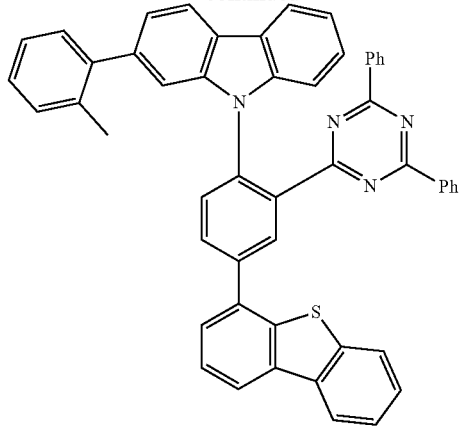
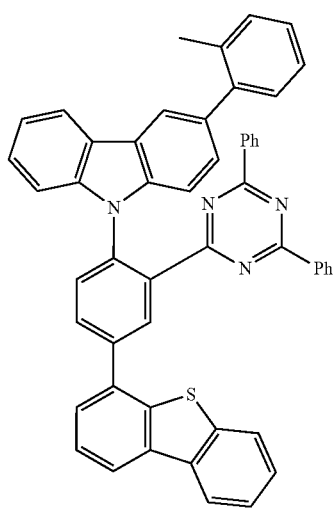
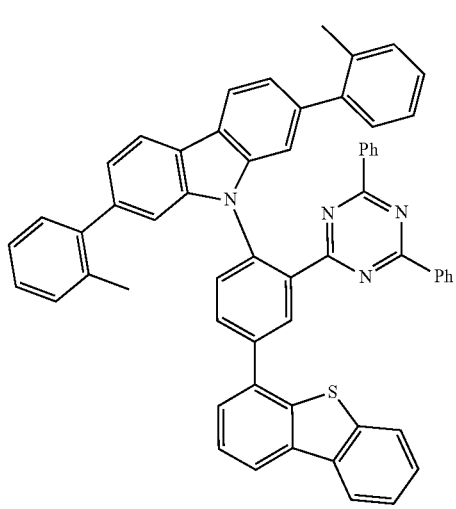

203
-continued
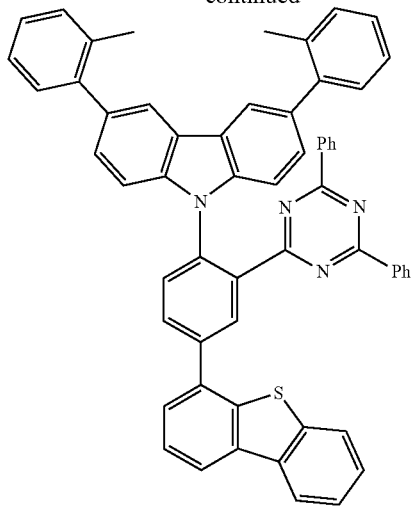
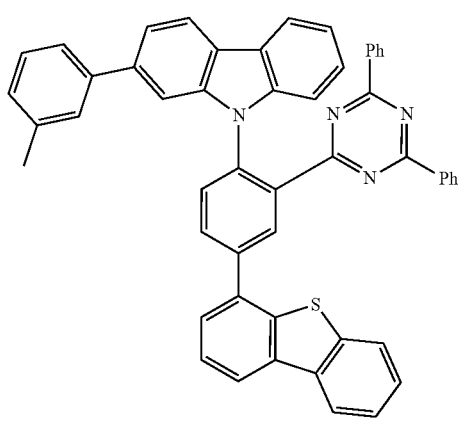
204
-continued
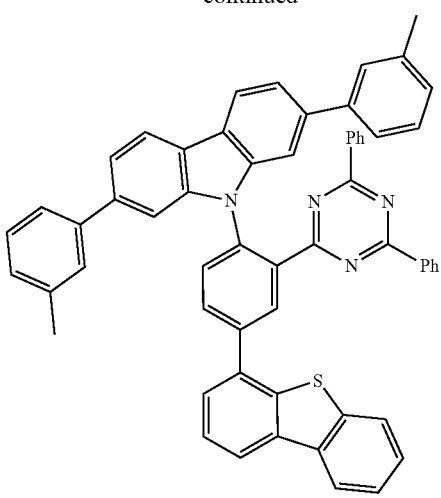
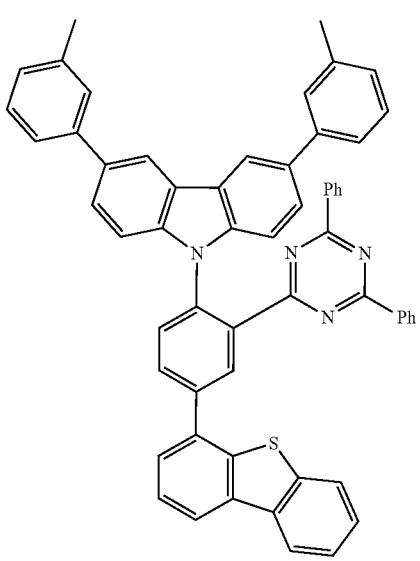
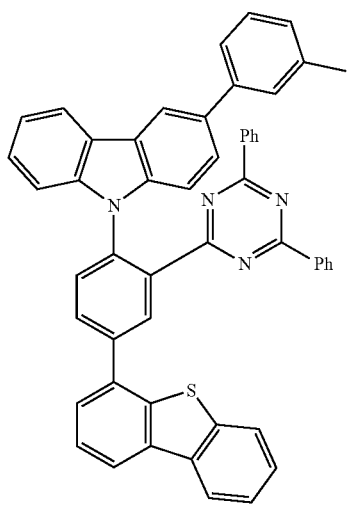
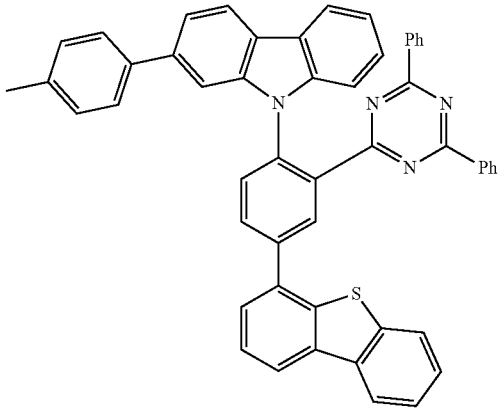

205
-continued
206
-continued
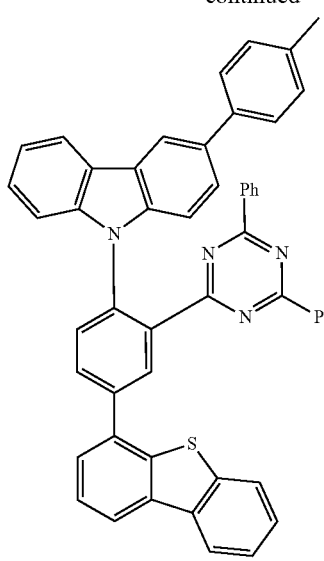
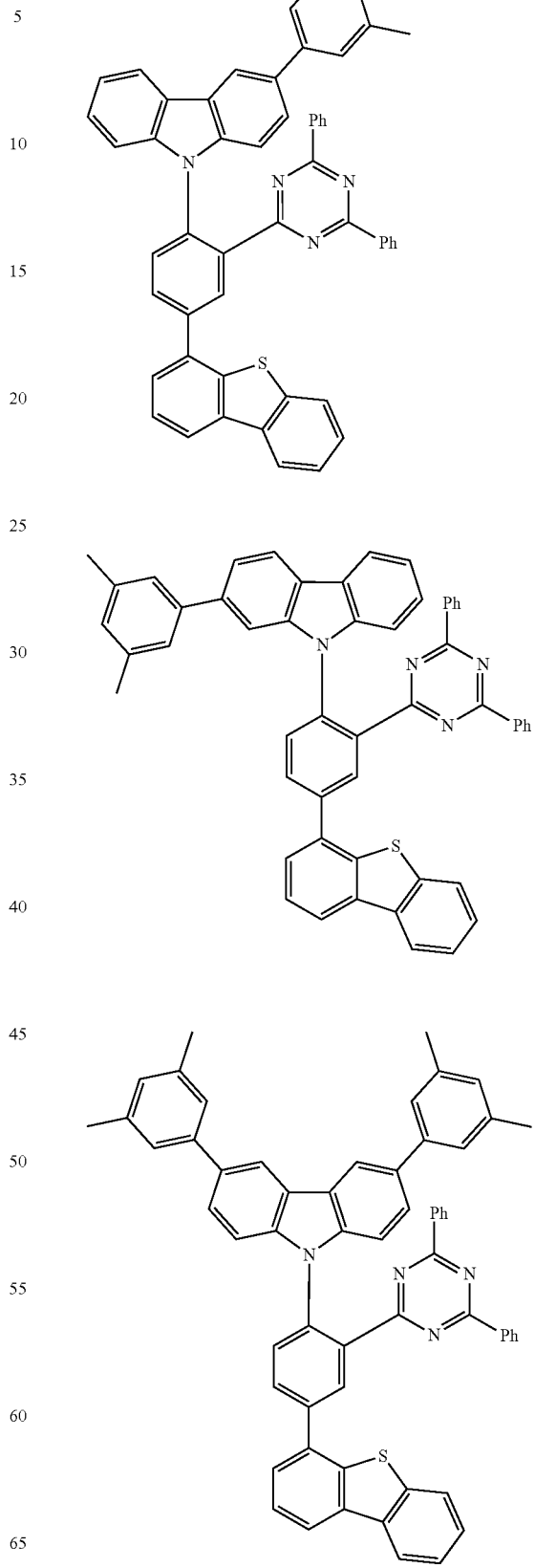

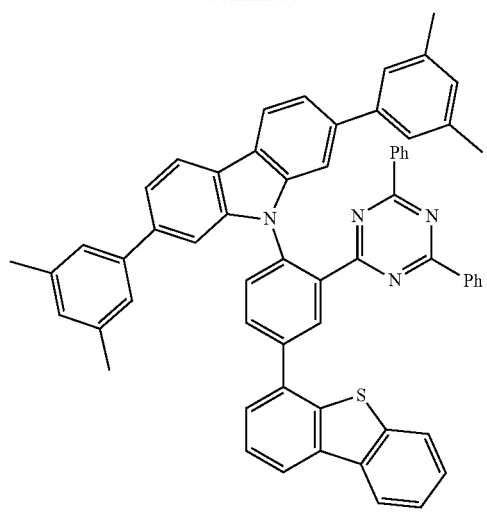
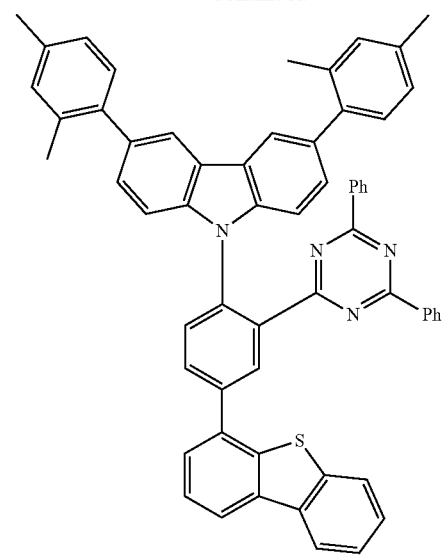
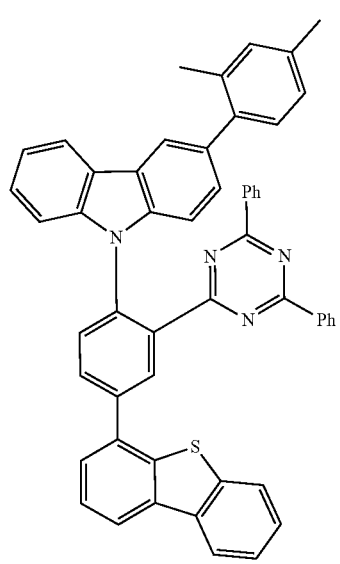
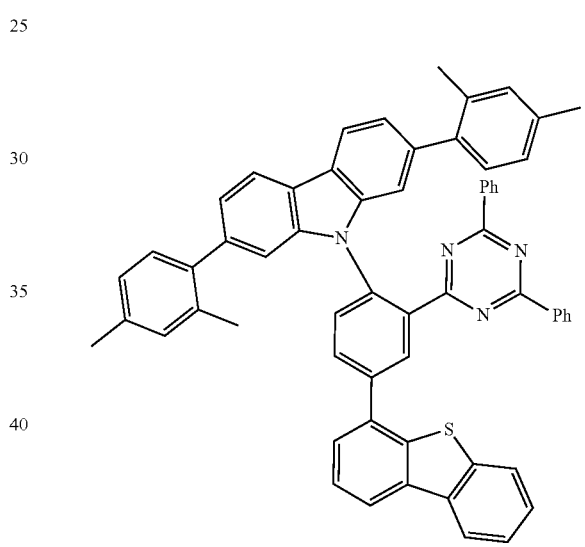
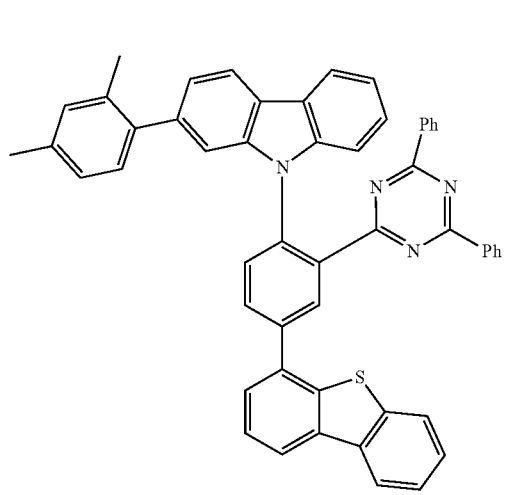

209
-continued
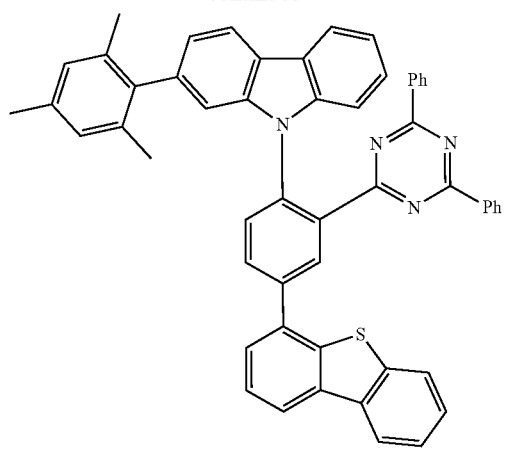
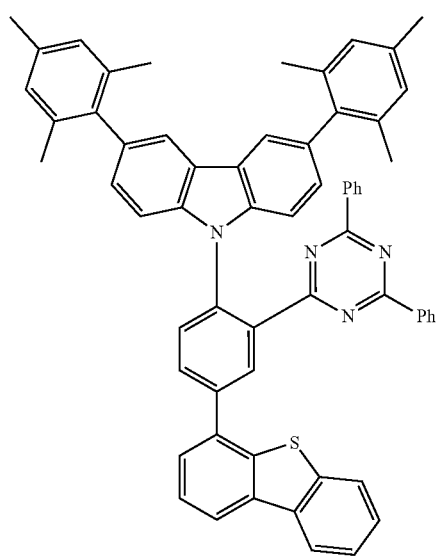
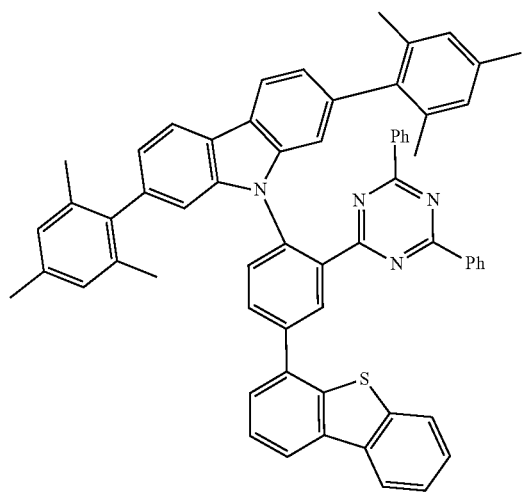
210
-continued
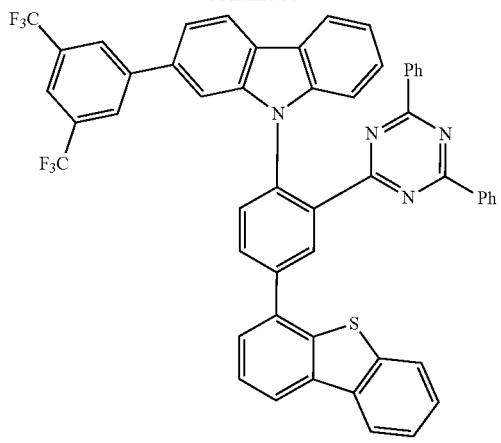
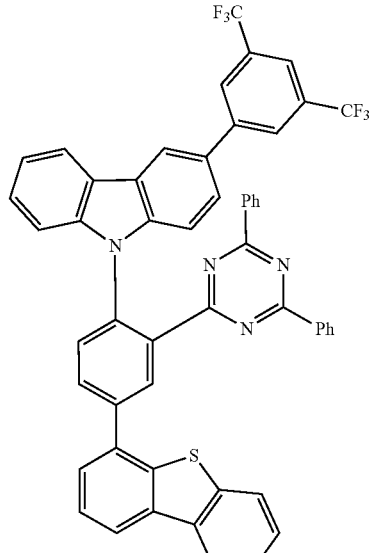
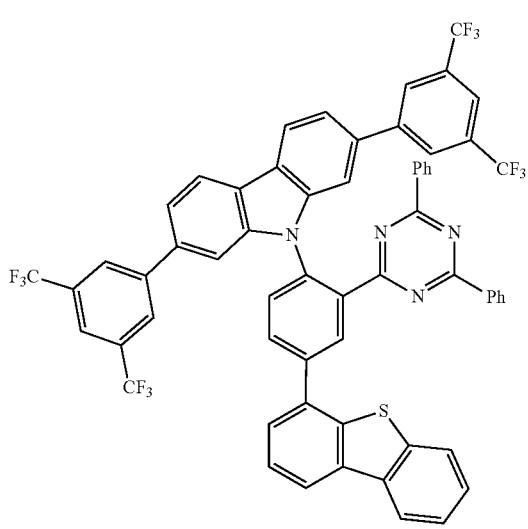

211
-continued
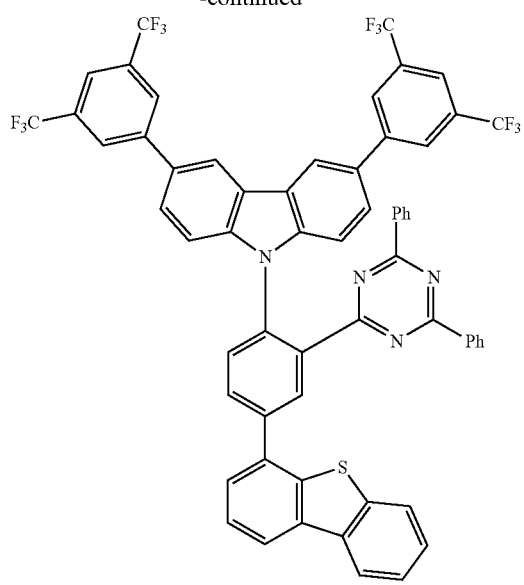
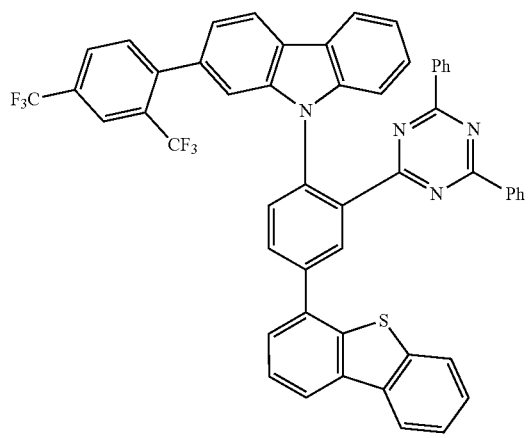
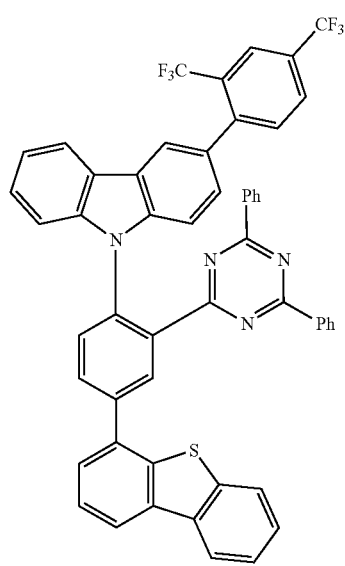
212
-continued
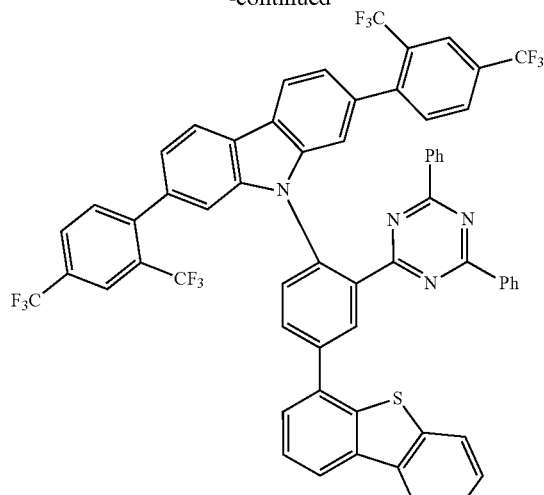
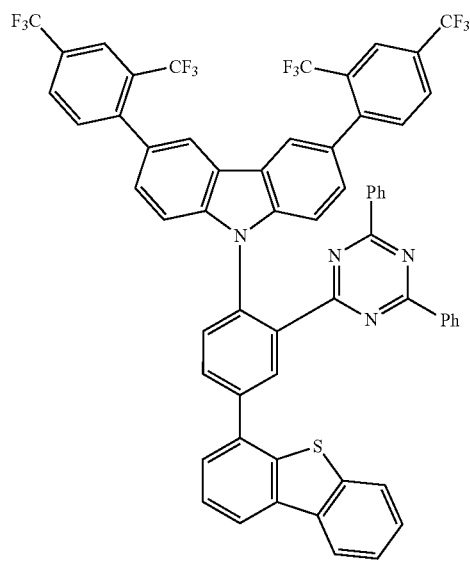
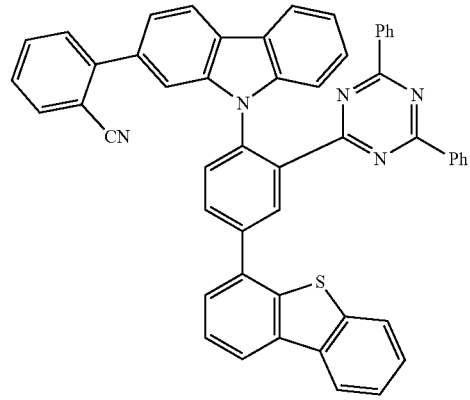

213
-continued
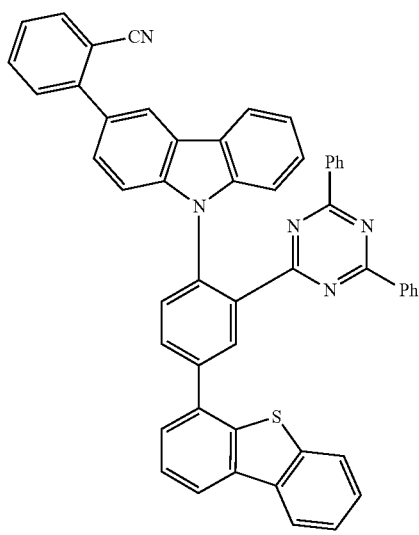
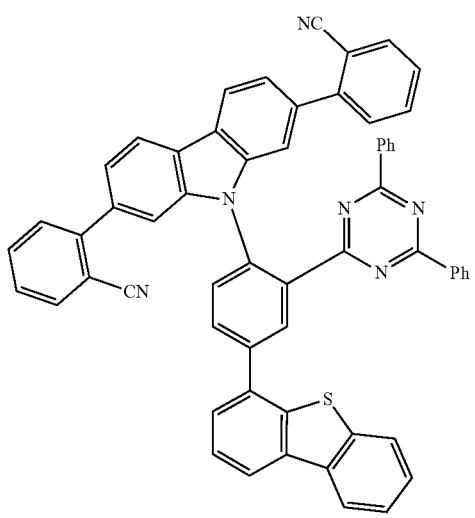 [SMILES: N#Cc1ccccc1-c1ccc2c3ccc(-c4ccccc4C#N)cc3n(-c3ccc(-c4cccc5c4sc4ccccc45)cc3-c3nc(-c4ccccc4)nc(-c4ccccc4)n3)c2c1]
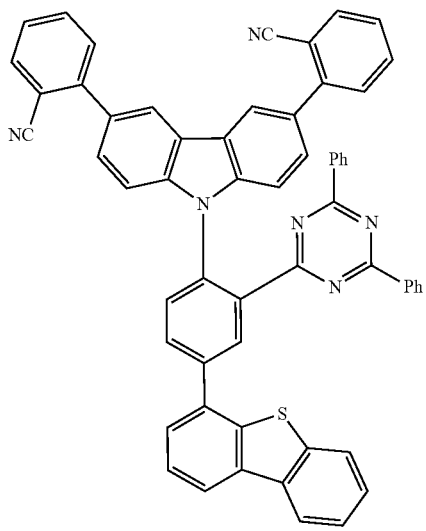
214
-continued
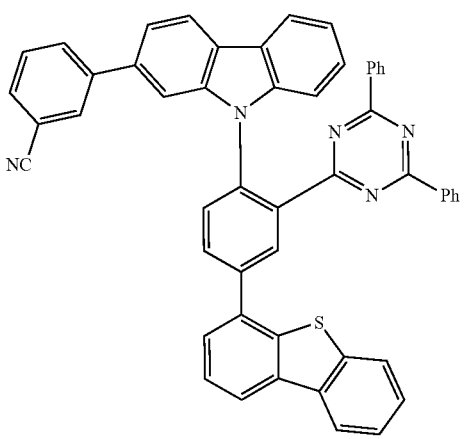
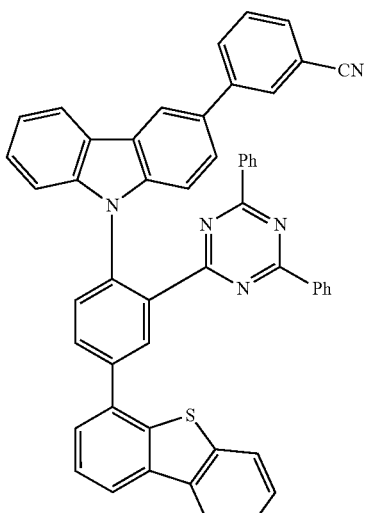
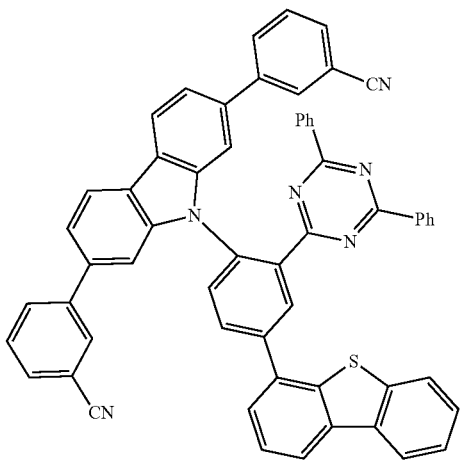

215
-continued
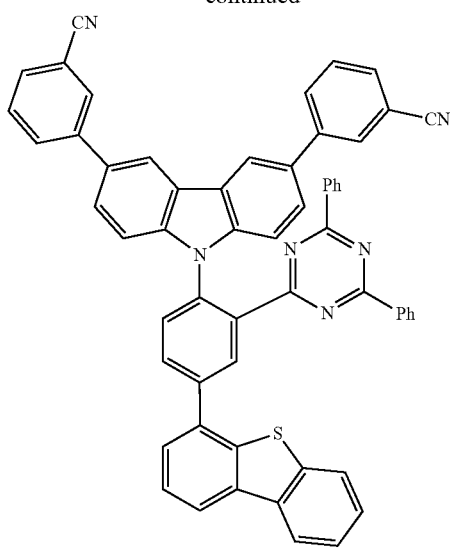
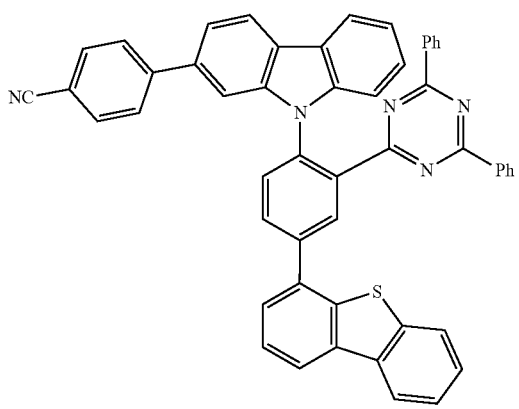
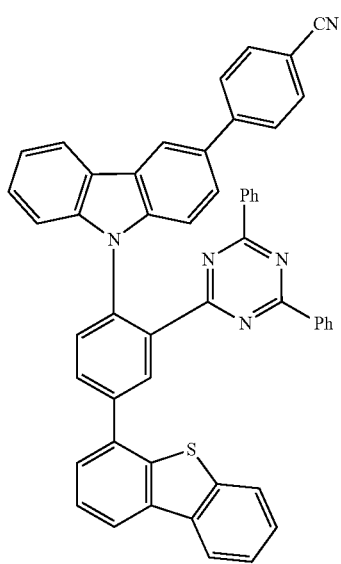
216
-continued
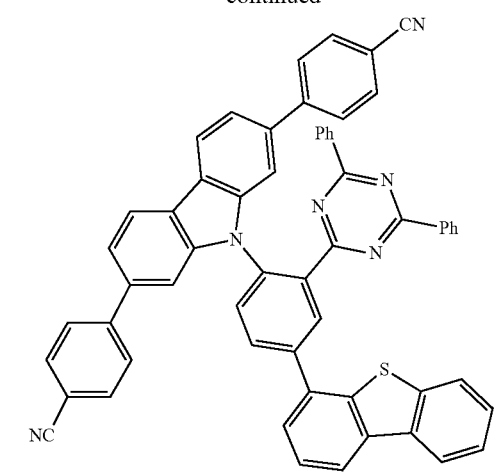
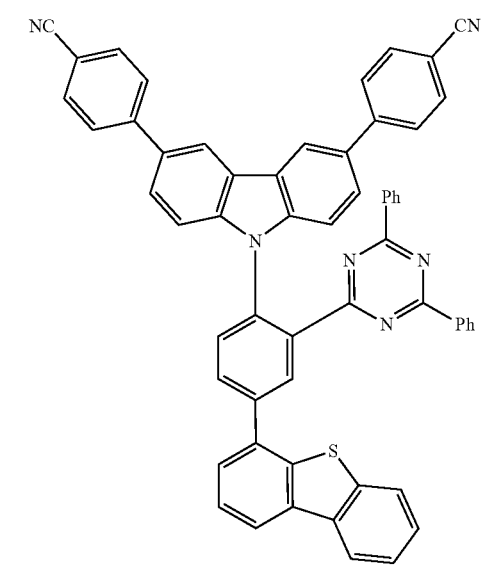
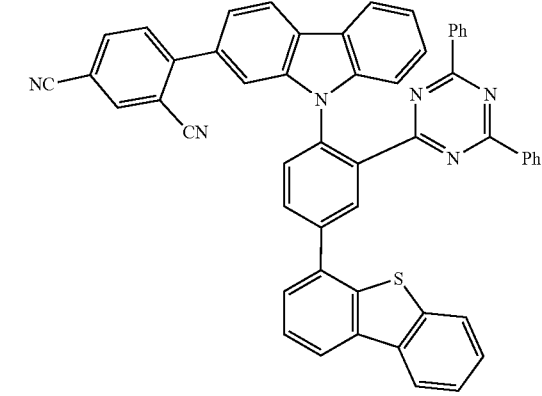

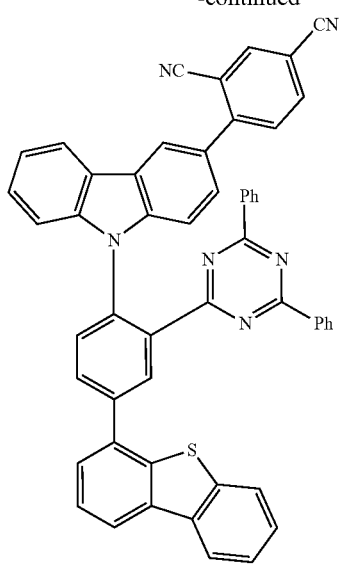
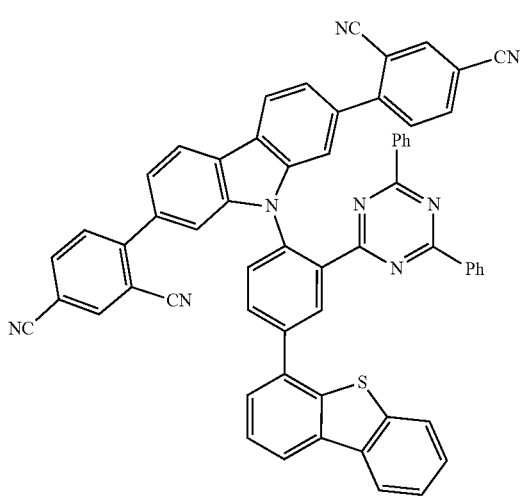
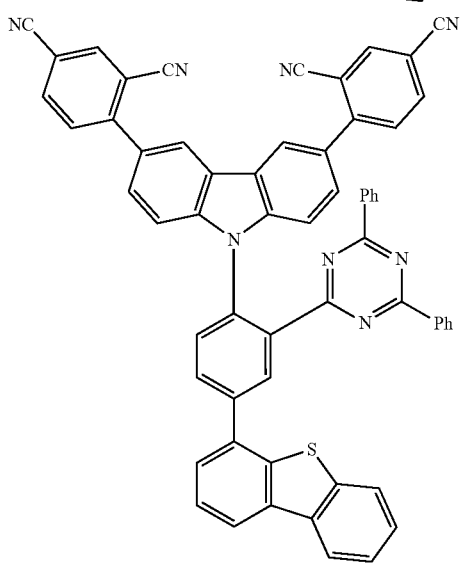
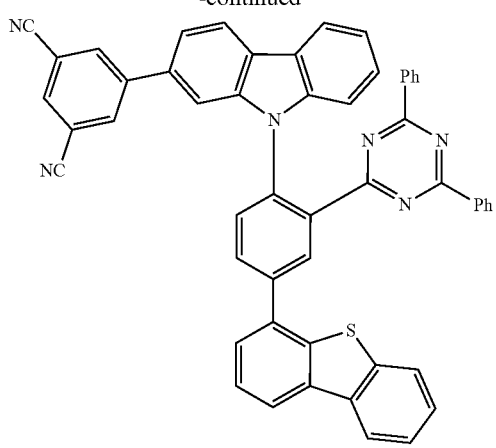
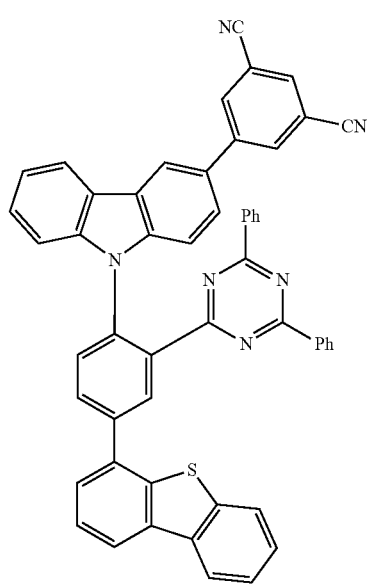
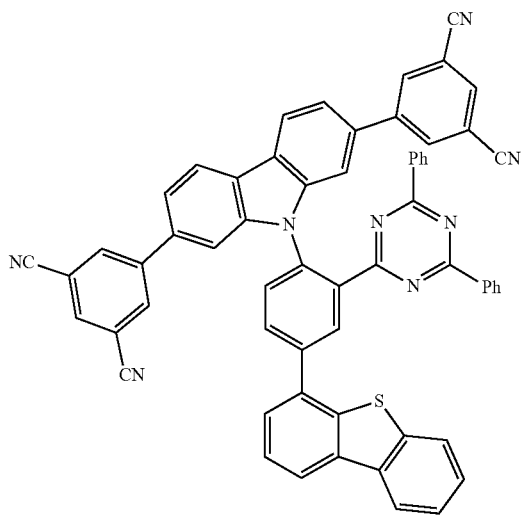

219
-continued
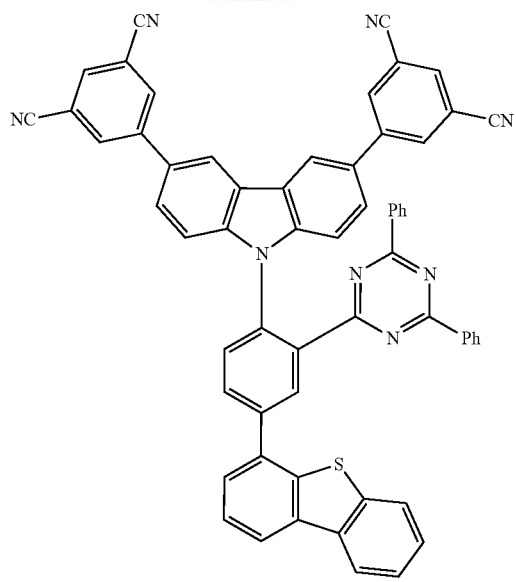
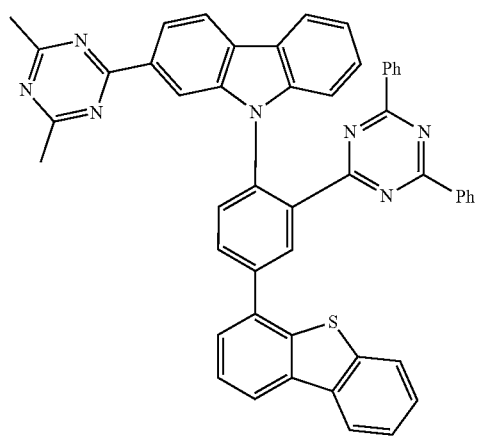
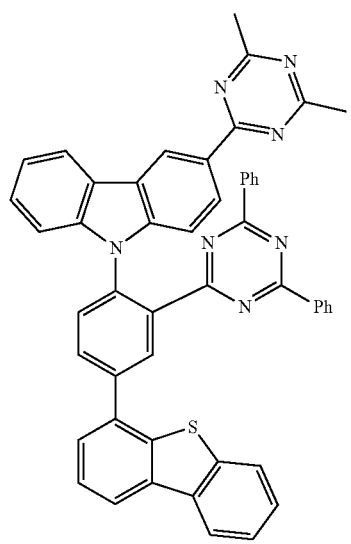
220
-continued
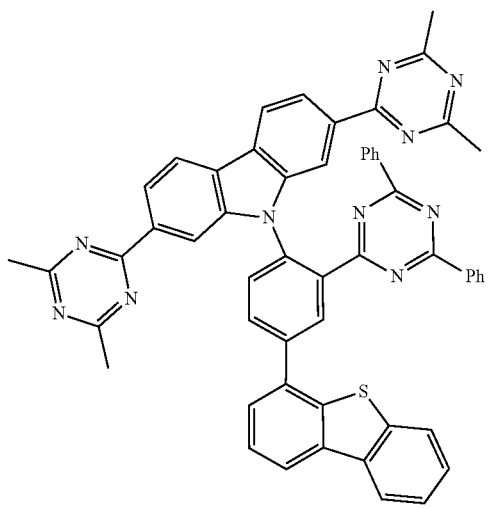
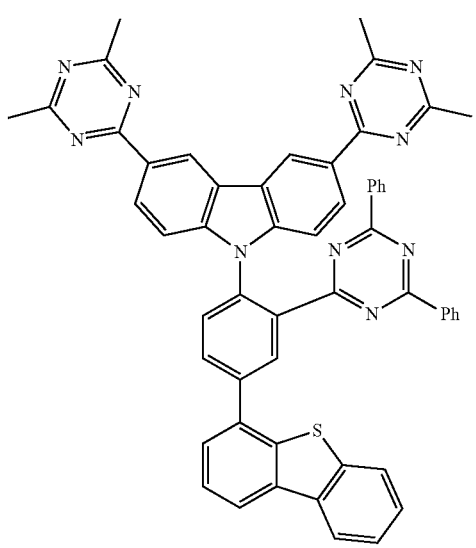
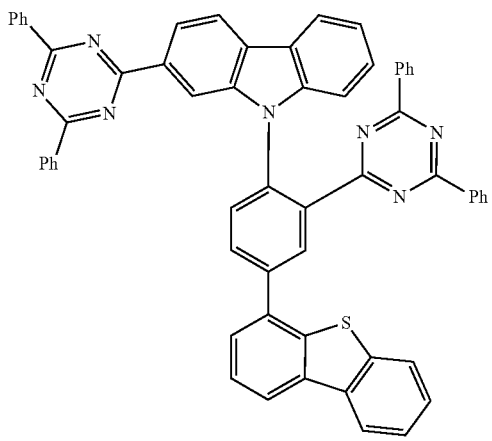

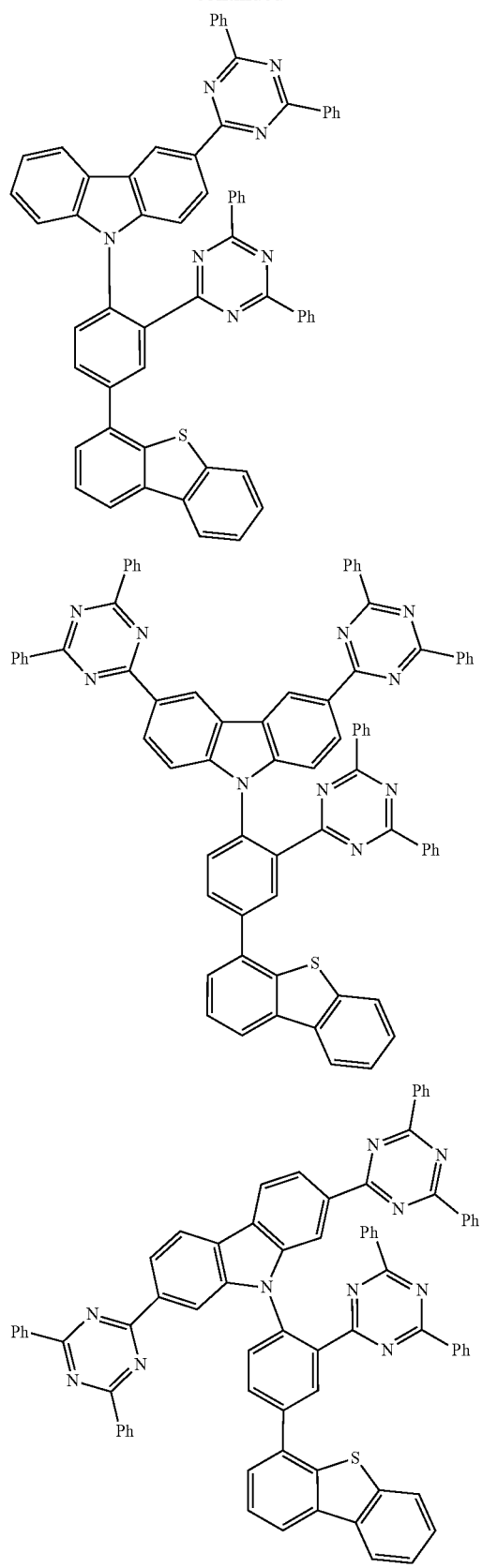
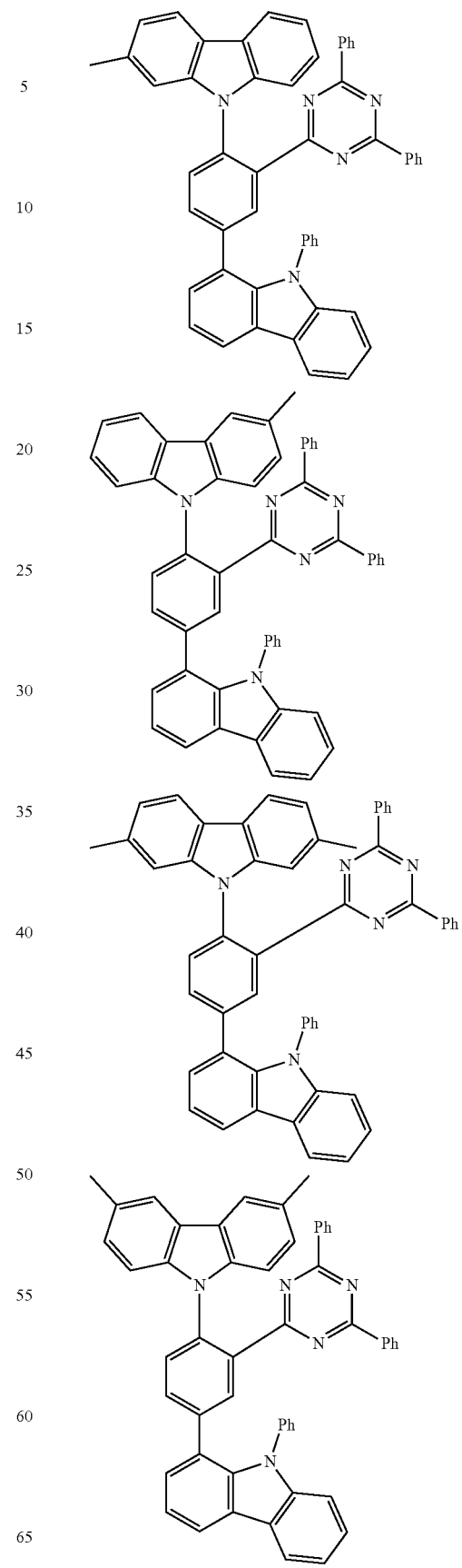

223
-continued
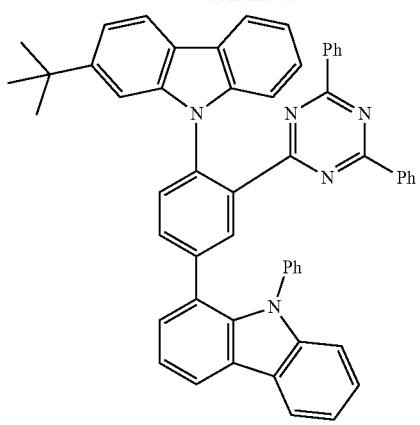
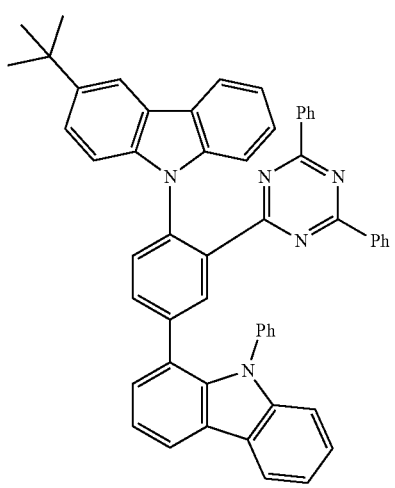
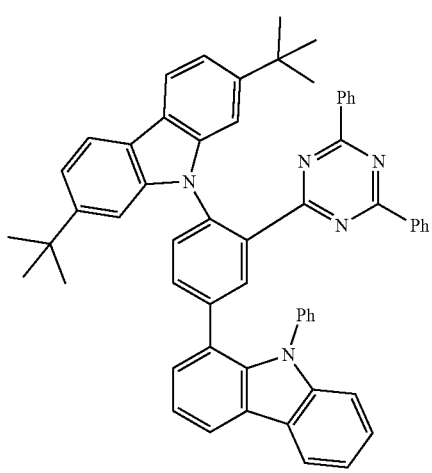
224
-continued
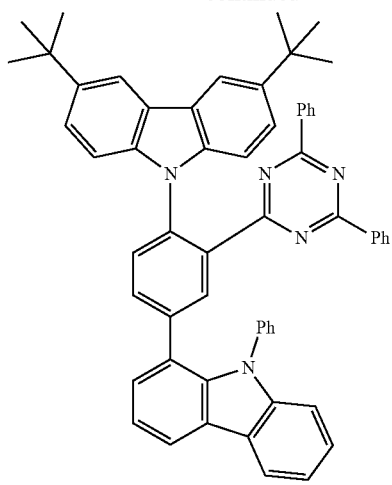
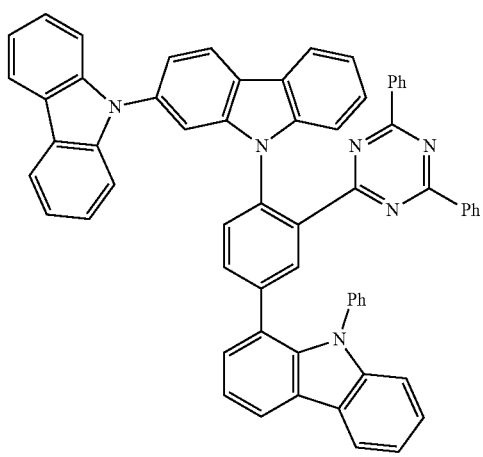
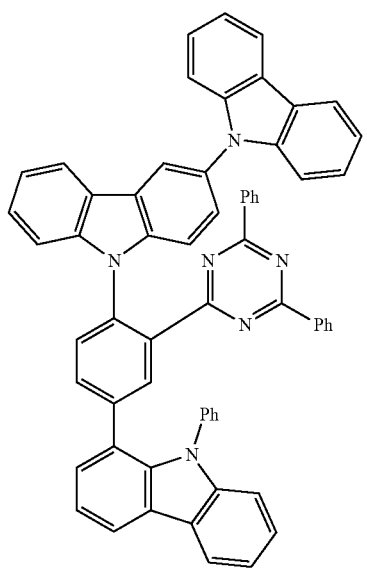

225
-continued
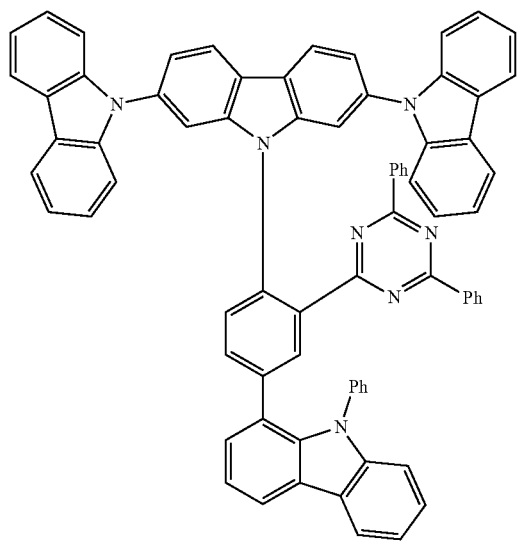
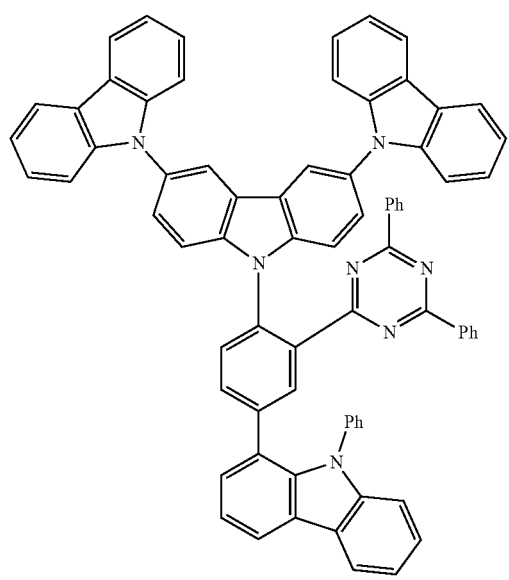
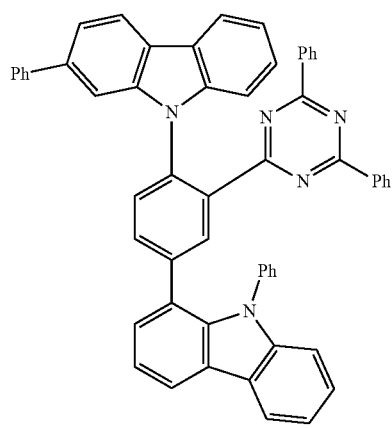
226
-continued
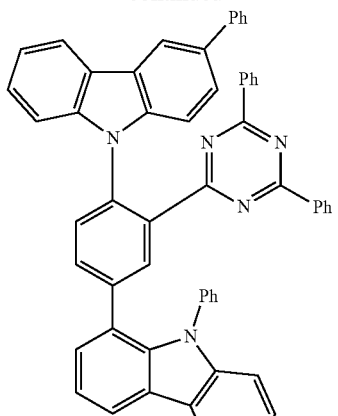
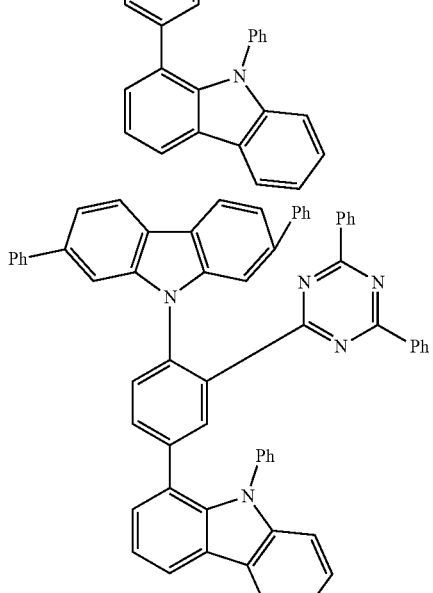
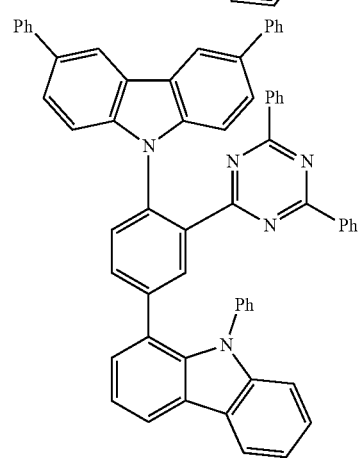
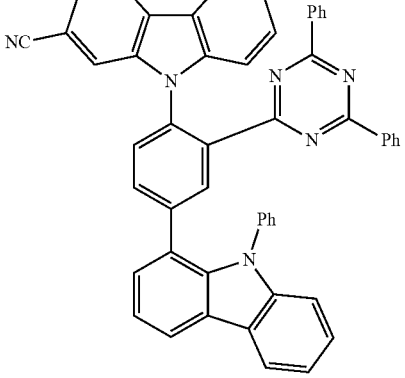

-continued
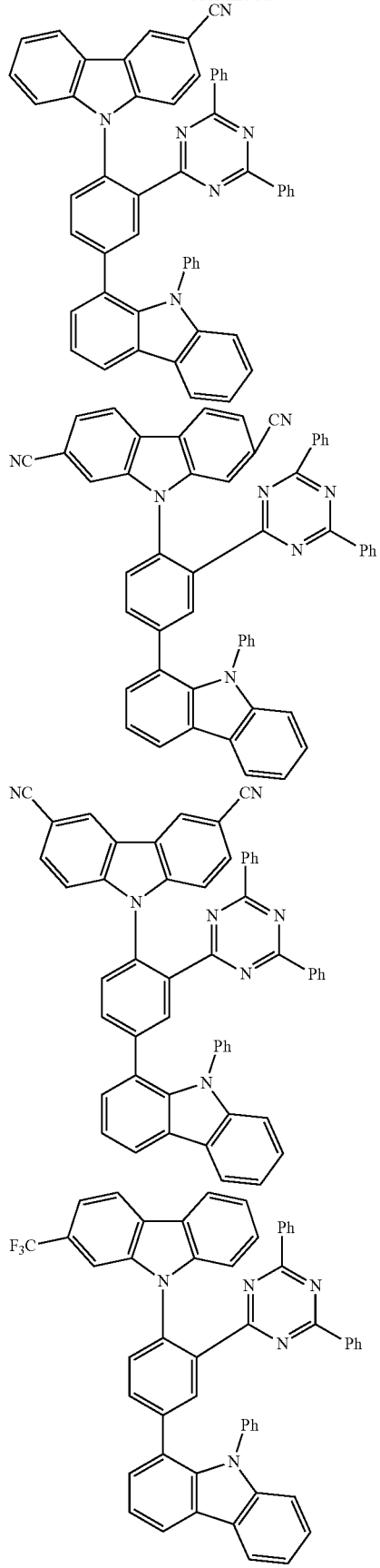
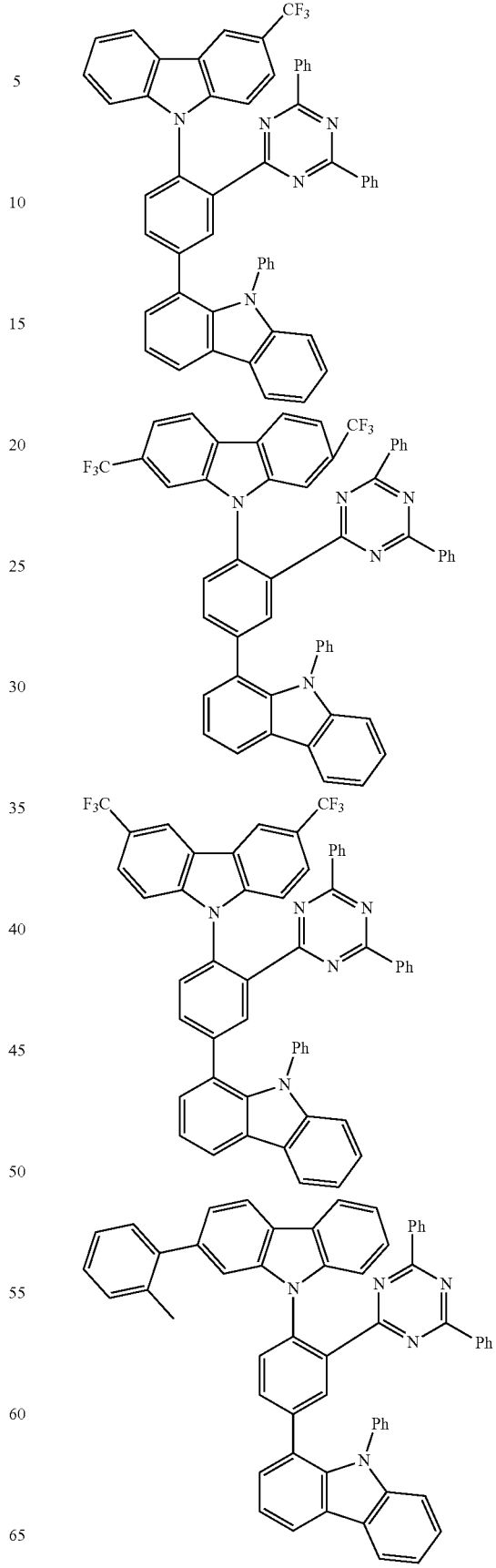

229
-continued
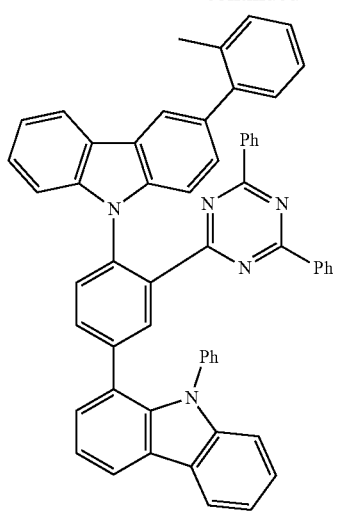
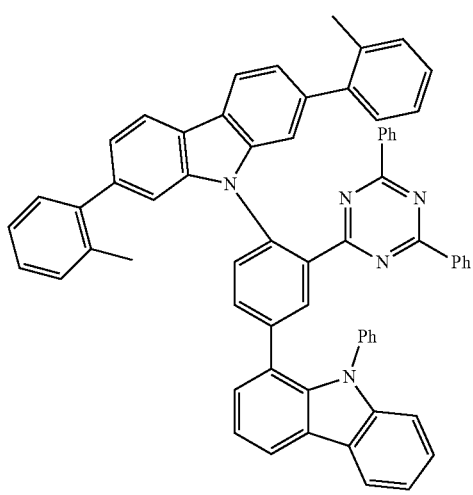
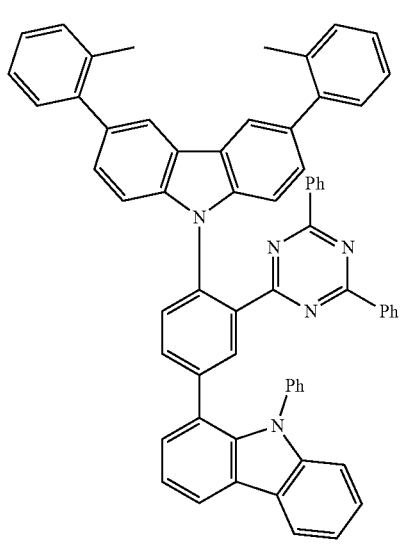
230
-continued
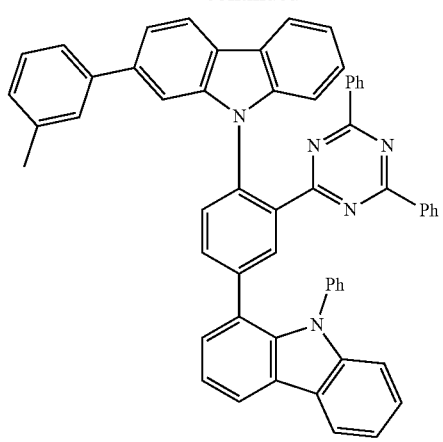
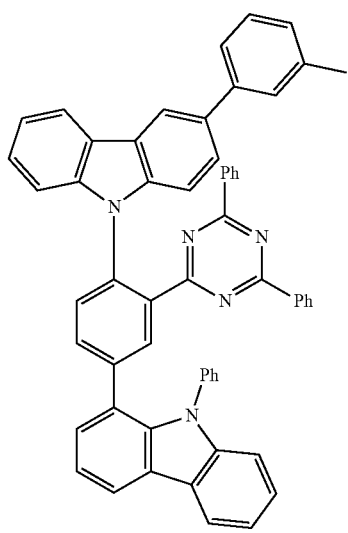
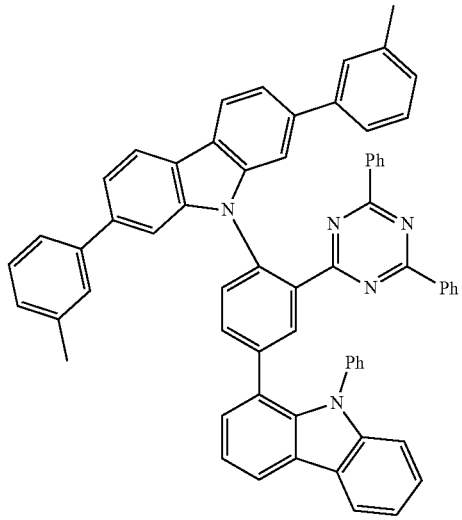

231
-continued
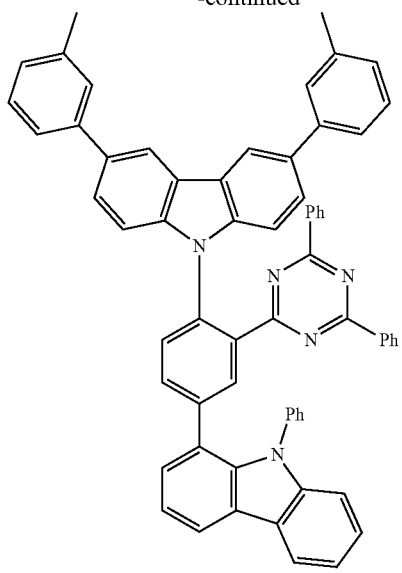
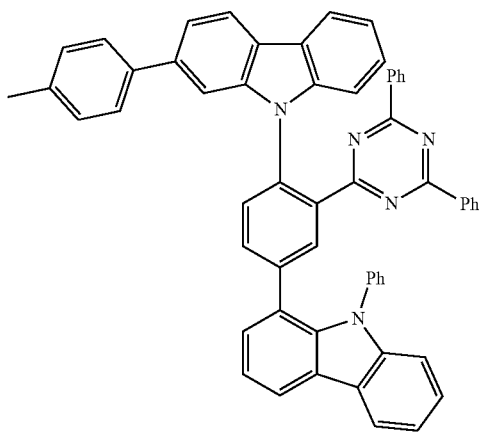
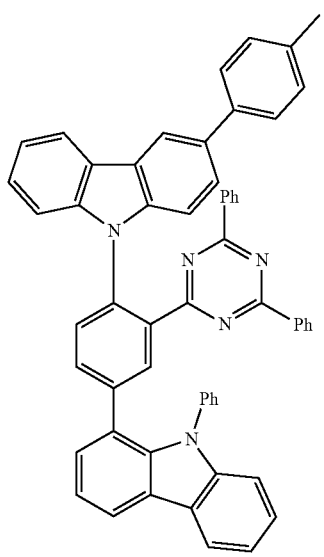
232
-continued
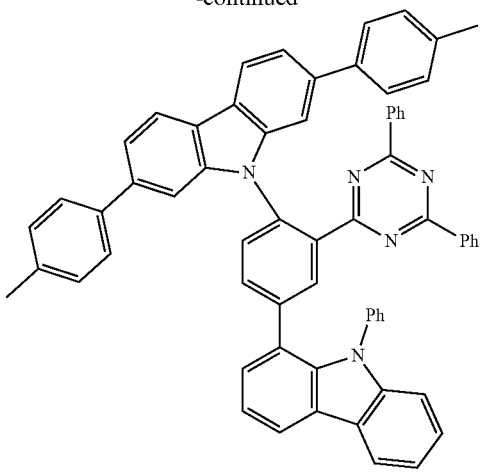
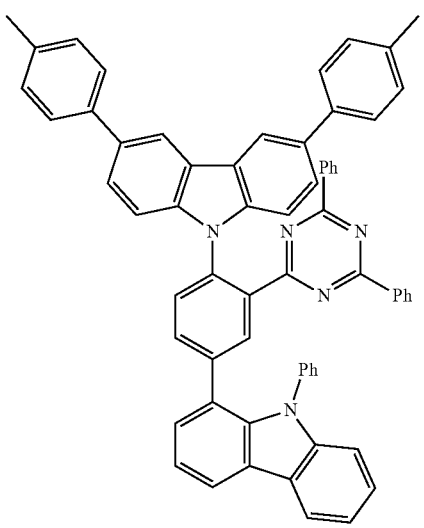
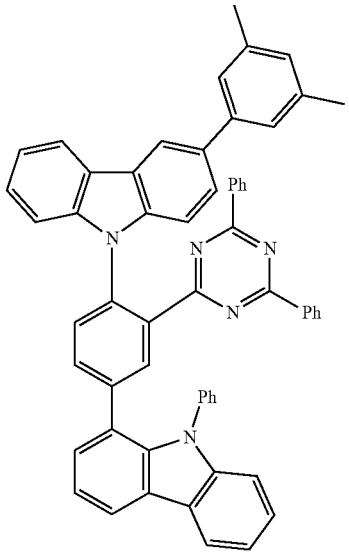

233
-continued
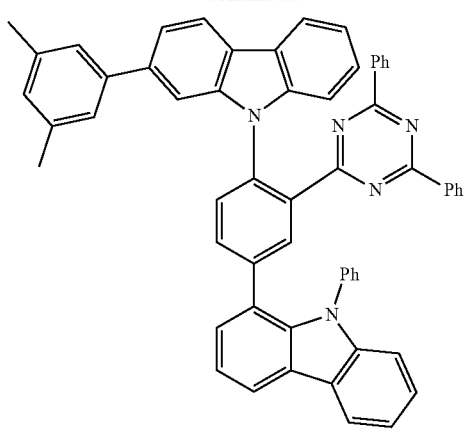
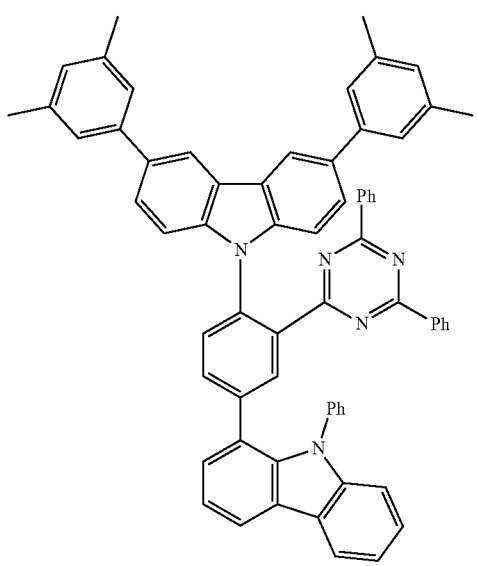
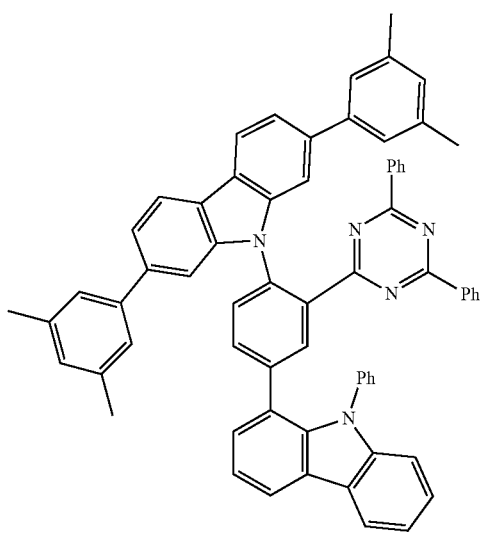
234
-continued
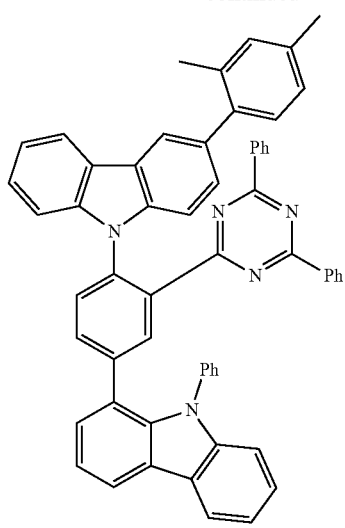
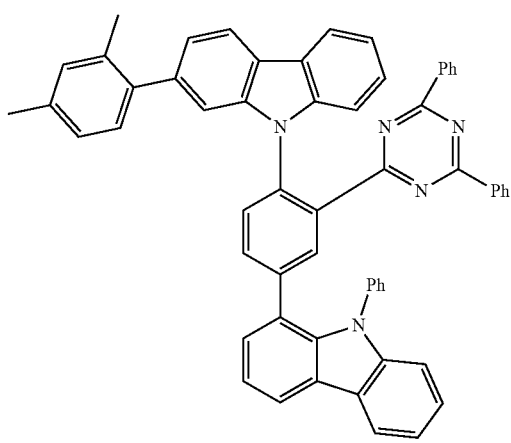
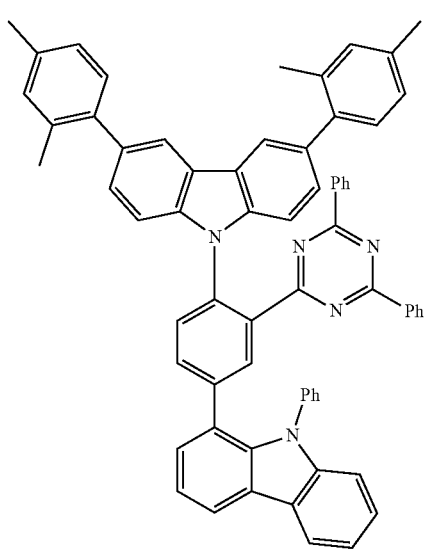

235
-continued
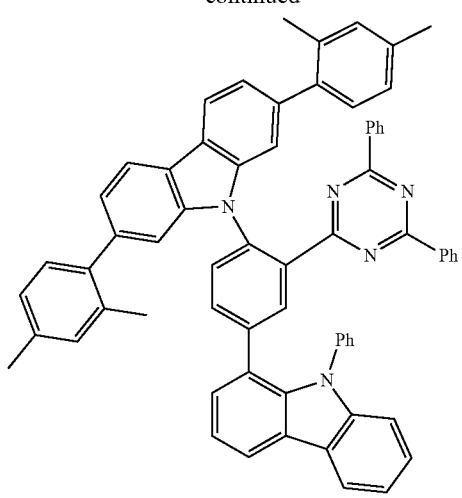
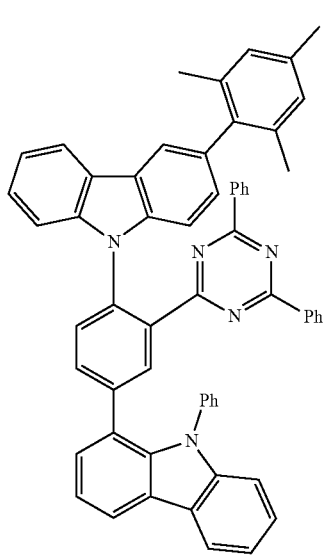
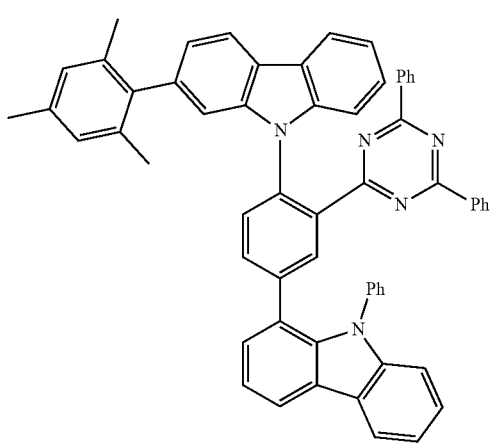
236
-continued
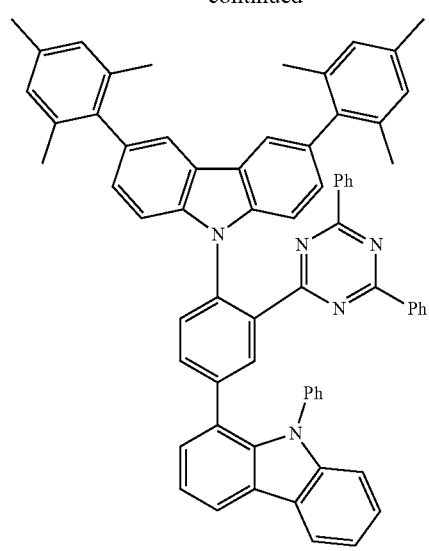
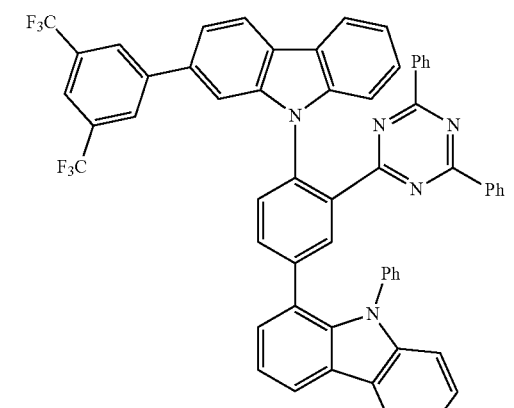

237
-continued
238
-continued
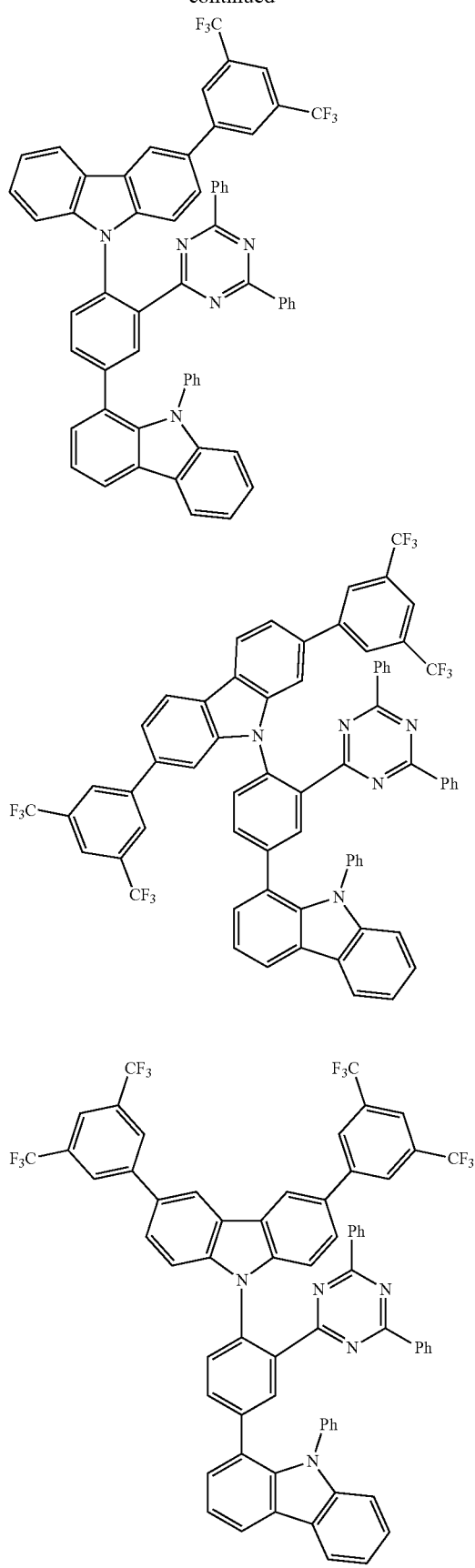
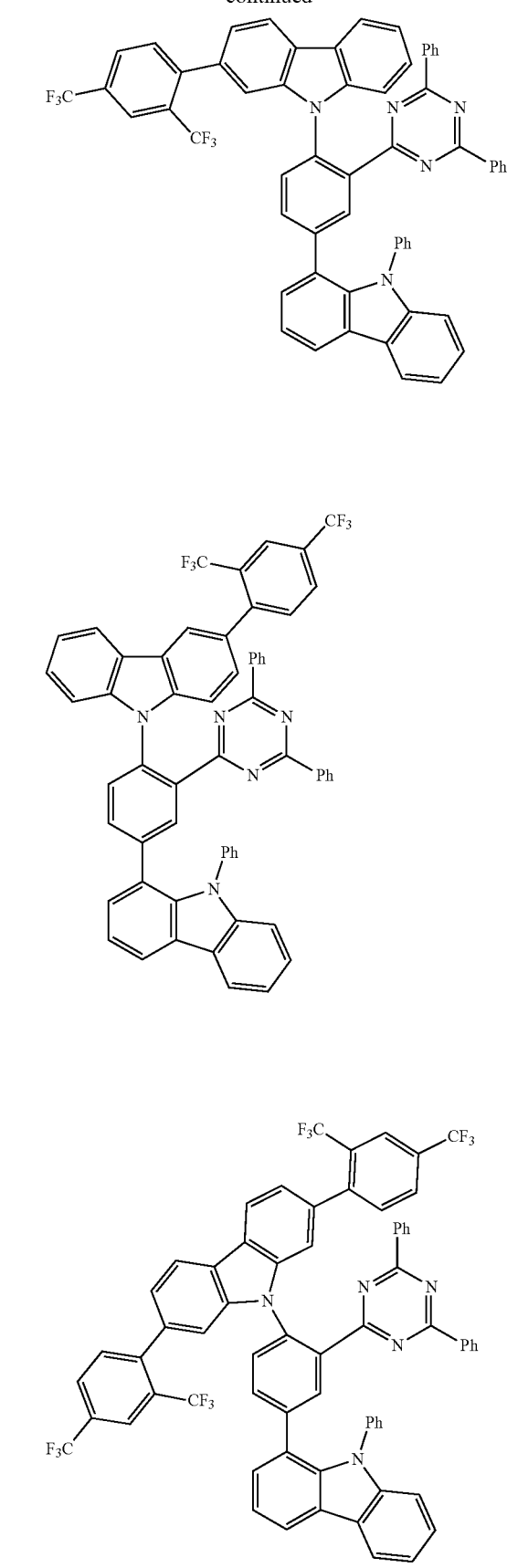

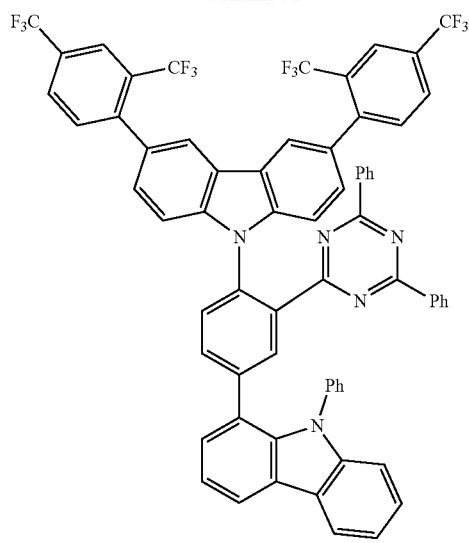
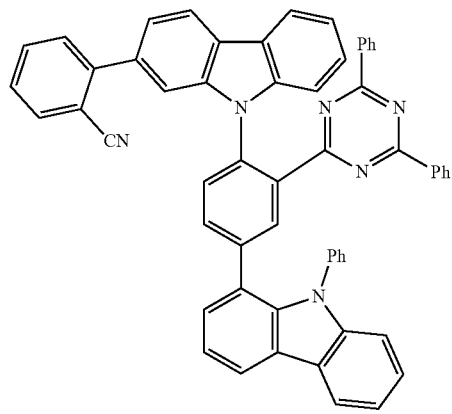
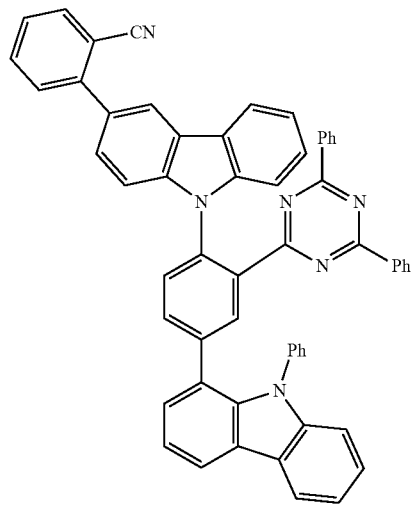
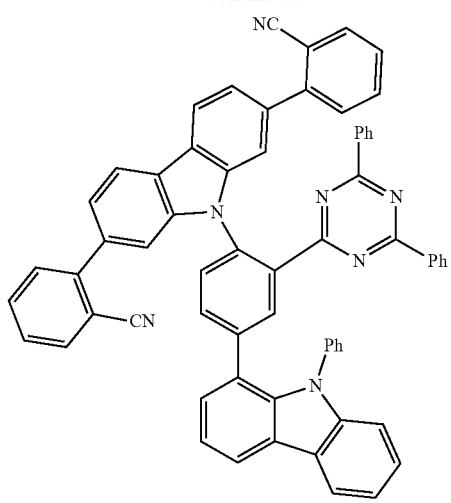
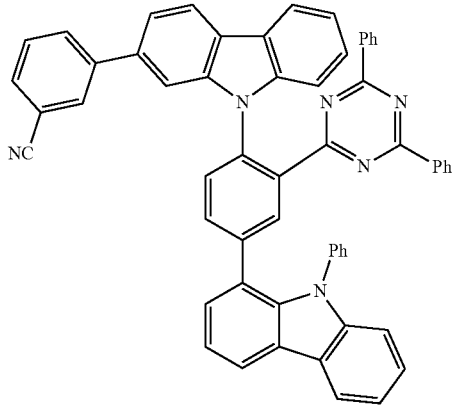

241
-continued
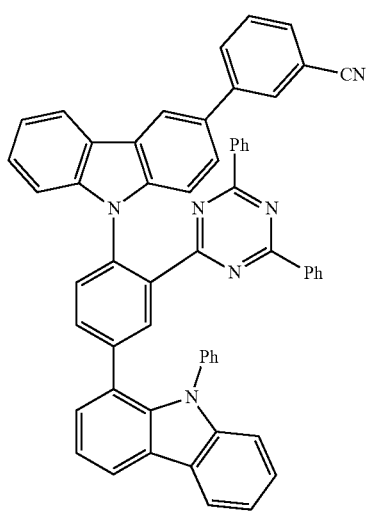
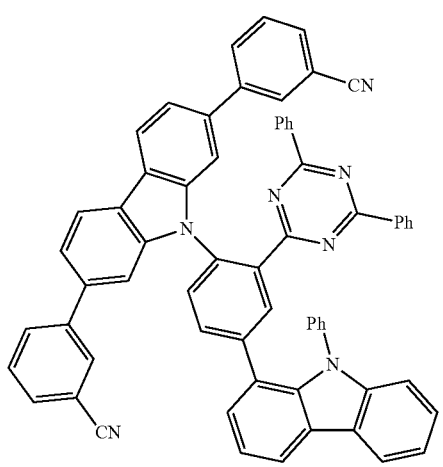
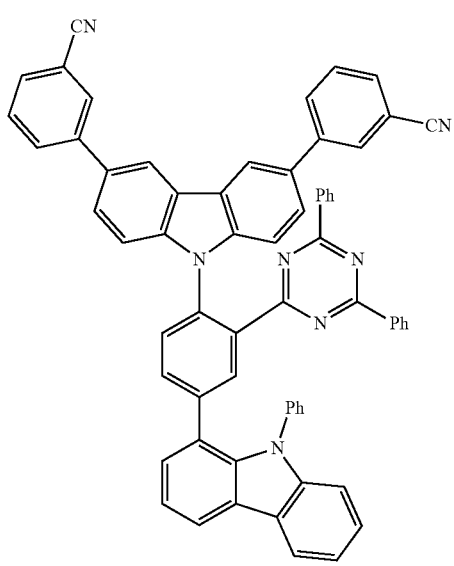
242
-continued
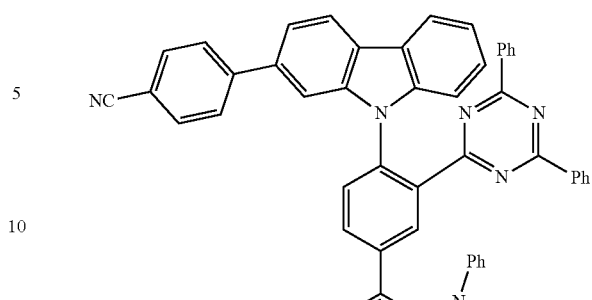
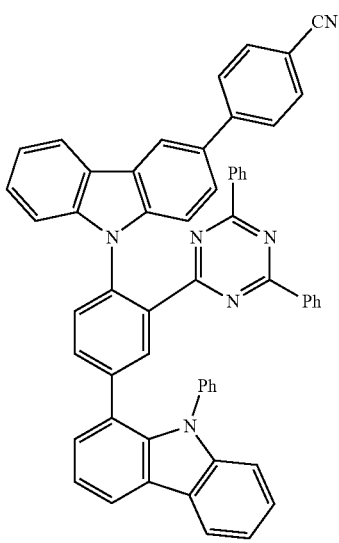
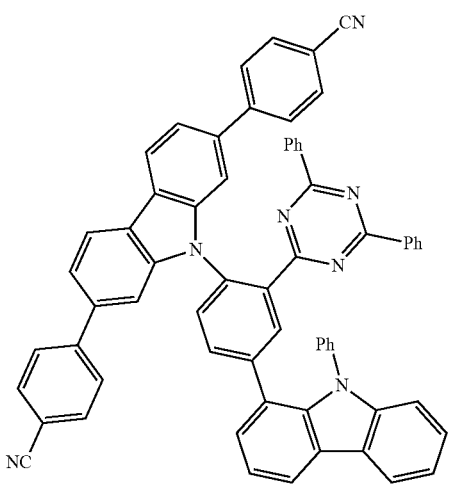

243
-continued
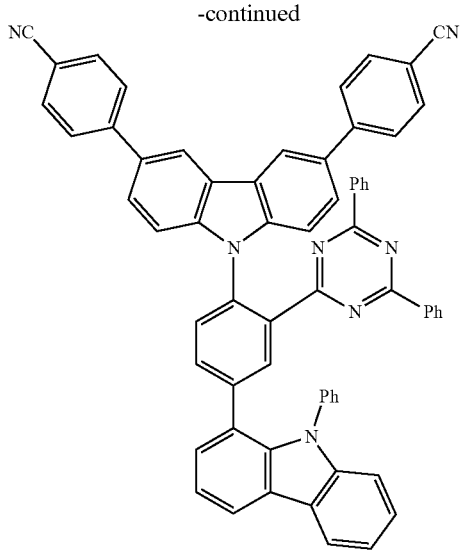
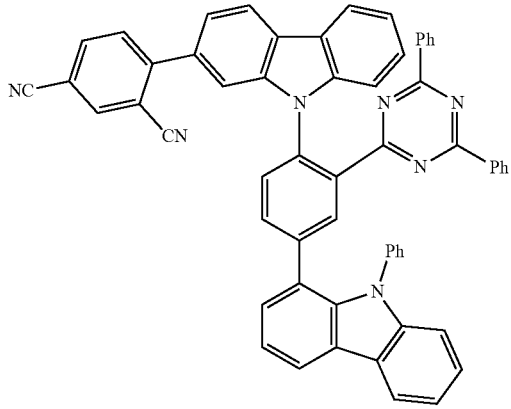
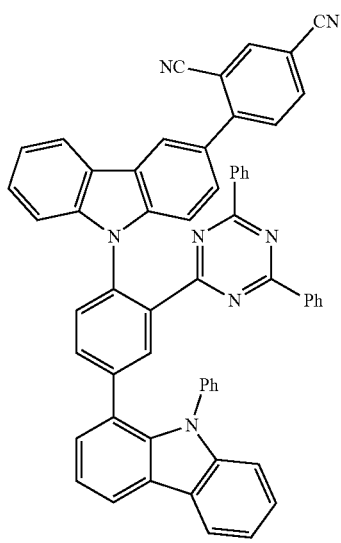
244
-continued
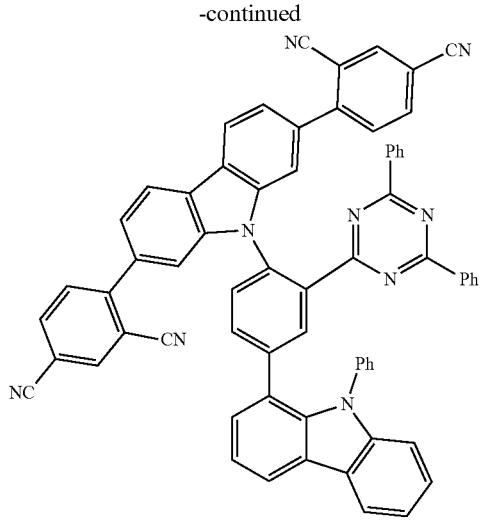
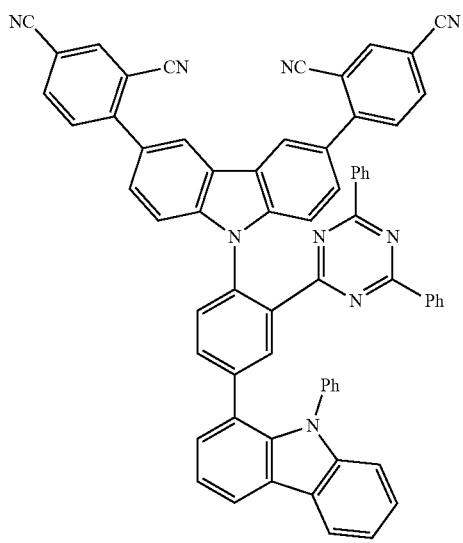
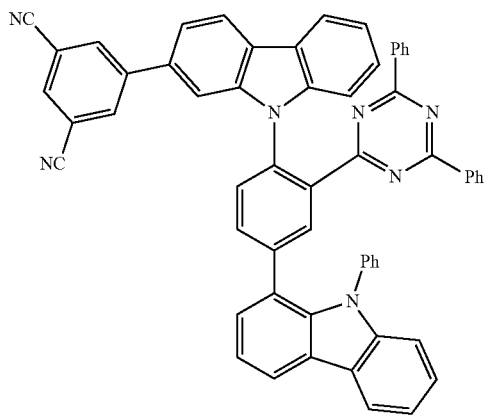

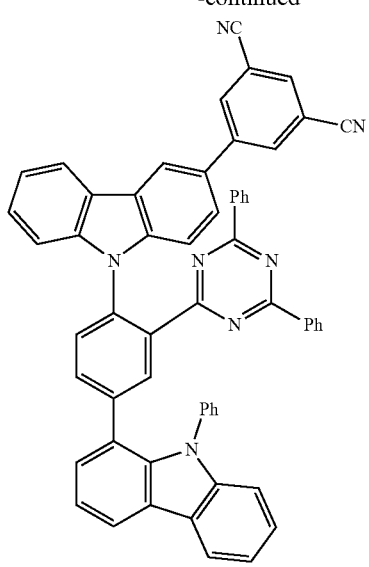
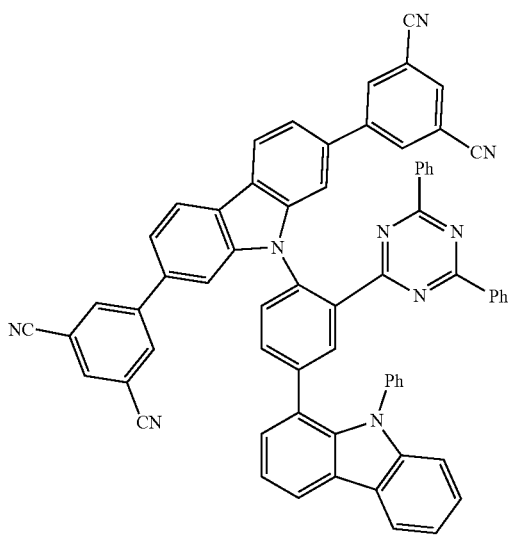
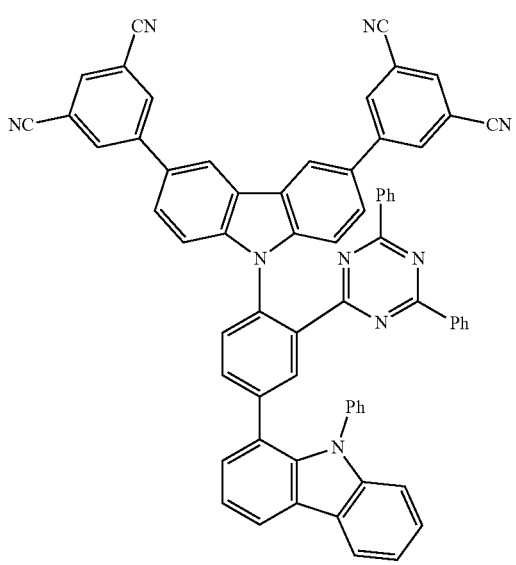
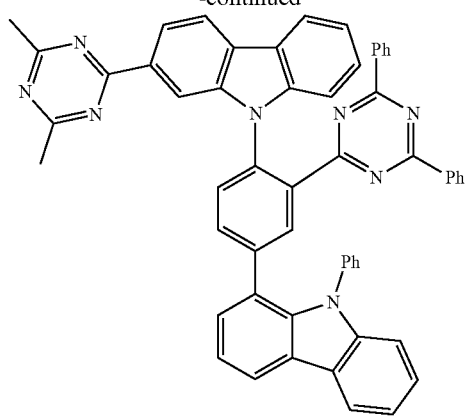
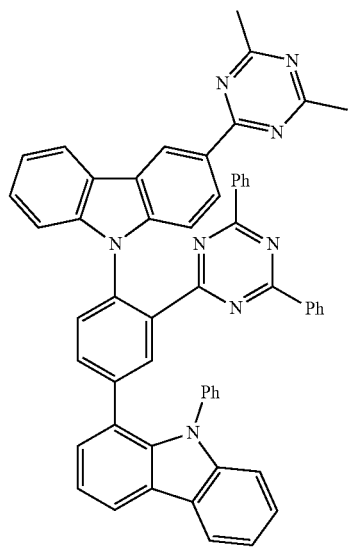
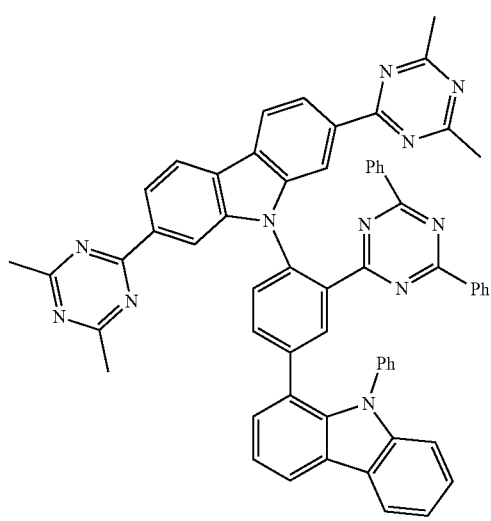

247
-continued
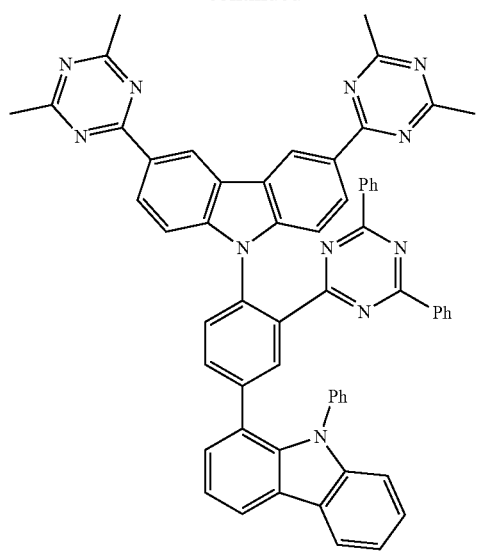
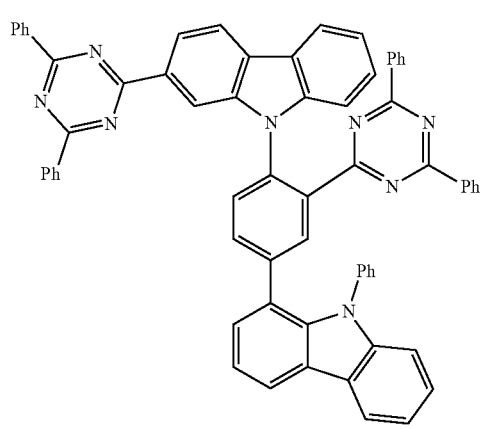
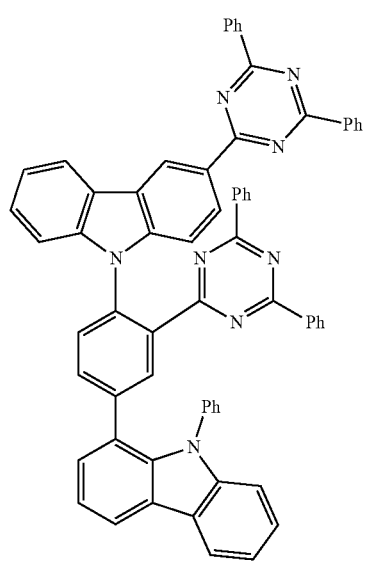
248
-continued
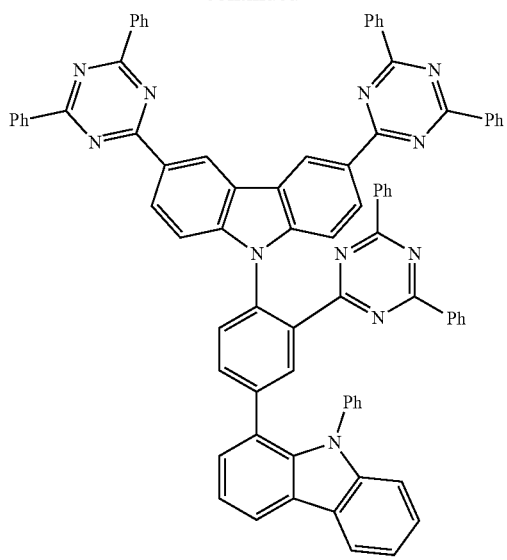
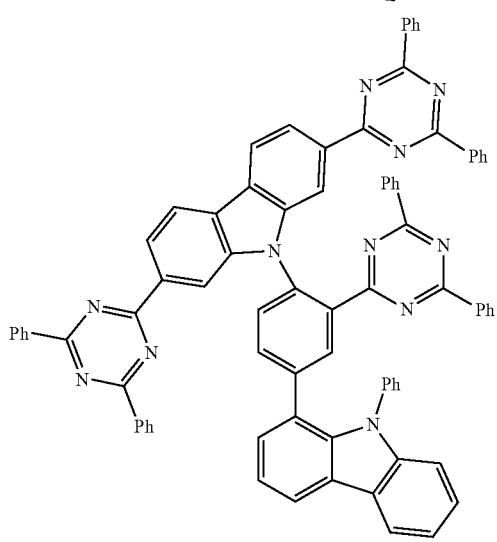
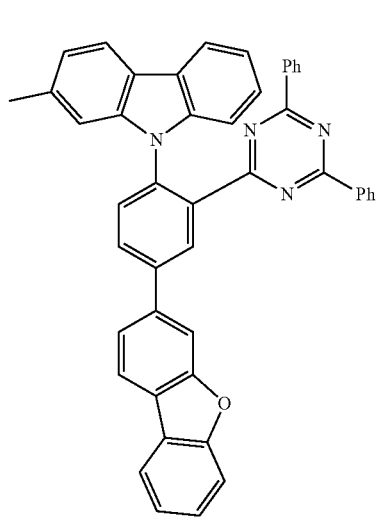

249
-continued
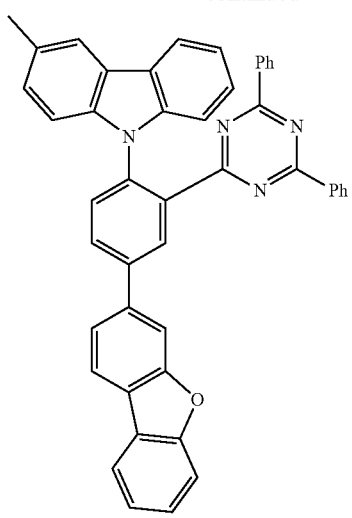
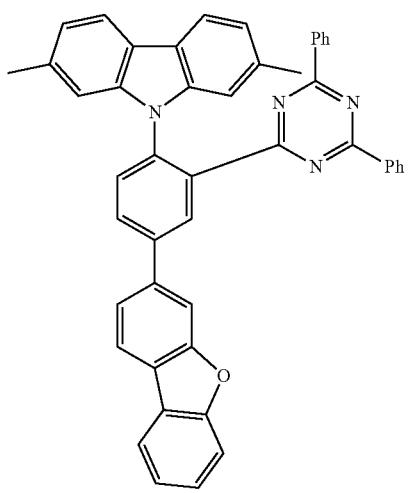
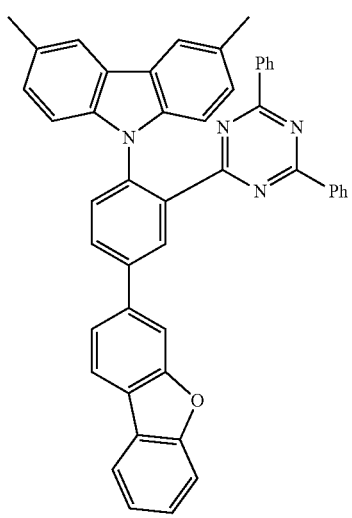
250
-continued
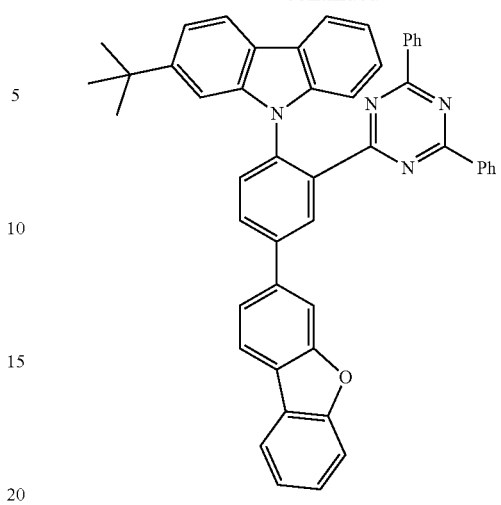
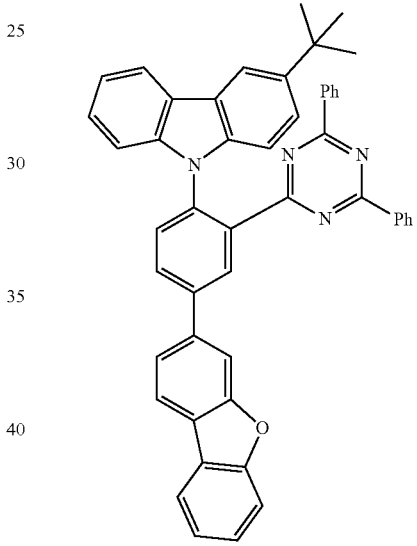
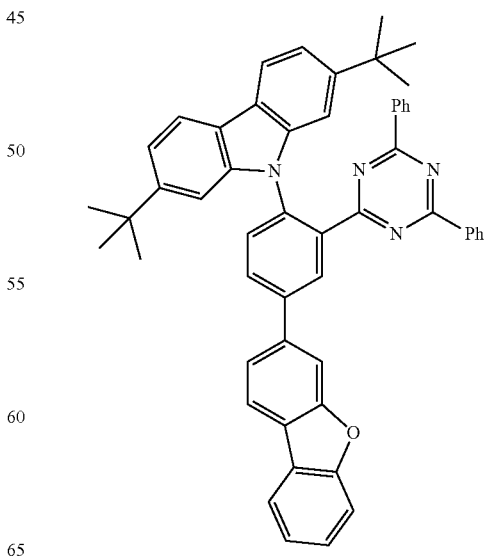

251
-continued
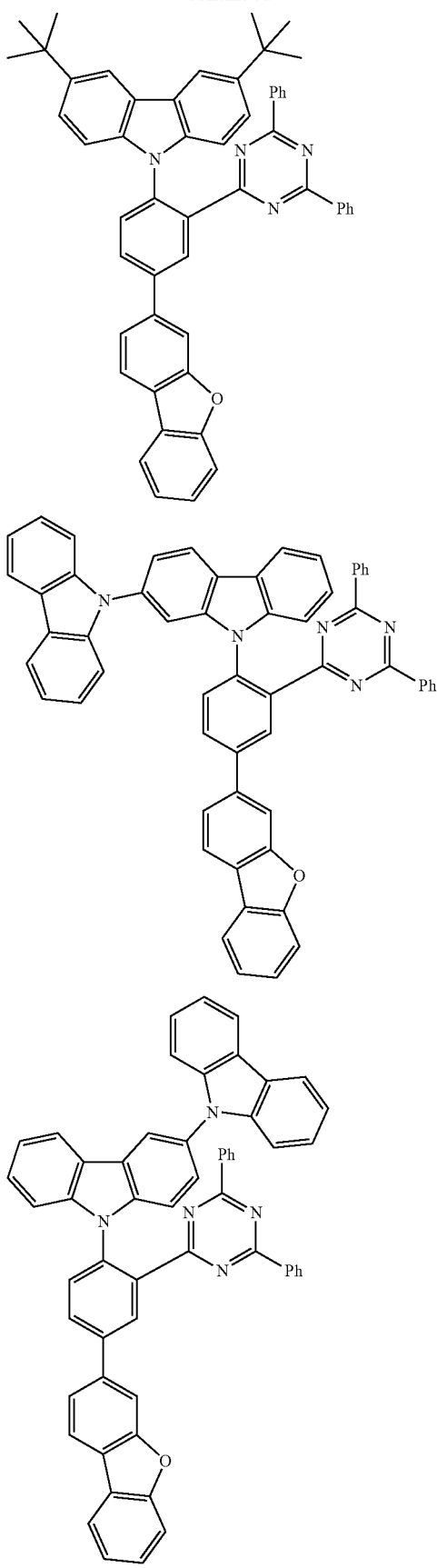
252
-continued
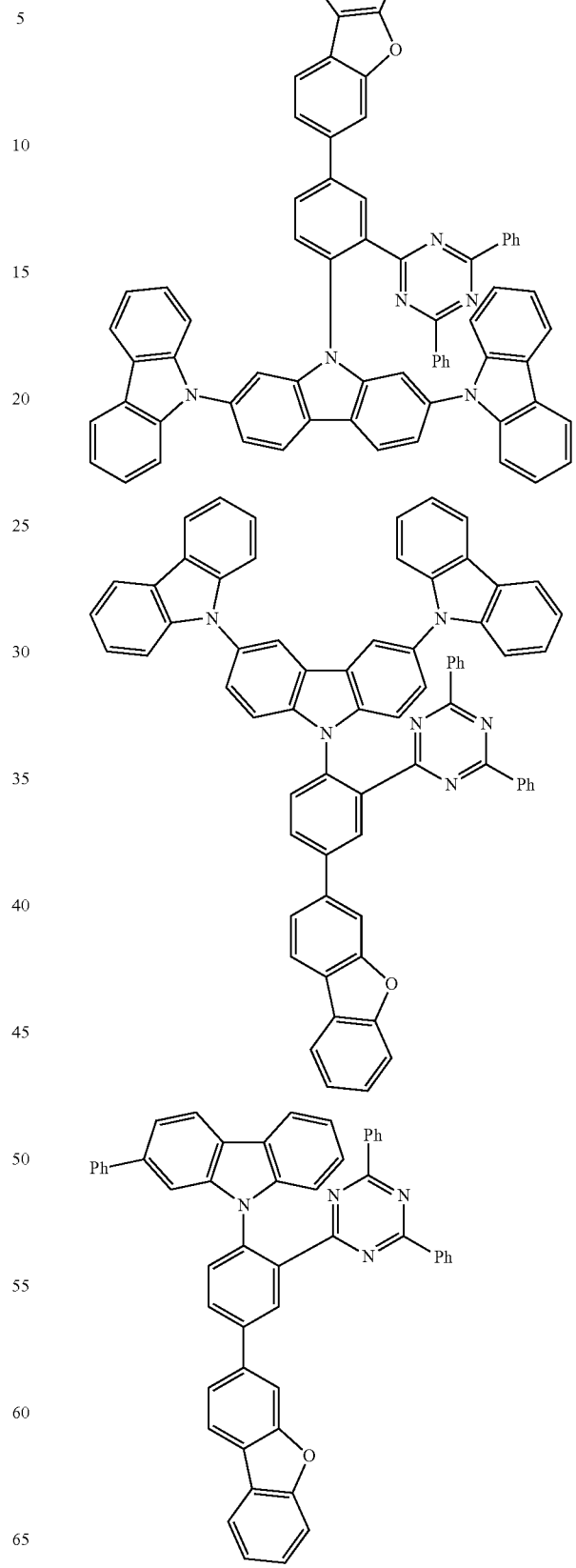

253
-continued
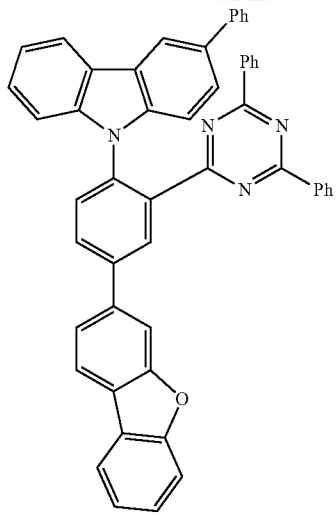
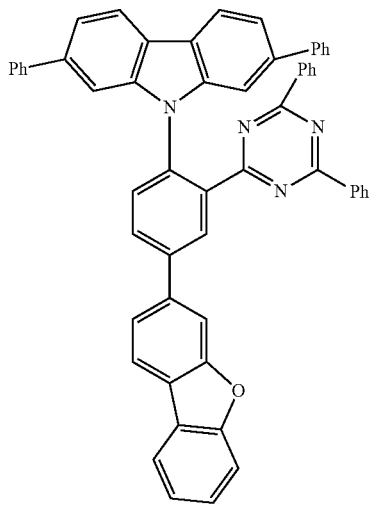
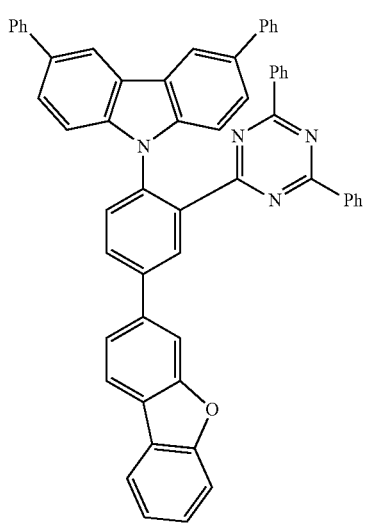
254
-continued
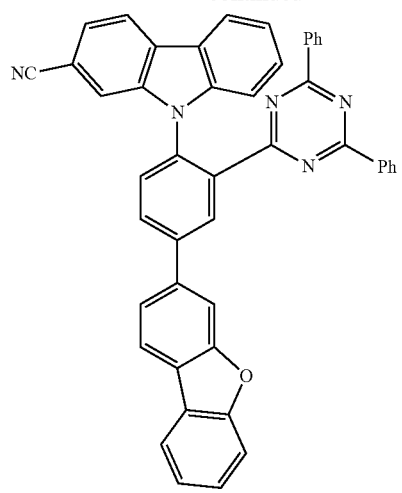
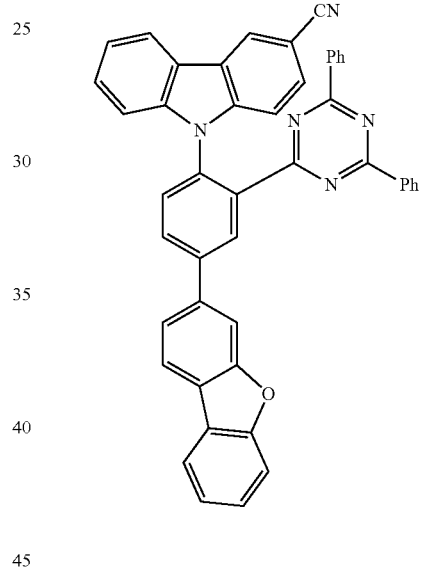
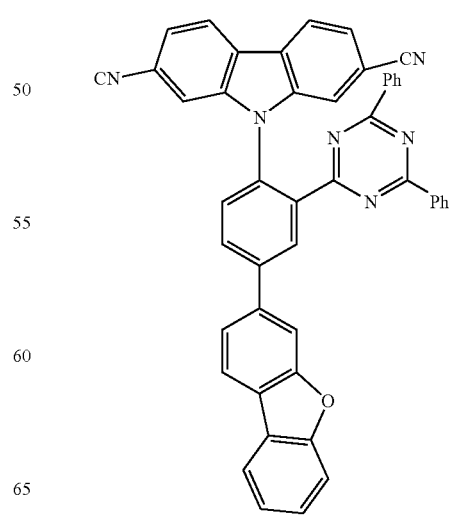

255
-continued
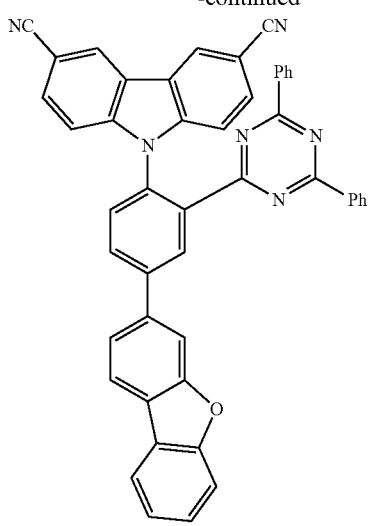
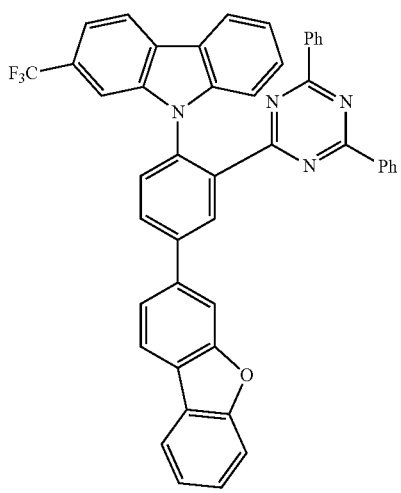
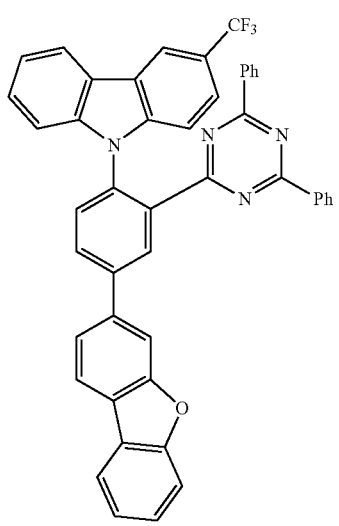
256
-continued
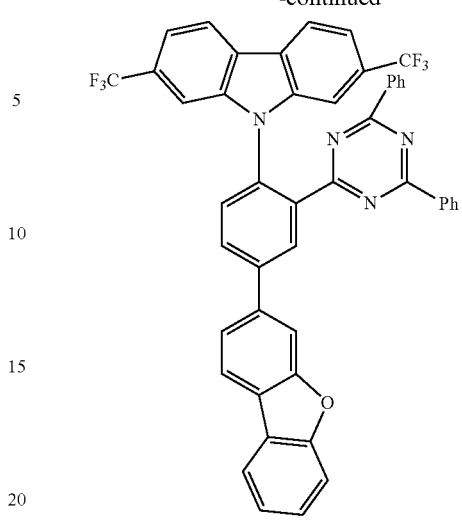
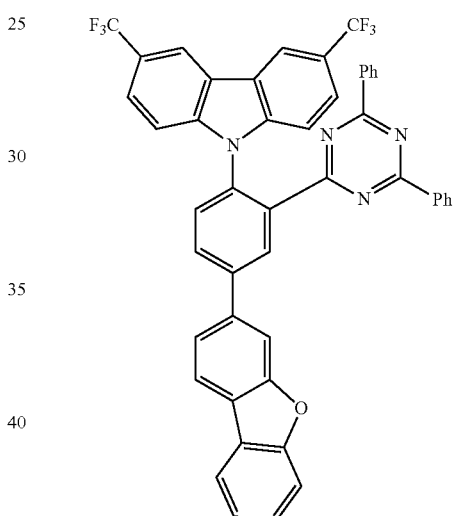
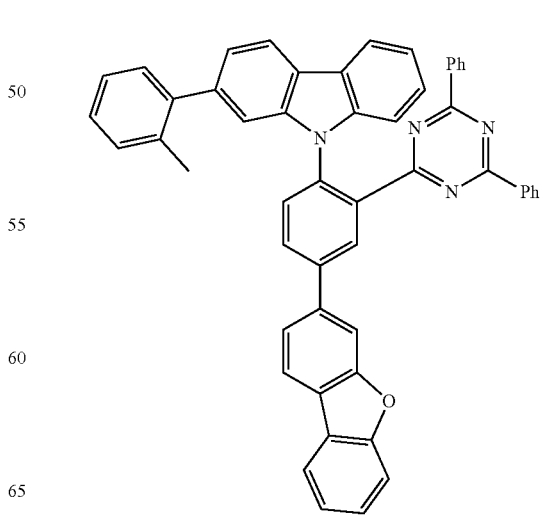

257 258
-continued -continued
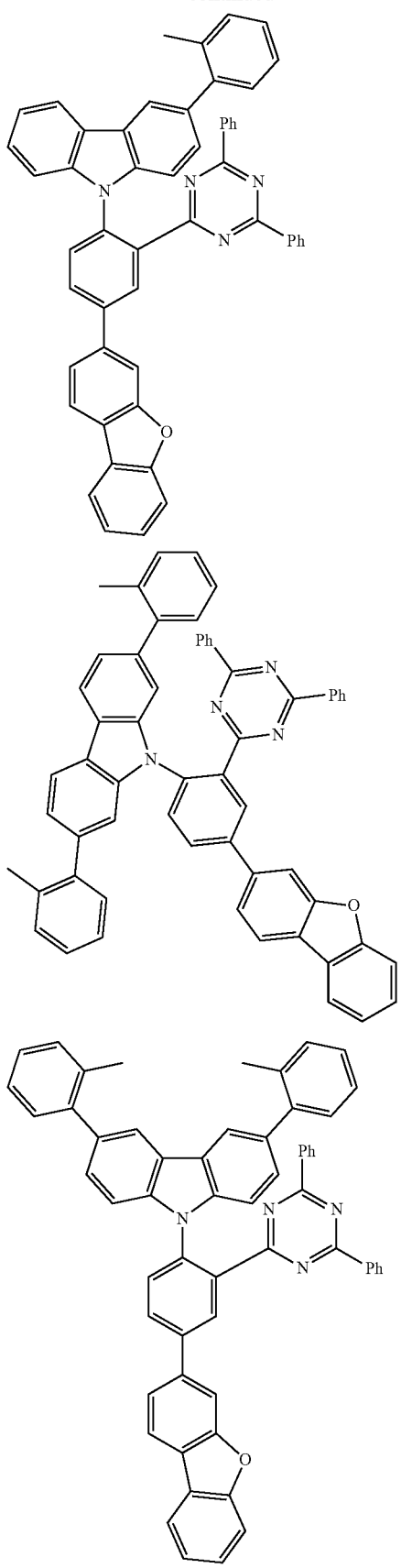
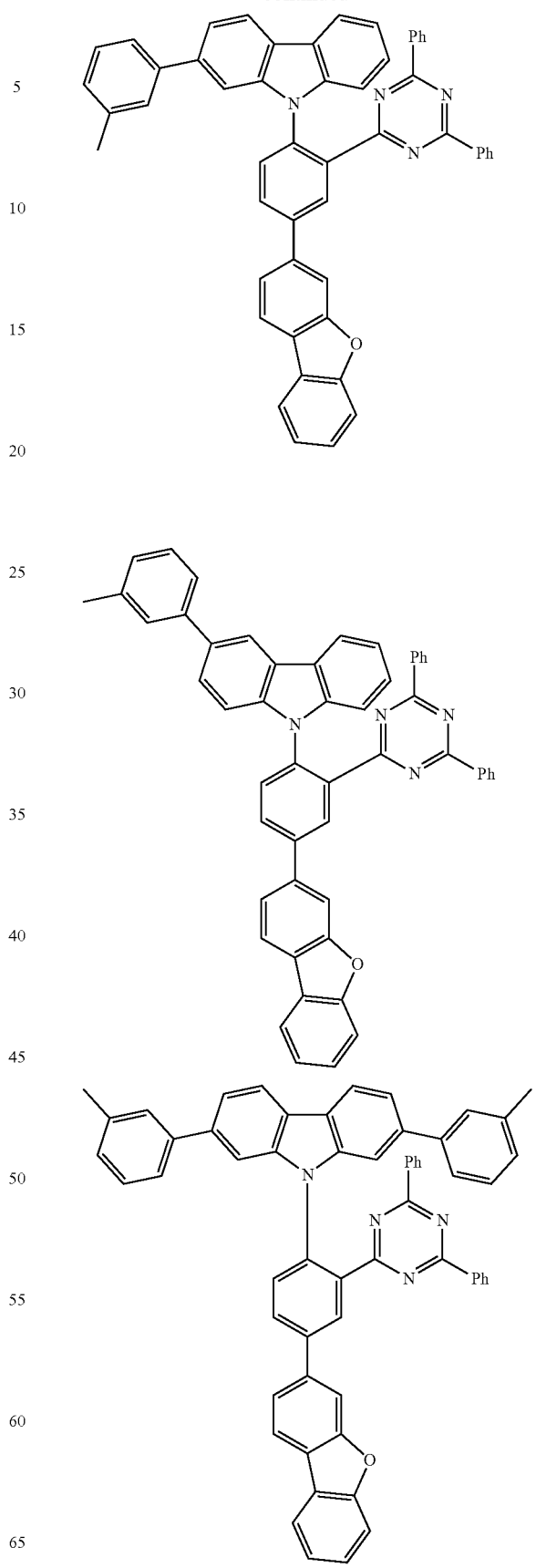

259
-continued
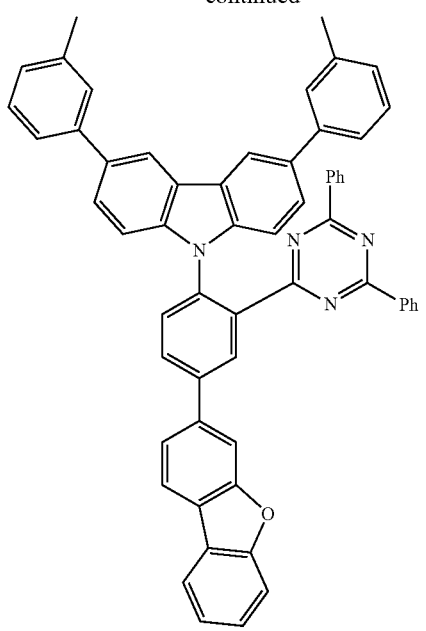
260
-continued
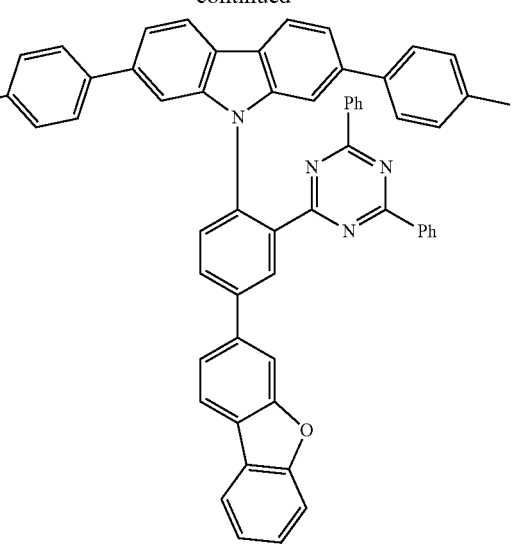
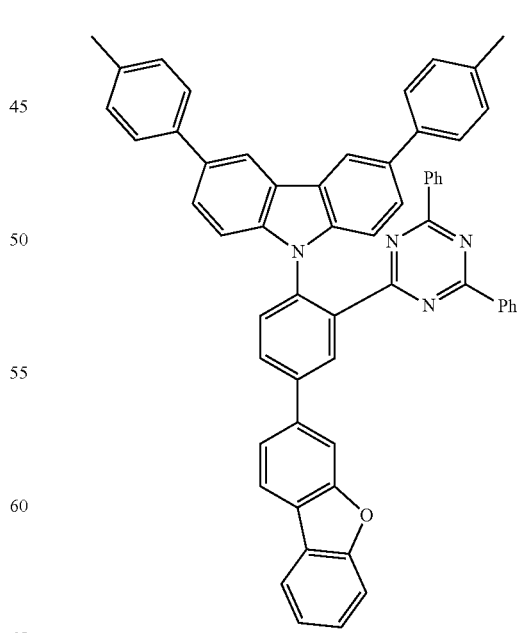

261
-continued
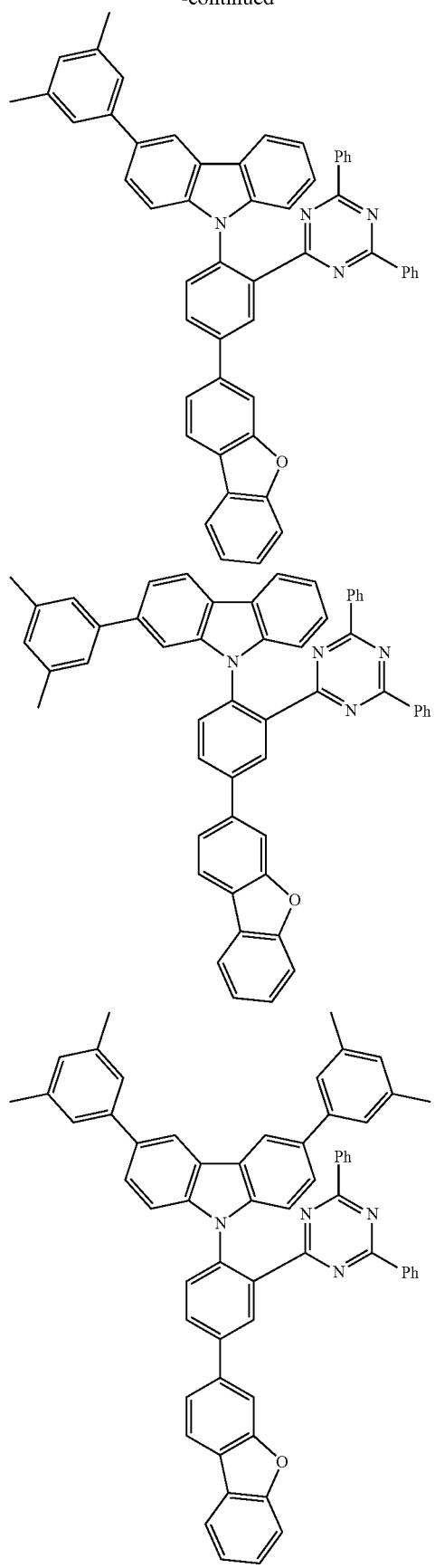
262
-continued
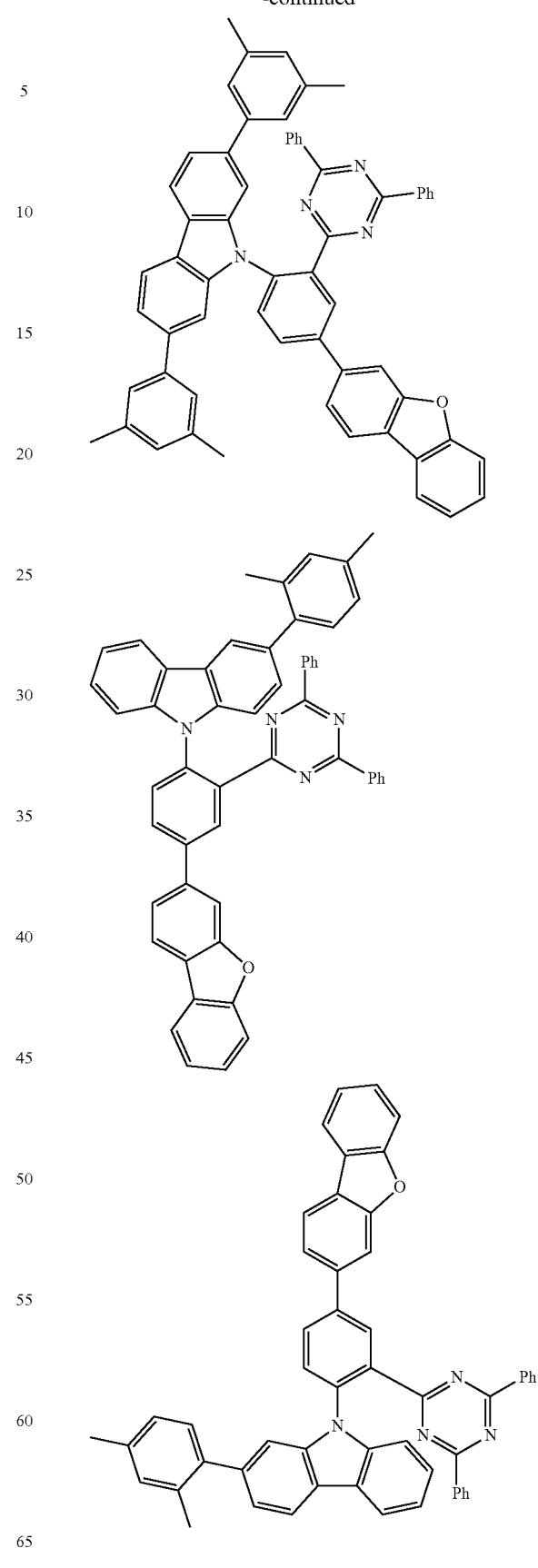

263
-continued
264
-continued
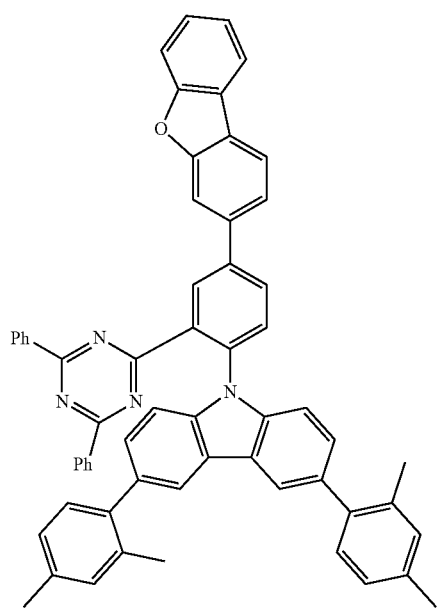
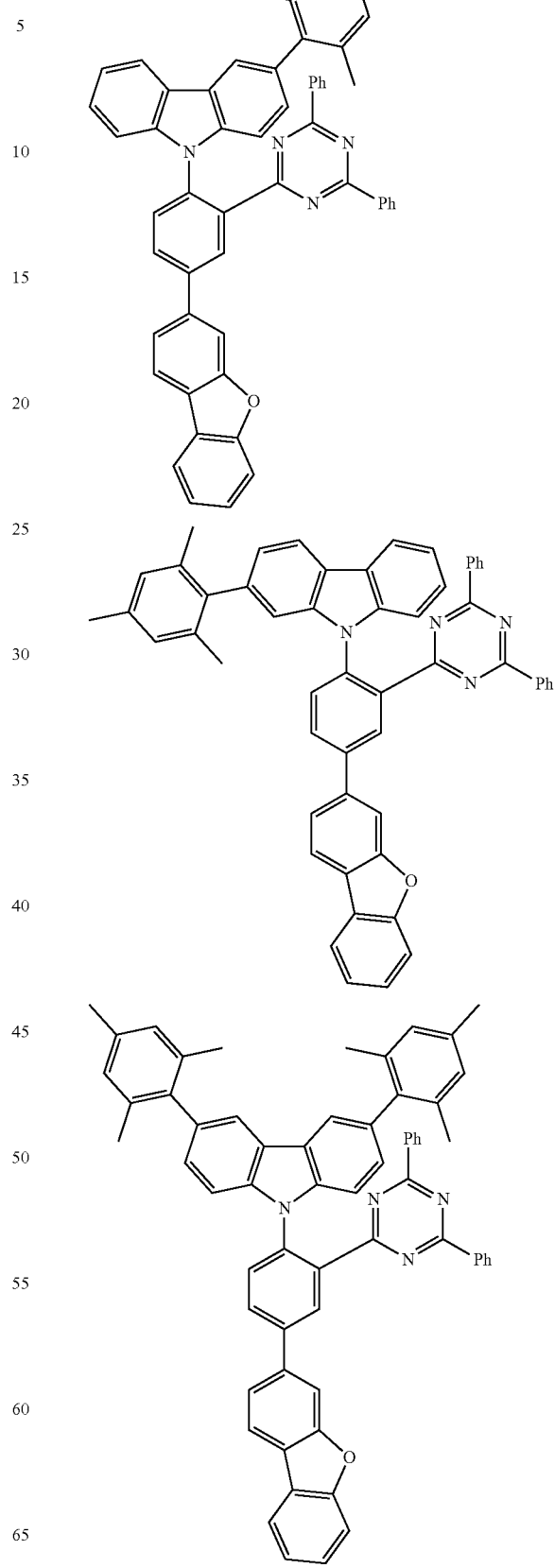

265
-continued
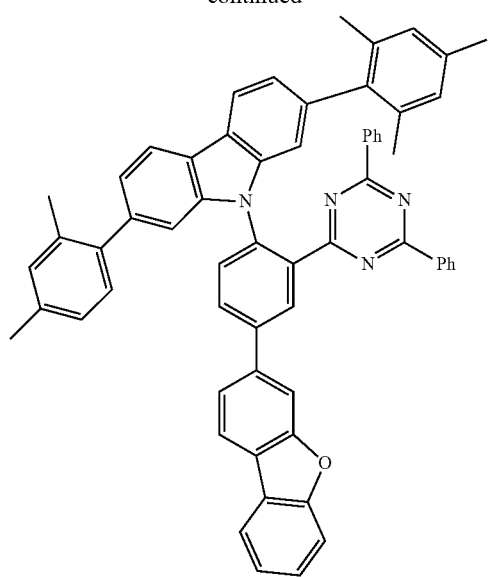
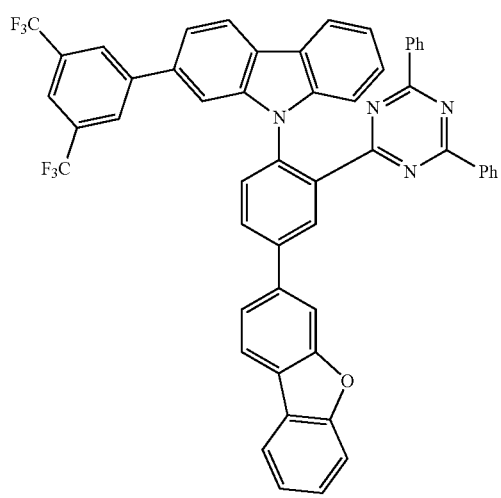
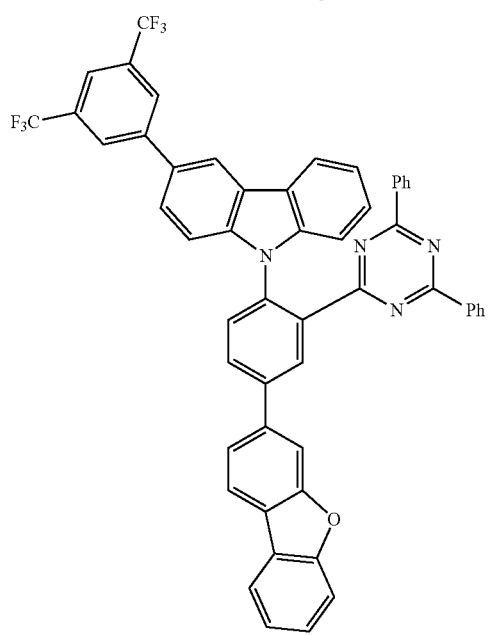
266
-continued
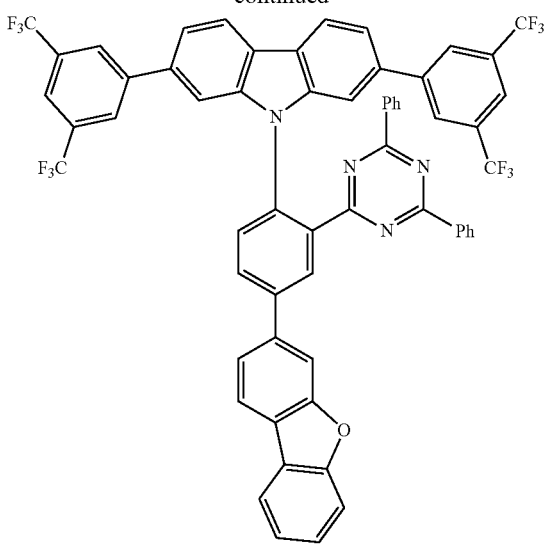
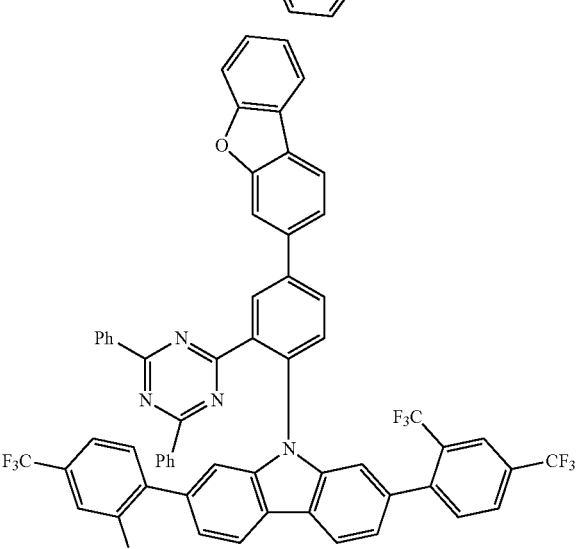
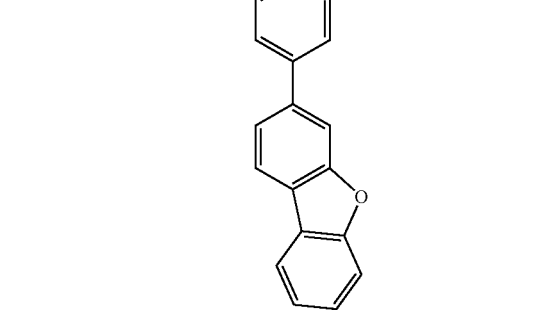

267
-continued
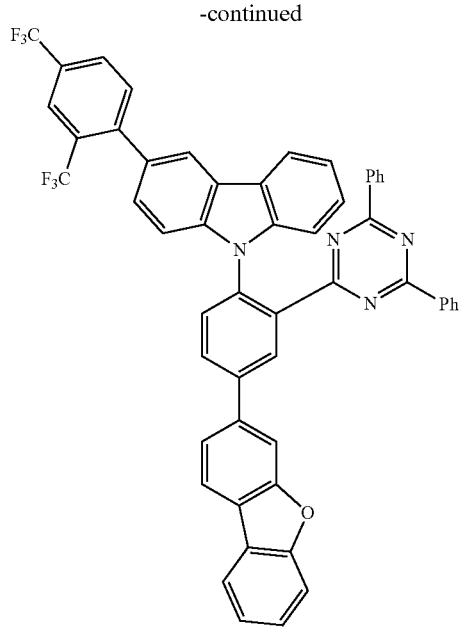
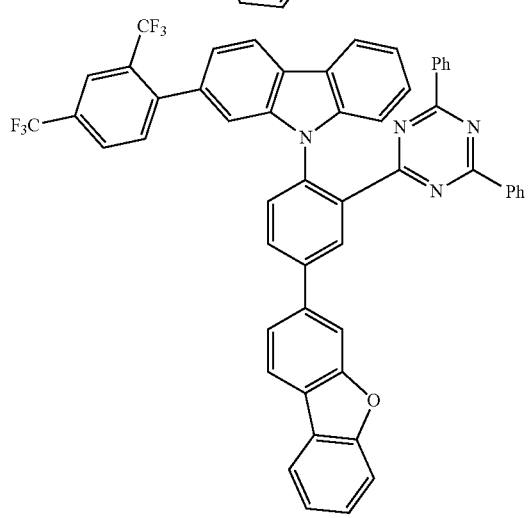
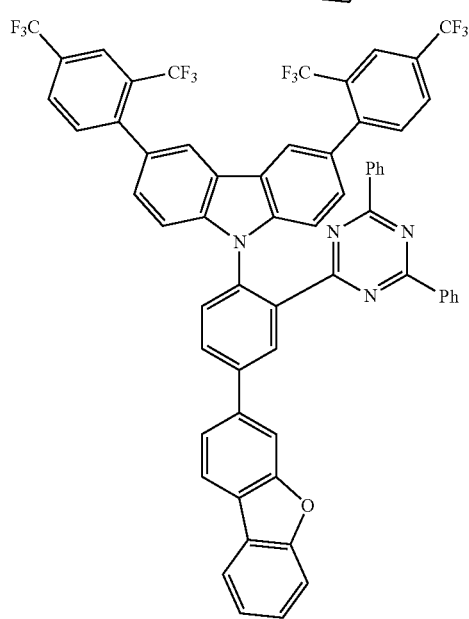
268
-continued
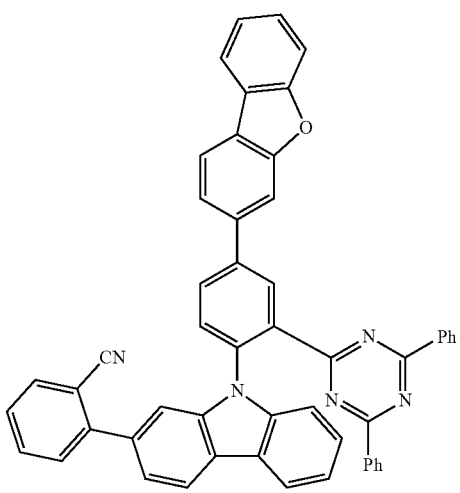
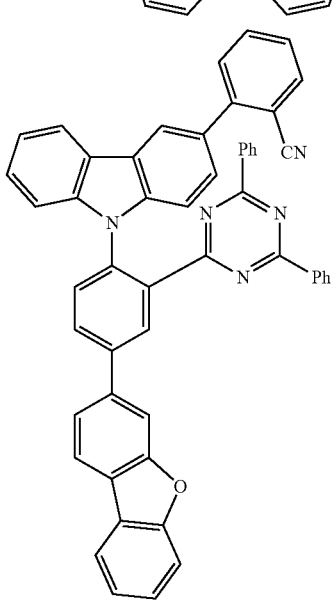
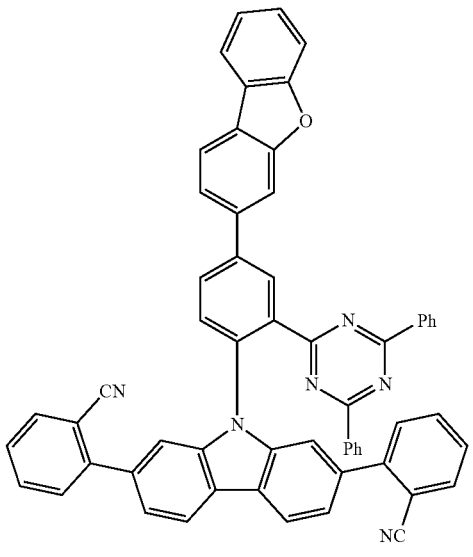

269
-continued
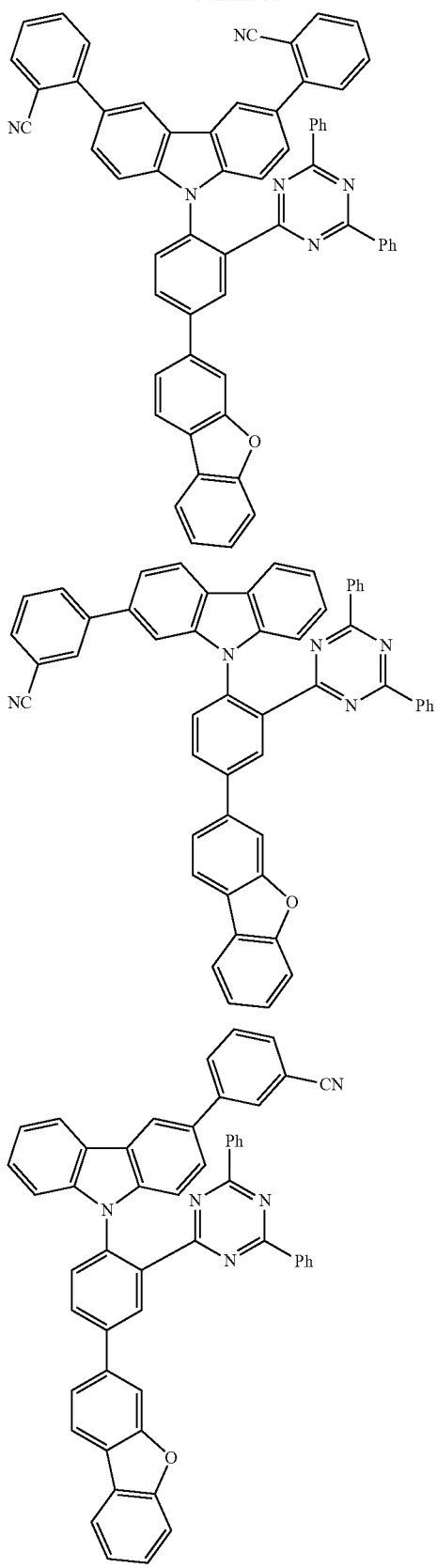
270
-continued
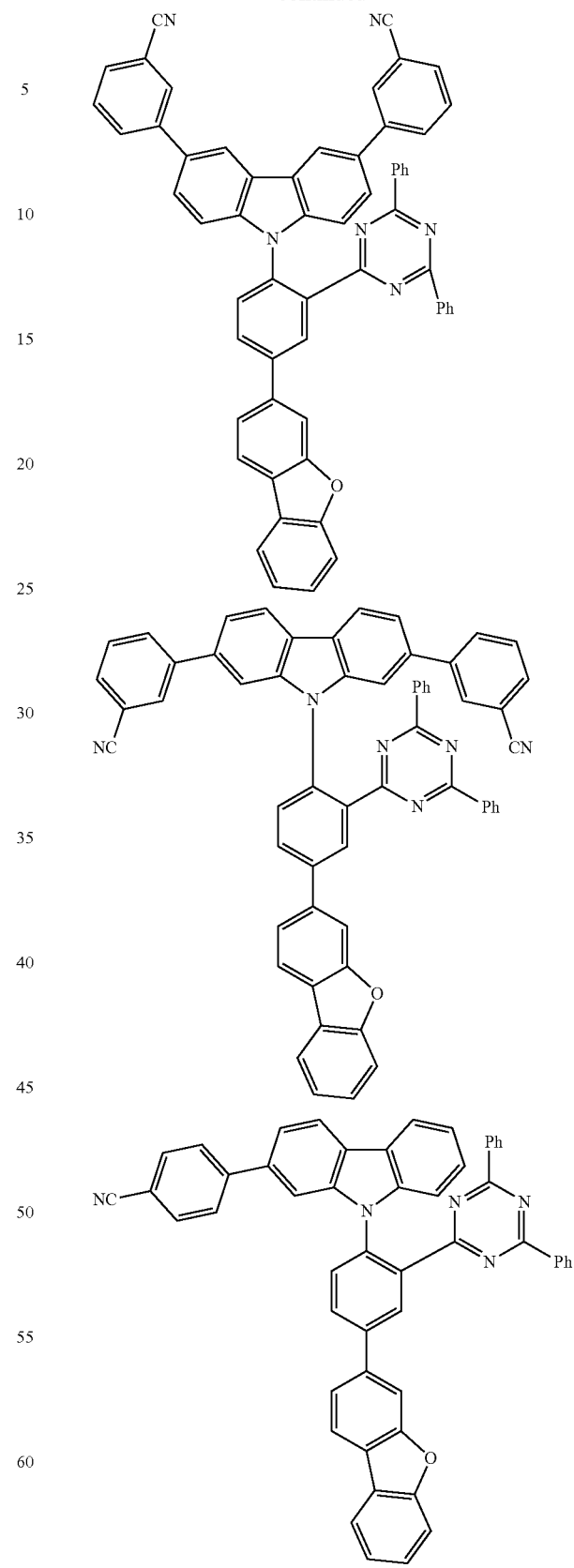

271
-continued
272
-continued
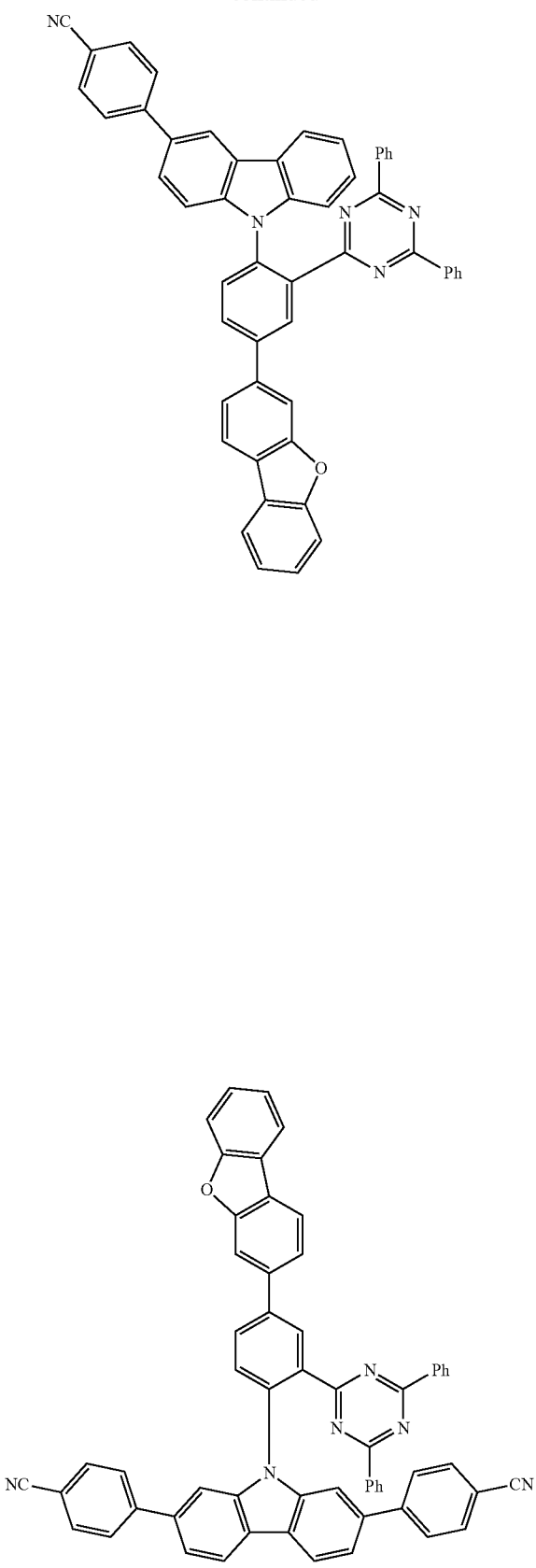
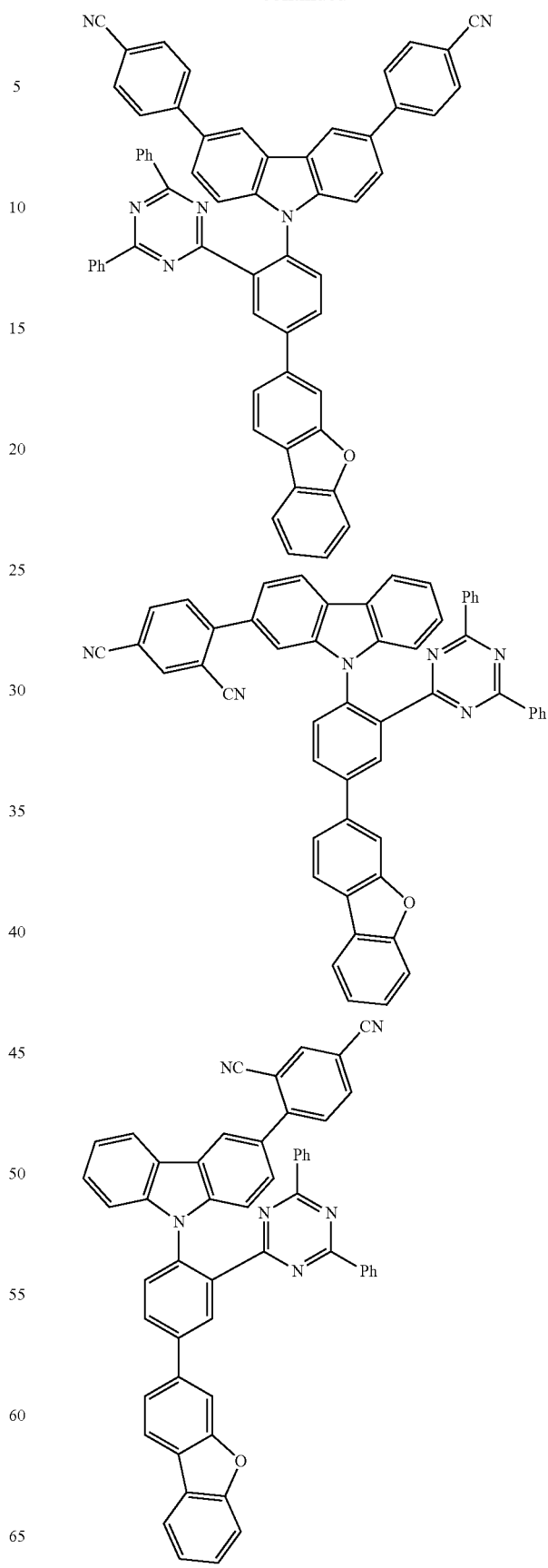

273
-continued
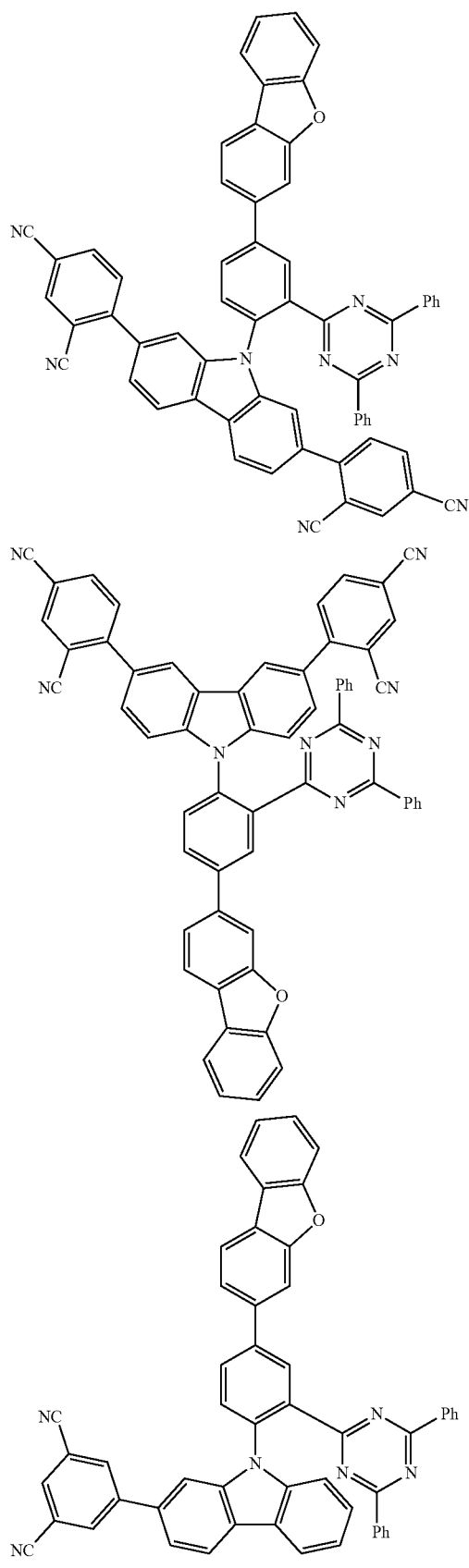
274
-continued
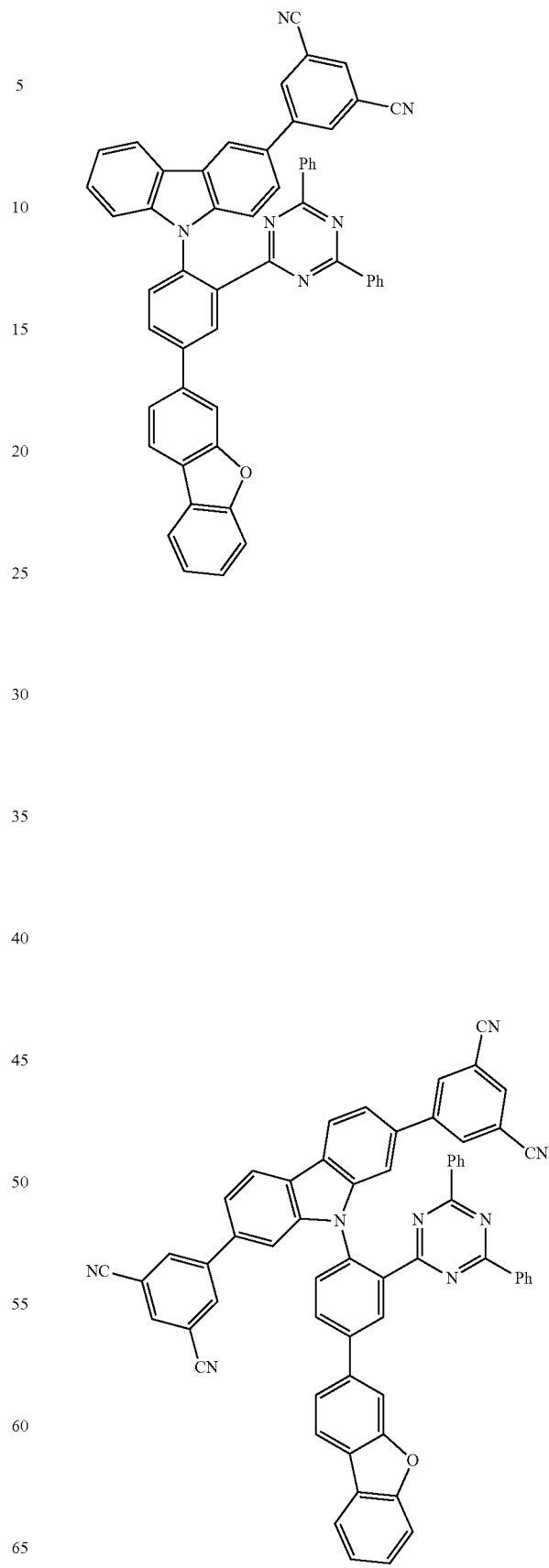

275
-continued
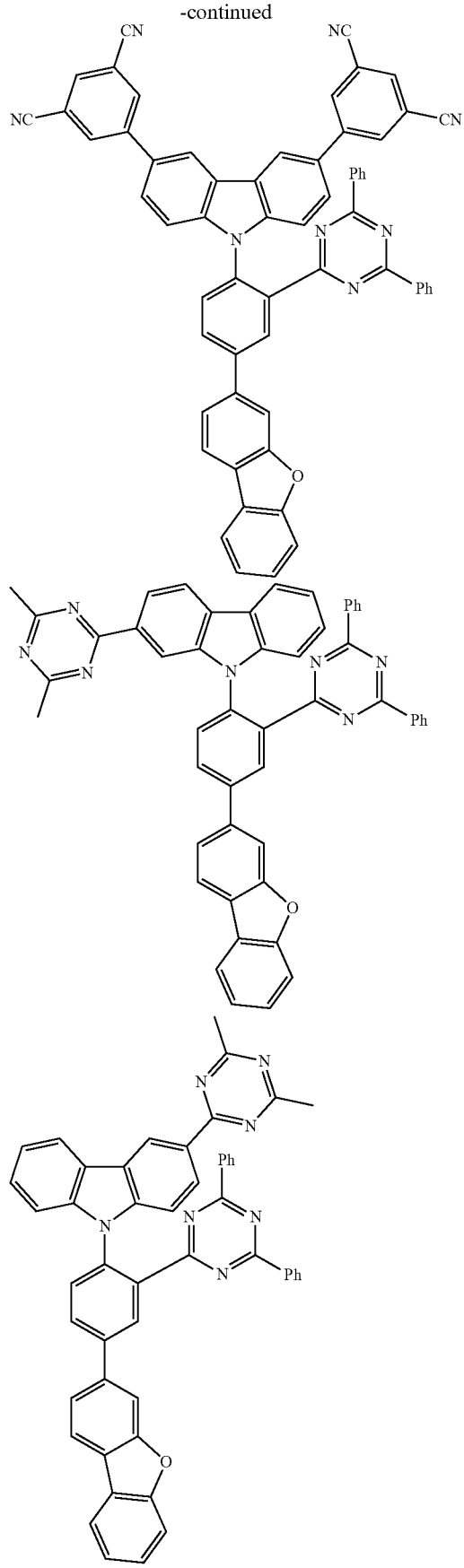
276
-continued
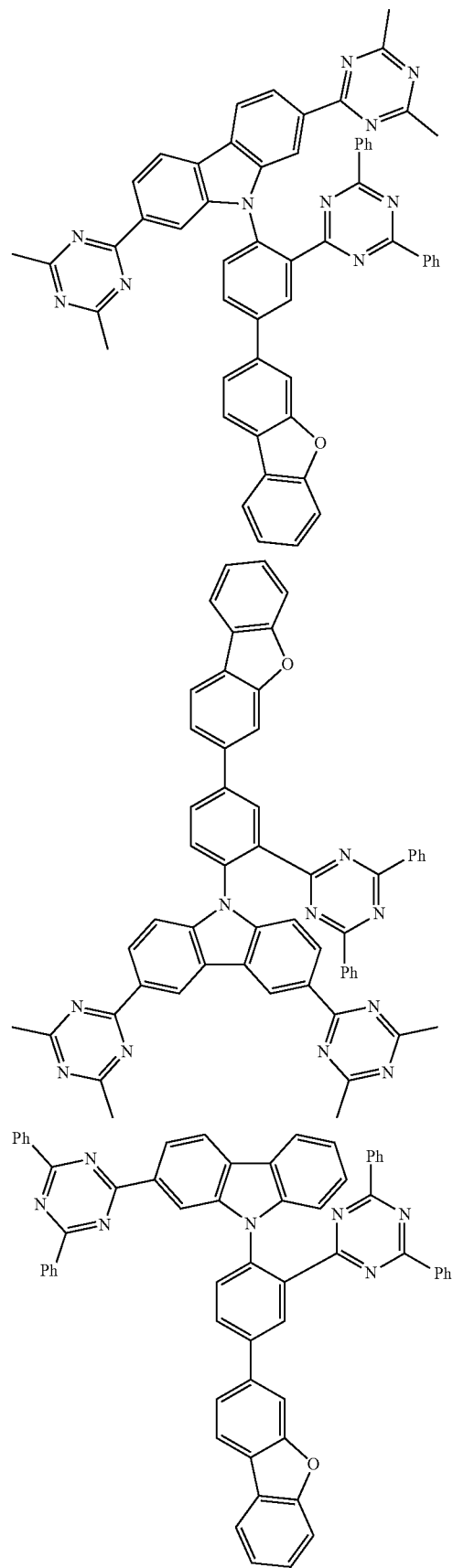

-continued
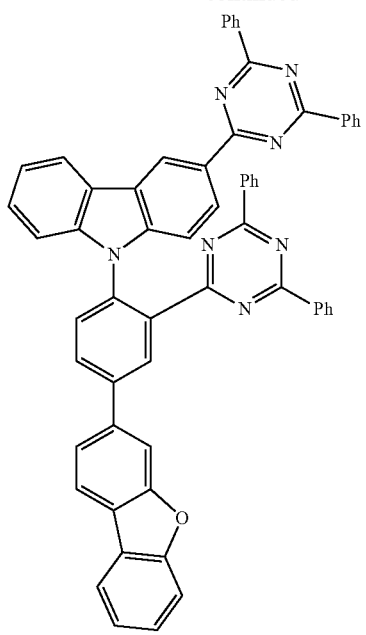
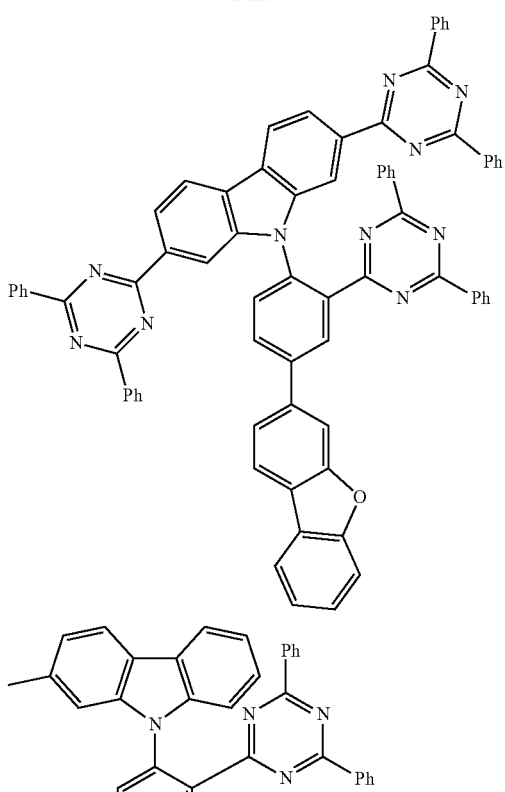
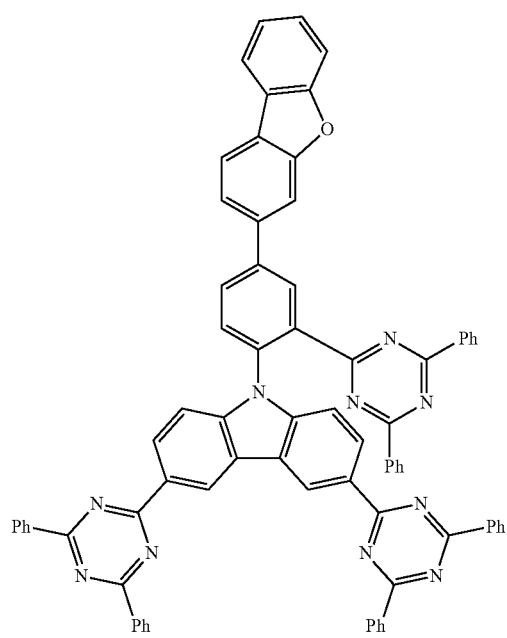
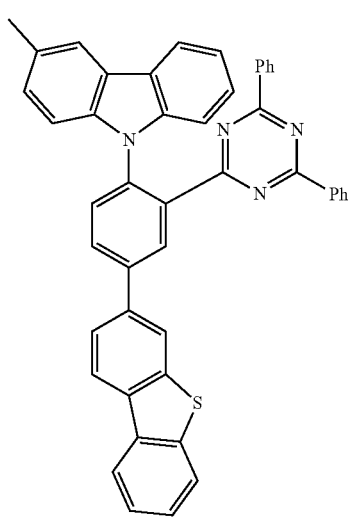

279
-continued
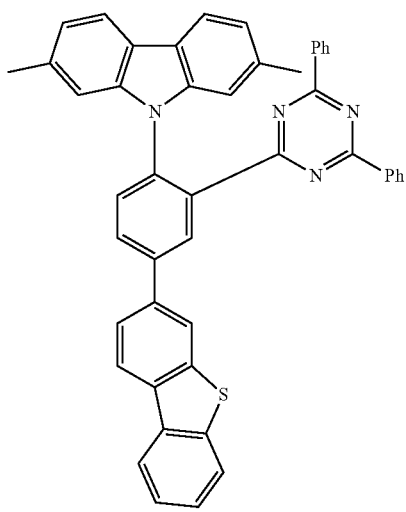
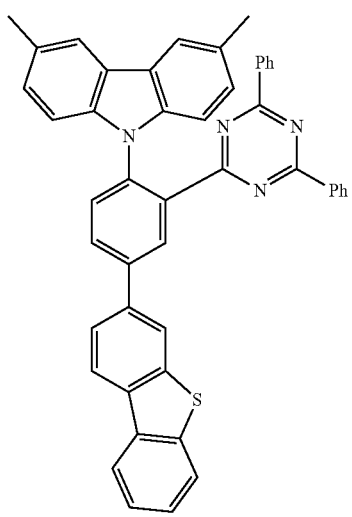
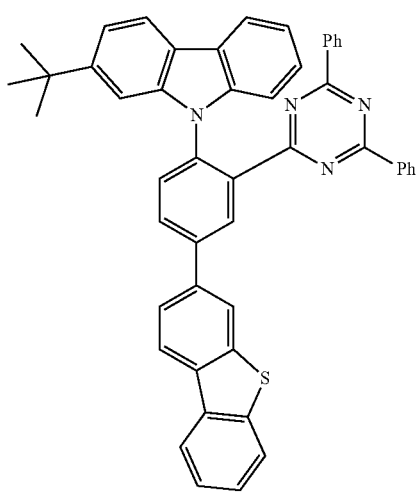
280
-continued
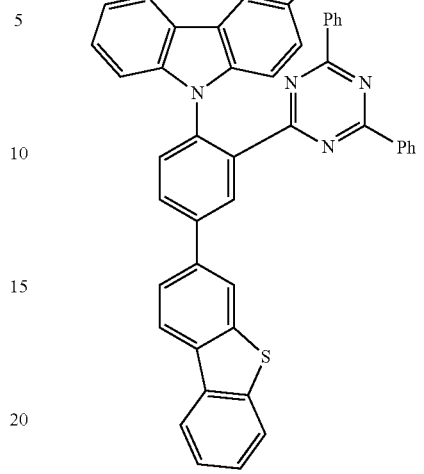
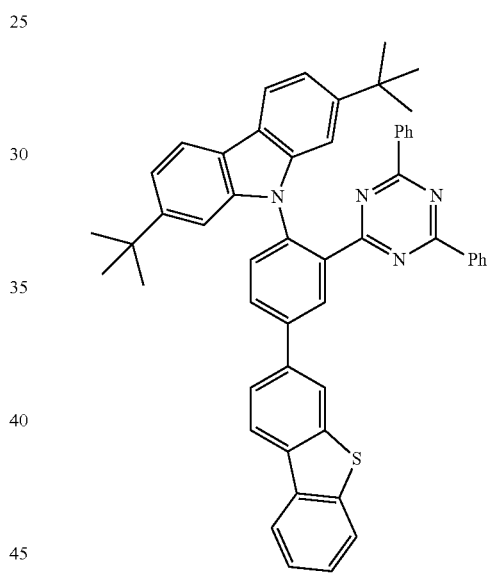
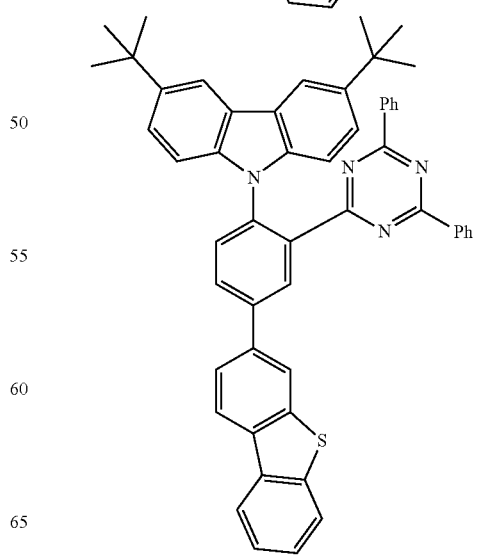

281
-continued
282
-continued
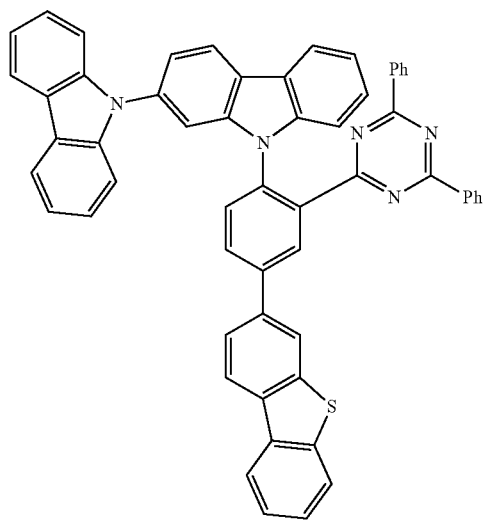
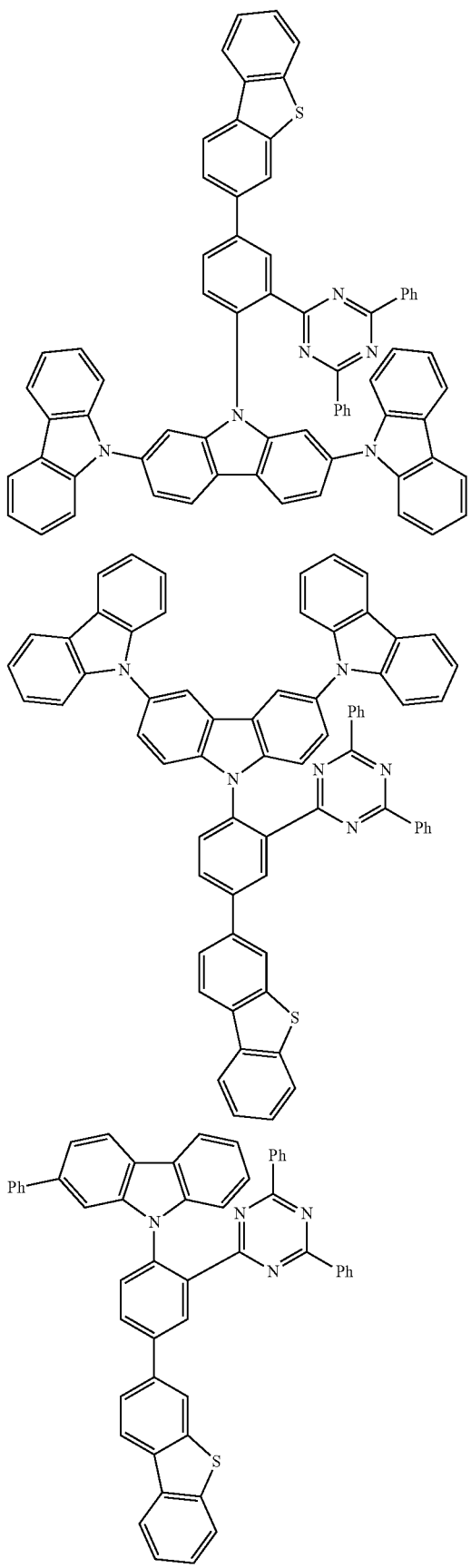

283
-continued
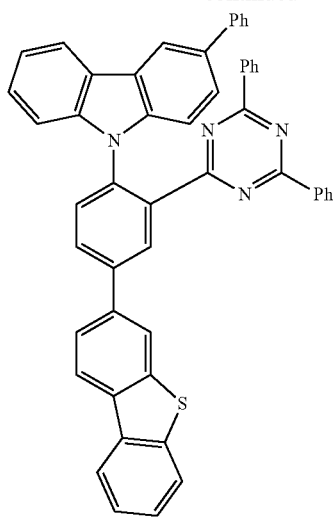
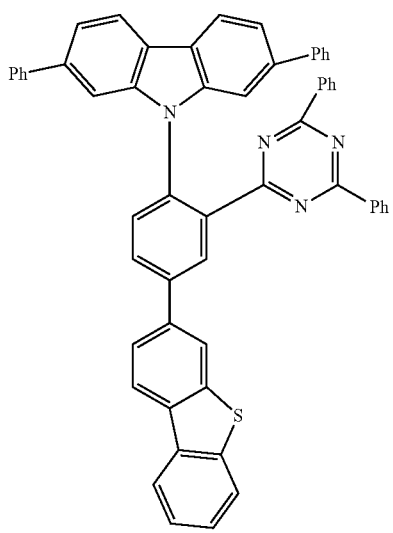 [SMILES: c1ccc(-c2ccc3c4ccc(-c5ccccc5)cc4n(-c4ccc(-c5ccc6c(c5)sc5ccccc56)cc4-c4nc(-c5ccccc5)nc(-c5ccccc5)n4)c3c2)cc1]
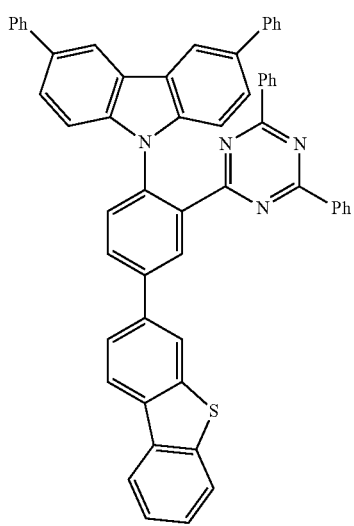
284
-continued
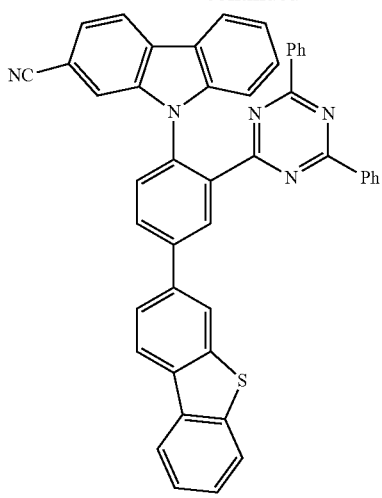
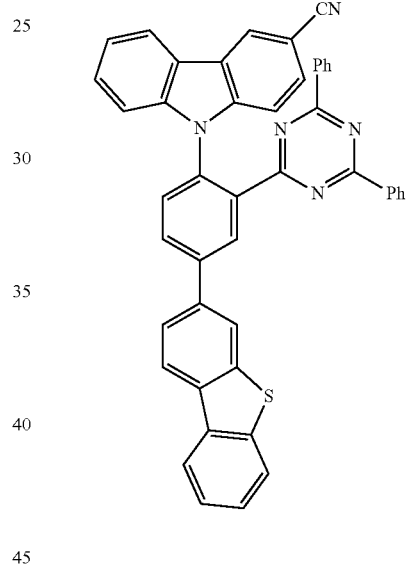
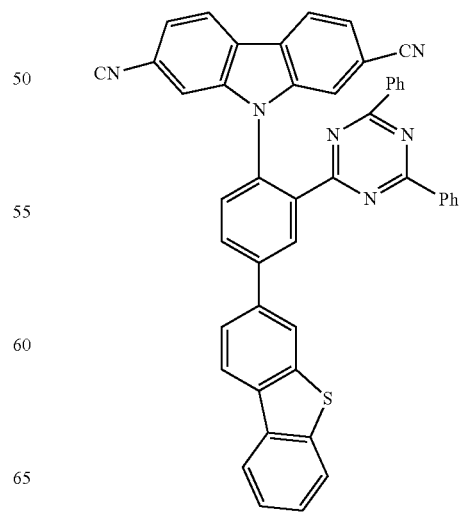

285
-continued
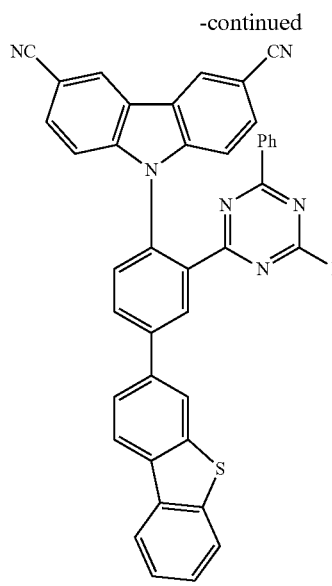
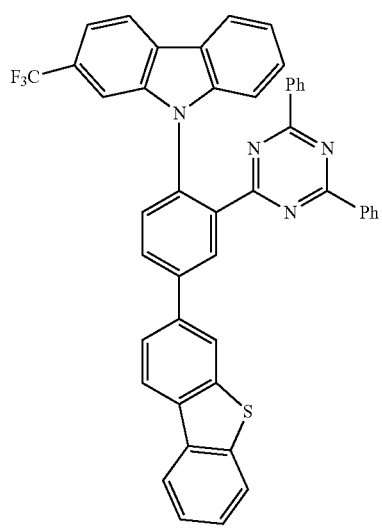
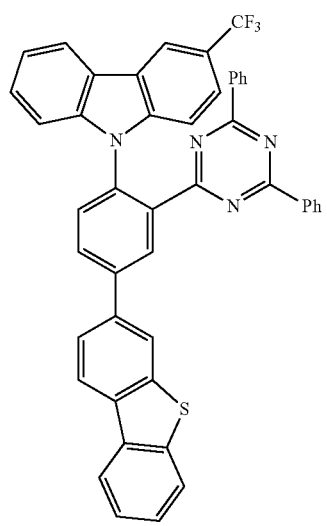
286
-continued
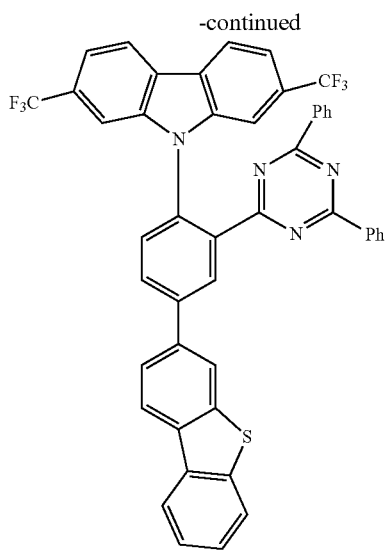
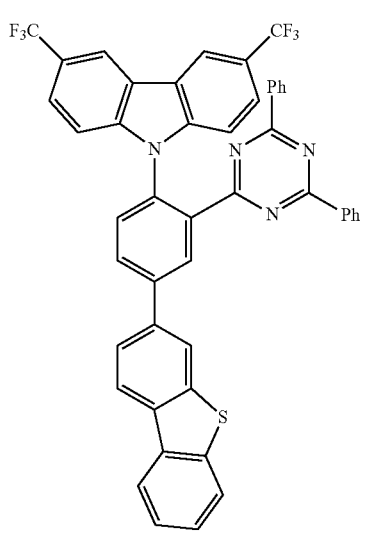
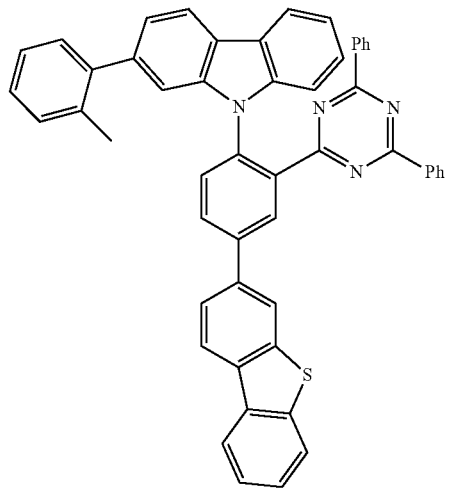

287
-continued
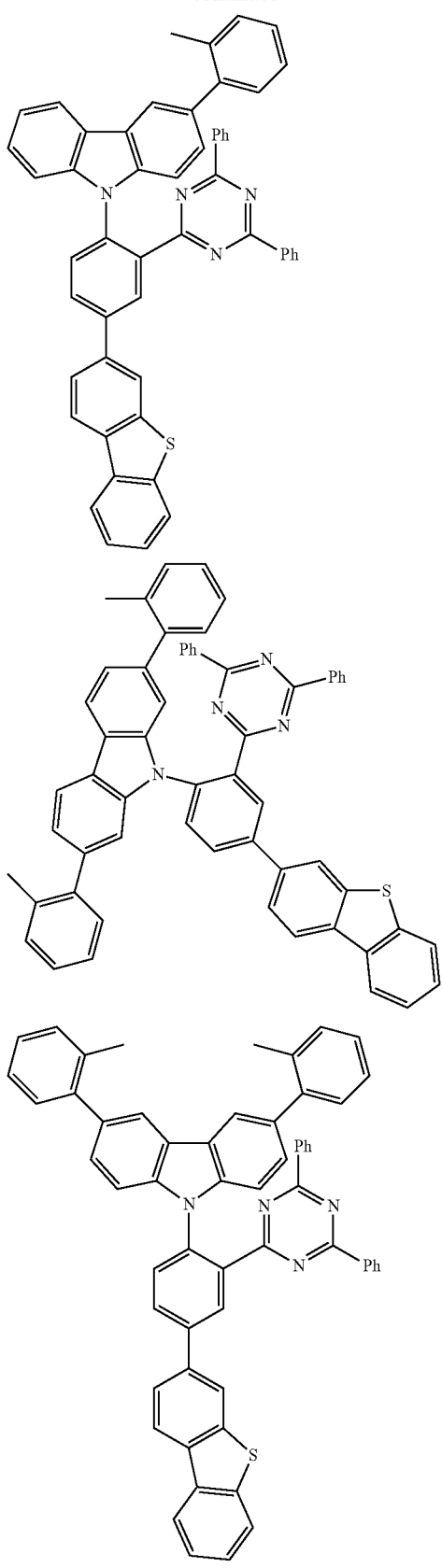
288
-continued
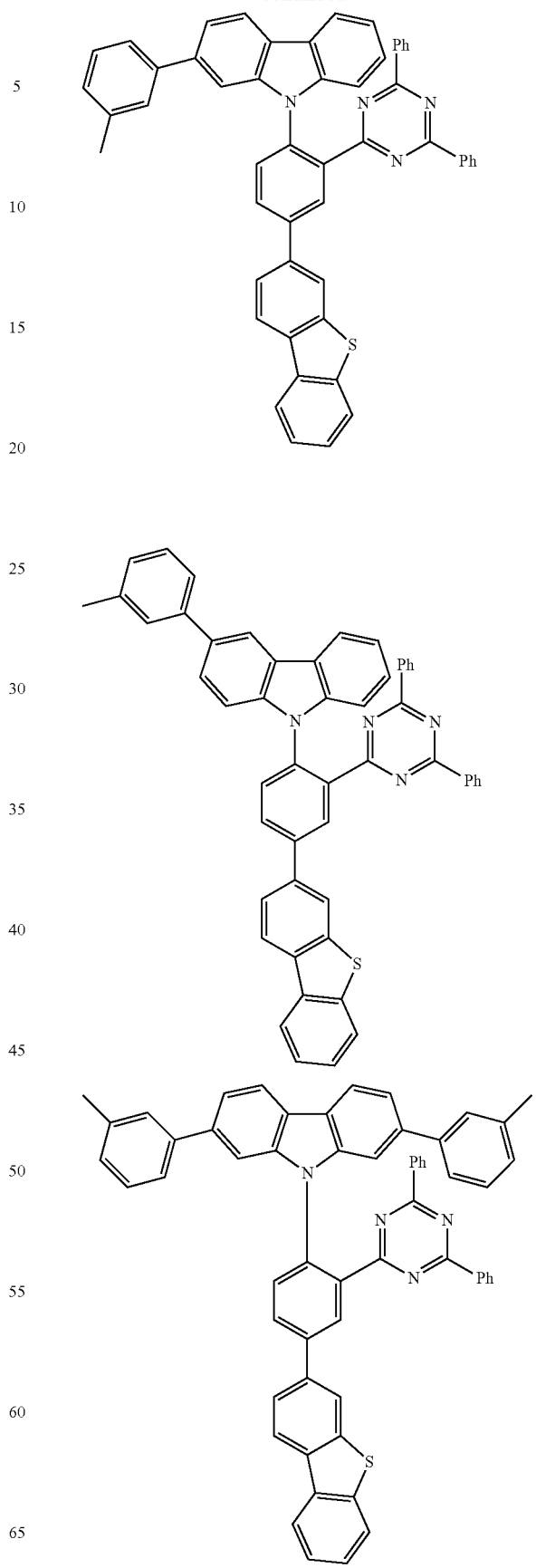

289
-continued
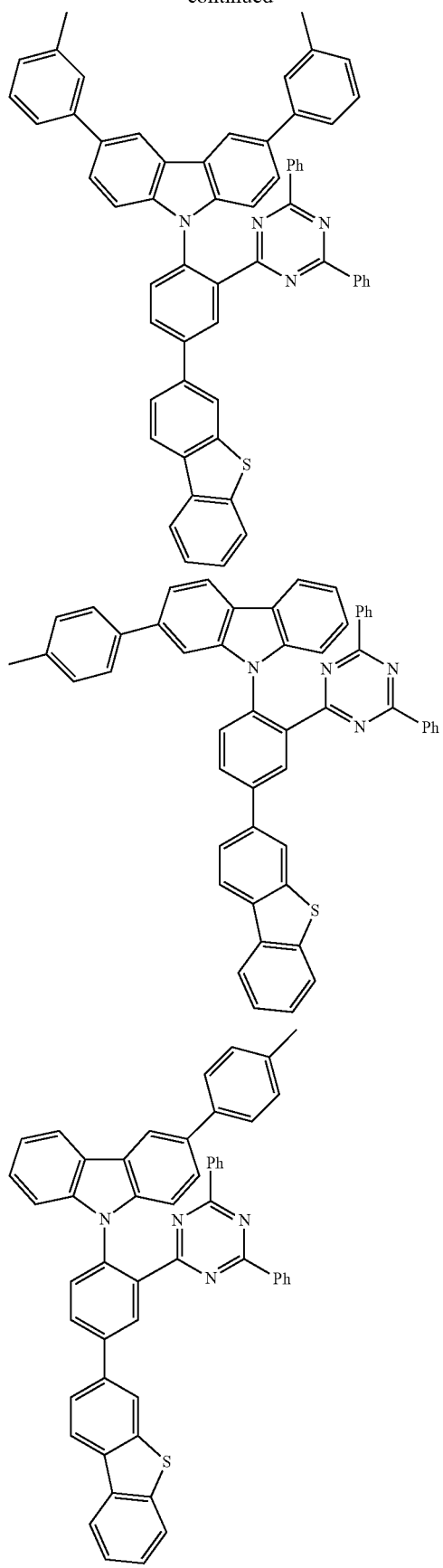
290
-continued
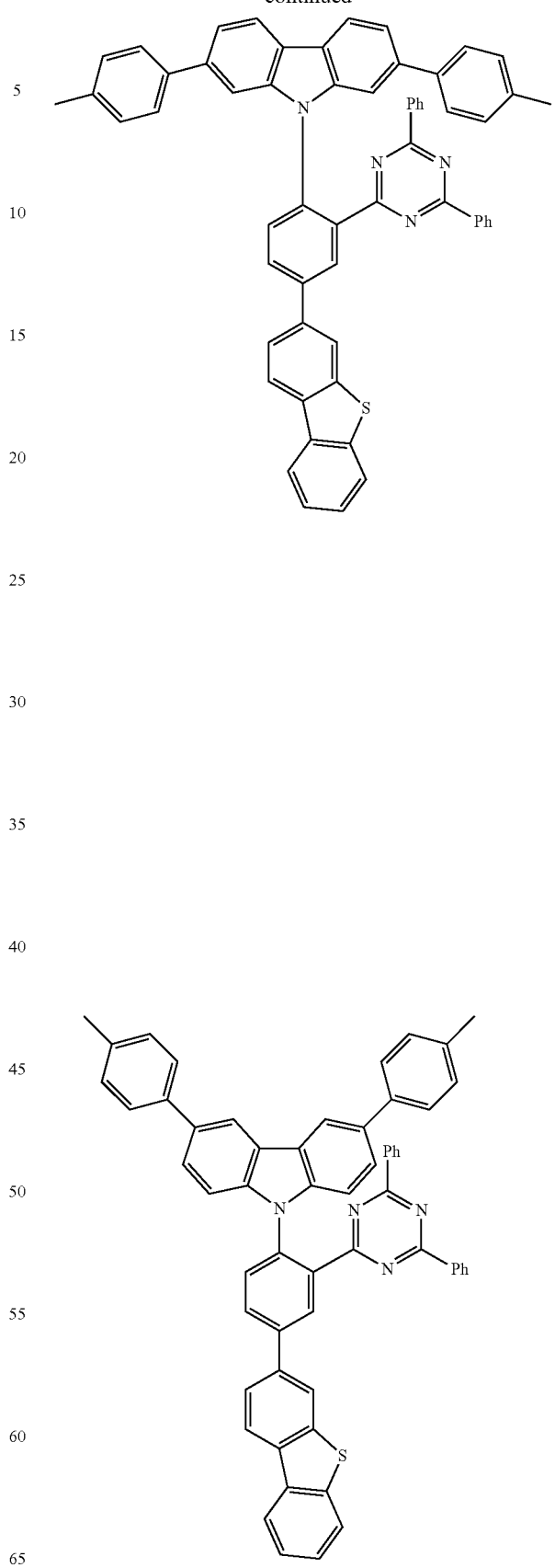

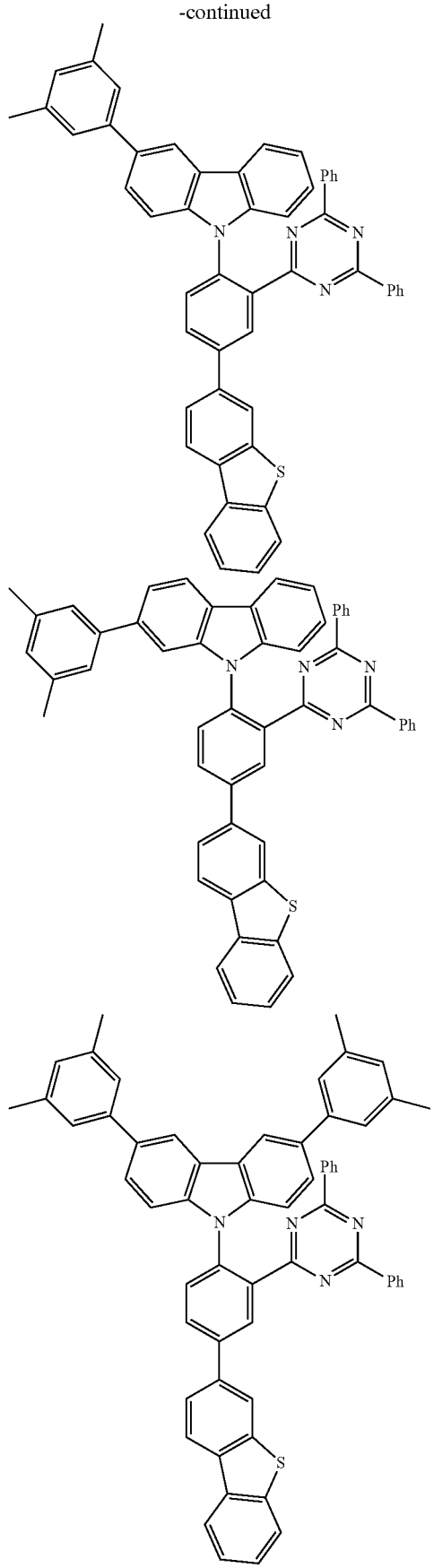
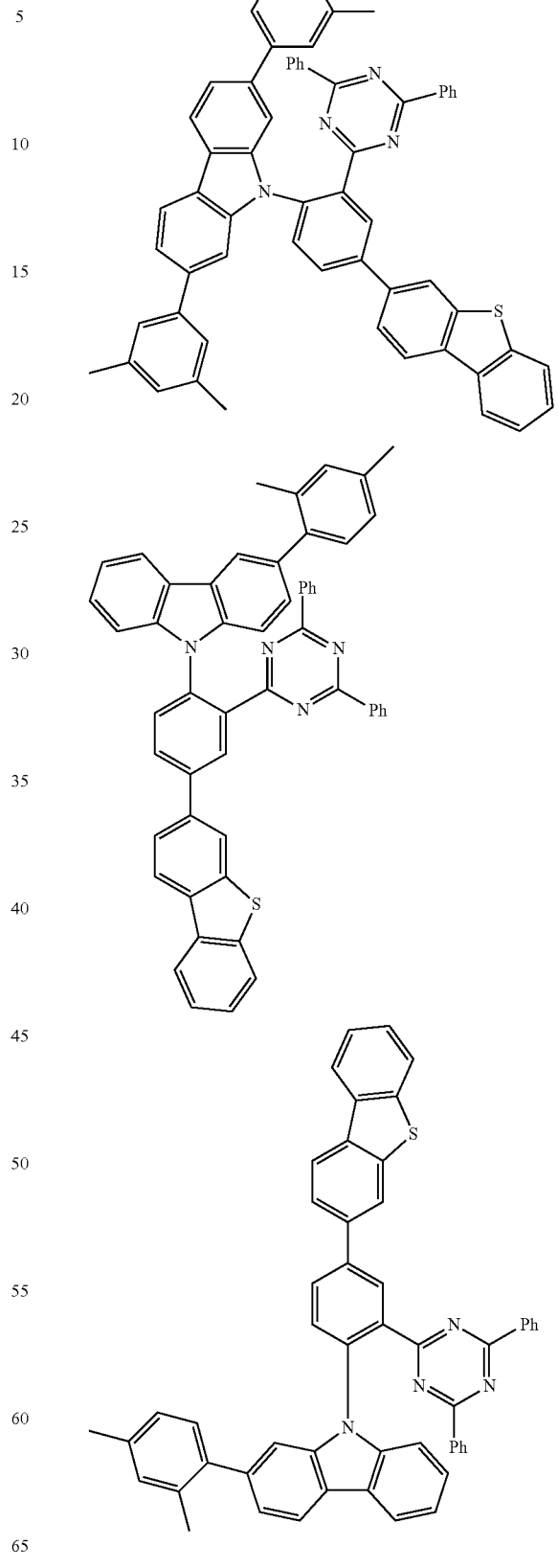

293
-continued
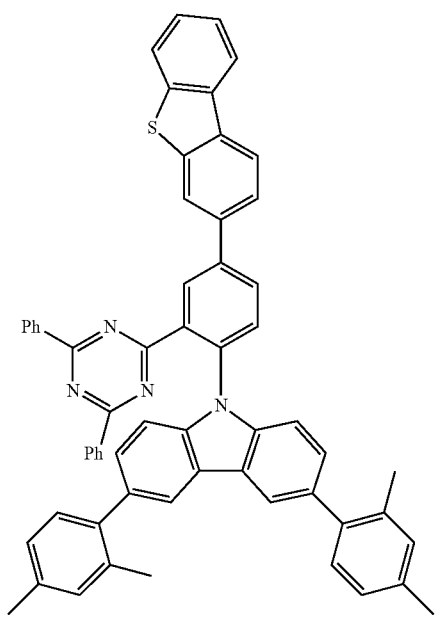
294
-continued
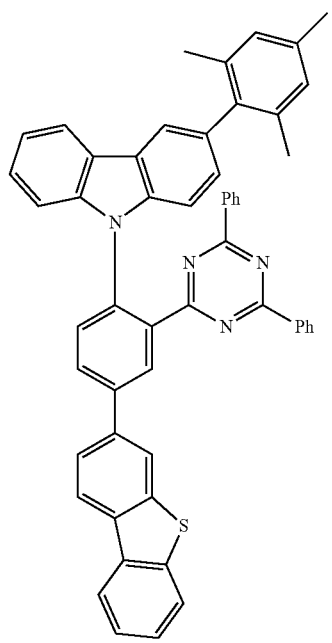
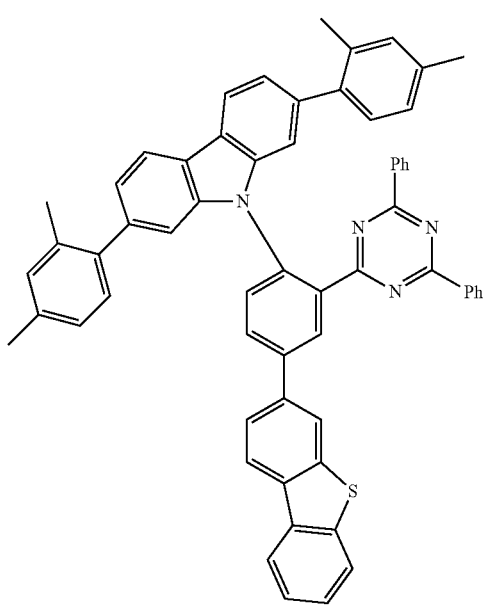
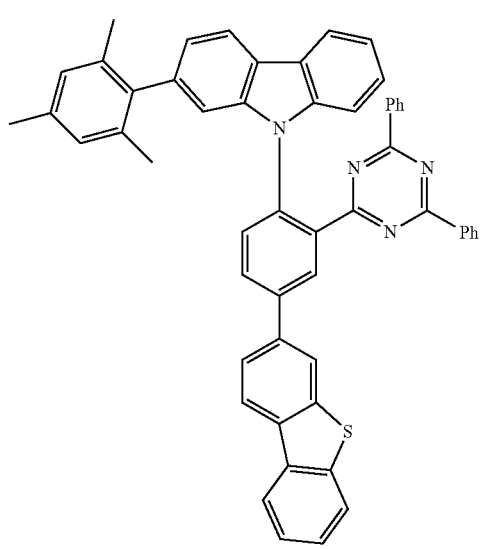

295
-continued
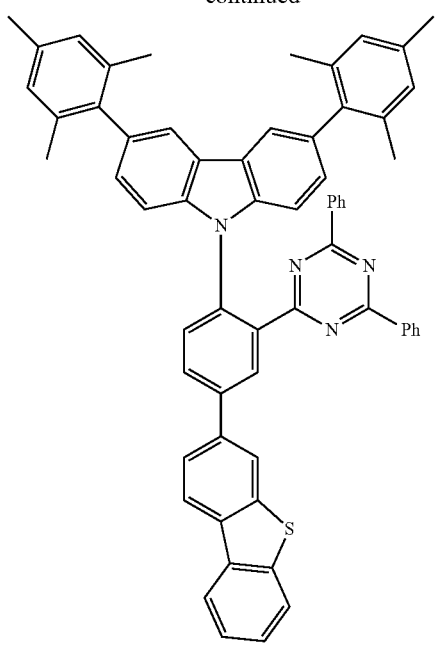
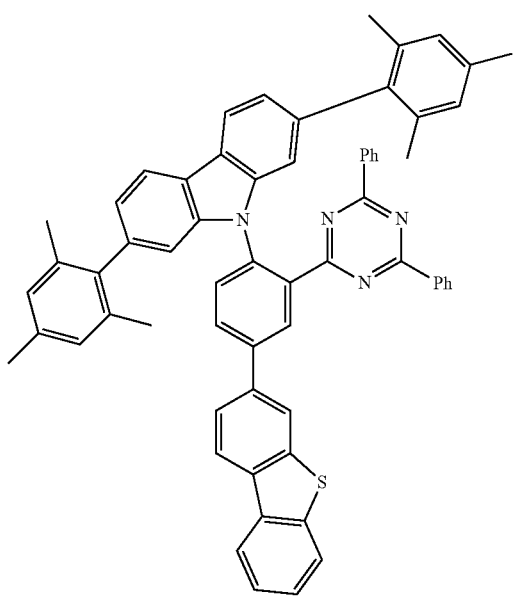
296
-continued
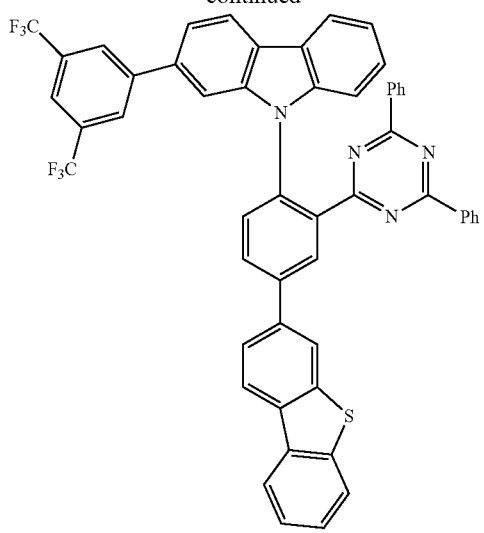
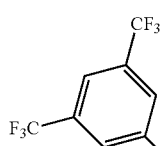
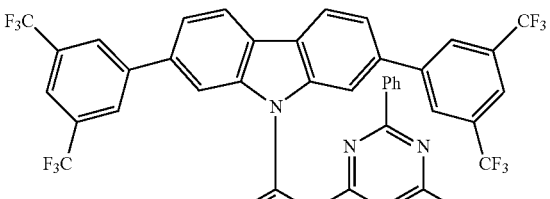
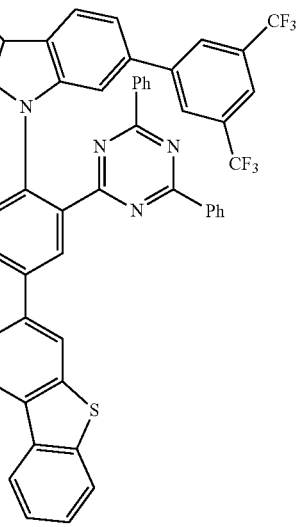

297
-continued
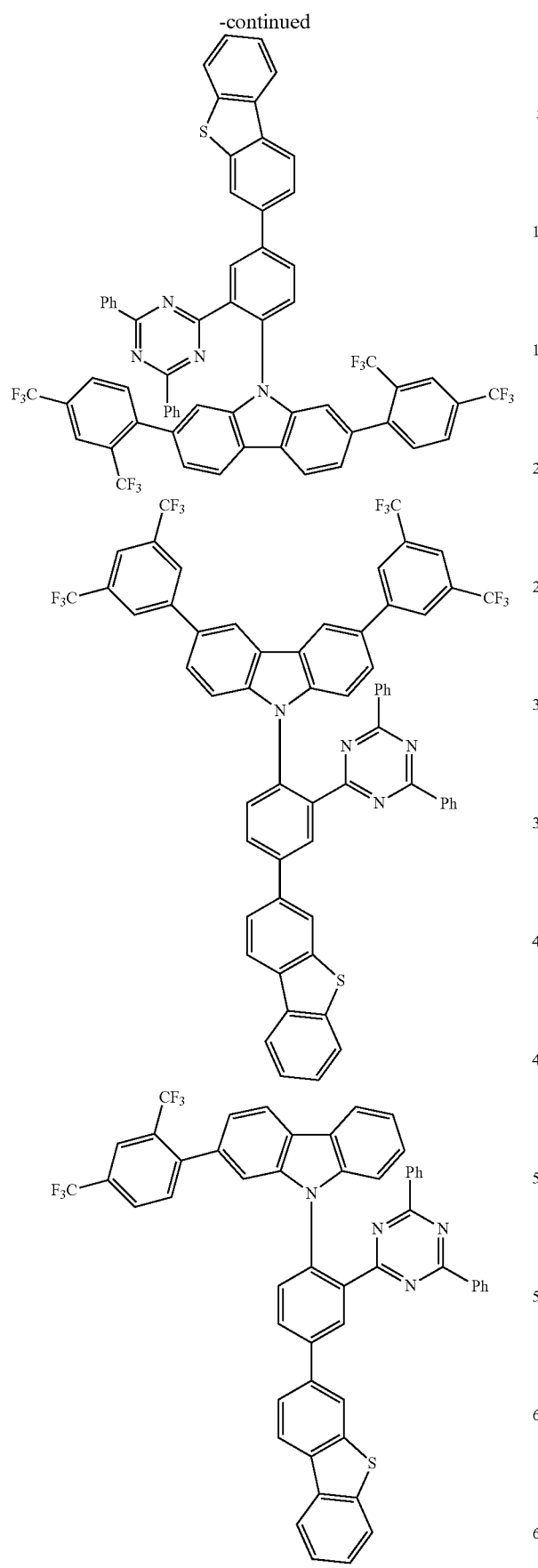
298
-continued
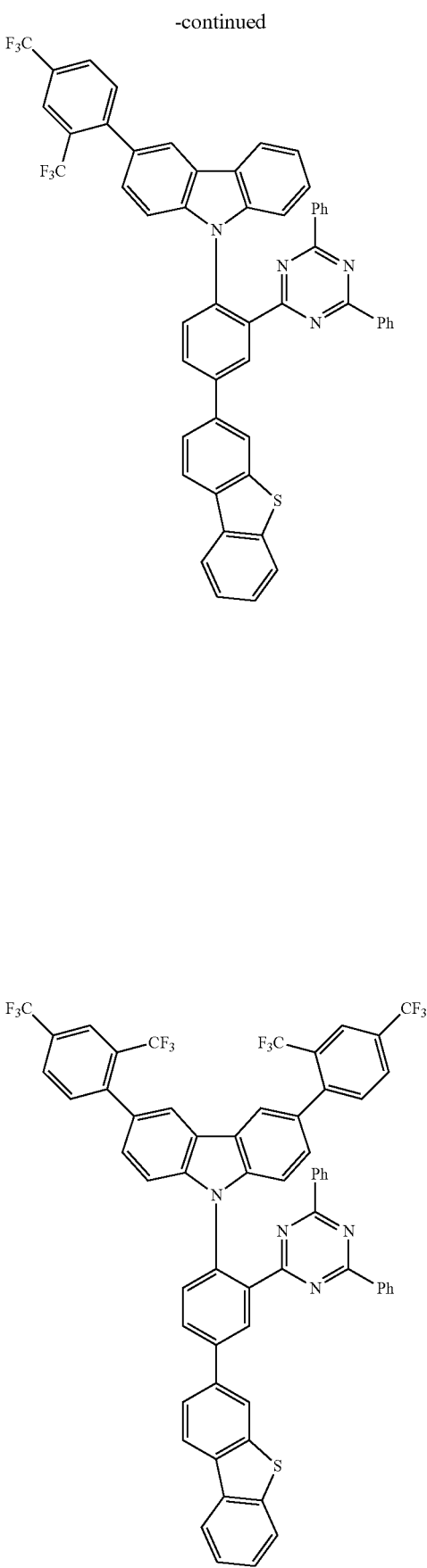

299
-continued
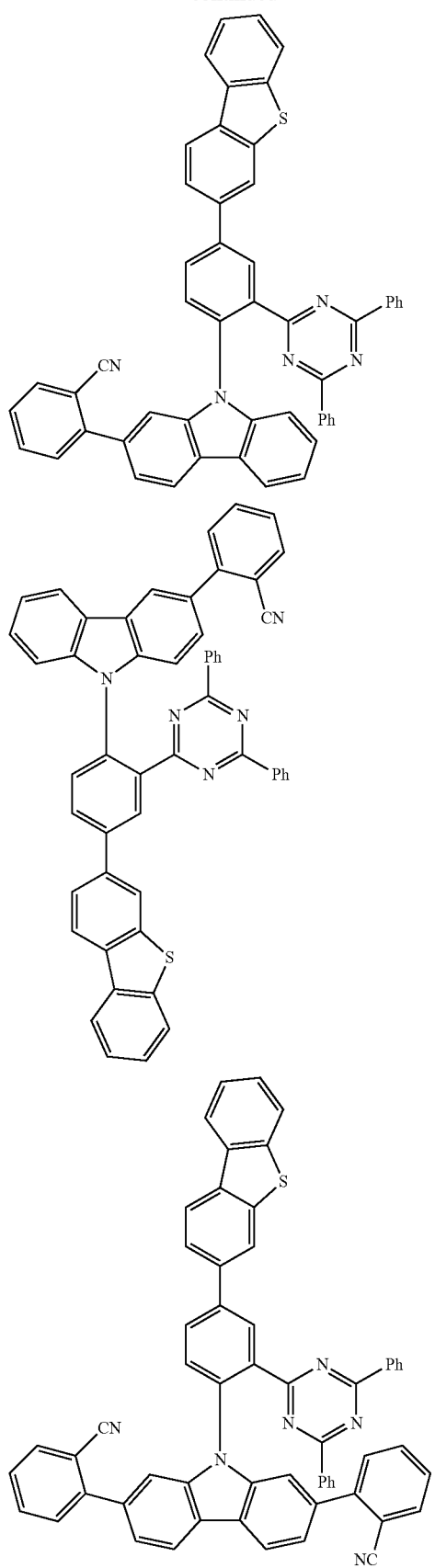
300
-continued
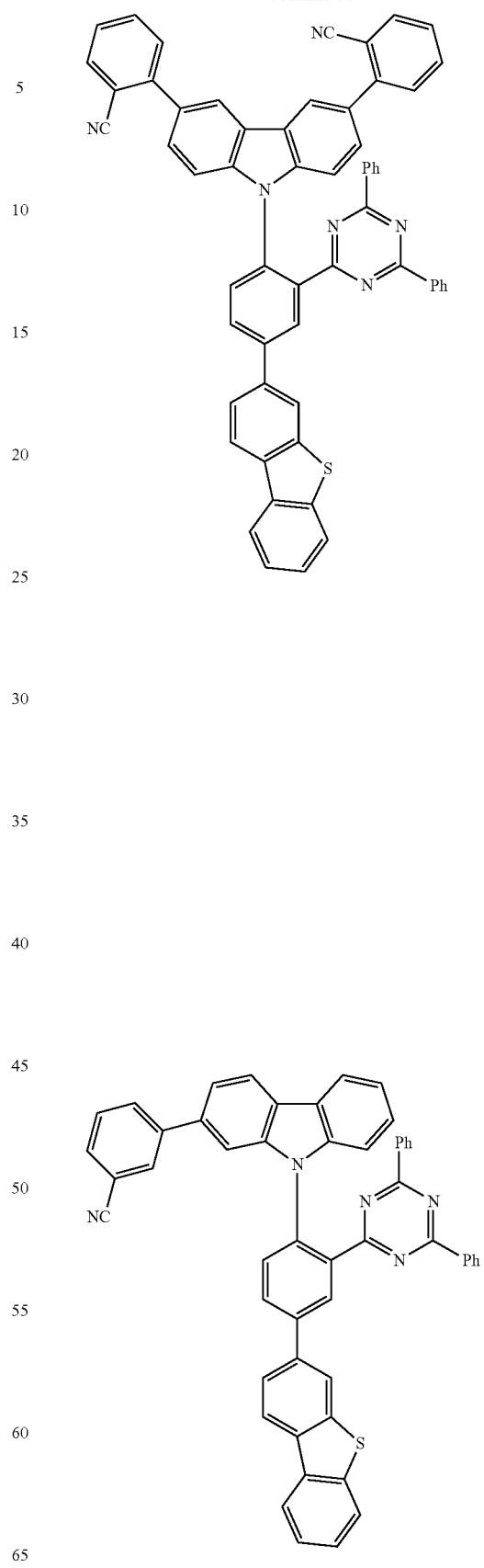

301
-continued
302
-continued
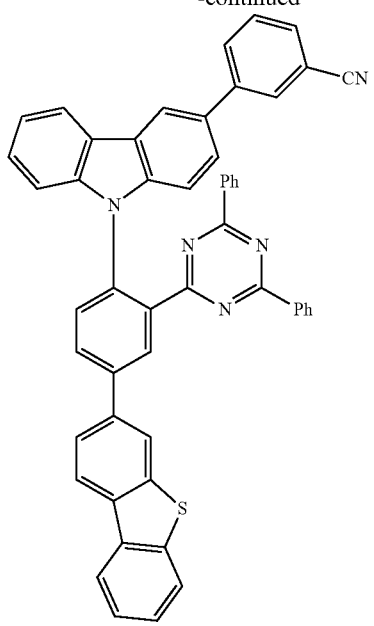
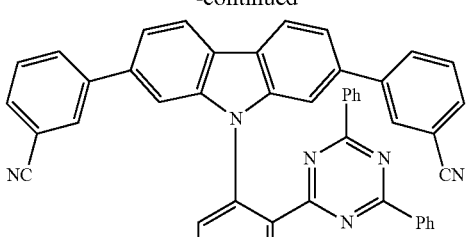
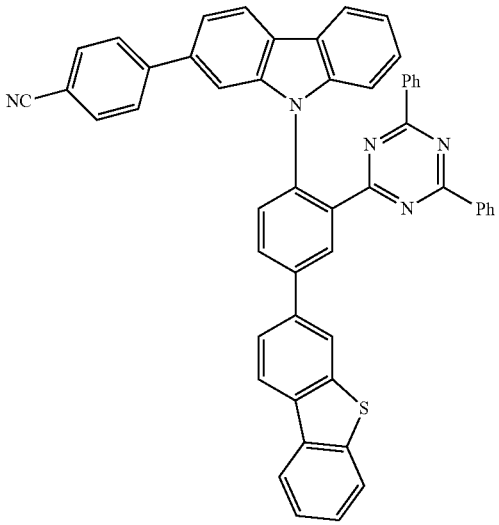
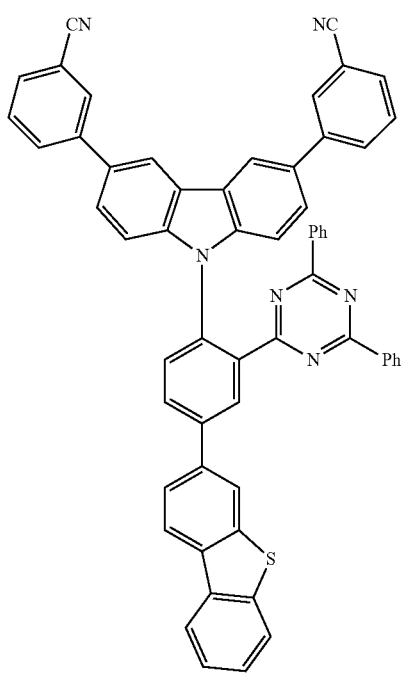

303
-continued
304
-continued
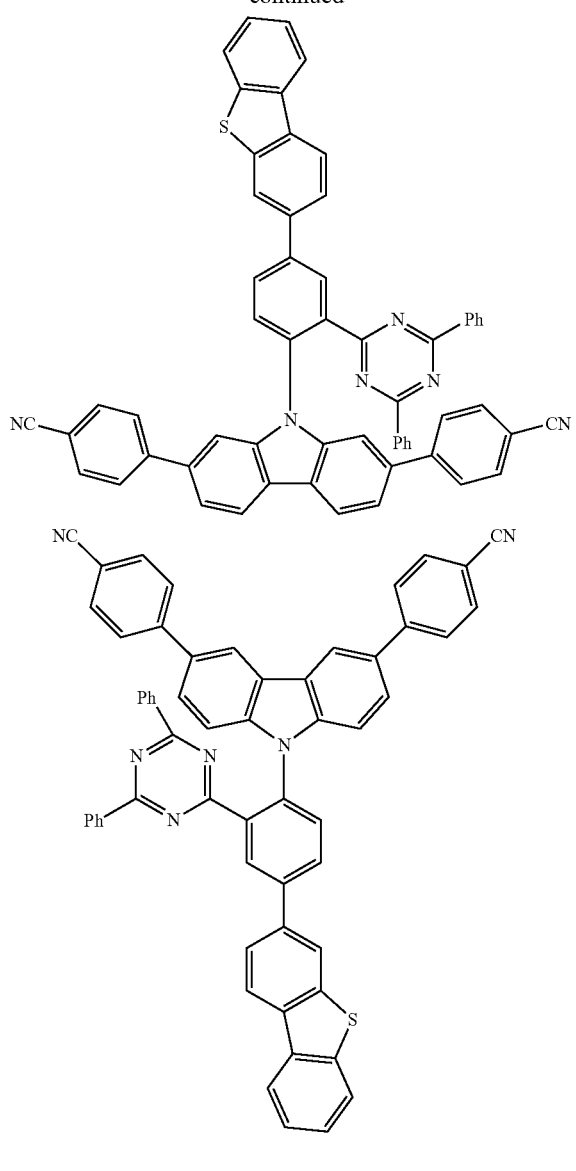
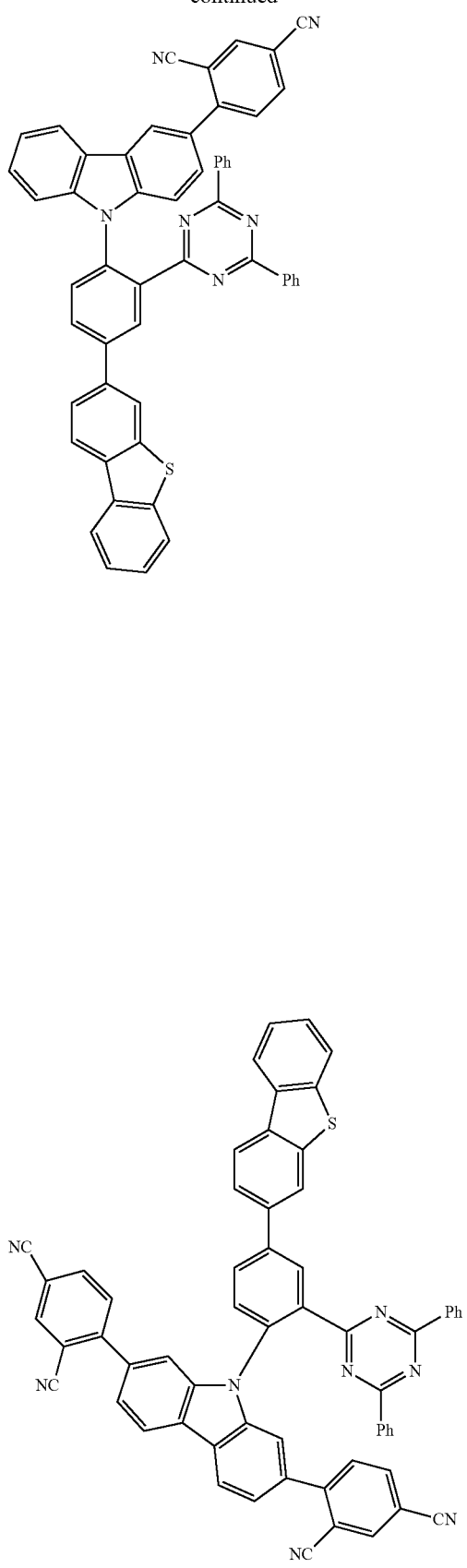

305
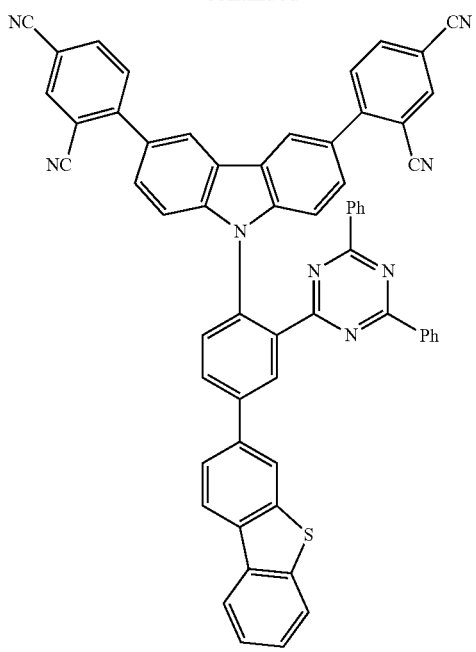
306
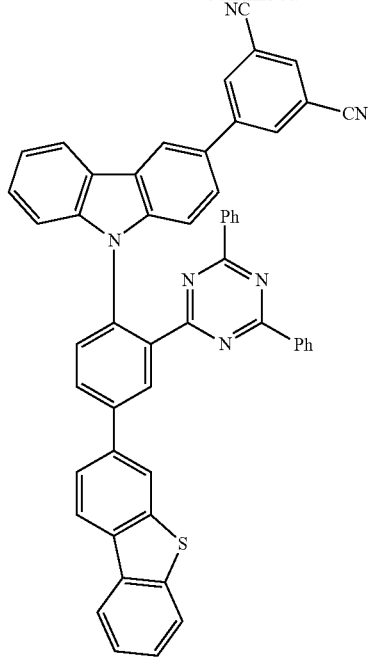
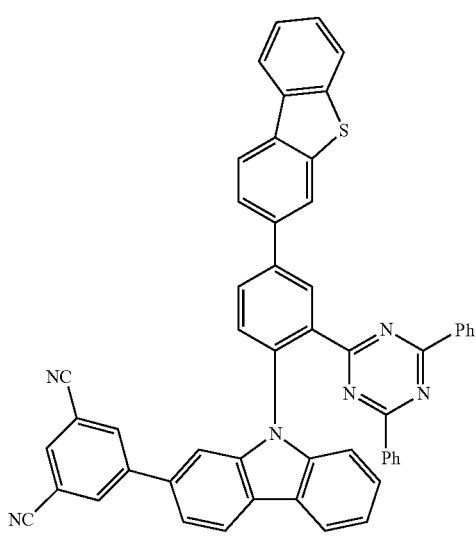
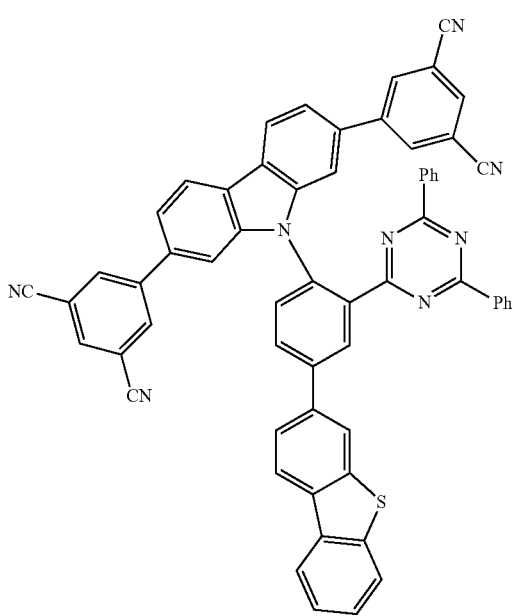

307
-continued
308
-continued
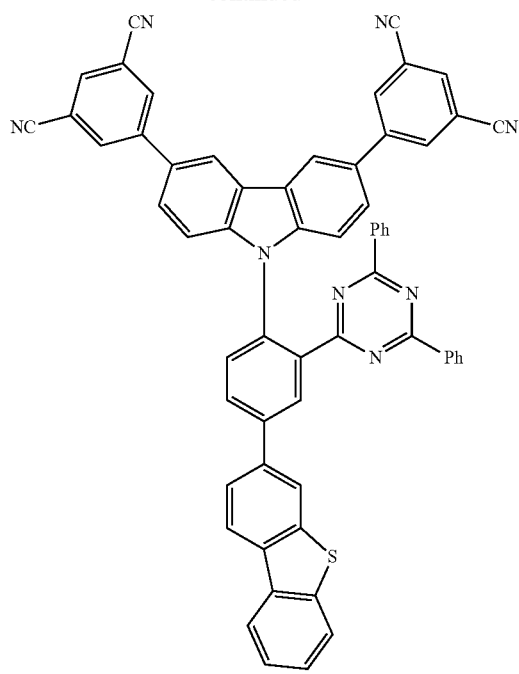
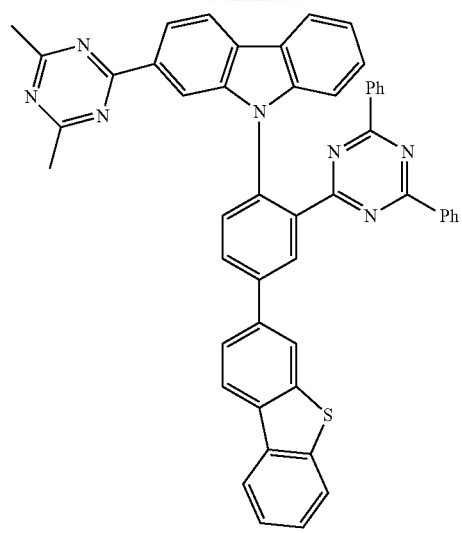

309
-continued
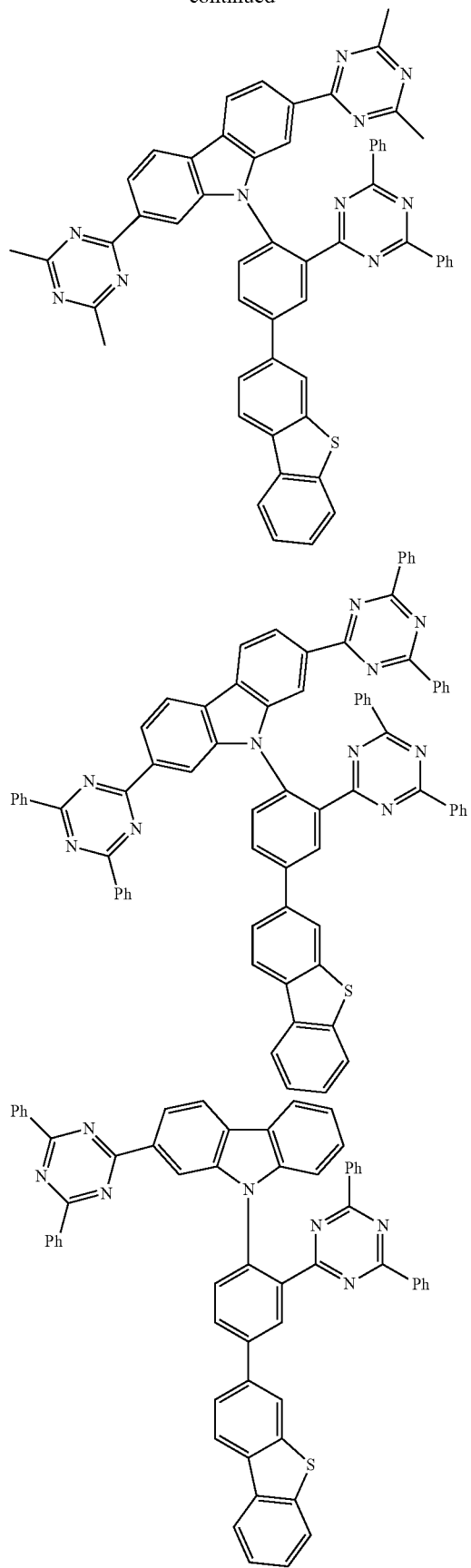
310
-continued
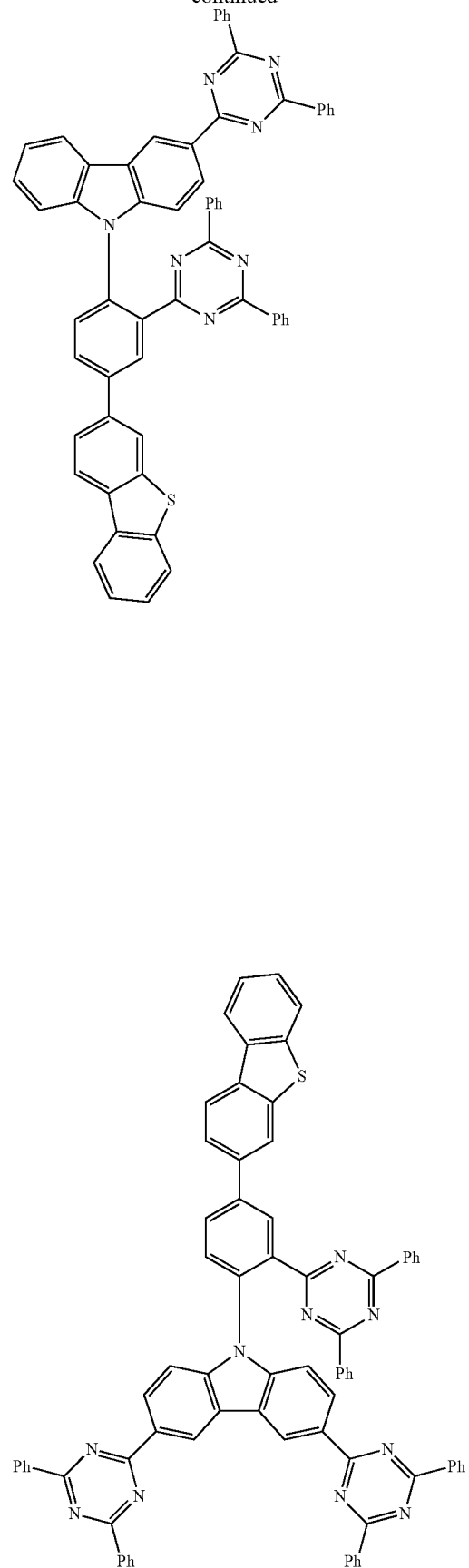

311
-continued
312
-continued
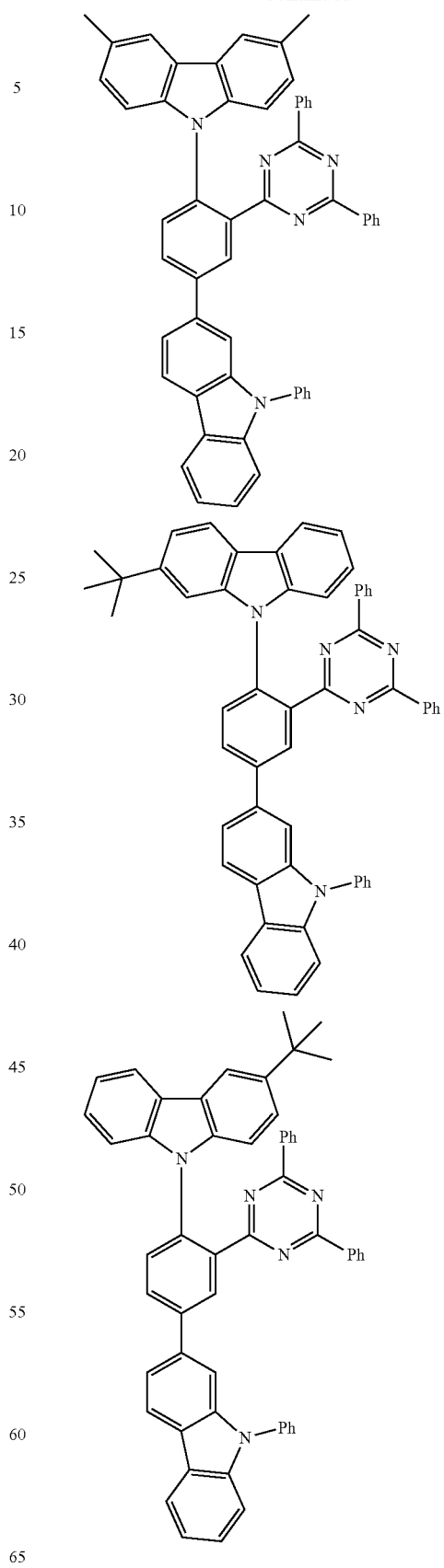

313
-continued
314
-continued
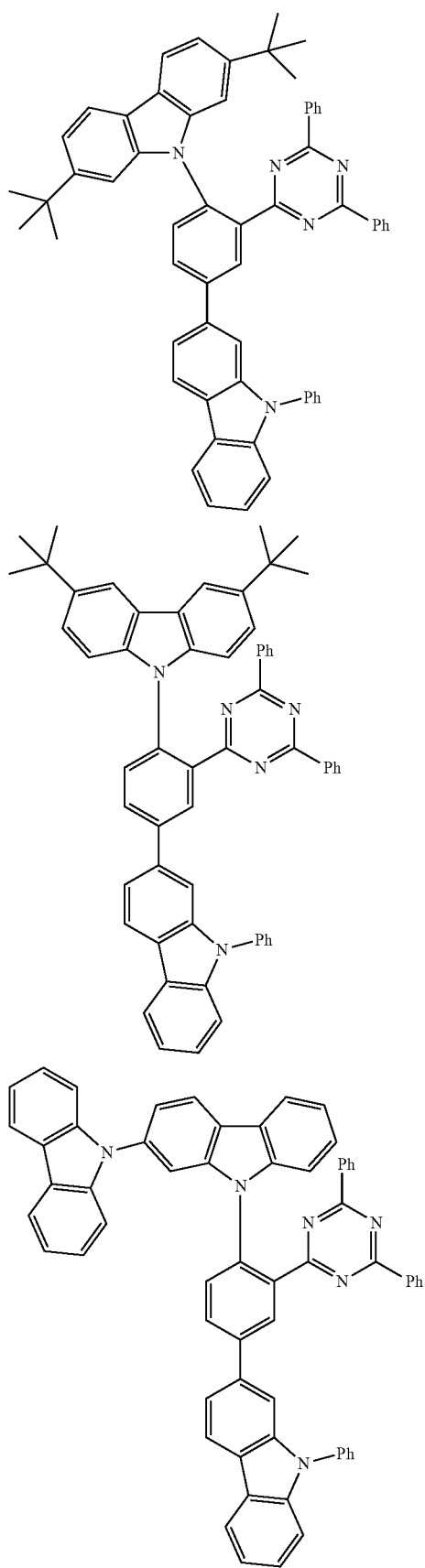
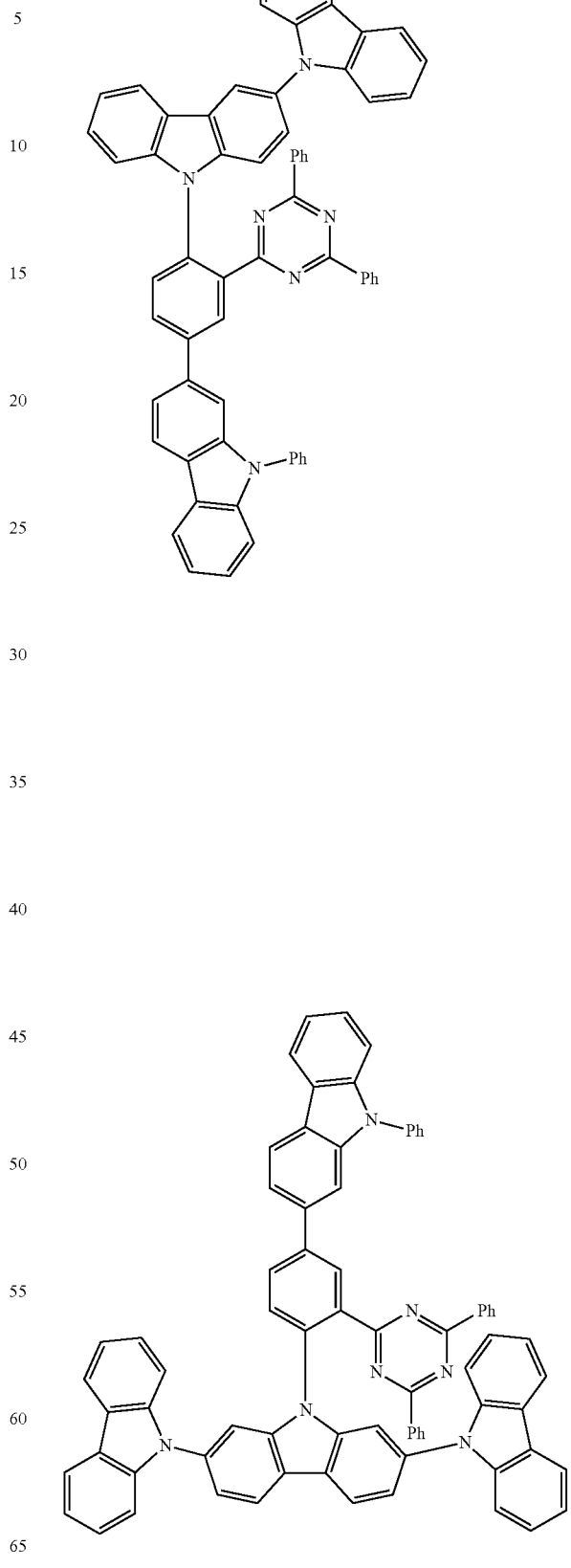

315
-continued
316
-continued
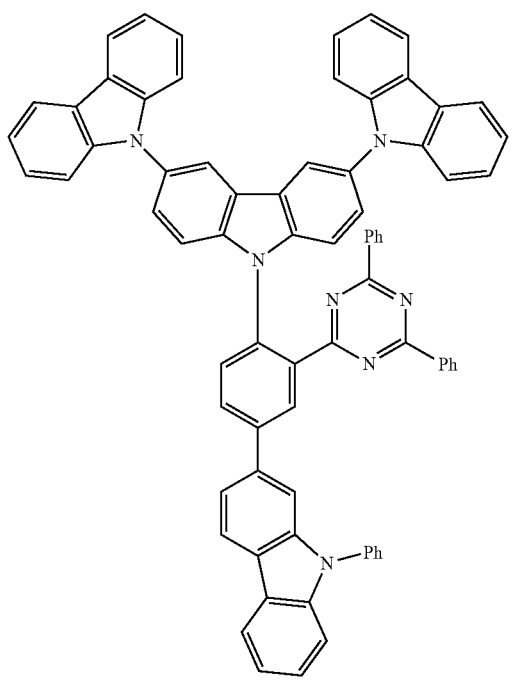
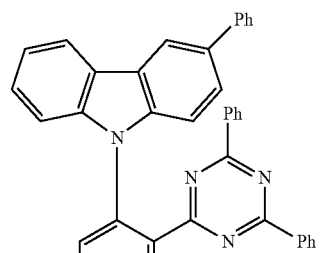
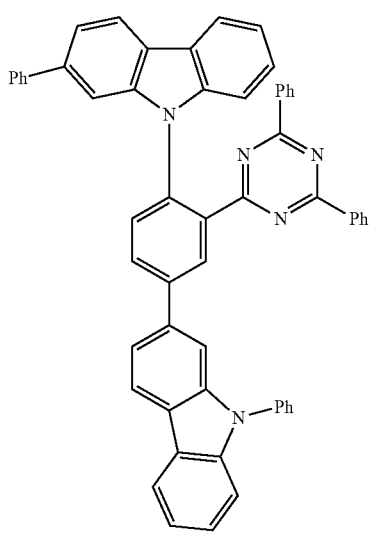
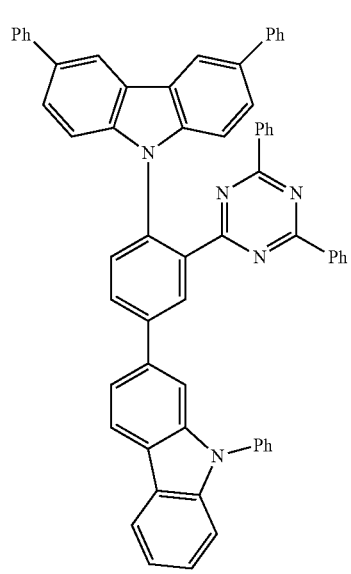

317
-continued
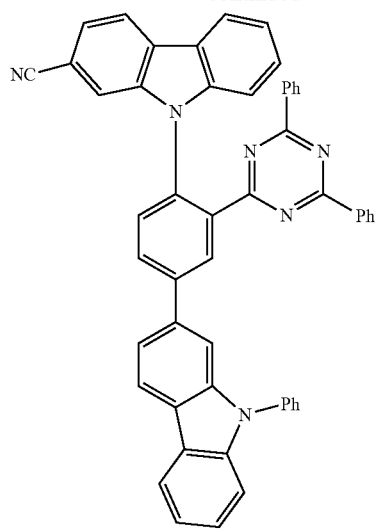
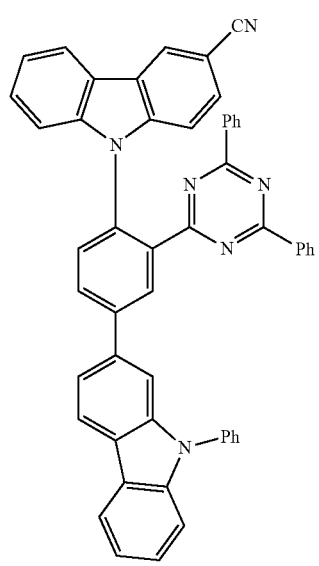
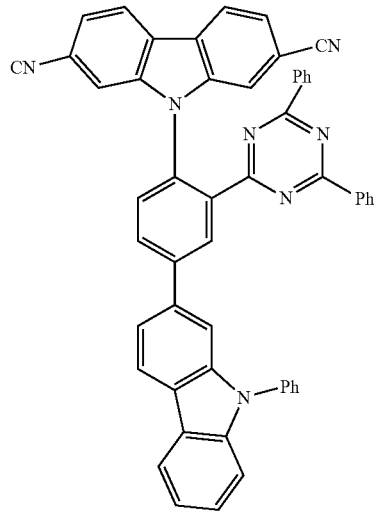
318
-continued
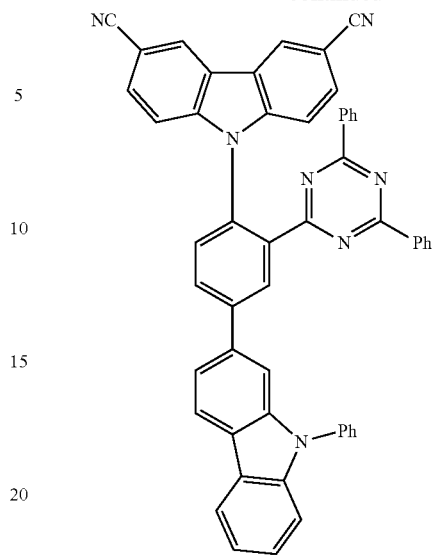
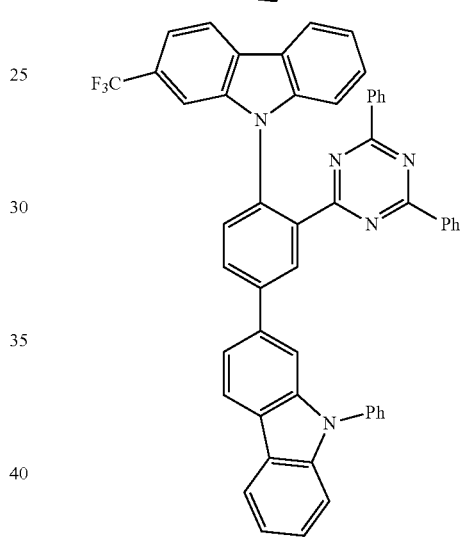
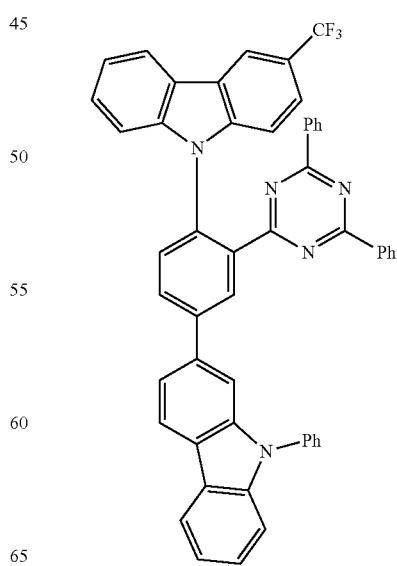

319
-continued
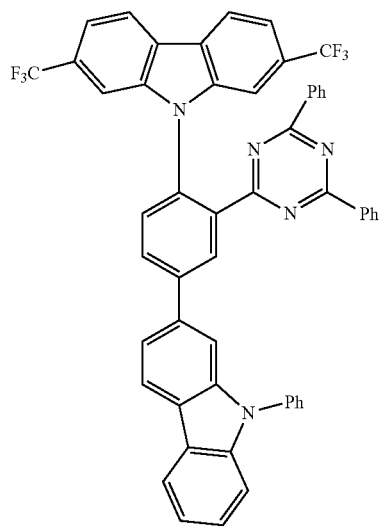
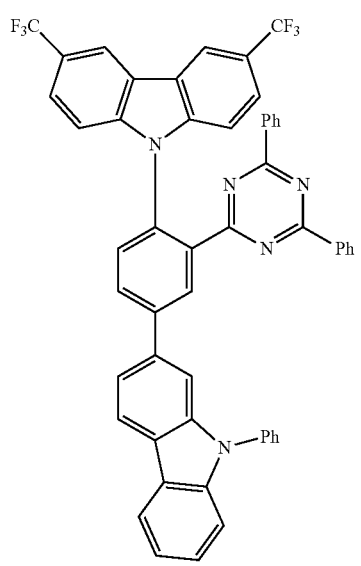
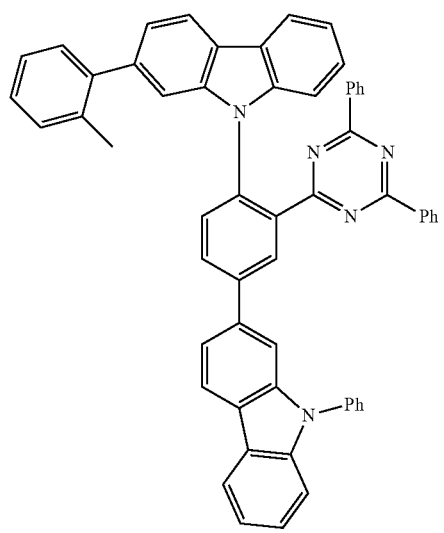
320
-continued
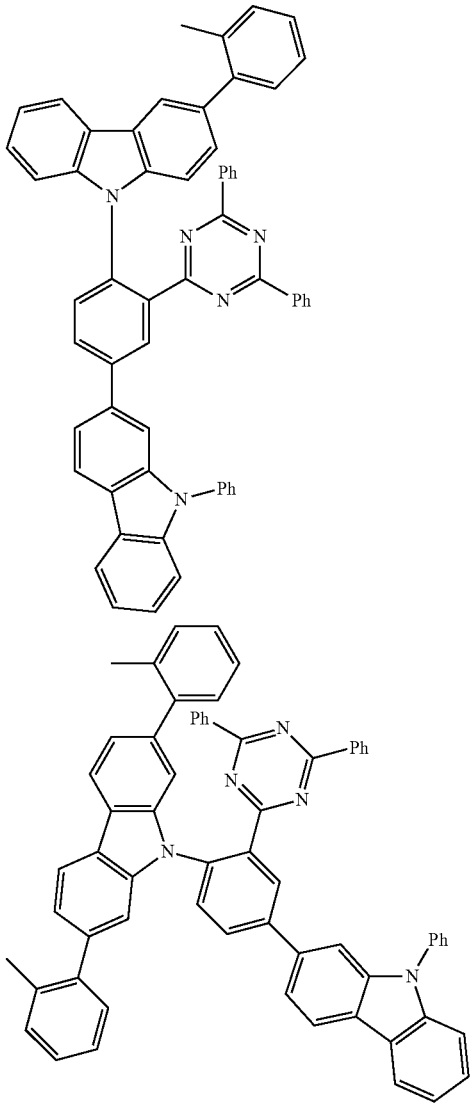
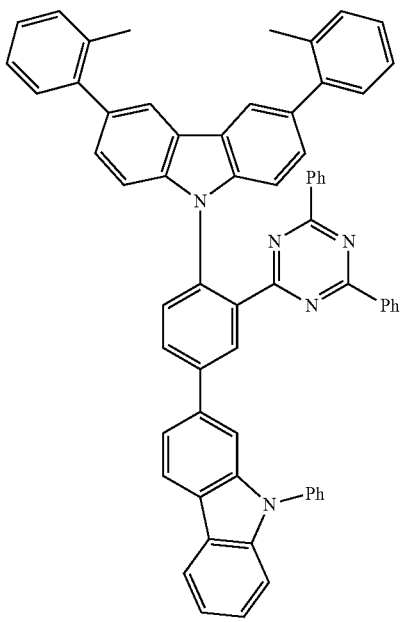

321
-continued
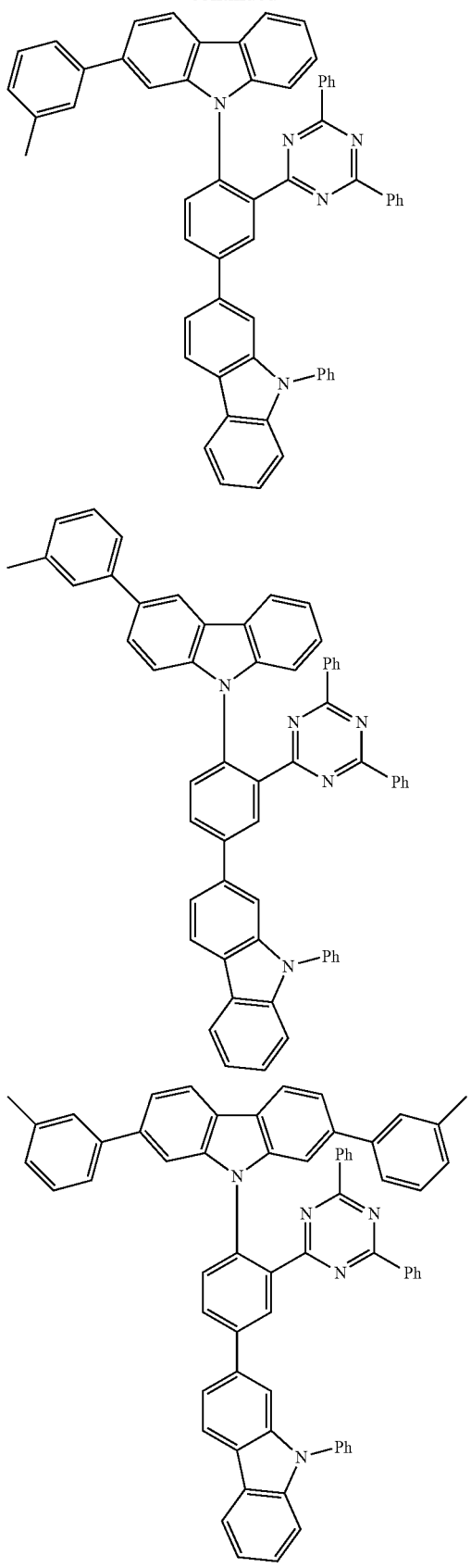
322
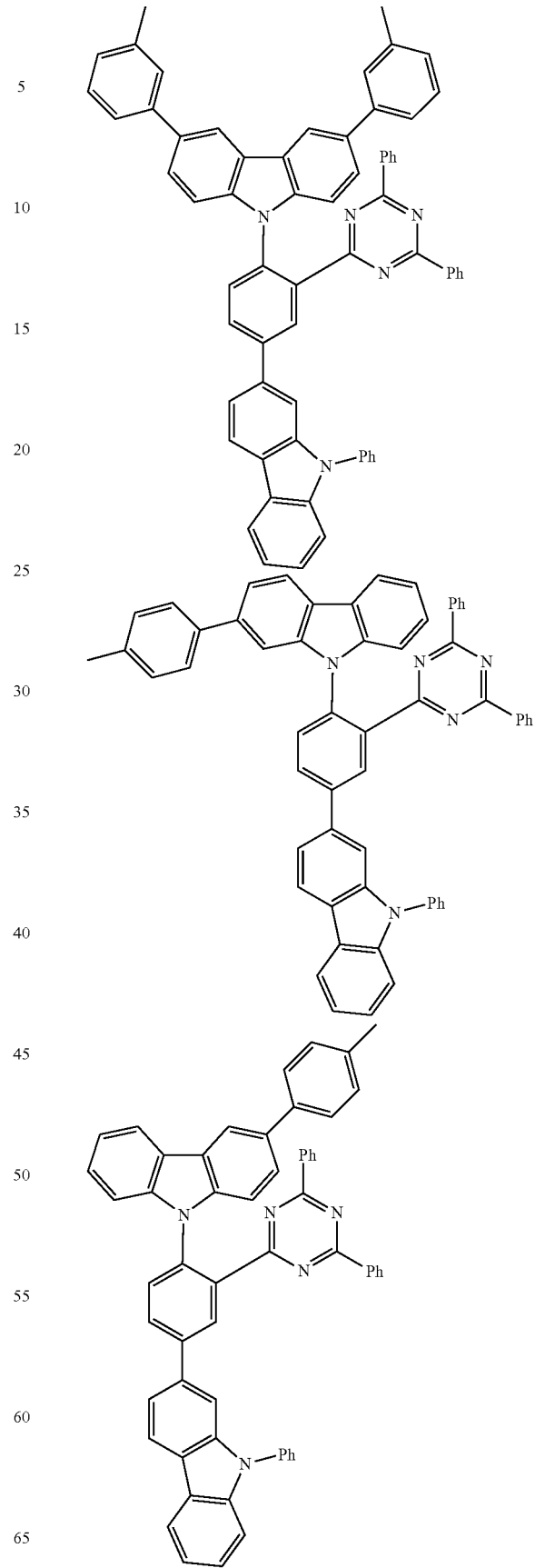

323
-continued
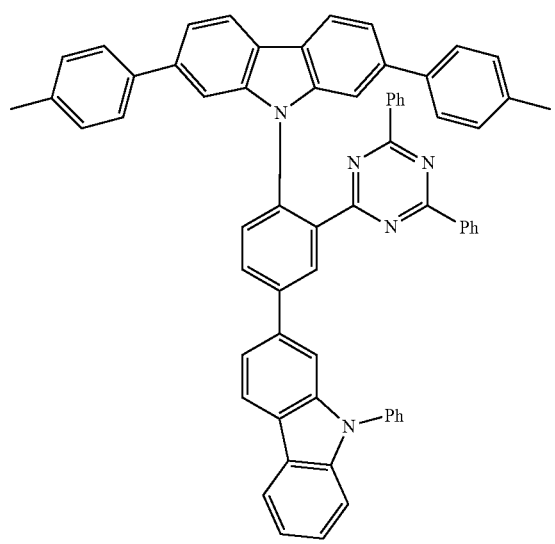
324
-continued
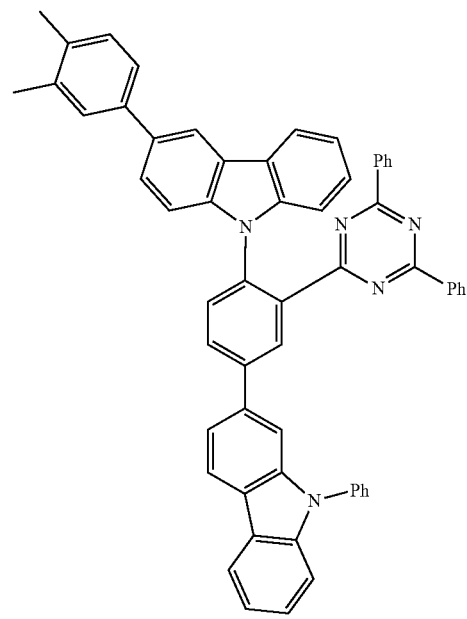
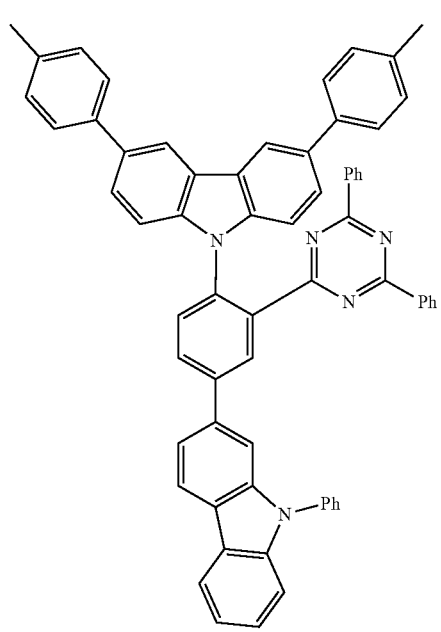
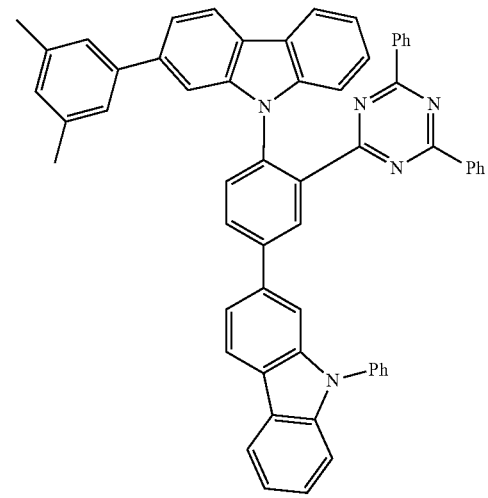

325
-continued
326
-continued
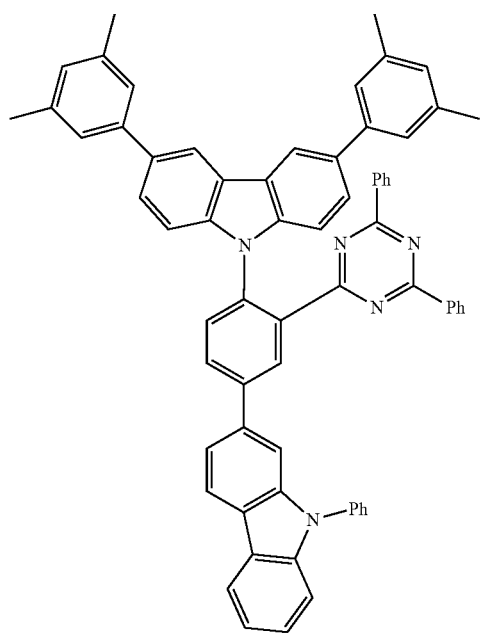
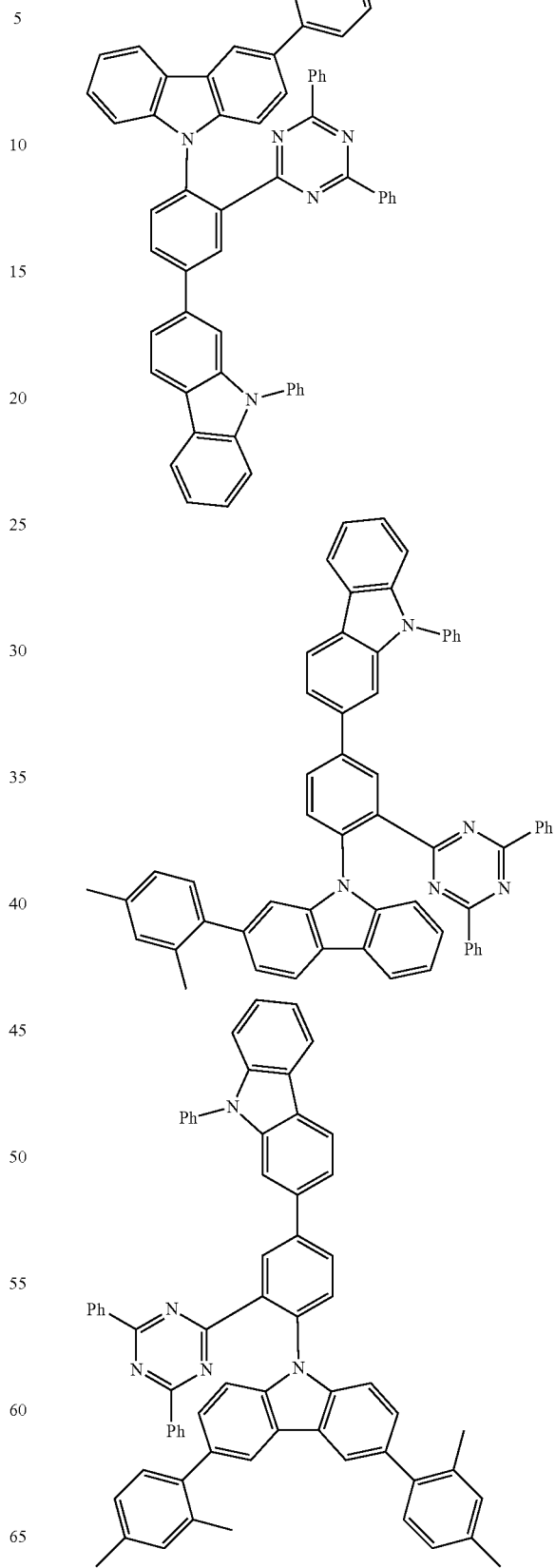

327
-continued
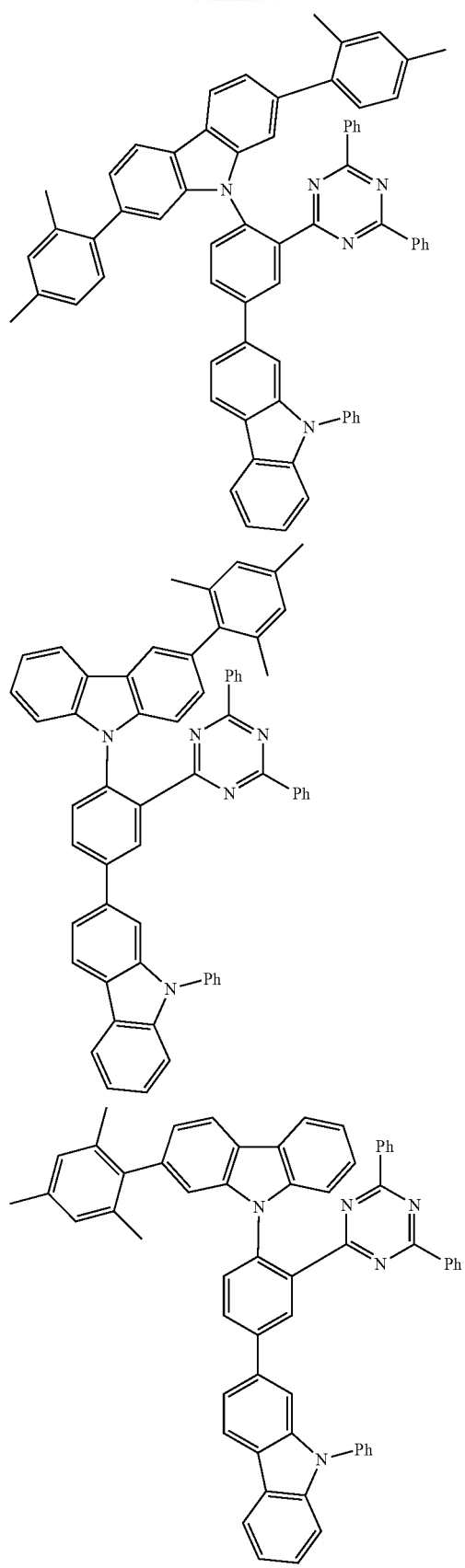
328
-continued
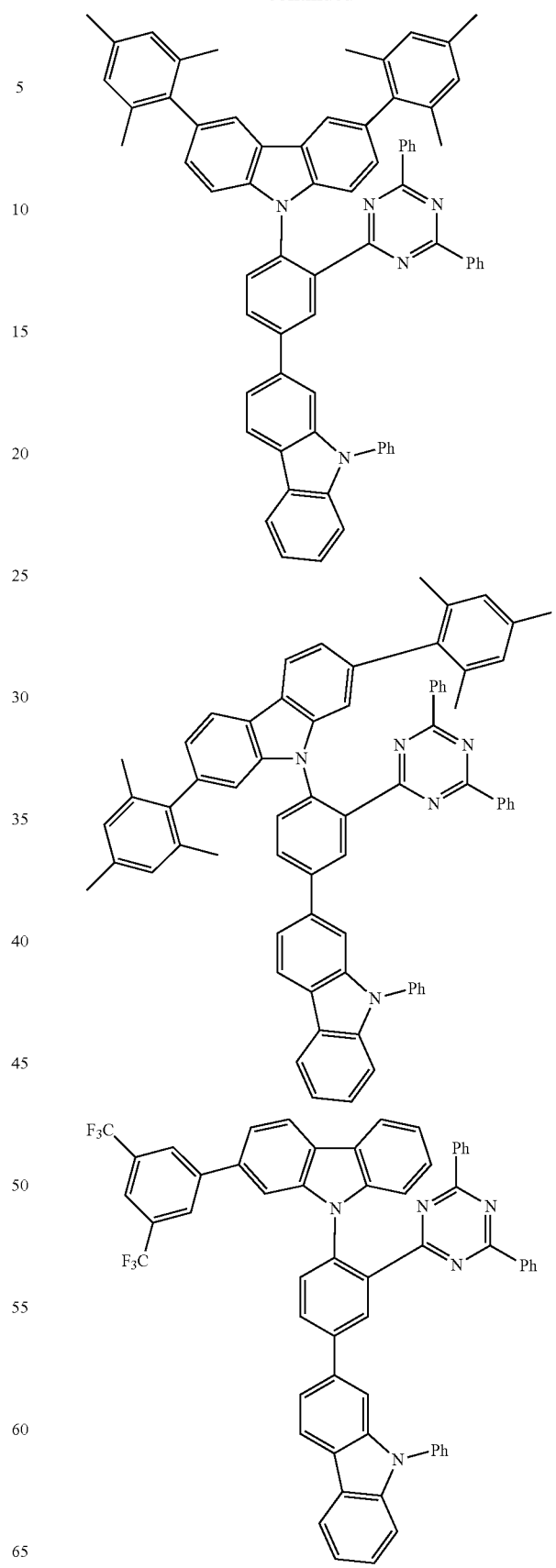

329
-continued
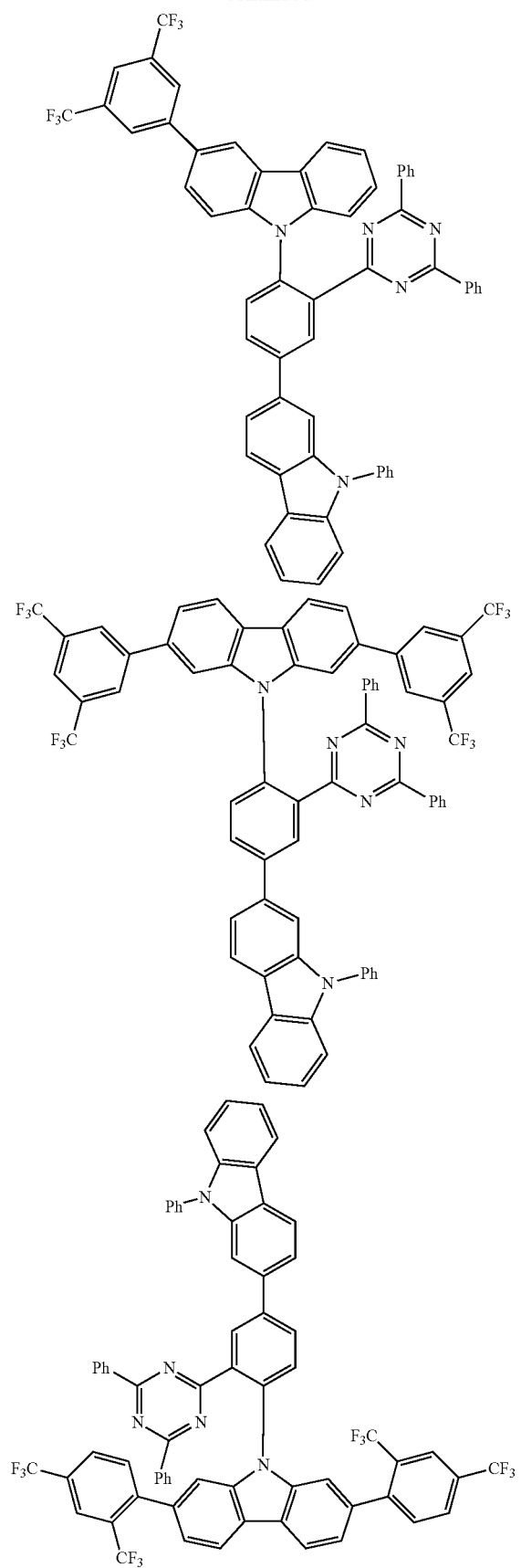
330
-continued
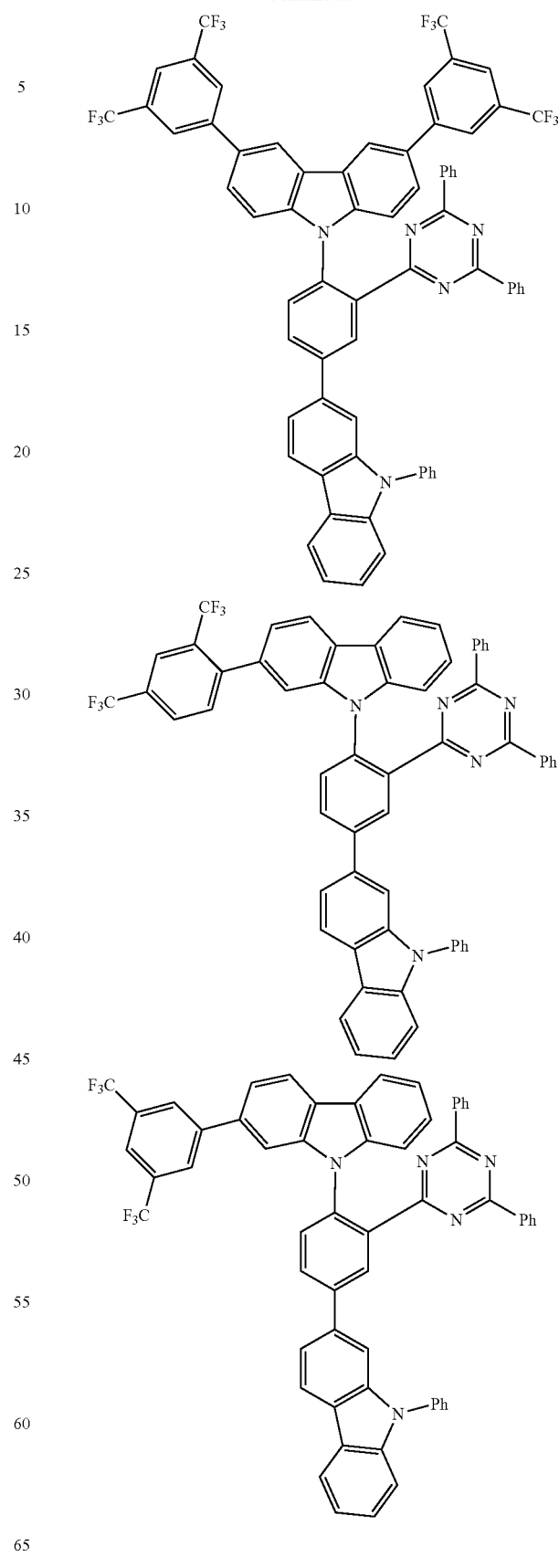

331
-continued
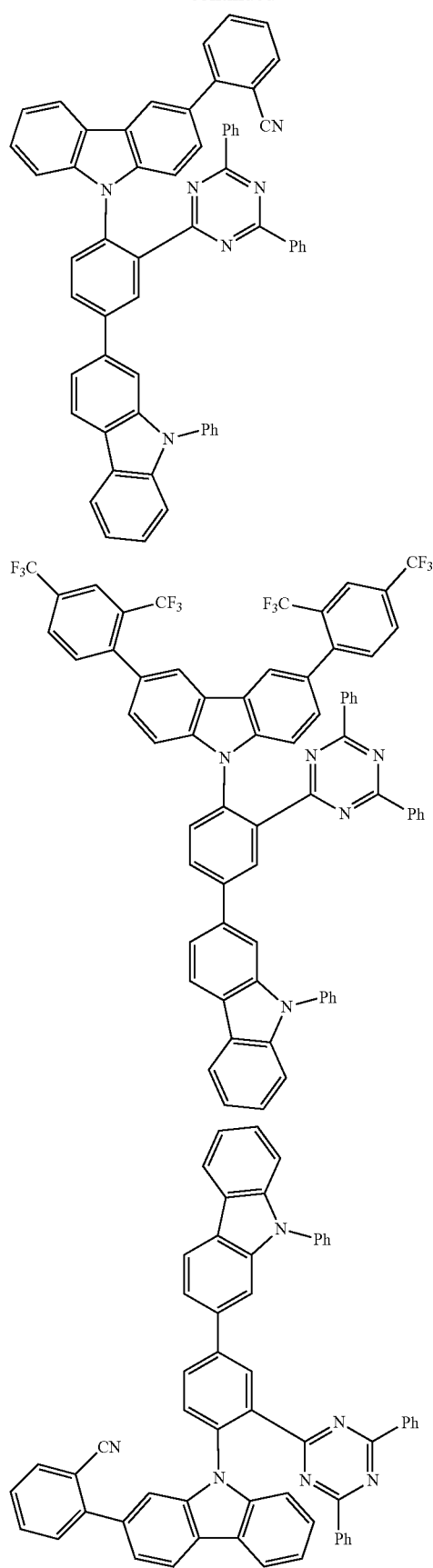
332
-continued

333
-continued
334
-continued
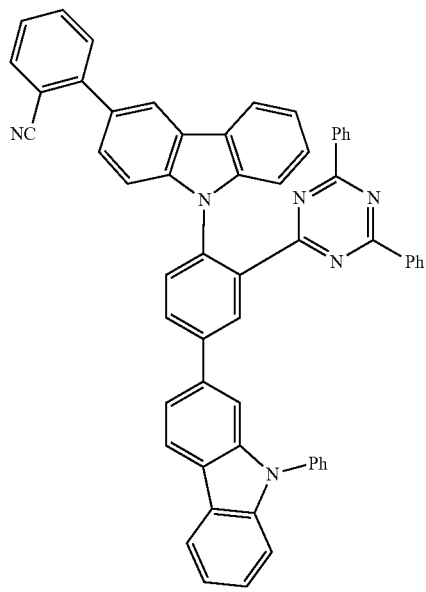
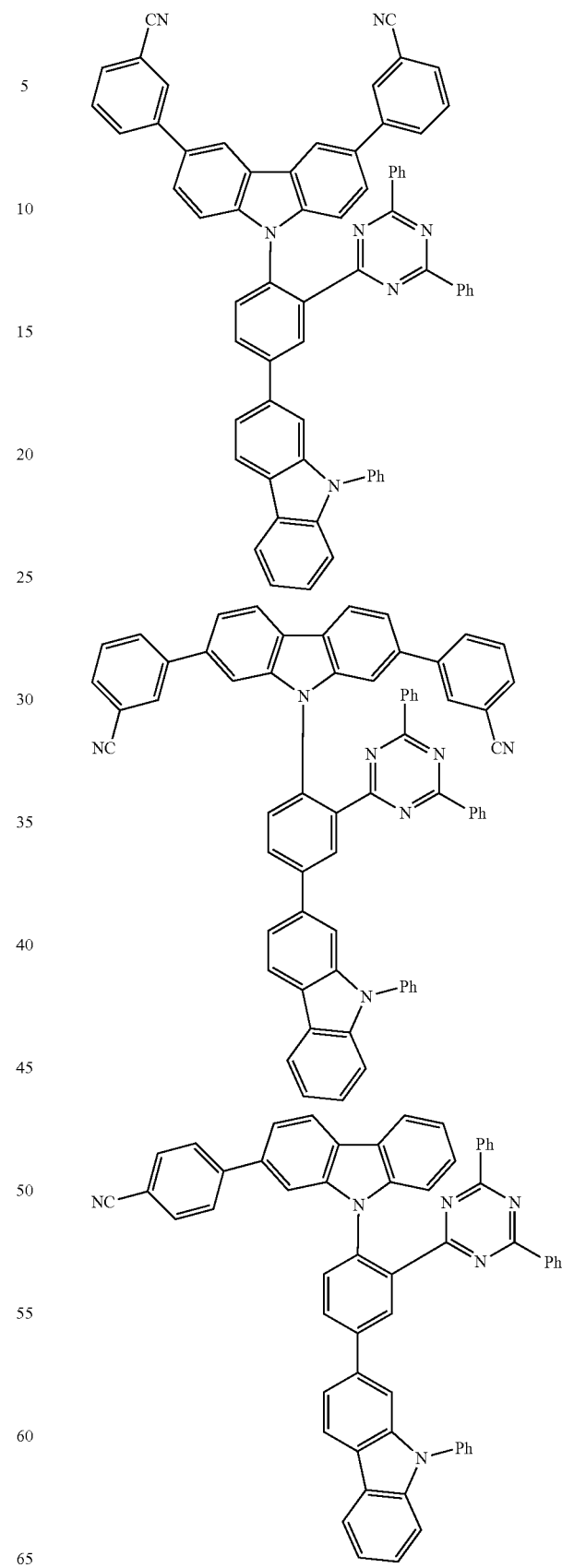

335
-continued
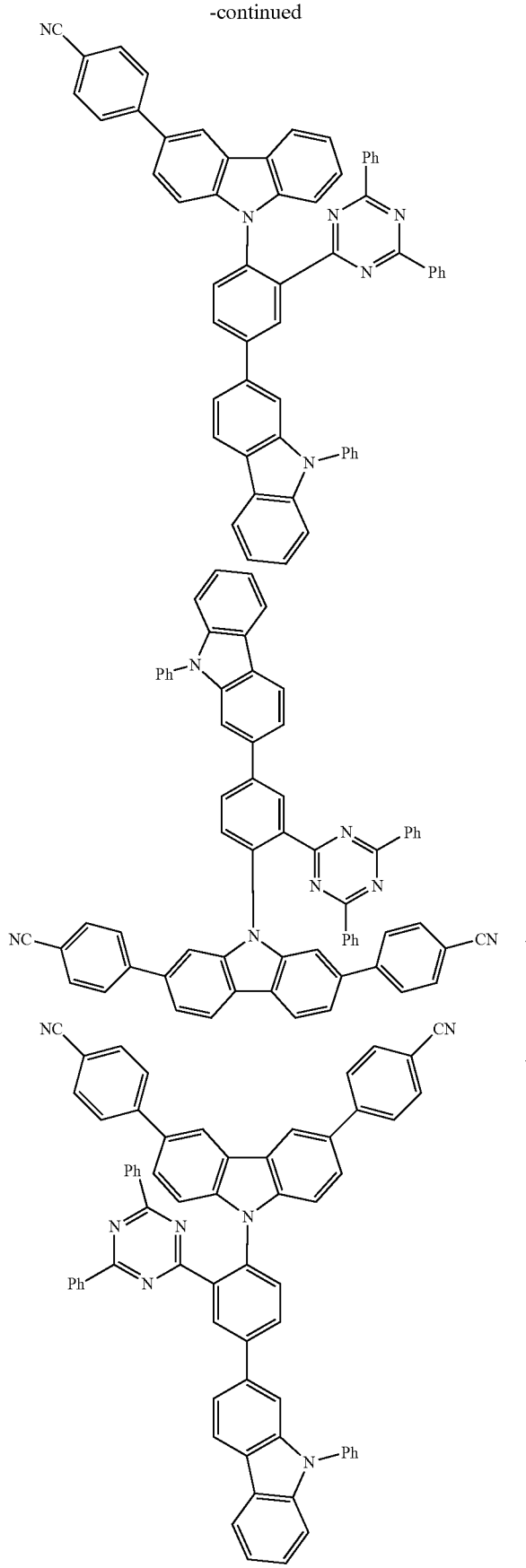
336
-continued
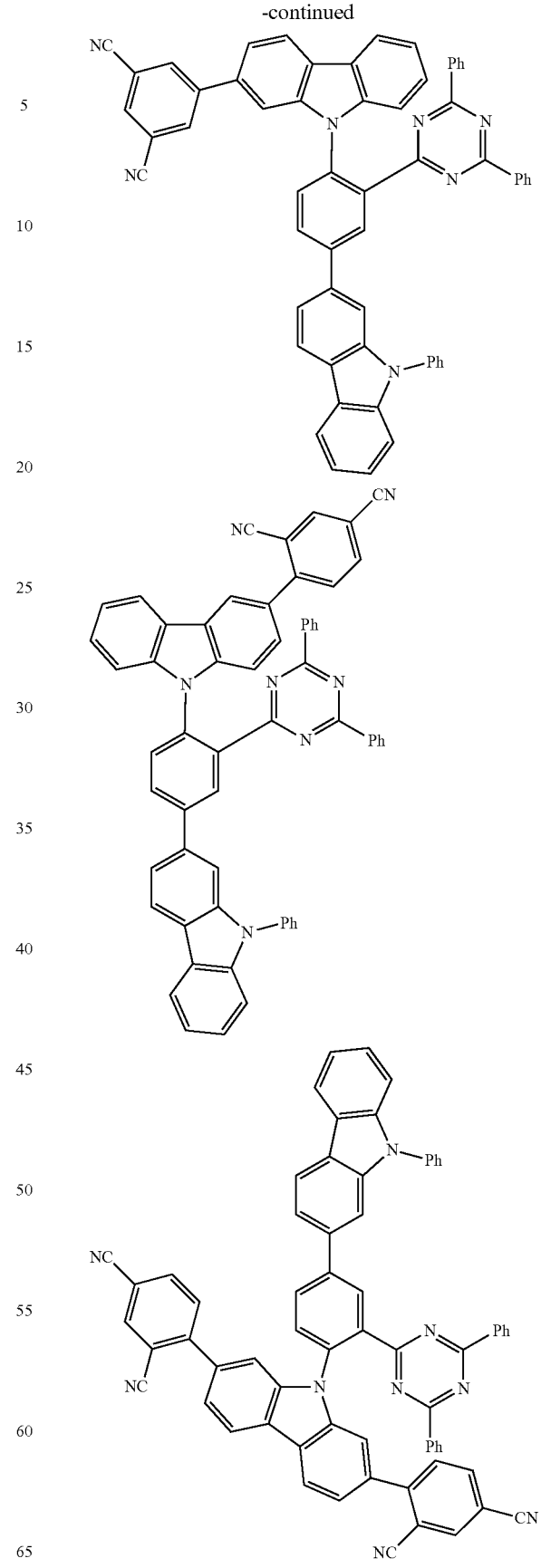

337
-continued
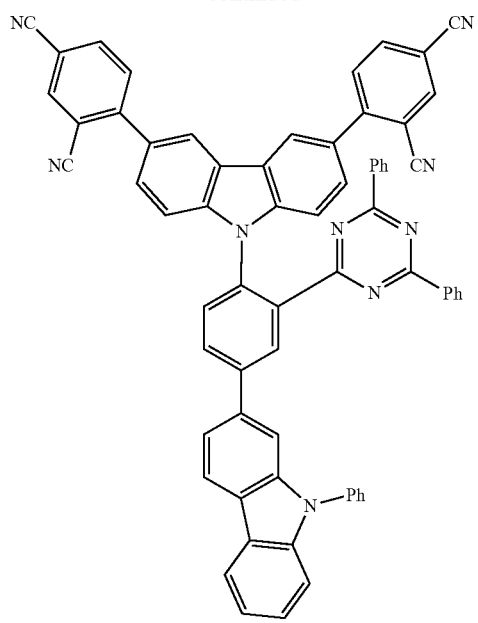
338
-continued
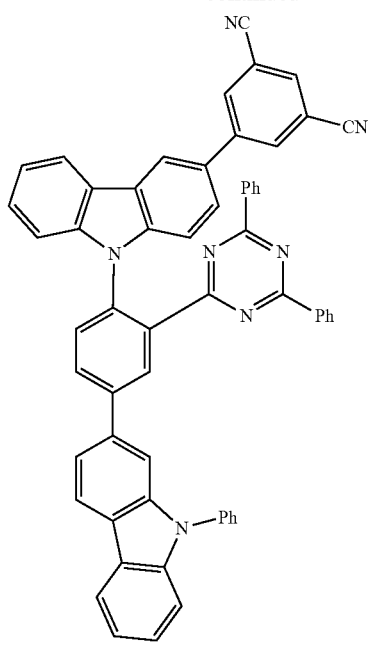
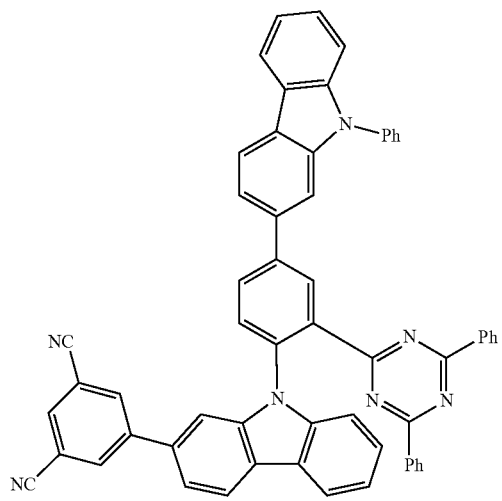

339
-continued
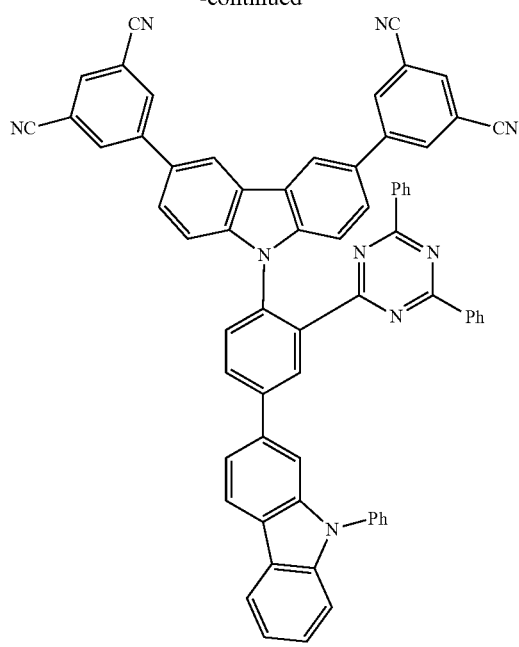
340
-continued
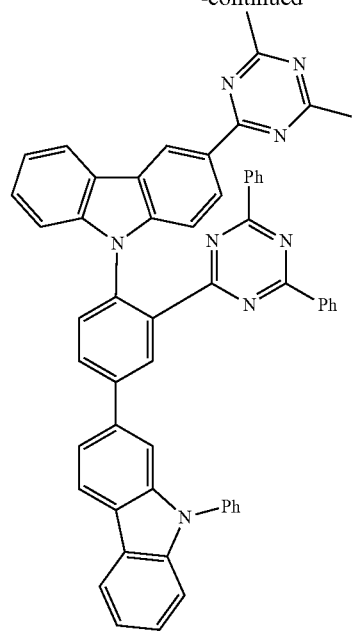
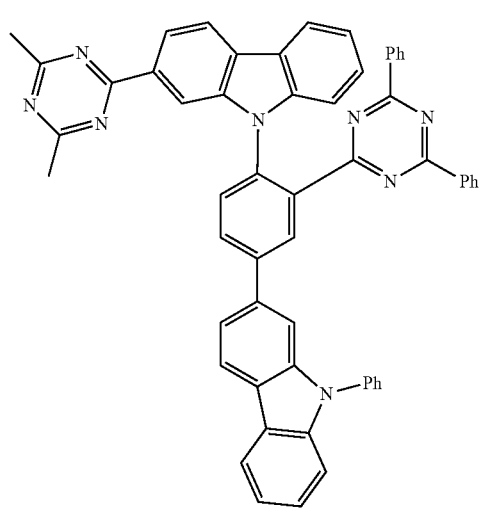
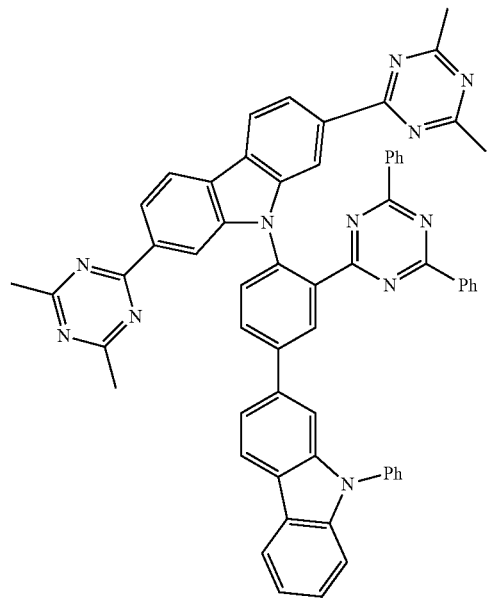

341
-continued
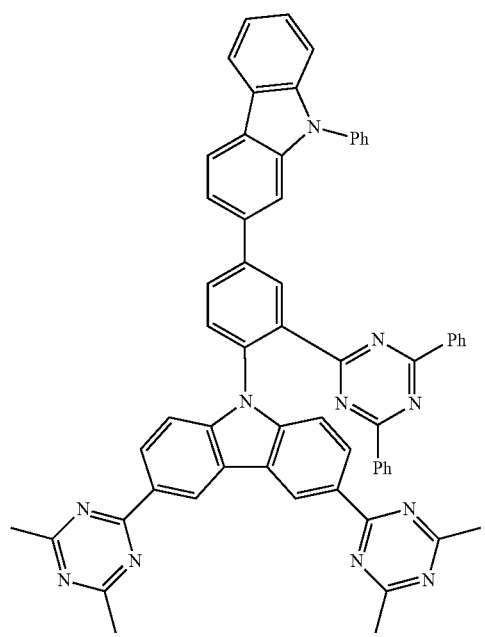
342
-continued
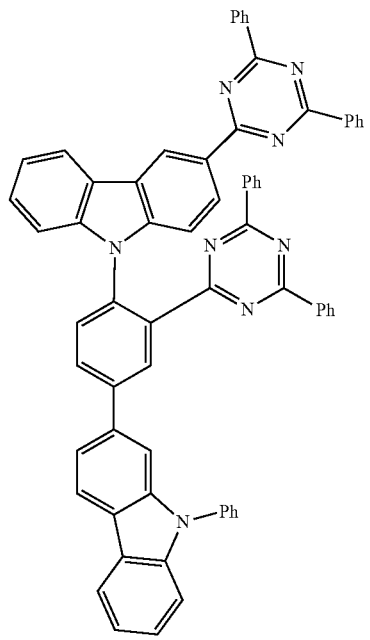
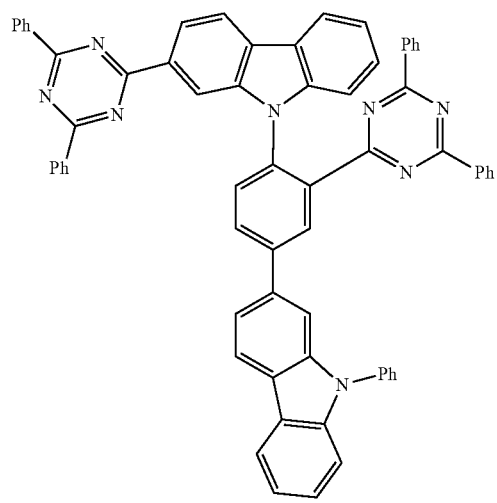
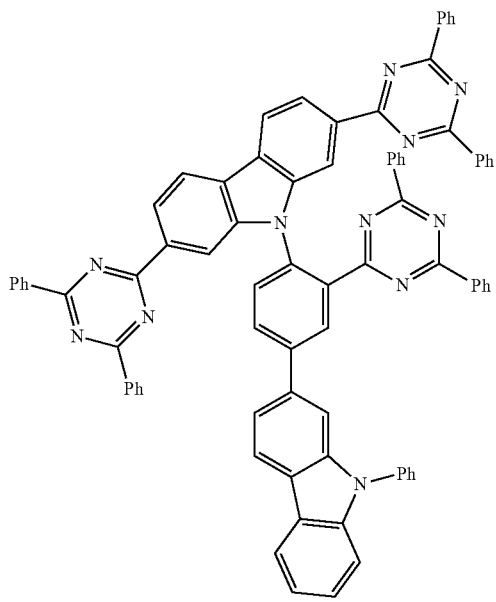

343
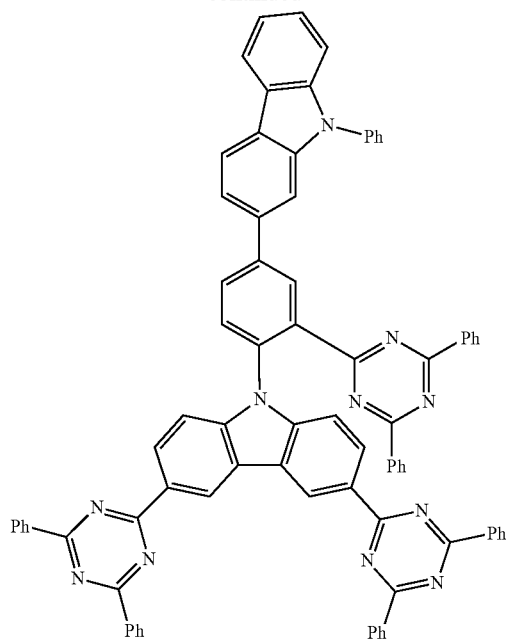
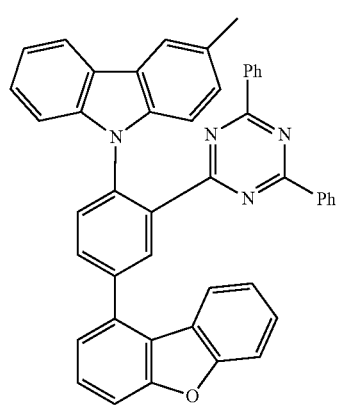
344
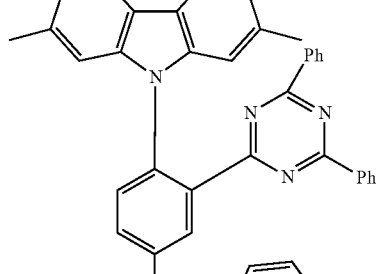
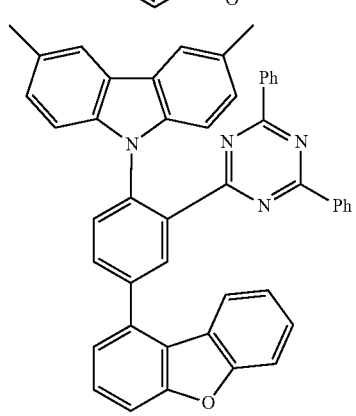
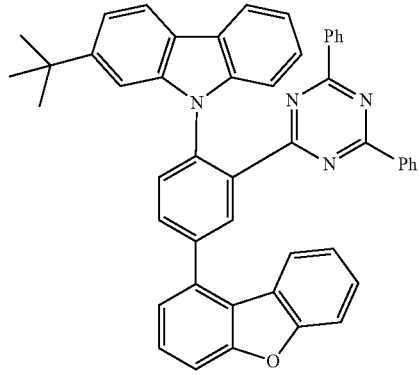
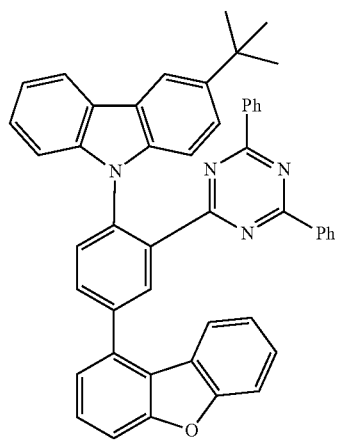

345
-continued
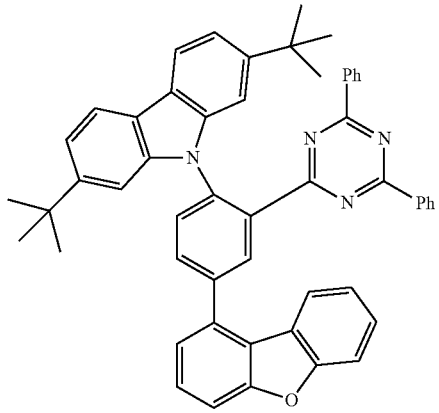
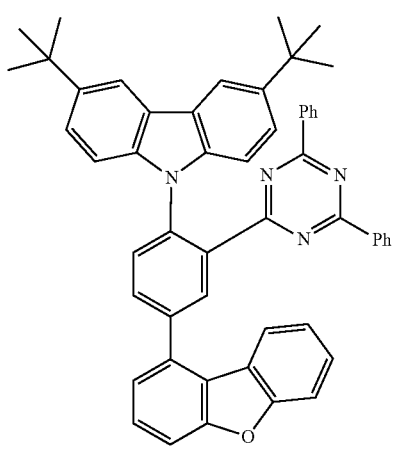
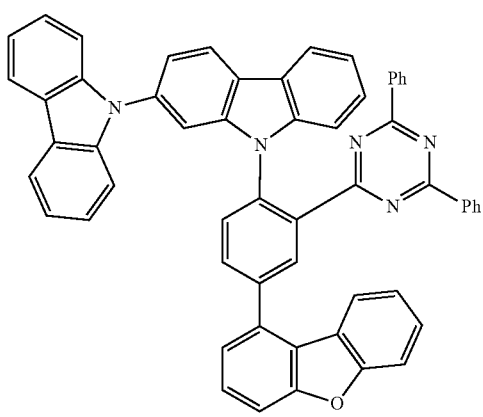
346
-continued
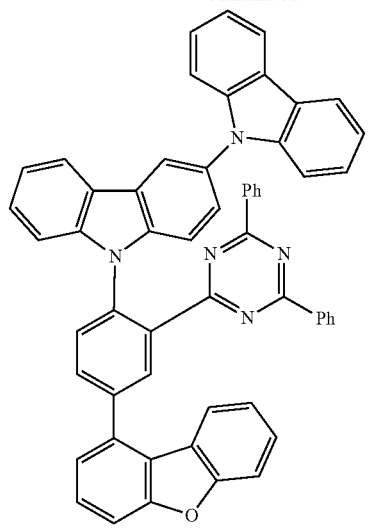
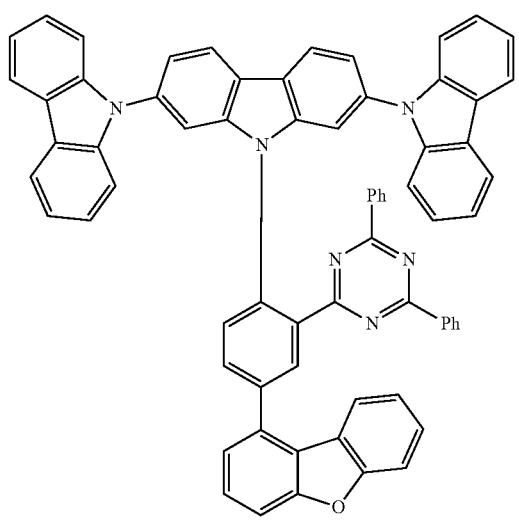
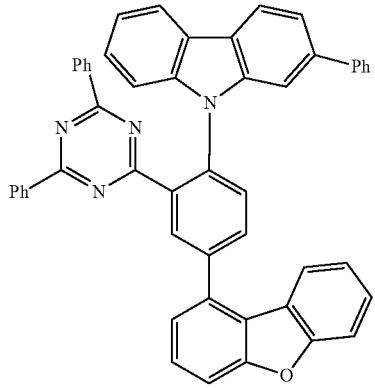

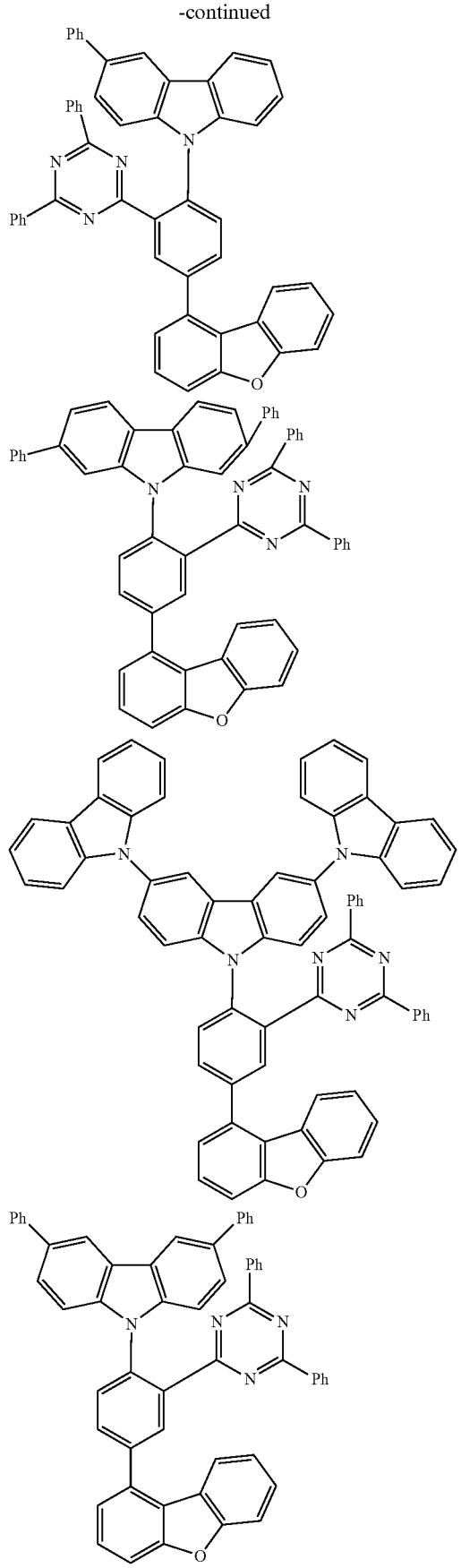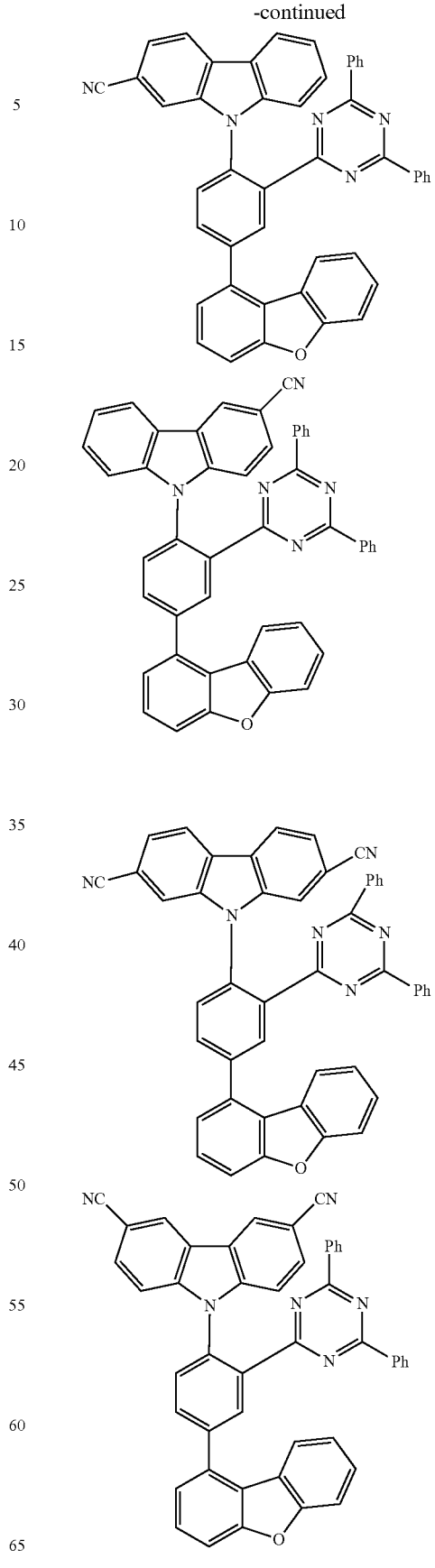

349
-continued
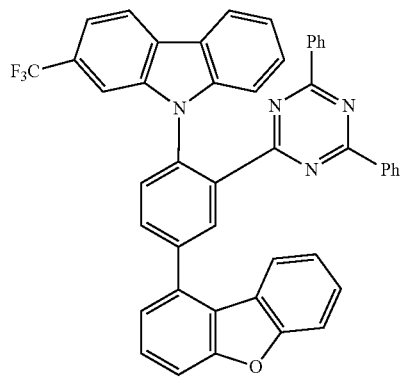
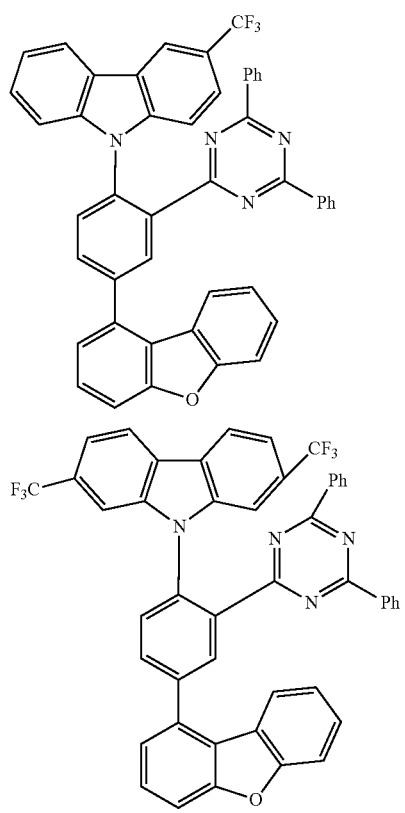
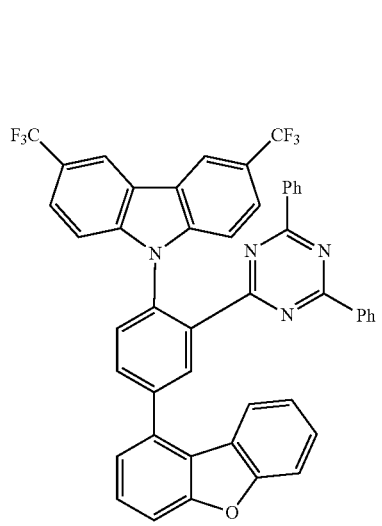
350
-continued
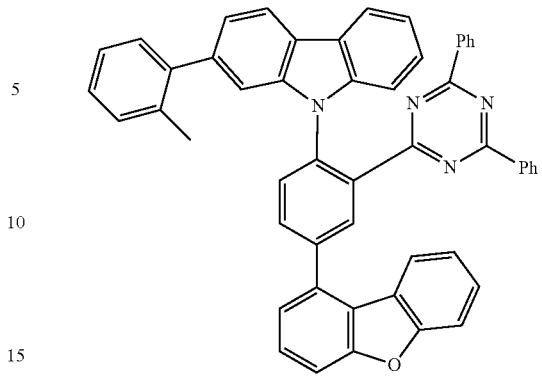
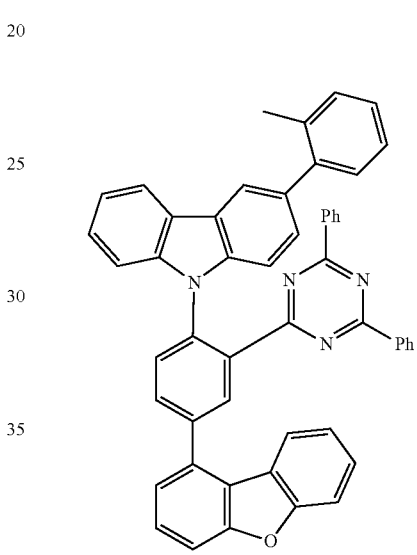
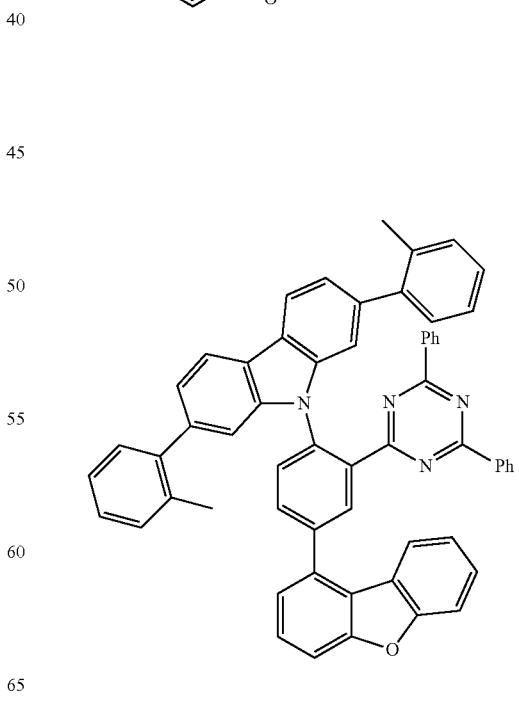

351
-continued
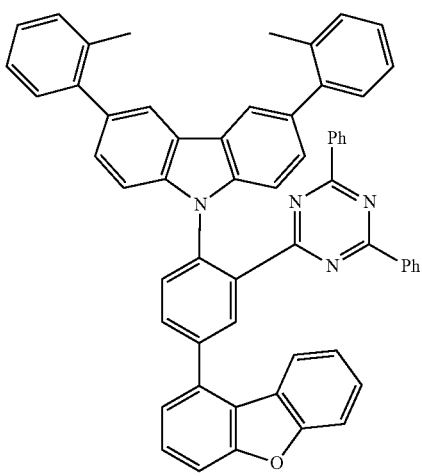
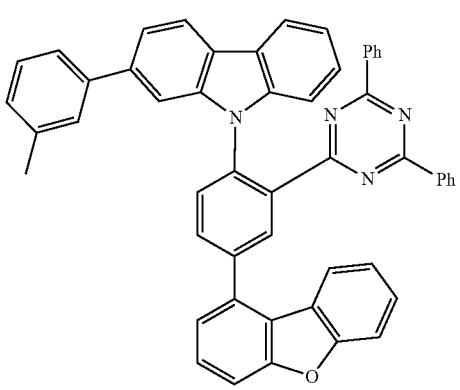
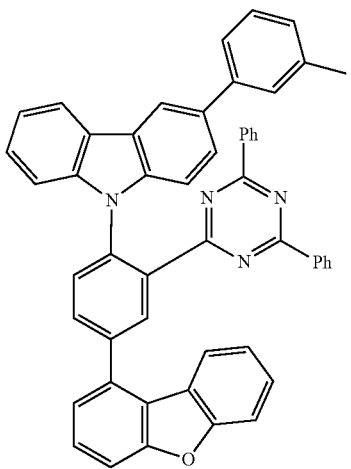
352
-continued
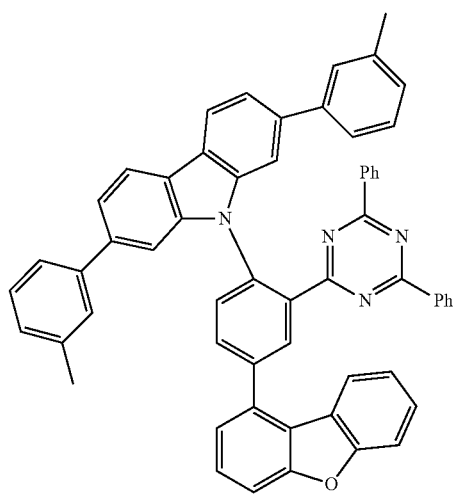
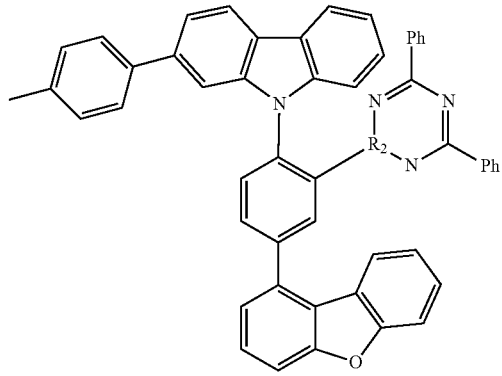

353
-continued
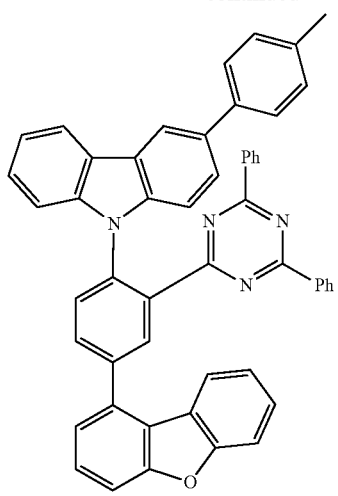
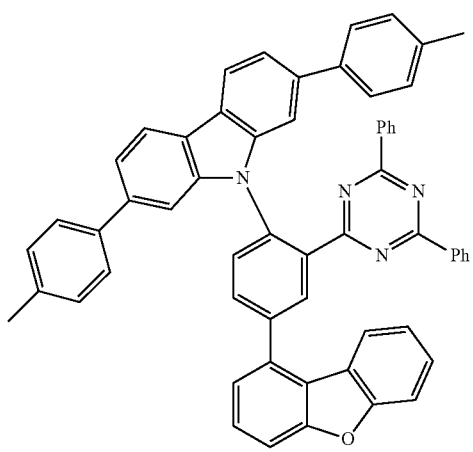
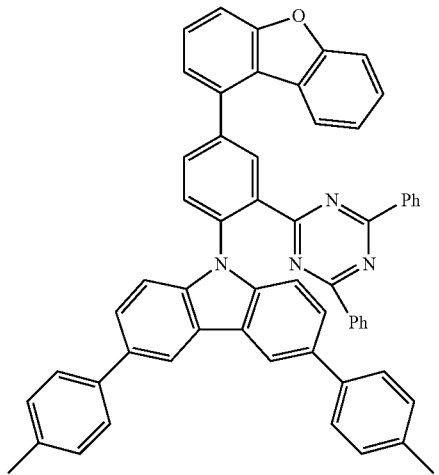
354
-continued
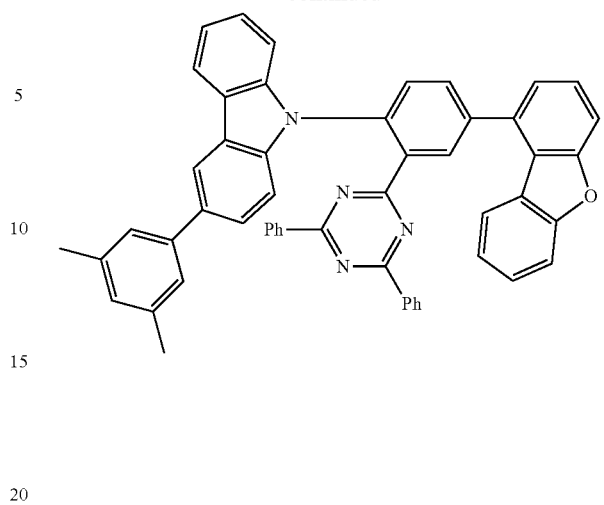
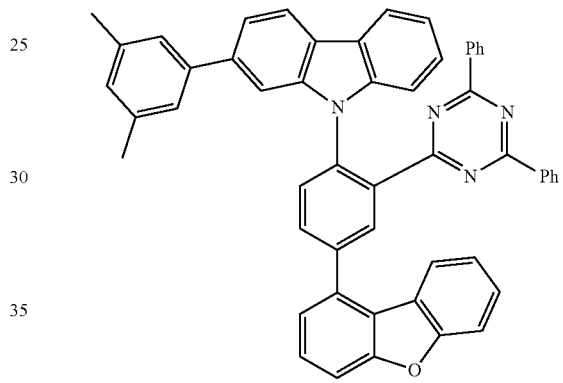
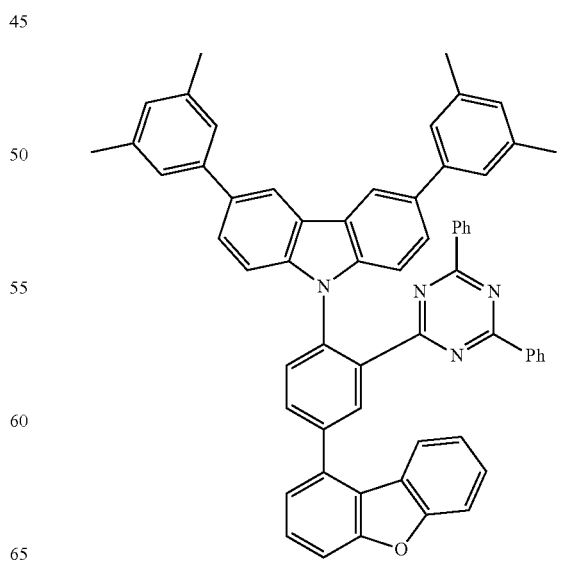

355
-continued
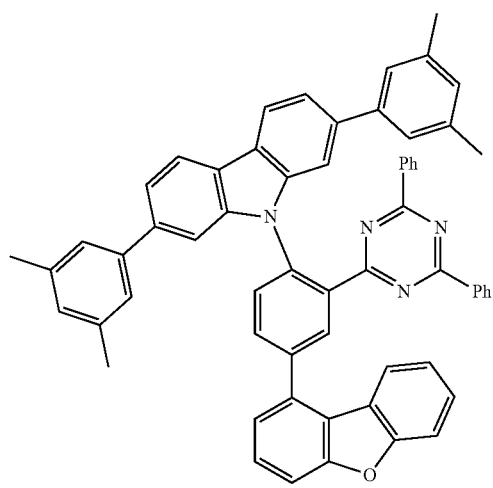
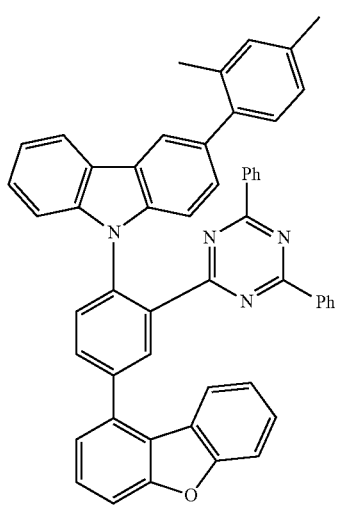
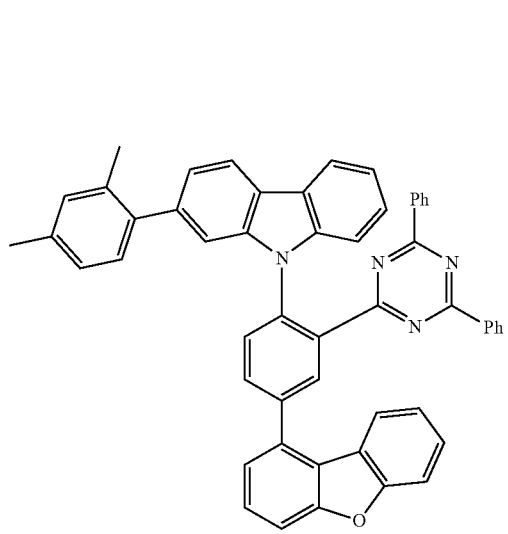
356
-continued
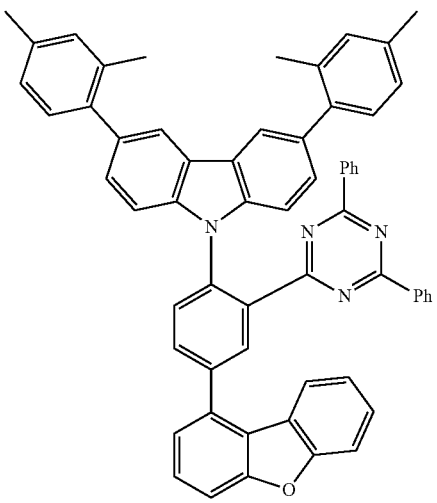
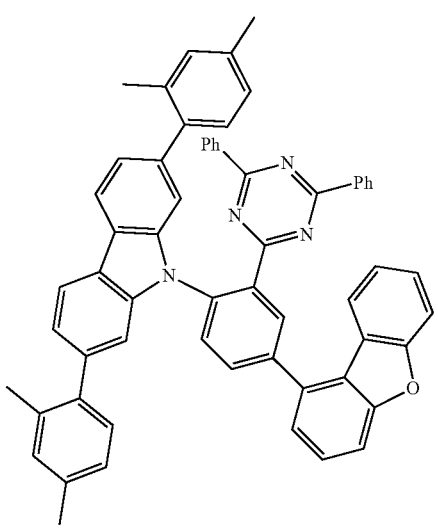

357
-continued
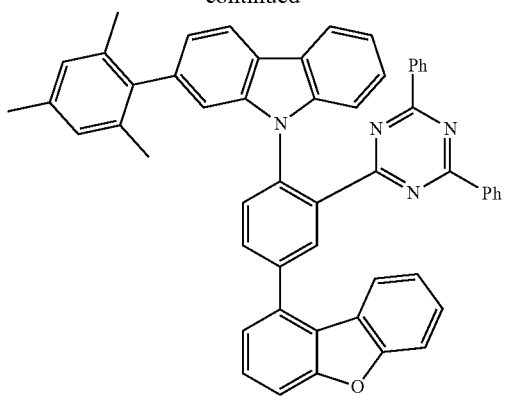
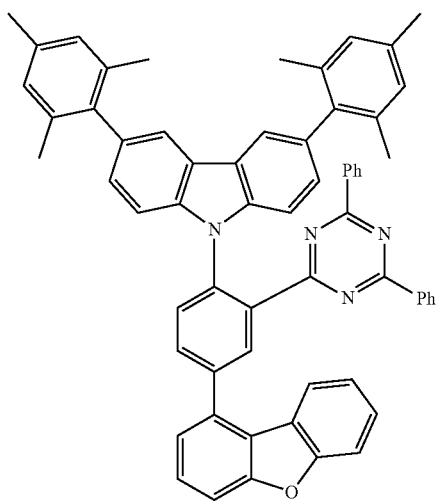
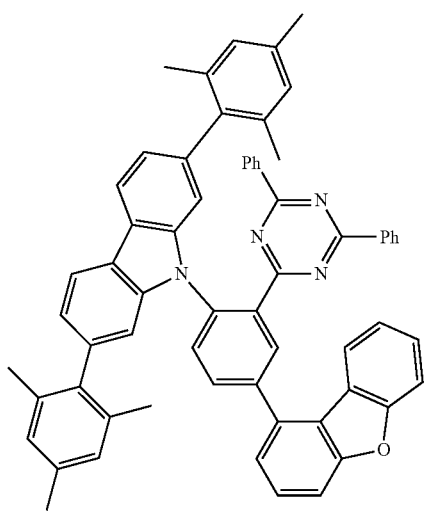
358
-continued
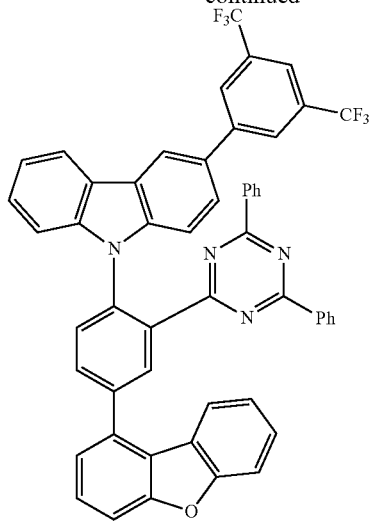
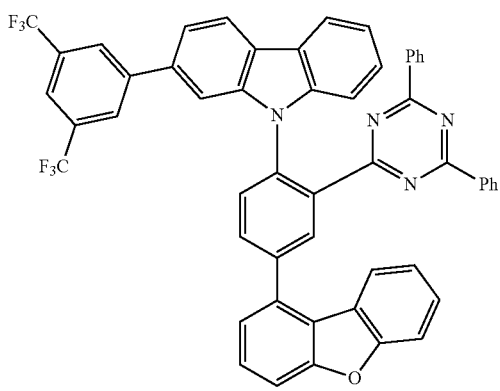
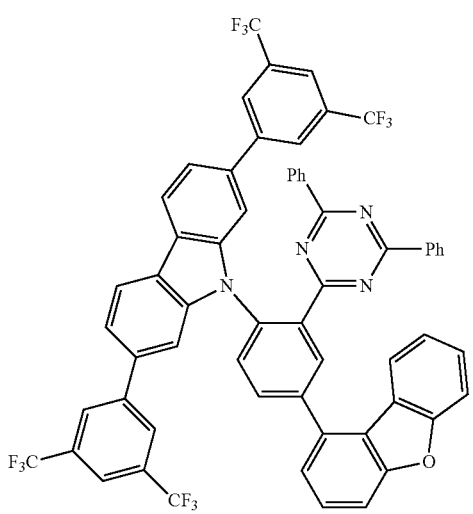

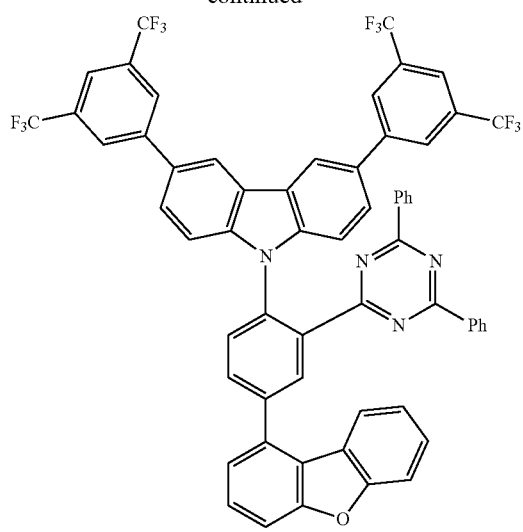
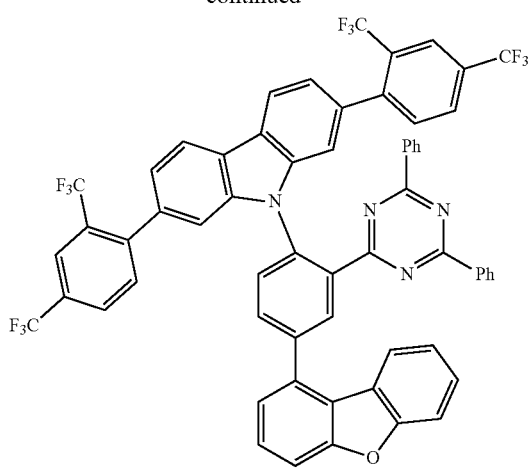
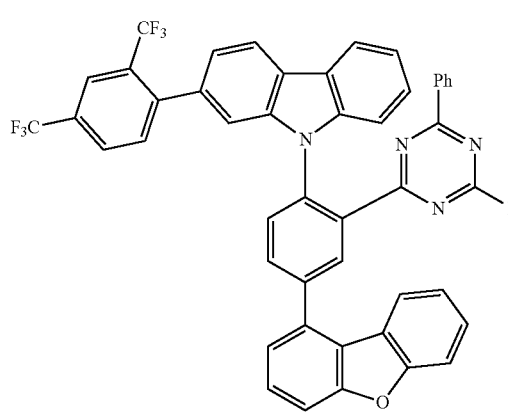
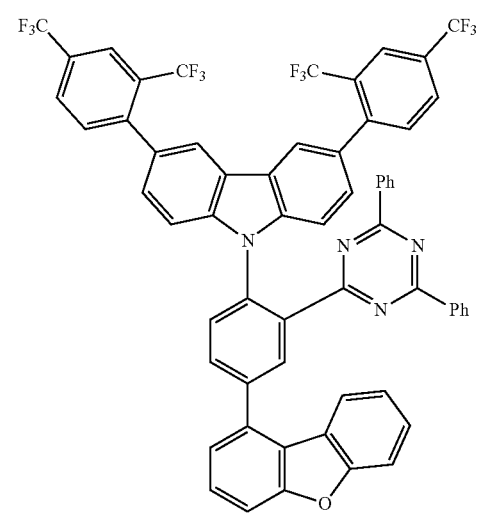
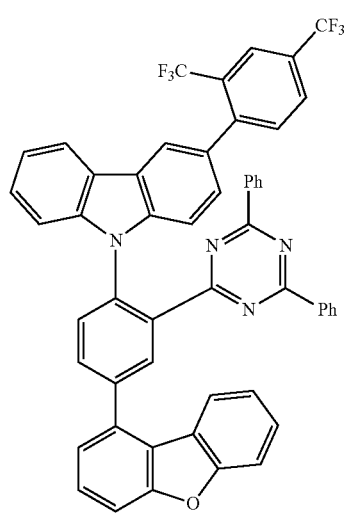
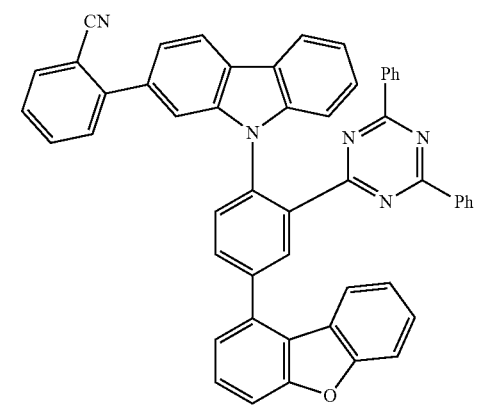

361
-continued
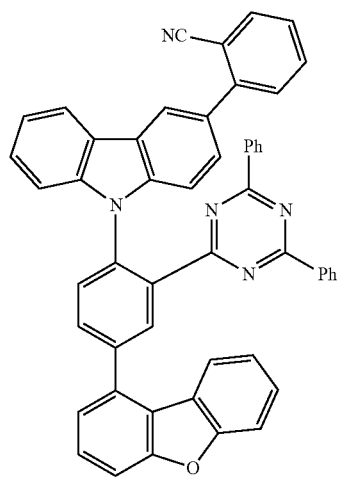
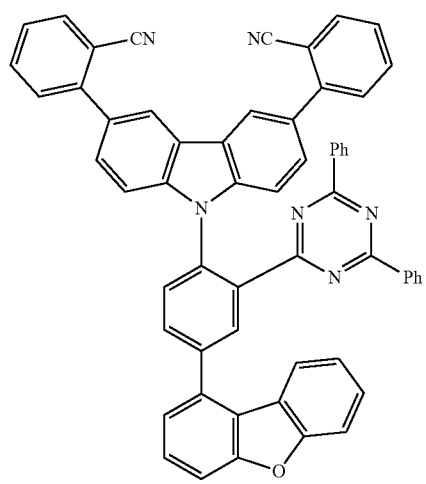
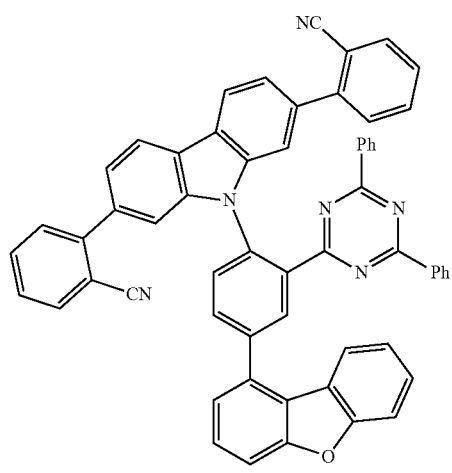
362
-continued
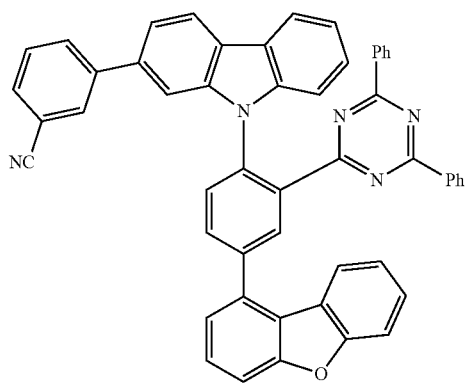
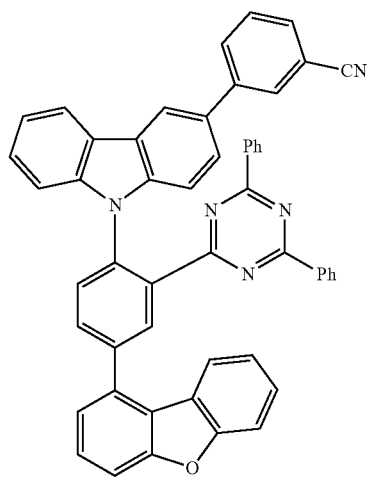
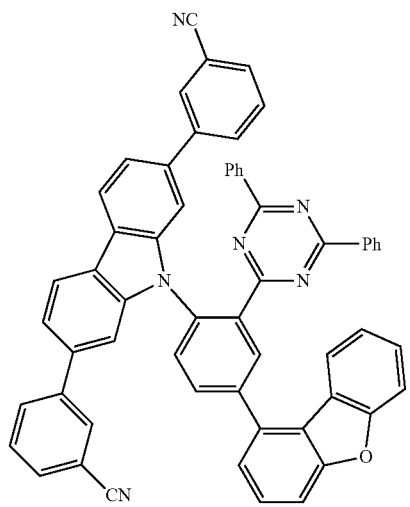

363
-continued
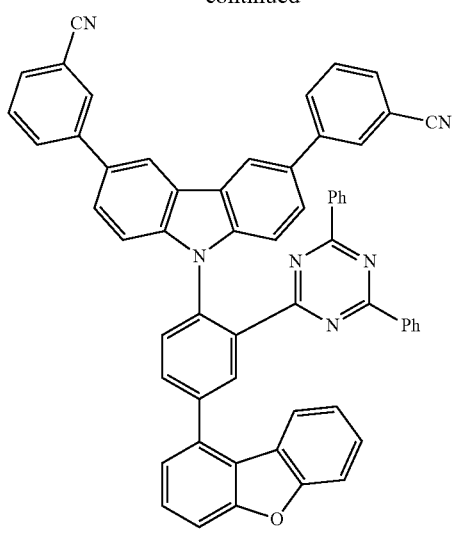
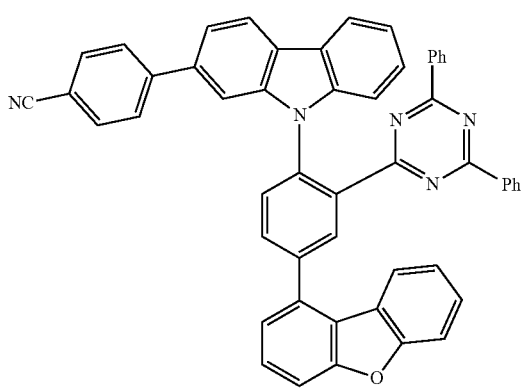
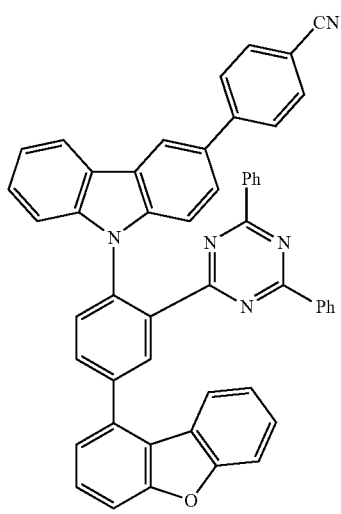
364
-continued
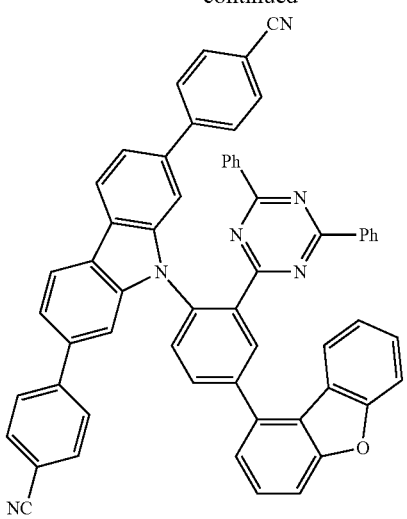
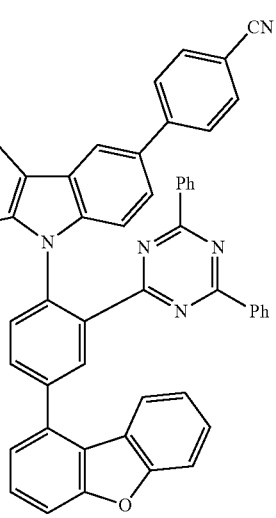

365
-continued
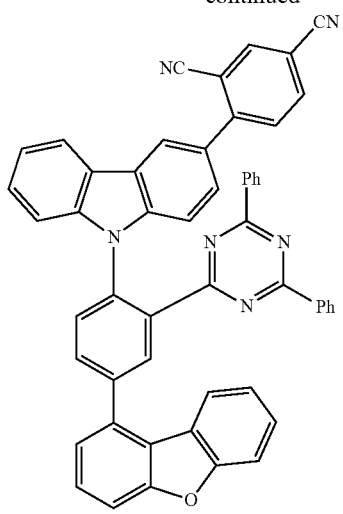
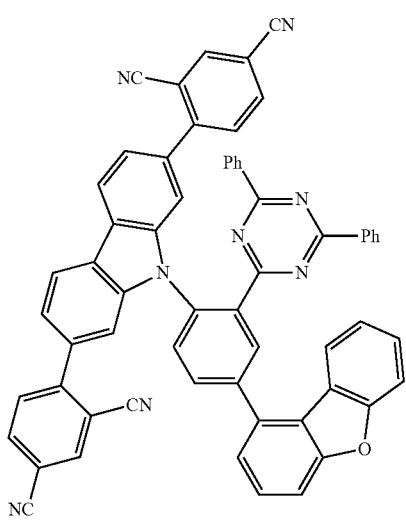
366
-continued
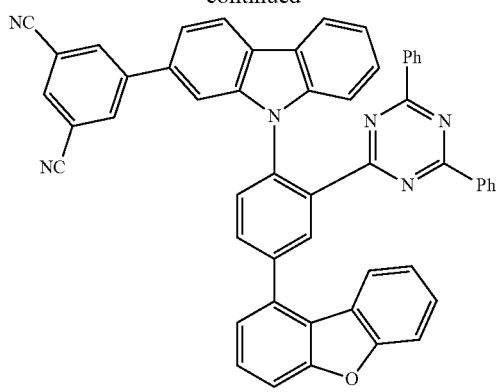
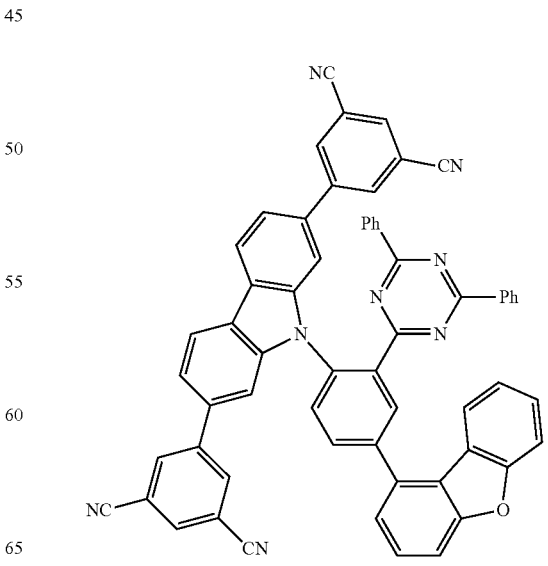

367
-continued
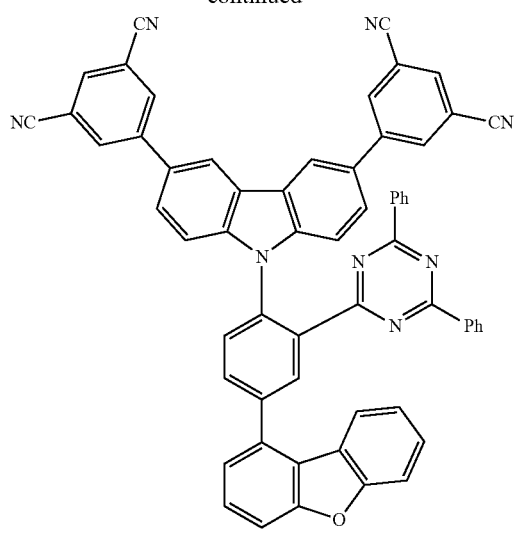
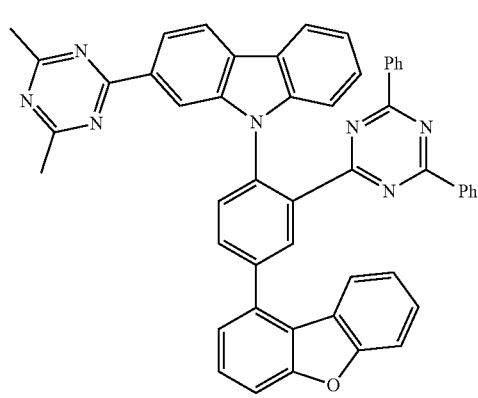
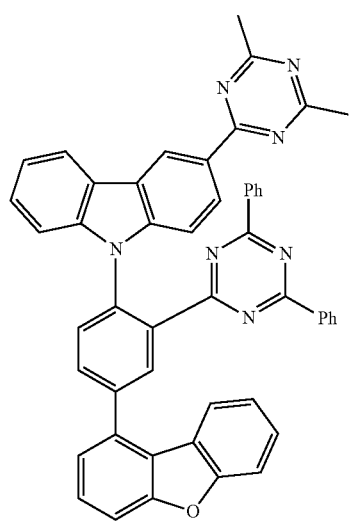
368
-continued
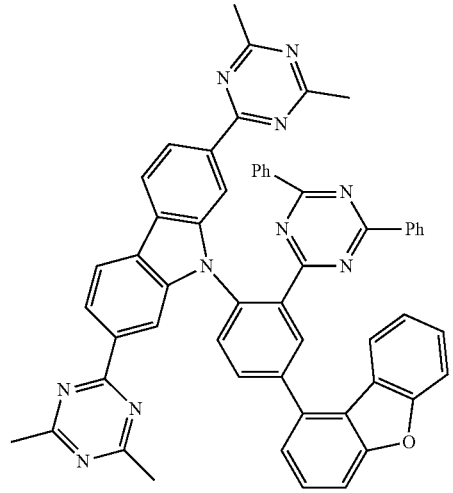
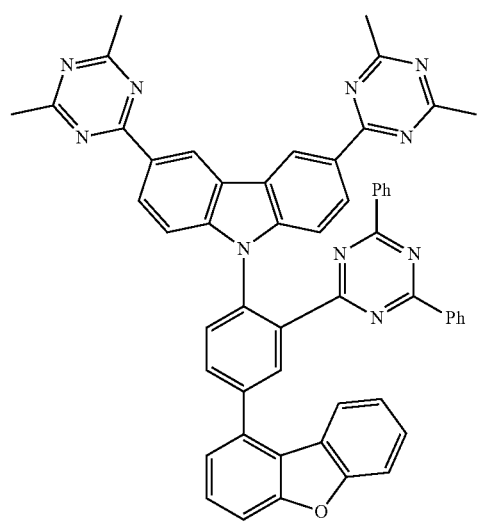
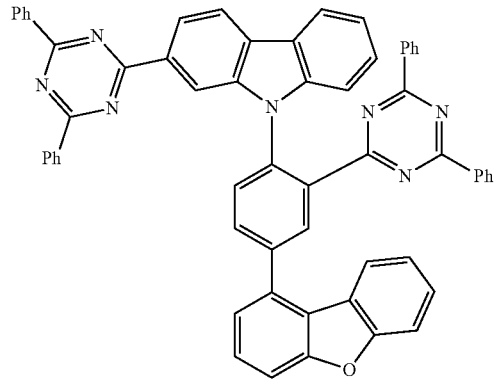

-continued
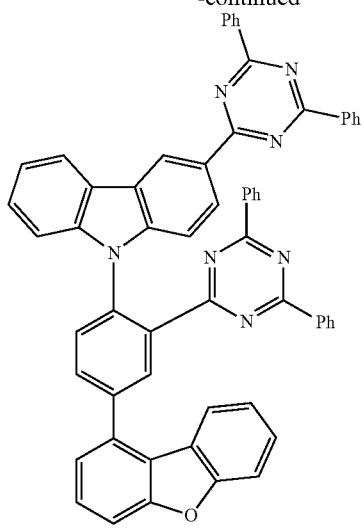
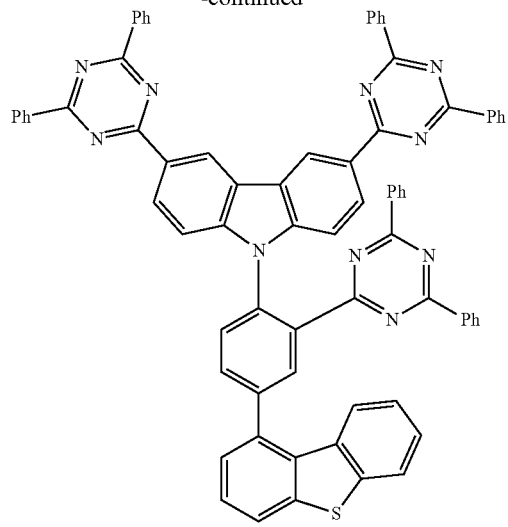
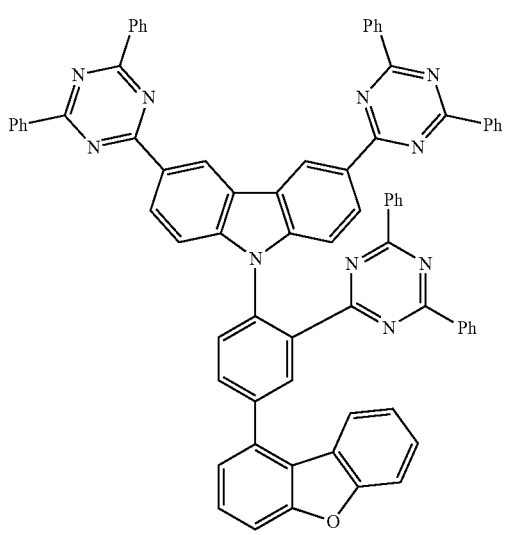
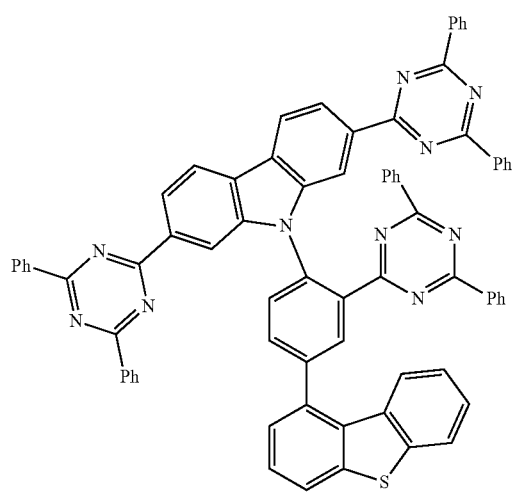
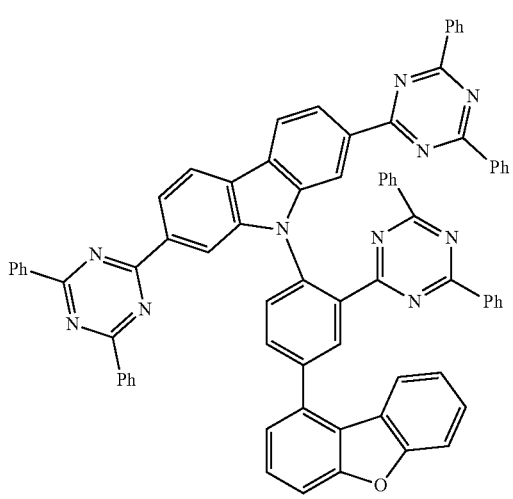
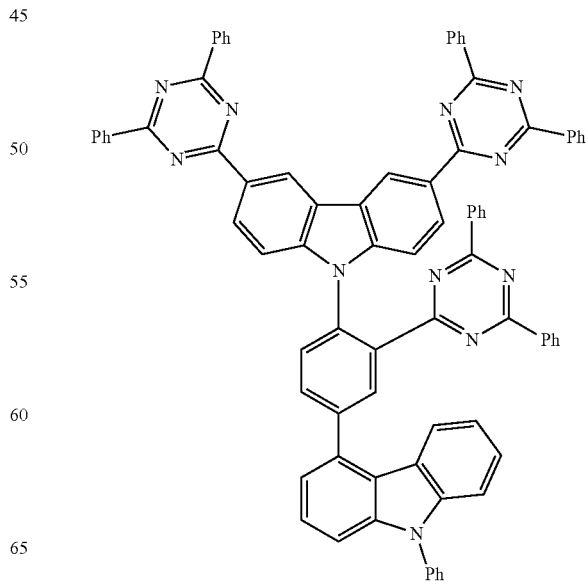

371
-continued
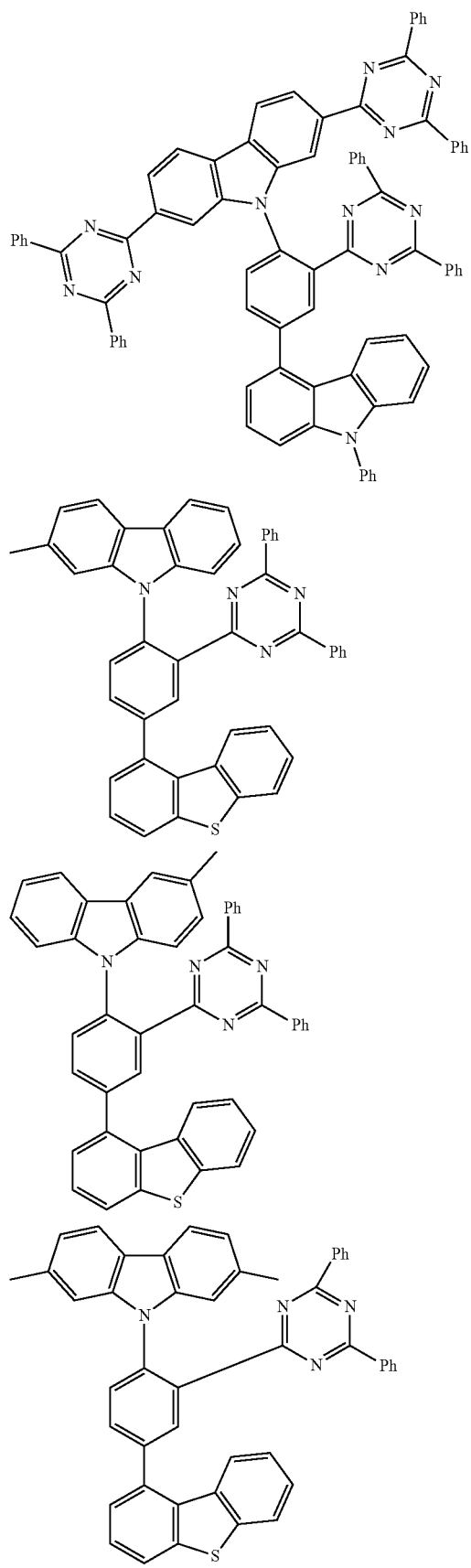
372
-continued
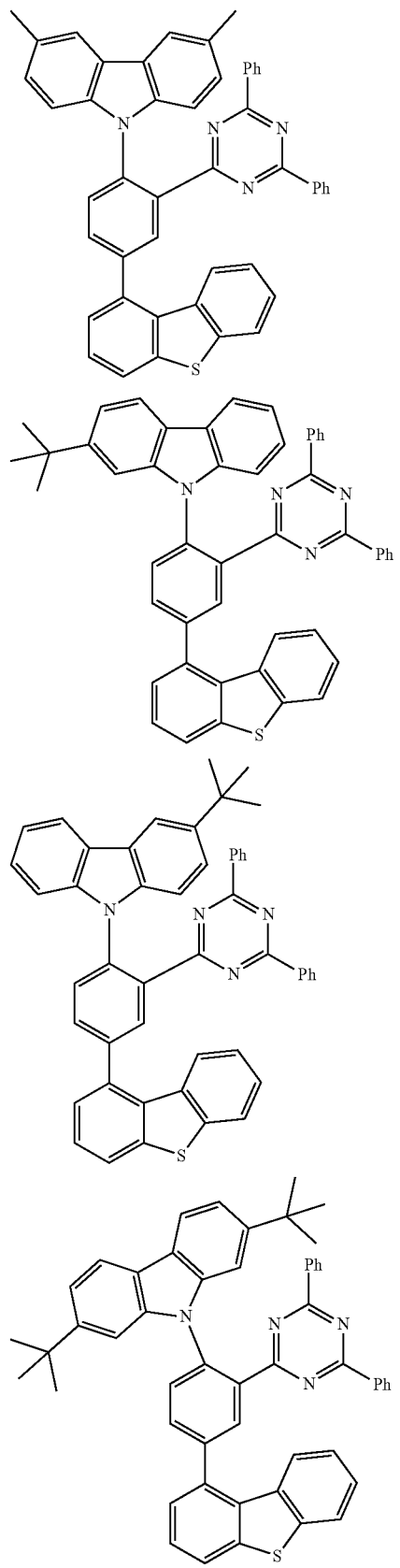

373
-continued
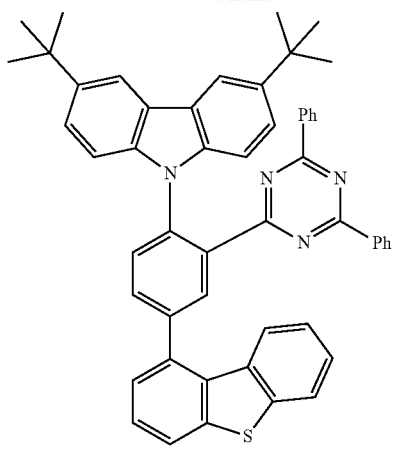
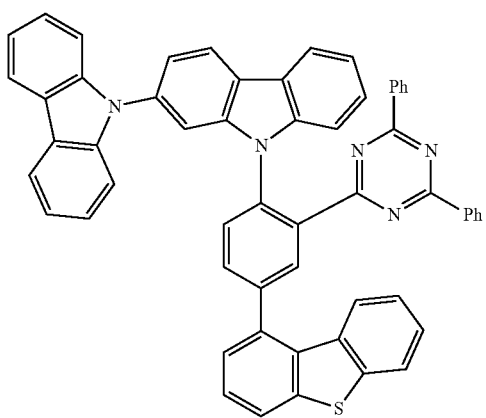
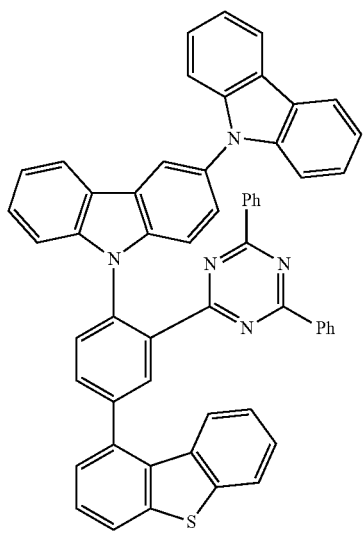
374
-continued
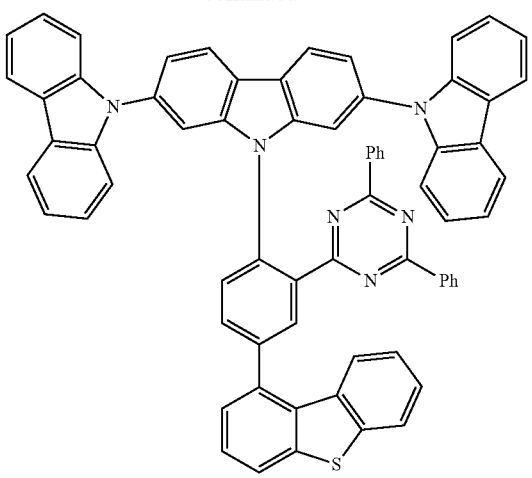
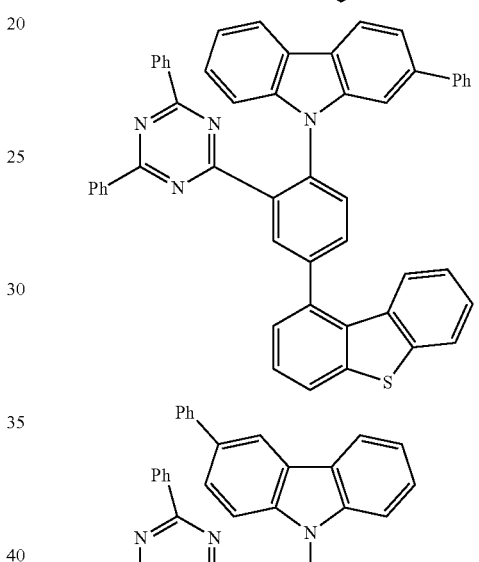
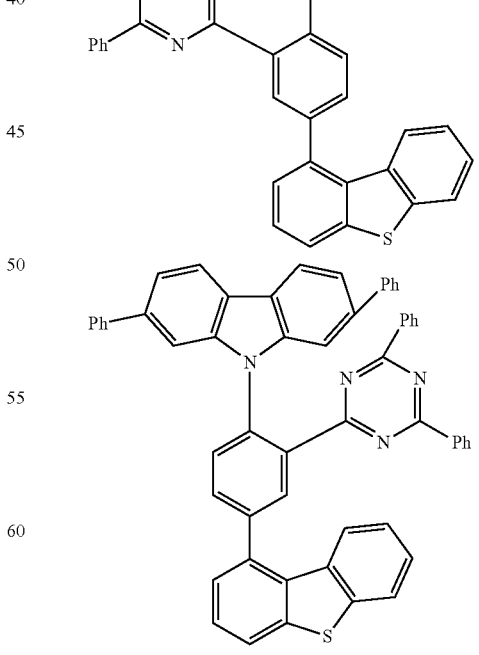

375
-continued
376
-continued
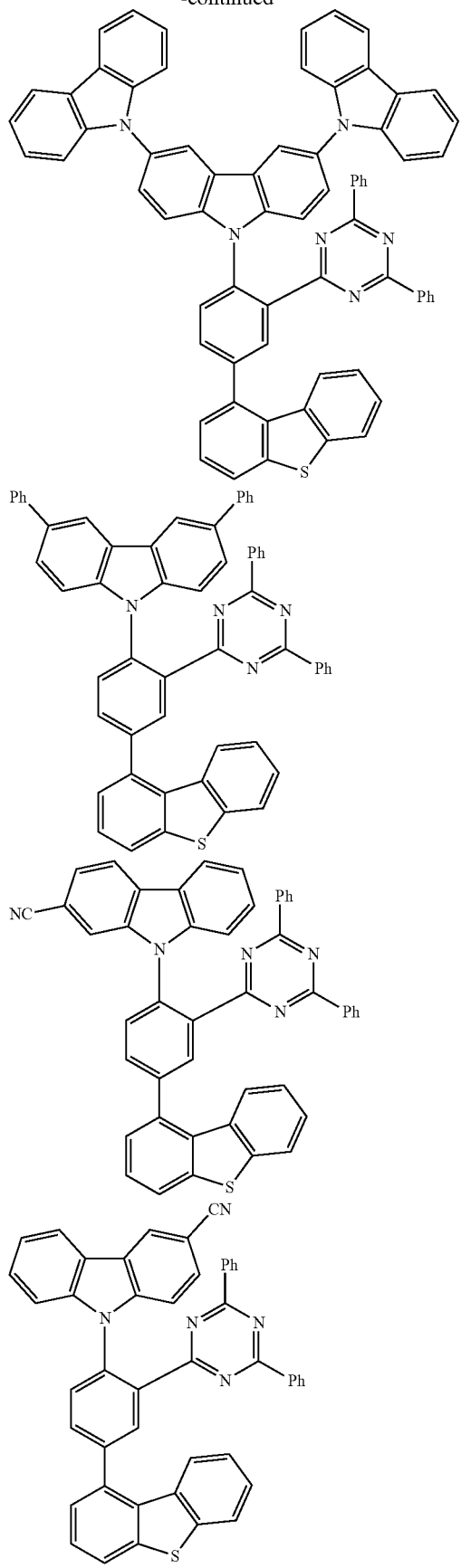
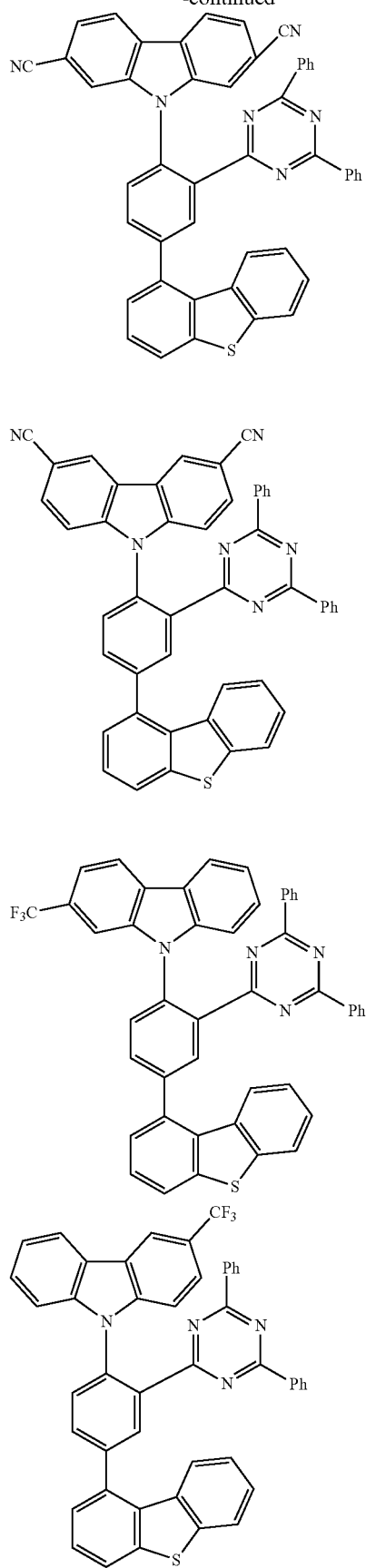

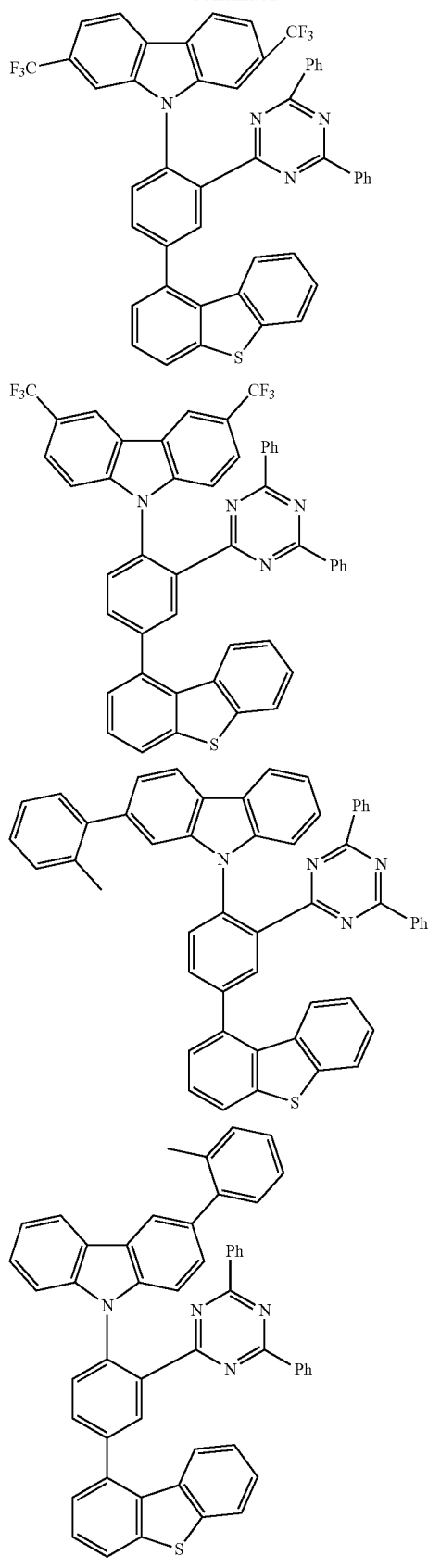
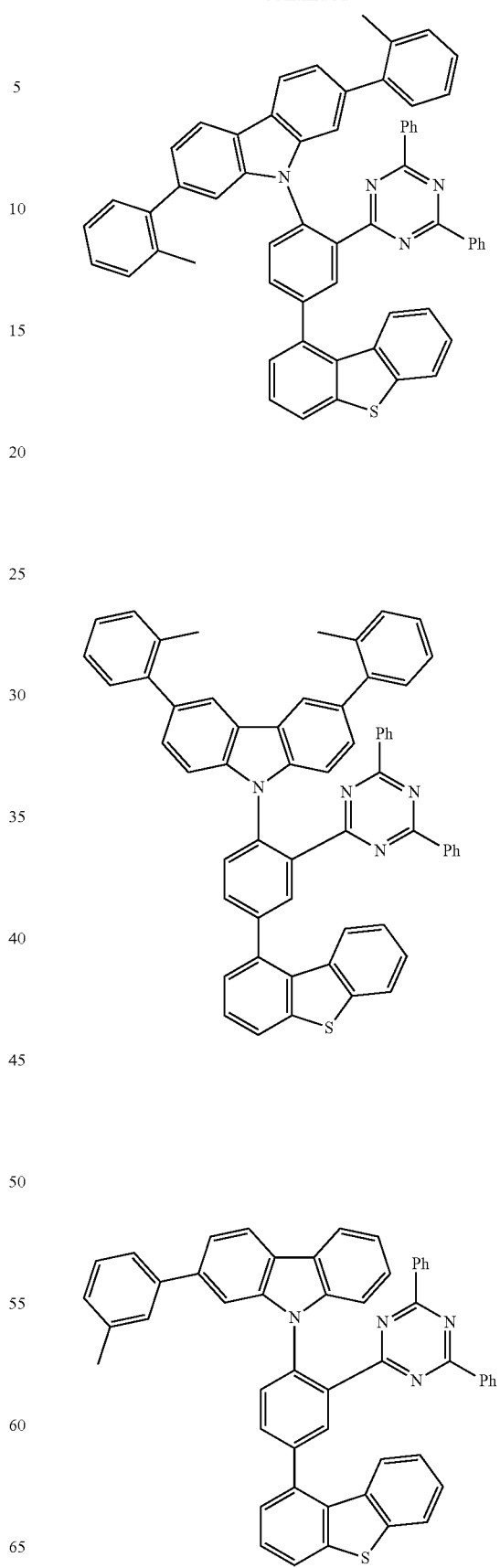

379
-continued
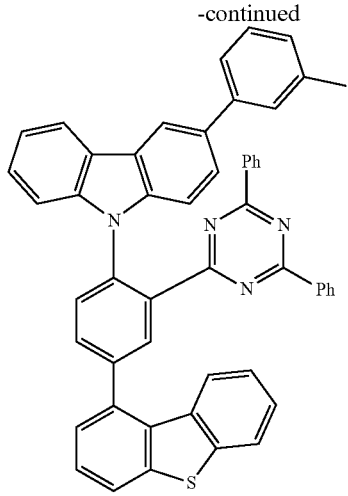
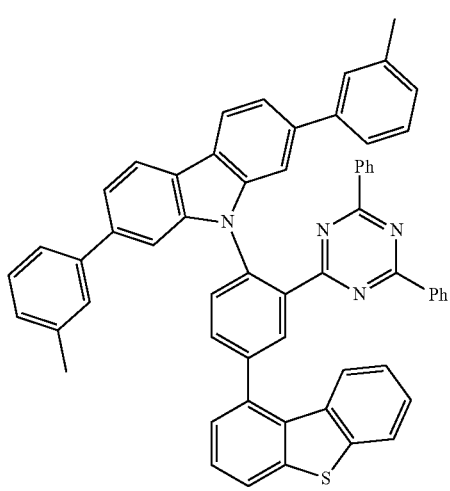
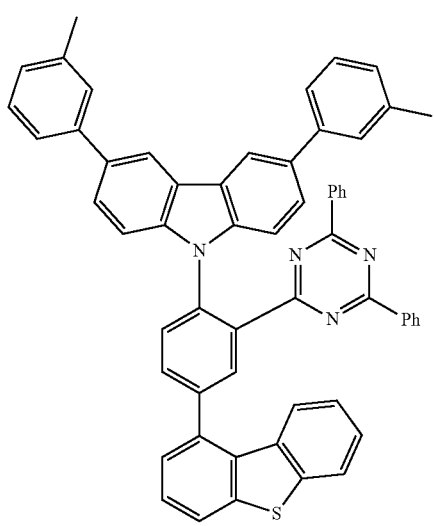
380
-continued
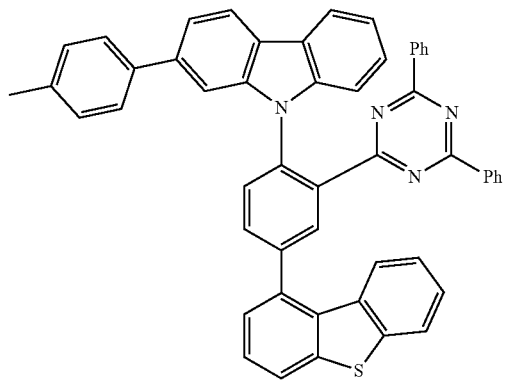
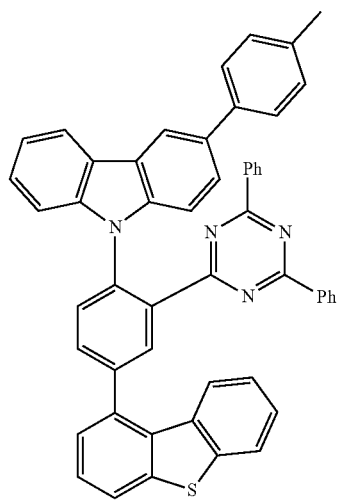
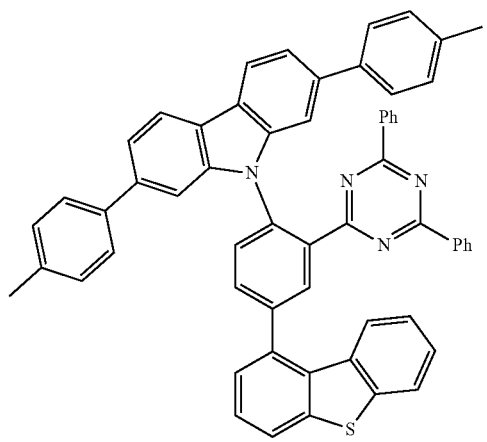

381
-continued
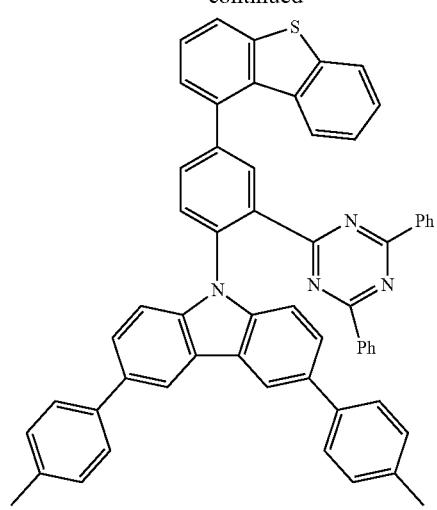
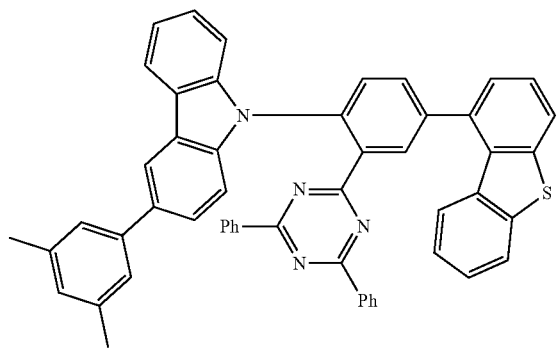
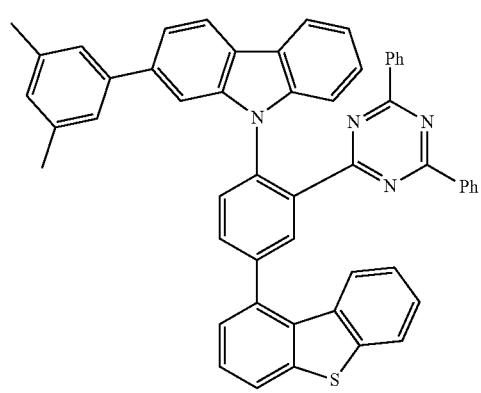
382
-continued
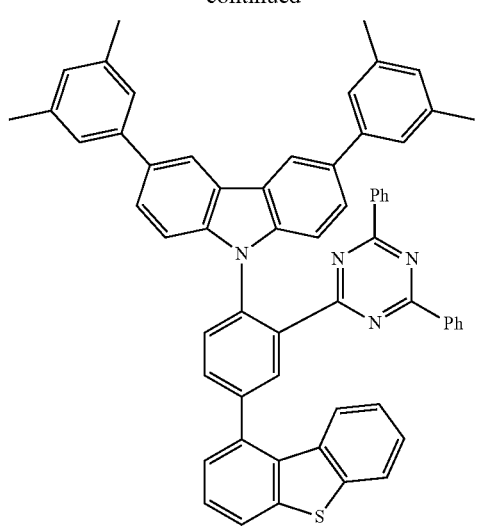
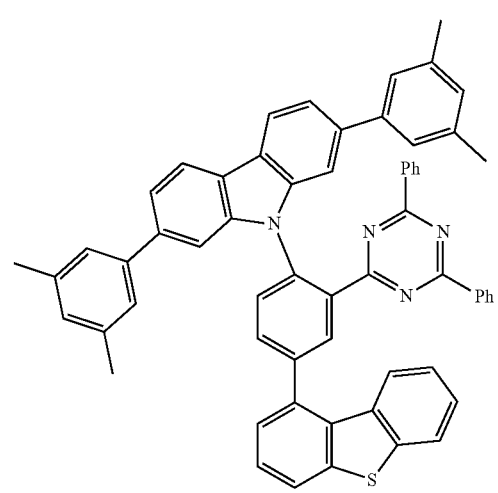
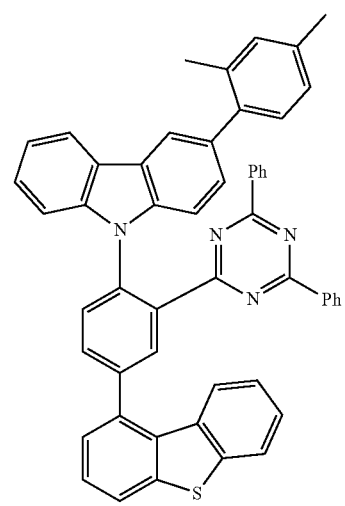

383
-continued
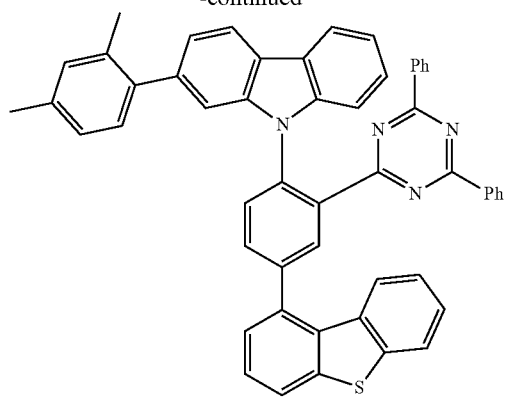
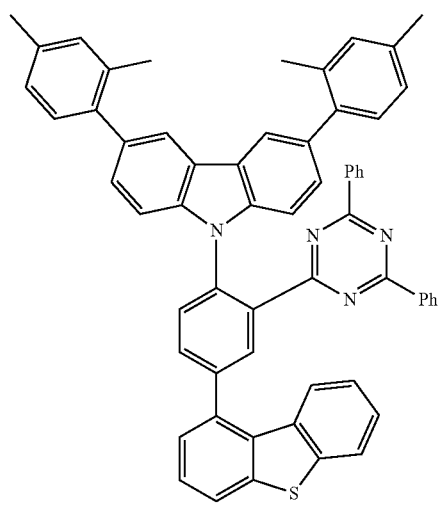
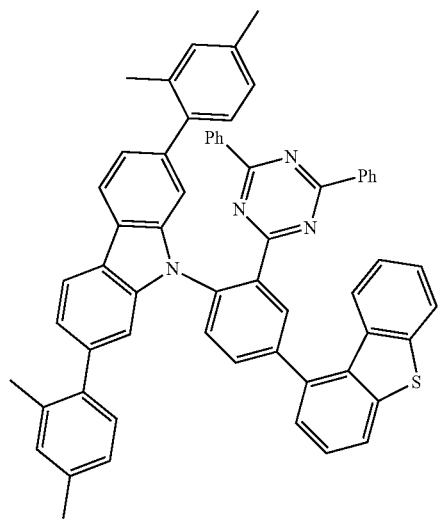
384
-continued
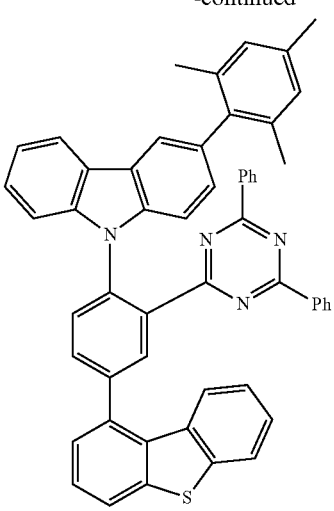
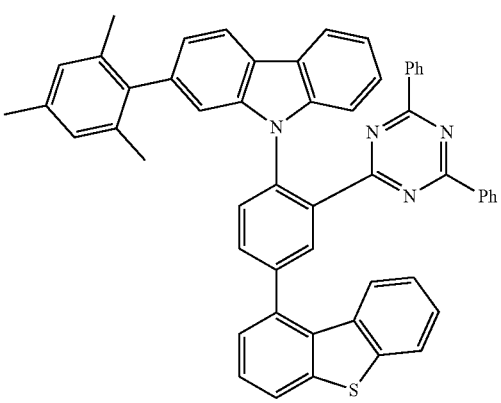
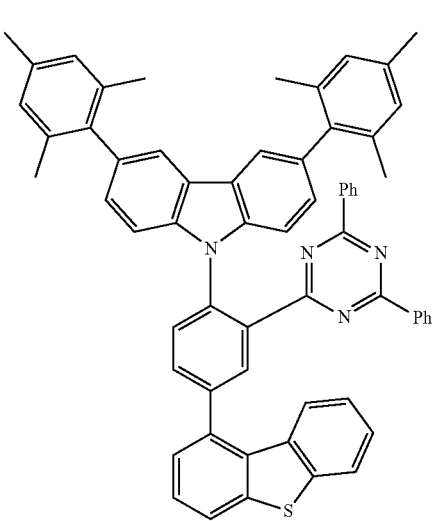

385
-continued
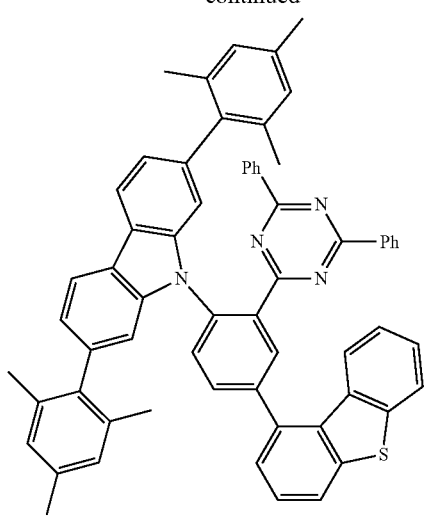
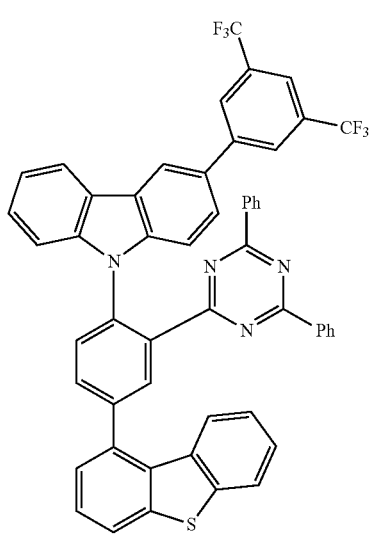
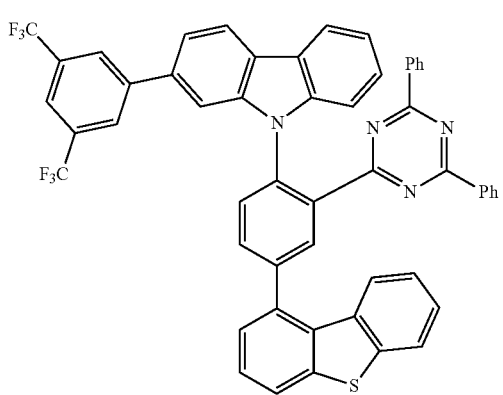
386
-continued
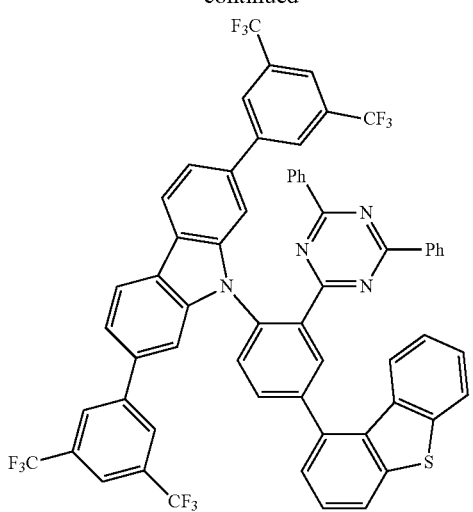
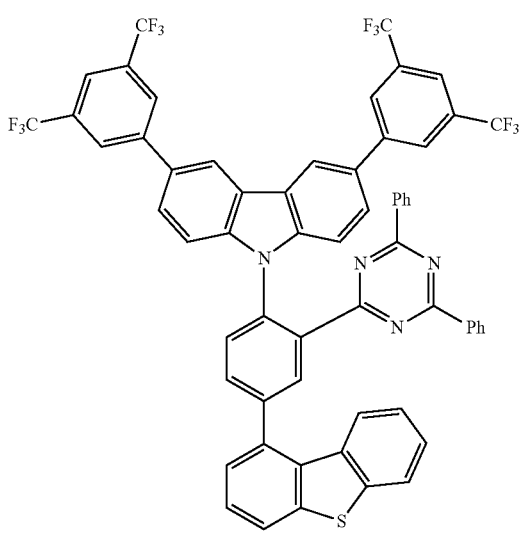
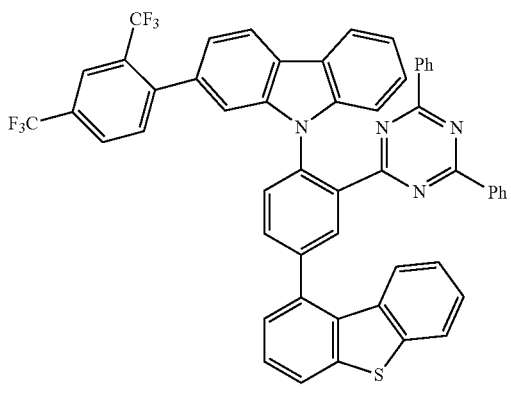

387
-continued
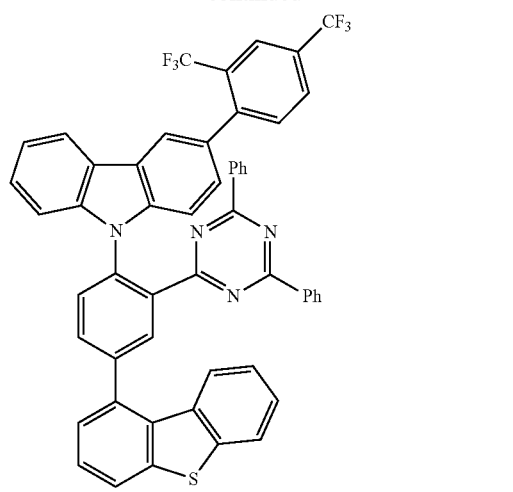
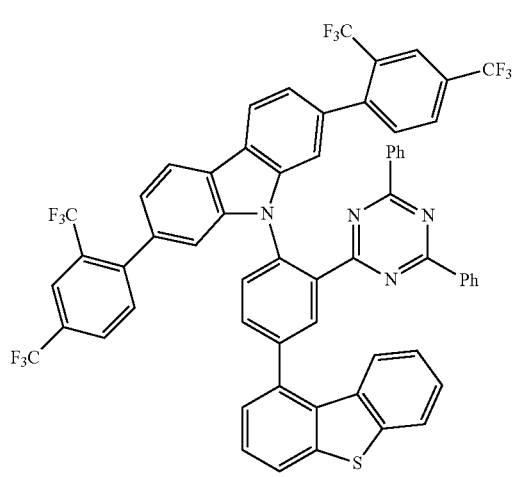
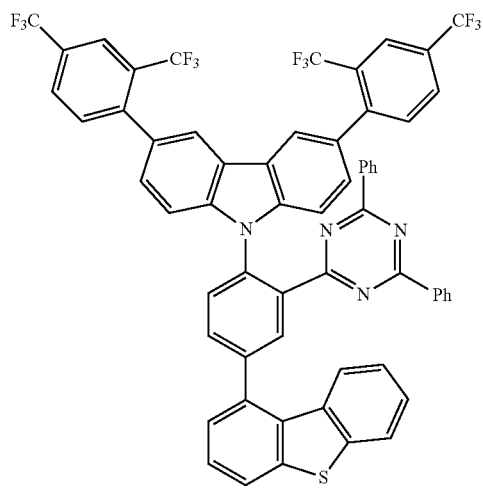
388
-continued
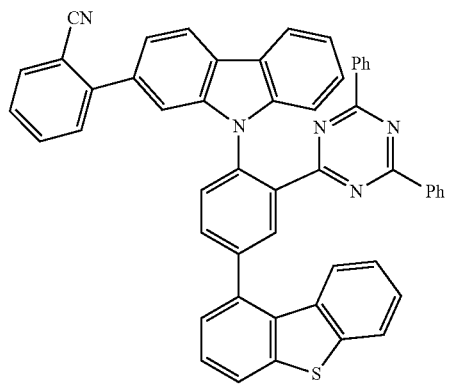
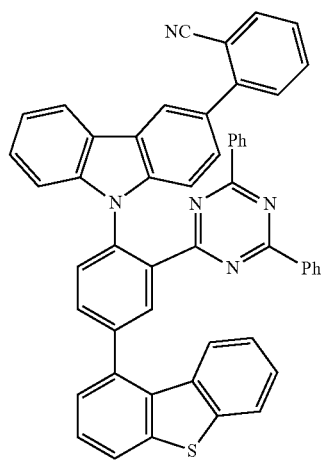
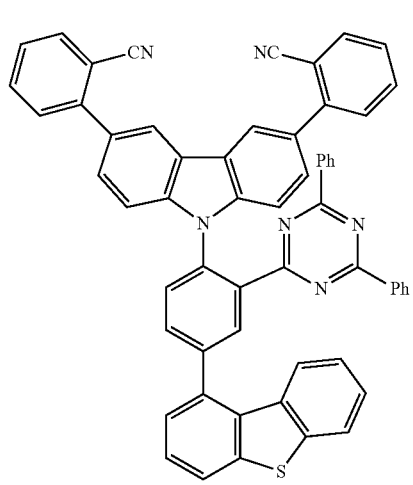

389
-continued
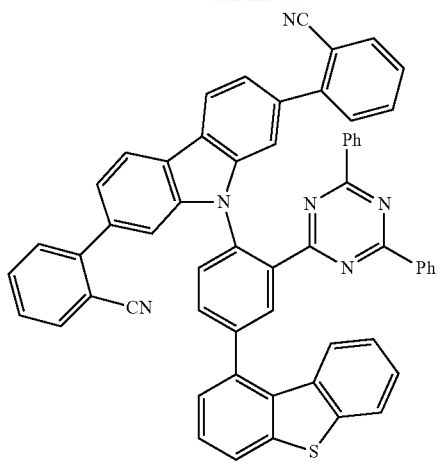
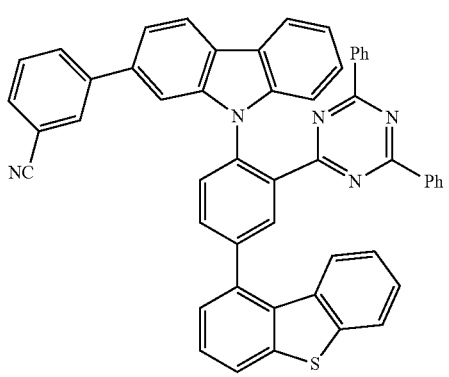
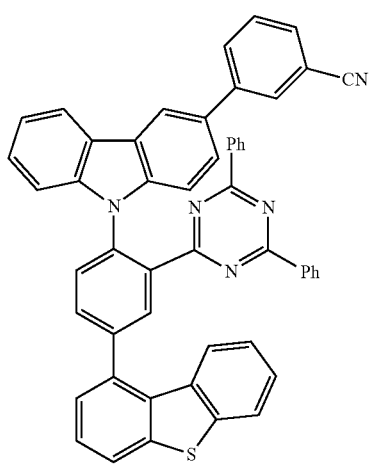
390
-continued
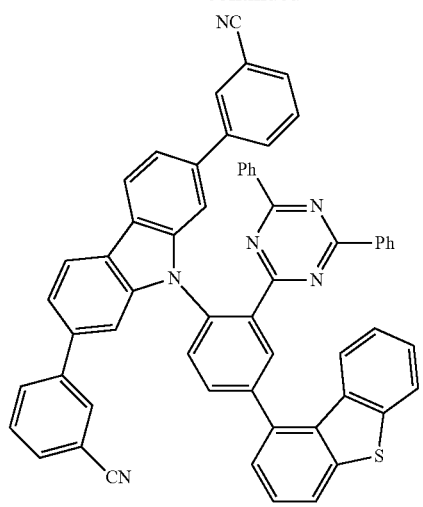
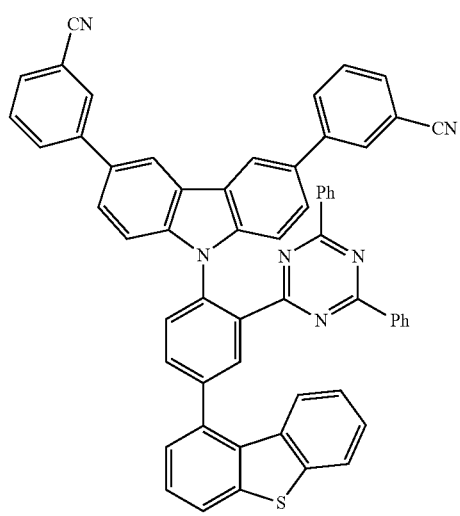
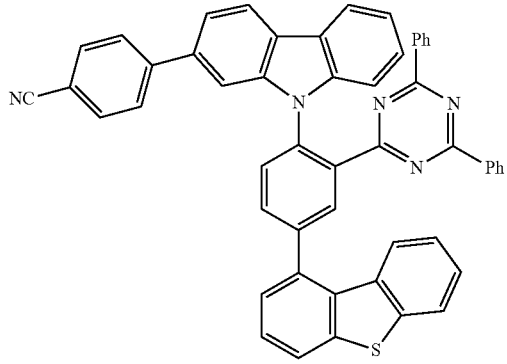

391
-continued
392
-continued
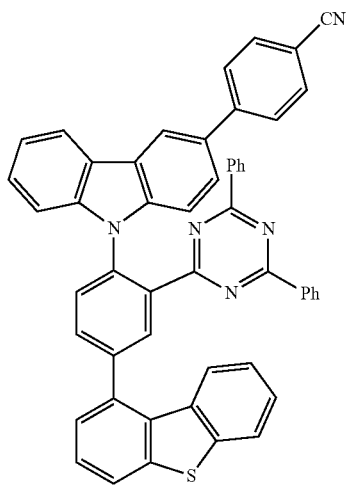
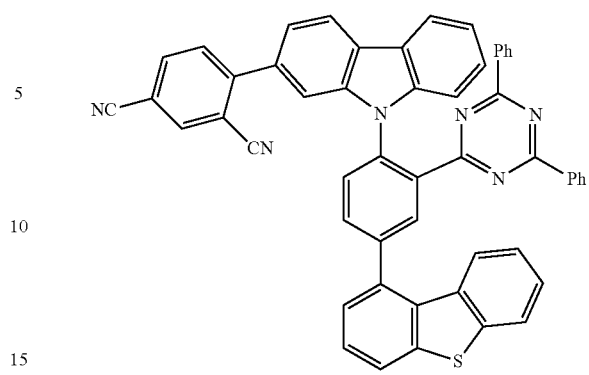
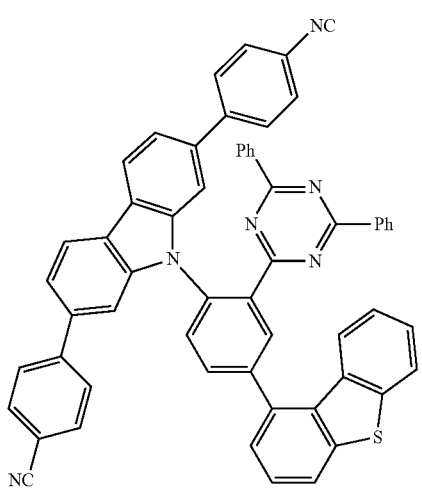
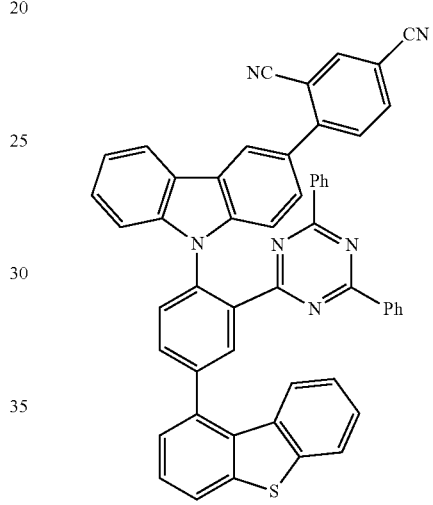
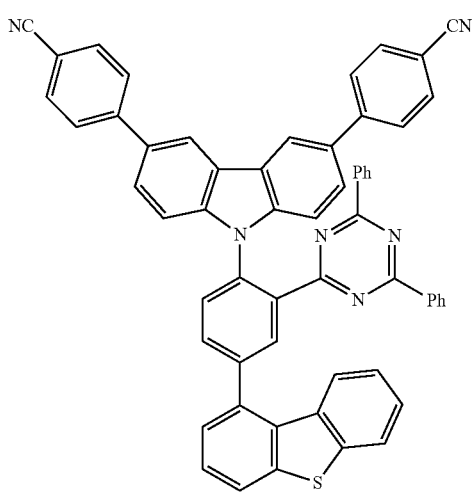
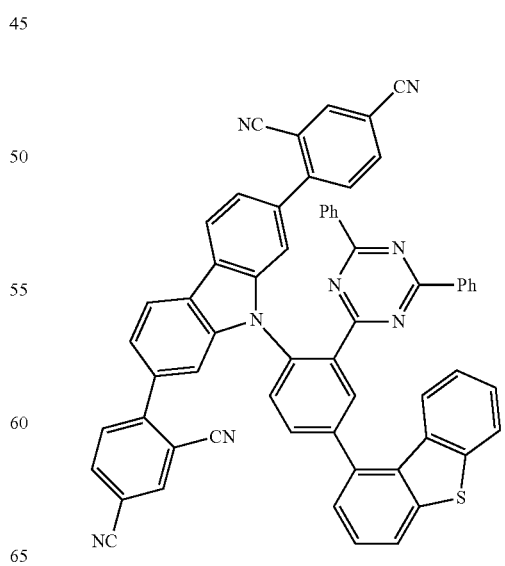

393
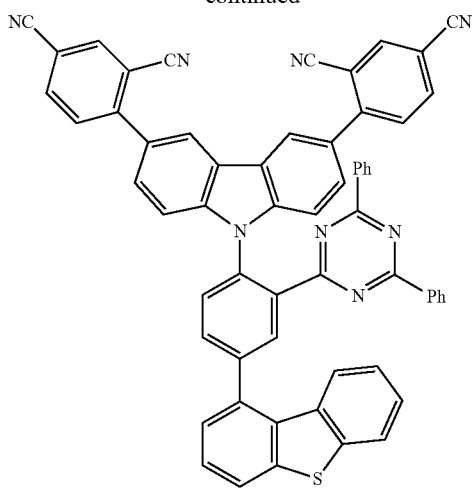
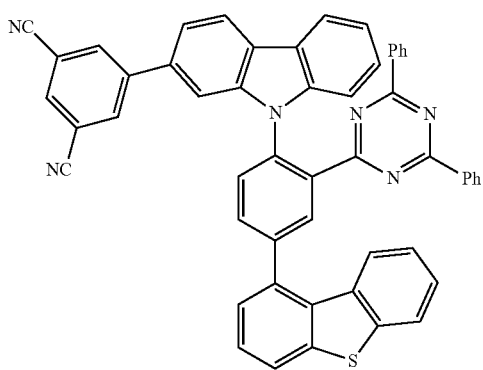
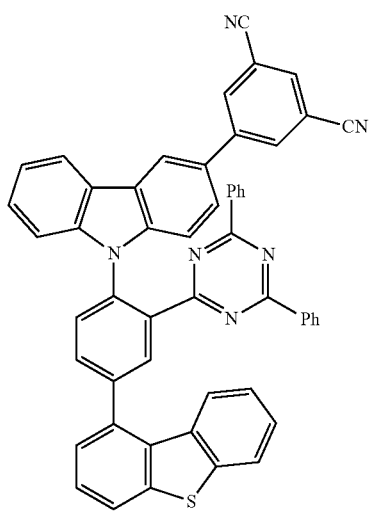
394
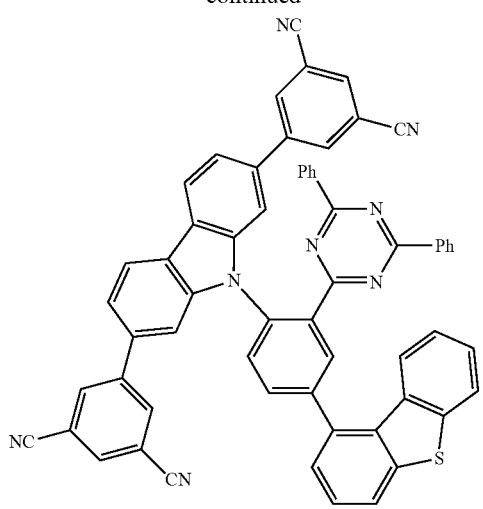
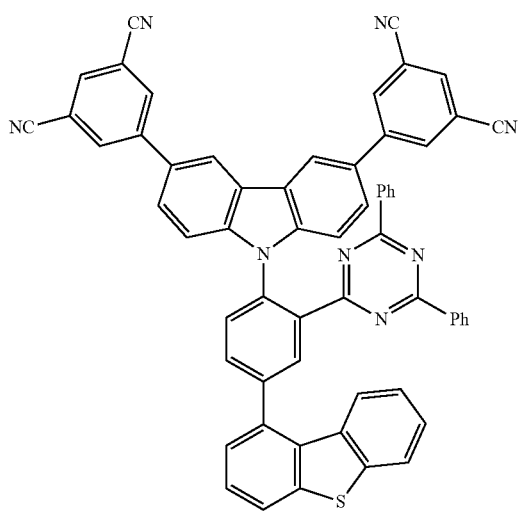
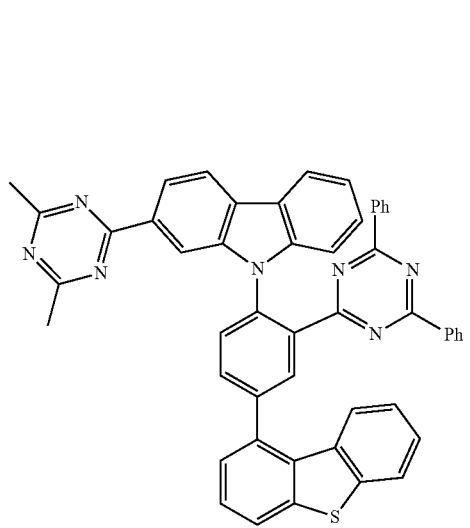

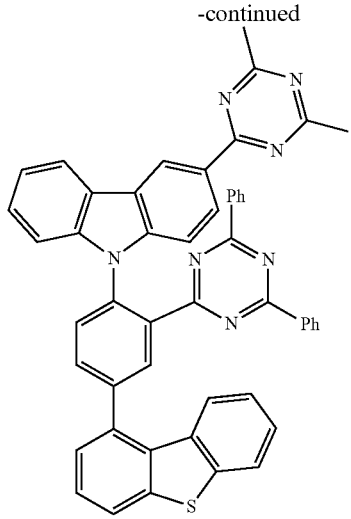
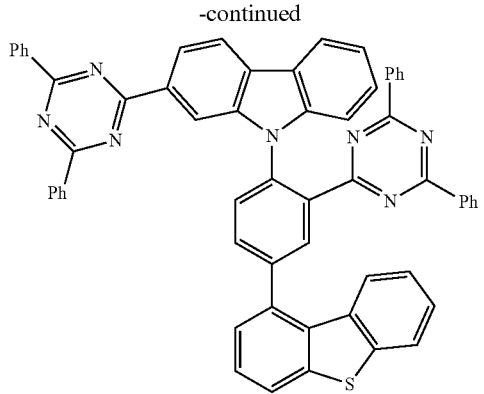
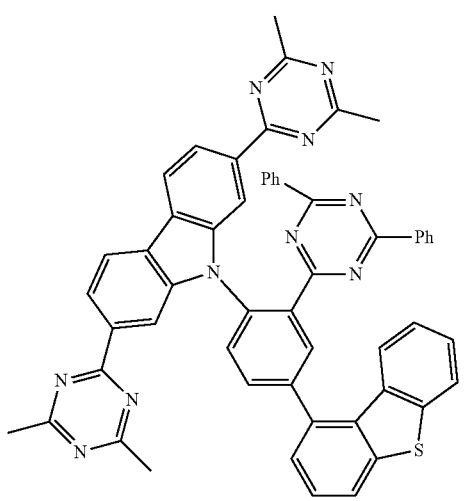
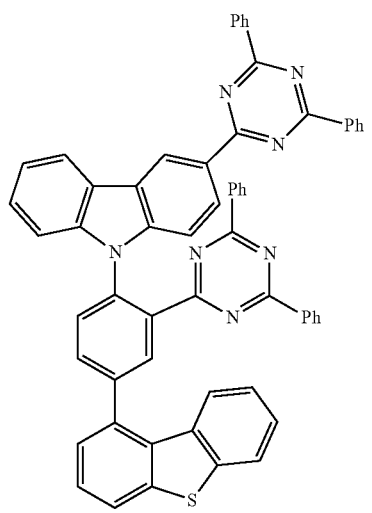
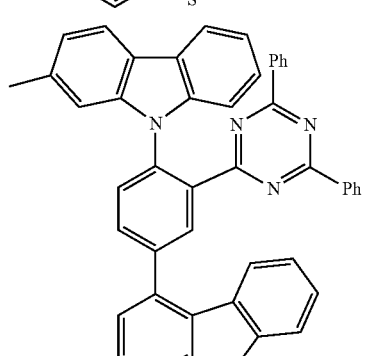
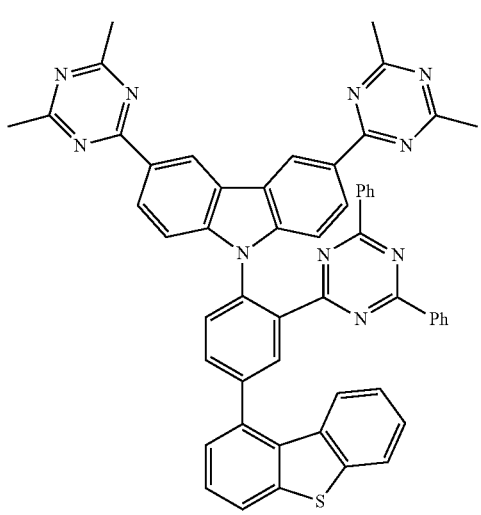
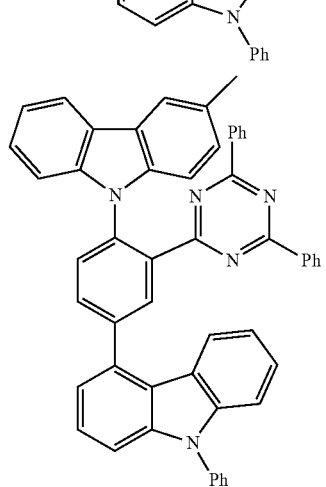

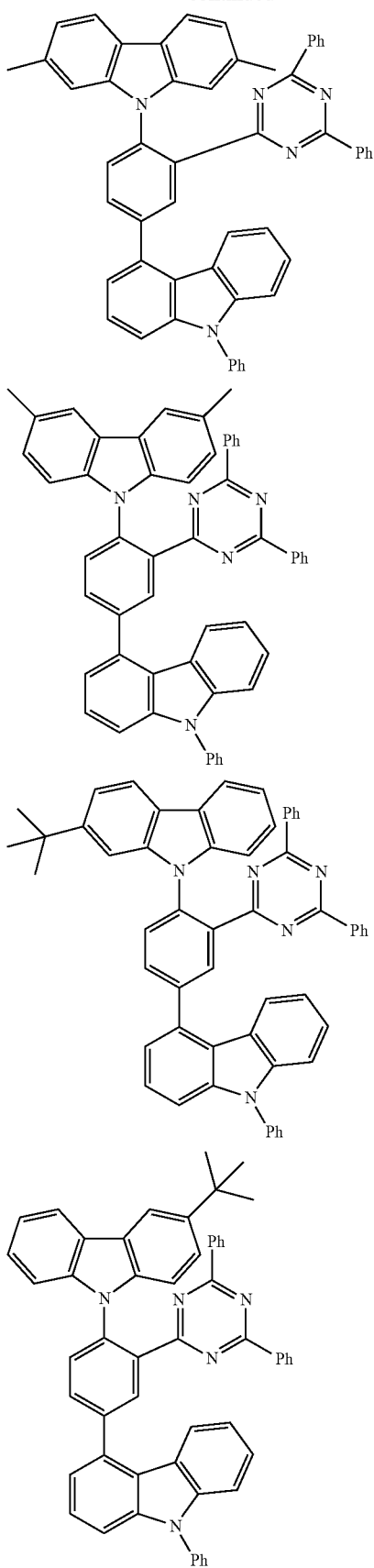
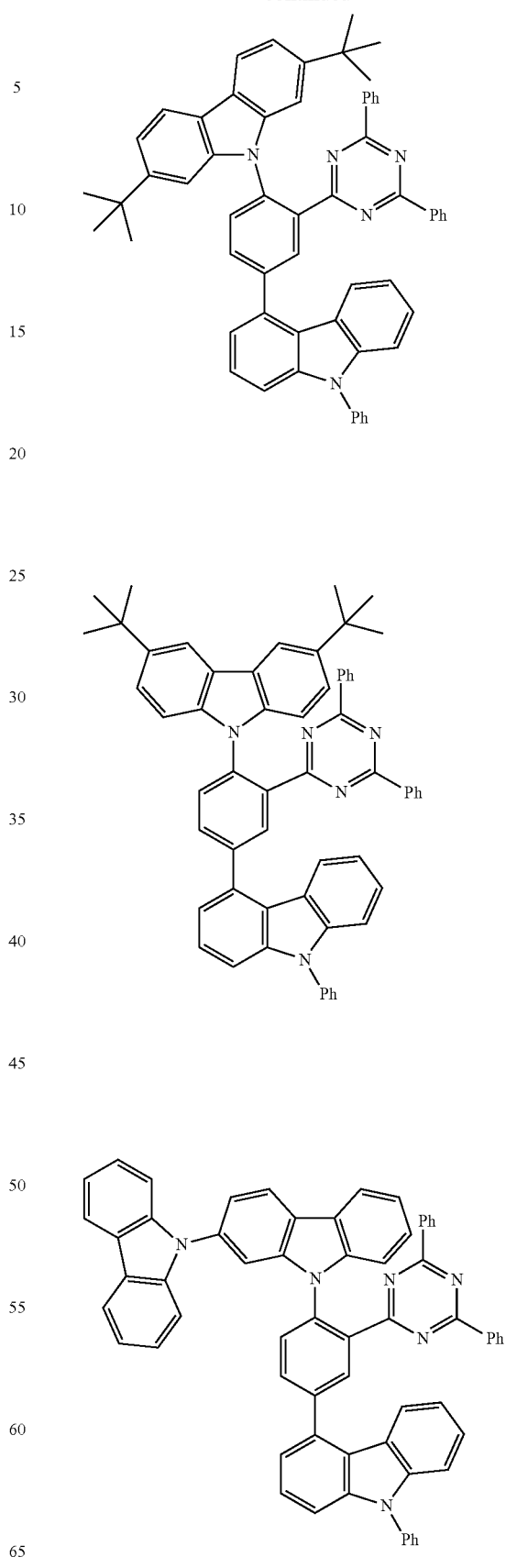

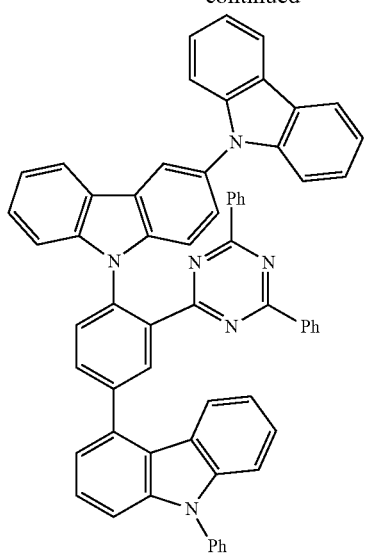
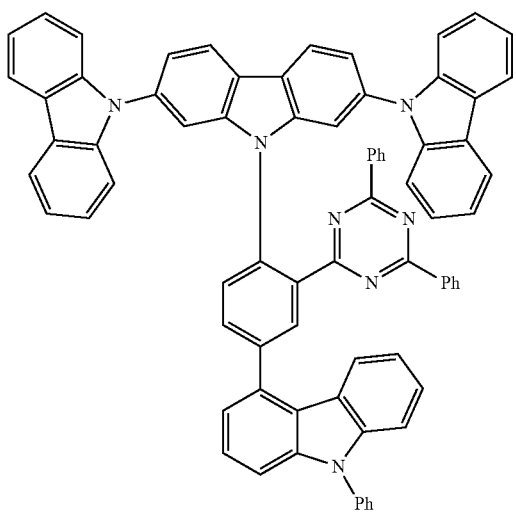
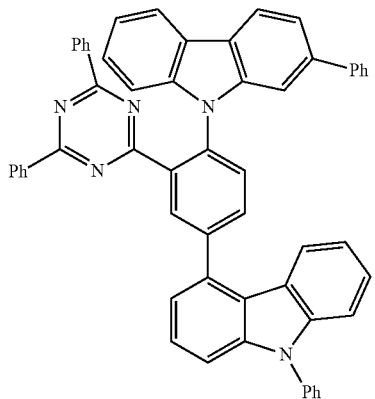
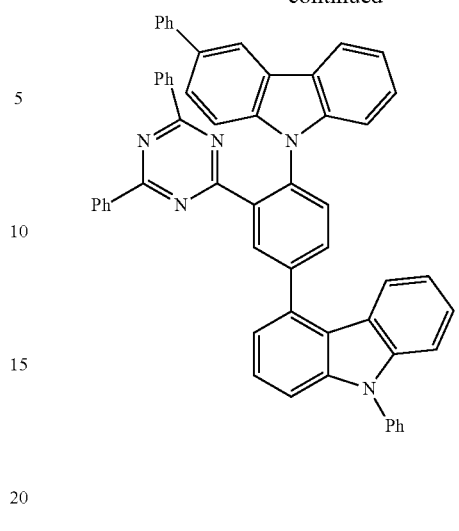
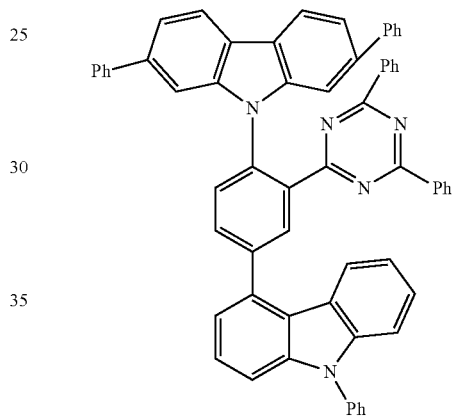
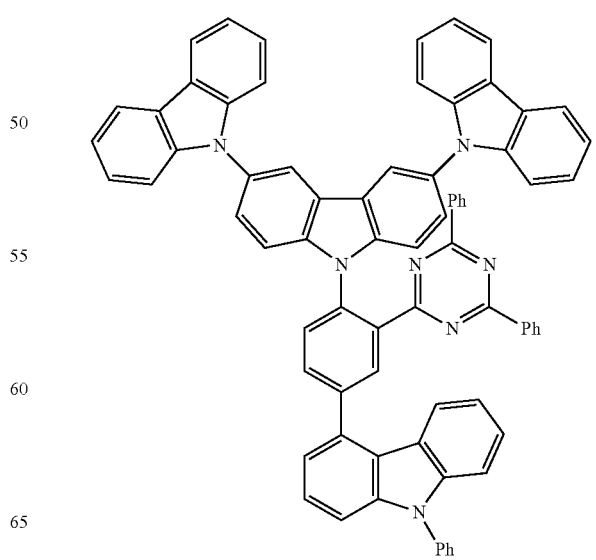

401
-continued
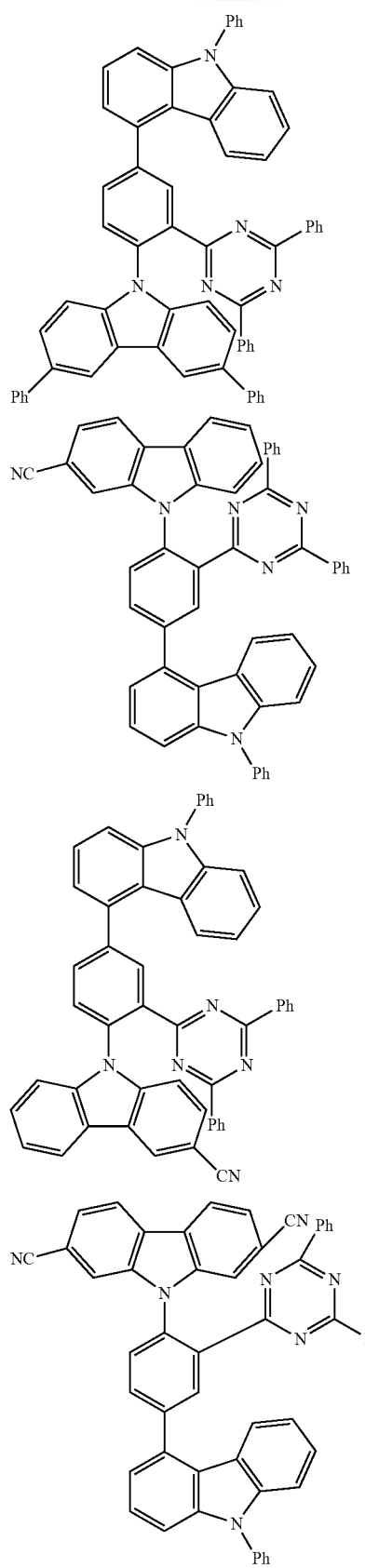
402
-continued
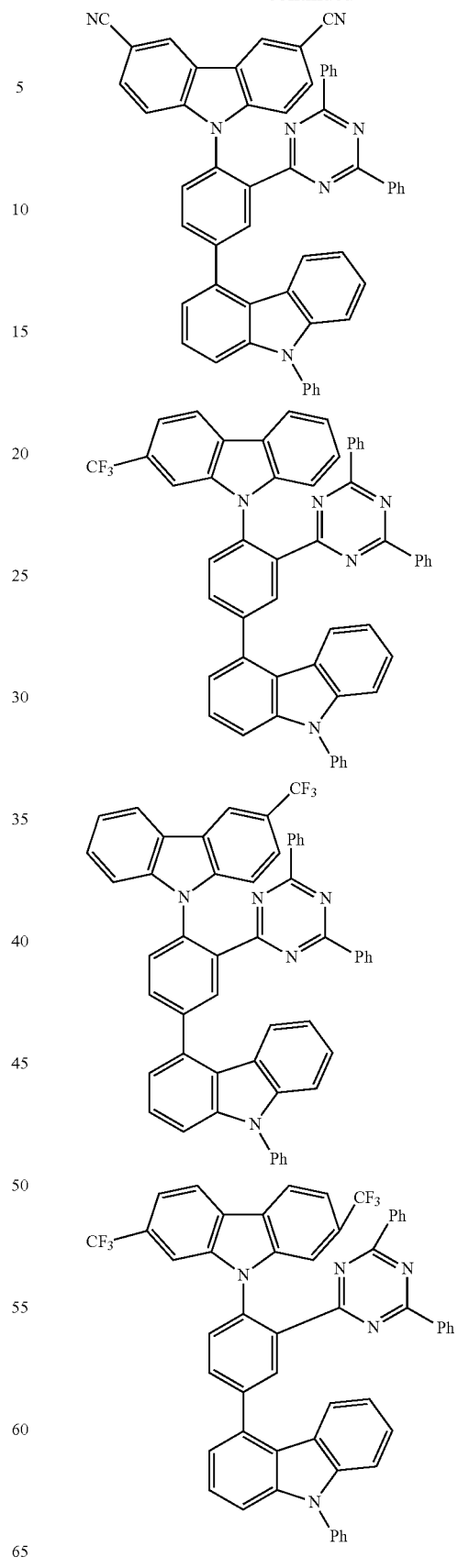

403
-continued
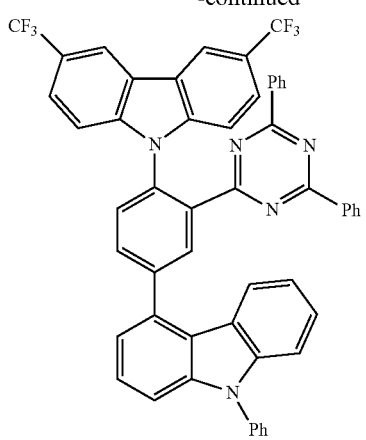
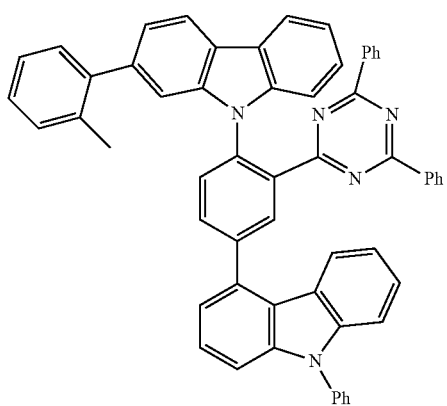
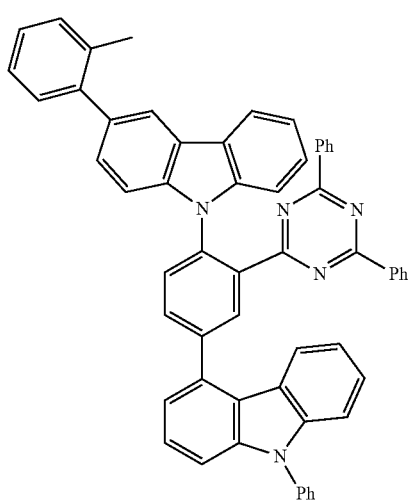
404
-continued
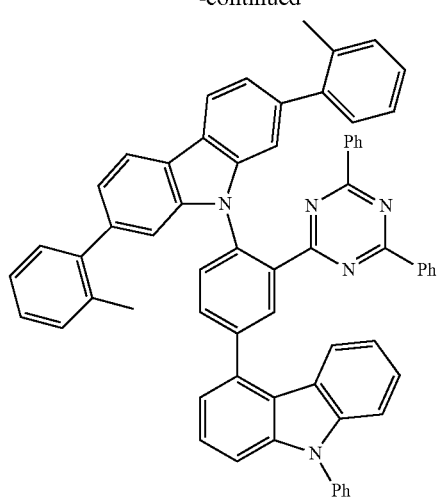
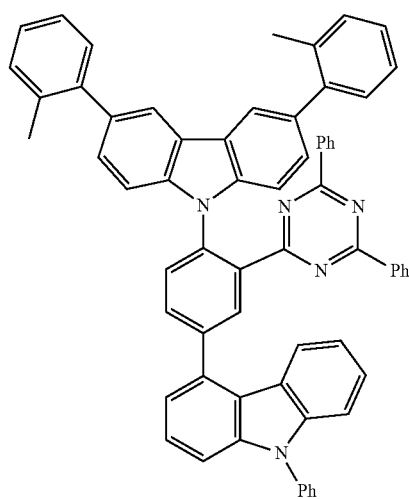

405
-continued
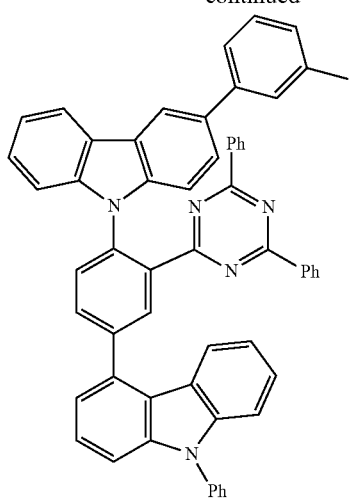
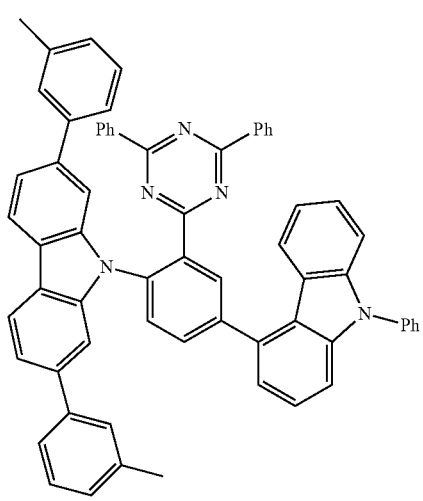
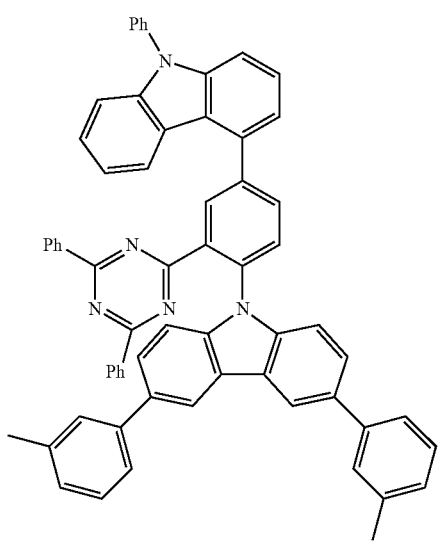
406
-continued
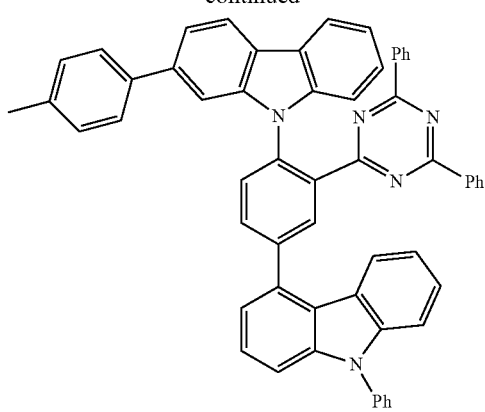
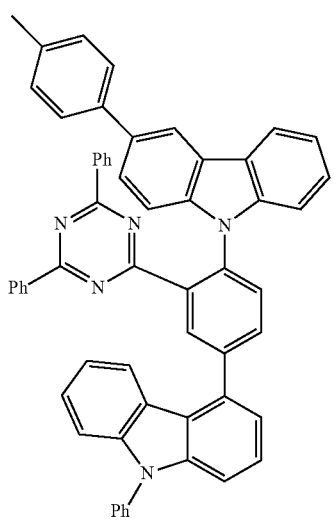
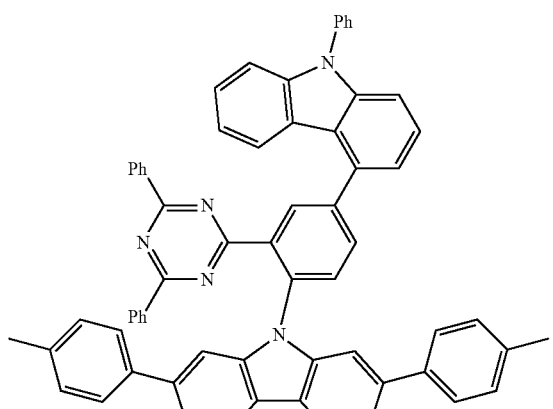

407
-continued
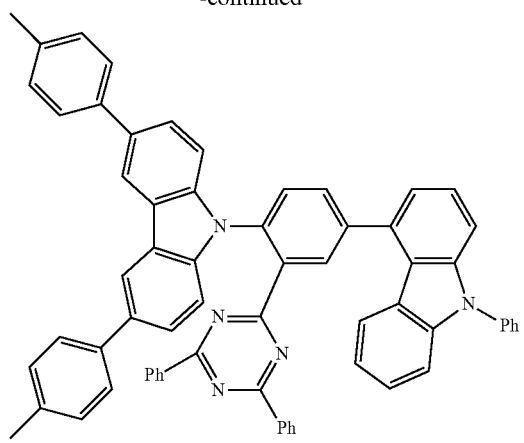
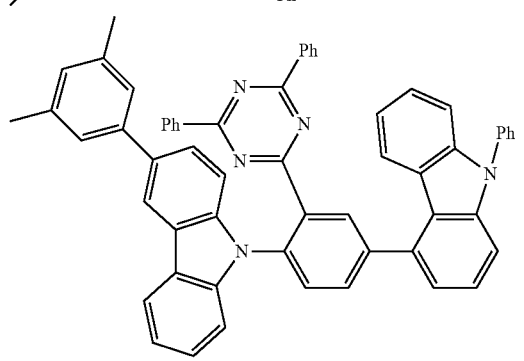
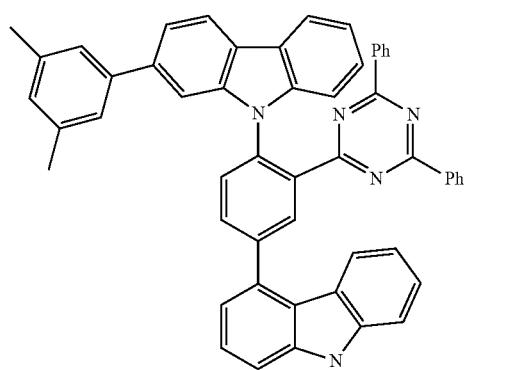
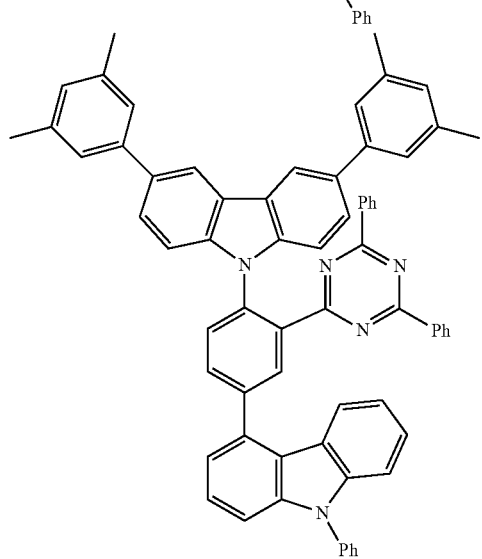
408
-continued
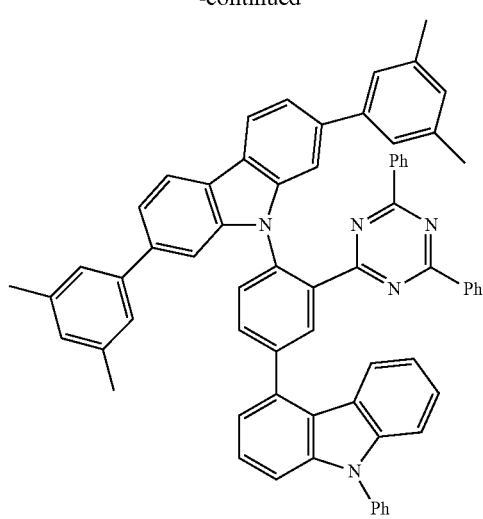
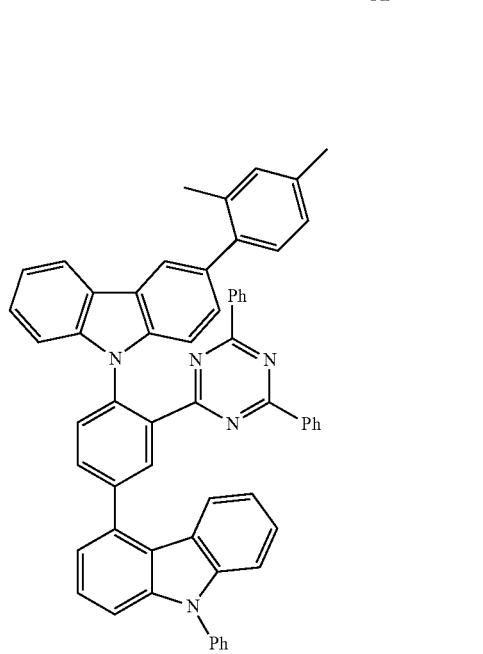
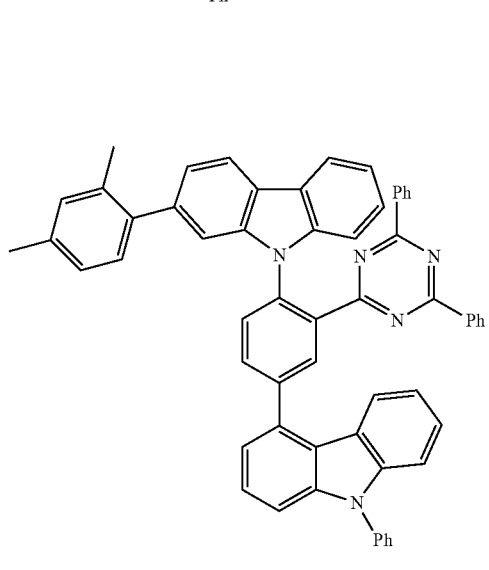

409
-continued
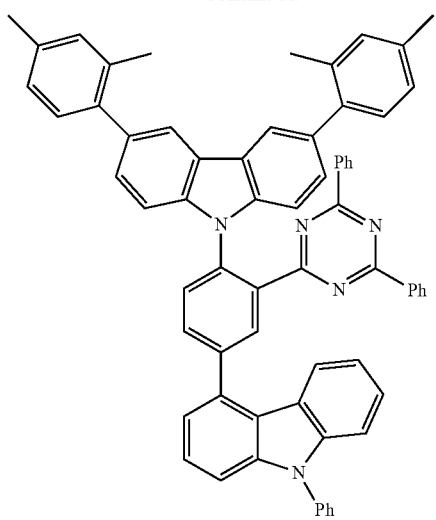
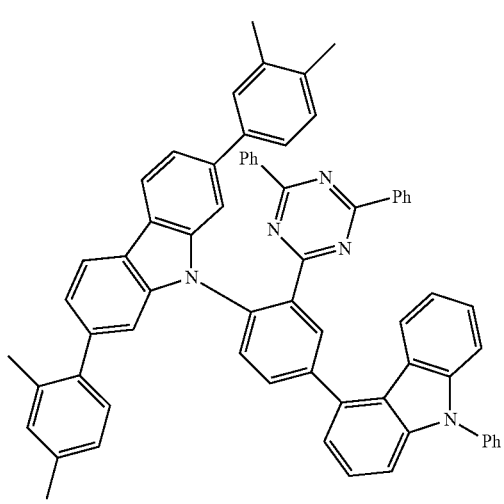
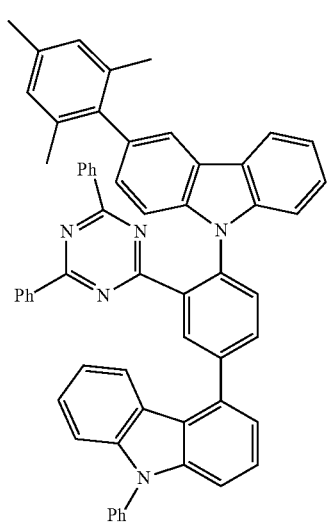
410
-continued
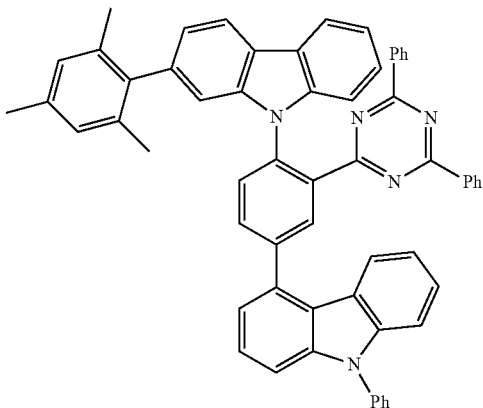
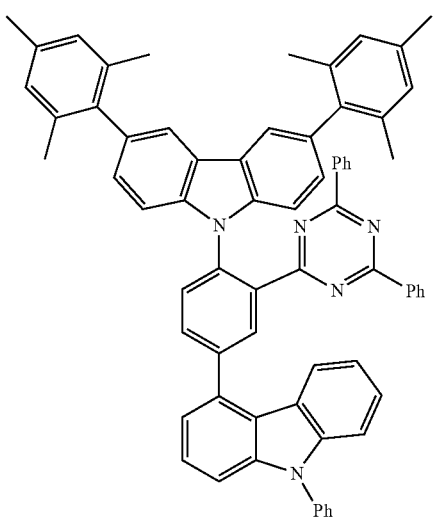
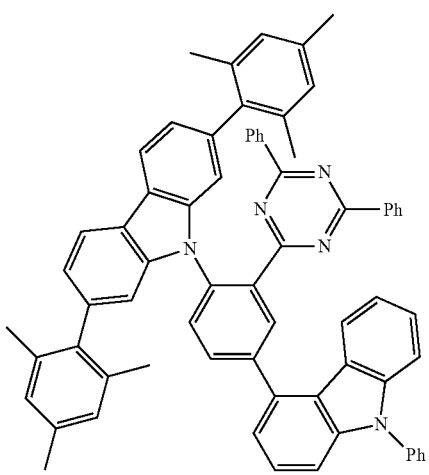

411
-continued
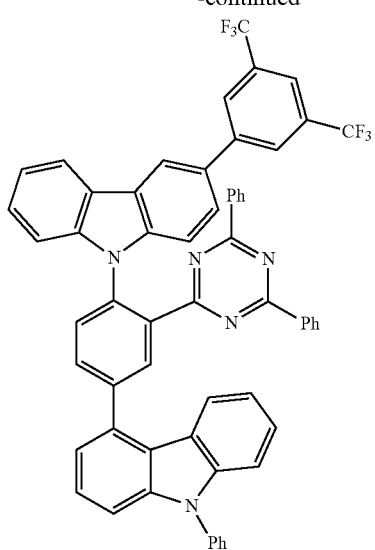
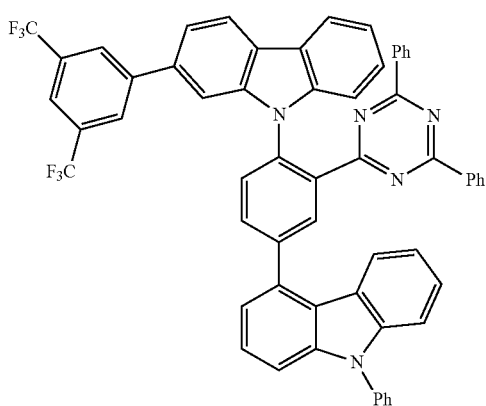
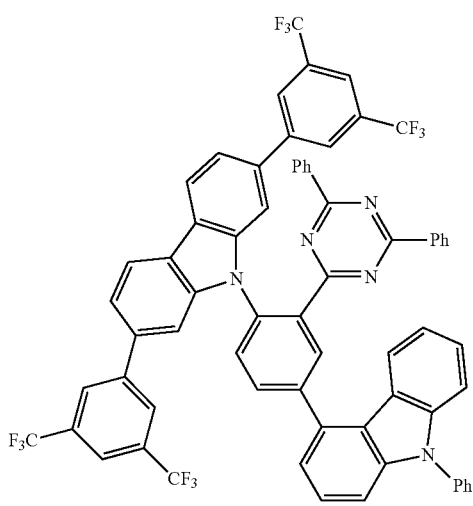
412
-continued
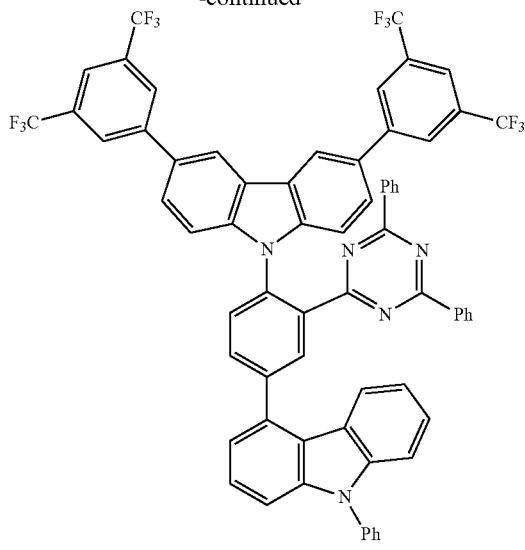
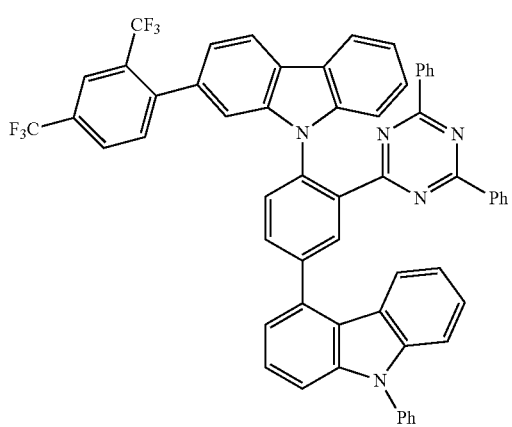
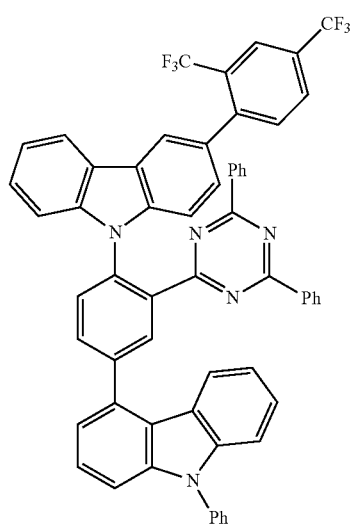

413
-continued
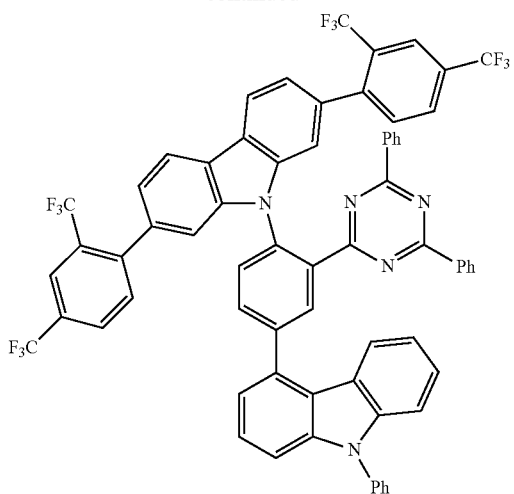
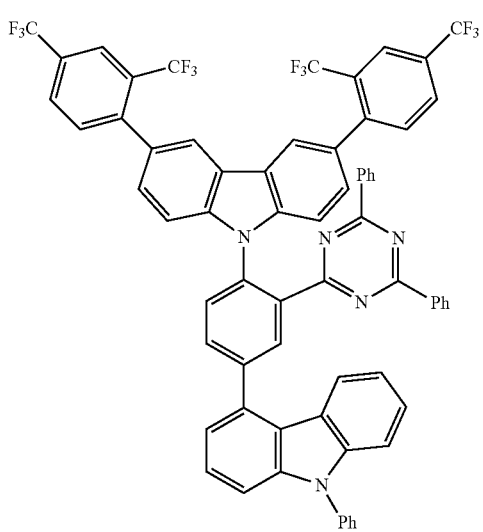
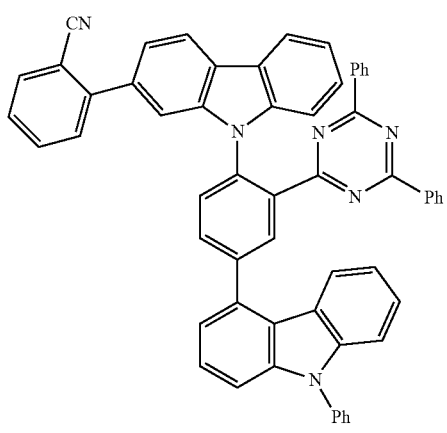
414
-continued
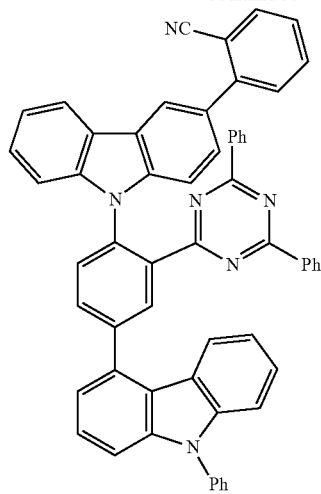
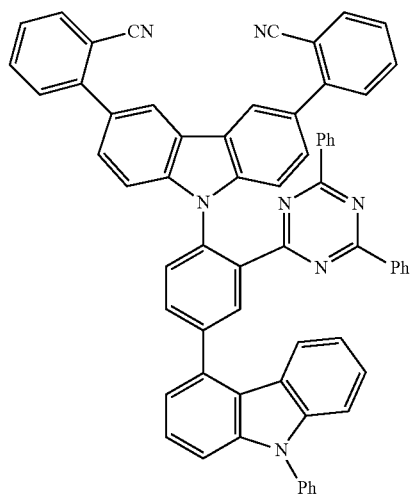
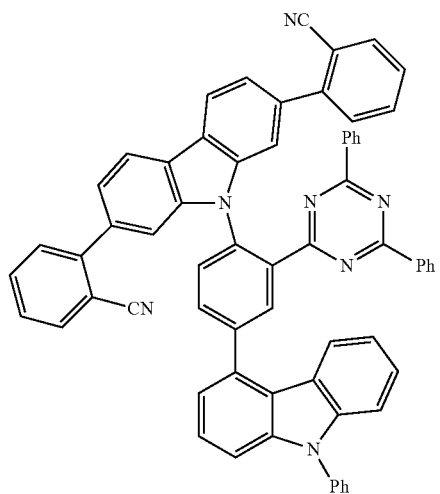

415
-continued
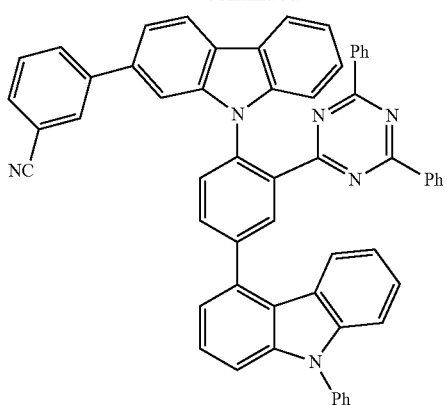
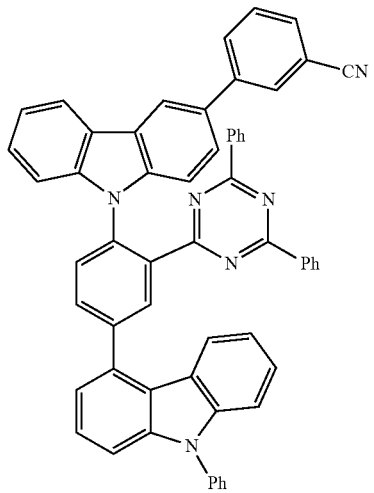
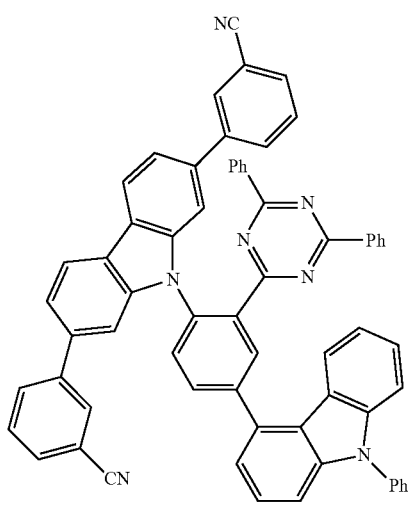
416
-continued
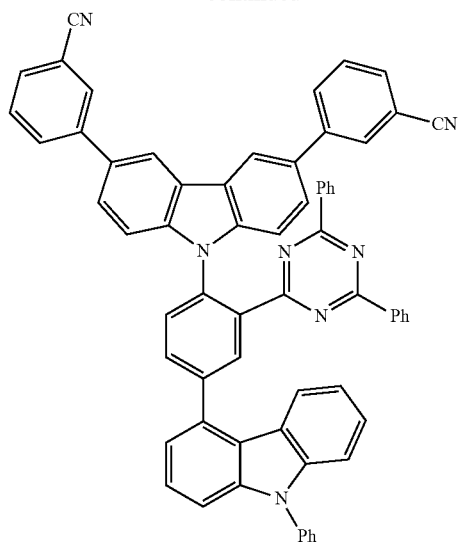
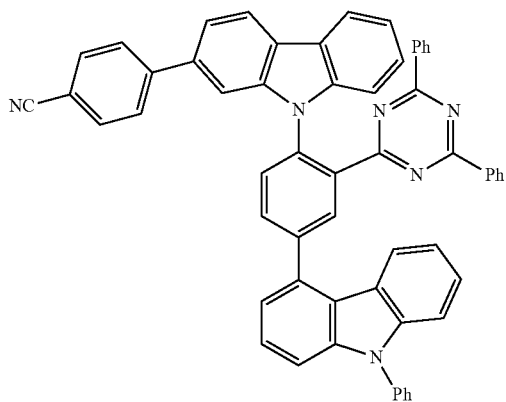
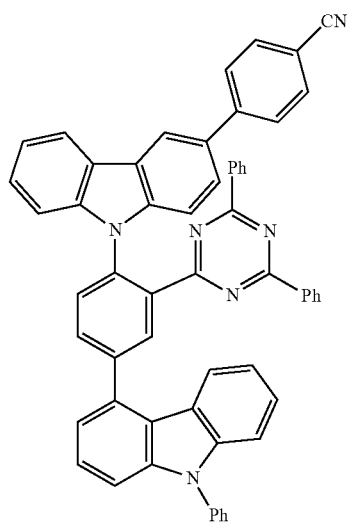

417
-continued
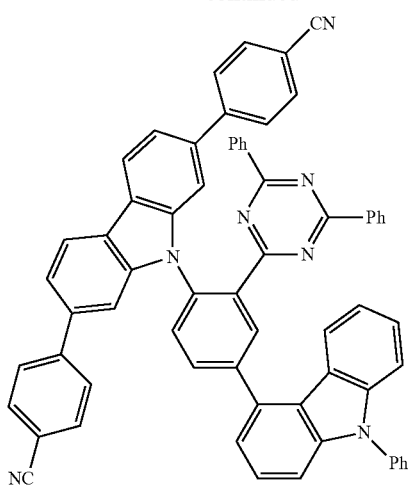
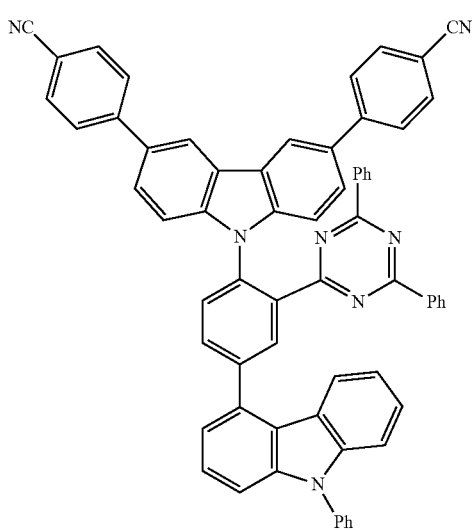
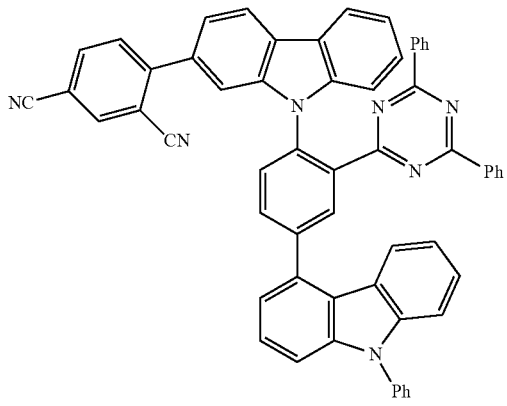
418
-continued
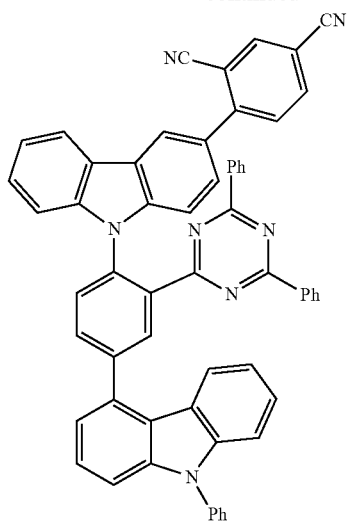
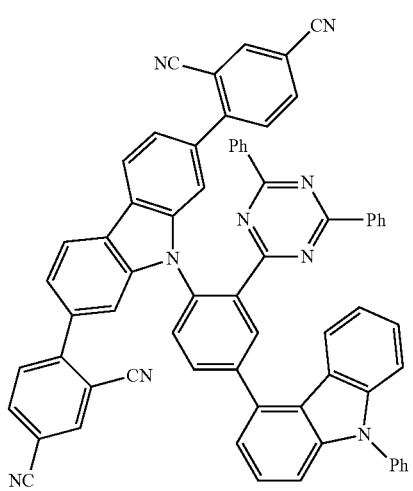
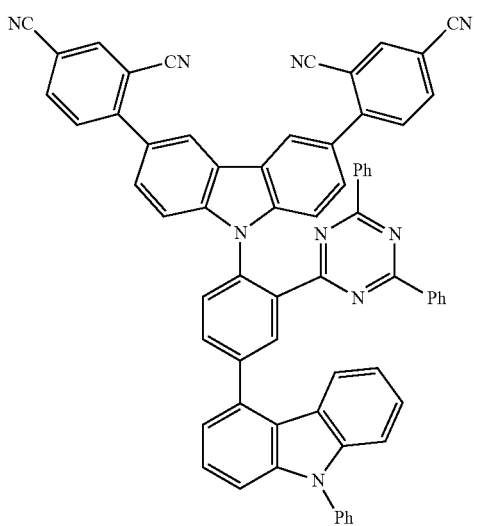

419
-continued
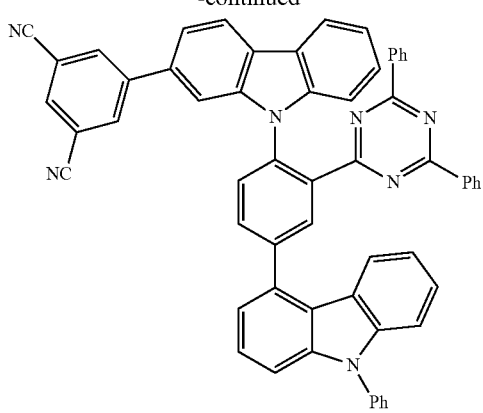
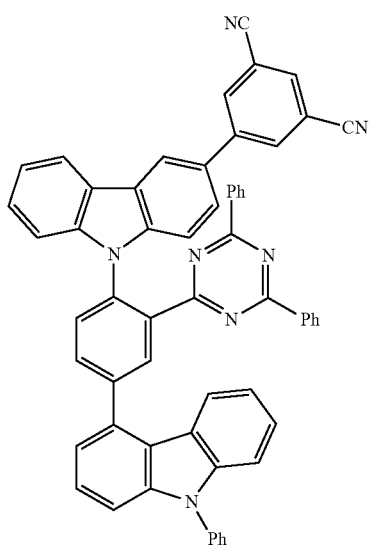
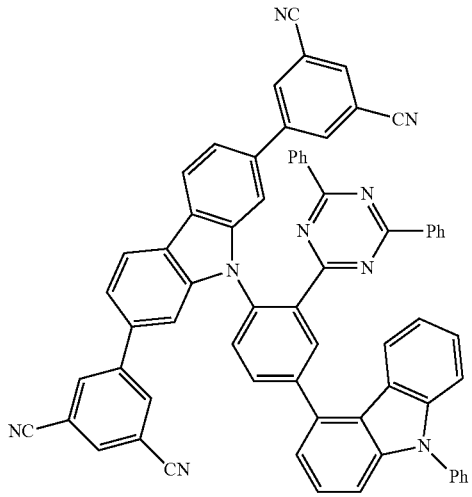
420
-continued
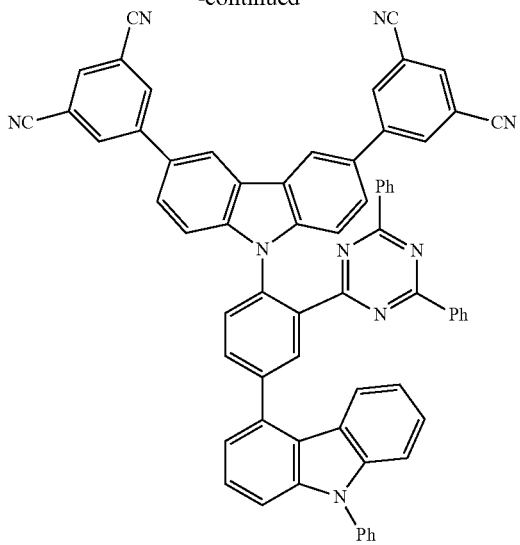
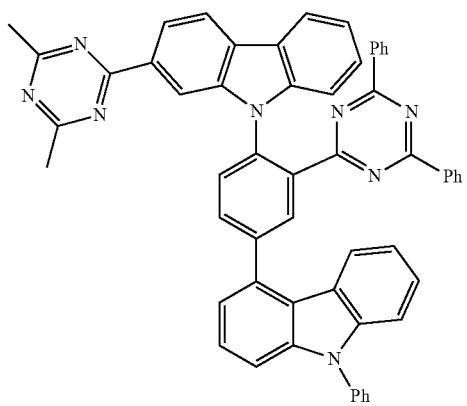
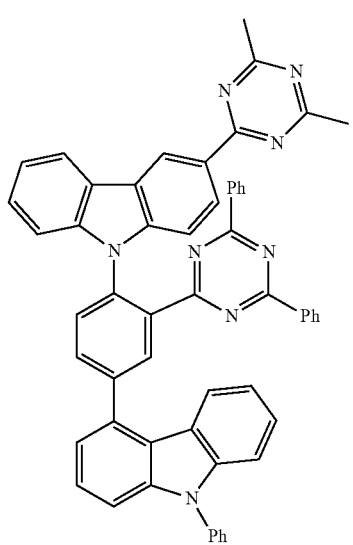

421
-continued
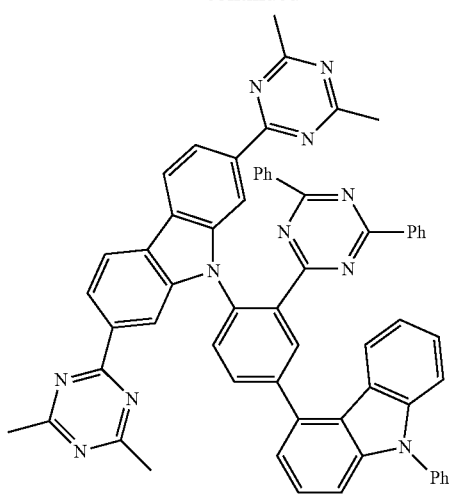
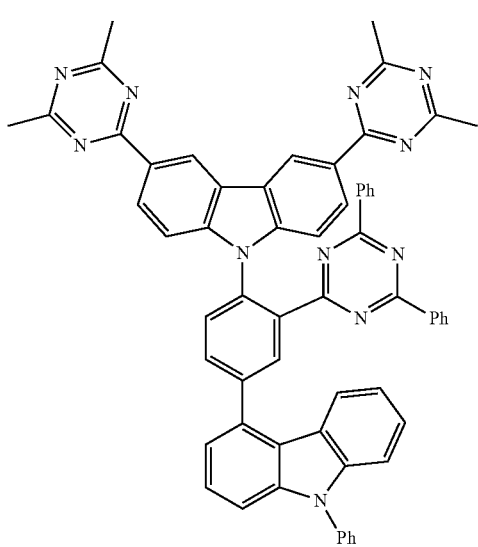
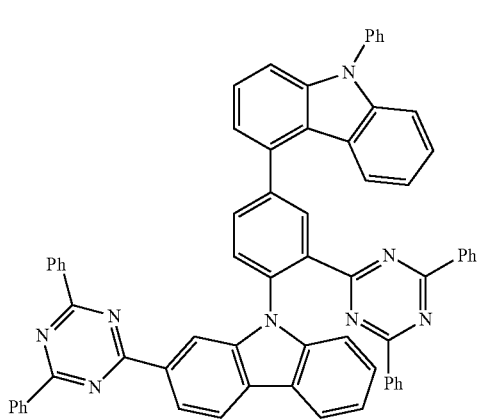
422
-continued
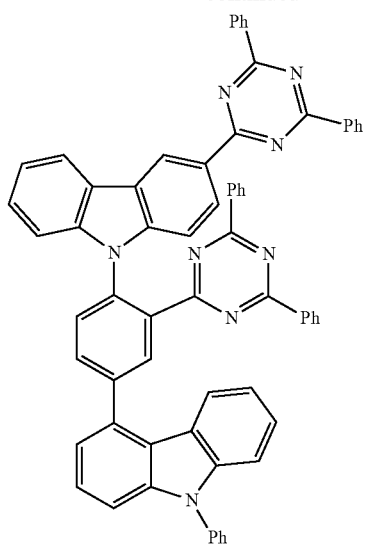
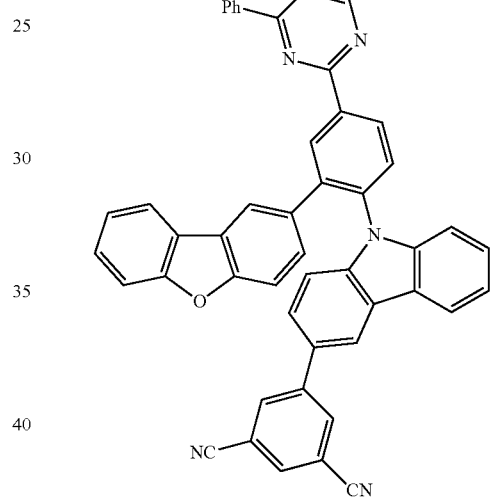
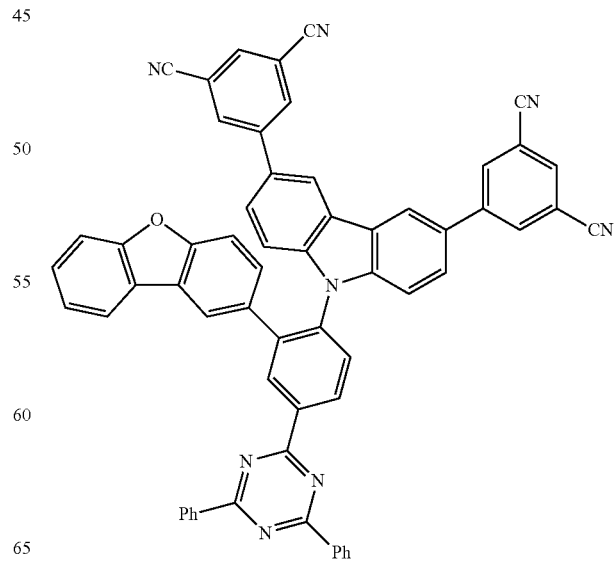

-continued
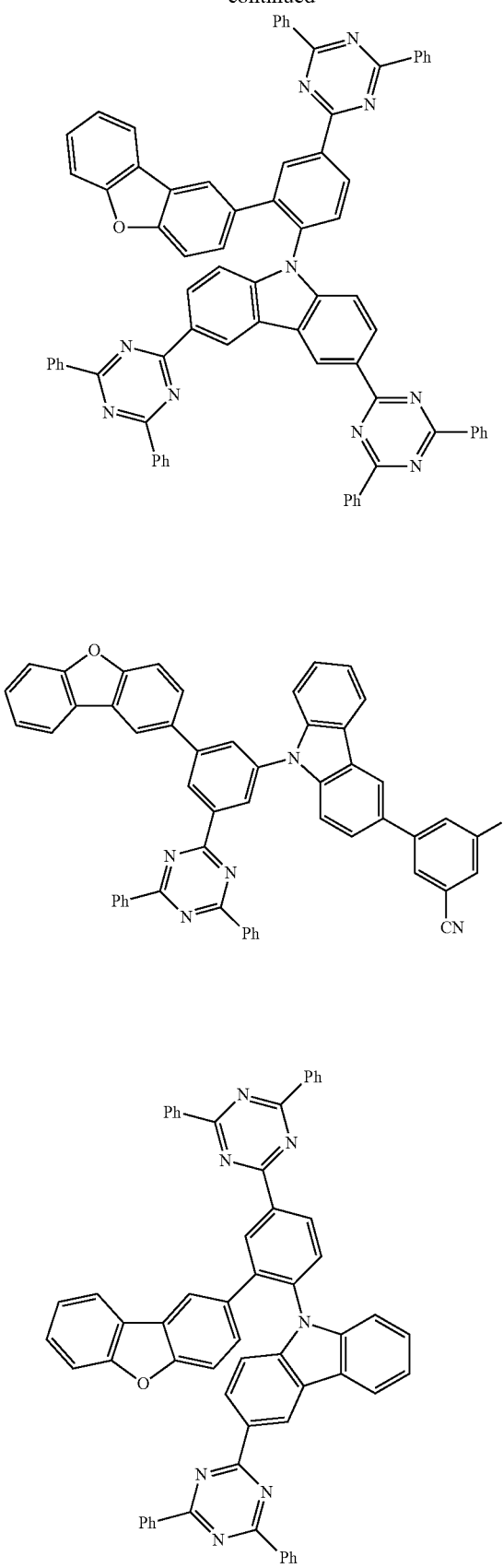
-continued
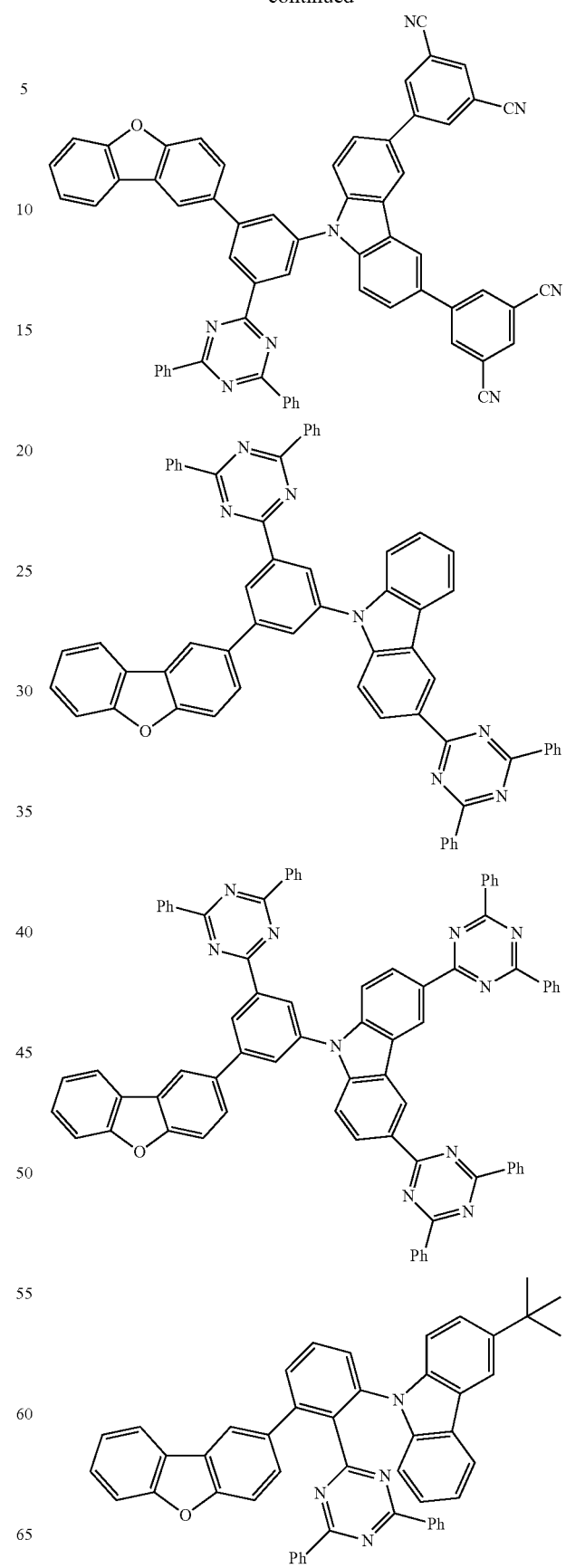

-continued

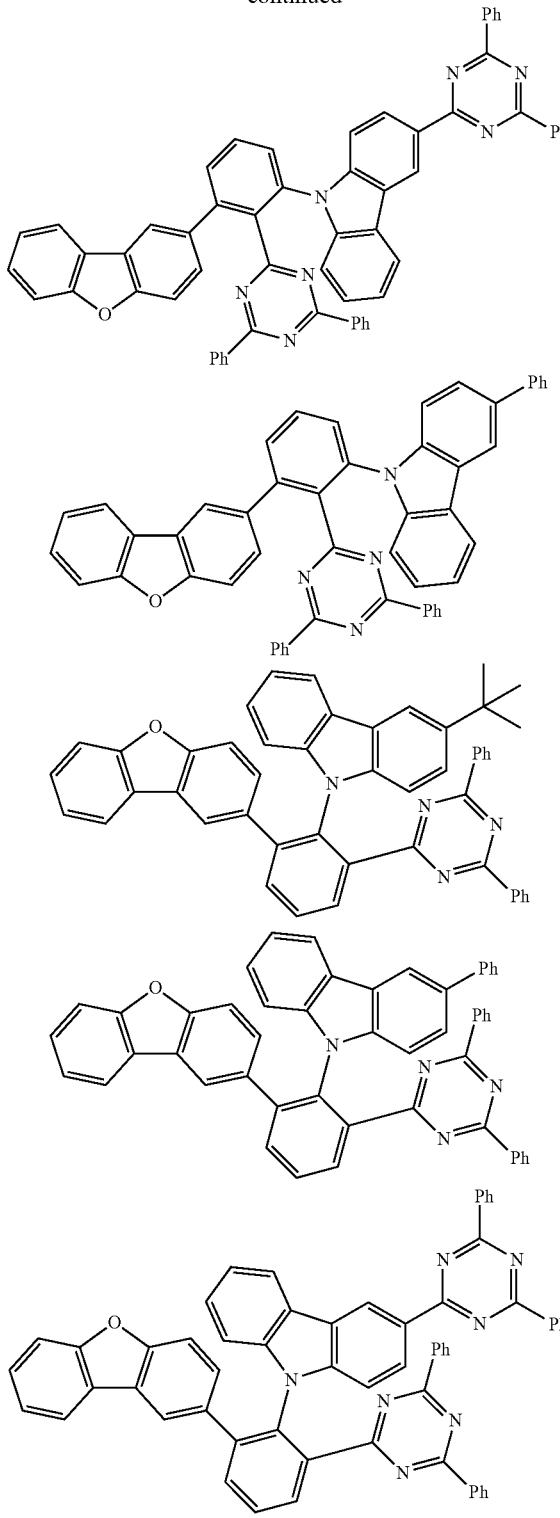

The invention claimed is:
1. An organic molecule, consisting of:
one first chemical moiety represented by a structure of Formula I:

Formula I

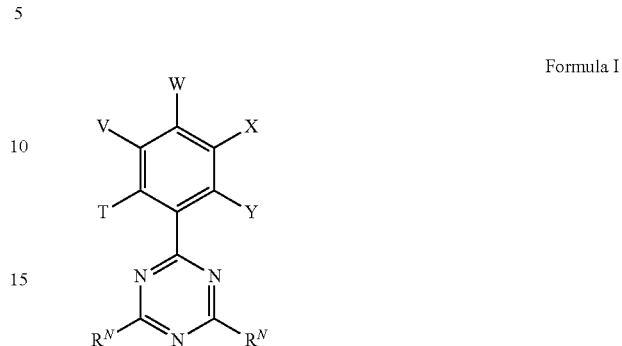

one second chemical moiety represented by a structure of Formula II:

Formula II

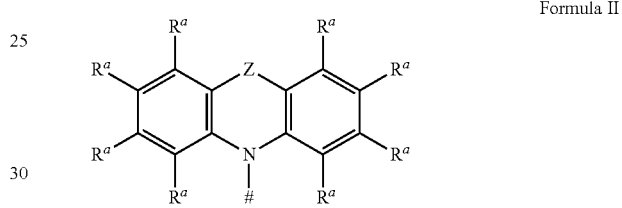

wherein the first chemical moiety is linked to the second chemical moiety via a single bond; and
one third chemical moiety represented by a structure of Formula III:

Formula III

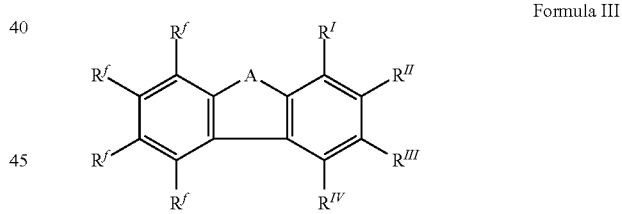

wherein the first chemical moiety is linked to the third chemical moiety via a single bond;
wherein
one of T or W is a binding site of the single bond linking the first chemical moiety to the second chemical moiety;
another one of T or W is $R^1$;
one of X, V or Y is a binding site of the single bond linking the first chemical moiety to the third chemical moiety;
other two of X, V or Y are each independently $R^1$;
represents the binding site of the single bond linking the first chemical moiety to the second chemical moiety;
A is selected from the group consisting of O, S and N-Ph;
Z is a direct bond;
$R^N$ is at each occurrence independently from another selected from the group consisting of:
hydrogen,
deuterium,
$C_1$-$C_5$-alkyl, wherein one or more hydrogen atoms of the $C_1$-$C_5$-alkyl are optionally substituted by deuterium;

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the inventions.

$C_2$-$C_8$-alkenyl, wherein one or more hydrogen atoms of the $C_2$-$C_8$-alkenyl are optionally substituted by deuterium;

$C_2$-$C_8$-alkynyl, wherein one or more hydrogen atoms of the $C_2$-$C_8$-alkynyl are optionally substituted by deuterium;

$C_6$-$C_{18}$-aryl, which is optionally substituted with one or more substituents $R^6$; and $C_3$-$C_{17}$-heteroaryl, which is optionally substituted with one or more substituents $R^6$:

$R^I$, $R^{II}$, $R^{III}$, and $R^{IV}$ are at each occurrence independently from another selected from the group consisting of $ and Rd;

$R^d$ is at each occurrence independently from another selected from the group consisting of:
hydrogen,
deuterium,
$C_6$-$C_{18}$-aryl, which is optionally substituted with one or more substituents independently from another selected from the group consisting of:
$C_1$-$C_5$-alkyl, wherein optionally one or more hydrogen atoms of the $C_1$-$C_5$-alkyl are independently from each other substituted by deuterium, CN, $CF_3$, or F; and
$C_6$-$C_{18}$-aryl, which is optionally substituted with one or more $C_1$-$C_5$-alkyl substituents;

$ represents the binding site of the single bond linking the first chemical moiety to the third chemical moiety;

$R^1$ is at each occurrence independently from another selected from the group consisting of:
hydrogen,
deuterium,
$C_1$-$C_5$-alkyl, wherein one or more hydrogen atoms of the $C_1$-$C_5$-alkyl are optionally substituted by deuterium;
$C_2$-$C_8$-alkenyl, wherein one or more hydrogen atoms of the $C_2$-$C_8$-alkenyl are optionally substituted by deuterium;
$C_2$-$C_8$-alkynyl, wherein one or more hydrogen atoms of the $C_2$-$C_8$-alkynyl are optionally substituted by deuterium; and
$C_6$-$C_{18}$-aryl, which is optionally substituted with one or more substituents independently from another selected from the group consisting of:
$C_1$-$C_5$-alkyl, wherein optionally one or more hydrogen atoms of the $C_1$-$C_5$-alkyl are independently from each other substituted by deuterium, CN, $CF_3$, or F; and
$C_6$-$C_{18}$-aryl, which is optionally substituted with one or more $C_1$-$C_5$-alkyl substituents;

$R^a$ is at each occurrence independently from another selected from the group consisting of:
hydrogen,
deuterium,
$N(R^5)_2$,
$OR^5$,
$Si(R^5)_3$,
$B(OR^5)_2$,
$R^5$,
$CF_3$,
CN,
F,
Br,
I,
$C_1$-$C_{40}$-alkyl,
which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_1$-$C_{40}$-alkoxy,
which is optionally substituted with one or more substituents $R^5$ and wherein one or more non-adjacent $CH_2$-groups are optionally substituted by $R^5C{=}CR^5$, C=C, $Si(R^5)_2$, $Ge(R^5)_2$, $Sn(R^5)_2$, C=O, C=S, C=Se, C=$NR^5$ P(=O)($R^5$), SO, $SO_2$, $NR^5$, O, S or $CONR^5$;

$C_1$-$C_{40}$-thioalkoxy,
which is optionally substituted with one or more substituents $R^5$ and wherein one or more non-adjacent $CH_2$-groups are optionally substituted by $R^5C{=}CR^5$, C=C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_2$-$C_{40}$-alkenyl,
which is optionally substituted with one or more substituents $R^5$ and wherein one or more non-adjacent $CH_2$-groups are optionally substituted by $R^5C{=}CR^5$, C=C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_2$-$C_{40}$-alkynyl,
which is optionally substituted with one or more substituents $R^5$ and wherein one or more non-adjacent $CH_2$-groups are optionally substituted by $R^5C{=}CR^5$, C=C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_6$-$C_{60}$-aryl, which is optionally substituted with one or more substituents $R^5$ and $C_3$-$C_{57}$-heteroaryl, which is optionally substituted with one or more substituents $R^5$;

$R^5$ is at each occurrence independently from another selected from the group consisting of:
hydrogen,
deuterium,
$N(R^6)_2$,
$OR^6$,
$Si(R^6)_3$,
$B(OR^6)_2$,
$OSO_2R^6$,
$CF_3$,
CN,
F,
Br,
I,
$C_1$-$C_{40}$-alkyl,
which is optionally substituted with one or more substituents $R^6$ and wherein one or more non-adjacent $CH_2$-groups are optionally substituted by $R^6C{=}CR^6$, C=C, $Si(R^6)_2$, $Ge(R^6)_2$, $Sn(R^6)_2$, C=O, C=S, C=Se, C=$NR^6$ P(=O)($R^6$), SO, $SO_2$, $NR^6$, O, S or $CONR^6$;

$C_1$-$C_{40}$-alkoxy,
which is optionally substituted with one or more substituents $R^6$ and wherein one or more non-adjacent $CH_2$-groups are optionally substituted by $R^6C{=}CR^6$, C=C, $Si(R^6)_2$, $Ge(R^6)_2$, $Sn(R^6)_2$, C=O, C=S, C=Se, C=$NR^6$, P(=O)($R^6$), SO, $SO_2$, $NR^6$, O, S or $CONR^6$;

$C_1$-$C_{40}$-thioalkoxy,
which is optionally substituted with one or more substituents $R^6$ and wherein one or more non-adjacent $CH_2$-groups are optionally substituted by $R^6C{=}CR^6$, CEC, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_2$-C$_{40}$-alkenyl,
    which is optionally substituted with one or more substituents R$^6$ and wherein one or more non-adjacent CH$_2$-groups are optionally substituted by R$^6$C=CR$^6$, C=C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_2$-C$_{40}$-alkynyl,
    which is optionally substituted with one or more substituents R$^6$ and wherein one or more non-adjacent CH$_2$-groups are optionally substituted by R$^6$C=CR$^6$, CEC, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_6$-C$_{60}$-aryl, which is optionally substituted with one or more substituents R$^6$; and C$_3$-C$_{57}$-heteroaryl, which is optionally substituted with one or more substituents R$^6$;

R$^f$ is at each occurrence independently from another selected from the group consisting of:
hydrogen,
deuterium,
N(R$^{5f}$)$_2$,
OR$^{5f}$,
Si(R$^{5f}$)$_3$,
B(OR$^{5f}$)$_2$,
OSO$_2$R$^{5f}$,
CF$_3$,
CN,
F,
Br
I, C$_1$-C$_{40}$-alkyl,
    which is optionally substituted with one or more substituents R$^{5f}$ and wherein one or more non-adjacent CH$_2$-groups are optionally substituted by R$^{5f}$C=CR$^{5f}$, C=C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$, O, S or CONR$^{5f}$, C$_1$-C$_{40}$-alkoxy,
    which is optionally substituted with one or more substituents R$^{5f}$ and wherein one or more non-adjacent CH$_2$-groups are optionally substituted by R$^{5f}$C=CR$^{5f}$, CEC, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$, O, S or CONR$^{5f}$;

C$_1$-C$_{40}$-thioalkoxy,
    which is optionally substituted with one or more substituents R$^{5f}$ and wherein one or more non-adjacent CH$_2$-groups are optionally substituted by R$^{5f}$C=CR$^{5f}$, C=C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$, O, S or CONR$^{5f}$, C$_2$-C$_{40}$-alkenyl,
    which is optionally substituted with one or more substituents R$^{5f}$ and wherein one or more non-adjacent CH$_2$-groups are optionally substituted by R$^{5f}$C=CR$^{5f}$, C=C, Si(R$^{5f}$)$_2$, Ge(R$^{5f}$)$_2$, Sn(R$^{5f}$)$_2$, C=O, C=S, C=Se, C=NR$^{5f}$, P(=O)(R$^{5f}$), SO, SO$_2$, NR$^{5f}$, O, S or CONR$^{5f}$, C$_2$-C$_{40}$-alkynyl,
    which is optionally substituted with one or more substituents R$^{5f}$ and wherein one or more non-adjacent CH$_2$-groups are optionally substituted by R$^{5f}$C=CR$^{5f}$, C=C, Si(R$^{5f}$)$_2$, Ge(R$^{5f}$)$_2$, Sn(R$^{5f}$)$_2$, C=O, C=S, C=Se, C=NR$^{5f}$ P(=O)(R$^{5f}$), SO, SO$_2$, NR$^{5f}$, O, S or CONR$^{5f}$;

C$_6$-C$_{60}$-aryl, which is optionally substituted with one or more substituents R$^{5f}$, and C$_3$-C$_{57}$-heteroaryl, which is optionally substituted with one or more substituents R$^{5f}$;

R$^{5f}$ is at each occurrence independently from another selected from the group consisting of:
hydrogen,
deuterium,
N(R$^6$)$_2$,
OR$^6$,
Si(R$^6$)$_3$,
B(OR$^6$)$_2$,
OSO$_2$R$^6$
CF$_3$,
CN,
F,
Br,
I, C$_1$-C$_{40}$-alkyl,
    which is optionally substituted with one or more substituents R$^6$ and wherein one or more non-adjacent CH$_2$-groups are optionally substituted by R$^6$C=CR$^6$, CEC, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_1$-C$_{40}$-alkoxy,
    which is optionally substituted with one or more substituents R$^6$ and wherein one or more non-adjacent CH$_2$-groups are optionally substituted by R$^6$C=CR$^6$, C=C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_1$-C$_{40}$-thioalkoxy,
    which is optionally substituted with one or more substituents R$^6$ and wherein one or more non-adjacent CH$_2$-groups are optionally substituted by R$^6$C=CR$^6$, CEC, Si(R$^6$)$_2$, Ge(R$^6$)$_2$, Sn(R$^6$)$_2$, C=O, C=S, C=Se, C=NR$^6$ P(=O)(R$^6$), SO, SO$_2$, NR$^6$, O, S or CONR$^6$;

C$_2$-C$_{40}$-alkenyl,
    which is optionally substituted with one or more substituents R$^6$ and wherein one or more non-adjacent CH$_2$-groups are optionally substituted by R$^6$C=CR$^6$, CEC, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_2$-C$_{40}$-alkynyl,
    which is optionally substituted with one or more substituents R$^6$ and wherein one or more non-adjacent CH$_2$-groups are optionally substituted by R$^6$C=CR$^6$, CEC, Si(R$^6$)$_2$, Ge(R$^6$)$_2$, Sn(R$^6$)$_2$, C=O, C=S, C=Se, C=NR$^6$ P(=O)(R$^6$), SO, SO$_2$, NR$^6$, O, S or CONR$^6$;

C$_6$-C$_{60}$-aryl, which is optionally substituted with one or more substituents R$^6$; and C$_3$-C$_{57}$-heteroaryl, which is optionally substituted with one or more substituents R$^6$;

R$^6$ is at each occurrence independently from another selected from the group consisting of:
hydrogen,
deuterium,
OPh,
CF$_3$,
CN,
F, C$_1$-C$_5$-alkyl, wherein optionally one or more hydrogen atoms of the C$_1$-C$_5$-alkyl are independently from each other substituted by deuterium, CN, CF$_3$, or F;

C$_1$-C$_5$-alkoxy, wherein optionally one or more hydrogen atoms of the C$_1$-C$_5$-alkoxy are independently from each other substituted by deuterium, CN, CF$_3$, or F;

C$_1$-C$_5$-thioalkoxy, wherein optionally one or more hydrogen atoms of the C$_1$-C$_5$-thioalkoxy are independently from each other substituted by deuterium, CN, CF$_3$, or F;

C$_2$-C$_5$-alkenyl, wherein optionally one or more hydrogen atoms of the C$_2$-C$_5$-alkenyl are independently from each other substituted by deuterium, CN, CF$_3$, or F;

C$_2$-C$_5$-alkynyl, wherein optionally one or more hydrogen atoms of the C$_2$-C$_5$-alkynyl are independently from each other substituted by deuterium, CN, CF$_3$, or F;

C$_6$-C$_{18}$-aryl, which is optionally substituted with one or more C$_1$-C$_5$-alkyl substituents;

C$_3$-C$_{17}$-heteroaryl, which is optionally substituted with one or more C$_1$-C$_5$-alkyl substituents;

N (C$_6$-C$_{18}$-aryl)$_2$;

N (C$_3$-C$_{17}$-heteroaryl)$_2$; and

N (C$_3$-C$_{17}$-heteroaryl) (C$_6$-C$_{18}$-aryl);

wherein the substituents R$^a$ or R$^5$ independently from each other optionally form a mono- or polycyclic, aliphatic, aromatic and/or benzo-fused ring system with one or more substituents R$^a$ or R$^5$;

wherein the substituents R$^f$ or R$^{5f}$ independently from each other optionally form a mono- or polycyclic, aliphatic, aromatic and/or benzo-fused ring system with one or more substituents R$^f$ or R$^{5f}$; and wherein exactly one substituent selected from the group consisting of R$^I$, R$^{II}$, R$^{III}$ and R$^{IV}$ is the binding site of the single bond linking the first chemical moiety to the third chemical moiety.

2. The organic molecule according to claim 1, wherein R$^1$, R$^d$, R$^f$ and R$^N$ are at each occurrence independently from another selected from the group consisting of H and phenyl.

3. The organic molecule according to claim 1, wherein X represents the binding site of the single bond linking the first chemical moiety and the third chemical moiety, and W represents the binding site of the single bond linking the first chemical moiety and the second chemical moiety.

4. The organic molecule according to claim 1, wherein the second chemical moiety is represented by Formula IIa:

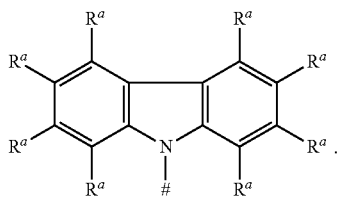

Formula IIa

5. The organic molecule according to claim 1, wherein the second chemical moiety is represented by Formula IIb:

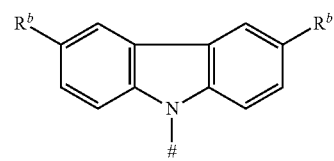

Formula IIb wherein

R$^b$ is at each occurrence independently from another selected from the group consisting of deuterium, N(R$^5$)$_2$, OR$^5$, Si(R$^5$)$_3$, B(OR$^5$)$_2$, OSO$_2$R$^5$, CF$_3$, CN, F, Br, I, C$_1$-C$_{40}$-alkyl,
which is optionally substituted with one or more substituents R$^5$ and wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_1$-C$_{40}$-alkoxy,
which is optionally substituted with one or more substituents R$^5$ and wherein one or more non-adjacent CH$_2$-groups are optionally substituted by R$^5$C=CR$^5$, C=C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_1$-C$_{40}$-thioalkoxy,
which is optionally substituted with one or more substituents R$^5$ and wherein one or more non-adjacent CH$_2$-groups are optionally substituted by R$^5$C=CR$^5$, C=C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_2$-C$_{40}$-alkenyl,
which is optionally substituted with one or more substituents R$^5$ and wherein one or more non-adjacent CH$_2$-groups are optionally substituted by R$^5$C=CR$^5$, C=C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_2$-C$_{40}$-alkynyl,
which is optionally substituted with one or more substituents R$^5$ and wherein one or more non-adjacent CH$_2$-groups are optionally substituted by R$^5$C=CR$^5$, C=C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_6$-C$_{60}$-aryl,
which is optionally substituted with one or more substituents R$^5$; and C$_3$-C$_{57}$-heteroaryl,
which is optionally substituted with one or more substituents R$^5$.

6. The organic molecule according to claim 1 wherein the second chemical moiety is represented by formula IIc:

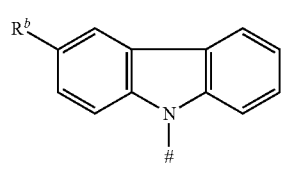

Formula IIc wherein $R^b$ is at each occurrence independently from another selected from the group consisting of deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl, which is optionally substituted with one or more substituents $R^5$ and wherein one or more non-adjacent $CH_2$-groups are optionally substituted by $R^5C$=$CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C$=$CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C$=$CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C$=$CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C$=$CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$.

7. The organic molecule according to claim 5, wherein $R^b$ is at each occurrence independently from another selected from the group consisting of Me, $^i$Pr, $^t$Bu, CN, $CF_3$, Ph, which is optionally substituted with one or more substituents independently from each other selected from the group consisting of Me, $^i$Pr, $^t$Bu, CN, $CF_3$ and Ph;

pyridinyl, which is optionally substituted with one or more substituents independently from each other selected from the group consisting of Me, $^i$Pr, $^t$Bu, CN, $CF_3$ and Ph;

pyrimidinyl, which is optionally substituted with one or more substituents independently from each other selected from the group consisting of Me, $^i$Pr, $^t$Bu, CN, $CF_3$ and Ph;

carbazolyl, which is optionally substituted with one or more substituents independently from each other selected from the group consisting of Me, $^i$Pr, Bu, CN, $CF_3$ and Ph;

triazinyl, which is optionally substituted with one or more substituents independently from each other selected from the group consisting of Me, $^i$Pr, $^t$Bu, CN, $CF_3$ and Ph; and N (Ph)$_2$.

8. A composition comprising at least one organic molecule according to claim 1 as an emitter and/or host.

9. An optoelectronic device comprising the organic molecule according to claim 1.

10. The optoelectronic device according to claim 9, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

11. The optoelectronic device according to claim 10, comprising:
a substrate;
an anode;
a cathode, wherein the anode or the cathode is applied to the substrate; and
at least one light-emitting layer disposed between the anode and the cathode and which comprises the organic molecule.

12. An optoelectronic device comprising the organic molecule according to claim 1, wherein the organic molecule is one of a luminescent emitter, an electron transport material, a hole injection material or a hole blocking material in the optoelectronic device.

13. The optoelectronic device according to claim 12, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

14. An optoelectronic device comprising the organic molecule according to claim 1, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

15. The optoelectronic device according to claim 14, comprising:
a substrate;
an anode;
a cathode, wherein the anode or the cathode is applied to the substrate; and
at least one light-emitting layer disposed between the anode and the cathode and which comprises the organic molecule.

16. An optoelectronic device comprising the organic molecule according to claim 2, wherein the organic molecule is one of a luminescent emitter, an electron transport material, a hole injection material or a hole blocking material in the optoelectronic device.

17. An optoelectronic device comprising the composition according to claim 8, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

18. The optoelectronic device according to claim 17, comprising:
a substrate;
an anode;

a cathode, wherein the anode or the cathode is applied to the substrate; and at least one light-emitting layer disposed between the anode and the cathode and which comprises the composition.

19. A process for producing an optoelectronic device, comprising processing of the organic molecule according to claim 1 by a vacuum evaporation method or from a solution.

20. A process for producing an optoelectronic device, comprising processing of the composition according to claim 8 by a vacuum evaporation method or from a solution.

* * * * *